(12) United States Patent
Trager et al.

(10) Patent No.: US 11,253,547 B2
(45) Date of Patent: *Feb. 22, 2022

(54) CD19-DIRECTED CHIMERIC ANTIGEN RECEPTORS AND USES THEREOF IN IMMUNOTHERAPY

(71) Applicant: Nkarta, Inc., South San Francisco, CA (US)

(72) Inventors: James Barnaby Trager, Albany, CA (US); Luxuan Guo Buren, San Francisco, CA (US); Chao Guo, San Francisco, CA (US); Mira Tohmé, San Francisco, CA (US); Ivan Chan, Millbrae, CA (US); Alexandra Leida Liana Lazetic, San Jose, CA (US)

(73) Assignee: Nkarta, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/089,449

(22) Filed: Nov. 4, 2020

(65) Prior Publication Data

US 2021/0070856 A1 Mar. 11, 2021

Related U.S. Application Data

(63) Continuation of application No. PCT/US2020/020824, filed on Mar. 3, 2020.

(60) Provisional application No. 62/932,165, filed on Nov. 7, 2019, provisional application No. 62/895,910, filed on Sep. 4, 2019, provisional application No. 62/814,180, filed on Mar. 5, 2019.

(51) Int. Cl.
| | |
|---|---|
| *C07K 14/54* | (2006.01) |
| *A61K 35/17* | (2015.01) |
| *A61P 35/00* | (2006.01) |
| *C07K 14/55* | (2006.01) |
| *C07K 14/725* | (2006.01) |
| *C07K 14/705* | (2006.01) |
| *C07K 16/28* | (2006.01) |
| *C12N 5/0783* | (2010.01) |

(52) U.S. Cl.
CPC ............. *A61K 35/17* (2013.01); *A61P 35/00* (2018.01); *C07K 14/5443* (2013.01); *C07K 14/55* (2013.01); *C07K 14/7051* (2013.01); *C07K 14/70517* (2013.01); *C07K 14/70578* (2013.01); *C07K 16/2803* (2013.01); *C07K 16/2878* (2013.01); *C12N 5/0646* (2013.01); *C07K 2317/56* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 4,650,764 A | 3/1987 | Temin et al. |
| 4,690,915 A | 9/1987 | Rosenberg et al. |
| 4,844,893 A | 7/1989 | Honsik et al. |
| 4,980,289 A | 12/1990 | Temin et al. |
| 5,124,263 A | 6/1992 | Temin et al. |
| 5,359,046 A | 10/1994 | Capon |
| 5,399,346 A | 3/1995 | Anderson et al. |
| 5,415,874 A | 5/1995 | Bender et al. |
| 5,653,977 A | 8/1997 | Saleh |
| 5,674,704 A | 10/1997 | Goodwin et al. |
| 5,686,281 A | 11/1997 | Roberts |
| 5,712,149 A | 1/1998 | Roberts |
| 5,902,733 A | 5/1999 | Hirt et al. |
| 6,103,521 A | 8/2000 | Capon et al. |
| 6,261,839 B1 | 7/2001 | Multhoff et al. |
| 6,303,121 B1 | 10/2001 | Kwon |
| 6,319,494 B1 | 11/2001 | Capon et al. |
| 6,355,476 B1 | 3/2002 | Kwon et al. |
| 6,410,319 B1 | 6/2002 | Raubitschek et al. |
| 6,464,973 B1 | 10/2002 | Levitsky et al. |
| 6,797,514 B2 | 9/2004 | Berenson et al. |
| 7,052,906 B1 | 5/2006 | Lawson et al. |
| 7,070,995 B2 | 7/2006 | Jensen |
| 7,390,483 B2 | 6/2008 | Levitsky et al. |

(Continued)

FOREIGN PATENT DOCUMENTS

| | | |
|---|---|---|
| CN | 101684456 | 3/2010 |
| CN | 105838677 | 8/2016 |

(Continued)

OTHER PUBLICATIONS

International Search Report and Written Opinion for International Application No. PCT/US20/20824, dated Jul. 30, 2020, in 23 pages.
Caratelli et al., "Fcγ Chimeric Receptor-Engineered T Cells: Methodology, Advantages, Limitations, and Clinical Relevance," Front Immunol., vol. 8, Article 457, 8 pages (Apr. 27, 2017).
Gillet et al., Selectable markers for gene therapy, Chapter 26 of Gene and Cell Therapy: Therapeutic Mechanisms and Strategies, 3rd Ed. N.S. Templeton Ed, (CRC Press: Bpca Ratpm. FL), pp. 555 and 558, 2009.

(Continued)

*Primary Examiner* — Michael D Burkhart
(74) *Attorney, Agent, or Firm* — Knobbe Martens Olson & Bear LLP

(57) ABSTRACT

Provided for herein in several embodiments are immune cell-based (e.g., natural killer (NK) cell) compositions comprising CD19-directed chimeric antigen receptors. In some embodiments the anti-CD19 binder portion of the CAR is humanized. In several embodiments, the humanized anti-CD19 CAR expressing cells exhibit enhanced expression of the CAR as well as enhanced cytotoxicity and/or persistence. Several embodiments include methods of using of the anti-CD19 CAR expressing immune cells in immunotherapy.

19 Claims, 124 Drawing Sheets

Specification includes a Sequence Listing.

(56) References Cited

U.S. PATENT DOCUMENTS

| | | |
|---|---|---|
| 7,435,596 B2 | 10/2008 | Campana et al. |
| 7,446,179 B2 | 11/2008 | Jensen et al. |
| 7,446,190 B2 | 11/2008 | Sadelain et al. |
| 7,740,871 B2 | 6/2010 | Ambinder et al. |
| 7,994,298 B2 | 8/2011 | Zhang et al. |
| 8,012,469 B2 | 9/2011 | Levitsky et al. |
| 8,026,097 B2 | 9/2011 | Campana et al. |
| 8,252,914 B2 | 8/2012 | Zhang et al. |
| 8,383,096 B2 | 2/2013 | Ambinder et al. |
| 8,389,282 B2 | 3/2013 | Sadelain et al. |
| 8,399,645 B2 | 3/2013 | Campana et al. |
| 8,802,374 B2 | 8/2014 | Jensen |
| 8,877,182 B2 | 11/2014 | Alici |
| 8,906,682 B2 | 12/2014 | June et al. |
| 8,911,993 B2 | 12/2014 | June et al. |
| 8,916,381 B1 | 12/2014 | June et al. |
| 8,926,964 B2 | 1/2015 | Hariri et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,212,229 B2 | 12/2015 | Schönfeld et al. |
| 9,328,156 B2 | 5/2016 | June et al. |
| 9,365,641 B2 | 6/2016 | June et al. |
| 9,447,194 B2 | 9/2016 | Jensen |
| 9,464,140 B2 | 10/2016 | June et al. |
| 9,464,274 B2 | 10/2016 | Hariri et al. |
| 9,481,728 B2 | 11/2016 | June et al. |
| 9,487,800 B2 | 11/2016 | Schönfeld et al. |
| 9,499,629 B2 | 11/2016 | June et al. |
| 9,511,092 B2 | 12/2016 | Campana et al. |
| 9,518,523 B2 | 12/2016 | June et al. |
| 9,540,445 B2 | 1/2017 | June et al. |
| 9,580,685 B2 | 2/2017 | Jensen |
| 9,605,049 B2 | 3/2017 | Campana et al. |
| 9,623,082 B2 | 4/2017 | Copik et al. |
| 9,629,877 B2 | 4/2017 | Cooper et al. |
| 9,701,758 B2 | 7/2017 | Cooper et al. |
| 9,834,590 B2 | 12/2017 | Campana et al. |
| 9,856,322 B2 | 1/2018 | Campana et al. |
| 10,100,281 B2 | 10/2018 | Jensen |
| 10,125,193 B2 | 11/2018 | Cooper et al. |
| 2002/0018783 A1 | 2/2002 | Sadelain et al. |
| 2002/0037282 A1 | 3/2002 | Levitsky et al. |
| 2003/0147869 A1 | 8/2003 | Riley |
| 2003/0157713 A1 | 8/2003 | Ohno et al. |
| 2003/0215427 A1 | 11/2003 | Jensen |
| 2004/0038886 A1 | 2/2004 | Finney et al. |
| 2004/0043401 A1 | 3/2004 | Sadelain et al. |
| 2004/0126363 A1 | 7/2004 | Jensen et al. |
| 2004/0161433 A1 | 8/2004 | Teshigawara et al. |
| 2005/0048549 A1 | 3/2005 | Cao et al. |
| 2005/0113564 A1 | 5/2005 | Campana et al. |
| 2005/0255118 A1 | 11/2005 | Wehner |
| 2006/0057680 A1 | 3/2006 | Zheng et al. |
| 2006/0093605 A1 | 5/2006 | Campana et al. |
| 2006/0140922 A1 | 6/2006 | Levitsky et al. |
| 2006/0233770 A1 | 10/2006 | Ambinder et al. |
| 2006/0247191 A1 | 11/2006 | Finney et al. |
| 2007/0077241 A1 | 4/2007 | Spies et al. |
| 2007/0160578 A1 | 7/2007 | Waldmann et al. |
| 2007/0166327 A1 | 7/2007 | Cooper et al. |
| 2008/0026413 A1 | 1/2008 | Savage |
| 2008/0260758 A1 | 10/2008 | Levitsky et al. |
| 2008/0299137 A1 | 12/2008 | Svendsen et al. |
| 2009/0011498 A1 | 1/2009 | Campana et al. |
| 2009/0202501 A1 | 8/2009 | Zhang et al. |
| 2010/0029749 A1 | 2/2010 | Zhang et al. |
| 2010/0178276 A1 | 7/2010 | Sadelain et al. |
| 2010/0272760 A1 | 10/2010 | Ambinder et al. |
| 2011/0059137 A1 | 3/2011 | Antonia et al. |
| 2011/0287058 A1 | 11/2011 | Levitsky et al. |
| 2012/0015434 A1 | 1/2012 | Campana et al. |
| 2012/0029063 A1 | 2/2012 | Zhang et al. |
| 2012/0148552 A1 | 6/2012 | Jensen |
| 2012/0148553 A1 | 6/2012 | Hariri et al. |
| 2012/0258085 A1 | 10/2012 | Alici |
| 2012/0282256 A1 | 11/2012 | Campana et al. |
| 2013/0052158 A1 | 2/2013 | Van Rhee |
| 2013/0058921 A1 | 3/2013 | Van Rhee |
| 2013/0071414 A1 | 3/2013 | Dotti et al. |
| 2013/0121960 A1 | 5/2013 | Sadelain et al. |
| 2013/0216509 A1 | 8/2013 | Campana et al. |
| 2013/0251752 A1 | 9/2013 | Antonia et al. |
| 2013/0266551 A1 | 10/2013 | Campana et al. |
| 2013/0280221 A1 | 10/2013 | Schönfeld et al. |
| 2013/0280285 A1 | 10/2013 | Schönfeld et al. |
| 2013/0288368 A1 | 10/2013 | June et al. |
| 2013/0309258 A1 | 11/2013 | June et al. |
| 2014/0023626 A1 | 1/2014 | Peled et al. |
| 2014/0099309 A1 | 4/2014 | Powell, Jr. et al. |
| 2014/0099340 A1 | 4/2014 | June et al. |
| 2014/0115198 A1 | 6/2014 | Spies et al. |
| 2014/0227237 A1 | 8/2014 | June et al. |
| 2014/0271635 A1 | 9/2014 | Brogdon et al. |
| 2014/0286934 A1 | 9/2014 | Blein et al. |
| 2014/0286973 A1 | 9/2014 | Powell, Jr. |
| 2014/0302608 A1 | 10/2014 | Dominici et al. |
| 2014/0322183 A1 | 10/2014 | Milone et al. |
| 2014/0328812 A1 | 11/2014 | Campana et al. |
| 2014/0341869 A1 | 11/2014 | Campana et al. |
| 2015/0072425 A1 | 3/2015 | Hariri et al. |
| 2015/0139943 A1 | 5/2015 | Campana et al. |
| 2015/0190471 A1 | 7/2015 | Copik et al. |
| 2015/0218649 A1 | 8/2015 | Saenger et al. |
| 2015/0225470 A1 | 8/2015 | Zhang et al. |
| 2015/0273089 A1 | 10/2015 | Gray |
| 2015/0306141 A1 | 10/2015 | Jensen et al. |
| 2015/0329640 A1 | 11/2015 | Finer |
| 2015/0344844 A1 | 12/2015 | Better et al. |
| 2015/0368342 A1 | 12/2015 | Wu et al. |
| 2016/0000828 A1 | 1/2016 | Campana et al. |
| 2016/0008398 A1 | 1/2016 | Sadelain et al. |
| 2016/0009784 A1 | 1/2016 | Campana et al. |
| 2016/0030659 A1 | 2/2016 | Cheney |
| 2016/0045551 A1 | 2/2016 | Brentjens et al. |
| 2016/0046729 A1 | 2/2016 | Schönfeld et al. |
| 2016/0122766 A1 | 5/2016 | Wucherpfenning et al. |
| 2016/0122782 A1 | 5/2016 | Crisman et al. |
| 2016/0152723 A1 | 6/2016 | Chen et al. |
| 2016/0158285 A1 | 6/2016 | Cooper et al. |
| 2016/0185862 A1 | 6/2016 | Wu et al. |
| 2016/0207989 A1 | 7/2016 | Short |
| 2016/0228547 A1 | 8/2016 | Wagner et al. |
| 2016/0235787 A1 | 8/2016 | June et al. |
| 2016/0250258 A1 | 9/2016 | Delaney et al. |
| 2016/0272718 A1 | 9/2016 | Wang et al. |
| 2016/0289293 A1 | 10/2016 | Pulé et al. |
| 2016/0289294 A1 | 10/2016 | Pulé et al. |
| 2016/0296562 A1 | 10/2016 | Pulé et al. |
| 2016/0326265 A1 | 11/2016 | June et al. |
| 2016/0333108 A1 | 11/2016 | Forman et al. |
| 2017/0002322 A1 | 1/2017 | Hariri et al. |
| 2017/0014508 A1 | 1/2017 | Pulé et al. |
| 2017/0015975 A1 | 1/2017 | Fu et al. |
| 2017/0016025 A1 | 1/2017 | Poirot et al. |
| 2017/0044227 A1 | 2/2017 | Schönfeld et al. |
| 2017/0049819 A1 | 2/2017 | Friedman et al. |
| 2017/0073638 A1 | 3/2017 | Campana et al. |
| 2017/0081411 A1 | 3/2017 | Engels et al. |
| 2017/0107178 A1 | 4/2017 | Cowley et al. |
| 2017/0107286 A1 | 4/2017 | Kochenderfer |
| 2017/0137515 A1 | 5/2017 | Chang et al. |
| 2017/0158749 A1 | 6/2017 | Cooper et al. |
| 2017/0183415 A1 | 6/2017 | Brogdon et al. |
| 2017/0226223 A1 | 8/2017 | Williams et al. |
| 2017/0232070 A1 | 8/2017 | Junghans |
| 2017/0239294 A1 | 8/2017 | Thomas-Tikhonenko et al. |
| 2017/0260594 A1 | 9/2017 | Molinero et al. |
| 2017/0281766 A1 | 10/2017 | Wiltzius |
| 2017/0283482 A1 | 10/2017 | Campana et al. |
| 2017/0283775 A1 | 10/2017 | June et al. |
| 2017/0296678 A1 | 10/2017 | Sezc et al. |
| 2017/0333481 A1 | 11/2017 | Jantz et al. |

(56) References Cited

U.S. PATENT DOCUMENTS

| | | |
|---|---|---|
| 2017/0334968 A1 | 11/2017 | Cooper et al. |
| 2018/0002435 A1 | 1/2018 | Sasu et al. |
| 2018/0008638 A1 | 1/2018 | Campana et al. |
| 2018/0044391 A1 | 2/2018 | Gundram et al. |
| 2018/0044417 A1 | 2/2018 | Pulé et al. |
| 2018/0057609 A1 | 3/2018 | June et al. |
| 2018/0057795 A1 | 3/2018 | Childs et al. |
| 2018/0086846 A1 | 3/2018 | Wiltzius et al. |
| 2018/0118845 A1 | 5/2018 | Campana et al. |
| 2018/0125889 A1 | 5/2018 | Leek et al. |
| 2018/0133296 A1 | 5/2018 | Barrett et al. |
| 2018/0134787 A1 | 5/2018 | Liu et al. |
| 2018/0135015 A1 | 5/2018 | Campana et al. |
| 2018/0153977 A1 | 6/2018 | Wu et al. |
| 2018/0186878 A1 | 7/2018 | Rosenthal |
| 2018/0187149 A1 | 7/2018 | Ma et al. |
| 2018/0200298 A1 | 7/2018 | Jensen et al. |
| 2018/0244748 A1 | 8/2018 | Gill et al. |
| 2018/0258391 A1 | 9/2018 | June et al. |
| 2018/0312580 A1 | 11/2018 | Chen et al. |
| 2018/0312588 A1 | 11/2018 | Wiltzius et al. |
| 2018/0319862 A1 | 11/2018 | Thompson et al. |
| 2018/0325955 A1 | 11/2018 | Terrett et al. |
| 2019/0290693 A1 | 9/2019 | Qi et al. |
| 2019/0338011 A1 | 11/2019 | Zhang et al. |
| 2020/0123217 A1 | 4/2020 | Zhang et al. |
| 2020/0255803 A1 | 8/2020 | Zhang et al. |
| 2020/0407686 A1 | 12/2020 | Campana et al. |
| 2021/0017271 A1 | 1/2021 | Tan et al. |
| 2021/0046115 A1 | 2/2021 | Seow et al. |
| 2021/0054409 A1 | 2/2021 | Zhu et al. |
| 2021/0070856 A1* | 3/2021 | Trager ............ A61K 45/06 |

FOREIGN PATENT DOCUMENTS

| | | |
|---|---|---|
| CN | 105985931 | 10/2016 |
| CN | 107827990 | 3/2018 |
| EP | 0952213 A1 | 10/1999 |
| EP | 830599 B1 | 4/2000 |
| EP | 1231262 A1 | 8/2002 |
| EP | 1306427 A1 | 5/2003 |
| EP | 1053301 B1 | 4/2004 |
| EP | 1233058 B1 | 12/2006 |
| EP | 1820017 A2 | 8/2007 |
| EP | 2411507 A1 | 2/2012 |
| EP | 2493485 A1 | 9/2012 |
| EP | 2493486 A1 | 9/2012 |
| EP | 2141997 B1 | 10/2012 |
| EP | 2593542 A1 | 5/2013 |
| EP | 2614151 A1 | 7/2013 |
| EP | 2756521 A2 | 7/2014 |
| EP | 2537416 B1 | 11/2014 |
| EP | 2856876 A1 | 4/2015 |
| EP | 2866834 A1 | 5/2015 |
| EP | 2903637 A1 | 8/2015 |
| EP | 2904106 A2 | 8/2015 |
| EP | 2948544 A1 | 12/2015 |
| EP | 2956175 A1 | 12/2015 |
| EP | 2961831 A1 | 1/2016 |
| EP | 2964753 A1 | 1/2016 |
| EP | 2968492 A1 | 1/2016 |
| EP | 2970426 A2 | 1/2016 |
| EP | 2986636 A1 | 2/2016 |
| EP | 3008173 A2 | 4/2016 |
| EP | 3012268 A1 | 4/2016 |
| EP | 2614077 B1 | 8/2016 |
| EP | 3057986 A1 | 8/2016 |
| EP | 3063175 A2 | 9/2016 |
| EP | 3071221 A1 | 9/2016 |
| EP | 3071222 A1 | 9/2016 |
| EP | 3071223 A1 | 9/2016 |
| EP | 3083671 A1 | 10/2016 |
| EP | 3083691 A2 | 10/2016 |
| EP | 3094653 A1 | 11/2016 |
| EP | 3105318 A1 | 12/2016 |
| EP | 3105335 A1 | 12/2016 |
| EP | 3115373 A1 | 1/2017 |
| EP | 3126380 A1 | 2/2017 |
| EP | 3134432 A2 | 3/2017 |
| EP | 3180359 A1 | 6/2017 |
| EP | 2649086 B1 | 7/2017 |
| EP | 3189132 A1 | 7/2017 |
| EP | 3214091 B1 | 10/2018 |
| EP | 3567049 | 11/2019 |
| EP | 3119425 B1 | 9/2020 |
| WO | WO 1995/007358 | 3/1995 |
| WO | WO 1996/023814 | 8/1996 |
| WO | WO 1996/024671 | 8/1996 |
| WO | WO 1996/041163 A1 | 12/1996 |
| WO | WO 1997/023613 | 7/1997 |
| WO | WO 1998/026061 | 6/1998 |
| WO | WO 1999/000494 | 1/1999 |
| WO | WO 1999/038954 A1 | 8/1999 |
| WO | WO 1999/06557 | 11/1999 |
| WO | WO 1999/057268 | 11/1999 |
| WO | WO 2000/014257 | 3/2000 |
| WO | WO00/23573 | 4/2000 |
| WO | WO 2001/029191 A1 | 4/2001 |
| WO | WO 2001/038494 A1 | 5/2001 |
| WO | WO 2002/010350 A1 | 2/2002 |
| WO | WO 2002/033101 | 4/2002 |
| WO | WO 2002/077029 | 10/2002 |
| WO | WO 2003/089616 | 10/2003 |
| WO | WO 2004/027036 A3 | 1/2004 |
| WO | WO 2004/027036 A2 | 4/2004 |
| WO | WO 2004/039840 | 5/2004 |
| WO | WO 2005/044996 A2 | 5/2005 |
| WO | WO 2005/118788 A2 | 12/2005 |
| WO | WO 2006/036445 | 4/2006 |
| WO | WO 2006/052534 | 5/2006 |
| WO | WO 2006//061626 A3 | 7/2006 |
| WO | WO 2007/046006 | 4/2007 |
| WO | WO 2008/121420 A1 | 10/2008 |
| WO | WO 2009/091826 | 7/2009 |
| WO | WO 2009/117566 A1 | 9/2009 |
| WO | WO 2010/071836 | 6/2010 |
| WO | WO 2010/110734 A1 | 9/2010 |
| WO | WO 2011/020047 | 2/2011 |
| WO | WO 2011/053321 | 5/2011 |
| WO | WO 2011/053322 A1 | 5/2011 |
| WO | WO 2011/080740 | 7/2011 |
| WO | WO 2011/150976 | 12/2011 |
| WO | WO 2012/009422 | 1/2012 |
| WO | WO 2012/031744 A1 | 3/2012 |
| WO | WO 2012/071411 | 5/2012 |
| WO | WO 2012/079000 | 6/2012 |
| WO | WO 2012/136231 | 10/2012 |
| WO | WO 2013/040371 | 3/2013 |
| WO | WO 2013/040557 A2 | 3/2013 |
| WO | WO 2013/040557 A3 | 3/2013 |
| WO | WO 2013/126720 A2 | 8/2013 |
| WO | WO 2013/126726 A1 | 8/2013 |
| WO | WO 2014/005072 | 1/2014 |
| WO | WO 2014/011993 A2 | 1/2014 |
| WO | WO 2014/055413 A2 | 4/2014 |
| WO | WO 2014/055442 A2 | 4/2014 |
| WO | WO 2014/055657 A1 | 4/2014 |
| WO | WO 2014/055668 A1 | 4/2014 |
| WO | WO 2014/099671 A1 | 6/2014 |
| WO | WO 2014/117121 | 7/2014 |
| WO | WO 2014/127261 A1 | 8/2014 |
| WO | WO 2014/134165 A1 | 9/2014 |
| WO | WO 2014/138704 A1 | 9/2014 |
| WO | WO 2014/145252 A2 | 9/2014 |
| WO | WO 2014/164554 A1 | 10/2014 |
| WO | WO 2014/172584 A1 | 10/2014 |
| WO | WO 2014/186469 | 11/2014 |
| WO | WO 2014/201021 A2 | 12/2014 |
| WO | WO 2015/058018 A1 | 4/2015 |
| WO | WO 2015/066551 A2 | 5/2015 |
| WO | WO 2015/075468 A1 | 5/2015 |
| WO | WO 2015/075469 A1 | 5/2015 |
| WO | WO 2015/075470 A1 | 5/2015 |
| WO | WO 2015/092024 A2 | 6/2015 |

(56) References Cited

FOREIGN PATENT DOCUMENTS

| WO | WO 2015/095895 | A1 | 6/2015 |
| WO | WO 2015/105522 | A1 | 7/2015 |
| WO | WO 2015/120421 | A1 | 7/2015 |
| WO | WO 2015/123642 | A1 | 8/2015 |
| WO | WO 2015/142314 | A1 | 9/2015 |
| WO | WO 2015/142661 | A1 | 9/2015 |
| WO | WO 2015/150771 | A1 | 10/2015 |
| WO | WO 2015/154012 | A1 | 10/2015 |
| WO | WO 2015/164759 | A2 | 10/2015 |
| WO | WO 2015/174928 | | 11/2015 |
| WO | WO 2016/011210 | A2 | 1/2016 |
| WO | WO 2016/025880 | A1 | 2/2016 |
| WO | WO 2016/030691 | A1 | 3/2016 |
| WO | WO 2016/033331 | A1 | 3/2016 |
| WO | WO 2016/033690 | A1 | 3/2016 |
| WO | WO 2016/040441 | A1 | 3/2016 |
| WO | WO 2016/042041 | A1 | 3/2016 |
| WO | WO 2016/042461 | A1 | 3/2016 |
| WO | WO 2016/061574 | A1 | 4/2016 |
| WO | WO 2016/069607 | | 5/2016 |
| WO | WO 2016/073602 | A2 | 5/2016 |
| WO | WO 2016/073629 | A1 | 5/2016 |
| WO | WO 2016/073755 | A2 | 5/2016 |
| WO | WO 2016/075612 | A1 | 5/2016 |
| WO | WO 2016/100985 | A2 | 6/2016 |
| WO | WO 2016/109661 | A1 | 7/2016 |
| WO | WO 2016/109668 | A1 | 7/2016 |
| WO | WO 2016/115482 | A1 | 7/2016 |
| WO | WO 2016/123122 | A1 | 8/2016 |
| WO | WO 2016/123333 | A1 | 8/2016 |
| WO | WO 2016/124765 | A1 | 8/2016 |
| WO | WO 2016/124930 | A1 | 8/2016 |
| WO | WO 2016/126608 | A1 | 8/2016 |
| WO | WO 2016/141357 | A1 | 9/2016 |
| WO | WO 2016/142314 | | 9/2016 |
| WO | WO 2016/149254 | A1 | 9/2016 |
| WO | WO 2016/151315 | A1 | 9/2016 |
| WO | WO 2016/154055 | A1 | 9/2016 |
| WO | WO 2016/154585 | A1 | 9/2016 |
| WO | WO 2016/172537 | A1 | 10/2016 |
| WO | WO 2016/172583 | A1 | 10/2016 |
| WO | WO 2016/174405 | A1 | 11/2016 |
| WO | WO 2016/174406 | A1 | 11/2016 |
| WO | WO 2016/174407 | A1 | 11/2016 |
| WO | WO 2016/174408 | A1 | 11/2016 |
| WO | WO 2016/174409 | A1 | 11/2016 |
| WO | WO 2016/174461 | A1 | 11/2016 |
| WO | WO 2016/174652 | A1 | 11/2016 |
| WO | WO 2016/179684 | A1 | 11/2016 |
| WO | WO 2016/191587 | A1 | 12/2016 |
| WO | WO 2016/191755 | A1 | 12/2016 |
| WO | WO 2016/196388 | A1 | 12/2016 |
| WO | WO 2016/197108 | A1 | 12/2016 |
| WO | WO 2016/201304 | A1 | 12/2016 |
| WO | WO 2016/210293 | A1 | 12/2016 |
| WO | WO 2017/004150 | A1 | 1/2017 |
| WO | WO 2017/011804 | A1 | 1/2017 |
| WO | WO 2017/021701 | A1 | 2/2017 |
| WO | WO 2017/023859 | A1 | 2/2017 |
| WO | WO 2017/024131 | | 2/2017 |
| WO | WO 2017/028374 | | 2/2017 |
| WO | WO 2017/029511 | A1 | 2/2017 |
| WO | WO 2017/032777 | A1 | 3/2017 |
| WO | WO 2017/034615 | A1 | 3/2017 |
| WO | WO 2017/037083 | A1 | 3/2017 |
| WO | WO 2017/041749 | A1 | 3/2017 |
| WO | WO 2017/049166 | A1 | 3/2017 |
| WO | WO 2017/058752 | A1 | 4/2017 |
| WO | WO 2017/058753 | A1 | 4/2017 |
| WO | WO 2017/069958 | A2 | 4/2017 |
| WO | WO 2017/079705 | A1 | 5/2017 |
| WO | WO 2017/079881 | A1 | 5/2017 |
| WO | WO 2017/093969 | | 6/2017 |
| WO | WO 2017/096329 | A1 | 6/2017 |
| WO | WO 2017/127729 | A1 | 7/2017 |
| WO | WO 2017/172952 | | 10/2017 |
| WO | WO 2017/182643 | | 10/2017 |
| WO | WO 2017/214207 | | 12/2017 |
| WO | WO 2017/222593 | | 12/2017 |
| WO | WO 2018/013918 | | 1/2018 |
| WO | WO 2018/023025 | | 2/2018 |
| WO | WO 2018/026819 | | 2/2018 |
| WO | WO 2018/049248 | A1 | 3/2018 |
| WO | WO 2018/103503 | | 6/2018 |
| WO | WO 2018/124766 | | 7/2018 |
| WO | WO 2018/161017 | | 9/2018 |
| WO | WO 2018/183385 | | 10/2018 |
| WO | WO 2019/062817 | | 4/2019 |
| WO | WO 2019/118885 | | 6/2019 |
| WO | WO 2019/129002 | | 7/2019 |
| WO | WO 2020/083282 | | 4/2020 |
| WO | WO 2021/009694 | | 1/2021 |

OTHER PUBLICATIONS

Kober, J., et al. "The capacity of the TNF family members 4-1BBL, OX40L, CD70, GITRL, CD30L, and LIGHT to costimulate human T cells", Eur J Immuno, vol. 38, No. 10, pp. 2678-2688 (Oct. 28, 2008).
Sokolic et al., A selectable bicistronic retroviral vector corrects the molecular defect in a cell line derived from a patient with leukocyte adhesion deficiency, Biol. Blood Marrow Transp. 12(2) Suppl 1:20-21, Feb. 2006.
Sureth et al. Efficient generation of gene-modified human natural killer cells via alpharetroviral vectors, J. Mol. Med. 94:83-93, 2016., published online Aug. 25, 2015.
Murad, et al. "Manufacturing development and clinical production of NKG2D Chimeric Antigen Receptor-expressing T cells for autologous adoptive cell therapy" Cytotherapy, Jul. 2018; 20(7): 952-963.
Abken et al., "Chimeric T-cell receptors: highly specific tools to target cytotoxic T-lymphocytes to tumour cells," Cancer Treat Rev., 23(2):97-112, Mar. 1997.
Abken, H., et al., "Tuning tumor-specific T-cell activation: a matter of costimulation?" Trends in Immunol. 23: 240-245 (2002).
Aguera-Gonzales et al. 2011, Eur. J. Immunol. 41:3667-3676.
Alderson et al., "Molecular and Biological Characterization of Human 4-1BB and its Ligand," Eur. J. Immunol., 1994, 24: 2219-2227.
Allison and Lanier, "Structure, function, and serology of the T-cell antigen receptor complex," Annu Rev Immunol, 1987, 5:503-40.
Alvarez-Vallina, L. and Hawkins, R.E., "Antigen-specific targeting of CD28-mediated T cell co-stimulation using chimeric single-chain antibody variable fragment-CD28 receptors," Eur. J. Immunol. 26: 2304-2309 (1996).
Ang S.O. et al, "Avoiding the need for clinical-grade OKT3: ex vivo expansion of T cells using artificial antigen presenting cells genetically modified to crosslink CD3." Biology of Blood and Marrow Transplantation, Jan. 9, 2012, vol. 18, No. 2, pp. S258.
Annenkov, A., and Chernajovsky, Y., "Engineering mouse T lymphocytes specific to type II collagen by transduction with a chimeric receptor consisting of a single chain Fv and TCR zeta," Gene Therapy 7: 714-722 (2000).
Antony, G.K., et al., "Interleukin 2 in cancer therapy," Curr Med Chem., 17(29): 3297-3302 (2010).
Aoudjit and Vuori., "Integrin Signaling in Cancer Cell Survival and Chemoresistance," Chemotherapy Research and Practice., 2012(Article ID 283181), 16 pages, 2012.
Appelbaum, "Haematopoietic cell transplantation as immunotherapy," Nature, 2001, 411(6835):385-9.
ATCC No. CCL-243, 1975.
Baek, H.J. et al., "Ex vivo expansion of natural killer cells using cryopreserved irradiated feeder cells," Anticancer Research, 33: Feb. 20, 2011 (2013).
Barber et al. 2008, Exp. Hematol., 36:1318:1328.
Barber et al. 2009, J. Immunol. 183:6939-6947.
Barber, et al. 2007, Cancer Res 67(10):5003-5008.
Barber, et al. 2011, Gene Therapy 18:509-516.

(56) References Cited

OTHER PUBLICATIONS

Barber, et al. 2008, J. Immunol 180:72-78.
Barber et al. 2009, J. Immunol 183: 2365-2372.
Barrett, D.M., et al., "Chimeric Antigen Receptor Therapy for Cancer," Annu Rev. Med. 65:333-347 (2014).
Bartholomew et al., "Mesenchymal stem cells suppress lymphocyte proliferation in vitro and prolong skin graft survival in vivo," Exp Hematol, Jan. 2002, 30(1): 42-8.
Batlevi, C.L., et al. "Novel immunotherapies in lymphoid malignancies," Nature Rev. Clin. Oncol. 13:25-40 (2016).
Bedouelle, et al. "Diversity and junction residues as hotspots of binding energy in an antibody neutralizing the dengue virus" the FEBS Journal, (Jan. 2006) 273, 34-46.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," Blood, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana.
Billadeau et al. "NKG2D-DAP10 triggers human NK cell-mediated killing via a Syk-independent regulatory pathway" Nature Immunology (2003), vol. 4, No. 6, pp. 557-564.
Bischof et al., "Autonomous induction of proliferation, JNK and NF-alphaB activation in primary resting T cells by mobilized CD28," Eur J Immunol., 30(3):876-882, Mar. 2000.
Boyman, O. et al., "The role of interleukin-2 during homeostasis and activation of the immune system," Nat Rev Immunol., 12(3): 180-190 (2012).
Brentjens et al., "Eradication of Systemic B-Cell Tumors by Genetically Targeted Human T Lymphocytes Co-Stimulated B Cd80 and Interleukin-15," Nature Medicine, 2003, 9: 279-286.
Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).
Brentjens, R.J., et al., "Safety and persistence of adoptively transferred autologous CD19-targeted T cells in patients with relapsed or chemotherapy refractory B-cell leukemias," Blood 119(18):4817-4828 (2011).
Bridgeman, J.S., et al., "Building Better Chimeric Antigen Receptors for Adoptive T Cell Therapy," Current Gene Therapy 10: 77-90 (2010).
Brocker et al., "New simplified molecular design for functional T cell receptor," Eur J Immunol., 23(7):1435-1439, Jul. 1993.
Bronte, V., and Mocellin, S., "Suppressive Influences in the Immune Response to Cancer," J. Immunother. 32: 1-11 (2009).
Brown et al. "Tolerance to Single, but Not Multiple, Amino Acid Replacements in Antibody VH CDR2" The Journal of Immunology (May 1, 1996) 156, 3285-3291.
Budagian, V. et al., "IL-15/IL-15 receptor biology: A guided tour through an expanding universe," Cytokine & Growth Factor Reviews, 17(4): 259-280 (2006).
Bukczynski et al., "Costimulation of Human CD28-T Cells by 4-1BB Ligand," Eur. J. Immunol., 2003, 33: 446-454.
Burkett, P.R. et al., "Coordinate expression and trans presentation of interleukin (IL)-15Ralpha and IL-15 supports natural killer cell and memory CD8+ T cell homeostasis," J Exp Med., 200(7): 825-834 (2004).
Caligiuri et al., "Immunotherapeutic approaches for hematologic malignancies," Hematology Am Soc Hematol Educ Program, 2004, 37-53.
Campana et al., "Immunophenotyping of Leukemia," Jour of Immunol Methods, 2000, 243:59-75.
Cardoso AA, et al. Pre-B acute lymphoblastic leukemia cells may induce T-cell anergy to alloantigen. Blood 88:41-48 (1996).
Carlsten et al., "Genetic manipulation of NK cells for cancer immunotherapy: techniques and clinical implications," Frontiers in Immunology, vol. 6, Article 266, Jun. 2015.
Carson, W.E. et al., "A potential role for interleukin-15 in the regulation of human natural killer cell survival," J Clin Invest., 99(5): 937-943 (1997).
Carter, P., et al., "Identification and validation of cell surface antigens for antibody targeting in oncology," Endocrine-Related Cnacer 11: 659-687 (2004).
Cesano, A., et al. "Reversal of Acute Myelogenous Leukemia in Humanized SCID Mice Using a Novel Adoptive Transfer Approach," J. Clin. Invest. 94: 1076-1084 (1994).
Chambers, C.A., "The expanding world of co-stimulation: the two-signal model revisited," Trends in Immunol., 2001, 22(4):217-223.
Champlin R. "T-cell depletion to prevent graft-versus-host disease after bone marrow transplantation," Hematol Oncol Clin North Am. Jun. 1990;4(3):687-98.
Chang, Y.H. et al., "A chimeric receptor with NKG2D specificity enhances natural killer cell activation and killing of tumor cells," Cancer Res., 73(6): 1777-1786 (2013).
Chertova, E. et al., "Characterization and favorable in vivo properties of heterodimeric soluble IL-15.IL-15Ralpha cytokine compared to IL-15 monomer," J Biol Chem., 288(25): 18093-18103 (2013).
Cheung et al., "Anti-Idiotypic Antibody Facilitates scFv Chimeric Immune Receptor-Gene Transduction and Clonal expansion of Human Lymphocytes for Tumor Therapy," Hybridoma and Hybridomics, 2003, 24(4): 209-218.
Chiorean and Miller, "The biology of natural killer cells and implications for therapy of human disease," J Hematother Stem Cell Res, Aug. 2001, 10(4): 451-63.
Cho, D. et al., "Expansion and activation of natural killer cells for cancer immunotherapy," The Korean Journal of Laboratory Medicine, 29(2): 89-96 (2009).
ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480.
ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216.
ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313.
ClinicalTrials.gov, "A Study Evaluating KTE-C19 in Adult Subjects With Relapsed/Refractory Bprecursor Acute Lymphoblastic Leukemia (r/r ALL) (ZUMA-3) (ZUMA-3)," available at https://clinicaltrials.gov/show/NCT02614066, NCT02614066.
ClinicalTrials.gov, "Administration of Anti-CD19-chimeric-antigen-receptor-transduced T Cells From the Original Transplant Donor to Patients With Recurrent or Persistent B-cell Malignancies After Allogeneic Stem Cell Transplantation," available at https://clinicaltrials.gov/show/NCT01087294, NCT01087294.
ClinicalTrials.gov, "Anti-CD19 White Blood Cells for Children and Young Adults With B Cell Leukemia or Lymphoma," available at https://clinicaltrials.gov/show/NCT01593696, NCT01593696.
ClinicalTrials.gov, "CAR T Cell Receptor Immunotherapy for Patients With B-cell Lymphoma," available at https://clinicaltrials.gov/show/NCT00924326, NCT00924326.
ClinicalTrials.gov, "CD19 CAR T Cells for B Cell Malignancies After Allogeneic Transplant," available at https://clinicaltrials.gov/show/NCT01475058, NCT01475058.
ClinicalTrials.gov, "CD19 Chimeric Receptor Expressing T Lymphocytes In B-Cell Non Hodgkin's Lymphoma, ALL & CLL (CRETI-NH)," available at https://clinicaltrials.gov/show/NCT00586391, NCT00586391.

(56) References Cited

OTHER PUBLICATIONS

ClinicalTrials.gov, "CD19+ CAR T Cells for Lymphoid Malignancies," available at https://clinicaltrials.gov/show/NCT02529813, NCT02529813.

ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.gov/show/NCT01416974, NCT01416974.

ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366.

ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.gov/show/NCT01840566, NCT01840566.

ClinicalTrials.gov, "In Vitro Expanded Allogeneic Epstein-Barr Virus Specific Cytotoxic Tlymphocytes (EBV-CTLs) Genetically Targeted to the CD19 Antigen in B-cell Malignancies," available at https://clinicaltrials.gov/show/NCT01430390, NCT01430390.

ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069.

ClinicalTrials.gov, "Study Evaluating the Efficacy and Safety of JCAR015 in Adult B-cell Acute Lymphoblastic Leukemia (B-ALL) (ROCKET)," available at https://clinicaltrials.gov/show/NCT02535364, NCT02535364.

ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943.

ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937.

ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD19", Available at: https://clinicaltrials.gov/show/NCT00466531, NCT00466531.

Colman, P.M., "Effects of amino acid sequence changes on antibody-antigen interactions" Biomolecular Research Institute, (1994) 145, 33-36.

Cooper, M.A. et al., "In vivo evidence for a dependence on interleukin 15 for survival of natural killer cells," Blood, 100(10): 3633-3638 (2002).

Cooper et al., "T-Cell Clones can be Rendered Specific for CD I 9: Toward the Selective Augmentation Of the Graft-Versus-B Lineage Leukemia Effect," Blood, 2003, pp. 1637-1644, vol. 101.

Cruz et al., "Infusion of donor-derived CD19-redirected virus-specific T cells for B-cell malignancies relapsed after allogeneic stem cell transplant: a phase 1 study," Blood 122(17):2965-2973 (2013).

Damle et al., "Differential regulatory signals delivered by antibody binding to the CD28 (Tp44) molecule during the activation of human T lymphocytes," J Immunol., 140(6):1753-1761, Mar. 15, 1988.

Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).

Davila, M.L., et al., "Efficacy and Toxicity Management of 19-28z CAR T Cell Therapy in B Cell Acute Lymphoblastic Leukemia," Science Translat. Med. 6(24) (2014).

DeBenedette et al., "Role of 4-1BB ligand in costimulation of T lymphocyte growth and its upregulation on M12 B lymphomas by cAMP," J Exp Med, Mar. 1995, 181(3): 985-92.

DeBenedette, MA, et al.. "Costimulatin ofCD28-T Lymphocytes by 4-1 BB Ligand," J. Jmmzmol., 1997, pp. 551-559, vol. 158.

Diefenbach et al. "Selective associations with signaling proteins determine stimulatory versus costimulatory activity of NKG2D", 2002, Nat. Immunol. 3:1142-1149.

Dotti et al., "Design and Development of Therapies using Chimeric Antigen Receptor-Expressing T cells," Immunol Rev., 257(1), 35 pages Jan. 2014.

Dubois, S. et al., "IL-15Ra recycles and presents IL-15 In trans to neighboring cells," Immunity,17(5): 537-547 (2002).

Dubois, S., et al., "Preassociation of IL-15 with IL-15R alpha-IgG1-Fc enhances its activity on proliferation of NK and CD8+/CD44high T cells and its antitumor action," Journal of Immunology, 180(4):2099-2106 (2008).

Ellis et al., "Interactions of CD80 and CD86 with CD28 and CTLA4," J Immunol., 156(8):2700-2709, Apr. 15, 1996.

Eshhar et al., "Specific activation and targeting of cytotoxic lymphocytes through chimeric single chains consisting of antibody-binding domains and the y or C subunits of the immunoglobulin and T-cell receptors," Proc. Natl. Acad. Sci. USA, 1993, 90(2):720-724.

Eshhar, Z, et al .. "Functioual Expression of Chimeric Receptor Genes in Human T Cells," J. Immunol. Methods, 2001, 248(1-2):67-76.

Eshhar, Z., "Tumor-specific T-bodies: towards clinical application," Cancer Immunol. Immunother. 45: 131-136 (1997).

Fagan, E.A., and Eddleston, A.L.W.F., "Immunotherapy for cancer: the use of lymphokine activated killer (LAK) cells," Gut 28: 113-116 (1987).

Farag et al., "Natural killer cell receptors: new biology and insights into the Graft-versus-leukemia effect," Blood, 2002, 100(6):1935-1947.

Fehniger, T.A. et al., "Interleukin 15: biology and relevance to human disease," Blood, 97(1):14-32 (2001).

Fehniger TA, et al.; "Ontogeny and expansion of human natural killer cells: clinical implications", Int Rev Immunol. Jun. 2001; 20(3-4):503-534.

Ferlazzo, G. et al., "Distinct roles of IL-12 and IL-15 in human natural killer cell activation by dendritic cells from secondary lymphoid organs," PNAS, 101(47): 16606-16611 (2004).

Fernández-Messina, L. et al., "Human NKG2D-ligands: cell biology strategies to ensure immune recognition," Frontiers in Immunology, Sep. 2012, vol. 3, Article 299.

Finney et al., "Chimeric receptors providing both primary and costimulatory signaling in T cells from a single gene product," J Immunol. Sep. 15, 1998;161(6):2791-2797.

Finney et al., "Activation of resting human primary T cells with chimeric receptors: costimulation from CD28, inducible costimulator, CD134, and CD137 in series with signals from the TCR zeta chain", J Immunol. Jan. 1, 2004; 172(1):104-113.

Fujisaki, H. et al., "Expansion of highly cytotoxic human natural killer cells for cancer cell therapy," Cancer Res., 69(9): 4010-4017 (2009).

Fujisaki, H. et al., "Replicative potential of human natural killer cells," Br J Haematol,145(5):606-613 (2009).

Gardner, R., et al., "Acquisition of a CD19 negative myeloid phenotype allows immune escape of MLL-rearranged B-ALL from CD19 CAR-T cell therapy," Blood (forthcoming 2016).

Garrity et al. "The activating NKG2D receptor assembles in the membrane with two signaling dimers into a hexameric structure", 2005, Proc. Natl. Acad. Sci. USA. 102:7641-7646.

Geiger and Jyothi, "Development and application for receptor-modified T lymphocytes for adoptive immunotherapy," Transfus Med Rev, Jan. 2001, 15(1): 21-34.

Geiger et al., "Integrated src kinase and costimulatory activity enhances signal transduction through single-chain chimeric receptors in T lymphocytes", Blood. Oct. 15, 2001; 98(8):2364-2371.

GenBank Accession No. AF072844.1, "*Homo sapiens* membrane protein DAP10 (DAP10) mRNA, complete cds", Aug. 4, 1999, 2 pages total.

(56) References Cited

OTHER PUBLICATIONS

GenBank Accession No. NM_011612 GI: 6755830, Mus musculus tumor necrosis factor receptor superfamily, member 9 (Tnfrsf9), mRNA, dated Oct. 26, 2004, 8 pages.
GenBank Accession No. NM_000734 GI: 37595563, *Homo sapiens* CD3Z antigen, zeta polypeptide (TiT3 complex) (CD3Z), transcript variant 2, mRNA, dated Oct. 27, 2004, 8 pages.
GenBank Accession No. NM_001768 GI: 27886640, *Homo sapiens* CD8 antigen, alpha polypeptide (p32) (CD8A), transcript variant 1, mRNA, dated Oct. 27, 2004, 5 pages.
GenBank Accession No. NM_007360.3, "*Homo sapiens* killer cell lectin like receptor K1 (KLRK1), mRNA", Sequence ID 315221123, Jan. 12, 2013.
Germain et al., "T-cell signaling: the importance of receptor clustering," Curr Biol., 7(10):R640- R644, Oct. 1, 1997.
Ghobadi, et al., "Updated Phase 1 Results from ZUMA-1: A Phase 1-2 Multicenter Study Evaluating the Safety and Efficacy of KTE-C19 (Anti-CD19 CAR T Cells) in Subjects With Refractory Aggressive Non-Hodgkin Lymphoma," Slides accompanying oral presentation at the American Association for Cancer Research Annual Meeting, New Orleans, Louisiana.
Ghorashian, S., et al., "CD19 chimeric antigen receptor T cell therapy for haematological malignancies," Br. J. Haematol. 169:463-478 (2015).
Gilfillan et al. "NKG2D recruits two distinct adapters to trigger NK cell activation and costimulation" Nature Immunnology (2002), vol. 3, No. 12, pp. 1150-1155.
Gill, S., et al., "Chimeric antigen receptor T cell therapy: 25 years in the making," Blood Rev. (2015).
Ginaldi, L., et al., "Levels of expression of CD19 and CD20 in chronic B cell leukaemias," J. Clin. Pathol. 51: 364-369 (1998).
Giuliani, M. et al., "Generation of a novel regulatory NK cell subset from peripheral blood CD34+ progenitors promoted by membrane-bound IL-15," PLos One, 3(5): e2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human CD3− CD56+ natural killer cells to lipopolysaccharide: a role for T cells," Immunology, Apr. 2004, 111(4):384-90.
Goodwin et al., "Molecular cloning of a ligand for the inducible T cell gene 4-1 BB: a member of an emerging family of cytokines with homology to tumor necrosis factor", Eur J Immunol. Oct. 1993. 23 (10):2631-2641.
Gross and Eshhar, "Endowing T cells with antibody specificity using chimeric T cell receptors," FASEB J. Dec. 1992;6(15):3370-3378.
Grupp et al., "Chimeric antigen receptor-modified T cells for acute lymphoid leukemia," N Engl J Med. Apr. 18, 2013; 368(16):1509-1518.
Harada H, et al., "Selective expansion of human natural killer cells from peripheral blood mononuclear cells by the cell line, HFWT", Jpn J Cancer Res. Mar. 2002; 93(3):313-319.
Harada H, et al.; "A Wilms tumor cell line, HFWT, can greatly stimulate proliferation of CD56+human natural killer cells and their novel precursors in blood mononuclear cells", Exp Hematol. Jul. 2004; 32(7):614-621.
Harding et al., "CD28-mediated signalling co-stimulates murine T cells and prevents induction of anergy in T-cell clones," Nature, 356(6370):607-609, Apr. 16, 1992.
Hayashi. T. et a!., "Identification of the NKG2D Haplotypes Associated with Natural Cytotoxic Activity of Peripheral Blood Lymphocytes and Cancer Immunosurveillance", Cancer Research (2006), vol. 66 No. 01. pp. 563-570.
Haynes NM, et al., "Rejection of syngeneic colon carcinoma by CTLs expressing single-chain antibody receptors codelivering CD28 costimulation", J Immunol. Nov. 15, 2002; 169(10):5780-5786.
Haynes NM, et al., "Single-chain antigen recognition receptors that costimulate potent rejection of established experimental tumors", Blood. Nov. 1, 2002; 100(9):3155-3163.
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Ho E.L. et al., "Murine Nkg2d and Cd94 are clustered within the natural killer complex and are expressed independently in natural killer cells," Proc. Natl. Acad. Sci. USA, vol. 95, pp. 6320-6325, May 1998.
Hollyman, D., et al., "Manufacturing Validation of Biologically Functional T Cells Targeted to CD19 Antigen for Autologous Adoptive T cell Therapy," J. Immunother. 32: 169-180 (2009).
Hombach , et al., Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule, J Immunol. Dec. 1, 2001; 167(11 ):6123-6131.
Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., 2001, 61:1976-1982.
Hombach et al., "The recombinant T cell receptor strategy: insights into structure and function of recombinant immunoreceptors on the way towards an optimal receptor design for cellular irnrnunotherapy," Curr Gene Ther. May 2002;2(2):211-226.
Hombach, A., et al., "Adoptive immunotherapy with genetically engineered T cells: modification of the IgG1 Fc 'spacer' domain in the extracellular moiety of chimeric antigen receptors avoids 'offtarget' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigendependent T cell activation but not antigen recognition," Gene Therapy 7: 1067-1075 (2000).
Horng et al. 2007, Nat. Immunol. 8:1345-1352.
Hsu, C. et al., "Cytokine-independent growth and clonal expansion of a primary human CD8+ T-cell clone following retroviral transduction with the IL-15 gene," Blood, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Huang Q.S. et al, Expansion of human natural killer cells ex vivo. Chine J Cell Mol Immunol, Dec. 31, 2008, vol. 24, No. 12, pp. 1167-1170.
Huang, et al. "Abstract A207: Utilizing human OX40 knock-in mice (HuGEMM™) to assess antitumor efficacy of OX40-agonistic antibodies" Molecular Cancer Therapeutics, (Jan. 1, 2018) vol. 17, Issue 1 Supplement in 4 pages.
Hurtado et al., "Potential role of 4-1BB in T cell activation. Comparison with the costimulatory molecule CD28," J Immunol, Oct. 1995, 155(7): 3360-7.
Ignacio et al., "Monoclonal antibodies against the 4-1BB T-cell activation molecule eradicate established tumors," Nature Med., 1997, 3:682-685.
Imai C, et al., "Chimeric receptors with 4-1BB signaling capacity provoke potent cytotoxicity against acute lymphoblastic leukemia", Leukemia. Feb. 12, 2004; 18(4):676-684.
Imai, C. et al., "Genetic modification of primary natural killer cells overcomes inhibitory signals and induces specific killing of leukemic cells," Blood, 106: 376-383 (2005).
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a.
Imai et al. "Genetic modification of T cells for cancer therapy", Journal of Biological Regulators and Homeostatic Agents, 18 (1): p. 62-71; Jan. 2004; (abstract only).
Imai, C., et al; "A novel method for propagating primary natural killer (NK) cells allows highly Efficient expression of anti-CD19

(56) References Cited

OTHER PUBLICATIONS chimeric receptors and generation of powerful cytotoxicity Against NK-resistent acute lymphoblastic leukemia cells." Abstract# 306 Blood 104 (Nov. 16, 2004).

Imamura, M. et al., "Autonomous growth and increased cytotoxicity of natural killer cells expressing membrane-bound interleukin-15," Blood, 124(7): 1081-1088 (Jul. 8, 2014).

Ishii, H. et al., "Monocytes enhance cell proliferation and LMP1 expression of nasal natural killer/T-cell lymphoma cells by cell contact-dependent interaction through membrane-bound IL-15," International Journal of Cancer, 130(1): 48-58 (2012).

Ishiwata I, et al., "Carcinoembryonic proteins produced by Wilms' tumor cells in vitro and in vivo", Exp Pathol. 1991; 41(1):1-9.

Jena et al., "Redirecting T-cell specificity by introducing a tumor-specific chimeric antigen receptor," Blood, 2010, 116(7):1035-1044.

Jenkins et al., "Inhibition of antigen-specific proliferation of type 1 murine T cell clones after stimulation with immobilized anti-CD3 monoclonal antibody," J Immunol., 144(1):16-22, Jan. 1, 1990.

Jensen, M.C., et al., "Anti-transgene Rejection Responses Contribute to Attenuated Persistence of Adoptively Transferred CD20/CD19-Specific Chimeric Antigen Receptor Redirected T Cells in Humans," Biol. Blood Marrow Transplant 16: 1245-1256 (2010).

Jiang, W. et al., "hIL-15 gene-modified human natural killer cells (NKL-IL15) augments the anti-human hepatocellular carcinoma effect in vivo," Immunobiology, 219: 547-553 (Mar. 12, 2014).

Kabalak, G. et al., "Assocaition of an NKG2D gene variant with systematic lupus erythematosus in two populations," Human Immunology 71 (2010) 74-78.

Kalos et al, "T Cells with Chimeric Antigen Receptors Have Potent Antitumor Effects and Can Establish Memory in Patienis with Advanced Leukemia," Sci Transl Med. Aug. 10, 2011;3(95):95ra73.

Kershaw, M.H., et al., "A Phase I Study on Adoptive Immunotherapy Using Gene-Modified T Cells for Ovarian Cancer," Clin. Cancer Res. 12:6106-6115 (2006).

Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).

Kim Y J, et al., "Human 4-1 BB regulates CD28 co-stimulation to promote Th1 cell responses. Eur J Immunol", Mar. 1998; 28(3):881-890.

Kim Y J, et al., "Novel T cell antigen 4-1 BB associates with the protein tyrosine kinase p56lck1", J Immunol.Aug. 1, 1993; 151(3):1255-1262.

Kitaya, K. et al., "IL-15 expression at human endometrium and decidua," Biology of Reproduction, 63(3): 683-687 (2000).

Kitaya, K. et al., "Regulatory role of membrane-bound form interleukin-15 on human uterine microvascular endothelial cells in circulating CD16(−) natural killer cell extravasation into human endometrium," Biology of Reproduction, 89(3): 70 (2013).

Klein E, et al., "Properties of the K562 cell line, derived from a patient with chronic myeloid leukemia", Int J Cancer. Oct. 15, 1976; 18(4):421-431.

Klingemann HG, et al., "Ex vivo expansion of natural killer cells for clinical applications", Cytotherapy. 2004; 6(1):15-22.

Kobayashi, H. et al., "Role of trans-cellular IL-15 presentation in the activation of NK cell-mediated killing, which leads to enhanced tumor immunosurveillance," Blood, 105(2): 721-727 (Jan. 2005).

Kochenderfer, J.N. et al. "Construction and Preclinical Evaluation of an Anti-CD19 Chimeric Antigen Receptor," J. Immunother. 32(7):689-702 (2009).

Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. (2014).

Kochenderfer, J.N., et al. "Donor-derived CD19-targeted T cells cause regression of malignancy persisting after allogeneic hematopoietic stem cell transplantation," Blood 122(25): 4129-4139 (2013).

Kochenderfer, J.N., et al., "B-cell depletion and remissions of malignancy along with cytokineassociated toxicity in a clinical trial of anti-CD19 chimeric-antigen-receptor-transduced T cells," Blood 119(12):2709-2720 (2012).

Kochenderfer, J.N., et al., "Eradication of B-lineage cells and regression of lymphoma in a patient treated with autologous T cells genetically engineered to recognize CD19," Blood 116(20):4099-4102 (2010).

Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060.

Kohn et al. "CARs on track in the clinic," Mar. 2011, Molecular Therapy:The Journal of the American Society of Gene Therapy, 19:432-438.

Koka, R. et al., "Cutting edge: murine dendritic cells require IL-15R alpha to prime NK cells," J Immunol., 173(6): 3594-3598 (Sep. 2004).

Kolb HJ, et al., "Graft-versus-leukemia effect of donor lymphocyte transfusions in marrow grafted patients," Blood, 1995, 6:2041-2050.

Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66: 10995-11004 (2006).

Lafreniere, R. and Rosenberg, S.A., "Successful Immunotherapy of Murine Experimental Hepatic Metastases with Lymphokine-activated Killer Cells and Recombinant Interleukin 2," Cancer Res. 45: 3735-3741 (1985).

Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Poster session presented at the American Association for Cancer Research Annual Meeting, New Orleans, Louisiana, 2016.

Lapteva, N. et al., "Large-scale ex vivo expansion and characterization of natural killer cells for clinical applications," Cytotherapy, 14(9): 1131-1143 (2012).

Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.

Lee, D.W., et al., "T cells expressing CD19 chimeric antigen receptors for acute lymphoblastic leukaemia in children and young adults: a phase 1 dose-escalation trial," Lancet 385:517-528 (2015).

Lehner at al. "Redirecting T Cells to Ewing's Sarcoma family of Tumors by a Chimeric NKG2D Receptor Expressed by Lentiviral Transduction or Mrna Transfection", 2012, PloS. One 7:e31210.

Leung, W. et al., "Determinants of antileukemia effects of allogeneic NK cells," J Immunol., 172(1): 644-650 (Jan. 2004).

Li et al., "Human iPSC-Derived Natural Killer Cells Engineered with Chimeric Antigen Receptors Enhance Anti-tumor Activity," Cell Stem Cell 23, 1-12, Aug. 2, 2018.

Liao, W. et al., "Interleukin-2 at the crossroads of effector responses, tolerance, and immunotherapy," Immunity, 38(1): 13-25 (2013).

Liebowitz et al., "Costimulatory approaches to adoptive immunotherapy," Curr Opin Oncol, Nov. 1998, 10(6): 533-41.

Lozzio et al., "Properties and Usefulness of the Originl K-562 Human Myelogenous Leukemia Cell Line," Leukemia Research, vol. 3, No. 6, pp. 363-370, 1979.

Lode et al., "Targeted cytokines for cancer immunotherapy," Immunol Res., 21(2-3):279-288, 2000.

Lozzio CB, et al., "Human chronic myelogenous leukemia cell-line with positive Philadelphia chromosome", Blood. Mar. 1975; 45(3):321-334.

Lugli, E. et al., "Transient and persistent effects of IL-15 on lymphocyte homeostasis in nonhuman primates," Blood, 116(17): 3238-3248 (2010).

Martinez et al. "Cutting Edge: NKG2D-Dependent Cytotoxicity Is Controlled by Ligand Distribution in the Target Cell Membrane", 2011, J. Immunol. 186:5538-5542.

Maude et al., "Chimeric antigen receptor T cells for sustained remissions in leukemia," N Engl J Med., 371(16):1507-1517, Oct. 16, 2014.

(56) References Cited

OTHER PUBLICATIONS

McLaughlin et al., "Adoptive T-cell therapies for refractory/relapsed leukemia and lymphoma: current strategies and recent advances," Ther Adv Hematol., 6(6):295-307, Dec. 2015.
Melero I, et al., "Amplification of tumor immunity by gene transfer of the co-stimulatory 4-1 BB ligand: synergy with the CD2S co-stimulatory pathway," Eur J Immunol., 1998, 28(3):1116-1121.
Melero I, et al., "NK1 .1 cells express 4-1BB(CDw137) costimulatory molecule and are required for tumor immunity elicited by anti-4-1 BB monoclonal antibodies," Cell Immunol., 1998, 190(2):167-172.
Miller et al., "Role of monocytes in the expansion of human activated natural killer cells," Blood, Nov. 1992, 80(9): 2221-9.
Miller, J.S., "Therapeutic applications: natural killer cells in the clinic," Hematology Am Soc Hematol Educ Program 2013: 247-253 (2013).
Miller, J.S et al., "Successful adoptive transfer and in vivo expansion of human haploidentical NK cells in cancer patients," Blood, 105: 3051-3057 (Apr. 2005).
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Mishra, A. et al., "Aberrant overexpression of IL-15 initiates large granular lymphocyte leukemia through chromosomal instability and DNA hypermethylation," Cancer Cell, 22(5):645-655 (2012).
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," EMBO J., 2004, 23(2):255-259.
Moritz and Groner, "A spacer region between the single chain antibody- and the CD3 Cchain domain of chimeric T cell receptor components is required for efficient ligand binding and signaling activity," Gene Ther. Oct. 1995;2(8):539-546.
Mortier, E., et al., "IL-15Ralpha chaperones IL-15 to stable dendritic cell membrane complexes that activate NK cells via trans presentation," The Journal of Experimental Medicine, 205(5): 1213-1225 (2008).
Musso, T. et al., "Human monocytes constitutively express membrane-bound, biologically active, and interferon-gamma-upregulated interleukin-15," Blood, 93(10): 3531-3539 (1999).
Nagashima et al., "Stable transduction of the interleukin-2 gene into human natural killer cell lines and their phenotypic and functional characterization in vitro and in vivo," Blood, May 1998, 91(10): 3850-61.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.
NCBI Reference Sequence NM_ 198053, "*Homo sapiens* CD247 molecule (CD247), transcript variant 1, mRNA", Jan. 20, 2008, 11 pages total.
NCBI Reference Sequence NM_007360.2, "*Homo sapiens* killer cell lectin-like receptor subfamily K, member 1 (KLRK1 ), mRNA", Dec. 5, 2010, 10 pages total.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Scoiety of Hematology Annual Meeting, Orlando, Florida.
Negrini, S. et al., "Membrane-bound IL-15 stimulation of peripheral blood natural killer progenitors leads to the generation of an adherent subset co-expressing dendritic cells and natural killer functional markers," Haematologica, 96(5): 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.
Wu et al., 1999, An Activating Immunoreceptor Complex Formed by NKG2D and DAP10, Science 285:730-732.
Olsen, S.K. et al., "Crystal structure of the interleukin-15 interleukin-15 receptor α complex Insights into trans and cis presentation," The Journal of Biological Chemistry, 282(51): 37191-37204.
Pan et al., "Regulation of dendritic cell function by NK cells: mechanisms underlying the synergism in the combination therapy of IL-12 and 4-1BB activation," J Immunol, Apr. 2004, 172(8): 4779-89.
Park et al. "Complex regulation of human NKG2D-DAP10 cell surface expression: opposing roles of the Yc cytokines and TGF-B1 ", 2011, Blood 118:3019-3027.
Park, J.H., and Brentjens, R.J., "Are All Chimeric Antigen Receptors Created Equal?" J. Clin. Oncol. 33: 651-653 (2015).
Park, J.H., et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html.
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/webprogram/Paper86688.html.
Parkhurst, M.R. et al., "Adoptive transfer of autologous natural killer cells leads to high levels of circulating natural killer cells but does not mediate tumor regression," Clin Cancer Res., 17(19): 6287-97 (2011).
Patel, S.D., et al., "Impact of chimeric immune receptor extracellular protein domains on T cell function," Gene Therapy 6: 412-419 (1999).
Perussia et al., "Preferential proliferation of natural killer cells among peripheral blood mononuclear cells cocultured with B lymphoblastoid cell lines," Nat Immun Cell Growth Regul, 1987, 6(4): 171-88.
Porter and Antin, "The graft-versus-leukemia of allogeneic cell therapy," Annu Rev Med, 1999, 50:369-86.
Porter DL et al., "Chimeric Antigen Receptor-Modified T Cells in Chronic Lymphoid Leukemia", N. Eng. J. Med. Aug. 25, 2011; 365(8):725-733.
Porter et al., "Induction of graft-versus-host disease as immunotherapy for relapsed chronic myeloid leukemia," N Engl J Med, Jan. 1994, 330(2): 100-6.
Qi L. et al, "Multiple effects of IL-21 on the ex vivo expansion of human primary NK cells." Immunology, Nov. 28, 2014, vol. 143, No. S2, p. 62-176.
Qian, L. et al., "Construction of a plasmid for co-expression of mouse membrane-bound form of IL-15 and RAE-1ε and its biological activity," Plasmid, 65(3): 239-245 (2011).
Ramos and Dotti, "Chimeric antigen receptor (CAR)-engineered lymphocytes for cancer therapy," Expert Opin Biol Ther., 2011, 11(7):855-873.
Ramos, C.A., et al., "CD19-CAR Trials," The Cancer J. 20: 112-118 (2014).
Riddell, S.R., et al., "T-Cell Therapy of Leukemia," Cancer Control 9: 114-122 (2002).
Roberts et al., "Antigen-specific cytolysis by neutrophils and NK cells expressing chimeric immune receptors bearing zeta or gamma signaling domains," J Immunol, Jul. 1998, 161(1):375-84.
Robertson MJ, et al.; "Costimulation of human natural killer cell proliferation: role of accessory cytokines and cell contact-dependent signals", Nat Immun. 1996-1997; 15(5):213-226.
Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-C19) in Subjects with Refractory Aggressive Non-Hodgkin Lymphoma (NHL)," Abstract presented at the American Society of Hematology Annual

(56) References Cited

OTHER PUBLICATIONS

Meeting, Orlando, Florida, available at https://ash.confex.com/ash/2015/webprogramscheduler/Paper80339.html.
Roszak, A. et al., "Prevalence of the NKG2D Thr72Ala Polymorphism in Patients with Cervical Carcinoma", Genetic Testing and Molecular Biornarkers {2012), Vo!. 16, No. 08, pp. 841-845.
Rowley, J. et al., "Expression of IL-15RA or an IL-15/IL-15RA fusion on CD8+ T cells modifies adoptively transferred T-cell function in cis," European Journal of Immunology, 39:491-506 (2009).
Rubnitz, J.E. et al., "NKAML: a pilot study to determine the safety and feasibility of haploidentical natural killer cell transplantation in childhood acute myeloid leukemia," J Clin Oncol, 28(6): 955-959 (2010).
Rudikoff, et al. "Single amino acid substitution altering antigen-binding specificity", Nov. 23, 1981, 79, 1979-1983.
Ruggeri, L. et al., "Effectiveness of donor natural killer cell alloreactivity in mismatched hematopoietic transplants," Science, 295(5562): 2097-2100 (2002), https://pubmed.ncbi.nlm.nih.gov/11896281/.
Sadelain et al., "The promise and potential pitfalls of chimeric antigen receptors," Curr Opin Immunol., 2009, 21(2):215-223.
Sadelain, M., "CAR Therapy: the CD19 Paradigm," J. Clin. Investigation 125: 3392-3400 (2015).
Sahm et al., Expression of IL-15 in NK cells results in rapid enruchment and selective cytotoxicity of gene-modified effectors that carry a tumor-specific antigen receptor. Cancer Immunol. Immunother. 61(9):1451-1461, Feb. 2012.
Salih et al., Cutting Edge: Down-Regulation of MICA on Human Tumors by Proteolytic Shedding, 2002, J. Immunol. 169:4098-4102.
Sambrook et al, "Molecular Cloning: A Laboratory Manual," (1989) [Table of Contents and Preface Only].
Sankhla, S.K., et al., "Adoptive immunotherapy using lymphokineactivated killer (LAK) cells and interleukin-2 for recurrent malignant primary brain tumors," J Neurooncol. 27: 133-140 (1995).
Santegoets S.J. et al, "IL-21 promotes the expansion of CD27+ CD28+ tumor infiltrating lymphocytes with high cytotoxic potential and low collateral expansion of regulatory T cells." Journal of Translational Medicine, Feb. 12, 2013, vol. 11, No. 37, pp. e1-10.
Sattler, S. et al., "Evolution of the C-Type Lectin-Like Receptor Genes od the DECTIN-1 Cluster in the NK Gene Complex," The Scientific World Journal, vol. 2012, 2011.
Sentman, et al., "NK Cell Receptors as Tools in Cancer Immunotherapy," Department of Microbiology and Immunology, Dartmouth Medical School, Lebanon, New Hampshire 03756, 2006.
Sentman, et al., "NKG2D CARs as Cell Therapy for Cancer," 2014, The Cancer Journal 20(2):156-159.
Shook D. R. et al., Natural killer cell engineering for cellular therapy of cancer. Tissue Antigens, Nov. 13, 2011, vol. 78, No. 6, pp. 409-415 p. 410 right column 2nd para and p. 411 left column.
Shimasaki, N. et al., "A clinically adaptable method to enhance the cytotoxicity of natural killer cells against B-cell malignancies," Cytotherapy, 14(7): 830-840 (2012).
Sica G, Chen L. Modulation of the immune response through 4-1BB. In: Habib N, ed. Cancer gene therapy: past achievements and future challenges. New York: Kluwer Academic/Plenum Publishers; 355-362 (2000) [Book].
Slavin et al., "Allogeneic cell therapy with donor peripheral blood cells and recombinant human interleukin-2 to treat leukemia relapse after allogeneic bone marrow transplantation," Blood, Mar. 1996, 87(6): 2195-204.
Sneller, M.C. et al., "IL-15 administered by continuous infusion to rhesus macaques induces massive expansion of CD8+ T effector memory population in peripheral blood," Blood, 118(26): 6845-6848 (2011).
Somanchi, S.S. et al., "Expansion, purification, and functional assessment of human peripheral blood NK cells," Journal of Visualized Experiments, 48A: 2540 (2011).

Song, De-Gang et al., "In vivo persistence, tumor localization and anti-tumor activity of CAR engineered T cells is enhanced by costimulatory signaling through CD137 (4-1BB)," Cancer Res. Jul. 1, 2011; 71(13): 4617-4627.
Song, De-Gang et al., "Chimeric NKG2D CAR-Expressing T Cell-Meditated Attack of Human Ovarian Cancer Is Enhanced by Histone Deacetylase Inhibition," Human Gene Therapy, 24:295-305 (Mar. 2013).
Spear, et al. 2012, J. Immunol 188: 6389-6398.
Spear, et al. 2013, Immunology and Cell Biology 91: 435-440.
Spear, et al. 2013, OncoImmunology 2(4): e23564-1-e23564-12.
Sun, J., et al., "Early transduction produces highly functional chimeric antigen receptor-modified virus-specific T-cells with central memory markers: a Production Assistant for Cell Therapy (PACT) translational application," J. Immunother. Cancer (2015).
Tagaya, Y. et al., "IL-15: a pleiotropic cytokine with diverse receptor/signaling pathways whose expression is controlled at multiple levels," Immunity, 4(4): 329-336 (1996).
Takahashi C, et al., "Cutting edge: 4-1 BB is a bona fide CDS T cell survival signal", J Immunol. May 1, 1999; 162(9):5037-5040.
Topp, M.S., et al., "Universal chimeric immunoreceptors for targeting B-cell malignancies with engineered CTL: combining CD19-specific TCR zeta signaling with engineered CD28-mediated costimulation," Mol. Ther. 3(5)(part 2 of 2): S21 (2001).
Trinchieri et al., "Response of resting human peripheral blood natural killer cells to interleukin 2," J Exp Med, Oct. 1984, 160(4): 1147-69.
Tsukamoto, K. et al., "Juxtacrine function of interleukin-15/interleukin-15 receptor system in tumour derived human B-cell lines," Clinical and Experimental Immunology, 146(3): 559-566 (2006).
Turaj, et al. "Augmentation of CD134 (OX40)-dependent NK anti-tumour activity is dependent on antibody cross-linking" Scientific Reports, (2018) 8, 2278.
Turtle, "Therapy of B Cell Malignancies with CD19-Specific Chimeric Antigen Receptor Modified T Cells of Defined Subset Composition," Blood 124(21): 384-384, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered To Express a CD19-Specific Chimeric Antigen Receptor" Mol. Ther., 2014, 22(Supp.1):296.
Vajdos, et al. "Comprehensive Functional Maps of the Antigen-binding Site of an Anti-ErbB2 Antibody Obtained with Shotgun Scanning Mutagenesis" J. Mol. Biol. (Jul. 5, 2002) 320, 415-428.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-63.
Vujanovic, L. et al., "Virally infected and matured human dendritic cells activate natural killer cells via cooperative activity of plasma membrane-bound TNF and IL-15," Blood, 116(4): 575-583 (2010).
Waldmann, T.A. et al., "Safety (toxicity), pharmacokinetics, immunogenicity, and impact on elements of the normal immune system of recombinant human IL-15 in rhesus macaques," Blood, 117(18): 4787-4795 (2011).
Wang, et al., "Phase I Studies of central-memory-derived CD19 CAR T cell therapy following autologous HSCT in patients with B-Cell NHL," Blood (forthcoming 2016).
Watzl, C. et al., "Signal Transduction During Activation and Inhibition of Natural Killer Cells," Curr Protoc Immunol. Author Manuscript; available in PMC Dec. 9, 2013.
Weissman et al., "Molecular cloning and chromosomal localization of the human T-cell receptor ~ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).

(56) References Cited

OTHER PUBLICATIONS

Wu and Lanier, "Natural killer cells and cancer," Adv Cancer Res, 2003, 90: 127-56.

Xu, Y., et al., "Closely related T-memory stem cells correlate with in vivo expansion of CAR.CD19-T cells and are preserved by IL-7 and IL-15," Blood 123(24):3750-3759 (2014).

Ye L. et al, "Effects of target cell overexpression of IL-15, 4-1BBL and IL-18 combine with IL-2 on NK cell activation and cytotoxicity during ex vivo expansion." Chin J Cancer Biother, Oct. 31, 2014, vol. 21, No. 5, pp. 537-542.

Yim et al., "Molecular cloning and characterization of pig immunoreceptor DAP10 and NKG2D," Immunogenetics—Jan. 2001.

Zanoni, I. et al., "IL-15 cis presentation is required for optimal NK cell activation in lipopolysaccharide-mediated inflammatory conditions," Cell Reports, 4: 1235-1249 (2013).

Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.

Zhang, J. et al., "Characterization of interleukin-15-gene-modified human natural killer cells: implications for adoptive cellular immunotherapy," Haematologica, 89(3): 338-347 (2004).

Zhang et al., "Chimeric NKG2D-Modified T Cells Inhibit Systematic T-Cell Lymphoma Growth in a Manner Involving Multiple Cytokines and Cytotoxic Pathways," 2007, Cancer Res. 67:11029-11036.

Zhang et al. Chimeric NK-receptor-bearing T cells mediate antitumor immunotherapy, Sep. 1, 2005, Blood Journal 106(5): 1544-1551.

Zhang et al., "Generation of Antitumor Response by Genetic Modification of Primary Human T Cells with a Chimeric NKG2D Receptor," 2006, Cancer Res 66(11):5927-5933.

Zhang, et al. Mouse Tumor vasculature Expresses NKG2D Ligands and can be Targeted by Chimeric NKG2D-Modified T Cells, 2013, J. Immunol 190:2455-2463.

Steel et al., Interleukin-15 biology and its therapeutic implications in cancer, Trends Pharmacol, Sci. 33(1):35-41, Jan. 2012.

Cecele J. Denman, et al., "Membrane-Bound IL-21 Promotes Sustained Ex Vivo Proliferation of Human Natural Killer Cells" PLOS One, www.plosone.org, Jan. 18, 2012, vol. 7, in 13 pages.

Wang, et al., "Human NK cells maintain licensing status and are subject to killer immunoglobulin-like receptor (KIR) and KIR-ligand inhibition following ex vivo expansion", Cancer Immunology, Immunotherapy, vol. 65, No. 9, Jul. 8, 2016, pp. 1047-1059.

Bridgeman, J.S., et al., "The Optimal Antigen Response of Chimeric Antigen Receptors Harboring the CD3 ζ Transmembrane Domain Is Dependent upon Incorporation of the Receptor into the Endogenous TCR/CD3 Complex" The Journal of Immunology, Oct. 15, 2019, in 13 pages.

Zah, et al., "T Cells Expressing CD19/CD20 Bispecific Chimeric Antigen Receptors Prevent Antigen Escape by Malignant B Cells", Cancer Immunology Research, Apr. 8, 2016, in 15 pages.

Parihar, et al., "NK cells expressing a chimeric activating receptor eliminate MDSCs and rescue impaired CAR-T cell activity against solid tumors", cancerimmunolres.aacrjournals.org, Jan. 19, 2019, in 47 pages.

Jiang, W. et al., "Functional characterization of interleukin-15 gene transduction into the human natural killer cell line NKL" International Society for Cellular Therapy, (2008), vol. 10, No. 3, 265-274.

Schirrmann, et al. "Human natural killer cell line modified with a chimeric immunoglobulin T-cell receptor gene leads to tumor growth inhibition in vivo" Cancer Gene Therapy (2002) 9, 390-398.

* cited by examiner

| Construct | Structure |
|---|---|
| NK19 | CD19 scFv – CD8α Hinge – CD8α TM – 41BB – CD3ζ ITAM – 2A – mIL-15 |
| NK19 opt. | CD19 scFv – CD8α Hinge – CD8α TM – 41BB – CD3ζ ITAM |
| NK19-1a | Flag-CD19scFv – CD8α Hinge – CD8α TM – OX40 – CD3ζ ITAM |
| NK19-1b | Flag-CD19scFv – CD8α Hinge – CD8α TM – OX40 – CD3ζ ITAM – 2A – mIL-15 |
| NK19-2a | Flag-CD19scFv – CD8α Hinge – CD8α TM – CD28 – CD3ζ ITAM |
| NK19-2b | Flag-CD19scFv – CD8α Hinge – CD8α TM – CD28 – CD3ζ ITAM – 2A – mIL-15 |
| NK19-3a | Flag-CD19scFv – CD8α Hinge – CD8α TM – ICOS – CD3ζ ITAM |
| NK19-3b | Flag-CD19scFv – CD8α Hinge – CD8α TM – ICOS – CD3ζ ITAM – 2A – mIL-15 |
| NK19-4a | Flag-CD19scFv – CD8α Hinge – CD8α TM – CD28 – 41BB – CD3ζ ITAM |
| NK19-4b | Flag-CD19scFv – CD8α Hinge – CD8α TM – CD28 – 41BB – CD3ζ ITAM – 2A – mIL-15 |

NK19-9a: Flag-CD19 scFv | CD8α Hinge | CD8α TM | CD27 | CD3ζ ITAM

NK19-9b: Flag-CD19 scFv | CD8α Hinge | CD8α TM | CD27 | CD3ζ ITAM | 2A | mIL-15

NK19-10a: Flag-CD19 scFv | CD8α Hinge | CD8α TM | CD70 | CD3ζ ITAM

NK19-10b: Flag-CD19 scFv | CD8α Hinge | CD8α TM | CD70 | CD3ζ ITAM | 2A | mIL-15

NK19-11a: Flag-CD19 scFv | CD8α Hinge | CD8α TM | CD161 | CD3ζ ITAM

NK19-11b: Flag-CD19 scFv | CD8α Hinge | CD8α TM | CD161 | CD3ζ ITAM | 2A | mIL-15

Figure 3C Cont.

NK19-12a: Flag-CD19 scFv | CD8α Hinge | CD8α TM | CD40L | CD3ζ ITAM

NK19-12b: Flag-CD19 scFv | CD8α Hinge | CD8α TM | CD40L | CD3ζ ITAM | 2A | mIL-15

NK19-13a: Flag-CD19 scFv | CD8α Hinge | CD8α TM | CD44 | CD3ζ ITAM

NK19-13b: Flag-CD19 scFv | CD8α Hinge | CD8α TM | CD44 | CD3ζ ITAM | 2A | mIL-15

NK19-14a: Flag-CD19 scFv | CD8α Hinge | CD8α TM | CD44 | OX40 | CD27 | CD3ζ ITAM NK19-14b: Flag-CD19 scFv | CD8α Hinge | CD8α TM | CD44 | OX40 | CD27 | CD3ζ ITAM | 2A | mIL-15

NK19H-NF-1a: Humanized CD19 scFv (L1/H1) | CD8α Hinge | CD8α TM | OX40 | CD3ζ ITAM NK19H-NF-1b: Humanized CD19 scFv (L1/H1) | CD8α Hinge | CD8α TM | OX40 | CD3ζ ITAM | 2A | mIL-15

NK19H-NF-2a: Humanized CD19 scFv (L2/H1) | CD8α Hinge | CD8α TM | OX40 | CD3ζ ITAM NK19H-NF-2b: Humanized CD19 scFv (L2/H1) | CD8α Hinge | CD8α TM | OX40 | CD3ζ ITAM | 2A | mIL-15

NK19H-NF-3a: Humanized CD19 scFv (L3/H1) | CD8α Hinge | CD8α TM | OX40 | CD3ζ ITAM NK19H-NF-3b: Humanized CD19 scFv (L3/H1) | CD8α Hinge | CD8α TM | OX40 | CD3ζ ITAM | 2A | mIL-15

NK19H-NF-4a: Humanized CD19 scFv (L1/H2) | CD8α Hinge | CD8α TM | OX40 | CD3ζ ITAM NK19H-NF-4b: Humanized CD19 scFv (L1/H2) | CD8α Hinge | CD8α TM | OX40 | CD3ζ ITAM | 2A | mIL-15

NK19H-NF-8a: Humanized CD19 scFv (L2/H3) | CD8α Hinge | CD8α TM | OX40 | CD3ζ ITAM NK19H-NF-8b: Humanized CD19 scFv (L2/H3) | CD8α Hinge | CD8α TM | OX40 | CD3ζ ITAM | 2A | mIL-15

NK19H-NF-9a: Humanized CD19 scFv (L3/H3) | CD8α Hinge | CD8α TM | OX40 | CD3ζ ITAM NK19H-NF-9b: Humanized CD19 scFv (L3/H3) | CD8α Hinge | CD8α TM | OX40 | CD3ζ ITAM | 2A | mIL-15

NK19H-NF-10a: Humanized CD19 scFv (L1/H4) | CD8α Hinge | CD8α TM | OX40 | CD3ζ ITAM NK19H-NF-10b: Humanized CD19 scFv (L1/H4) | CD8α Hinge | CD8α TM | OX40 | CD3ζ ITAM | 2A | mIL-15

Figure 3I

NK19H-NF-11a: Humanized CD19 scFv (L2/H4) | CD8α Hinge | CD8α TM | OX40 | CD3ζ ITAM NK19H-NF-11b: Humanized CD19 scFv (L2/H4) | CD8α Hinge | CD8α TM | OX40 | CD3ζ ITAM | 2A | miL-15

NK19H-NF-12a: Humanized CD19 scFv (L3/H4) | CD8α Hinge | CD8α TM | OX40 | CD3ζ ITAM NK19H-NF-12b: Humanized CD19 scFv (L3/H4) | CD8α Hinge | CD8α TM | OX40 | CD3ζ ITAM | 2A | miL-15

NK19H-NF-13a: Humanized CD19 scFv | CD8α Hinge | CD8α TM | CD44 | OX40 | CD27 | CD3ζ ITAM NK19H-NF-13b: Humanized CD19 scFv | CD8α Hinge | CD8α TM | CD44 | OX40 | CD27 | CD3ζ ITAM | 2A | miL-15

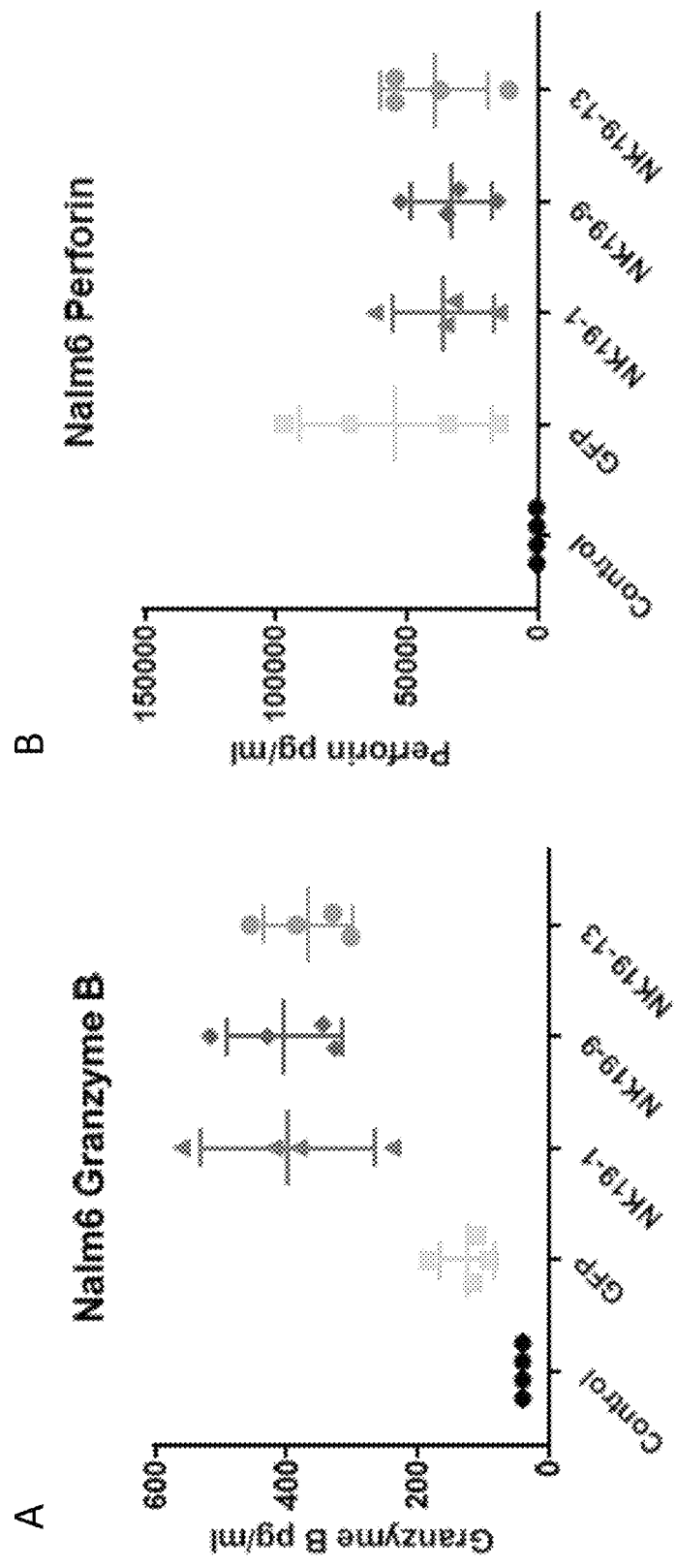
Figure 11A-B

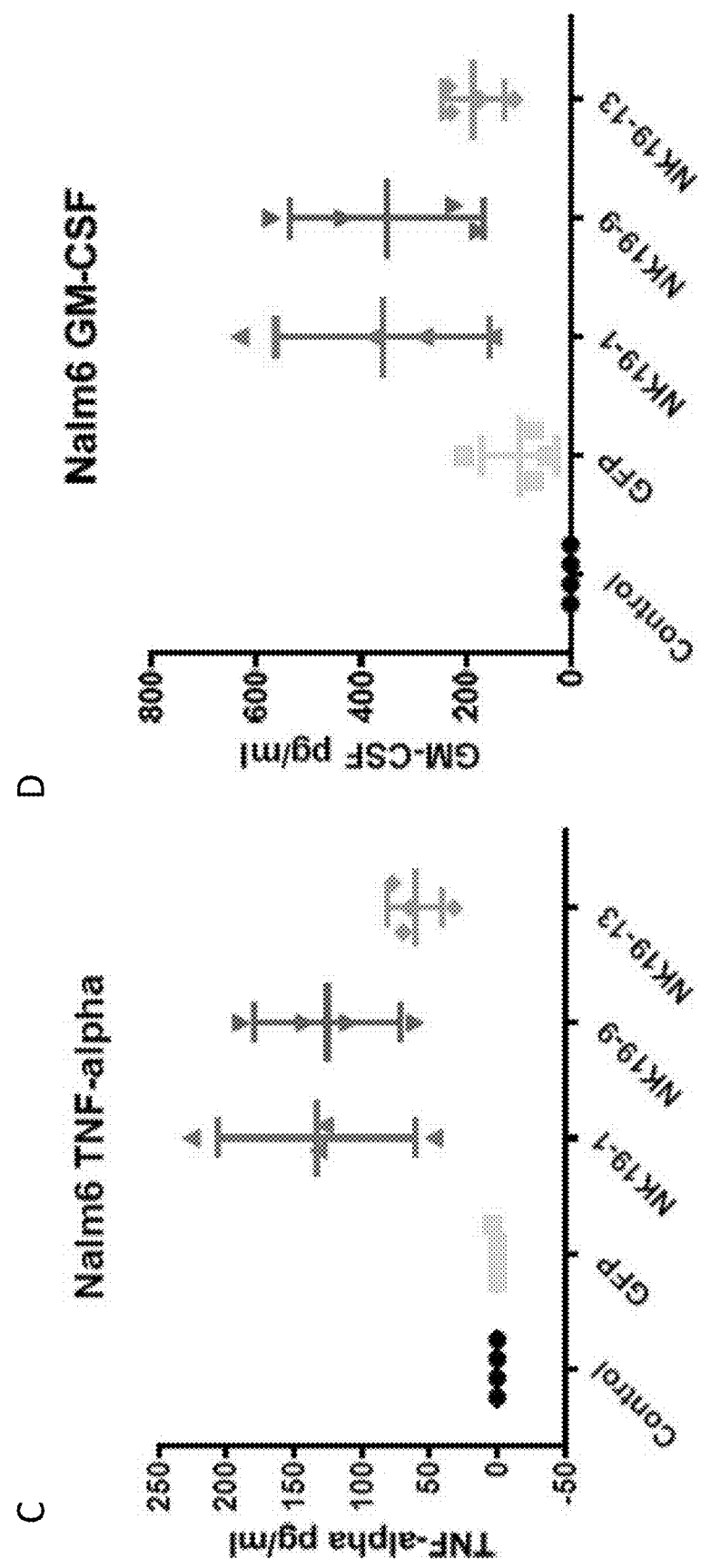
Figure 11C-D

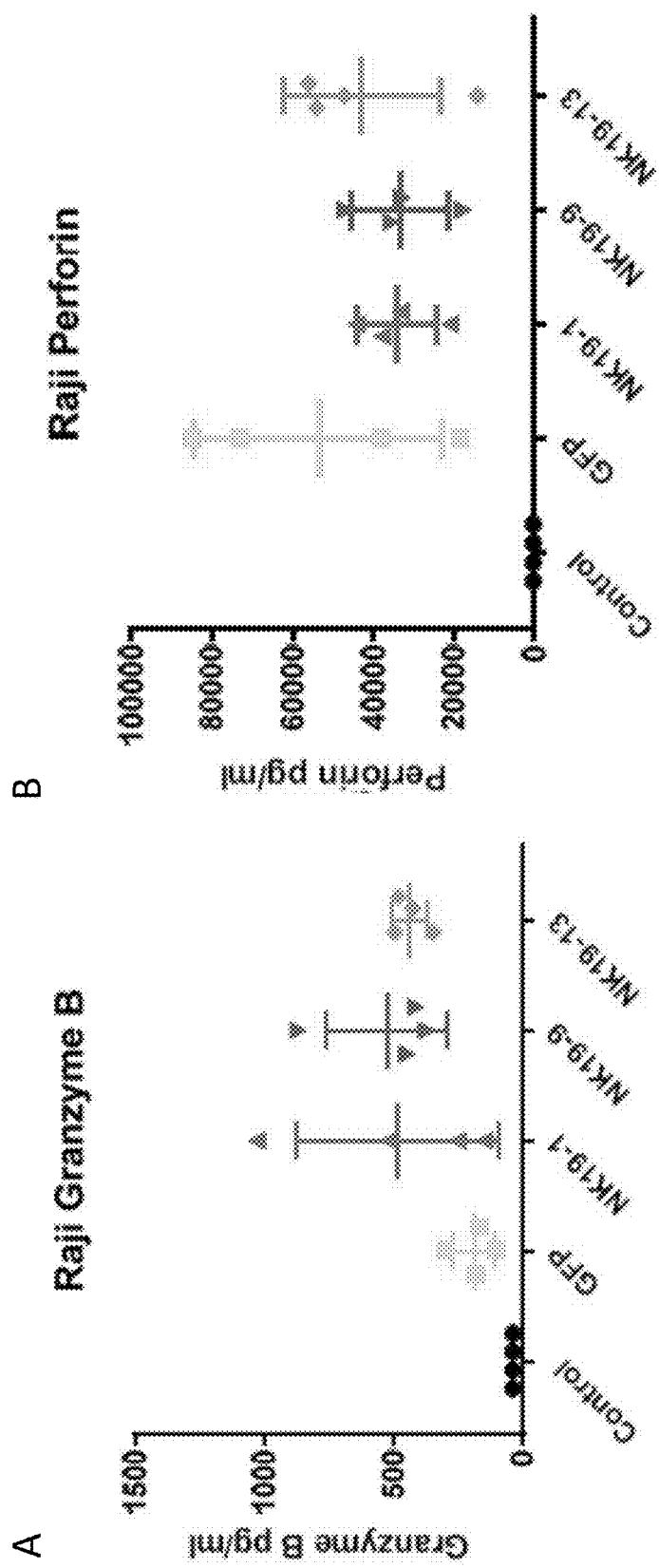
Figure 12A-B

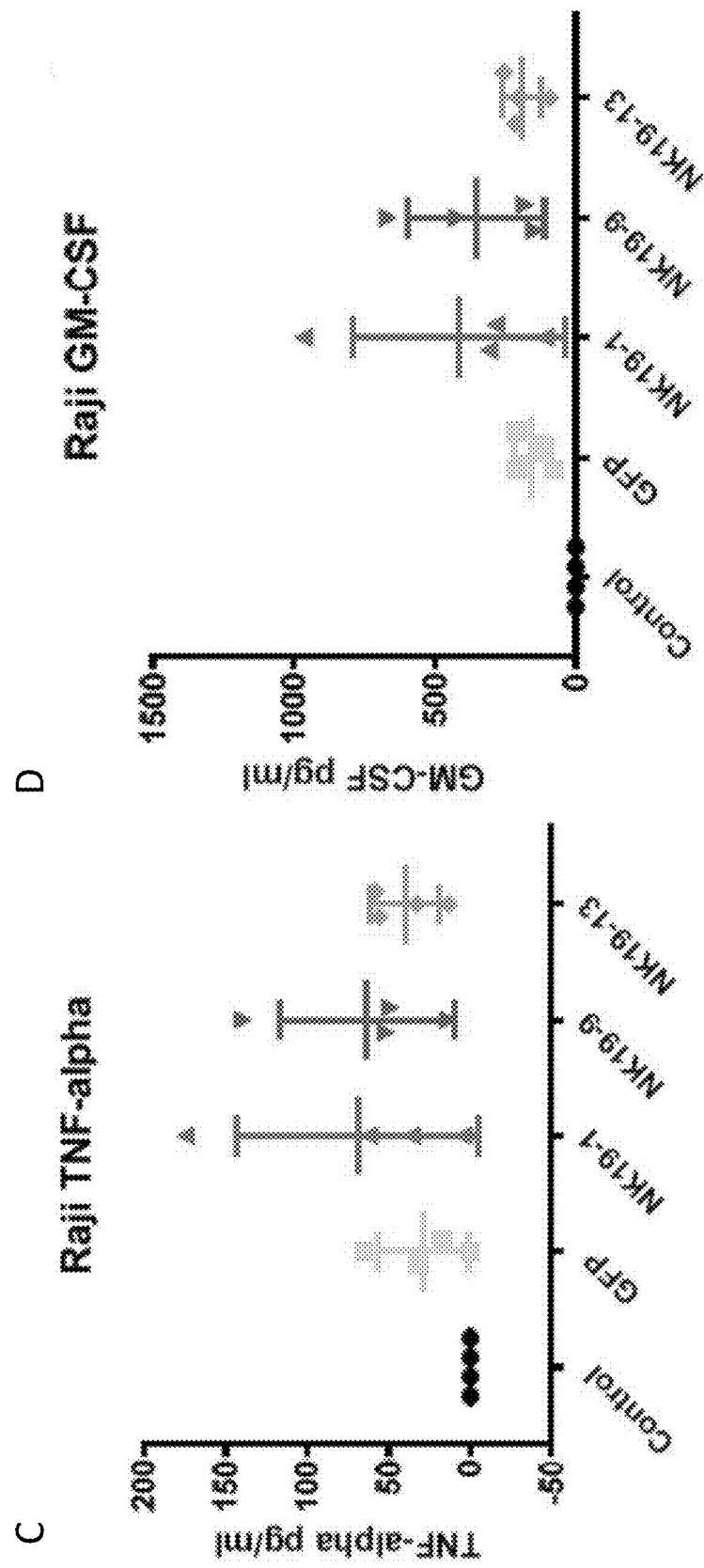
Figure 12C-D

| MFI | Unheating | | | Heating | | |
|---|---|---|---|---|---|---|
| | 0.5 | 0.25 | 0.125 | | 0.5 | 0.25 | 0.125 |
| H1L1 | 385 | 285 | 169 | H1L1 | 389 | 270 | 159 |
| H1L2 | 396 | 303 | 202 | H1L2 | 395 | 288 | 196 |
| H1L3 | 406 | 306 | 99.3 | H1L3 | 392 | 278 | 190 |
| H2L1 | 399 | 292 | 181 | H2L1 | 378 | 270 | 186 |
| H2L2 | 390 | 274 | 180 | H2L2 | 398 | 271 | 177 |
| H2L3 | 431 | 327 | 213 | H2L3 | 432 | 305 | 202 |
| H3L1 | 359 | 246 | 164 | H3L1 | 350 | 227 | 137 |
| H3L2 | 379 | 253 | 132 | H3L2 | 348 | 229 | 151 |
| H3L3 | 415 | 299 | 203 | H3L3 | 418 | 310 | 217 |
| H4L1 | 390 | 274 | 188 | H4L1 | 400 | 285 | 199 |
| H4L2 | 387 | 281 | 199 | H4L2 | 383 | 279 | 183 |
| H4L3 | 445 | 329 | 235 | H4L3 | 420 | 334 | 245 |
| HOLO | 433 | 312 | 194 | HOLO | 435 | 321 | 207 |

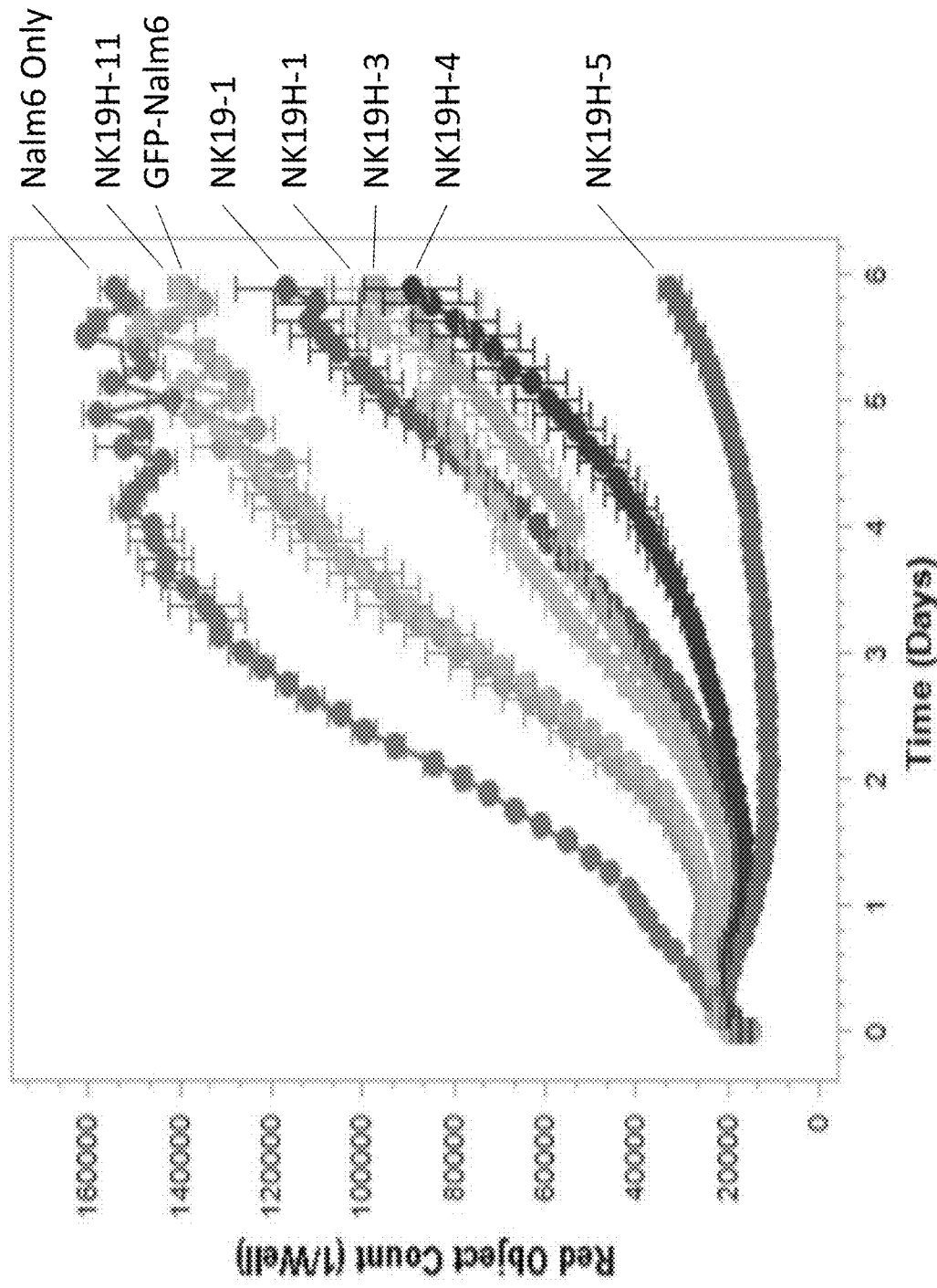

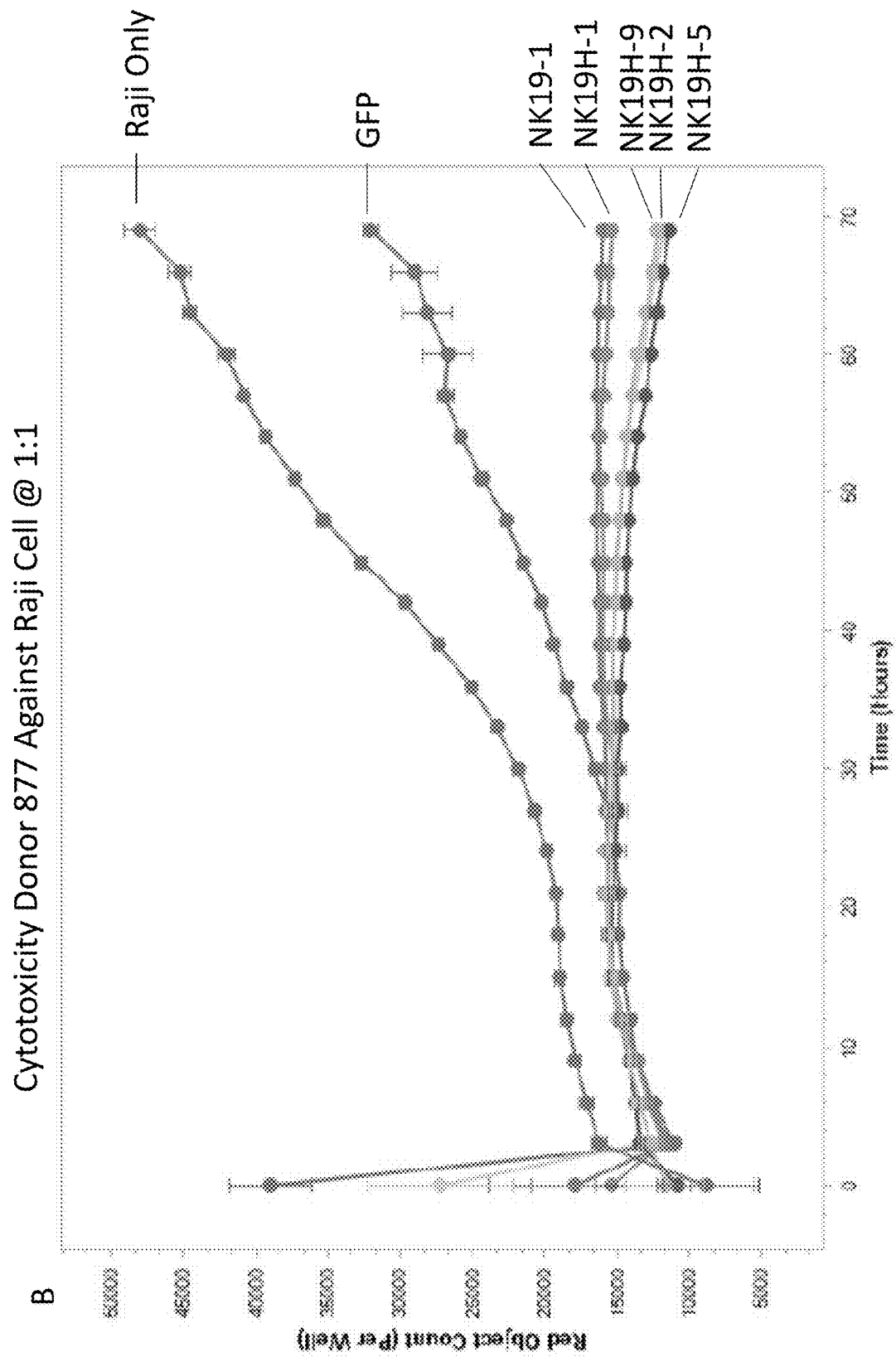

Longitudinal Imaging Results for NK19 IL12/18 Fresh vs Frozen Days 1-56

SEQUENCE LISTING

<160> NUMBER OF SEQ ID NOS: 207

<210> SEQ ID NO 1
<211> LENGTH: 135
<212> TYPE: DNA
<213> ORGANISM: Homo sapiens
<220> FEATURE:
<221> NAME/KEY: misc_feature
<223> OTHER INFORMATION: CD8alpha hinge - DNA

<400> SEQUENCE: 1
accacgacgc cagcgccgcg accaccaaca ccggcgccca ccatcgcgtc gcagcccctg    60
tccctgcgcc cagaggcgtg ccggccagcg gcggggggcg cagtgcacac gaggggggctg   120 gacttcgcct gtgat                                                    135

<210> SEQ ID NO 2
<211> LENGTH: 45
<212> TYPE: PRT
<213> ORGANISM: Homo sapiens
<220> FEATURE:
<221> NAME/KEY: MISC_FEATURE
<223> OTHER INFORMATION: CD8a hinge - protein

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 3
<211> LENGTH: 63
<212> TYPE: DNA
<213> ORGANISM: Homo sapiens
<220> FEATURE:
<221> NAME/KEY: misc_feature
<223> OTHER INFORMATION: CD8 TM - DNA

<400> SEQUENCE: 3
atctacatct gggcgccctt ggccgggact tgtggggtcc ttctcctgtc actggttatc    60
acc                                                                 63

```
<210> SEQ ID NO 4
<211> LENGTH: 21
<212> TYPE: PRT
<213> ORGANISM: Homo sapiens
<220> FEATURE:
<221> NAME/KEY: MISC_FEATURE
<223> OTHER INFORMATION: CD8 TM - protein

<400> SEQUENCE: 4

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 5
<211> LENGTH: 111
<212> TYPE: DNA
<213> ORGANISM: Homo sapiens
<220> FEATURE:
<221> NAME/KEY: misc_feature
<223> OTHER INFORMATION: OX40 - DNA

<400> SEQUENCE: 5
cggagggacc agaggctgcc ccccgatgcc cacaagcccc ctgggggagg cagtttccgg        60 accccccatcc aagaggagca ggccgacgcc cactccaccc tggccaagat c              111

<210> SEQ ID NO 6
<211> LENGTH: 37
<212> TYPE: PRT
<213> ORGANISM: Homo sapiens
<220> FEATURE:
<221> NAME/KEY: MISC_FEATURE
<223> OTHER INFORMATION: OX40 - protein

<400> SEQUENCE: 6

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 7
<211> LENGTH: 336
<212> TYPE: DNA
<213> ORGANISM: Homo sapiens
<220> FEATURE:
<221> NAME/KEY: misc_feature
<223> OTHER INFORMATION: CD3zeta - DNA

<400> SEQUENCE: 7
agagtgaagt tcagcaggag cgcagacgcc cccgcgtacc agcagggcca gaaccagctc        60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga agataagat ggcggaggcc tacagtgaga ttgggatgaa aggcgagcgc       240 cggagggca aggggcacga tggcctttac cagggtctca gtacagccac caaggacacc       300
tacgacgccc ttcacatgca ggccctgccc cctcgc                                336

<210> SEQ ID NO 8
<211> LENGTH: 112
<212> TYPE: PRT
```

<213> ORGANISM: Homo sapiens
<220> FEATURE:
<221> NAME/KEY: MISC_FEATURE
<223> OTHER INFORMATION: CD3zeta - protein

<400> SEQUENCE: 8

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 9
<211> LENGTH: 63
<212> TYPE: DNA
<213> ORGANISM: Homo sapiens
<220> FEATURE:
<221> NAME/KEY: misc_feature
<223> OTHER INFORMATION: T2A - DNA

<400> SEQUENCE: 9

```
ggctctggcg agggaagggg ttccctgctt acttgcggcg acgtcgaaga gaatcccggt    60
ccg                                                                  63
```

<210> SEQ ID NO 10
<211> LENGTH: 21
<212> TYPE: PRT
<213> ORGANISM: Homo sapiens
<220> FEATURE:
<221> NAME/KEY: MISC_FEATURE
<223> OTHER INFORMATION: T2A - protein

<400> SEQUENCE: 10

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 11
<211> LENGTH: 342
<212> TYPE: DNA
<213> ORGANISM: Homo sapiens
<220> FEATURE:
<221> NAME/KEY: misc_feature
<223> OTHER INFORMATION: IL15 - DNA

<400> SEQUENCE: 11

```
aactgggtca acgtgattag cgatttgaag aaaatcgagg accttataca gtctatgcat    60
attgacgcta cactgtatac tgagagtgat gtacacccgt cctgtaaggt aacggccatg   120
aaatgctttc ttctggagct ccaggtcatc agcttggagt ctggggacgc aagcatccac   180
gatacggttg aaaacctcat catccttgcg aacaactctc tctcatctaa tggaaacgtt   240
```

```
acagagagtg ggtgtaagga gtgcgaagag ttggaagaaa aaaacatcaa agaatttctt    300
caatccttcg ttcacatagt gcaaatgttc attaacacgt cc                       342
```

<210> SEQ ID NO 12
<211> LENGTH: 114
<212> TYPE: PRT
<213> ORGANISM: Homo sapiens
<220> FEATURE:
<221> NAME/KEY: MISC_FEATURE
<223> OTHER INFORMATION: IL15 - protein

<400> SEQUENCE: 12

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 13
<211> LENGTH: 207
<212> TYPE: DNA
<213> ORGANISM: Homo sapiens
<220> FEATURE:
<221> NAME/KEY: misc_feature
<223> OTHER INFORMATION: CD8hinge/TM - DNA

<400> SEQUENCE: 13

```
actaccacac ccgccccgag gccacctacg ccggcaccga ctatcgccag tcaacccctc    60
tctctgcgcc ccgaggcttg ccggcctgcg gctggtgggg cggtccacac ccggggcctg   120
gattttgcgt gcgatatata catctgggca cctcttgccg gcacctgcgg agtgctgctt   180
ctctcactcg ttattacgct gtactgc                                        207
```

<210> SEQ ID NO 14
<211> LENGTH: 66
<212> TYPE: PRT
<213> ORGANISM: Homo sapiens
<220> FEATURE:
<221> NAME/KEY: MISC_FEATURE
<223> OTHER INFORMATION: CD8hinge/TM - protein

<400> SEQUENCE: 14

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60
```

Ile Thr
65

<210> SEQ ID NO 15
<211> LENGTH: 30
<212> TYPE: DNA
<213> ORGANISM: Homo sapiens
<220> FEATURE:
<221> NAME/KEY: misc_feature
<223> OTHER INFORMATION: Linker 1 (used after FLAG tag)  - DNA

<400> SEQUENCE: 15
ggcggtggtg gctctggtgg tggcggcagc                                    30

<210> SEQ ID NO 16
<211> LENGTH: 10
<212> TYPE: PRT
<213> ORGANISM: Homo sapiens
<220> FEATURE:
<221> NAME/KEY: MISC_FEATURE
<223> OTHER INFORMATION: Linker 1 (used after FLAG tag)  - protein

<400> SEQUENCE: 16

Gly Gly Gly Gly Ser Gly Gly Gly Gly Ser
1               5                   10

<210> SEQ ID NO 17
<211> LENGTH: 30
<212> TYPE: DNA
<213> ORGANISM: Homo sapiens
<220> FEATURE:
<221> NAME/KEY: misc_feature
<223> OTHER INFORMATION: Linker 2 - after neg. control binding domain -
      DNA

<400> SEQUENCE: 17
ggccaggccg gctccggagg aggaggatcc                                    30

<210> SEQ ID NO 18
<211> LENGTH: 10
<212> TYPE: PRT
<213> ORGANISM: Homo sapiens
<220> FEATURE:
<221> NAME/KEY: MISC_FEATURE
<223> OTHER INFORMATION: Linker 2 - after neg. control binding domain -
      Protein

<400> SEQUENCE: 18

Gly Gln Ala Gly Ser Gly Gly Gly Gly Ser
1               5                   10

<210> SEQ ID NO 19
<211> LENGTH: 12
<212> TYPE: DNA
<213> ORGANISM: Homo sapiens
<220> FEATURE:
<221> NAME/KEY: misc_feature
<223> OTHER INFORMATION: Linker post scFv - DNA

<400> SEQUENCE: 19
ggccaggccg gc                                                       12

<210> SEQ ID NO 20
<211> LENGTH: 4
<212> TYPE: PRT
<213> ORGANISM: Homo sapiens
<220> FEATURE:

```
<221> NAME/KEY: MISC_FEATURE
<223> OTHER INFORMATION: Linker post scFv - protein

<400> SEQUENCE: 20

Gly Gln Ala Gly
1

<210> SEQ ID NO 21
<211> LENGTH: 33
<212> TYPE: DNA
<213> ORGANISM: Homo sapiens
<220> FEATURE:
<221> NAME/KEY: misc_feature
<223> OTHER INFORMATION: Linker - DNA
<220> FEATURE:
<221> NAME/KEY: misc_feature
<223> OTHER INFORMATION: Misc Linker - DNA

<400> SEQUENCE: 21
ggcggcggcg gtagcggtgg tggcggctcc gga                                   33

<210> SEQ ID NO 22
<211> LENGTH: 11
<212> TYPE: PRT
<213> ORGANISM: Homo sapiens
<220> FEATURE:
<221> NAME/KEY: MISC_FEATURE
<223> OTHER INFORMATION: Misc Linker - protein

<400> SEQUENCE: 22

Gly Gly Gly Gly Ser Gly Gly Gly Ser Gly
1               5                   10

<210> SEQ ID NO 23
<211> LENGTH: 18
<212> TYPE: DNA
<213> ORGANISM: Homo sapiens
<220> FEATURE:
<221> NAME/KEY: misc_feature
<223> OTHER INFORMATION: Linker - DNA

<400> SEQUENCE: 23
ggccaggccg gctccgga                                                    18

<210> SEQ ID NO 24
<211> LENGTH: 6
<212> TYPE: PRT
<213> ORGANISM: Homo sapiens
<220> FEATURE:
<221> NAME/KEY: MISC_FEATURE
<223> OTHER INFORMATION: Linker - protein

<400> SEQUENCE: 24

Gly Gln Ala Gly Ser Gly
1               5

<210> SEQ ID NO 25
<211> LENGTH: 405
<212> TYPE: DNA
<213> ORGANISM: Homo sapiens
<220> FEATURE:
<221> NAME/KEY: misc_feature
<223> OTHER INFORMATION: NKG2D Extracellular Fragment - DNA

<400> SEQUENCE: 25
ttattcaacc aagaagttca aattcccttg accgaaagtt actgtggccc atgtcctaaa      60
aactggatat gttacaaaaa taactgctac caatttttg atgagagtaa aaactggtat     120
```

```
gagagccagg cttcttgtat gtctcaaaat gccagccttc tgaaagtata cagcaaagag    180
gaccaggatt tacttaaact ggtgaagtca tatcattgga tgggactagt acacattcca    240
acaaatggat cttggcagtg ggaagatggc tccattctct cacccaacct actaacaata    300
attgaaatgc agaagggaga ctgtgcactc tatgcctcga gctttaaagg ctatatagaa    360
aactgttcaa ctccaaatac gtacatctgc atgcaaagga ctgtg                   405
```

```
<210> SEQ ID NO 26
<211> LENGTH: 135
<212> TYPE: PRT
<213> ORGANISM: Homo sapiens
<220> FEATURE:
<221> NAME/KEY: MISC_FEATURE
<223> OTHER INFORMATION: NKG2D Extracellular Fragment - protein

<400> SEQUENCE: 26
```

```
Leu Phe Asn Gln Glu Val Gln Ile Pro Leu Thr Glu Ser Tyr Cys Gly
 1               5                  10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val
    130                 135
```

```
<210> SEQ ID NO 27
<211> LENGTH: 645
<212> TYPE: DNA
<213> ORGANISM: Homo sapiens
<220> FEATURE:
<221> NAME/KEY: misc_feature
<223> OTHER INFORMATION: Full Human NKG2D - DNA

<400> SEQUENCE: 27
gggtggattc gtggtcggag gtctcgacac agctgggaga tgagtgaatt tcataattat    60
aacttggatc tgaagaagag tgattttcca acacgatggc aaaagcaaag atgtccagta   120
gtcaaaagca aatgtagaga aaatgcatct ccattttttt tctgctgctt catcgctgta   180
gccatgggaa tccgtttcat tattatggta acaaatggat gtgctgtatt cctaaactca   240
ttattcaacc aagaagttca aattcccttg accgaaagtt actgtggccc atgtcctaaa   300
aactggatat gttacaaaaa taactgctac caattttttg atgagagtaa aaactggtat   360
gagagccagg cttcttgtat gtctcaaaat gccagccttc tgaaagtata cagcaaagag   420
gaccaggatt tacttaaact ggtgaagtca tatcattgga tgggactagt acacattcca   480
acaaatggat cttggcagtg ggaagatggc tccattctct cacccaacct actaacaata   540
attgaaatgc agaagggaga ctgtgcactc tatgcctcga gctttaaagg ctatatagaa   600
```

```
aactgttcaa ctccaaatac gtacatctgc atgcaaagga ctgtg              645
```

<210> SEQ ID NO 28
<211> LENGTH: 405
<212> TYPE: DNA
<213> ORGANISM: Homo sapiens
<220> FEATURE:
<221> NAME/KEY: misc_feature
<223> OTHER INFORMATION: Codon optimized human NKG2D fragment - DNA

<400> SEQUENCE: 28

```
ctgttcaatc aggaagtcca gatcccctg acagagtctt actgcggccc atgtcccaag    60
aactggatct gctacaagaa caattgttat cagttctttg acgagagcaa gaactggtat  120
gagtcccagg cctcttgcat gagccagaat gcctctctgc tgaaggtgta cagcaaggag  180
gaccaggatc tgctgaagct ggtgaagtcc tatcactgga tgggcctggt gcacatccct  240
acaaacggct cttggcagtg ggaggacggc tccatcctgt ctccaaatct gctgaccatc  300
atcgagatgc agaagggcga ttgcgccctg tacgccagtc ccttcaaggg ctatatcgag  360
aactgctcca cacccaatac ctacatctgt atgcagagga ccgtg                  405
```

<210> SEQ ID NO 29
<211> LENGTH: 126
<212> TYPE: DNA
<213> ORGANISM: Homo sapiens
<220> FEATURE:
<221> NAME/KEY: misc_feature
<223> OTHER INFORMATION: 4-1BB

<400> SEQUENCE: 29

```
aaacggggca gaaagaaact cctgtatata ttcaaacaac catttatgag accagtacaa    60
actactcaag aggaagatgg ctgtagctgc cgatttccag aagaagaaga aggaggatgt  120
gaactg                                                              126
```

<210> SEQ ID NO 30
<211> LENGTH: 29
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 Transmembrane domain

<400> SEQUENCE: 30

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser
            20                  25
```

<210> SEQ ID NO 31
<211> LENGTH: 39
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 IC domain

<400> SEQUENCE: 31

```
Lys Arg Ser Arg Leu Leu His Ser Asp Tyr Met Asn Met Thr Pro Arg
1               5                   10                  15

Arg Pro Gly Pro Thr Arg Lys His Tyr Gln Pro Tyr Ala Pro Pro Arg
            20                  25                  30
```

Asp Phe Ala Ala Tyr Arg Ser
        35

<210> SEQ ID NO 32
<211> LENGTH: 123
<212> TYPE: PRT
<213> ORGANISM: Homo sapiens
<220> FEATURE:
<221> NAME/KEY: MISC_FEATURE
<223> OTHER INFORMATION: VL Nicholson et al.

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Arg Ala Asp Ala Ala
            100                 105                 110

Pro Thr Val Ser Ile Phe Pro Pro Ser Ser Asn
        115                 120

<210> SEQ ID NO 33
<211> LENGTH: 120
<212> TYPE: PRT
<213> ORGANISM: Homo sapiens
<220> FEATURE:
<221> NAME/KEY: MISC_FEATURE
<223> OTHER INFORMATION: VH Nicholson et al.

<400> SEQUENCE: 33

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 34
<211> LENGTH: 634
<212> TYPE: PRT
<213> ORGANISM: Homo sapiens
<220> FEATURE:

<221> NAME/KEY: MISC_FEATURE
<223> OTHER INFORMATION: PRT Artificial Sequence CD19R zeta chimeric
      receptor

<400> SEQUENCE: 34

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
            210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Val Glu Pro Lys Ser
            260                 265                 270

Ser Asp Lys Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
```

```
                385                 390                 395                 400
Val Tyr Thr Leu Pro Pro Ser Arg Asp Glu Leu Thr Lys Asn Gln Val
                    405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
        450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                    485                 490                 495

Ser Pro Gly Lys Met Ala Leu Ile Val Leu Gly Gly Val Ala Gly Leu
                500                 505                 510

Leu Leu Phe Ile Gly Leu Gly Ile Phe Phe Arg Val Lys Phe Ser Arg
            515                 520                 525

Ser Ala Asp Ala Pro Ala Tyr Gln Gln Gly Gln Asn Gln Leu Tyr Asn
        530                 535                 540

Glu Leu Asn Leu Gly Arg Arg Glu Glu Tyr Asp Val Leu Asp Lys Arg
545                 550                 555                 560

Arg Gly Arg Asp Pro Glu Met Gly Gly Lys Pro Arg Arg Lys Asn Pro
                565                 570                 575

Gln Glu Gly Leu Tyr Asn Glu Leu Gln Lys Asp Lys Met Ala Glu Ala
                580                 585                 590

Tyr Ser Glu Ile Gly Met Lys Gly Glu Arg Arg Arg Gly Lys Gly His
            595                 600                 605

Asp Gly Leu Tyr Gln Gly Leu Ser Thr Ala Thr Lys Asp Thr Tyr Asp
        610                 615                 620

Ala Leu His Met Gln Ala Leu Pro Pro Arg
625                 630

<210> SEQ ID NO 35
<211> LENGTH: 120
<212> TYPE: PRT
<213> ORGANISM: Homo sapiens
<220> FEATURE:
<221> NAME/KEY: MISC_FEATURE
<223> OTHER INFORMATION: anti-CD19 scFv HCV

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ser Val Ile Trp Gly Ser Glu Thr Thr Tyr Tyr Asn Ser Ala Leu Lys
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110
```

```
Gly Thr Leu Val Thr Val Ser Ser
        115             120

<210> SEQ ID NO 36
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti-CD19 scFv HCV

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 37
<211> LENGTH: 11
<212> TYPE: PRT
<213> ORGANISM: Homo sapiens
<220> FEATURE:
<221> NAME/KEY: MISC_FEATURE
<223> OTHER INFORMATION: LC CDR1

<400> SEQUENCE: 37

Arg Ala Ser Gln Asp Ile Ser Lys Tyr Leu Asn
1               5                   10

<210> SEQ ID NO 38
<211> LENGTH: 7
<212> TYPE: PRT
<213> ORGANISM: Homo sapiens
<220> FEATURE:
<221> NAME/KEY: MISC_FEATURE
<223> OTHER INFORMATION: LC CDR2

<400> SEQUENCE: 38

His Thr Ser Arg Leu His Ser
1               5

<210> SEQ ID NO 39
<211> LENGTH: 9
<212> TYPE: PRT
<213> ORGANISM: Homo sapiens
<220> FEATURE:
<221> NAME/KEY: MISC_FEATURE
<223> OTHER INFORMATION: LC CDR3

<400> SEQUENCE: 39

Gln Gln Gly Asn Thr Leu Pro Tyr Thr
1               5

<210> SEQ ID NO 40
```

```
<211> LENGTH: 10
<212> TYPE: PRT
<213> ORGANISM: Homo sapiens
<220> FEATURE:
<221> NAME/KEY: MISC_FEATURE
<223> OTHER INFORMATION: HC CDR1

<400> SEQUENCE: 40

Gly Val Ser Leu Pro Asp Tyr Gly Val Ser
1               5                   10

<210> SEQ ID NO 41
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2

<400> SEQUENCE: 41

Val Ile Trp Gly Ser Glu Thr Thr Tyr Tyr Ser Ser Ser Leu Lys Ser
1               5                   10                  15

<210> SEQ ID NO 42
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2 - alternative

<400> SEQUENCE: 42

Val Ile Trp Gly Ser Glu Thr Thr Tyr Tyr Gln Ser Ser Leu Lys Ser
1               5                   10                  15

<210> SEQ ID NO 43
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2 - alternative 2

<400> SEQUENCE: 43

Val Ile Trp Gly Ser Glu Thr Thr Tyr Tyr Asn Ser Ser Leu Lys Ser
1               5                   10                  15

<210> SEQ ID NO 44
<211> LENGTH: 12
<212> TYPE: PRT
<213> ORGANISM: Homo sapiens
<220> FEATURE:
<221> NAME/KEY: MISC_FEATURE
<223> OTHER INFORMATION: HC CDR3

<400> SEQUENCE: 44

His Tyr Tyr Tyr Gly Gly Ser Tyr Ala Met Asp Tyr
1               5                   10

<210> SEQ ID NO 45
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 1

<400> SEQUENCE: 45
```

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 46
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 2

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 47
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 3

<400> SEQUENCE: 47

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Gly Asn Thr Leu Pro Tyr
            85                  90                  95

Thr Phe Gly Gln Gly Thr Lys Leu Glu Ile Lys
            100                 105
```

<210> SEQ ID NO 48
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 4

<400> SEQUENCE: 48

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
            35                  40                  45

Lys His Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
            85                  90                  95

Thr Phe Gly Gln Gly Thr Lys Leu Glu Ile Lys
            100                 105
```

<210> SEQ ID NO 49
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 1

<400> SEQUENCE: 49

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Asn Ser Ala Leu Lys
        50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120
```

<210> SEQ ID NO 50
<211> LENGTH: 120
<212> TYPE: PRT
<213> ORGANISM: Homo sapiens
<220> FEATURE:

<221> NAME/KEY: MISC_FEATURE
<223> OTHER INFORMATION: Heavy chain variable region 2

<400> SEQUENCE: 50

Gln Val Gln Leu Gln Glu Ser Gly Pro Gly Leu Val Lys Pro Ser Glu
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Thr Ser Lys Asn Gln Val Phe Leu
65                  70                  75                  80

Lys Met Ser Ser Leu Thr Ala Ala Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 51
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 3

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Thr Ala Ser Gly Val Ser Leu Pro Asp Tyr
            20                  25                  30

Gly Val Ser Trp Val Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 52
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 4

<400> SEQUENCE: 52

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Leu Pro Asp Tyr

```
                    20                  25                  30
Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
        50                  55                  60

Ser Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser
        115                 120

<210> SEQ ID NO 53
<211> LENGTH: 8
<212> TYPE: PRT
<213> ORGANISM: Homo sapiens
<220> FEATURE:
<221> NAME/KEY: MISC_FEATURE
<223> OTHER INFORMATION: LC CDR1

<400> SEQUENCE: 53

Arg Ala Ser Gln Asp Ile Ser Lys
1               5

<210> SEQ ID NO 54
<211> LENGTH: 7
<212> TYPE: PRT
<213> ORGANISM: Homo sapiens
<220> FEATURE:
<221> NAME/KEY: MISC_FEATURE
<223> OTHER INFORMATION: LC CDR2

<400> SEQUENCE: 54

Ile Tyr His Thr Ser Arg Leu
1               5

<210> SEQ ID NO 55
<211> LENGTH: 9
<212> TYPE: PRT
<213> ORGANISM: Homo sapiens
<220> FEATURE:
<221> NAME/KEY: MISC_FEATURE
<223> OTHER INFORMATION: LC CDR3

<400> SEQUENCE: 55

Gln Gln Gly Asn Thr Leu Pro Tyr Thr
1               5

<210> SEQ ID NO 56
<211> LENGTH: 10
<212> TYPE: PRT
<213> ORGANISM: Homo sapiens
<220> FEATURE:
<221> NAME/KEY: MISC_FEATURE
<223> OTHER INFORMATION: HC CDR1

<400> SEQUENCE: 56

Gly Val Ser Leu Pro Asp Tyr Gly Val Ser
1               5                   10

<210> SEQ ID NO 57
<211> LENGTH: 14
```

```
<212> TYPE: PRT
<213> ORGANISM: Homo sapiens
<220> FEATURE:
<221> NAME/KEY: MISC_FEATURE
<223> OTHER INFORMATION: HC CDR2

<400> SEQUENCE: 57

Val Ile Trp Gly Ser Glu Thr Thr Tyr Tyr Asn Ser Ala Leu
1               5                   10

<210> SEQ ID NO 58
<211> LENGTH: 12
<212> TYPE: PRT
<213> ORGANISM: Homo sapiens
<220> FEATURE:
<221> NAME/KEY: MISC_FEATURE
<223> OTHER INFORMATION: HC CDR3

<400> SEQUENCE: 58

His Tyr Tyr Tyr Gly Gly Ser Tyr Ala Met Asp Tyr
1               5                   10

<210> SEQ ID NO 59
<211> LENGTH: 2210
<212> TYPE: DNA
<213> ORGANISM: Homo sapiens
<220> FEATURE:
<221> NAME/KEY: misc_feature
<223> OTHER INFORMATION: NK19-1b DNA

<400> SEQUENCE: 59
ggatccgaat cgccgccac  catggcctta ccagtgaccg  ccttgctcct gccgctggcc     60
ttgctgctcc acgccgccag gccggactac aaagacgatg acgataaagg cggtggtggc    120
tctggtggtg gcggcagcga catccagatg acacagacta catcctccct gtctgcctct    180
ctgggagaca gagtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttactttt gccaacaggg taatacgctt    420
ccgtacacgt tcggagggg  gaccaagctg gagatcacag gtggcggtgg ctcgggcggt    480
ggtgggtcgg gtggcggcgg atctgaggtg aaactgcagg agtcaggacc tggcctggtg    540
gcgccctcac agagcctgtc cgtcacatgc actgtctcag ggtctcatt  acccgactat    600 ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtgggtcct  tctcctgtca ctggttatca ccctttactg ccggagggac   1080
cagaggctgc ccccgatgc  ccacaagccc ctgggggag  gcagtttccg gacccccatc   1140
caagaggagc aggccgacgc ccactccacc ctggccaaga tcagagtgaa gttcagcagg   1200
agcgcagacg cccccgcgta ccagcagggc cagaaccagc tctataacga gctcaatcta   1260
ggacgaagag aggagtacga tgttttggac aagagacgtg gccgggaccc tgagatgggg   1320
```

```
ggaaagccga gaaggaagaa ccctcaggaa ggcctgtaca atgaactgca gaaagataag    1380
atggcggagg cctacagtga gattgggatg aaaggcgagc gccggagggg caaggggcac    1440
gatggccttt accagggtct cagtacagcc accaaggaca cctacgacgc ccttcacatg    1500
caggccctgc cccctcgcgg ctctggcgag ggaaggggtt ccctgcttac ttgcggcgac    1560
gtcgaagaga atcccggtcc gatggccctc ccagtaactg ccctccttt gcccctcgca    1620 ctccttcttc atgccgctcg ccccaactgg gtcaacgtga ttagcgattt gaagaaaatc    1680
gaggacctta tacagtctat gcatattgac gctacactgt atactgagag tgatgtacac    1740
ccgtcctgta aggtaacggc catgaaatgc tttcttctgg agctccaggt catcagcttg    1800
gagtctgggg acgcaagcat ccacgatacg gttgaaaacc tcatcatcct gcgaacaac    1860 tctctctcat ctaatggaaa cgttacagag agtgggtgta aggagtgcga agagttggaa    1920
gaaaaaaaca tcaaagaatt tcttcaatcc ttcgttcaca tagtgcaaat gttcattaac    1980
acgtccacta ccacacccgc cccgaggcca cctacgccgg caccgactat cgccagtcaa    2040
cccctctctc tgcgccccga ggcttgccgg cctgcggctg gtgggcggt ccacacccgg    2100 ggcctggatt ttgcgtgcga tatatacatc tgggcacctc ttgccggcac ctgcggagtg    2160
ctgcttctct cactcgttat tacgctgtac tgctaagcgg ccgcgtcgac              2210
```

<210> SEQ ID NO 60
<211> LENGTH: 724
<212> TYPE: PRT
<213> ORGANISM: Homo sapiens
<220> FEATURE:
<221> NAME/KEY: MISC_FEATURE
<223> OTHER INFORMATION: NK19-1b Protein

<400> SEQUENCE: 60

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
```

-continued

```
                195                 200                 205
Leu Gly Val Ile Trp Gly Ser Glu Thr Thr Tyr Tyr Asn Ser Ala Leu
210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
                260                 265                 270

Gln Gly Thr Ser Val Thr Val Ser Ser Thr Thr Thr Pro Ala Pro Arg
                275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
                340                 345                 350

Asp Gln Arg Leu Pro Pro Asp Ala His Lys Pro Pro Gly Gly Gly Ser
                355                 360                 365

Phe Arg Thr Pro Ile Gln Glu Glu Gln Ala Asp Ala His Ser Thr Leu
370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
                420                 425                 430

Gly Gly Lys Pro Arg Arg Lys Asn Pro Gln Glu Gly Leu Tyr Asn Glu
                435                 440                 445

Leu Gln Lys Asp Lys Met Ala Glu Ala Tyr Ser Glu Ile Gly Met Lys
450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
                500                 505                 510

Asp Val Glu Glu Asn Pro Gly Pro Met Ala Leu Pro Val Thr Ala Leu
                515                 520                 525

Leu Leu Pro Leu Ala Leu Leu Leu His Ala Ala Arg Pro Asn Trp Val
530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
                580                 585                 590

Leu Glu Ser Gly Asp Ala Ser Ile His Asp Thr Val Glu Asn Leu Ile
                595                 600                 605

Ile Leu Ala Asn Asn Ser Leu Ser Ser Asn Gly Asn Val Thr Glu Ser
610                 615                 620
```

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
            645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Gly Gly
        675                 680                 685

Ala Val His Thr Arg Gly Leu Asp Phe Ala Cys Asp Ile Tyr Ile Trp
690                 695                 700

Ala Pro Leu Ala Gly Thr Cys Gly Val Leu Leu Leu Ser Leu Val Ile
705                 710                 715                 720

Thr Leu Tyr Cys

<210> SEQ ID NO 61
<211> LENGTH: 2231
<212> TYPE: DNA
<213> ORGANISM: Homo sapiens
<220> FEATURE:
<221> NAME/KEY: misc_feature
<223> OTHER INFORMATION: NK19-2b DNA

<400> SEQUENCE: 61
ggatccgaat cgccgccac catggcctta ccagtgaccg ccttgctcct gccgctggcc      60
ttgctgctcc acgccgccag gccggactac aaagacgatg acgataaagg cggtggtggc     120
tctggtggtg gcggcagcga catccagatg acacagacta tcctccct gtctgcctct      180 ctgggagaca gagtcaccat cagttgcagg gcaagtcagg acattagtaa atatttaaat     240
tggtatcagc agaaaccaga tggaactgtt aaactcctga tctaccatac atcaagatta    300
cactcaggag tcccatcaag gttcagtggc agtgggtctg gaacagatta ttctctcacc   360
attagcaacc tggagcaaga agatattgcc acttactttt gccaacaggg taatacgctt    420
ccgtacacgt tcggagggg gaccaagctg gagatcacag gtggcggtgg ctcgggcggt     480
ggtgggtcgg gtggcggcgg atctgaggtg aaactgcagg agtcaggacc tggcctggtg    540
gcgccctcac agagcctgtc cgtcacatgc actgtctcag gggtctcatt acccgactat    600
ggtgtaagct ggattcgcca gcctccacga aagggtctgg agtggctggg agtaatatgg     660
ggtagtgaaa ccacatacta taattcagct ctcaaatcca gactgaccat catcaaggac     720
aactccaaga gccaagttttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg   960
ggcgcagtgc acacgagggg gctggacttc gcctgtgatt tttgggtgct ggtggtggtt  1020
ggtggagtcc tggcttgcta tagcttgcta gtaacagtgg cctttattat tttctgggtg   1080
aggagtaaga ggagcaggct cctgcacagt gactacatga acatgactcc ccgccgcccc  1140
gggcccaccc gcaagcatta ccagccctat gccccaccac gcgacttcgc agcctatcgc   1200
tccagagtga agttcagcag gagcgcagac gccccgcgt accagcaggg ccagaaccag   1260
ctctataacg agctcaatct aggacgaaga gaggagtacg atgttttgga caagagacgt    1320
ggccgggacc ctgagatggg gggaaagccg agaaggaaga accctcagga aggcctgtac   1380
aatgaactgc agaaagataa gatggcggag cctacagtg agattgggat gaaaggcgag   1440

```
cgccggaggg gcaaggggca cgatggcctt taccagggtc tcagtacagc caccaaggac    1500
acctacgacg cccttcacat gcaggccctg cccctcgcg gctctggcga gggaaggggt     1560
tccctgctta cttgcggcga cgtcgaagag aatcccggtc cgatggccct cccagtaact    1620
gccctccttt tgcccctcgc actccttctt catgccgctc gccccaactg ggtcaacgtg    1680
attagcgatt tgaagaaaat cgaggacctt atacagtcta tgcatattga cgctacactg    1740
tatactgaga gtgatgtaca cccgtcctgt aaggtaacgg ccatgaaatg ctttcttctg    1800
gagctccagg tcatcagctt ggagtctggg gacgcaagca tccacgatac ggttgaaaac    1860
ctcatcatcc ttgcgaacaa ctctctctca tctaatggaa acgttacaga gagtgggtgt    1920
aaggagtgcg aagagttgga agaaaaaaac atcaaagaat tcttcaatc cttcgttcac     1980 atagtgcaaa tgttcattaa cacgtccact accacacccg ccccgaggcc acctacgccg    2040
gcaccgacta tcgccagtca acccctctct ctgcgccccg aggcttgccg gcctgcggct    2100
ggtggggcgg tccacacccg gggcctggat tttgcgtgcg atatatacat ctgggcacct    2160
cttgccggca cctgcggagt gctgcttctc tcactcgtta ttacgctgta ctgctaagcg    2220
gccgcgtcga c                                                         2231
```

<210> SEQ ID NO 62
<211> LENGTH: 731
<212> TYPE: PRT
<213> ORGANISM: Homo sapiens
<220> FEATURE:
<221> NAME/KEY: MISC_FEATURE
<223> OTHER INFORMATION: NK19-2b Protein

<400> SEQUENCE: 62

```
Met Ala Leu Pro Val Thr Ala Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205
```

```
Leu Gly Val Ile Trp Gly Ser Glu Thr Thr Tyr Tyr Asn Ser Ala Leu
210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Thr Ala Ile Tyr Tyr Cys
            245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Gly Gly Val
            325                 330                 335

Leu Ala Cys Tyr Ser Leu Leu Val Thr Val Ala Phe Ile Ile Phe Trp
        340                 345                 350

Val Arg Ser Lys Arg Ser Arg Leu Leu His Ser Asp Tyr Met Asn Met
    355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg Gly Ser Gly Glu Gly Arg
            500                 505                 510

Gly Ser Leu Leu Thr Cys Gly Asp Val Glu Glu Asn Pro Gly Pro Met
            515                 520                 525

Ala Leu Pro Val Thr Ala Leu Leu Leu Pro Leu Ala Leu Leu Leu His
            530                 535                 540

Ala Ala Arg Pro Asn Trp Val Asn Val Ile Ser Asp Leu Lys Lys Ile
545                 550                 555                 560

Glu Asp Leu Ile Gln Ser Met His Ile Asp Ala Thr Leu Tyr Thr Glu
            565                 570                 575

Ser Asp Val His Pro Ser Cys Lys Val Thr Ala Met Lys Cys Phe Leu
            580                 585                 590

Leu Glu Leu Gln Val Ile Ser Leu Glu Ser Gly Asp Ala Ser Ile His
            595                 600                 605

Asp Thr Val Glu Asn Leu Ile Ile Leu Ala Asn Asn Ser Leu Ser Ser
            610                 615                 620

Asn Gly Asn Val Thr Glu Ser Gly Cys Lys Glu Cys Glu Glu Leu Glu
```

```
                625                630                635                640
Glu Lys Asn Ile Lys Glu Phe Leu Gln Ser Phe Val His Ile Val Gln
                       645                650                655

Met Phe Ile Asn Thr Ser Thr Thr Thr Pro Ala Pro Arg Pro Pro Thr
                660                665                670

Pro Ala Pro Thr Ile Ala Ser Gln Pro Leu Ser Leu Arg Pro Glu Ala
                675                680                685

Cys Arg Pro Ala Ala Gly Gly Ala Val His Thr Arg Gly Leu Asp Phe
    690                695                700

Ala Cys Asp Ile Tyr Ile Trp Ala Pro Leu Ala Gly Thr Cys Gly Val
705                710                715                720

Leu Leu Leu Ser Leu Val Ile Thr Leu Tyr Cys
                725                730

<210> SEQ ID NO 63
<211> LENGTH: 2213
<212> TYPE: DNA
<213> ORGANISM: Homo sapiens
<220> FEATURE:
<221> NAME/KEY: misc_feature
<223> OTHER INFORMATION: NK19-3b DNA

<400> SEQUENCE: 63
ggatccgaat cgccgccac  catggcctta ccagtgaccg ccttgctcct gccgctggcc    60
ttgctgctcc acgccgccag gccggactac aaagacgatg acgataaagg cggtggtggc   120
tctggtggtg gcggcagcga catccagatg acacagacta catcctccct gtctgcctct   180
ctgggagaca gagtcaccat cagttgcagg gcaagtcagg acattagtaa atatttaaat   240
tggtatcagc agaaaccaga tggaactgtt aaactcctga tctaccatac atcaagatta   300
cactcaggag tcccatcaag gttcagtggc agtgggtctg gaacagatta ttctctcacc   360
attagcaacc tggagcaaga agatattgcc acttacttt  gccaacaggg taatacgctt   420
ccgtacacgt tcggagggg  gaccaagctg gagatcacag gtggcggtgg ctcgggcggt   480
ggtgggtcgg gtggcggcgg atctgaggtg aaactgcagg agtcaggacc tggcctggtg   540
gcgccctcac agagcctgtc cgtcacatgc actgtctcag gggtctcatt acccgactat   600
ggtgtaagct ggattcgcca gcctccacga aagggtctgg agtggctggg agtaatatgg   660
ggtagtgaaa ccacatacta taattcagct ctcaaatcca gactgaccat catcaaggac   720
aactccaaga gccaagtttt cttaaaaatg aacagtctgc aaactgatga cacagccatt   780
tactactgtg ccaaacatta ttactacggt ggtagctatg ctatggacta ctggggccaa   840
ggaacctcag tcaccgtctc ctcaaccacg acgccagcgc cgcgaccacc aacaccggcg   900
cccaccatcg cgtcgcagcc cctgtccctg cgcccagagg cgtgccggcc agcggcgggg   960
ggcgcagtgc acacgagggg gctggacttc gcctgtgata tctacatctg ggcgcccttg  1020
gccgggactt gtgggtcct  tctcctgtca ctggttatca cccttactg  ctgttggctt  1080
acaaaaaaga gtattcatc  cagtgtgcac gaccctaacg tgaatacat  gttcatgaga  1140
gcagtgaaca gccaaaaaa  atctagactc acagatgtga ccctaagagt gaagttcagc  1200
aggagcgcag acgcccccgc gtaccagcag gccagaacc  agctctataa cgagctcaat  1260
ctaggacgaa gagaggagta cgatgttttg gacaagagac gtggccggga ccctgagatg  1320
gggggaaagc cgagaaggaa gaaccctcag gaaggcctgt acaatgaact gcagaaagat  1380
aagatggcgg aggcctacag tgagattggg atgaaaggcg agcgccggag gggcaagggg  1440
```

-continued

```
cacgatggcc tttaccaggg tctcagtaca gccaccaagg acacctacga cgcccttcac    1500
atgcaggccc tgcccctcg cggctctggc gagggaaggg gttccctgct tacttgcggc     1560
gacgtcgaag agaatcccgg tccgatggcc ctcccagtaa ctgccctcct tttgcccctc    1620
gcactccttc ttcatgccgc tcgcccaac tgggtcaacg tgattagcga tttgaagaaa     1680
atcgaggacc ttatacagtc tatgcatatt gacgctacac tgtatactga gagtgatgta    1740
cacccgtcct gtaaggtaac ggccatgaaa tgctttcttc tggagctcca ggtcatcagc    1800
ttggagtctg gggacgcaag catccacgat acggttgaaa acctcatcat ccttgcgaac    1860
aactctctct catctaatgg aaacgttaca gagagtgggt gtaaggagtg cgaagagttg    1920
gaagaaaaaa acatcaaaga atttcttcaa tccttcgttc acatagtgca aatgttcatt    1980
aacacgtcca ctaccacacc cgccccgagg ccacctacgc cggcaccgac tatcgccagt    2040 caaccctct ctctgcgccc cgaggcttgc cggcctgcgg ctggtggggc ggtccacacc     2100
cggggcctgg attttgcgtg cgatatatac atctgggcac tcttgccgg cacctgcgga     2160 gtgctgcttc tctcactcgt tattacgctg tactgctaag cggccgcgtc gac            2213
```

<210> SEQ ID NO 64
<211> LENGTH: 725
<212> TYPE: PRT
<213> ORGANISM: Homo sapiens
<220> FEATURE:
<221> NAME/KEY: MISC_FEATURE
<223> OTHER INFORMATION: NK19-3b Protein

<400> SEQUENCE: 64

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220
```

-continued

```
Lys Ser Arg Leu Thr Ile Ile Lys Asp Asn Ser Lys Ser Gln Val Phe
225                 230                 235                 240

Leu Lys Met Asn Ser Leu Gln Thr Asp Thr Ala Ile Tyr Tyr Cys
            245                 250                 255

Ala Lys His Tyr Tyr Tyr Gly Gly Ser Tyr Ala Met Asp Tyr Trp Gly
        260                 265                 270

Gln Gly Thr Ser Val Thr Val Ser Ser Thr Thr Thr Pro Ala Pro Arg
    275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Cys Trp
            340                 345                 350

Leu Thr Lys Lys Lys Tyr Ser Ser Ser Val His Asp Pro Asn Gly Glu
        355                 360                 365

Tyr Met Phe Met Arg Ala Val Asn Thr Ala Lys Lys Ser Arg Leu Thr
370                 375                 380

Asp Val Thr Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg Gly Ser Gly Glu Gly Arg Gly Ser Leu Leu Thr Cys
            500                 505                 510

Gly Asp Val Glu Glu Asn Pro Gly Pro Met Ala Leu Pro Val Thr Ala
        515                 520                 525

Leu Leu Leu Pro Leu Ala Leu Leu Leu His Ala Ala Arg Pro Asn Trp
    530                 535                 540

Val Asn Val Ile Ser Asp Leu Lys Lys Ile Glu Asp Leu Ile Gln Ser
545                 550                 555                 560

Met His Ile Asp Ala Thr Leu Tyr Thr Glu Ser Asp Val His Pro Ser
                565                 570                 575

Cys Lys Val Thr Ala Met Lys Cys Phe Leu Leu Glu Leu Gln Val Ile
            580                 585                 590

Ser Leu Glu Ser Gly Asp Ala Ser Ile His Asp Thr Val Glu Asn Leu
        595                 600                 605

Ile Ile Leu Ala Asn Asn Ser Leu Ser Ser Asn Gly Asn Val Thr Glu
    610                 615                 620

Ser Gly Cys Lys Glu Cys Glu Glu Leu Glu Glu Lys Asn Ile Lys Glu
625                 630                 635                 640

Phe Leu Gln Ser Phe Val His Ile Val Gln Met Phe Ile Asn Thr Ser
```

```
              645                 650                 655
Thr Thr Thr Pro Ala Pro Arg Pro Pro Thr Pro Ala Pro Thr Ile Ala
            660                 665                 670

Ser Gln Pro Leu Ser Leu Arg Pro Glu Ala Cys Arg Pro Ala Ala Gly
        675                 680                 685

Gly Ala Val His Thr Arg Gly Leu Asp Phe Ala Cys Asp Ile Tyr Ile
    690                 695                 700

Trp Ala Pro Leu Ala Gly Thr Cys Gly Val Leu Leu Leu Ser Leu Val
705                 710                 715                 720

Ile Thr Leu Tyr Cys
                725

<210> SEQ ID NO 65
<211> LENGTH: 2357
<212> TYPE: DNA
<213> ORGANISM: Homo sapiens
<220> FEATURE:
<221> NAME/KEY: misc_feature
<223> OTHER INFORMATION: NK19-4b DNA

<400> SEQUENCE: 65
ggatccgaat tcgccgccac catggcctta ccagtgaccg ccttgctcct gccgctggcc      60
ttgctgctcc acgccgccag gccggactac aaagacgatg acgataaagg cggtggtggc    120
tctggtggtg gcggcagcga catccagatg acacagacta tcctcccct gtctgcctct    180 ctgggagaca gagtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttactttt gccaacaggg taatacgctt    420
ccgtacacgt tcggaggggg gaccaagctg gagatcacag gtggcggtgg ctcgggcggt    480
ggtgggtcgg gtggcggcgg atctgaggtg aaactgcagg agtcaggacc tggcctggtg    540
gcgccctcac agagcctgtc cgtcacatgc actgtctcag ggtctcatt acccgactat    600 ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgatt tttgggtgct ggtggtggtt    1020
ggtggagtcc tggcttgcta tagcttgcta gtaacagtgg cctttattat tttctgggtg    1080
aggagtaaga ggagcaggct cctgcacagt gactacatga acatgactcc ccgccgcccc    1140
gggcccaccc gcaagcatta ccagccctat gccccaccac gcgacttcgc agcctatcgc    1200
tccaaacggg gcagaaagaa actcctgtat atattcaaac aaccatttat gagaccagta    1260
caaactactc aagaggaaga tggctgtagc tgccgatttc agaagaaga agaaggagga    1320 tgtgaactga gagtgaagtt cagcaggagc gcagacgccc ccgcgtacca gcagggccag    1380
aaccagctct ataacgagct caatctagga cgaagagagg agtacgatgt tttggacaag    1440
agacgtggcc gggaccctga gatgggggga aagccgagaa ggaagaaccc tcaggaaggc    1500
ctgtacaatg aactgcagaa agataagatg gcggaggcct acagtgagat tgggatgaaa    1560
```

```
ggcgagcgcc ggaggggcaa ggggcacgat ggcctttacc agggtctcag tacagccacc    1620
aaggacacct acgacgccct tcacatgcag gccctgcccc ctcgcggctc tggcgaggga    1680
aggggttccc tgcttacttg cggcgacgtc gaagagaatc ccggtccgat ggccctccca    1740
gtaactgccc tccttttgcc cctcgcactc cttcttcatg ccgctcgccc caactgggtc    1800
aacgtgatta gcgatttgaa gaaaatcgag gaccttatac agtctatgca tattgacgct    1860
acactgtata ctgagagtga tgtacacccg tcctgtaagg taacggccat gaaatgcttt    1920
cttctggagc tccaggtcat cagcttggag tctggggacg caagcatcca cgatacggtt    1980
gaaaacctca tcatccttgc gaacaactct ctctcatcta atggaaacgt tacagagagt    2040
gggtgtaagg agtgcgaaga gttggaagaa aaaaacatca agaatttctc tcaatccttc    2100
gttcacatag tgcaaatgtt cattaacacg tccactacca cacccgcccc gaggccacct    2160
acgccggcac cgactatcgc cagtcaaccc ctctctctgc gccccgaggc ttgccggcct    2220
gcggctggtg gggcggtcca cacccggggc ctggattttg cgtgcgatat atacatctgg    2280
gcacctcttg ccggcacctg cggagtgctg cttctctcac tcgttattac gctgtactgc    2340
taagcggccg cgtcgac                                                   2357
```

<210> SEQ ID NO 66
<211> LENGTH: 773
<212> TYPE: PRT
<213> ORGANISM: Homo sapiens
<220> FEATURE:
<221> NAME/KEY: MISC_FEATURE
<223> OTHER INFORMATION: NK19-4b Protein

<400> SEQUENCE: 66

Met Ala Leu Pro Val Thr Ala Leu Leu Pro Leu Ala Leu Leu Leu
1               5                   10                  15

His Ala Ala Arg Pro Asp Tyr Lys Asp Asp Asp Lys Gly Gly Gly
                20                  25                  30

Gly Ser Gly Gly Gly Gly Ser Asp Ile Gln Met Thr Gln Thr Thr Ser
            35                  40                  45

Ser Leu Ser Ala Ser Leu Gly Asp Arg Val Thr Ile Ser Cys Arg Ala
        50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
                100                 105                 110

Thr Ile Ser Asn Leu Glu Gln Glu Asp Ile Ala Thr Tyr Phe Cys Gln
            115                 120                 125

Gln Gly Asn Thr Leu Pro Tyr Thr Phe Gly Gly Gly Thr Lys Leu Glu
        130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

```
Leu Gly Val Ile Trp Gly Ser Glu Thr Thr Tyr Tyr Asn Ser Ala Leu
210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Thr Ala Ile Tyr Tyr Cys
            245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
            275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Gly Gly Val
            325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
            355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Lys Arg Gly Arg Lys Lys
385                 390                 395                 400

Leu Leu Tyr Ile Phe Lys Gln Pro Phe Met Arg Pro Val Gln Thr Thr
                405                 410                 415

Gln Glu Glu Asp Gly Cys Ser Cys Arg Phe Pro Glu Glu Glu Glu Gly
            420                 425                 430

Gly Cys Glu Leu Arg Val Lys Phe Ser Arg Ser Ala Asp Ala Pro Ala
        435                 440                 445

Tyr Gln Gln Gly Gln Asn Gln Leu Tyr Asn Glu Leu Asn Leu Gly Arg
    450                 455                 460

Arg Glu Glu Tyr Asp Val Leu Asp Lys Arg Arg Gly Arg Asp Pro Glu
465                 470                 475                 480

Met Gly Gly Lys Pro Arg Arg Lys Asn Pro Gln Glu Gly Leu Tyr Asn
                485                 490                 495

Glu Leu Gln Lys Asp Lys Met Ala Glu Ala Tyr Ser Glu Ile Gly Met
            500                 505                 510

Lys Gly Glu Arg Arg Arg Gly Lys Gly His Asp Gly Leu Tyr Gln Gly
        515                 520                 525

Leu Ser Thr Ala Thr Lys Asp Thr Tyr Asp Ala Leu His Met Gln Ala
    530                 535                 540

Leu Pro Pro Arg Gly Ser Gly Glu Gly Arg Gly Ser Leu Leu Thr Cys
545                 550                 555                 560

Gly Asp Val Glu Glu Asn Pro Gly Pro Met Ala Leu Pro Val Thr Ala
                565                 570                 575

Leu Leu Leu Pro Leu Ala Leu Leu Leu His Ala Ala Arg Pro Asn Trp
            580                 585                 590

Val Asn Val Ile Ser Asp Leu Lys Lys Ile Glu Asp Leu Ile Gln Ser
            595                 600                 605

Met His Ile Asp Ala Thr Leu Tyr Thr Glu Ser Asp Val His Pro Ser
    610                 615                 620

Cys Lys Val Thr Ala Met Lys Cys Phe Leu Leu Glu Leu Gln Val Ile
```

```
                    625              630              635              640
        Ser Leu Glu Ser Gly Asp Ala Ser Ile His Asp Thr Val Glu Asn Leu
                        645              650              655

Ile Ile Leu Ala Asn Asn Ser Leu Ser Ser Asn Gly Asn Val Thr Glu
                    660              665              670

Ser Gly Cys Lys Glu Cys Glu Leu Glu Glu Lys Asn Ile Lys Glu
                675              680              685

Phe Leu Gln Ser Phe Val His Ile Val Gln Met Phe Ile Asn Thr Ser
                690              695              700

Thr Thr Thr Pro Ala Pro Arg Pro Pro Thr Pro Ala Pro Thr Ile Ala
        705              710              715              720

Ser Gln Pro Leu Ser Leu Arg Pro Glu Ala Cys Arg Pro Ala Ala Gly
                        725              730              735

Gly Ala Val His Thr Arg Gly Leu Asp Phe Ala Cys Asp Ile Tyr Ile
                    740              745              750

Trp Ala Pro Leu Ala Gly Thr Cys Gly Val Leu Leu Leu Ser Leu Val
                        755              760              765

Ile Thr Leu Tyr Cys
            770

<210> SEQ ID NO 67
<211> LENGTH: 2201
<212> TYPE: DNA
<213> ORGANISM: Homo sapiens
<220> FEATURE:
<221> NAME/KEY: misc_feature
<223> OTHER INFORMATION: NK19-5b DNA

<400> SEQUENCE: 67
ggatccgaat cgccgccac  catggcctta ccagtgaccg ccttgctcct gccgctggcc      60
ttgctgctcc acgccgccag gccggactac aaagacgatg acgataaagg cggtggtggc     120
tctggtggtg gcggcagcga catccagatg acacagacta catcctccct gtctgcctct     180
ctgggagaca gagtcaccat cagttgcagg gcaagtcagg acattagtaa atatttaaat     240
tggtatcagc agaaaccaga tggaactgtt aaactcctga tctaccatac atcaagatta     300
cactcaggag tcccatcaag gttcagtggc agtgggtctg gaacagatta ttctctcacc     360
attagcaacc tggagcaaga agatattgcc acttactttt gccaacaggg taatacgctt     420
ccgtacacgt tcggaggggg gaccaagctg gagatcacag gtggcggtgg ctcgggcggt     480
ggtgggtcgg gtggcggcgg atctgaggtg aaactgcagg agtcaggacc tggcctggtg     540
gcgccctcac agagcctgtc cgtcacatgc actgtctcag gggtctcatt acccgactat     600
ggtgtaagct ggattcgcca gcctccacga aagggtctgg agtggctggg agtaatatgg     660
ggtagtgaaa ccacatacta taattcagct ctcaaatcca gactgaccat catcaaggac     720
aactccaaga gccaagtttt cttaaaaatg aacagtctgc aaactgatga cacagccatt     780
tactactgtg ccaaacatta ttactacggt ggtagctatg ctatggacta ctggggccaa     840
ggaacctcag tcaccgtctc ctcaaccacg acgccagcgc cgcgaccacc aacaccggcg     900
cccaccatcg cgtcgcagcc cctgtccctg cgcccagagg cgtgccggcc agcggcgggg     960
ggcgcagtgc acacgagggg gctggacttc gcctgtgatc atttttttt ctgctgcttc    1020 atcgctgtag ccatgggaat ccgtttcatt attatggtaa cacggaggga ccagaggctg    1080 cccccgatg cccacaagcc ccctggggga ggcagtttcc ggacccccat ccaagaggag    1140
caggccgacg cccactccac cctggccaag atcagagtga agttcagcag gagcgcagac    1200
```

-continued

```
gcccccgcgt accagcaggg ccagaaccag ctctataacg agctcaatct aggacgaaga    1260
gaggagtacg atgttttgga caagagacgt ggccgggacc ctgagatggg gggaaagccg    1320
agaaggaaga accctcagga aggcctgtac aatgaactgc agaaagataa gatggcggag    1380
gcctacagtg agattgggat gaaaggcgag cgccggaggg gcaaggggca cgatggcctt    1440
taccagggtc tcagtacagc caccaaggac acctacgacg cccttcacat gcaggccctg    1500 cccccctcgcg gctctggcga gggaaggggt tccctgctta cttgcggcga cgtcgaagag    1560
aatcccggtc cgatggccct cccagtaact gccctccttt tgcccctcgc actccttctt    1620
catgccgctc gccccaactg ggtcaacgtg attagcgatt tgaagaaaat cgaggacctt    1680
atacagtcta tgcatattga cgctacactg tatactgaga gtgatgtaca cccgtcctgt    1740
aaggtaacgg ccatgaaatg ctttcttctg gagctccagg tcatcagctt ggagtctggg    1800
gacgcaagca tccacgatac ggttgaaaac ctcatcatcc ttgcgaacaa ctctctctca    1860
tctaatggaa acgttacaga gagtgggtgt aaggagtgcg aagagttgga agaaaaaaac    1920
atcaaagaat tcttcaatc cttcgttcac atagtgcaaa tgttcattaa cacgtccact    1980
accacacccg ccccgaggcc acctacgccg gcaccgacta cgccagtca acccctctct    2040 ctgcgccccg aggcttgccg gcctgcggct ggtggggcgg tccacacccg gggcctggat    2100
tttgcgtgcg atatatacat ctgggcacct cttgccggca cctgcggagt gctgcttctc    2160
tcactcgtta ttacgctgta ctgctaagcg gccgcgtcga c                       2201
```

<210> SEQ ID NO 68
<211> LENGTH: 721
<212> TYPE: PRT
<213> ORGANISM: Homo sapiens
<220> FEATURE:
<221> NAME/KEY: MISC_FEATURE
<223> OTHER INFORMATION: NK19-5b Protein

<400> SEQUENCE: 68

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175
```

```
Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
            195                 200                 205

Leu Gly Val Ile Trp Gly Ser Glu Thr Thr Tyr Tyr Asn Ser Ala Leu
            210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
            245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
            275                 280                 285

Pro Pro Thr Pro Ala Pro Thr Ile Ala Ser Gln Pro Leu Ser Leu Arg
            290                 295                 300

Pro Glu Ala Cys Arg Pro Ala Ala Gly Gly Ala Val His Thr Arg Gly
305                 310                 315                 320

Leu Asp Phe Ala Cys Asp Pro Phe Phe Phe Cys Cys Phe Ile Ala Val
            325                 330                 335

Ala Met Gly Ile Arg Phe Ile Ile Met Val Thr Arg Arg Asp Gln Arg
            340                 345                 350

Leu Pro Pro Asp Ala His Lys Pro Gly Gly Gly Ser Phe Arg Thr
            355                 360                 365

Pro Ile Gln Glu Glu Gln Ala Asp Ala His Ser Thr Leu Ala Lys Ile
            370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
            485                 490                 495

Gly Ser Gly Glu Gly Arg Gly Ser Leu Leu Thr Cys Gly Asp Val Glu
            500                 505                 510

Glu Asn Pro Gly Pro Met Ala Leu Pro Val Thr Ala Leu Leu Leu Pro
            515                 520                 525

Leu Ala Leu Leu Leu His Ala Ala Arg Pro Asn Trp Val Asn Val Ile
            530                 535                 540

Ser Asp Leu Lys Lys Ile Glu Asp Leu Ile Gln Ser Met His Ile Asp
545                 550                 555                 560

Ala Thr Leu Tyr Thr Glu Ser Asp Val His Pro Ser Cys Lys Val Thr
            565                 570                 575

Ala Met Lys Cys Phe Leu Leu Glu Leu Gln Val Ile Ser Leu Glu Ser
            580                 585                 590

Gly Asp Ala Ser Ile His Asp Thr Val Glu Asn Leu Ile Ile Leu Ala
```

| | | 595 | | | 600 | | | 605 | | | |
|---|---|---|---|---|---|---|---|---|---|---|---|
| Asn | Asn | Ser | Leu | Ser | Ser | Asn | Gly | Asn | Val | Thr | Glu | Ser | Gly | Cys | Lys |
| | | 610 | | | | | 615 | | | | | 620 | | | |

Glu Cys Glu Glu Leu Glu Glu Lys Asn Ile Lys Glu Phe Leu Gln Ser
625                     630                     635                     640

Phe Val His Ile Val Gln Met Phe Ile Asn Thr Ser Thr Thr Thr Pro
                        645                     650                     655

Ala Pro Arg Pro Pro Thr Pro Ala Pro Thr Ile Ala Ser Gln Pro Leu
            660                     665                     670

Ser Leu Arg Pro Glu Ala Cys Arg Pro Ala Ala Gly Gly Ala Val His
        675                     680                     685

Thr Arg Gly Leu Asp Phe Ala Cys Asp Ile Tyr Ile Trp Ala Pro Leu
    690                     695                     700

Ala Gly Thr Cys Gly Val Leu Leu Leu Ser Leu Val Ile Thr Leu Tyr
705                     710                     715                     720

Cys

<210> SEQ ID NO 69
<211> LENGTH: 1805
<212> TYPE: DNA
<213> ORGANISM: Homo sapiens
<220> FEATURE:
<221> NAME/KEY: misc_feature
<223> OTHER INFORMATION: NK19-6b DNA

<400> SEQUENCE: 69

```
ggatccgaat cgccgccac  catggcctta  ccagtgaccg  ccttgctcct  gccgctggcc      60
ttgctgctcc acgccgccag gccggactac aaagacgatg acgataaagg cggtggtggc     120
tctggtggtg gcggcagcga catccagatg acacagacta tcctccct gtctgcctct        180
ctgggagaca gagtcaccat cagttgcagg gcaagtcagg acattagtaa atatttaaat     240
tggtatcagc agaaaccaga tggaactgtt aaactcctga tctaccatac atcaagatta     300
cactcaggag tcccatcaag gttcagtggc agtgggtctg gaacagatta ttctctcacc     360
attagcaacc tggagcaaga agatattgcc acttacttt gccaacaggg taatacgctt      420
ccgtacacgt tcggagggg gaccaagctg gagatcacaa ccacgacgcc agcgccgcga      480
ccaccaacac cggcgcccac catcgcgtcg cagcccctgt ccctgcgccc agaggcgtgc      540
cggccagcgg cgggggcgc agtgcacacg aggggctgg acttcgcctg tgatatctac       600
atctgggcgc ccttggccgg gacttgtggg gtccttctcc tgtcactggt tatcaccctt     660
tactgccgga gggaccagag gctgccccc gatgcccaca gcccctgg gggaggcagt       720
ttccggaccc ccatccaaga ggagcaggcc gacgcccact ccaccctggc caagatcaga     780
gtgaagttca gcaggagcgc agacgccccc gcgtaccagc agggccagaa ccagctctat     840
aacgagctca atctaggacg aagagaggag tacgatgttt tggacaagag acgtggccgg     900
gaccctgaga tgggggaaa gccgagaagg aagaaccctc aggaaggcct gtacaatgaa     960
ctgcagaaag ataagatggc ggaggcctac agtgagattg gatgaaagg cgagcgccgg    1020
agggcaagg ggcacgatgg cctttaccag ggtctcagta cagccaccaa ggacacctac    1080
gacgccttc acatgcaggc cctgcccct cgcggctctg gcgagggaag gggttccctg     1140
cttacttgcg gcgacgtcga agagaatccc ggtccgatgg ccctcccagt aactgccctc    1200
cttttgcccc tcgcactcct tcttcatgcc gctcgcccca actgggtcaa cgtgattagc    1260
gatttgaaga aaatcgagga ccttatacag tctatgcata ttgacgctac actgtatact    1320
```

-continued

```
gagagtgatg tacacccgtc ctgtaaggta acggccatga aatgctttct tctggagctc    1380
caggtcatca gcttggagtc tggggacgca agcatccacg atacggttga aaacctcatc    1440
atccttgcga caactctct ctcatctaat ggaaacgtta cagagagtgg gtgtaaggag     1500
tgcgaagagt tggaagaaaa aaacatcaaa gaatttcttc aatccttcgt tcacatagtg    1560
caaatgttca ttaacacgtc cactaccaca cccgccccga ggccacctac gccggcaccg    1620
actatcgcca gtcaacccct ctctctgcgc cccgaggctt gccggcctgc ggctggtggg    1680
gcggtccaca cccggggcct ggattttgcg tgcgatatat acatctgggc acctcttgcc    1740
ggcacctgcg gagtgctgct tctctcactc gttattacgc tgtactgcta agcggccgcg    1800
tcgac                                                                1805
```

<210> SEQ ID NO 70
<211> LENGTH: 589
<212> TYPE: PRT
<213> ORGANISM: Homo sapiens
<220> FEATURE:
<221> NAME/KEY: MISC_FEATURE
<223> OTHER INFORMATION: NK19-6b Protein

<400> SEQUENCE: 70

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Arg Arg Asp Gln Arg Leu Pro Pro Asp
    210                 215                 220

Ala His Lys Pro Pro Gly Gly Gly Ser Phe Arg Thr Pro Ile Gln Glu
225                 230                 235                 240

Glu Gln Ala Asp Ala His Ser Thr Leu Ala Lys Ile Arg Val Lys Phe
                245                 250                 255

Ser Arg Ser Ala Asp Ala Pro Ala Tyr Gln Gln Gly Gln Asn Gln Leu
```

```
                    260                 265                 270
Tyr Asn Glu Leu Asn Leu Gly Arg Arg Glu Glu Tyr Asp Val Leu Asp
            275                 280                 285
Lys Arg Arg Gly Arg Asp Pro Glu Met Gly Gly Lys Pro Arg Arg Lys
        290                 295                 300
Asn Pro Gln Glu Gly Leu Tyr Asn Glu Leu Gln Lys Asp Lys Met Ala
305                 310                 315                 320
Glu Ala Tyr Ser Glu Ile Gly Met Lys Gly Glu Arg Arg Arg Gly Lys
                325                 330                 335
Gly His Asp Gly Leu Tyr Gln Gly Leu Ser Thr Ala Thr Lys Asp Thr
            340                 345                 350
Tyr Asp Ala Leu His Met Gln Ala Leu Pro Pro Arg Gly Ser Gly Glu
        355                 360                 365
Gly Arg Gly Ser Leu Leu Thr Cys Gly Asp Val Glu Glu Asn Pro Gly
    370                 375                 380
Pro Met Ala Leu Pro Val Thr Ala Leu Leu Leu Pro Leu Ala Leu Leu
385                 390                 395                 400
Leu His Ala Ala Arg Pro Asn Trp Val Asn Val Ile Ser Asp Leu Lys
                405                 410                 415
Lys Ile Glu Asp Leu Ile Gln Ser Met His Ile Asp Ala Thr Leu Tyr
            420                 425                 430
Thr Glu Ser Asp Val His Pro Ser Cys Lys Val Thr Ala Met Lys Cys
        435                 440                 445
Phe Leu Leu Glu Leu Gln Val Ile Ser Leu Glu Ser Gly Asp Ala Ser
    450                 455                 460
Ile His Asp Thr Val Glu Asn Leu Ile Ile Leu Ala Asn Asn Ser Leu
465                 470                 475                 480
Ser Ser Asn Gly Asn Val Thr Glu Ser Gly Cys Lys Glu Cys Glu Glu
                485                 490                 495
Leu Glu Glu Lys Asn Ile Lys Glu Phe Leu Gln Ser Phe Val His Ile
            500                 505                 510
Val Gln Met Phe Ile Asn Thr Ser Thr Thr Thr Pro Ala Pro Arg Pro
        515                 520                 525
Pro Thr Pro Ala Pro Thr Ile Ala Ser Gln Pro Leu Ser Leu Arg Pro
    530                 535                 540
Glu Ala Cys Arg Pro Ala Ala Gly Gly Ala Val His Thr Arg Gly Leu
545                 550                 555                 560
Asp Phe Ala Cys Asp Ile Tyr Ile Trp Ala Pro Leu Ala Gly Thr Cys
                565                 570                 575
Gly Val Leu Leu Leu Ser Leu Val Ile Thr Leu Tyr Cys
            580                 585

<210> SEQ ID NO 71
<211> LENGTH: 3347
<212> TYPE: DNA
<213> ORGANISM: Homo sapiens
<220> FEATURE:
<221> NAME/KEY: misc_feature
<223> OTHER INFORMATION: NK19-7b DNA

<400> SEQUENCE: 71
ggatccgaat cgccgccac catggcctta ccagtgaccg ccttgctcct gccgctggcc    60
ttgctgctcc acgccgccag gccggactac aaagacgatg acgataaagg cggtggtggc   120
tctggtggtg gcggcagcga catccagatg acacagacta catcctccct gtctgcctct   180
```

```
ctgggagaca gagtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttactttt gccaacaggg taatacgctt    420
ccgtacacgt tcggagggggg gaccaagctg gagatcacag gtggcggtgg ctcgggcggt    480
ggtgggtcgg gtggcggcgg atctgaggtg aaactgcagg agtcaggacc tggcctggtg    540
gcgccctcac agagcctgtc cgtcacatgc actgtctcag gggtctcatt acccgactat    600
ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg    1020
gccgggactt gtggggtcct tctcctgtca ctggttatca ccctttactg ccggagggac    1080
cagaggctgc cccccgatgc ccacaagccc ctgggggag gcagtttccg gacccccatc    1140
caagaggagc aggccgacgc ccactccacc ctggccaaga tcagagtgaa gttcagcagg    1200
agcgcagacg cccccgcgta ccagcagggc cagaaccagc tctataacga gctcaatcta    1260
ggacgaagag aggagtacga tgttttggac aagagacgtg gccgggaccc tgagatgggg    1320
ggaaagccga gaaggaagaa ccctcaggaa ggcctgtaca atgaactgca gaaagataag    1380
atggcggagg cctacagtga gattgggatg aaaggcgagc gccggagggg caaggggcac    1440
gatggccttt accagggtct cagtacagcc accaaggaca cctacgacgc ccttcacatg    1500
caggccctgc cccctcgcgg ctctggcgag ggaaggggtt ccctgcttac ttgcggcgac    1560
gtcgaagaga atcccggtcc gatggccctc ccagtaactg ccctcctttt gcccctcgca    1620
ctccttcttc atgccgctcg ccccaactgg gtcaacgtga ttagcgattt gaagaaaatc    1680
gaggacctta tacagtctat gcatattgac gctacactgt atactgagag tgatgtacac    1740
ccgtcctgta aggtaacggc catgaaatgc tttcttctgg agctccaggt catcagcttg    1800
gagtctgggg acgcaagcat ccacgatacg gttgaaaacc tcatcatcct tgcgaacaac    1860
tctctctcat ctaatggaaa cgttacgag agtgggtgta aggagtgcga agagttggaa    1920
gaaaaaaaca tcaaagaatt tcttcaatcc ttcgttcaca tagtgcaaat gttcattaac    1980
acgtccacta ccacacccgc cccgaggcca cctacgccgg caccgactat cgccagtcaa    2040
cccctctctc tgcgccccga ggcttgccgg cctgcggctg gtgggcggt ccacacccgg    2100 ggcctggatt ttgcgtgcga tatatacatc tgggcacctc ttgccggcac ctgcggagtg    2160
ctgcttctct cactcgttat tacgctgtac tgcggcagcg cgccacaaa cttctctctg    2220 ctaaagcaag caggtgatgt tgaagaaaac cccgggccta tgcttctcct ggtgacaagc    2280
cttctgctct gtgagttacc acacccagca ttcctcctga tcccacgcaa agtgtgtaac    2340
ggaataggta ttggtgaatt taaagactca ctctccataa atgctacgaa tattaaacac    2400
ttcaaaaact gcacctccat cagtggcgat ctccacatct gccgtggc attagggt    2460 gactccttca cacatactcc tcctctggat ccacaggaac tggatattct gaaaccgta    2520 aaggaaatca cagggttttt gctgattcag gcttggcctg aaaacaggac ggacctccat    2580
```

```
gcctttgaga acctagaaat catacgcggc aggaccaagc aacatggtca gttttctctt     2640
gcagtcgtca gcctgaacat aacatccttg ggattacgct ccctcaagga gataagtgat     2700
ggagatgtga taatttcagg aaacaaaaat ttgtgctatg caaatacaat aaactggaaa     2760
aaactgtttg ggacctccgg tcagaaaacc aaaattataa gcaacagagg tgaaaacagc     2820
tgcaaggcca caggccaggt ctgccatgcc ttgtgctccc ccgagggctg ctggggcccg     2880
gagcccaggg actgcgtctc ttgccggaat gtcagccgag cagggaatg cgtggacaag      2940 tgcaaccttc tggagggtga gccaagggag tttgtggaga actctgagtg catacagtgc     3000
cacccagagt gcctgcctca ggccatgaac atcacctgca caggacgggg accagacaac     3060
tgtatccagt gtgcccacta cattgacggc ccccactgcg tcaagacctg cccggcagga     3120
gtcatgggag aaaacaacac cctggtctgg aagtacgcag acgccggcca tgtgtgccac     3180
ctgtgccatc caaactgcac ctacggatgc actgggccag tcttgaagg ctgtccaacg      3240 aatgggccta agatcccgtc catcgccact gggatggtgg gggccctcct cttgctgctg     3300
gtggtggccc tggggatcgg cctcttcatg tgagcggccg cgtcgac                   3347
```

<210> SEQ ID NO 72
<211> LENGTH: 1103
<212> TYPE: PRT
<213> ORGANISM: Homo sapiens
<220> FEATURE:
<221> NAME/KEY: MISC_FEATURE
<223> OTHER INFORMATION: NK19-7b Protein

<400> SEQUENCE: 72

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220
```

```
Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
            405                 410                 415

Glu Glu Tyr Asp Val Leu Asp Lys Arg Arg Gly Arg Asp Pro Glu Met
        420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
        450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
        530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
        610                 615                 620

Gly Cys Lys Glu Cys Glu Glu Leu Glu Glu Lys Asn Ile Lys Glu Phe
625                 630                 635                 640
```

```
Leu Gln Ser Phe Val His Ile Val Gln Met Phe Ile Asn Thr Ser Thr
                    645                 650                 655

Thr Thr Pro Ala Pro Arg Pro Pro Thr Pro Ala Pro Thr Ile Ala Ser
        660                 665                 670

Gln Pro Leu Ser Leu Arg Pro Glu Ala Cys Arg Pro Ala Ala Gly Gly
            675                 680                 685

Ala Val His Thr Arg Gly Leu Asp Phe Ala Cys Asp Ile Tyr Ile Trp
690                 695                 700

Ala Pro Leu Ala Gly Thr Cys Gly Val Leu Leu Ser Leu Val Ile
705                 710                 715                 720

Thr Leu Tyr Cys Gly Ser Gly Ala Thr Asn Phe Ser Leu Leu Lys Gln
            725                 730                 735

Ala Gly Asp Val Glu Glu Asn Pro Gly Pro Met Leu Leu Leu Val Thr
                740                 745                 750

Ser Leu Leu Leu Cys Glu Leu Pro His Pro Ala Phe Leu Leu Ile Pro
            755                 760                 765

Arg Lys Val Cys Asn Gly Ile Gly Ile Gly Glu Phe Lys Asp Ser Leu
770                 775                 780

Ser Ile Asn Ala Thr Asn Ile Lys His Phe Lys Asn Cys Thr Ser Ile
785                 790                 795                 800

Ser Gly Asp Leu His Ile Leu Pro Val Ala Phe Arg Gly Asp Ser Phe
                805                 810                 815

Thr His Thr Pro Pro Leu Asp Pro Gln Glu Leu Asp Ile Leu Lys Thr
            820                 825                 830

Val Lys Glu Ile Thr Gly Phe Leu Leu Ile Gln Ala Trp Pro Glu Asn
        835                 840                 845

Arg Thr Asp Leu His Ala Phe Glu Asn Leu Glu Ile Ile Arg Gly Arg
    850                 855                 860

Thr Lys Gln His Gly Gln Phe Ser Leu Ala Val Val Ser Leu Asn Ile
865                 870                 875                 880

Thr Ser Leu Gly Leu Arg Ser Leu Lys Glu Ile Ser Asp Gly Asp Val
                885                 890                 895

Ile Ile Ser Gly Asn Lys Asn Leu Cys Tyr Ala Asn Thr Ile Asn Trp
            900                 905                 910

Lys Lys Leu Phe Gly Thr Ser Gly Gln Lys Thr Lys Ile Ile Ser Asn
        915                 920                 925

Arg Gly Glu Asn Ser Cys Lys Ala Thr Gly Gln Val Cys His Ala Leu
    930                 935                 940

Cys Ser Pro Glu Gly Cys Trp Gly Pro Glu Pro Arg Asp Cys Val Ser
945                 950                 955                 960

Cys Arg Asn Val Ser Arg Gly Arg Glu Cys Val Asp Lys Cys Asn Leu
                965                 970                 975

Leu Glu Gly Glu Pro Arg Glu Phe Val Glu Asn Ser Glu Cys Ile Gln
            980                 985                 990

Cys His Pro Glu Cys Leu Pro Gln Ala Met Asn Ile Thr Cys Thr Gly
        995                 1000                1005

Arg Gly Pro Asp Asn Cys Ile Gln Cys Ala His Tyr Ile Asp Gly
    1010                1015                1020

Pro His Cys Val Lys Thr Cys Pro Ala Gly Val Met Gly Glu Asn
    1025                1030                1035

Asn Thr Leu Val Trp Lys Tyr Ala Asp Ala Gly His Val Cys His
    1040                1045                1050

Leu Cys His Pro Asn Cys Thr Tyr Gly Cys Thr Gly Pro Gly Leu
```

```
                    1055                1060                1065
Glu Gly Cys Pro Thr Asn Gly Pro Lys Ile Pro Ser Ile Ala Thr
        1070                1075                1080

Gly Met Val Gly Ala Leu Leu Leu Leu Leu Val Val Ala Leu Gly
        1085                1090                1095

Ile Gly Leu Phe Met
        1100

<210> SEQ ID NO 73
<211> LENGTH: 1844
<212> TYPE: DNA
<213> ORGANISM: Homo sapiens
<220> FEATURE:
<221> NAME/KEY: misc_feature
<223> OTHER INFORMATION: NK19-8b DNA

<400> SEQUENCE: 73
ggatccgaat cgccgccac catggcctta ccagtgaccg ccttgctcct gccgctggcc      60
ttgctgctcc acgccgccag gccggactac aaagacgatg acgataaagg cggtggtggc     120
tctggtggtg gcggcagcga ggtgaaactg caggagtcag gacctggcct ggtggcgccc     180
tcacagagcc tgtccgtcac atgcactgtc tcagggggtct cattacccga ctatggtgta    240
agctggattc gccagcctcc acgaaagggt ctggagtggc tgggagtaat atggggtagt     300
gaaaccacat actataattc agctctcaaa tccagactga ccatcatcaa ggacaactcc     360
aagagccaag ttttcttaaa aatgaacagt ctgcaaactg atgacacagc catttactac     420
tgtgccaaac attattacta cggtggtagc tatgctatgg actactgggg ccaaggaacc     480
tcagtcaccg tctcctcaac cacgacgcca gcgccgcgac caccaacacc ggcgcccacc     540
atcgcgtcgc agcccctgtc cctgcgccca gaggcgtgcc ggccagcggc gggggggcgca   600 gtgcacacga gggggctgga cttcgcctgt gatatctaca tctgggcgcc cttggccggg    660
acttgtgggg tccttctcct gtcactggtt atcacccttt actgccggag ggaccagagg    720
ctgccccccg atgcccacaa gccccctggg ggaggcagtt tccggacccc catccaagag     780
gagcaggccg acgcccactc caccctggcc aagatcagag tgaagttcag caggagcgca     840
gacgcccccg cgtaccagca gggccagaac cagctctata cgagctcaa tctaggacga      900 agagaggagt acgatgtttt ggacaagaga cgtggccggg accctgagat gggggggaaag    960 ccgagaagga agaaccctca ggaaggcctg tacaatgaac tgcagaaaga taagatggcg    1020
gaggcctaca gtgagattgg gatgaaaggc gagcgccgga ggggcaaggg gcacgatggc    1080
ctttaccagg gtctcagtac agccaccaag gacacctacg acgcccttca catgcaggcc    1140 ctgcccccctc gcggctctgg cgagggaagg ggttccctgc ttacttgcgg cgacgtcgaa    1200
gagaatcccg gtccgatggc cctcccagta actgccctcc ttttgcccct cgcactcctt    1260
cttcatgccg ctcgcccaa ctgggtcaac gtgattagcg atttgaagaa aatcgaggac     1320
cttatacagt ctatgcatat tgacgctaca ctgtatactg agagtgatgt acacccgtcc    1380
tgtaaggtaa cggccatgaa atgctttctt ctggagctcc aggtcatcag cttggagtct   1440
ggggacgcaa gcatccacga tacgttgaa aacctcatca tccttgcgaa caactctctc    1500
tcatctaatg gaaacgttac agagagtggg tgtaaggagt gcgaagagtt ggaagaaaaa   1560
aacatcaaag aatttcttca atccttcgtt cacatagtgc aaatgttcat taacacgtcc   1620
actaccacac ccgccccgag gccacctacg ccggcaccga ctatcgccag tcaacccctc    1680
tctctgcgcc ccgaggcttg ccggcctgcg gctggtgggg cggtccacac ccggggcctg    1740
```

```
gattttgcgt gcgatatata catctgggca cctcttgccg gcacctgcgg agtgctgctt    1800
ctctcactcg ttattacgct gtactgctaa gcggccgcgt cgac                    1844
```

<210> SEQ ID NO 74
<211> LENGTH: 602
<212> TYPE: PRT
<213> ORGANISM: Homo sapiens
<220> FEATURE:
<221> NAME/KEY: MISC_FEATURE
<223> OTHER INFORMATION: NK19-8b Protein

<400> SEQUENCE: 74

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Gly Ser Gly Gly Gly Gly Ser Glu Val Lys Leu Gln Glu Ser Gly Pro
        35                  40                  45

Gly Leu Val Ala Pro Ser Gln Ser Leu Ser Val Thr Cys Thr Val Ser
    50                  55                  60

Gly Val Ser Leu Pro Asp Tyr Gly Val Ser Trp Ile Arg Gln Pro Pro
65                  70                  75                  80

Arg Lys Gly Leu Glu Trp Leu Gly Val Ile Trp Gly Ser Glu Thr Thr
                85                  90                  95

Tyr Tyr Asn Ser Ala Leu Lys Ser Arg Leu Thr Ile Ile Lys Asp Asn
            100                 105                 110

Ser Lys Ser Gln Val Phe Leu Lys Met Asn Ser Leu Gln Thr Asp Asp
        115                 120                 125

Thr Ala Ile Tyr Tyr Cys Ala Lys His Tyr Tyr Gly Gly Ser Tyr
    130                 135                 140

Ala Met Asp Tyr Trp Gly Gln Gly Thr Ser Val Thr Val Ser Ser Thr
145                 150                 155                 160

Thr Thr Pro Ala Pro Arg Pro Pro Thr Pro Ala Pro Thr Ile Ala Ser
                165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Ile Tyr Ile Trp
        195                 200                 205

Ala Pro Leu Ala Gly Thr Cys Gly Val Leu Leu Leu Ser Leu Val Ile
    210                 215                 220

Thr Leu Tyr Cys Arg Arg Asp Gln Arg Leu Pro Pro Asp Ala His Lys
225                 230                 235                 240

Pro Pro Gly Gly Gly Ser Phe Arg Thr Pro Ile Gln Glu Glu Gln Ala
                245                 250                 255

Asp Ala His Ser Thr Leu Ala Lys Ile Arg Val Lys Phe Ser Arg Ser
            260                 265                 270

Ala Asp Ala Pro Ala Tyr Gln Gln Gly Gln Asn Gln Leu Tyr Asn Glu
        275                 280                 285

Leu Asn Leu Gly Arg Arg Glu Glu Tyr Asp Val Leu Asp Lys Arg Arg
    290                 295                 300

Gly Arg Asp Pro Glu Met Gly Gly Lys Pro Arg Arg Lys Asn Pro Gln
305                 310                 315                 320

Glu Gly Leu Tyr Asn Glu Leu Gln Lys Asp Lys Met Ala Glu Ala Tyr
                325                 330                 335
```

| | | | | | | | | | | |
|---|---|---|---|---|---|---|---|---|---|---|
|Ser|Glu|Ile|Gly|Met|Lys|Gly|Glu|Arg|Arg|Gly|Lys|Gly|His|Asp|
| | | |340| | | |345| | | |350| | | |

Ser Glu Ile Gly Met Lys Gly Glu Arg Arg Gly Lys Gly His Asp
                340                 345                 350

Gly Leu Tyr Gln Gly Leu Ser Thr Ala Thr Lys Asp Thr Tyr Asp Ala
            355                 360                 365

Leu His Met Gln Ala Leu Pro Pro Arg Gly Ser Gly Glu Gly Arg Gly
    370                 375                 380

Ser Leu Leu Thr Cys Gly Asp Val Glu Glu Asn Pro Gly Pro Met Ala
385                 390                 395                 400

Leu Pro Val Thr Ala Leu Leu Leu Pro Leu Ala Leu Leu Leu His Ala
                405                 410                 415

Ala Arg Pro Asn Trp Val Asn Val Ile Ser Asp Leu Lys Lys Ile Glu
            420                 425                 430

Asp Leu Ile Gln Ser Met His Ile Asp Ala Thr Leu Tyr Thr Glu Ser
    435                 440                 445

Asp Val His Pro Ser Cys Lys Val Thr Ala Met Lys Cys Phe Leu Leu
450                 455                 460

Glu Leu Gln Val Ile Ser Leu Glu Ser Gly Asp Ala Ser Ile His Asp
465                 470                 475                 480

Thr Val Glu Asn Leu Ile Ile Leu Ala Asn Asn Ser Leu Ser Ser Asn
                485                 490                 495

Gly Asn Val Thr Glu Ser Gly Cys Lys Glu Cys Glu Glu Leu Glu Glu
            500                 505                 510

Lys Asn Ile Lys Glu Phe Leu Gln Ser Phe Val His Ile Val Gln Met
    515                 520                 525

Phe Ile Asn Thr Ser Thr Thr Thr Pro Ala Pro Arg Pro Pro Thr Pro
530                 535                 540

Ala Pro Thr Ile Ala Ser Gln Pro Leu Ser Leu Arg Pro Glu Ala Cys
545                 550                 555                 560

Arg Pro Ala Ala Gly Gly Ala Val His Thr Arg Gly Leu Asp Phe Ala
                565                 570                 575

Cys Asp Ile Tyr Ile Trp Ala Pro Leu Ala Gly Thr Cys Gly Val Leu
            580                 585                 590

Leu Leu Ser Leu Val Ile Thr Leu Tyr Cys
    595                 600

<210> SEQ ID NO 75
<211> LENGTH: 2243
<212> TYPE: DNA
<213> ORGANISM: Homo sapiens
<220> FEATURE:
<221> NAME/KEY: misc_feature
<223> OTHER INFORMATION: NK19-9b DNA

<400> SEQUENCE: 75

```
ggatccgaat cgccgccac catggcctta ccagtgaccg ccttgctcct gccgctggcc      60
ttgctgctcc acgccgccag gccggactac aaagacgatg acgataaagg cggtggtggc    120
tctggtggtg gcggcagcga catccagatg acacagacta catcctccct gtctgcctct    180
ctgggagaca gagtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttacttt gccaacaggg taatacgctt    420
ccgtacacgt tcggaggggg gaccaagctg gagatcacag gtggcggtgg ctcgggcggt    480
ggtgggtcgg gtggcggcgg atctgaggtg aaactgcagg agtcaggacc tggcctggtg    540
```

```
gcgccctcac agagcctgtc cgtcacatgc actgtctcag gggtctcatt acccgactat    600
ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtggggtcct tctcctgtca ctggttatca ccctttactg ccaacgaagg   1080
aaatatagat caaacaaagg agaaagtcct gtggagcctg cagagccttg tcgttacagc   1140
tgccccaggg aggaggaggg cagcaccatc cccatccagg aggattaccg aaaaccggag   1200
cctgcctgct cccccagagt gaagttcagc aggagcgcag acgcccccgc gtaccagcag   1260
ggccagaacc agctctataa cgagctcaat ctaggacgaa gagaggagta cgatgttttg   1320
gacaagagac gtggccggga ccctgagatg ggggaaaagc cgagaaggaa gaaccctcag   1380
gaaggcctgt acaatgaact gcagaaagat aagatggcgg aggcctacag tgagattggg   1440
atgaaaggcg agcgccggag gggcaagggg cacgatggcc tttaccaggg tctcagtaca   1500
gccaccaagg acacctacga cgcccttcac atgcaggccc tgccccctcg cggctctggc   1560
gagggaaggg gttccctgct tacttgcggc gacgtcgaag agaatcccgg tccgatggcc   1620
ctcccagtaa ctgccctcct tttgcccctc gcactccttc ttcatgccgc tcgccccaac   1680
tgggtcaacg tgattagcga tttgaagaaa atcgaggacc ttatacagtc tatgcatatt   1740
gacgctacac tgtatactga gagtgatgta caccccgtcct gtaaggtaac ggccatgaaa   1800
tgctttcttc tggagctcca ggtcatcagc ttggagtctg gggacgcaag catccacgat   1860
acggttgaaa acctcatcat ccttgcgaac aactctctct catctaatgg aaacgttaca   1920
gagagtgggt gtaaggagtg cgaagagttg gaagaaaaaa acatcaaaga atttcttcaa   1980
tccttcgttc acatagtgca aatgttcatt aacacgtcca ctaccacacc cgccccgagg   2040
ccacctacgc cggcaccgac tatcgccagt caacccctct ctctgcgccc cgaggcttgc   2100
cggcctgcgg ctggtgggc ggtccacacc cggggcctgg attttgcgtg cgatatatac   2160
atctgggcac ctcttgccgg cacctgcgga gtgctgcttc tctcactcgt tattacgctg   2220
tactgctaag cggccgcgtc gac                                           2243
```

<210> SEQ ID NO 76
<211> LENGTH: 735
<212> TYPE: PRT
<213> ORGANISM: Homo sapiens
<220> FEATURE:
<221> NAME/KEY: MISC_FEATURE
<223> OTHER INFORMATION: NK19-9b Protein

<400> SEQUENCE: 76

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
                20                  25                  30

Gly Ser Gly Gly Gly Gly Ser Asp Ile Gln Met Thr Gln Thr Thr Ser
            35                  40                  45

-continued

```
Ser Leu Ser Ala Ser Leu Gly Asp Arg Val Thr Ile Ser Cys Arg Ala
 50                  55                  60

Ser Gln Asp Ile Ser Lys Tyr Leu Asn Trp Tyr Gln Gln Lys Pro Asp
 65                  70                  75                  80

Gly Thr Val Lys Leu Leu Ile Tyr His Thr Ser Arg Leu His Ser Gly
                 85                  90                  95

Val Pro Ser Arg Phe Ser Gly Ser Gly Ser Gly Thr Asp Tyr Ser Leu
                100                 105                 110

Thr Ile Ser Asn Leu Glu Gln Glu Asp Ile Ala Thr Tyr Phe Cys Gln
            115                 120                 125

Gln Gly Asn Thr Leu Pro Tyr Thr Phe Gly Gly Gly Thr Lys Leu Glu
        130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Gln Arg
            340                 345                 350

Arg Lys Tyr Arg Ser Asn Lys Gly Glu Ser Pro Val Glu Pro Ala Glu
        355                 360                 365

Pro Cys Arg Tyr Ser Cys Pro Arg Glu Glu Glu Gly Ser Thr Ile Pro
    370                 375                 380

Ile Gln Glu Asp Tyr Arg Lys Pro Glu Pro Ala Cys Ser Pro Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
```

```
                    465                 470                 475                 480
            Gly Lys Gly His Asp Gly Leu Tyr Gln Gly Leu Ser Thr Ala Thr Lys
                            485                 490                 495

Asp Thr Tyr Asp Ala Leu His Met Gln Ala Leu Pro Pro Arg Gly Ser
                        500                 505                 510

Gly Glu Gly Arg Gly Ser Leu Leu Thr Cys Gly Asp Val Glu Glu Asn
                        515                 520                 525

Pro Gly Pro Met Ala Leu Pro Val Thr Ala Leu Leu Leu Pro Leu Ala
                        530                 535                 540

Leu Leu Leu His Ala Ala Arg Pro Asn Trp Val Asn Val Ile Ser Asp
            545                 550                 555                 560

Leu Lys Lys Ile Glu Asp Leu Ile Gln Ser Met His Ile Asp Ala Thr
                            565                 570                 575

Leu Tyr Thr Glu Ser Asp Val His Pro Ser Cys Lys Val Thr Ala Met
                        580                 585                 590

Lys Cys Phe Leu Leu Glu Leu Gln Val Ile Ser Leu Glu Ser Gly Asp
                        595                 600                 605

Ala Ser Ile His Asp Thr Val Glu Asn Leu Ile Ile Leu Ala Asn Asn
                        610                 615                 620

Ser Leu Ser Ser Asn Gly Asn Val Thr Glu Ser Gly Cys Lys Glu Cys
            625                 630                 635                 640

Glu Glu Leu Glu Glu Lys Asn Ile Lys Glu Phe Leu Gln Ser Phe Val
                            645                 650                 655

His Ile Val Gln Met Phe Ile Asn Thr Ser Thr Thr Thr Pro Ala Pro
                        660                 665                 670

Arg Pro Pro Thr Pro Ala Pro Thr Ile Ala Ser Gln Pro Leu Ser Leu
                        675                 680                 685

Arg Pro Glu Ala Cys Arg Pro Ala Ala Gly Gly Ala Val His Thr Arg
                        690                 695                 700

Gly Leu Asp Phe Ala Cys Asp Ile Tyr Ile Trp Ala Pro Leu Ala Gly
            705                 710                 715                 720

Thr Cys Gly Val Leu Leu Leu Ser Leu Val Ile Thr Leu Tyr Cys
                            725                 730                 735

<210> SEQ ID NO 77
<211> LENGTH: 2150
<212> TYPE: DNA
<213> ORGANISM: Homo sapiens
<220> FEATURE:
<221> NAME/KEY: misc_feature
<223> OTHER INFORMATION: NK19-10b DNA

<400> SEQUENCE: 77
ggatccgaat cgccgccac catggcctta ccagtgaccg ccttgctcct gccgctggcc      60
ttgctgctcc acgccgccag gccggactac aaagacgatg acgataaagg cggtggtggc     120
tctggtggtg gcggcagcga catccagatg acacagacta catcctccct gtctgcctct     180
ctgggagaca gagtcaccat cagttgcagg gcaagtcagg acattagtaa atatttaaat     240
tggtatcagc agaaaccaga tggaactgtt aaactcctga tctaccatac atcaagatta     300
cactcaggag tcccatcaag gttcagtggc agtgggtctg gaacagatta ttctctcacc     360
attagcaacc tggagcaaga agatattgcc acttactttt gccaacaggg taatacgctt     420
ccgtacacgt tcgagggggg gaccaagctg gagatcacag gtggcggtgg ctcgggcggt     480
ggtgggtcgg gtggcggcgg atctgaggtg aaactgcagg agtcaggacc tggcctggtg     540
```

| | |
|---|---|
| gcgccctcac agagcctgtc cgtcacatgc actgtctcag gggtctcatt acccgactat | 600 |
| ggtgtaagct ggattcgcca gcctccacga aagggtctgg agtggctggg agtaatatgg | 660 |
| ggtagtgaaa ccacatacta taattcagct ctcaaatcca gactgaccat catcaaggac | 720 |
| aactccaaga gccaagtttt cttaaaaatg aacagtctgc aaactgatga cacagccatt | 780 |
| tactactgtg ccaaacatta ttactacggt ggtagctatg ctatggacta ctggggccaa | 840 |
| ggaacctcag tcaccgtctc ctcaaccacg acgccagcgc cgcgaccacc aacaccggcg | 900 |
| cccaccatcg cgtcgcagcc cctgtccctg cgcccagagg cgtgccggcc agcggcgggg | 960 |
| ggcgcagtgc acacgagggg gctggacttc gcctgtgata tctacatctg ggcgcccttg | 1020 |
| gccgggactt gtggggtcct tctcctgtca ctggttatca ccctttactg catgccggag | 1080 |
| gagggttcgg gctgctcggt gcggcgcagg ccctatgggt gcagagtgaa gttcagcagg | 1140 |
| agcgcagacg cccccgcgta ccagcagggc cagaaccagc tctataacga gctcaatcta | 1200 |
| ggacgaagag aggagtacga tgttttggac aagagacgtg gccgggaccc tgagatgggg | 1260 |
| ggaaagccga aaggaagaa ccctcaggaa ggcctgtaca tgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc cccctcgcgg ctctggcgag ggaaggggtt ccctgcttac ttgcggcgac | 1500 |
| gtcgaagaga atcccggtcc gatggccctc ccagtaactg ccctccttt gcccctcgca | 1560 |
| ctccttcttc atgccgctcg ccccaactgg gtcaacgtga ttagcgattt gaagaaaatc | 1620 |
| gaggacctta tacagtctat gcatattgac gctacactgt atactgagag tgatgtacac | 1680 |
| ccgtcctgta aggtaacggc catgaaatgc tttcttctgg agctccaggt catcagcttg | 1740 |
| gagtctgggg acgcaagcat ccacgatacg gttgaaaacc tcatcatcct tgcgaacaac | 1800 |
| tctctctcat ctaatggaaa cgttacagag agtgggtgta aggagtgcga agagttggaa | 1860 |
| gaaaaaaaca tcaaagaatt tcttcaatcc ttcgttcaca tagtgcaaat gttcattaac | 1920 |
| acgtccacta ccacacccgc cccgaggcca cctacgccgg caccgactat cgccagtcaa | 1980 |
| cccctctctc tgcgccccga ggcttgccgg cctcgggctg gtggggcggt ccacacccgg | 2040 |
| ggcctggatt ttgcgtgcga tatatacatc tgggcacctc ttgccggcac ctgcggagtg | 2100 |
| ctgcttctct cactcgttat tacgctgtac tgctaagcgg ccgcgtcgac | 2150 |

<210> SEQ ID NO 78
<211> LENGTH: 704
<212> TYPE: PRT
<213> ORGANISM: Homo sapiens
<220> FEATURE:
<221> NAME/KEY: MISC_FEATURE
<223> OTHER INFORMATION: NK19-10b Protein

<400> SEQUENCE: 78

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
                20                  25                  30

Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80
```

```
Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Met Pro
            340                 345                 350

Glu Glu Gly Ser Gly Cys Ser Val Arg Arg Arg Pro Tyr Gly Cys Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg Gly
465                 470                 475                 480

Ser Gly Glu Gly Arg Gly Ser Leu Leu Thr Cys Gly Asp Val Glu Glu
                485                 490                 495
```

```
Asn Pro Gly Pro Met Ala Leu Pro Val Thr Ala Leu Leu Pro Leu
            500                 505                 510

Ala Leu Leu Leu His Ala Ala Arg Pro Asn Trp Val Asn Val Ile Ser
        515                 520                 525

Asp Leu Lys Lys Ile Glu Asp Leu Ile Gln Ser Met His Ile Asp Ala
        530                 535                 540

Thr Leu Tyr Thr Glu Ser Asp Val His Pro Ser Cys Lys Val Thr Ala
545                 550                 555                 560

Met Lys Cys Phe Leu Glu Leu Gln Val Ile Ser Leu Glu Ser Gly
                565                 570                 575

Asp Ala Ser Ile His Asp Thr Val Glu Asn Leu Ile Ile Leu Ala Asn
        580                 585                 590

Asn Ser Leu Ser Ser Asn Gly Asn Val Thr Glu Ser Gly Cys Lys Glu
        595                 600                 605

Cys Glu Glu Leu Glu Glu Lys Asn Ile Lys Glu Phe Leu Gln Ser Phe
        610                 615                 620

Val His Ile Val Gln Met Phe Ile Asn Thr Ser Thr Thr Thr Pro Ala
625                 630                 635                 640

Pro Arg Pro Pro Thr Pro Ala Pro Thr Ile Ala Ser Gln Pro Leu Ser
                645                 650                 655

Leu Arg Pro Glu Ala Cys Arg Pro Ala Ala Gly Gly Ala Val His Thr
        660                 665                 670

Arg Gly Leu Asp Phe Ala Cys Asp Ile Tyr Ile Trp Ala Pro Leu Ala
        675                 680                 685

Gly Thr Cys Gly Val Leu Leu Leu Ser Leu Val Ile Thr Leu Tyr Cys
        690                 695                 700

<210> SEQ ID NO 79
<211> LENGTH: 2234
<212> TYPE: DNA
<213> ORGANISM: Homo sapiens
<220> FEATURE:
<221> NAME/KEY: misc_feature
<223> OTHER INFORMATION: NK19-11b DNA

<400> SEQUENCE: 79
ggatccgaat cgccgccac catggcctta ccagtgaccg ccttgctcct gccgctggcc      60
ttgctgctcc acgccgccag gccggactac aaagacgatg acgataaagg cgtggtggc    120 tctggtggtg gcggcagcga catccagatg acacagacta tcctccct gtctgcctct     180 ctggagacag agtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttactttt gccaacaggg taatacgctt    420
ccgtacacgt tcgagggggg gaccaagctg gagatcacag gtggcggtgg ctcgggcggt    480
ggtgggtcgg gtggcggcgg atctgaggtg aaactgcagg agtcaggacc tggcctggtg    540
gcgccctcac agagcctgtc cgtcacatgc actgtctcag ggtctcatt acccgactat    600 ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
```

```
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtggggtcct tctcctgtca ctggttatca ccctttactg catggaccaa   1080
caagcaatat atgctgagtt aaacttaccc acagactcag gcccagaaag ttcttcacct   1140
tcatctcttc ctcgggatgt ctgtcagggt tcaccttggc atcaatttgc cctgaaactt   1200
agctgtagag tgaagttcag caggagcgca acgcccccg cgtaccagca gggccagaac    1260
cagctctata acgagctcaa tctaggacga agagaggagt acgatgtttt ggacaagaga   1320
cgtggccggg accctgagat ggggggaaag ccgagaagga agaaccctca ggaaggcctg   1380
tacaatgaac tgcagaaaga taagatggcg gaggcctaca gtgagattgg gatgaaaggc   1440
gagcgccgga ggggcaaggg gcacgatggc ctttaccagg gtctcagtac agccaccaag   1500
gacacctacg acgcccttca catgcaggcc ctgccccctc gcggctctgg cgagggaagg   1560
ggttccctgc ttacttgcgg cgacgtcgaa gagaatcccg gtccgatggc cctcccagta   1620
actgccctcc ttttgcccct cgcactcctt cttcatgccg ctcgccccaa ctgggtcaac   1680
gtgattagcg atttgaagaa aatcgaggac cttatacagt ctatgcatat tgacgctaca   1740
ctgtatactg agagtgatgt acacccgtcc tgtaaggtaa cggccatgaa atgctttctt   1800
ctggagctcc aggtcatcag cttggagtct ggggacgcaa gcatccacga tacggttgaa   1860
aacctcatca tccttgcgaa caactctctc tcatctaatg gaaacgttac agagagtggg   1920
tgtaaggagt gcgaagagtt ggaagaaaaa aacatcaaag aatttcttca atccttcgtt   1980
cacatagtgc aaatgttcat taacacgtcc actaccacac ccgccccgag gccacctacg   2040
ccggcaccga ctatcgccag tcaacccctc tctctgcgcc ccgaggcttg ccggcctgcg   2100
gctggtgggg cggtccacac ccggggcctg gattttgcgt gcgatatata catctgggca   2160
cctcttgccg gcacctgcgg agtgctgctt ctctcactcg ttattacgct gtactgctaa   2220
gcggccgcgt cgac                                                      2234
```

<210> SEQ ID NO 80
<211> LENGTH: 732
<212> TYPE: PRT
<213> ORGANISM: Homo sapiens
<220> FEATURE:
<221> NAME/KEY: MISC_FEATURE
<223> OTHER INFORMATION: NK19-11b Protein

<400> SEQUENCE: 80

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110
```

```
Thr Ile Ser Asn Leu Glu Gln Glu Asp Ile Ala Thr Tyr Phe Cys Gln
            115                 120                 125

Gln Gly Asn Thr Leu Pro Tyr Thr Phe Gly Gly Gly Thr Lys Leu Glu
        130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Met Asp
            340                 345                 350

Gln Gln Ala Ile Tyr Ala Glu Leu Asn Leu Pro Thr Asp Ser Gly Pro
        355                 360                 365

Glu Ser Ser Ser Pro Ser Ser Leu Pro Arg Asp Val Cys Gln Gly Ser
    370                 375                 380

Pro Trp His Gln Phe Ala Leu Lys Leu Ser Cys Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg Gly Ser Gly Glu Gly
            500                 505                 510

Arg Gly Ser Leu Leu Thr Cys Gly Asp Val Glu Glu Asn Pro Gly Pro
        515                 520                 525

Met Ala Leu Pro Val Thr Ala Leu Leu Leu Pro Leu Ala Leu Leu Leu
```

|     | 530 |     |     | 535 |     |     | 540 |     |     |     |
|-----|-----|-----|-----|-----|-----|-----|-----|-----|-----|-----|

His Ala Ala Arg Pro Asn Trp Val Asn Val Ile Ser Asp Leu Lys Lys
545                 550                 555                 560

Ile Glu Asp Leu Ile Gln Ser Met His Ile Asp Ala Thr Leu Tyr Thr
                565                 570                 575

Glu Ser Asp Val His Pro Ser Cys Lys Val Thr Ala Met Lys Cys Phe
                    580                 585                 590

Leu Leu Glu Leu Gln Val Ile Ser Leu Glu Ser Gly Asp Ala Ser Ile
            595                 600                 605

His Asp Thr Val Glu Asn Leu Ile Ile Leu Ala Asn Asn Ser Leu Ser
            610                 615                 620

Ser Asn Gly Asn Val Thr Glu Ser Gly Cys Lys Glu Cys Glu Glu Leu
625                 630                 635                 640

Glu Glu Lys Asn Ile Lys Glu Phe Leu Gln Ser Phe Val His Ile Val
                    645                 650                 655

Gln Met Phe Ile Asn Thr Ser Thr Thr Thr Pro Ala Pro Arg Pro Pro
                660                 665                 670

Thr Pro Ala Pro Thr Ile Ala Ser Gln Pro Leu Ser Leu Arg Pro Glu
                    675                 680                 685

Ala Cys Arg Pro Ala Ala Gly Gly Ala Val His Thr Arg Gly Leu Asp
            690                 695                 700

Phe Ala Cys Asp Ile Tyr Ile Trp Ala Pro Leu Ala Gly Thr Cys Gly
705                 710                 715                 720

Val Leu Leu Leu Ser Leu Val Ile Thr Leu Tyr Cys
                725                 730

<210> SEQ ID NO 81
<211> LENGTH: 2165
<212> TYPE: DNA
<213> ORGANISM: Homo sapiens
<220> FEATURE:
<221> NAME/KEY: misc_feature
<223> OTHER INFORMATION: NK19-12b DNA

<400> SEQUENCE: 81

| | | | | |
|---|---|---|---|---|
| ggatccgaat tcgccgccac catggcctta ccagtgaccg ccttgctcct gccgctggcc | | | | 60 |
| ttgctgctcc acgccgccag gccggactac aaagacgatg acgataaagg cggtggtggc | | | | 120 |
| tctggtggtg gcggcagcga catccagatg acacagacta tcctccct gtctgcctct | | | | 180 |
| ctgggagaca gagtcaccat cagttgcagg gcaagtcagg acattagtaa atatttaaat | | | | 240 |
| tggtatcagc agaaaccaga tggaactgtt aaactcctga tctaccatac atcaagatta | | | | 300 |
| cactcaggag tcccatcaag gttcagtggc agtgggtctg gaacagatta ttctctcacc | | | | 360 |
| attagcaacc tggagcaaga agatattgcc acttactttt gccaacaggg taatacgctt | | | | 420 |
| ccgtacacgt tcggaggggg gaccaagctg gagatcacag gtggcggtgg ctcgggcggt | | | | 480 |
| ggtgggtcgg gtggcggcgg atctgaggtg aaactgcagg agtcaggacc tggcctggtg | | | | 540 |
| gcgccctcac agagcctgtc cgtcacatgc actgtctcag gggtctcatt accgactat | | | | 600 |
| ggtgtaagct ggattcgcca gcctccacga aagggtctgg agtggctggg agtaatatgg | | | | 660 |
| ggtagtgaaa ccacatacta taattcagct ctcaaatcca gactgaccat catcaaggac | | | | 720 |
| aactccaaga gccaagtttt cttaaaaatg aacagtctgc aaactgatga cacagccatt | | | | 780 |
| tactactgtg ccaaacatta ttactacggt ggtagctatg ctatggacta ctggggccaa | | | | 840 |
| ggaacctcag tcaccgtctc ctcaaccacg acgccagcgc cgcgaccacc aacaccggcg | | | | 900 |

```
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtggggtcct tctcctgtca ctggttatca cccttttactg catgatcgaa   1080 acatacaacc aaacttctcc ccgatctgcg gccactggac tgcccatcag catgaaaaga   1140
gtgaagttca gcaggagcgc agacgccccc gcgtaccagc agggccagaa ccagctctat   1200
aacgagctca atctaggacg aagagaggag tacgatgttt tggacaagag acgtggccgg   1260
gaccctgaga tgggggaaa gccgagaagg aagaaccctc aggaaggcct gtacaatgaa    1320
ctgcagaaag ataagatggc ggaggcctac agtgagattg gatgaaaagg cgagcgccgg   1380
aggggcaagg ggcacgatgg cctttaccag ggtctcagta cagccaccaa ggacacctac   1440 gacgccttc acatgcaggc cctgccccct cgcggctctg gcgagggaag gggttccctg    1500
cttacttgcg gcgacgtcga agagaatccc ggtccgatgg ccctcccagt aactgccctc   1560
cttttgcccc tcgcactcct tcttcatgcc gctcgcccca actgggtcaa cgtgattagc   1620
gatttgaaga aaatcgagga ccttatacag tctatgcata ttgacgctac actgtatact   1680
gagagtgatg tacacccgtc ctgtaaggta acggccatga aatgctttct tctggagctc   1740
caggtcatca gcttggagtc tggggacgca agcatccacg atacggttga aaacctcatc   1800
atccttgcga caactctct ctcatctaat ggaaacgtta cagagagtgg gtgtaaggag    1860
tgcgaagagt tggaagaaaa aaacatcaaa gaatttcttc aatccttcgt tcacatagtg   1920
caaatgttca ttaacacgtc cactaccaca cccgccccga ggccacctac gccggcaccg   1980
actatcgcca gtcaacccct ctctctgcgc cccgaggctt gccggcctgc ggctggtggg   2040
gcggtccaca cccgggggcct ggattttgcg tgcgatatat acatctgggc acctcttgcc   2100
ggcacctgcg gagtgctgct tctctcactc gttattacgc tgtactgcta agcggccgcg   2160
tcgac                                                               2165
```

<210> SEQ ID NO 82
<211> LENGTH: 709
<212> TYPE: PRT
<213> ORGANISM: Homo sapiens
<220> FEATURE:
<221> NAME/KEY: MISC_FEATURE
<223> OTHER INFORMATION: NK19-12b Protein

<400> SEQUENCE: 82

```
Met Ala Leu Pro Val Thr Ala Leu Leu Pro Leu Ala Leu Leu Leu
1               5                   10                  15

His Ala Ala Arg Pro Asp Tyr Lys Asp Asp Asp Lys Gly Gly Gly
                20                  25                  30

Gly Ser Gly Gly Gly Gly Ser Asp Ile Gln Met Thr Gln Thr Thr Ser
            35                  40                  45

Ser Leu Ser Ala Ser Leu Gly Asp Arg Val Thr Ile Ser Cys Arg Ala
        50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125
```

-continued

```
Gln Gly Asn Thr Leu Pro Tyr Thr Phe Gly Gly Gly Thr Lys Leu Glu
    130                 135                 140
Ile Thr Gly Gly Gly Ser Gly Gly Gly Ser Gly Gly Gly Gly
145                 150                 155                 160
Ser Glu Val Lys Leu Gln Glu Ser Gly Pro Gly Leu Val Ala Pro Ser
                165                 170                 175
Gln Ser Leu Ser Val Thr Cys Thr Val Ser Gly Val Ser Leu Pro Asp
            180                 185                 190
Tyr Gly Val Ser Trp Ile Arg Gln Pro Pro Arg Lys Gly Leu Glu Trp
        195                 200                 205
Leu Gly Val Ile Trp Gly Ser Glu Thr Thr Tyr Tyr Asn Ser Ala Leu
    210                 215                 220
Lys Ser Arg Leu Thr Ile Ile Lys Asp Asn Ser Lys Ser Gln Val Phe
225                 230                 235                 240
Leu Lys Met Asn Ser Leu Gln Thr Asp Asp Thr Ala Ile Tyr Tyr Cys
                245                 250                 255
Ala Lys His Tyr Tyr Gly Gly Ser Tyr Ala Met Asp Tyr Trp Gly
            260                 265                 270
Gln Gly Thr Ser Val Thr Val Ser Ser Thr Thr Thr Pro Ala Pro Arg
        275                 280                 285
Pro Pro Thr Pro Ala Pro Thr Ile Ala Ser Gln Pro Leu Ser Leu Arg
    290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
                325                 330                 335
Cys Gly Val Leu Leu Leu Ser Leu Val Ile Thr Leu Tyr Cys Met Ile
            340                 345                 350
Glu Thr Tyr Asn Gln Thr Ser Pro Arg Ser Ala Ala Thr Gly Leu Pro
        355                 360                 365
Ile Ser Met Lys Arg Val Lys Phe Ser Arg Ser Ala Asp Ala Pro Ala
    370                 375                 380
Tyr Gln Gln Gly Gln Asn Gln Leu Tyr Asn Glu Leu Asn Leu Gly Arg
385                 390                 395                 400
Arg Glu Glu Tyr Asp Val Leu Asp Lys Arg Arg Gly Arg Asp Pro Glu
                405                 410                 415
Met Gly Gly Lys Pro Arg Arg Lys Asn Pro Gln Glu Gly Leu Tyr Asn
            420                 425                 430
Glu Leu Gln Lys Asp Lys Met Ala Glu Ala Tyr Ser Glu Ile Gly Met
        435                 440                 445
Lys Gly Glu Arg Arg Arg Gly Lys Gly His Asp Gly Leu Tyr Gln Gly
    450                 455                 460
Leu Ser Thr Ala Thr Lys Asp Thr Tyr Asp Ala Leu His Met Gln Ala
465                 470                 475                 480
Leu Pro Pro Arg Gly Ser Gly Glu Gly Arg Gly Ser Leu Leu Thr Cys
                485                 490                 495
Gly Asp Val Glu Glu Asn Pro Gly Pro Met Ala Leu Pro Val Thr Ala
            500                 505                 510
Leu Leu Leu Pro Leu Ala Leu Leu His Ala Ala Arg Pro Asn Trp
        515                 520                 525
Val Asn Val Ile Ser Asp Leu Lys Lys Ile Glu Asp Leu Ile Gln Ser
    530                 535                 540
Met His Ile Asp Ala Thr Leu Tyr Thr Glu Ser Asp Val His Pro Ser
```

```
                545                 550                 555                 560
Cys Lys Val Thr Ala Met Lys Cys Phe Leu Leu Glu Leu Gln Val Ile
                    565                 570                 575

Ser Leu Glu Ser Gly Asp Ala Ser Ile His Asp Thr Val Glu Asn Leu
                580                 585                 590

Ile Ile Leu Ala Asn Asn Ser Leu Ser Ser Asn Gly Asn Val Thr Glu
                595                 600                 605

Ser Gly Cys Lys Glu Cys Glu Glu Leu Glu Lys Asn Ile Lys Glu
            610                 615                 620

Phe Leu Gln Ser Phe Val His Ile Val Gln Met Phe Ile Asn Thr Ser
625                 630                 635                 640

Thr Thr Thr Pro Ala Pro Arg Pro Pro Thr Pro Ala Pro Thr Ile Ala
                645                 650                 655

Ser Gln Pro Leu Ser Leu Arg Pro Glu Ala Cys Arg Pro Ala Ala Gly
                660                 665                 670

Gly Ala Val His Thr Arg Gly Leu Asp Phe Ala Cys Asp Ile Tyr Ile
                675                 680                 685

Trp Ala Pro Leu Ala Gly Thr Cys Gly Val Leu Leu Leu Ser Leu Val
            690                 695                 700

Ile Thr Leu Tyr Cys
705

<210> SEQ ID NO 83
<211> LENGTH: 2315
<212> TYPE: DNA
<213> ORGANISM: Homo sapiens
<220> FEATURE:
<221> NAME/KEY: misc_feature
<223> OTHER INFORMATION: NK19-13b DNA

<400> SEQUENCE: 83
ggatccgaat tcgccgccac catggcctta ccagtgaccg ccttgctcct gccgctggcc      60
ttgctgctcc acgccgccag gccggactac aaagacgatg acgataaagg cggtggtggc     120
tctggtggtg gcggcagcga catccagatg acacagacta catcctccct gtctgcctct     180
ctgggagaca gagtcaccat cagttgcagg gcaagtcagg acattagtaa atatttaaat     240
tggtatcagc agaaaccaga tggaactgtt aaactcctga tctaccatac atcaagatta     300
cactcaggag tcccatcaag gttcagtggc agtgggtctg gaacagatta ttctctcacc     360
attagcaacc tggagcaaga agatattgcc acttactttt gccaacaggg taatacgctt     420
ccgtacacgt tcggaggggg gaccaagctg gagatcacag gtggcggtgg ctcgggcggt     480
ggtgggtcgg gtggcggcgg atctgaggtg aaactgcagg agtcaggacc tggcctggtg     540
gcgccctcac agagcctgtc cgtcacatgc actgtctcag ggtctcatt acccgactat     600 ggtgtaagct ggattcgcca gcctccacga agggtctgg agtggctggg agtaatatgg     660
ggtagtgaaa ccacatacta taattcagct ctcaaatcca gactgaccat catcaaggac     720
aactccaaga gccaagtttt cttaaaaatg aacagtctgc aaactgatga cacagccatt     780
tactactgtg ccaaacatta ttactacggt ggtagctatg ctatggacta ctggggccaa     840
ggaacctcag tcaccgtctc ctcaaccacg acgccagcgc cgcgaccacc aacaccggcg     900
cccaccatcg cgtcgcagcc cctgtccctg cgcccagagg cgtgccggcc agcggcgggg     960
ggcgcagtgc acacgagggg gctggacttc gcctgtgata tctacatctg ggcgcccttg    1020
gccgggactt gtggggtcct tctcctgtca ctggttatca ccctttactg caacagtcga    1080
```

```
agaaggtgtg ggcagaagaa aaagctagtg atcaacagtg gcaatggagc tgtggaggac   1140
agaaagccaa gtggactcaa cggagaggcc agcaagtctc aggaaatggt gcatttggtg   1200
aacaaggagt cgtcagaaac tccagaccag tttatgacag ctgatgagac aaggaacctg   1260
cagaatgtgg acatgaagat tggggtgaga gtgaagttca gcaggagcgc agacgccccc   1320
gcgtaccagc agggccagaa ccagctctat aacgagctca atctaggacg aagagaggag   1380
tacgatgttt tggacaagag acgtggccgg gaccctgaga tggggggaaa gccgagaagg   1440
aagaaccctc aggaaggcct gtacaatgaa ctgcagaaag ataagatggc ggaggcctac   1500
agtgagattg ggatgaaagg cgagcgccgg aggggcaagg ggcacgatgg cctttaccag   1560
ggtctcagta cagccaccaa ggacacctac gacgcccttc acatgcaggc cctgccccct   1620
cgcggctctg gcgagggaag gggttccctg cttacttgcg cgacgtcga agagaatccc   1680 ggtccgatgg ccctcccagt aactgccctc cttttgcccc tcgcactcct tcttcatgcc   1740
gctcgcccca actgggtcaa cgtgattagc gatttgaaga aaatcgagga ccttatacag   1800
tctatgcata ttgacgctac actgtatact gagagtgatg tacacccgtc ctgtaaggta   1860
acggccatga aatgctttct tctggagctc caggtcatca gcttggagtc tggggacgca   1920
agcatccacg atacgcttga aaacctcatc atccttgcga caactctct ctcatctaat   1980 ggaaacgtta cagagagtgg ggtgtaagga gtgcgaagagt tggaagaaaa aaacatcaaa   2040
gaatttcttc aatccttcgt tcacatagtg caaatgttca ttaacacgtc cactaccaca   2100
cccgccccga ggccacctac gccggcaccg actatcgcca gtcaacccct ctctctgcgc   2160
cccgaggctt gccggcctgc ggctggtggg gcggtccaca cccgggggcct ggattttgcg   2220 tgcgatatat acatctgggc acctcttgcc ggcacctgcg gagtgctgct tctctcactc   2280
gttattacgc tgtactgcta agcggccgcg tcgac                               2315
```

<210> SEQ ID NO 84
<211> LENGTH: 759
<212> TYPE: PRT
<213> ORGANISM: Homo sapiens
<220> FEATURE:
<221> NAME/KEY: MISC_FEATURE
<223> OTHER INFORMATION: NK19-13b Protein

<400> SEQUENCE: 84

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
                20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140
```

```
Ile Thr Gly Gly Gly Ser Gly Gly Gly Ser Gly Gly Gly
145                 150                 155                 160

Ser Glu Val Lys Leu Gln Glu Ser Gly Pro Gly Leu Val Ala Pro Ser
            165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
            195                 200                 205

Leu Gly Val Ile Trp Gly Ser Glu Thr Thr Tyr Tyr Asn Ser Ala Leu
            210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
            245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
            275                 280                 285

Pro Pro Thr Pro Ala Pro Thr Ile Ala Ser Gln Pro Leu Ser Leu Arg
            290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
            325                 330                 335

Cys Gly Val Leu Leu Leu Ser Leu Val Ile Thr Leu Tyr Cys Asn Ser
            340                 345                 350

Arg Arg Arg Cys Gly Gln Lys Lys Lys Leu Val Ile Asn Ser Gly Asn
            355                 360                 365

Gly Ala Val Glu Asp Arg Lys Pro Ser Gly Leu Asn Gly Glu Ala Ser
            370                 375                 380

Lys Ser Gln Glu Met Val His Leu Val Asn Lys Glu Ser Ser Glu Thr
385                 390                 395                 400

Pro Asp Gln Phe Met Thr Ala Asp Glu Thr Arg Asn Leu Gln Asn Val
            405                 410                 415

Asp Met Lys Ile Gly Val Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
            435                 440                 445

Gly Arg Arg Glu Glu Tyr Asp Val Leu Asp Lys Arg Arg Gly Arg Asp
            450                 455                 460

Pro Glu Met Gly Gly Lys Pro Arg Arg Lys Asn Pro Gln Glu Gly Leu
465                 470                 475                 480

Tyr Asn Glu Leu Gln Lys Asp Lys Met Ala Glu Ala Tyr Ser Glu Ile
            485                 490                 495

Gly Met Lys Gly Glu Arg Arg Arg Gly Lys Gly His Asp Gly Leu Tyr
            500                 505                 510

Gln Gly Leu Ser Thr Ala Thr Lys Asp Thr Tyr Asp Ala Leu His Met
            515                 520                 525

Gln Ala Leu Pro Pro Arg Gly Ser Gly Glu Gly Arg Gly Ser Leu Leu
            530                 535                 540

Thr Cys Gly Asp Val Glu Glu Asn Pro Gly Pro Met Ala Leu Pro Val
545                 550                 555                 560
```

```
Thr Ala Leu Leu Leu Pro Leu Ala Leu Leu Leu His Ala Ala Arg Pro
                565                 570                 575

Asn Trp Val Asn Val Ile Ser Asp Leu Lys Lys Ile Glu Asp Leu Ile
            580                 585                 590

Gln Ser Met His Ile Asp Ala Thr Leu Tyr Thr Glu Ser Asp Val His
        595                 600                 605

Pro Ser Cys Lys Val Thr Ala Met Lys Cys Phe Leu Leu Glu Leu Gln
    610                 615                 620

Val Ile Ser Leu Glu Ser Gly Asp Ala Ser Ile His Asp Thr Val Glu
625                 630                 635                 640

Asn Leu Ile Ile Leu Ala Asn Asn Ser Leu Ser Ser Asn Gly Asn Val
                645                 650                 655

Thr Glu Ser Gly Cys Lys Glu Cys Glu Glu Leu Glu Glu Lys Asn Ile
            660                 665                 670

Lys Glu Phe Leu Gln Ser Phe Val His Ile Val Gln Met Phe Ile Asn
        675                 680                 685

Thr Ser Thr Thr Thr Pro Ala Pro Arg Pro Pro Thr Pro Ala Pro Thr
    690                 695                 700

Ile Ala Ser Gln Pro Leu Ser Leu Arg Pro Glu Ala Cys Arg Pro Ala
705                 710                 715                 720

Ala Gly Gly Ala Val His Thr Arg Gly Leu Asp Phe Ala Cys Asp Ile
                725                 730                 735

Tyr Ile Trp Ala Pro Leu Ala Gly Thr Cys Gly Val Leu Leu Leu Ser
            740                 745                 750

Leu Val Ile Thr Leu Tyr Cys
        755

<210> SEQ ID NO 85
<211> LENGTH: 6488
<212> TYPE: DNA
<213> ORGANISM: Homo sapiens
<220> FEATURE:
<221> NAME/KEY: misc_feature
<223> OTHER INFORMATION: NK19 DNA

<400> SEQUENCE: 85
atgaaagacc ccacctgtag gtttggcaag ctagcttaag taacgccatt ttgcaaggca      60
tggaaaatac ataactgaga atagagaagt tcagatcaag gttaggaaca gagagacagc     120
agaatatggg ccaaacagga tatctgtggt aagcagttcc tgccccggct cagggccaag     180
aacagatggt ccccagatgc ggtcccgccc tcagcagttt ctagagaacc atcagatgtt     240
tccagggtgc cccaaggacc tgaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540 accctgccc agggaccacc gaccccccg ccgggaggta agctggccag cggtcgtttc       600
gtgtctgtct ctgtctttgt gcgtgtttgt gccggcatct aatgtttgcg cctgcgtctg     660
tactagttag ctaactagct ctgtatctgg cggacccgtg gtggaactga cgagttctga     720
acacccggcc gcaaccctgg gagacgtccc agggactttg ggggccgttt tgtggcccg      780 acctgaggaa gggagtcgat gtggaatccg acccgtcag gatatgtggt tctggtagga      840
gacgagaacc taaacagtt cccgcctccg tctgaatttt tgctttcggt ttggaaccga      900
```

```
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtccccctac atcgtgacct gggaagcctt ggcttttgac   1260 cccctccct gggtcaagcc ctttgtacac cctaagcctc cgcctcctct tcctccatcc   1320
gccccgtctc tccccttga acctcctcgt tcgaccccgc ctcgatcctc cctttatcca   1380
gccctcactc cttctctagg cgccggaatt cgttaacctc gagcgggatc aattccgccc   1440 ccccctaac gttactggcc gaagccgctt ggaataaggc cggtgtgcgt ttgtctatat   1500
gttattttcc accatattgc cgtcttttgg caatgtgagg gcccggaaac ctggccctgt   1560
cttcttgacg agcattccta ggggtctttc ccctctcgcc aaaggaatgc aaggtctgtt   1620
gaatgtcgtg aaggaagcag ttcctctgga agcttcttga agacaaacaa cgtctgtagc   1680 gacccttgc aggcagcgga accccccacc tggcgacagg tgcctctgcg gccaaaagcc   1740
acgtgtataa gatacacctg caaaggcggc acaacccag tgccacgttg tgagttggat   1800
agttgtggaa agagtcaaat ggctctcctc aagcgtattc aacaagggc tgaaggatgc   1860 ccagaaggta ccccattgta tgggatctga tctggggcct cggtgcacat gctttacatg   1920
tgtttagtcg aggttaaaaa aacgtctagg ccccccgaac cacggggacg tggttttcct   1980
ttgaaaaaca cgataatacc atggtgagca agggcgagga gctgttcacc ggggtggtgc   2040
ccatcctggt cgagctggac ggcgacgtaa acggccacaa gttcagcgtg tccggcgagg   2100
gcgagggcga tgccacctac ggcaagctga ccctgaagtt catctgcacc accggcaagc   2160
tgcccgtgcc ctggcccacc ctcgtgacca ccctgaccta cggcgtgcag tgcttcagcc   2220
gctaccccga ccacatgaag cagcacgact tcttcaagtc cgccatgccc gaaggctacg   2280
tccaggagcg caccatcttc ttcaaggacg acggcaacta caagacccgc gccgaggtga   2340
agttcgaggg cgacaccctg gtgaaccgca tcgagctgaa gggcatcgac ttcaaggagg   2400
acggcaacat cctggggcac aagctggagt acaactacaa cagccacaac gtctatatca   2460
tggccgacaa gcagaagaac ggcatcaagg tgaacttcaa gatccgccac aacatcgagg   2520
acggcagcgt gcagctcgcc gaccactacc agcagaacac ccccatcggc gacggccccg   2580
tgctgctgcc cgacaaccac tacctgagca cccagtccgc cctgagcaaa gaccccaacg   2640
agaagcgcga tcacatggtc ctgctggagt tcgtgaccgc cgccgggatc actctcggca   2700
tggacgagct gtacaagtaa agcggccgcg actctagagt cgacctgcag gcatgcaagc   2760
ttcaggtagc cggctaacgt taacaaccgg tacctctaga actatagcta gcatgcgcaa   2820
atttaaagcg ctgatatcga taaaataaaa gatttttatt agtctccaga aaaggggggg   2880
aatgaaagac cccacctgta ggtttggcaa gctagcttaa gtaacgccat tttgcaaggc   2940
atggaaaata cataactgag aatagagaag ttcagatcaa ggttaggaac agagagacag   3000
cagaatatgg gccaaacagg atatctgtgg taagcagttc ctgccccggc tcagggccaa   3060
gaacagatgg tccccagatg cggtcccgcc ctcagcagtt tctagagaac catcagatgt   3120
ttccagggtg ccccaaggac ctgaaatgac cctgtgcctt atttgaacta accaatcagt   3180
tcgcttctcg cttctgttcg cgcgcttctg ctccccgagc tcaataaaag agcccacaac   3240
```

```
ccctcactcg gcgcgccagt cctccgatag actgcgtcgc ccgggtaccc gtgtatccaa    3300
taaaccctct tgcagttgca tccgacttgt ggtctcgctg ttccttggga gggtctcctc    3360
tgagtgattg actacccgtc agcggggggtc tttcatgggt aacagtttct tgaagttgga   3420
gaacaacatt ctgagggtag gagtcgaata ttaagtaatc ctgactcaat tagccactgt    3480
tttgaatcca catactccaa tactcctgaa atagttcatt atggacagcg cagaaagagc    3540
tggggagaat tgtgaaattg ttatccgctc acaattccac acaacatacg agccggaagc    3600
ataaagtgta aagcctgggg tgcctaatga gtgagctaac tcacattaat tgcgttgcgc    3660
tcactgcccg ctttccagtc gggaaacctg tcgtgccagc tgcattaatg aatcggccaa    3720
cgcgcgggga gaggcggttt gcgtattggg cgctcttccg cttcctcgct cactgactcg    3780
ctgcgctcgg tcgttcggct gcggcgagcg gtatcagctc actcaaaggc ggtaatacgg    3840
ttatccacag aatcagggga taacgcagga aagaacatgt gagcaaaagg ccagcaaaag    3900
gccaggaacc gtaaaaaggc cgcgttgctg gcgtttttcc ataggctccg ccccccctgac   3960 gagcatcaca aaaatcgacg ctcaagtcag aggtggcgaa acccgacagg actataaaga    4020
taccaggcgt ttccccctgg aagctccctc gtgcgctctc ctgttccgac cctgccgctt    4080
accggatacc tgtccgcctt tctcccttcg ggaagcgtgg cgctttctca tagctcacgc    4140
tgtaggtatc tcagttcggt gtaggtcgtt cgctccaagc tgggctgtgt gcacgaaccc    4200
cccgttcagc ccgaccgctg cgccttatcc ggtaactatc gtcttgagtc caacccggta    4260
agacacgact tatcgccact ggcagcagcc actggtaaca ggattagcag agcgaggtat    4320
gtaggcggtg ctacagagtt cttgaagtgg tggcctaact acggctacac tagaagaaca    4380
gtatttggta tctgcgctct gctgaagcca gttaccttcg gaaaaagagt tggtagctct    4440
tgatccggca acaaaccacc gctggtagc ggtggttttt tgtttgcaa gcagcagatt      4500 acgcgcagaa aaaaggatc tcaagaagat cctttgatct tttctacggg gtctgacgct     4560
cagtggaacg aaaactcacg ttaagggatt ttggtcatga gattatcaaa aaggatcttc    4620
acctagatcc ttttaaatta aaaatgaagt tttaaatcaa tctaaagtat atatgagtaa    4680
acttggtctg acagttacca atgcttaatc agtgaggcac ctatctcagc gatctgtcta    4740
tttcgttcat ccatagttgc ctgactcccc gtcgtgtaga taactacgat acgggagggc    4800
ttaccatctg gccccagtgc tgcaatgata ccgcgagacc cacgctcacc ggctccagat    4860
ttatcagcaa taaaccagcc agccggaagg gccgagcgca gaagtggtcc tgcaacttta   4920
tccgcctcca tccagtctat taattgttgc cgggaagcta gagtaagtag ttcgccagtt    4980
aatagtttgc gcaacgttgt tgccattgct acaggcatcg tggtgtcacg ctcgtcgttt    5040
ggtatggctt cattcagctc cggttcccaa cgatcaaggc gagttacatg atcccccatg    5100
ttgtgcaaaa aagcggttag ctccttcggt cctccgatcg ttgtcagaag taagttggcc    5160
gcagtgttat cactcatggt tatggcagca ctgcataatt ctcttactgt catgccatcc    5220
gtaagatgct tttctgtgac tggtgagtac tcaaccaagt cattctgaga atagtgtatg    5280
cggcgaccga gttgctcttg cccggcgtca atacgggata ataccgcgcc acatagcaga    5340
actttaaaag tgctcatcat tggaaaacgt tcttcggggc gaaaactctc aaggatctta    5400
ccgctgttga gatccagttc gatgtaaccc actcgtgcac ccaactgatc ttcagcatct    5460
tttactttca ccagcgtttc tgggtgagca aaaacaggaa ggcaaaatgc cgcaaaaaag    5520
ggaataaggg cgacacggaa atgttgaata ctcatactct tcctttttca atattattga    5580
agcatttatc agggttattg tctcatgagc ggatacatat ttgaatgtat ttagaaaaat    5640
```

```
aaacaaatag gggttccgcg cacatttccc cgaaaagtgc cacctgacgt ctaagaaacc    5700
attattatca tgacattaac ctataaaaat aggcgtatca cgaggccctt tcgtctcgcg    5760
cgtttcggtg atgacggtga aaacctctga cacatgcagc tcccggagac ggtcacagct    5820
tgtctgtaag cggatgccgg gagcagacaa gcccgtcagg gcgcgtcagc gggtgttggc    5880
gggtgtcggg gctggcttaa ctatgcggca tcagagcaga ttgtactgag agtgcaccat    5940
atgcggtgtg aaataccgca cagatgcgta aggagaaaat accgcatcag gcgccattcg    6000
ccattcaggc tgcgcaactg ttgggaaggg cgatcggtgc gggcctcttc gctattacgc    6060
cagctggcga aaggggggatg tgctgcaagg cgattaagtt gggtaacgcc agggttttcc    6120
cagtcacgac gttgtaaaac gacggcgcaa ggaatggtgc atgcaaggag atggcgccca    6180
acagtccccc ggccacgggg cctgccacca tacccacgcc gaaacaagcg ctcatgagcc    6240
cgaagtggcg agcccgatct tccccatcgg tgatgtcggc gatataggcg ccagcaaccg    6300
cacctgtggc gccggtgatg ccggccacga tgcgtccggc gtagaggcga ttagtccaat    6360
ttgttaaaga caggatatca gtggtccagg ctctagtttt gactcaacaa tatcaccagc    6420
tgaagcctat agagtacgag ccatagataa aataaaagat tttatttagt ctccagaaaa    6480
aggggggga                                                           6488
```

<210> SEQ ID NO 86
<211> LENGTH: 486
<212> TYPE: PRT
<213> ORGANISM: Homo sapiens
<220> FEATURE:
<221> NAME/KEY: MISC_FEATURE
<223> OTHER INFORMATION: NK19 PROTEIN

<400> SEQUENCE: 86

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser

```
                195                 200                 205
Arg Leu Thr Ile Ile Lys Asp Asn Ser Lys Ser Gln Val Phe Leu Lys
            210                 215                 220

Met Asn Ser Leu Gln Thr Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 87
<211> LENGTH: 6488
<212> TYPE: DNA
<213> ORGANISM: Homo sapiens
<220> FEATURE:
<221> NAME/KEY: misc_feature
<223> OTHER INFORMATION: MSCV-IRES-GFP expression plasmid

<400> SEQUENCE: 87
atgaaagacc ccacctgtag gtttggcaag ctagcttaag taacgccatt ttgcaaggca      60
tggaaaatac ataactgaga atagagaagt tcagatcaag gttaggaaca gagagacagc     120
agaatatggg ccaaacagga tatctgtggt aagcagttcc tgccccggct cagggccaag     180
aacagatggt ccccagatgc ggtcccgccc tcagcagttt ctagagaacc atcagatgtt     240
tccagggtgc cccaaggacc tgaaatgacc ctgtgcctta tttgaactaa ccaatcagtt     300
cgcttctcgc ttctgttcgc gcgcttctgc tccccgagct caataaaaga gcccacaacc     360
```

-continued

```
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540
accccctgccc agggaccacc gaccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtccccttac atcgtgacct gggaagcctt ggcttttgac   1260
cccctccct gggtcaagcc ctttgtacac cctaagcctc cgcctcctct tcctccatcc    1320
gccccgtctc tccccttga acctcctcgt tcgacccgc ctcgatcctc cctttatcca    1380
gccctcactc cttctctagg cgccggaatt cgttaacctc gagcgggatc aattccgccc    1440
ccccctaac gttactggcc gaagccgctt ggaataaggc cggtgtgcgt ttgtctatat    1500
gttattttcc accatattgc cgtcttttgg caatgtgagg gcccggaaac ctggccctgt    1560
cttcttgacg agcattccta ggggtctttc ccctctcgcc aaaggaatgc aaggtctgtt   1620
gaatgtcgtg aaggaagcag ttcctctgga agcttcttga agacaaacaa cgtctgtagc   1680
gacccttttgc aggcagcgga accccccacc tggcgacagg tgcctctgcg gccaaaagcc   1740
acgtgtataa gatacacctg caaaggcggc acaaccccag tgccacgttg tgagttggat   1800
agttgtggaa agagtcaaat ggctctcctc aagcgtattc aacaagggc tgaaggatgc    1860
ccagaaggta ccccattgta tgggatctga tctggggcct cggtgcacat gctttacatg   1920
tgtttagtcg aggttaaaaa aacgtctagg cccccccgaac cacggggacg tggttttcct   1980
ttgaaaaaca cgataatacc atggtgagca agggcgagga gctgttcacc ggggtggtgc   2040
ccatcctggt cgagctggac ggcgacgtaa acggccacaa gttcagcgtg tccggcgagg   2100
gcgagggcga tgccacctac ggcaagctga ccctgaagtt catctgcacc accggcaagc   2160
tgcccgtgcc ctggcccacc ctcgtgacca ccctgaccta cggcgtgcag tgcttcagcc   2220
gctacccga ccacatgaag cagcacgact tcttcaagtc cgccatgccc gaaggctacg   2280
tccaggagcg caccatcttc ttcaaggacg acggcaacta caagacccgc gccgaggtga   2340
agttcgaggg cgacaccctg gtgaaccgca tcgagctgaa gggcatcgac ttcaaggagg   2400
acggcaacat cctggggcac aagctggagt acaactacaa cagccacaac gtctatatca   2460
tggccgacaa gcagaagaac ggcatcaagg tgaacttcaa gatccgccac aacatcgagg   2520
acggcagcgt gcagctcgcc gaccactacc agcagaacac cccatcggc gacggccccg    2580
tgctgctgcc cgacaaccac tacctgagca cccagtccgc cctgagcaaa gaccccaacg   2640
agaagcgcga tcacatggtc ctgctggagt tcgtgaccgc cgccgggatc actctcggca   2700
tggacgagct gtacaagtaa agcggccgcg actctagagt cgacctgcag gcatgcaagc   2760
```

-continued

```
ttcaggtagc cggctaacgt taacaaccgg tacctctaga actatagcta gcatgcgcaa    2820
atttaaagcg ctgatatcga taaaataaaa gattttattt agtctccaga aaaggggggg    2880
aatgaaagac cccacctgta ggtttggcaa gctagcttaa gtaacgccat tttgcaaggc    2940
atggaaaata cataactgag aatagagaag ttcagatcaa ggttaggaac agagagacag    3000
cagaatatgg gccaaacagg atatctgtgg taagcagttc ctgccccggc tcagggccaa    3060
gaacagatgt tccccagatg cggtcccgcc ctcagcagtt tctagagaac catcagatgt    3120
ttccagggtg ccccaaggac ctgaaatgac cctgtgcctt atttgaacta accaatcagt    3180
tcgcttctcg cttctgttcg cgcgcttctg ctccccgagc tcaataaaag agcccacaac    3240
ccctcactcg gcgcgccagt cctccgatag actgcgtcgc ccgggtaccc gtgtatccaa    3300
taaaccctct tgcagttgca tccgacttgt ggtctcgctg ttccttggga gggtctcctc    3360
tgagtgattg actacccgtc agcggggggtc tttcatgggt aacagtttct tgaagttgga    3420
gaacaacatt ctgagggtag gagtcgaata ttaagtaatc ctgactcaat tagccactgt    3480
tttgaatcca catactccaa tactcctgaa atagttcatt atggacagcg cagaaagagc    3540
tggggagaat tgtgaaattg ttatccgctc acaattccac acaacatacg agccggaagc    3600
ataaagtgta aagcctgggg tgcctaatga gtgagctaac tcacattaat tgcgttgcgc    3660
tcactgcccg ctttccagtc gggaaacctg tcgtgccagc tgcattaatg aatcggccaa    3720
cgcgcgggga gaggcggttt gcgtattggg cgctcttccg cttcctcgct cactgactcg    3780
ctgcgctcgg tcgttcggct gcggcgagcg gtatcagctc actcaaaggc ggtaatacgg    3840
ttatccacag aatcagggga taacgcagga agaacatgt gagcaaaagg ccagcaaaag    3900
gccaggaacc gtaaaaaggc cgcgttgctg gcgtttttcc ataggctccg ccccctgac    3960 gagcatcaca aaaatcgacg ctcaagtcag aggtggcgaa acccgacagg actataaaga    4020
taccaggcgt ttccccctgg aagctccctc gtgcgctctc ctgttccgac cctgccgctt    4080
accggatacc tgtccgcctt tctcccttcg ggaagcgtgg cgctttctca tagctcacgc    4140
tgtaggtatc tcagttcggt gtaggtcgtt cgctccaagc tgggctgtgt gcacgaaccc    4200
cccgttcagc ccgaccgctg cgccttatcc ggtaactatc gtcttgagtc caacccggta    4260
agacacgact tatcgccact ggcagcagcc actggtaaca ggattagcag agcgaggtat    4320
gtaggcggtg ctacagagtt cttgaagtgg tggcctaact acggctacac tagaagaaca    4380
gtatttggta tctgcgctct gctgaagcca gttaccttcg gaaaaagagt tggtagctct    4440
tgatccggca aacaaaccac cgctggtagc ggtggttttt ttgtttgcaa gcagcagatt    4500
acgcgcagaa aaaaggatc tcaagaagat cctttgatct tttctacggg gtctgacgct    4560
cagtggaacg aaaactcacg ttaagggatt ttggtcatga gattatcaaa aaggatcttc    4620
acctagatcc ttttaaatta aaaatgaagt tttaaatcaa tctaaagtat atatgagtaa    4680
acttggtctg acagttacca atgcttaatc agtgaggcac ctatctcagc gatctgtcta    4740
tttcgttcat ccatagttgc ctgactcccc gtcgtgtaga taactacgat acgggagggc    4800
ttaccatctg gccccagtgc tgcaatgata ccgcgagacc cacgctcacc ggctccagat    4860
ttatcagcaa taaaccagcc agccggaagg gccgagcgca gaagtggtcc tgcaacttta    4920
tccgcctcca tccagtctat taattgttgc cgggaagcta gagtaagtag ttcgccagtt    4980
aatagtttgc gcaacgttgt tgccattgct acaggcatcg tggtgtcacg ctcgtcgttt    5040
ggtatggctt cattcagctc cggttcccaa cgatcaaggc gagttacatg atccccccatg    5100
```

```
ttgtgcaaaa aagcggttag ctccttcggt cctccgatcg ttgtcagaag taagttggcc      5160
gcagtgttat cactcatggt tatggcagca ctgcataatt ctcttactgt catgccatcc      5220
gtaagatgct tttctgtgac tggtgagtac tcaaccaagt cattctgaga atagtgtatg      5280
cggcgaccga gttgctcttg cccggcgtca atacgggata ataccgcgcc acatagcaga      5340
actttaaaag tgctcatcat tggaaaacgt tcttcgggc gaaaactctc aaggatctta      5400
ccgctgttga gatccagttc gatgtaaccc actcgtgcac ccaactgatc ttcagcatct      5460
tttactttca ccagcgtttc tgggtgagca aaaacaggaa ggcaaaatgc cgcaaaaaag      5520
ggaataaggg cgacacggaa atgttgaata ctcatactct ccttttttca atattattga      5580
agcatttatc agggttattg tctcatgagc ggatacatat ttgaatgtat ttagaaaaat      5640
aaacaaatag gggttccgcg cacatttccc cgaaaagtgc cacctgacgt ctaagaaacc      5700
attattatca tgacattaac ctataaaaat aggcgtatca cgaggccctt tcgtctcgcg      5760
cgtttcggtg atgacggtga aaacctctga cacatgcagc tcccggagac ggtcacagct      5820
tgtctgtaag cggatgccgg gagcagacaa gcccgtcagg gcgcgtcagc gggtgttggc      5880
gggtgtcggg gctggcttaa ctatgcggca tcagagcaga ttgtactgag agtgcaccat      5940
atgcggtgtg aaataccgca cagatgcgta aggagaaaat accgcatcag gcgccattcg      6000
ccattcaggc tgcgcaactg ttgggaaggg cgatcggtgc gggcctcttc gctattacgc      6060
cagctggcga aggggggatg tgctgcaagg cgattaagtt gggtaacgcc agggttttcc      6120
cagtcacgac gttgtaaaac gacggcgcaa ggaatggtgc atgcaaggag atggcgccca      6180
acagtccccc ggccacgggg cctgccacca tacccacgcc gaaacaagcg ctcatgagcc      6240
cgaagtggcg agcccgatct tccccatcgg tgatgtcggc gatataggcg ccagcaaccg      6300
cacctgtggc gccggtgatg ccggccacga tgcgtccggc gtagaggcga ttagtccaat      6360
ttgttaaaga caggatatca gtggtccagg ctctagtttt gactcaacaa tatcaccagc      6420
tgaagcctat agagtacgag ccatagataa aataaaagat tttatttagt ctccagaaaa      6480
agggggga                                                              6488
```

<210> SEQ ID NO 88
<211> LENGTH: 117
<212> TYPE: PRT
<213> ORGANISM: Homo sapiens
<220> FEATURE:
<221> NAME/KEY: MISC_FEATURE
<223> OTHER INFORMATION: anti CLDN6 heavy chain

<400> SEQUENCE: 88

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Ile
            35                  40                  45

Gly Leu Ile Asn Pro Tyr Asn Gly Gly Thr Ile Tyr Asn Gln Lys Phe
        50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110

Leu Thr Val Ser Ser
         115

<210> SEQ ID NO 89
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 1

<400> SEQUENCE: 89

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Leu
            20                  25                  30

His Trp Phe Gln Gln Lys Pro Gly Thr Ser Pro Lys Leu Trp Val Tyr
        35                  40                  45

Ser Thr Ser Asn Leu Pro Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ile Tyr Pro Pro Trp
            85                  90                  95

Thr Phe Gly Gly Gly Thr Lys Leu Glu Ile Lys
            100                 105

<210> SEQ ID NO 90
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 2

<400> SEQUENCE: 90

Gln Ile Val Leu Thr Gln Ser Pro Ser Ile Met Ser Val Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Gly Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
            85                  90                  95

Thr Phe Gly Gly Gly Thr Lys Leu Glu Ile Lys
            100                 105

<210> SEQ ID NO 91
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 3

<400> SEQUENCE: 91

```
Gln Ile Val Leu Thr Gln Ser Pro Ser Ile Met Ser Val Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Ser Ile Tyr
            35                  40                  45

Ser Thr Ser Asn Leu Ala Ser Gly Val Pro Ala Arg Phe Ser Gly Arg
        50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105
```

<210> SEQ ID NO 92
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR1

<400> SEQUENCE: 92

```
Gly Tyr Ser Phe Thr Gly Tyr Thr
1               5
```

<210> SEQ ID NO 93
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR2

<400> SEQUENCE: 93

```
Ile Asn Pro Tyr Asn Gly Gly Thr
1               5
```

<210> SEQ ID NO 94
<211> LENGTH: 10
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR3

<400> SEQUENCE: 94

```
Ala Arg Asp Tyr Gly Phe Val Leu Asp Tyr
1               5                   10
```

<210> SEQ ID NO 95
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 light chain 1 CDR1

<400> SEQUENCE: 95

```
Ser Ser Val Ser Tyr
1               5
```

<210> SEQ ID NO 96

```
<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 light chain 1  CDR2

<400> SEQUENCE: 96

Ser Thr Ser
1

<210> SEQ ID NO 97
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 light chain 1 CDR3

<400> SEQUENCE: 97

Gln Gln Arg Ser Ile Tyr Pro Pro
1               5

<210> SEQ ID NO 98
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 light chain 2 CDR1

<400> SEQUENCE: 98

Ser Ser Val Ser Tyr
1               5

<210> SEQ ID NO 99
<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 light chain 2  CDR2

<400> SEQUENCE: 99

Ser Thr Ser
1

<210> SEQ ID NO 100
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 light chain 2 CDR3

<400> SEQUENCE: 100

Gln Gln Arg Ser Asn Tyr Pro Pro
1               5

<210> SEQ ID NO 101
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 LC CDR1

<400> SEQUENCE: 101
```

```
Ser Ser Val Ser Tyr
1               5

<210> SEQ ID NO 102
<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 LC3 CDR2

<400> SEQUENCE: 102

Ser Thr Ser
1

<210> SEQ ID NO 103
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 LC3 CDR3

<400> SEQUENCE: 103

Gln Gln Arg Ser Asn Tyr Pro Pro
1               5

<210> SEQ ID NO 104
<211> LENGTH: 120
<212> TYPE: PRT
<213> ORGANISM: Homo sapiens
<220> FEATURE:
<221> NAME/KEY: MISC_FEATURE
<223> OTHER INFORMATION: anti CD19 heavy chain variable region

<400> SEQUENCE: 104

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 105
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CD19 light chain variable region

<400> SEQUENCE: 105

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys
            100                 105

<210> SEQ ID NO 106
<211> LENGTH: 450
<212> TYPE: PRT
<213> ORGANISM: Homo sapiens
<220> FEATURE:
<221> NAME/KEY: MISC_FEATURE
<223> OTHER INFORMATION: anti CD19 heavy chain variable

<400> SEQUENCE: 106

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
            260                 265                 270
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 107
<211> LENGTH: 214
<212> TYPE: PRT
<213> ORGANISM: Homo sapiens
<220> FEATURE:
<221> NAME/KEY: MISC_FEATURE
<223> OTHER INFORMATION: anti CD19 light chain variable

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 108
<211> LENGTH: 11
<212> TYPE: PRT
<213> ORGANISM: Homo sapiens
<220> FEATURE:
<221> NAME/KEY: MISC_FEATURE
<223> OTHER INFORMATION: anti CD19 LCCDR1

<400> SEQUENCE: 108

Arg Ala Ser Gln Asp Ile Ser Lys Tyr Leu Asn
1               5                   10

<210> SEQ ID NO 109
<211> LENGTH: 7
<212> TYPE: PRT
<213> ORGANISM: Homo sapiens
<220> FEATURE:
<221> NAME/KEY: MISC_FEATURE
<223> OTHER INFORMATION: anti CD19 LCCDR2

<400> SEQUENCE: 109

His Thr Ser Arg Leu His Ser
1               5

<210> SEQ ID NO 110
<211> LENGTH: 9
<212> TYPE: PRT
<213> ORGANISM: Homo sapiens
<220> FEATURE:
<221> NAME/KEY: MISC_FEATURE
<223> OTHER INFORMATION: anti CD19 LCCDR3

<400> SEQUENCE: 110

Gln Gln Gly Asn Thr Leu Pro Tyr Thr
1               5

<210> SEQ ID NO 111
<211> LENGTH: 10
<212> TYPE: PRT
<213> ORGANISM: Homo sapiens
<220> FEATURE:
<221> NAME/KEY: MISC_FEATURE
<223> OTHER INFORMATION: anti CD19 HCCDR1

<400> SEQUENCE: 111

Gly Val Ser Leu Pro Asp Tyr Gly Val Ser
1               5                   10

<210> SEQ ID NO 112
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 112

Val Ile Trp Gly Ser Glu Thr Thr Tyr Tyr Ser Ser Leu Lys Ser
1               5                   10                  15

<210> SEQ ID NO 113
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 113

Val Ile Trp Gly Ser Glu Thr Thr Tyr Tyr Gln Ser Ser Leu Lys Ser
1               5                   10                  15

<210> SEQ ID NO 114
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 114

Val Ile Trp Gly Ser Glu Thr Thr Tyr Tyr Asn Ser Ser Leu Lys Ser
1               5                   10                  15

<210> SEQ ID NO 115
<211> LENGTH: 12
<212> TYPE: PRT
<213> ORGANISM: Homo sapiens
<220> FEATURE:
<221> NAME/KEY: MISC_FEATURE
<223> OTHER INFORMATION: anti CD19 HCCDR3

<400> SEQUENCE: 115

His Tyr Tyr Tyr Gly Gly Ser Tyr Ala Met Asp Tyr
1               5                   10

<210> SEQ ID NO 116
<211> LENGTH: 242
<212> TYPE: PRT
<213> ORGANISM: Homo sapiens
<220> FEATURE:
<221> NAME/KEY: MISC_FEATURE
<223> OTHER INFORMATION: antiCD19CAR

<400> SEQUENCE: 116

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
            130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
                180                 185                 190

Lys Asp Asn Ser Lys Asn Gln Val Ser Leu Lys Leu Ser Ser Val Thr
            195                 200                 205

Ala Ala Asp Thr Ala Val Tyr Tyr Cys Ala Lys His Tyr Tyr Tyr Gly
            210                 215                 220

Gly Ser Tyr Ala Met Asp Tyr Trp Gly Gln Gly Thr Leu Val Thr Val
225                 230                 235                 240

Ser Ser

<210> SEQ ID NO 117
<211> LENGTH: 107
<212> TYPE: PRT
<213> ORGANISM: Homo sapiens
<220> FEATURE:
<221> NAME/KEY: MISC_FEATURE
<223> OTHER INFORMATION: huFMC63VLv1

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Thr
                100                 105

<210> SEQ ID NO 118
<211> LENGTH: 107
<212> TYPE: PRT
<213> ORGANISM: Homo sapiens
<220> FEATURE:
<221> NAME/KEY: MISC_FEATURE
<223> OTHER INFORMATION: HUFMC63VLV2

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Thr Val Lys Leu Leu Ile
        35                  40                  45

Tyr His Thr Ser Arg Leu His Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105
```

<210> SEQ ID NO 119
<211> LENGTH: 107
<212> TYPE: PRT
<213> ORGANISM: Homo sapiens
<220> FEATURE:
<221> NAME/KEY: MISC_FEATURE
<223> OTHER INFORMATION: HUFMC63VLV3

<400> SEQUENCE: 119

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
                 20                  25                  30

Leu Asn Trp Tyr Gln Gln Lys Pro Asp Gly Thr Val Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105
```

<210> SEQ ID NO 120
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV1

<400> SEQUENCE: 120

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Val Ser Leu Pro Asp Tyr
                 20                  25                  30

Gly Val Ser Trp Ile Arg Gln Pro Pro Gly Lys Gly Leu Glu Trp Ile
             35                  40                  45

Gly Val Ile Trp Gly Ser Glu Thr Thr Tyr Tyr Asn Ser Ala Leu Lys
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
            115                 120
```

<210> SEQ ID NO 121
<211> LENGTH: 120

```
<212> TYPE: PRT
<213> ORGANISM: Homo sapiens
<220> FEATURE:
<221> NAME/KEY: MISC_FEATURE
<223> OTHER INFORMATION: HUFMC63VHV2

<400> SEQUENCE: 121

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 122
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV3

<400> SEQUENCE: 122

Gln Val Gln Leu Gln Glu Ser Gly Pro Gly Leu Val Lys Pro Ser Gln
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 123
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV4

<400> SEQUENCE: 123

Gln Val Gln Leu Gln Glu Ser Gly Pro Gly Leu Val Lys Pro Ser Gln
```

```
                1               5                   10                  15
            Thr Leu Ser Val Thr Cys Thr Val Ser Gly Val Ser Leu Pro Asp Tyr
                            20                  25                  30

Gly Val Ser Trp Ile Arg Gln Pro Pro Arg Lys Gly Leu Glu Trp Leu
                        35                  40                  45

Gly Val Ile Trp Gly Ser Glu Thr Thr Tyr Tyr Asn Ser Ala Leu Lys
                    50                  55                  60

Ser Arg Leu Thr Ile Ser Lys Asp Asn Ser Lys Ser Gln Val Ser Leu
                65                  70                  75                  80

Lys Met Ser Ser Val Thr Ala Ala Asp Thr Ala Ile Tyr Tyr Cys Ala
                            85                  90                  95

Lys His Tyr Tyr Tyr Gly Gly Ser Tyr Ala Met Asp Tyr Trp Gly Gln
                            100                 105                 110

Gly Thr Ser Val Thr Val Ser Ser
                        115                 120

<210> SEQ ID NO 124
<211> LENGTH: 11
<212> TYPE: PRT
<213> ORGANISM: Homo sapiens
<220> FEATURE:
<221> NAME/KEY: MISC_FEATURE
<223> OTHER INFORMATION: huFMC63VLv1 CDR1

<400> SEQUENCE: 124

Arg Ala Ser Gln Asp Ile Ser Lys Tyr Leu Asn
1               5                   10

<210> SEQ ID NO 125
<211> LENGTH: 7
<212> TYPE: PRT
<213> ORGANISM: Homo sapiens
<220> FEATURE:
<221> NAME/KEY: MISC_FEATURE
<223> OTHER INFORMATION: huFMC63VLv1 CDR2

<400> SEQUENCE: 125

His Thr Ser Arg Leu His Ser
1               5

<210> SEQ ID NO 126

<400> SEQUENCE: 126

000

<210> SEQ ID NO 127
<211> LENGTH: 11
<212> TYPE: PRT
<213> ORGANISM: Homo sapiens
<220> FEATURE:
<221> NAME/KEY: MISC_FEATURE
<223> OTHER INFORMATION: HUFMC63VLV2 CDR1

<400> SEQUENCE: 127

Arg Ala Ser Gln Asp Ile Ser Lys Tyr Leu Asn
1               5                   10

<210> SEQ ID NO 128
<211> LENGTH: 7
<212> TYPE: PRT
<213> ORGANISM: Homo sapiens
<220> FEATURE:
<221> NAME/KEY: MISC_FEATURE
```

<223> OTHER INFORMATION: HUFMC63VLV2 CDR2

<400> SEQUENCE: 128

His Thr Ser Arg Leu His Ser
1               5

<210> SEQ ID NO 129
<211> LENGTH: 9
<212> TYPE: PRT
<213> ORGANISM: Homo sapiens
<220> FEATURE:
<221> NAME/KEY: MISC_FEATURE
<223> OTHER INFORMATION: HUFMC63VLV2 CDR3

<400> SEQUENCE: 129

Gln Gln Gly Asn Thr Leu Pro Tyr Thr
1               5

<210> SEQ ID NO 130
<211> LENGTH: 11
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR1

<400> SEQUENCE: 130

Arg Ala Ser Gln Asp Ile Ser Lys Tyr Leu Asn
1               5                   10

<210> SEQ ID NO 131
<211> LENGTH: 7
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR2

<400> SEQUENCE: 131

His Thr Ser Arg Leu His Ser
1               5

<210> SEQ ID NO 132
<211> LENGTH: 9
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR3

<400> SEQUENCE: 132

Gln Gln Gly Asn Thr Leu Pro Tyr Thr
1               5

<210> SEQ ID NO 133
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR1

<400> SEQUENCE: 133

Gly Val Ser Leu Pro Asp Tyr Gly Val Ser
1               5                   10

<210> SEQ ID NO 134

```
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR2

<400> SEQUENCE: 134

Val Ile Trp Gly Ser Glu Thr Thr Tyr Tyr Asn Ser Ala Leu Lys Ser
1               5                   10                  15

<210> SEQ ID NO 135
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR3

<400> SEQUENCE: 135

His Tyr Tyr Tyr Gly Gly Ser Tyr Ala Met Asp Tyr
1               5                   10

<210> SEQ ID NO 136
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR1

<400> SEQUENCE: 136

Gly Val Ser Leu Pro Asp Tyr Gly Val Ser
1               5                   10

<210> SEQ ID NO 137
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR2

<400> SEQUENCE: 137

Val Ile Trp Gly Ser Glu Thr Thr Tyr Tyr Asn Ser Ala Leu Lys Ser
1               5                   10                  15

<210> SEQ ID NO 138
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR3

<400> SEQUENCE: 138

His Tyr Tyr Tyr Gly Gly Ser Tyr Ala Met Asp Tyr
1               5                   10

<210> SEQ ID NO 139
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR1

<400> SEQUENCE: 139
```

```
Gly Val Ser Leu Pro Asp Tyr Gly Val Ser
1               5                   10
```

<210> SEQ ID NO 140
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR2

<400> SEQUENCE: 140

```
Val Ile Trp Gly Ser Glu Thr Thr Tyr Tyr Asn Ser Ala Leu Lys Ser
1               5                   10                  15
```

<210> SEQ ID NO 141
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR3

<400> SEQUENCE: 141

```
His Tyr Tyr Tyr Gly Gly Ser Tyr Ala Met Asp Tyr
1               5                   10
```

<210> SEQ ID NO 142
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR1

<400> SEQUENCE: 142

```
Gly Val Ser Leu Pro Asp Tyr Gly Val Ser
1               5                   10
```

<210> SEQ ID NO 143
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR2

<400> SEQUENCE: 143

```
Val Ile Trp Gly Ser Glu Thr Thr Tyr Tyr Asn Ser Ala Leu Lys Ser
1               5                   10                  15
```

<210> SEQ ID NO 144
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR3

<400> SEQUENCE: 144

```
His Tyr Tyr Tyr Gly Gly Ser Tyr Ala Met Asp Tyr
1               5                   10
```

<210> SEQ ID NO 145
<211> LENGTH: 1122
<212> TYPE: DNA
<213> ORGANISM: Homo sapiens
<220> FEATURE:

<221> NAME/KEY: misc_feature
<223> OTHER INFORMATION: DNA NKG2D-Ox40-CD3z

<400> SEQUENCE: 145

```
atggccttac cagtgaccgc cttgctcctg ccgctggcct tgctgctcca cgccgccagg        60
ccgttattca accaagaagt tcaaattccc ttgaccgaaa gttactgtgg cccatgtcct       120
aaaaactgga tatgttacaa aaataactgc taccaatttt ttgatgagag taaaaactgg       180
tatgagagcc aggcttcttg tatgtctcaa aatgccagcc ttctgaaagt atacagcaaa       240
gaggaccagg atttacttaa actggtgaag tcatatcatt ggatgggact agtacacatt       300
ccaacaaatg gatcttggca gtgggaagat ggctccattc tctcacccaa cctactaaca       360
ataattgaaa tgcagaaggg agactgtgca ctctatgcct cgagctttaa aggctatata       420
gaaaactgtt caactccaaa tacgtacatc tgcatgcaaa ggactgtgac cacgacgcca       480
gcgccgcgac caccaacacc ggcgcccacc atcgcgtcgc agcccctgtc cctgcgccca       540
gaggcgtgcc ggccagcggc gggggcgca gtgcacacga gggggctgga cttcgcctgt       600
gatatctaca tctgggcgcc cttggccggg acttgtgggg tcttctcct gtcactggtt       660
atcacccttt actgccggag ggaccagagg ctgccccccg atgcccacaa gccccctggg       720
ggaggcagtt tccggacccc catccaagag gagcaggccg acgcccactc caccctggcc       780
aagatcagag tgaagttcag caggagcgca gacgcccccg cgtaccagca gggccagaac       840
cagctctata acgagctcaa tctaggacga agagaggagt acgatgtttt ggacaagaga       900
cgtggccggg accctgagat gggggaaag ccgagaagga agaaccctca ggaaggcctg       960
tacaatgaac tgcagaaaga taagatggcg gaggcctaca gtgagattgg gatgaaaggc      1020
gagcgccgga ggggcaaggg gcacgatggc ctttaccagg gtctcagtac agccaccaag      1080
gacacctacg acgccttca catgcaggcc ctgccccctc gc                          1122
```

<210> SEQ ID NO 146
<211> LENGTH: 341
<212> TYPE: PRT
<213> ORGANISM: Homo sapiens
<220> FEATURE:
<221> NAME/KEY: MISC_FEATURE
<223> OTHER INFORMATION: Amino Acid NKG2D-OX40-CD3z

<400> SEQUENCE: 146

```
Met Ala Leu Pro Val Thr Ala Leu Leu Leu Pro Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
```

```
                130             135             140
Thr Pro Asn Thr Tyr Ile Cys Met Gln Arg Thr Val Glu Ser Lys Tyr
145                 150                 155                 160

Gly Pro Pro Cys Pro Ser Cys Pro Ile Tyr Ile Trp Ala Pro Leu Ala
                165                 170                 175

Gly Thr Cys Gly Val Leu Leu Leu Ser Leu Val Ile Thr Leu Tyr Cys
                180                 185                 190

Arg Arg Asp Gln Arg Leu Pro Pro Asp Ala His Lys Pro Pro Gly Gly
                195                 200                 205

Gly Ser Phe Arg Thr Pro Ile Gln Glu Glu Gln Ala Asp Ala His Ser
        210                 215                 220

Thr Leu Ala Lys Ile Arg Val Lys Phe Ser Arg Ser Ala Asp Ala Pro
225                 230                 235                 240

Ala Tyr Gln Gln Gly Gln Asn Gln Leu Tyr Asn Glu Leu Asn Leu Gly
                245                 250                 255

Arg Arg Glu Glu Tyr Asp Val Leu Asp Lys Arg Arg Gly Arg Asp Pro
                260                 265                 270

Glu Met Gly Gly Lys Pro Arg Arg Lys Asn Pro Gln Glu Gly Leu Tyr
                275                 280                 285

Asn Glu Leu Gln Lys Asp Lys Met Ala Glu Ala Tyr Ser Glu Ile Gly
        290                 295                 300

Met Lys Gly Glu Arg Arg Arg Gly Lys Gly His Asp Gly Leu Tyr Gln
305                 310                 315                 320

Gly Leu Ser Thr Ala Thr Lys Asp Thr Tyr Asp Ala Leu His Met Gln
                325                 330                 335

Ala Leu Pro Pro Arg
            340

<210> SEQ ID NO 147
<211> LENGTH: 1467
<212> TYPE: DNA
<213> ORGANISM: Homo sapiens
<220> FEATURE:
<221> NAME/KEY: misc_feature
<223> OTHER INFORMATION: DNA Sequence FMC63_CD28_CAR

<400> SEQUENCE: 147
atgcttctcc tggtgacaag ccttctttac cacacccagc attcctcctg atcccagaca     60
tccagataca tcctccctgt ctgcctctct gggagacaga gtcaccgggc aagtcaggac    120
attagtaaat atttaaattg gtatcagctc tgtgagtgac acagacatca gttgcagcag    180
aaaccagatg gaactgttaa actcctgatc taccatacat caagattaca ctcaggagtc    240
ccatcaaggt tcagtggcag tgggtctgga acagattatt ctctcaccat tagcaacctg    300
gagcaagaag atattgccac ttactttgc caacagggta atacgcttcc gtacacgttc    360
ggagggggga ctaagttgga aataacaggc tccacctctg gatccggcaa gcccggatct    420
ggcgagggat ccaccaaggg cgaggtgaaa ctgcaggagt caggacctgg cctggtggcg    480
ccctcacaga gcctgtccgt cacatgcact gtctcagggg tctcattacc cgactatggt    540
gtaagctgga ttcgccagcc tccacgaaag gtctggagt ggctgggagt aatatggggt    600
agtgaaacca catactataa ttcagctctc aaatccagac tgaccatcat caaggacaac    660
tccaagagcc aagttttctt aaaaatgaac agtctgcaaa ctgatgacac agccatttac    720
tactgtgcca acattatta ctacggtggt agctatgcta tggactactg ggtcaagga    780 acctcagtca ccgtctcctc agcggccgca attgaagtta tgtatcctcc tccttaccta    840
```

```
gacaatgaga agagcaatgg aaccattatc catgtgaaag ggaaacacct ttgtccaagt    900
cccctatttc ccggaccttc taagccctt tggtgctgg tggtggttgg gggagtcctg    960
gcttgctata gcttgctagt aacagtggcc tttattattt tctgggtgag gagtaagagg   1020
agcaggctcc tgcacagtga ctacatgaac atgactcccc gccgcccgg gcccacccgc   1080 aagcattacc agccctatgc cccaccacgc gacttcgcag cctatcgctc cagagtgaag   1140
ttcagcagga gcgcagacgc ccccgcgtac cagcagggcc agaaccagct ctataacgag   1200
ctcaatctag gacgaagaga ggagtacgat gttttggaca agagacgtgg ccgggaccct   1260
gagatggggg gaaagccgag aaggaagaac cctcaggaag gcctgtacaa tgaactgcag   1320
aaagataaga tggcggaggc ctacagtgag attgggatga aggcgagcg ccggagggc   1380 aaggggcacg atggccttta ccagggtctc agtacagcca ccaaggacac ctacgacgcc   1440
cttcacatgc aggccctgcc ccctcgc                                      1467
```

<210> SEQ ID NO 148
<211> LENGTH: 331
<212> TYPE: DNA
<213> ORGANISM: Homo sapiens
<220> FEATURE:
<221> NAME/KEY: misc_feature
<223> OTHER INFORMATION: DNA Sequence FCM63 Light Chain

<400> SEQUENCE: 148

```
gacatccaga tacatcctcc ctgtctgcct ctctgggaga cagagtcacc gggcaagtca     60
ggacattagt aaatatttaa attggtatca gctctgtgag tgacacagac atcagttgca    120
gcagaaacca gatggaactg ttaaactcct gatctaccat acatcaagat tacactcagg    180
agtcccatca aggttcagtg gcagtgggtc tggaacagat tattctctca ccattagcaa    240
cctggagcaa gaagatattg ccacttactt tgccaacag ggtaatacgc ttccgtacac    300
gttcggaggg gggactaagt tggaaataac a                                  331
```

<210> SEQ ID NO 149
<211> LENGTH: 54
<212> TYPE: DNA
<213> ORGANISM: Homo sapiens
<220> FEATURE:
<221> NAME/KEY: misc_feature
<223> OTHER INFORMATION: DNA Sequence FMC63 Linker

<400> SEQUENCE: 149

```
ggctccacct ctggatccgg caagcccgga tctggcgagg gatccaccaa gggc            54
```

<210> SEQ ID NO 150
<211> LENGTH: 360
<212> TYPE: DNA
<213> ORGANISM: Homo sapiens
<220> FEATURE:
<221> NAME/KEY: misc_feature
<223> OTHER INFORMATION: DNA Sequence FMC63 Heavy Chain

<400> SEQUENCE: 150

```
gaggtgaaac tgcaggagtc aggacctggc ctggtggcgc cctcacagag cctgtccgtc     60
acatgcactg tctcagggt ctcattaccc gactatggtg taagctggat tcgccagcct    120
ccacgaaagg gtctggagtg gctgggagta atatggggta gtgaaaccac atactataat    180
tcagctctca atccagact gaccatcatc aaggacaact ccaagagcca gttttctta    240 aaaatgaaca gtctgcaaac tgatgacaca gccatttact actgtgccaa acattattac    300
```

```
tacggtggta gctatgctat ggactactgg ggtcaaggaa cctcagtcac cgtctcctca    360

<210> SEQ ID NO 151
<211> LENGTH: 117
<212> TYPE: DNA
<213> ORGANISM: Homo sapiens
<220> FEATURE:
<221> NAME/KEY: misc_feature
<223> OTHER INFORMATION: DNA Sequence CD28 spacer

<400> SEQUENCE: 151
attgaagtta tgtatcctcc tccttaccta gacaatgaga agagcaatgg aaccattatc    60
catgtgaaag ggaaacacct tgtccaagt cccctatttc ccggaccttc taagccc       117

<210> SEQ ID NO 152
<211> LENGTH: 81
<212> TYPE: DNA
<213> ORGANISM: Homo sapiens
<220> FEATURE:
<221> NAME/KEY: misc_feature
<223> OTHER INFORMATION: DNA Sequence transmembrane region

<400> SEQUENCE: 152
ttttgggtgc tggtggtggt tgggggagtc ctggcttgct atagcttgct agtaacagtg    60
gcctttatta ttttctgggt g                                             81

<210> SEQ ID NO 153
<211> LENGTH: 123
<212> TYPE: DNA
<213> ORGANISM: Homo sapiens
<220> FEATURE:
<221> NAME/KEY: misc_feature
<223> OTHER INFORMATION: DNA Sequence CD28 Co-stim

<400> SEQUENCE: 153
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 154
<211> LENGTH: 336
<212> TYPE: DNA
<213> ORGANISM: Homo sapiens
<220> FEATURE:
<221> NAME/KEY: misc_feature
<223> OTHER INFORMATION: CD3zeta [repeat]

<400> SEQUENCE: 154
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc    240 cggagggggca aggggcacga tggcctttac cagggtctca gtacagccac caaggacacc   300
tacgacgccc ttcacatgca ggccctgccc cctcgc                             336

<210> SEQ ID NO 155
<211> LENGTH: 342
<212> TYPE: DNA
<213> ORGANISM: Homo sapiens
<220> FEATURE:
```

<221> NAME/KEY: misc_feature
<223> OTHER INFORMATION: Coding sequence for mbIL15

<400> SEQUENCE: 155

```
aactgggtca acgtgattag cgatttgaag aaaatcgagg accttataca gtctatgcat    60
attgacgcta cactgtatac tgagagtgat gtacacccgt cctgtaaggt aacggccatg   120
aaatgctttc ttctggagct ccaggtcatc agcttggagt ctggggacgc aagcatccac   180
gatacggttg aaaacctcat catccttgcg aacaactctc tctcatctaa tggaaacgtt   240
acagagagtg ggtgtaagga gtgcgaagag ttggaagaaa aaacatcaa agaatttctt    300
caatccttcg ttcacatagt gcaaatgttc attaacacgt cc                     342
```

<210> SEQ ID NO 156
<211> LENGTH: 135
<212> TYPE: DNA
<213> ORGANISM: Homo sapiens
<220> FEATURE:
<221> NAME/KEY: misc_feature
<223> OTHER INFORMATION: DNA seq of cd hinge rev. trans from No: 157

<400> SEQUENCE: 156

```
accaccaccc cggcgccgcg cccgccgacc ccggcgccga ccattgcgag ccagccgctg    60
agcctgcgcc cggaagcgtg ccgcccggcg gcgggcggcg cggtgcatac ccgcggcctg   120
gattttgcgt gcgat                                                   135
```

<210> SEQ ID NO 157
<211> LENGTH: 45
<212> TYPE: PRT
<213> ORGANISM: Homo sapiens
<220> FEATURE:
<221> NAME/KEY: MISC_FEATURE
<223> OTHER INFORMATION: Amino Acid CD8 Hinge

<400> SEQUENCE: 157

```
Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
            20                  25                  30
Gly Ala Val His Thr Arg Gly Leu Asp Phe Ala Cys Asp
        35                  40                  45
```

<210> SEQ ID NO 158
<211> LENGTH: 72
<212> TYPE: DNA
<213> ORGANISM: Homo sapiens
<220> FEATURE:
<221> NAME/KEY: misc_feature
<223> OTHER INFORMATION: DNA seq of CD8 TM rev trans from No: 159

<400> SEQUENCE: 158

```
atttatattt gggcgccgct ggcgggcacc tgcggcgtgc tgctgctgag cctggtgatt    60
accctgtatt gc                                                       72
```

<210> SEQ ID NO 159
<211> LENGTH: 24
<212> TYPE: PRT
<213> ORGANISM: Homo sapiens
<220> FEATURE:
<221> NAME/KEY: MISC_FEATURE
<223> OTHER INFORMATION: AA Sequence CD8 TM

<400> SEQUENCE: 159

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 160
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-1

<400> SEQUENCE: 160

| | | | | | |
|---|---|---|---|---|---|
| gaattcgccg | ccaccatggc | cttaccagtg | accgccttgc | tcctgccgct | ggccttgctg | 60 |
| ctccacgccg | ccaggccgga | ctacaaagac | gatgacgata | aaggcggtgg | tggctctggt | 120 |
| ggtggcggca | gcgatattca | gatgacccag | agcccgagca | gcctgagcgc | gagcgtgggc | 180 |
| gatcgcgtga | ccattacctg | ccgcgcgagc | caggatatta | gcaaatatct | gaactggtat | 240 |
| cagcagaaac | cgggcggcac | cgtgaaactg | ctgatttatc | ataccagccg | cctgcatagc | 300 |
| ggcgtgccga | gccgctttag | cggcagcggc | agcggcaccg | attttaccct | gaccattagc | 360 |
| agcctgcagc | cggaagatat | tgcgacctat | tattgccagc | agggcaacac | cctgccgtat | 420 |
| acctttggcg | gcgcaccaa | actggaaatt | accgtgggcg | gtggctcggg | cggtggtggg | 480 |
| tcgggtggcg | gcggatctca | ggtgcagctg | caggaaagcg | gcccgggcct | ggtgaaaccg | 540 |
| agccagaccc | tgagcctgac | ctgcaccgtg | agcggcgtga | gcctgccgga | ttatggcgtg | 600 |
| agctggattc | gccagccgcc | gggcaaaggc | ctggaatgga | ttggcgtgat | tggggcagc | 660 |
| gaaaccacct | attataacag | cgcgctgaaa | agccgcctga | ccattagcaa | agataacagc | 720 |
| aaaaaccagg | tgagcctgaa | actgagcagc | gtgaccgcgg | cggataccgc | ggtgtattat | 780 |
| tgcgcgaaac | attattatta | tggcggcagc | tatgcgatgg | attattgggg | ccagggcacc | 840 |
| agcgtgaccg | tgagcagcac | cacgacgcca | gcgcccgcgac | caccaacacc | ggcgcccacc | 900 |
| atcgcgtcgc | agcccctgtc | cctgcgccca | gaggcgtgcc | ggccagcggc | gggggcgca | 960 |
| gtgcacacga | gggggctgga | cttcgcctgt | gatatctaca | tctgggcgcc | cttggccggg | 1020 |
| acttgtgggg | tccttctcct | gtcactggtt | atcaccttt | actgccggag | ggaccagagg | 1080 |
| ctgcccccg | atgcccacaa | gcccctgggg | gaggcagtt | tccggacccc | catccaagag | 1140 |
| gagcaggccg | acgcccactc | caccctggcc | aagatcagag | tgaagttcag | caggagcgca | 1200 |
| gacgcccccg | cgtaccagca | gggccagaac | cagctctata | acgagctcaa | tctaggacga | 1260 |
| agagaggagt | acgatgtttt | ggacaagaga | cgtggccggg | accctgagat | ggggggaaag | 1320 |
| ccgagaagga | agaaccctca | ggaaggcctg | tacaatgaac | tgcagaaaga | taagatggcg | 1380 |
| gaggcctaca | gtgagattgg | gatgaaaggc | gagcgccgga | ggggcaaggg | gcacgatggc | 1440 |
| ctttaccagg | gtctcagtac | agccaccaag | gacacctacg | acgcccttca | catgcaggcc | 1500 |
| ctgccccctc | gcggctctgg | cgagggaagg | ggttccctgc | ttacttgcgg | cgacgtcgaa | 1560 |
| gagaatcccg | gtccgatggc | cctcccagta | actgccctcc | ttttgcccct | cgcactcctt | 1620 |
| cttcatgccg | ctcgccccaa | ctgggtcaac | gtgattagca | atttgaagaa | aatcgaggac | 1680 |
| cttatacagt | ctatgcatat | tgacgctaca | ctgtatactg | agagtgatgt | acacccgtcc | 1740 |
| tgtaaggtaa | cggccatgaa | atgctttctt | ctggagctcc | aggtcatcag | cttggagtct | 1800 |
| ggggacgcaa | gcatccacga | tacggttgaa | aacctcatca | tccttgcgaa | caactctctc | 1860 |

-continued

```
tcatctaatg gaaacgttac agagagtggg tgtaaggagt gcgaagagtt ggaagaaaaa    1920
aacatcaaag aatttcttca atccttcgtt cacatagtgc aaatgttcat taacacgtcc    1980
actaccacac ccgccccgag gccacctacg ccggcaccga ctatcgccag tcaacccctc    2040
tctctgcgcc ccgaggcttg ccggcctgcg gctggtgggg cggtccacac ccggggcctg    2100
gattttgcgt gcgatatata catctgggca cctcttgccg gcacctgcgg agtgctgctt    2160
ctctcactcg ttattacgct gtactgctaa gcggccgcgt cgac                    2204
```

<210> SEQ ID NO 161
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-1

<400> SEQUENCE: 161

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Lys Gly Leu Glu Trp
            195                 200                 205

Ile Gly Val Ile Trp Gly Ser Glu Thr Thr Tyr Tyr Asn Ser Ala Leu
210                 215                 220

Lys Ser Arg Leu Thr Ile Ser Lys Asp Asn Ser Lys Asn Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
```

```
            290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
                325                 330                 335
Cys Gly Val Leu Leu Leu Ser Leu Val Ile Thr Leu Tyr Cys Arg Arg
                340                 345                 350
Asp Gln Arg Leu Pro Pro Asp Ala His Lys Pro Gly Gly Gly Gly Ser
                355                 360                 365
Phe Arg Thr Pro Ile Gln Glu Glu Gln Ala Asp Ala His Ser Thr Leu
                370                 375                 380
Ala Lys Ile Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
                405                 410                 415
Glu Glu Tyr Asp Val Leu Asp Lys Arg Arg Gly Arg Asp Pro Glu Met
                420                 425                 430
Gly Gly Lys Pro Arg Arg Lys Asn Pro Gln Glu Gly Leu Tyr Asn Glu
                435                 440                 445
Leu Gln Lys Asp Lys Met Ala Glu Ala Tyr Ser Glu Ile Gly Met Lys
                450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                485                 490                 495
Pro Pro Arg Gly Ser Gly Gly Arg Gly Ser Leu Leu Thr Cys Gly
                500                 505                 510
Asp Val Glu Glu Asn Pro Gly Pro Met Ala Leu Pro Val Thr Ala Leu
                515                 520                 525
Leu Leu Pro Leu Ala Leu Leu Leu His Ala Ala Arg Pro Asn Trp Val
                530                 535                 540
Asn Val Ile Ser Asp Leu Lys Lys Ile Glu Asp Leu Ile Gln Ser Met
545                 550                 555                 560
His Ile Asp Ala Thr Leu Tyr Thr Glu Ser Asp Val His Pro Ser Cys
                565                 570                 575
Lys Val Thr Ala Met Lys Cys Phe Leu Leu Glu Leu Gln Val Ile Ser
                580                 585                 590
Leu Glu Ser Gly Asp Ala Ser Ile His Asp Thr Val Glu Asn Leu Ile
                595                 600                 605
Ile Leu Ala Asn Asn Ser Leu Ser Ser Asn Gly Asn Val Thr Glu Ser
                610                 615                 620
Gly Cys Lys Glu Cys Glu Glu Leu Glu Glu Lys Asn Ile Lys Glu Phe
625                 630                 635                 640
Leu Gln Ser Phe Val His Ile Val Gln Met Phe Ile Asn Thr Ser Thr
                645                 650                 655
Thr Thr Pro Ala Pro Arg Pro Pro Thr Pro Ala Pro Thr Ile Ala Ser
                660                 665                 670
Gln Pro Leu Ser Leu Arg Pro Glu Ala Cys Arg Pro Ala Ala Gly Gly
                675                 680                 685
Ala Val His Thr Arg Gly Leu Asp Phe Ala Cys Asp Ile Tyr Ile Trp
                690                 695                 700
Ala Pro Leu Ala Gly Thr Cys Gly Val Leu Leu Leu Ser Leu Val Ile
705                 710                 715                 720
```

Thr Leu Tyr Cys

<210> SEQ ID NO 162
<211> LENGTH: 2187
<212> TYPE: DNA
<213> ORGANISM: Homo sapiens
<220> FEATURE:
<221> NAME/KEY: misc_feature
<223> OTHER INFORMATION: DNA NK19H-2

<400> SEQUENCE: 162

| | | | | |
|---|---|---|---|---|
| gaattcgccg | ccaccatggc | cttaccagtg | accgccttgc | tcctgccgct ggccttgctg | 60 |
| ctccacgccg | ccaggccgga | ctacaaagac | gatgacgata | aaggcggtgg tggctctggt | 120 |
| ggtggcggca | gcgatattca | gatgacccag | agcccgagca | gcctgagcgc gagcgtgggc | 180 |
| gatcgcgtga | ccattacctg | ccgcgcgagc | caggatatta | gcaaatatct gaactggtat | 240 |
| cagcagaaac | cgggcggcac | cgtgaaactg | ctgatttatc | ataccagccg cctgcatagc | 300 |
| ggcgtgccga | gccgctttag | cggcagcggc | agcggcaccg | attttaccct gaccattagc | 360 |
| agcctgcagc | cggaagatat | tgcgacctat | ttttgccagc | agggcaacac cctgccgtat | 420 |
| acctttggcc | gcggcaccaa | actggaaatt | accgtggcg | gtggctcggg cggtggtggg | 480 |
| tcgggtggcg | gcggatctca | ggtgcagctg | caggaaagcg | gcccgggcct ggtgaaaccg | 540 |
| agccagaccc | tgagcctgac | ctgcaccgtg | agcggcgtga | gctgccgga ttatggcgtg | 600 |
| agctggattc | gccagccgcc | gggcaaaggc | ctggaatgga | ttggcgtgat tggggcagc | 660 |
| gaaaccacct | attataacag | cgcgctgaaa | agcgccctga | ccattagcaa agataacagc | 720 |
| aaaaaccagg | tgagcctgaa | actgagcagc | gtgaccgcgg | cggataccgc ggtgtattat | 780 |
| tgcgcgaaac | attattatta | tggcggcagc | tatgcgatgg | attattgggg ccagggcacc | 840 |
| agcgtgaccg | tgagcagcac | cacgacgcca | gcgccgcgac | caccaacacc ggcgcccacc | 900 |
| atcgcgtcgc | agcccctgtc | cctgcgccca | gaggcgtgcc | ggccagcggc gggggcgca | 960 |
| gtgcacacga | ggggctgga | cttcgcctgt | gatatctaca | tctgggcgcc cttggccggg | 1020 |
| acttgtgggg | tccttctcct | gtcactggtt | atcacccttt | actgccggag ggaccagagg | 1080 |
| ctgcccccg | atgcccacaa | gccccctggg | ggaggcagtt | tccggacccc catccaagag | 1140 |
| gagcaggccg | acgcccactc | caccctggcc | aagatcagag | tgaagttcag caggagcgca | 1200 |
| gacgcccccg | cgtaccagca | gggccagaac | cagctctata | acgagctcaa tctaggacga | 1260 |
| agagaggagt | acgatgtttt | ggacaagaga | cgtggccggg | accctgagat gggggaaag | 1320 |
| ccgagaagga | agaaccctca | ggaaggcctg | tacaatgaac | tgcagaaaga taagatggcg | 1380 |
| gaggcctaca | gtgagattgg | gatgaaaggc | gagcgccgga | ggggcaaggg gcacgatggc | 1440 |
| ctttaccagg | gtctcagtac | agccaccaag | gacacctacg | acgcccttca catgcaggcc | 1500 |
| ctgcccctc | gcggctctgg | cgagggaagg | ggttccctgc | ttacttgcgg cgacgtcgaa | 1560 |
| gagaatcccg | gtccgatggc | cctcccagta | actgccctcc | ttttgcccct cgcactcctt | 1620 |
| cttcatgccg | ctcgccccaa | ctgggtcaac | gtgattagcg | atttgaagaa aatcgaggac | 1680 |
| cttatacagt | ctatgcatat | tgacgctaca | ctgtatactg | agagtgatgt acacccgtcc | 1740 |
| tgtaaggtaa | cggccatgaa | atgctttctt | ctggagctcc | aggtcatcag cttggagtct | 1800 |
| ggggacgcaa | gcatccacga | tacggttgaa | aacctcatca | tccttgcgaa caactctctc | 1860 |
| tcatctaatg | gaaacgttac | agagagtggg | tgtaaggagt | gcgaagagtt ggaagaaaaa | 1920 |
| aacatcaaag | aatttcttca | atccttcgtt | cacatagtgc | aaatgttcat taacacgtcc | 1980 |

```
actaccacac cgccccgag gccacctacg ccggcaccga ctatcgccag tcaaccctc   2040 tctctgcgcc cgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgc                                      2187
```

<210> SEQ ID NO 163
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-2

<400> SEQUENCE: 163

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Ile Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Asn Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320
```

```
Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Gly Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

<210> SEQ ID NO 164
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-3

<400> SEQUENCE: 164

| | | | | | |
|---|---|---|---|---|---|
| gaattcgccg | ccaccatggc | cttaccagtg | accgccttgc | tcctgccgct | ggccttgctg | 60 |
| ctccacgccg | ccaggccgga | ctacaaagac | gatgacgata | aaggcggtgg | tggctctggt | 120 |
| ggtggcggca | gcgatattca | gatgacccag | agcccgagca | gcctgagcgc | gagcgtgggc | 180 |
| gatcgcgtga | ccattacctg | ccgcgcgagc | caggatatta | gcaaatatct | gaactggtat | 240 |
| cagcagaaac | cggatggcac | cgtgaaactg | ctgatttatc | ataccagccg | cctgcatagc | 300 |
| ggcgtgccga | gccgctttag | cggcagcggc | agcggcaccg | attataccct | gaccattagc | 360 |
| agcctgcagc | cggaagatat | tgcgacctat | ttttgccagc | agggcaacac | cctgccgtat | 420 |
| acctttggcc | gcgcaccaa | actggaaatt | accgtggcg | gtggctcggg | cggtggtggg | 480 |
| tcgggtggcg | gcggatctca | ggtgcagctg | caggaaagcg | gcccgggcct | ggtgaaaccg | 540 |
| agccagaccc | tgagcctgac | ctgcaccgtg | agcggcgtga | gctgccgga | ttatggcgtg | 600 |
| agctggattc | gccagccgcc | gggcaaaggc | ctggaatgga | ttggcgtgat | ttggggcagc | 660 |
| gaaaccacct | attataacag | cgcgctgaaa | agcgcctga | ccattagcaa | agataacagc | 720 |
| aaaaaccagg | tgagcctgaa | actgagcagc | gtgaccgcgg | cggataccgc | ggtgtattat | 780 |
| tgcgcgaaac | attattatta | tggcggcagc | tatgcgatgg | attattgggg | ccagggcacc | 840 |
| agcgtgaccg | tgagcagcac | cacgacgcca | gcgccgcgac | caccaacacc | ggcgcccacc | 900 |
| atcgcgtcgc | agccctgtc | cctgcgccca | gaggcgtgcc | ggccagcggc | gggggcgca | 960 |
| gtgcacacga | gggggctgga | cttcgcctgt | gatatctaca | tctgggcgcc | cttggccggg | 1020 |
| acttgtgggg | tccttctcct | gtcactggtt | atcaccctt | actgccggag | ggaccagagg | 1080 |
| ctgcccccg | atgcccacaa | gccccctggg | ggaggcagtt | ccggacccc | catccaagag | 1140 |
| gagcaggcc | acgcccactc | caccctggcc | aagatcagag | tgaagttcag | caggagcgca | 1200 |
| gacgcccccg | cgtaccagca | gggccagaac | cagctctata | acgagctcaa | tctaggacga | 1260 |
| agagaggagt | acgatgtttt | ggacaagaga | cgtggccggg | accctgagat | ggggggaaag | 1320 |
| ccgagaagga | agaaccctca | ggaaggcctg | tacaatgaac | tgcagaaaga | taagatggcg | 1380 |
| gaggcctaca | gtgagattgg | gatgaaaggc | gagcgccgga | ggggcaaggg | gcacgatggc | 1440 |
| ctttaccagg | gtctcagtac | agccaccaag | gacacctacg | acgcccttca | catgcaggcc | 1500 |
| ctgccccctc | gcggctctgg | cgagggaagg | ggttccctgc | ttacttgcgg | cgacgtcgaa | 1560 |
| gagaatcccg | gtccgatggc | cctcccagta | actgccctcc | ttttgcccct | cgcactcctt | 1620 |
| cttcatgccg | ctcgccccaa | ctgggtcaac | gtgattagcg | atttgaagaa | aatcgaggac | 1680 |
| cttatacagt | ctatgcatat | tgacgctaca | ctgtatactg | agagtgatgt | acaccccgtcc | 1740 |
| tgtaaggtaa | cggccatgaa | atgctttctt | ctggagctcc | aggtcatcag | cttggagtct | 1800 |
| ggggacgcaa | gcatccacga | tacggttgaa | aacctcatca | tccttgcgaa | caactctctc | 1860 |
| tcatctaatg | gaaacgttac | agagagtggg | tgtaaggagt | gcgaagagtt | ggaagaaaaa | 1920 |
| aacatcaaag | aatttcttca | atccttcgtt | cacatagtgc | aaatgttcat | taacacgtcc | 1980 |
| actaccacac | ccgccccgag | gccacctacg | ccggcaccga | ctatcgccag | tcaacccctc | 2040 |
| tctctgcgcc | ccgaggcttg | ccggcctgcg | gctggtgggg | cggtccacac | ccggggcctg | 2100 |

```
gattttgcgt gcgatatata catctgggca cctcttgccg gcacctgcgg agtgctgctt    2160
ctctcactcg ttattacgct gtactgctaa gcggccgcgt cgac                    2204
```

<210> SEQ ID NO 165
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-3

<400> SEQUENCE: 165

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Ile Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Asn Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335
```

```
Cys Gly Val Leu Leu Leu Ser Leu Val Ile Thr Leu Tyr Cys Arg Arg
                340                 345                 350

Asp Gln Arg Leu Pro Pro Asp Ala His Lys Pro Pro Gly Gly Gly Ser
            355                 360                 365

Phe Arg Thr Pro Ile Gln Glu Glu Gln Ala Asp Ala His Ser Thr Leu
        370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
        450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
690                 695                 700

Ala Pro Leu Ala Gly Thr Cys Gly Val Leu Leu Leu Ser Leu Val Ile
705                 710                 715                 720

Thr Leu Tyr Cys

<210> SEQ ID NO 166
<211> LENGTH: 2204
<212> TYPE: DNA
<213> ORGANISM: Homo sapiens
```

<220> FEATURE:
<221> NAME/KEY: misc_feature
<223> OTHER INFORMATION: DNA NK19H-4

<400> SEQUENCE: 166

```
gaattcgccg ccaccatggc cttaccagtg accgccttgc tcctgccgct ggccttgctg      60
ctccacgccg ccaggccgga ctacaaagac gatgacgata aaggcggtgg tggctctggt     120
ggtggcggca gcgatattca gatgacccag agcccgagca gcctgagcgc gagcgtgggc     180
gatcgcgtga ccattacctg ccgcgcgagc caggatatta gcaaatatct gaactggtat     240
cagcagaaac cgggcggcac cgtgaaactg ctgatttatc ataccagccg cctgcatagc     300
ggcgtgccga gccgctttag cggcagcggc agcggcaccg attttaccct gaccattagc     360
agcctgcagc cggaagatat tgcgacctat tattgccagc agggcaacac cctgccgtat     420
acctttggcg gcggcaccaa actggaaatt accgtggcg gtggctcggg cggtggtggg      480
tcgggtggcg gcggatctca ggtgcagctg caggaaagcg gcccgggcct ggtgaaaccg     540
agccagaccc tgagcctgac ctgcaccgtg agcggcgtga gcctgccgga ttatggcgtg     600
agctggattc gccagccgcc gggcaaaggc ctggaatggc tgggcgtgat ttggggcagc     660
gaaaccacct attataacag cgcgctgaaa agccgcctga ccattagcaa agataacagc     720
aaaagccagg tgagcctgaa actgagcagc gtgaccgcgg cggataccgc ggtgtattat     780
tgcgcgaaac attattatta tggcggcagc tatgcgatgg attattgggg ccagggcacc     840
agcgtgaccg tgagcagcac cacgacgcca gcgccgcgac caccaacacc ggcgcccacc     900
atcgcgtcgc agcccctgtc cctgcgccca gaggcgtgcc ggccagcggc gggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgccccccg atgcccacaa gcccctgggg gaggcagtt tccggacccc catccaagag   1140
gagcaggcc acgcccactc caccctggcc aagatcagag tgaagttcag caggagcgca   1200
gacgccccg cgtaccagca gggccagaac cagctctata cgagctcaa tctaggacga    1260
agagaggagt acgatgtttt ggacaagaga cgtggccggg accctgagat gggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa atcgaggac    1680
cttatacagt ctatgcatat tgacgctaca ctgtatactg agagtgatgt acaccgtcc    1740
tgtaaggtaa cggccatgaa atgctttctt ctggagctcc aggtcatcag cttgagtct    1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 167
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-4

<400> SEQUENCE: 167

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser

```
                355                 360                 365
Phe Arg Thr Pro Ile Gln Glu Glu Gln Ala Asp Ala His Ser Thr Leu
    370                 375                 380

Ala Lys Ile Arg Val Lys Phe Ser Arg Ser Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Gly Arg Asp Pro Glu Met
            420                 425                 430

Gly Gly Lys Pro Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
            515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
            595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
            675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys

<210> SEQ ID NO 168
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-5
```

<400> SEQUENCE: 168

```
gaattcgccg ccaccatggc cttaccagtg accgccttgc tcctgccgct ggccttgctg      60
ctccacgccg ccaggccgga ctacaaagac gatgacgata aaggcggtgg tggctctggt     120
ggtggcggca gcgatattca gatgacccag agcccgagca gcctgagcgc gagcgtgggc     180
gatcgcgtga ccattacctg ccgcgcgagc caggatatta gcaaatatct gaactggtat     240
cagcagaaac cgggcggcac cgtgaaactg ctgatttatc ataccagccg cctgcatagc     300
ggcgtgccga ccgctttag cggcagcggc agcggcaccg attttaccct gaccattagc     360
agcctgcagc cggaagatat tgcgacctat ttttgccagc agggcaacac cctgccgtat     420
acctttggcg gcggcaccaa actggaaatt accgtggcg gtggctcggg cggtggtggg     480
tcgggtggcg gcggatctca ggtgcagctg caggaaagcg gcccgggcct ggtgaaaccg     540
agccagaccc tgagcctgac ctgcaccgtg agcggcgtga gcctgccgga ttatggcgtg     600
agctggattc gccagccgcc gggcaaaggc ctggaatggc tgggcgtgat ttggggcagc     660
gaaaccacct attataacag cgcgctgaaa agccgcctga ccattagcaa agataacagc     720
aaaagccagg tgagcctgaa actgagcagc gtgaccgcgg cggataccgc ggtgtattat     780
tgcgcgaaac attattatta tggcggcagc tatgcgatgg attattgggg ccagggcacc     840
agcgtgaccg tgagcagcac cacgacgcca gcgccgcgac caccaacacc ggcgcccacc     900
atcgcgtcgc agccctgtc cctgcgccca gaggcgtgcc ggccagcggc gggggcgca     960
gtgcacacga gggggctgga cttcgcctgt gatatctaca tctgggcgcc cttggccggg    1020
acttgtgggg tccttctcct gtcactggtt atcacccttt actgccggag ggaccagagg    1080
ctgccccccg atgcccacaa gccccctggg ggaggcagtt ccggaccccc catccaagag    1140
gagcaggcca cgcccactc caccctggcc aagatcagag tgaagttcag caggagcgca    1200
gacgcccccg cgtaccagca gggccagaac cagctctata cgagctcaa tctaggacga    1260
agagaggagt acgatgtttt ggacaagaga cgtggccggg accctgagat gggggggaaag    1320
ccgagaagga agaaccctca ggaaggcctg tacaatgaac tgcagaaaga taagatggcg    1380
gaggcctaca gtgagattgg gatgaaaggc gagcgccgga ggggcaaggg gcacgatggc    1440
ctttaccagg gtctcagtac agccaccaag acacctacg acgcccttca catgcaggcc    1500
ctgcccctc gcggctctgg cgagggaagg ggttccctgc ttacttgcgg cgacgtcgaa    1560
gagaatcccg gtccgatggc cctcccagta actgccctcc ttttgccct cgcactcctt    1620
cttcatgccg ctcgccccaa ctgggtcaac gtgattagcg atttgaagaa aatcgaggac    1680
cttatacagt ctatgcatat tgacgctaca ctgtatactg agagtgatgt acaccgtcc    1740
tgtaaggtaa cggccatgaa atgctttctt ctggagctcc aggtcatcag cttggagtct    1800
ggggacgcaa gcatccacga tacggttgaa aacctcatca tccttgcgaa caactctctc    1860
tcatctaatg gaaacgttac agagagtggg tgtaaggagt gcgaagagtt ggaagaaaaa    1920
aacatcaaag aatttcttca atccttcgtt cacatagtgc aaatgttcat taacacgtcc    1980
actaccacac ccgccccgag gccacctacg ccggcaccga ctatcgccag tcaacccctc    2040
tctctgcgcc ccgaggcttg ccggcctgcg gctggtgggg cggtccacac ccggggcctg    2100
gattttgcgt gcgatatata catctgggca cctcttgccg gcacctgcgg agtgctgctt    2160
ctctcactcg ttattacgct gtactgctaa gcggccgcgt cgac                     2204
```

<210> SEQ ID NO 169
<211> LENGTH: 724

```
<212> TYPE: PRT
<213> ORGANISM: Homo sapiens
<220> FEATURE:
<221> NAME/KEY: MISC_FEATURE
<223> OTHER INFORMATION: AA NK19H-5

<400> SEQUENCE: 169
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Pro | Leu | Ala | Leu | Leu | Leu | |
| 1 | | | | 5 | | | | | 10 | | | | | 15 | |
| His | Ala | Ala | Arg | Pro | Asp | Tyr | Lys | Asp | Asp | Asp | Lys | Gly | Gly | Gly | |
| | | | 20 | | | | | 25 | | | | | 30 | | |
| Gly | Ser | Gly | Gly | Gly | Ser | Asp | Ile | Gln | Met | Thr | Gln | Ser | Pro | Ser | |
| | 35 | | | | | 40 | | | | | 45 | | | | |
| Ser | Leu | Ser | Ala | Ser | Val | Gly | Asp | Arg | Val | Thr | Ile | Thr | Cys | Arg | Ala |
| 50 | | | | | 55 | | | | | 60 | | | | | |
| Ser | Gln | Asp | Ile | Ser | Lys | Tyr | Leu | Asn | Trp | Tyr | Gln | Lys | Pro | Gly | |
| 65 | | | | | 70 | | | | | 75 | | | | | 80 |
| Gly | Thr | Val | Lys | Leu | Leu | Ile | Tyr | His | Thr | Ser | Arg | Leu | His | Ser | Gly |
| | | | | 85 | | | | | 90 | | | | | 95 | |
| Val | Pro | Ser | Arg | Phe | Ser | Gly | Ser | Gly | Ser | Gly | Thr | Asp | Phe | Thr | Leu |
| | | | 100 | | | | | 105 | | | | | 110 | | |
| Thr | Ile | Ser | Ser | Leu | Gln | Pro | Glu | Asp | Ile | Ala | Thr | Tyr | Phe | Cys | Gln |
| | | | 115 | | | | | 120 | | | | | 125 | | |
| Gln | Gly | Asn | Thr | Leu | Pro | Tyr | Thr | Phe | Gly | Gly | Gly | Thr | Lys | Leu | Glu |
| | 130 | | | | | 135 | | | | | 140 | | | | |
| Ile | Thr | Gly | Gly | Gly | Gly | Ser | Gly | Gly | Gly | Ser | Gly | Gly | Gly | Gly | |
| 145 | | | | | 150 | | | | | 155 | | | | | 160 |
| Ser | Gln | Val | Gln | Leu | Gln | Glu | Ser | Gly | Pro | Gly | Leu | Val | Lys | Pro | Ser |
| | | | | 165 | | | | | 170 | | | | | 175 | |
| Gln | Thr | Leu | Ser | Leu | Thr | Cys | Thr | Val | Ser | Gly | Val | Ser | Leu | Pro | Asp |
| | | | 180 | | | | | 185 | | | | | 190 | | |
| Tyr | Gly | Val | Ser | Trp | Ile | Arg | Gln | Pro | Pro | Gly | Lys | Gly | Leu | Glu | Trp |
| | | | 195 | | | | | 200 | | | | | 205 | | |
| Leu | Gly | Val | Ile | Trp | Gly | Ser | Glu | Thr | Thr | Tyr | Tyr | Asn | Ser | Ala | Leu |
| | 210 | | | | | 215 | | | | | 220 | | | | |
| Lys | Ser | Arg | Leu | Thr | Ile | Ser | Lys | Asp | Asn | Ser | Lys | Ser | Gln | Val | Ser |
| 225 | | | | | 230 | | | | | 235 | | | | | 240 |
| Leu | Lys | Leu | Ser | Ser | Val | Thr | Ala | Ala | Asp | Thr | Ala | Val | Tyr | Tyr | Cys |
| | | | | 245 | | | | | 250 | | | | | 255 | |
| Ala | Lys | His | Tyr | Tyr | Tyr | Gly | Gly | Ser | Tyr | Ala | Met | Asp | Tyr | Trp | Gly |
| | | | 260 | | | | | 265 | | | | | 270 | | |
| Gln | Gly | Thr | Ser | Val | Thr | Val | Ser | Ser | Thr | Thr | Thr | Pro | Ala | Pro | Arg |
| | | | 275 | | | | | 280 | | | | | 285 | | |
| Pro | Pro | Thr | Pro | Ala | Pro | Thr | Ile | Ala | Ser | Gln | Pro | Leu | Ser | Leu | Arg |
| | | 290 | | | | | 295 | | | | | 300 | | | |
| Pro | Glu | Ala | Cys | Arg | Pro | Ala | Ala | Gly | Gly | Ala | Val | His | Thr | Arg | Gly |
| 305 | | | | | 310 | | | | | 315 | | | | | 320 |
| Leu | Asp | Phe | Ala | Cys | Asp | Ile | Tyr | Ile | Trp | Ala | Pro | Leu | Ala | Gly | Thr |
| | | | | 325 | | | | | 330 | | | | | 335 | |
| Cys | Gly | Val | Leu | Leu | Leu | Ser | Leu | Val | Ile | Thr | Leu | Tyr | Cys | Arg | Arg |
| | | | 340 | | | | | 345 | | | | | 350 | | |
| Asp | Gln | Arg | Leu | Pro | Pro | Asp | Ala | His | Lys | Pro | Pro | Gly | Gly | Gly | Ser |
| | | 355 | | | | | 360 | | | | | 365 | | | |
| Phe | Arg | Thr | Pro | Ile | Gln | Glu | Glu | Gln | Ala | Asp | Ala | His | Ser | Thr | Leu |
| | 370 | | | | | 375 | | | | | 380 | | | | |

```
Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Gly Arg Asp Pro Glu Met
            420                 425                 430

Gly Gly Lys Pro Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
            515                 520                 525

Leu Leu Pro Leu Ala Leu Leu Leu His Ala Ala Arg Pro Asn Trp Val
530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
            595                 600                 605

Ile Leu Ala Asn Asn Ser Leu Ser Ser Asn Gly Asn Val Thr Glu Ser
610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
            675                 680                 685

Ala Val His Thr Arg Gly Leu Asp Phe Ala Cys Asp Ile Tyr Ile Trp
            690                 695                 700

Ala Pro Leu Ala Gly Thr Cys Gly Val Leu Leu Leu Ser Leu Val Ile
705                 710                 715                 720

Thr Leu Tyr Cys

<210> SEQ ID NO 170
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-6

<400> SEQUENCE: 170
gaattcgccg ccaccatggc cttaccagtg accgccttgc tcctgccgct ggccttgctg      60
```

```
ctccacgccg ccaggccgga ctacaaagac gatgacgata aaggcggtgg tggctctggt    120
ggtggcggca gcgacatcca gatgacacag agcccgtcct ccctgtctgc ctctgtggga    180
gacagagtca ccatcacctg cagggcaagt caggacatta gtaaatattt aaattggtat    240
cagcagaaac cagacggaac tgttaaactc ctgatctacc atacatcaag attacactca    300
ggagtcccat caaggttcag tggcagtggg tctggaacag attacaccct caccattagc    360
agcctgcaac cggaagatat tgccacttac ttctgccaac agggtaatac gcttccgtac    420
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccctgac atgcactgtc tcaggggtct cattacccga ctatggtgta    600
agctggattc gccagcctcc aggtaagggg ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc gggggcgca    960 gtgcacacga gggggctgga cttcgcctgt gatatctaca tctgggcgcc cttggccggg    1020
acttgtgggg tccttctcct gtcactggtt atcacccttt actgccggag ggaccagagg    1080 ctgcccccg atgccacaa gcccctggg ggaggcagtt tccggacccc catccaagag    1140 gagcaggcc acgccactc caccctggcc aagatcagag tgaagttcag caggagcgca    1200
gacgcccccg cgtaccagca gggccagaac cagctctata cgagctcaa tctaggacga    1260 agagaggagt acgatgtttt ggacaagaga cgtggccggg accctgagat gggggggaaag    1320 ccgagaagga agaaccctca ggaaggcctg tacaatgaac tgcagaaaga taagatggcg    1380
gaggcctaca gtgagattgg gatgaaaggc gagcgccgga ggggcaaggg gcacgatggc    1440
ctttaccagg gtctcagtac agccaccaag gacacctacg acgcccttca catgcaggcc    1500
ctgccccctc gcggctctgg cgagggaagg ggttccctgc ttacttgcgg cgacgtcgaa    1560
gagaatcccg gtccgatggc cctcccagta actgccctcc ttttgcccct cgcactcctt    1620
cttcatgccg ctcgccccaa ctgggtcaac gtgattagcg atttgaagaa aatcgaggac    1680
cttatacagt ctatgcatat tgacgctaca ctgtatactg agagtgatgt acacccgtcc    1740
tgtaaggtaa cggccatgaa atgctttctt ctggagctcc aggtcatcag cttggagtct    1800
ggggacgcaa gcatccacga tacggttgaa aacctcatca tccttgcgaa caactctctc    1860
tcatctaatg gaaacgttac agagagtggg tgtaaggagt gcgaagagtt ggaagaaaaa    1920
aacatcaaag aatttcttca atccttcgtt cacatagtgc aaatgttcat taacacgtcc    1980
actaccacac ccgccccgag gccacctacg ccggcaccga ctatcgccag tcaacccctc    2040
tctctgcgcc ccgaggcttg ccggcctgcg gctggtgggg cggtccacac ccggggcctg    2100
gattttgcgt gcgatatata catctgggca cctcttgccg gcacctgcgg agtgctgctt    2160
ctctcactcg ttattacgct gtactgctaa gcggccgcgt cgac                    2204
```

<210> SEQ ID NO 171
<211> LENGTH: 724
<212> TYPE: PRT
<213> ORGANISM: Homo sapiens
<220> FEATURE:
<221> NAME/KEY: MISC_FEATURE

<223> OTHER INFORMATION: AA NK19H-6

<400> SEQUENCE: 171

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
                20                  25                  30

Gly Ser Gly Gly Gly Gly Ser Asp Ile Gln Met Thr Gln Ser Pro Ser
            35                  40                  45

Ser Leu Ser Ala Ser Val Gly Asp Arg Val Thr Ile Thr Cys Arg Ala
50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

-continued

```
Gln Gln Gly Gln Asn Gln Leu Tyr Asn Glu Leu Asn Leu Gly Arg Arg
                405                 410                 415
Glu Glu Tyr Asp Val Leu Asp Lys Arg Arg Gly Arg Asp Pro Glu Met
            420                 425                 430
Gly Gly Lys Pro Arg Arg Lys Asn Pro Gln Glu Gly Leu Tyr Asn Glu
        435                 440                 445
Leu Gln Lys Asp Lys Met Ala Glu Ala Tyr Ser Glu Ile Gly Met Lys
    450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                485                 490                 495
Pro Pro Arg Gly Ser Gly Glu Gly Arg Gly Ser Leu Leu Thr Cys Gly
            500                 505                 510
Asp Val Glu Glu Asn Pro Gly Pro Met Ala Leu Pro Val Thr Ala Leu
        515                 520                 525
Leu Leu Pro Leu Ala Leu Leu Leu His Ala Ala Arg Pro Asn Trp Val
    530                 535                 540
Asn Val Ile Ser Asp Leu Lys Lys Ile Glu Asp Leu Ile Gln Ser Met
545                 550                 555                 560
His Ile Asp Ala Thr Leu Tyr Thr Glu Ser Asp Val His Pro Ser Cys
                565                 570                 575
Lys Val Thr Ala Met Lys Cys Phe Leu Leu Glu Leu Gln Val Ile Ser
            580                 585                 590
Leu Glu Ser Gly Asp Ala Ser Ile His Asp Thr Val Glu Asn Leu Ile
        595                 600                 605
Ile Leu Ala Asn Asn Ser Leu Ser Ser Asn Gly Asn Val Thr Glu Ser
    610                 615                 620
Gly Cys Lys Glu Cys Glu Glu Leu Glu Glu Lys Asn Ile Lys Glu Phe
625                 630                 635                 640
Leu Gln Ser Phe Val His Ile Val Gln Met Phe Ile Asn Thr Ser Thr
                645                 650                 655
Thr Thr Pro Ala Pro Arg Pro Pro Thr Pro Ala Pro Thr Ile Ala Ser
            660                 665                 670
Gln Pro Leu Ser Leu Arg Pro Glu Ala Cys Arg Pro Ala Ala Gly Gly
        675                 680                 685
Ala Val His Thr Arg Gly Leu Asp Phe Ala Cys Asp Ile Tyr Ile Trp
    690                 695                 700
Ala Pro Leu Ala Gly Thr Cys Gly Val Leu Leu Leu Ser Leu Val Ile
705                 710                 715                 720
Thr Leu Tyr Cys
```

<210> SEQ ID NO 172
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-7

<400> SEQUENCE: 172

```
gaattcgccg ccaccatggc cttaccagtg accgccttgc tcctgccgct ggccttgctg      60
ctccacgccg ccaggccgga ctacaaagac gatgacgata aaggcggtgg tggctctggt     120
ggtggcggca gcgacatcca gatgacacag agcccgtcct ccctgtctgc ctctgtggga     180
```

```
gacagagtca ccatcacctg cagggcaagt caggacatta gtaaatattt aaattggtat      240
cagcagaaac caggtggaac tgttaaactc ctgatctacc atacatcaag attacactca      300
ggagtcccat caaggttcag tggcagtggg tctggaacag atttcaccct caccattagc      360
agcctgcaac cggaagatat tgccacttac tactgccaac agggtaatac gcttccgtac      420
acgttcggag gggggaccaa gctggagatc acaggtggcg gtggctcggg cggtggtggg      480
tcgggtggcg gcggatctca ggtgcagctg caggagtcag gacctggcct ggtgaaaccc      540
tcacagactc tgtccgtgac atgcactgtc tcaggggtct cattacccga ctatggtgta      600
agctggattc gccagcctcc aggtaagggt ctggagtggc tgggagtaat atggggtagt      660
gaaaccacat actataattc agctctcaaa tccagactga ccatctccaa ggacaactcc      720
aagagccaag tttccttaaa attaagtagt gttactgctg ctgacacagc cgtctactac      780
tgtgccaaac attattacta cggtggtagc tatgctatgg actactgggg ccaaggaacc      840
tcagtcaccg tctcctcaac cacgacgcca gcgccgcgac caccaacacc ggcgcccacc      900
atcgcgtcgc agcccctgtc cctgcgccca gaggcgtgcc ggccagcggc ggggggcgca      960
gtgcacacga gggggctgga cttcgcctgt gatatctaca tctgggcgcc cttggccggg     1020
acttgtgggg tccttctcct gtcactggtt atcaccctt actgccggag ggaccagagg     1080 ctgcccccg atgcccacaa gccccctggg ggaggcagtt ccggacccc atccaagag      1140 gagcaggcca cgcccactc caccctggcc aagatcagag tgaagttcag caggagcgca     1200
gacgcccccg cgtaccagca gggccagaac cagctctata cgagctcaa tctaggacga     1260 agagaggagt acgatgtttt ggacaagaga cgtggccggg accctgagat ggggggaaag     1320
ccgagaagga agaaccctca ggaaggcctg tacaatgaac tgcagaaaga taagatggcg     1380
gaggcctaca gtgagattgg gatgaaaggc gagcgccgga ggggcaaggg gcacgatggc     1440
ctttaccagg gtctcagtac agccaccaag gacacctacg acgcccttca catgcaggcc     1500 ctgcccctc gcggctctgg cgagggaagg ggttccctgc ttacttgcgg cgacgtcgaa     1560
gagaatcccg gtccgatggc cctcccagta actgccctcc ttttgcccct cgcactcctt     1620
cttcatgccg ctcgccccaa ctgggtcaac gtgattagcg atttgaagaa aatcgaggac     1680
cttatacagt ctatgcatat tgacgctaca ctgtatactg agagtgatgt acaccgtcc     1740 tgtaaggtaa cggccatgaa atgctttctt ctggagctcc aggtcatcag cttggagtct     1800
ggggacgcaa gcatccacga tacggttgaa aacctcatca tccttgcgaa caactctctc     1860
tcatctaatg gaaacgttac agagagtggg tgtaaggagt gcgaagagtt ggaagaaaaa     1920
aacatcaaag aatttcttca atccttcgtt cacatagtgc aaatgttcat taacacgtcc     1980
actaccacac ccgccccgag gccacctacg ccggcaccga ctatcgccag tcaacccctc     2040
tctctgcgcc ccgaggcttg ccggcctgcg gctggtgggg cggtccacac ccggggcctg     2100
gattttgcgt gcgatatata catctgggca cctcttgccg gcacctgcgg agtgctgctt     2160
ctctcactcg ttattacgct gtactgctaa gcggccgcgt cgac                    2204
```

<210> SEQ ID NO 173
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-7

<400> SEQUENCE: 173

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
            115                 120                 125

Gln Gly Asn Thr Leu Pro Tyr Thr Phe Gly Gly Gly Thr Lys Leu Glu
        130                 135                 140

Ile Thr Gly Gly Gly Gly Ser Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
```

420                 425                 430
Gly Gly Lys Pro Arg Lys Asn Pro Gln Glu Gly Leu Tyr Asn Glu
            435                 440                 445
Leu Gln Lys Asp Lys Met Ala Glu Ala Tyr Ser Glu Ile Gly Met Lys
    450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                485                 490                 495
Pro Pro Arg Gly Ser Gly Glu Gly Arg Gly Ser Leu Leu Thr Cys Gly
            500                 505                 510
Asp Val Glu Glu Asn Pro Gly Pro Met Ala Leu Pro Val Thr Ala Leu
        515                 520                 525
Leu Leu Pro Leu Ala Leu Leu Leu His Ala Ala Arg Pro Asn Trp Val
        530                 535                 540
Asn Val Ile Ser Asp Leu Lys Lys Ile Glu Asp Leu Ile Gln Ser Met
545                 550                 555                 560
His Ile Asp Ala Thr Leu Tyr Thr Glu Ser Asp Val His Pro Ser Cys
                565                 570                 575
Lys Val Thr Ala Met Lys Cys Phe Leu Leu Glu Leu Gln Val Ile Ser
            580                 585                 590
Leu Glu Ser Gly Asp Ala Ser Ile His Asp Thr Val Glu Asn Leu Ile
        595                 600                 605
Ile Leu Ala Asn Asn Ser Leu Ser Ser Asn Gly Asn Val Thr Glu Ser
    610                 615                 620
Gly Cys Lys Glu Cys Glu Glu Leu Glu Glu Lys Asn Ile Lys Glu Phe
625                 630                 635                 640
Leu Gln Ser Phe Val His Ile Val Gln Met Phe Ile Asn Thr Ser Thr
                645                 650                 655
Thr Thr Pro Ala Pro Arg Pro Pro Thr Pro Ala Pro Thr Ile Ala Ser
            660                 665                 670
Gln Pro Leu Ser Leu Arg Pro Glu Ala Cys Arg Pro Ala Ala Gly Gly
        675                 680                 685
Ala Val His Thr Arg Gly Leu Asp Phe Ala Cys Asp Ile Tyr Ile Trp
        690                 695                 700
Ala Pro Leu Ala Gly Thr Cys Gly Val Leu Leu Leu Ser Leu Val Ile
705                 710                 715                 720
Thr Leu Tyr Cys

<210> SEQ ID NO 174
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-8

<400> SEQUENCE: 174
gaattcgccg ccaccatggc cttaccagtg accgccttgc tcctgccgct ggccttgctg      60
ctccacgccg ccaggccgga ctacaaagac gatgacgata aggcggtgg tggctctggt     120 ggtggcggca gcgacatcca gatgacacag agcccgtcct ccctgtctgc ctctgtggga     180
gacagagtca ccatcacctg cagggcaagt caggacatta gtaaatattt aaattggtat     240
cagcagaaac caggtggaac tgttaaactc ctgatctacc atacatcaag attacactca     300

```
ggagtcccat caaggttcag tggcagtggg tctggaacag atttcaccct caccattagc    360
agcctgcaac cggaagatat tgccacttac ttctgccaac agggtaatac gcttccgtac    420
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccgtgac atgcactgtc tcaggggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgcccccgc atgcccacaa gcccctgggg ggaggcagtt ccggacccc catccaagag    1140
gagcaggcca cgcccactc caccctggcc aagatcagag tgaagttcag caggagcgca   1200
gacgcccccg cgtaccagca gggccagaac cagctctata cgagctcaa tctaggacga   1260
agagaggagt acgatgtttt ggacaagaga cgtggccggg accctgagat ggggggaaag   1320
ccgagaagga gaaccctca ggaaggcctg tacaatgaac tgcagaaaga taagatggcg    1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa atcgaggac    1680
cttatacagt ctatgcatat tgacgctaca ctgtatactg agagtgatgt acaccgtcc    1740
tgtaaggtaa cggccatgaa atgctttctt ctggagctcc aggtcatcag cttggagtct   1800
gggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 175
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-8

<400> SEQUENCE: 175

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
```

```
                20                  25                  30
Gly Ser Gly Gly Gly Ser Asp Ile Gln Met Thr Gln Ser Pro Ser
            35                  40                  45
Ser Leu Ser Ala Ser Val Gly Asp Arg Val Thr Ile Thr Cys Arg Ala
 50                  55                  60
Ser Gln Asp Ile Ser Lys Tyr Leu Asn Trp Tyr Gln Gln Lys Pro Gly
 65                  70                  75                  80
Gly Thr Val Lys Leu Leu Ile Tyr His Thr Ser Arg Leu His Ser Gly
                85                  90                  95
Val Pro Ser Arg Phe Ser Gly Ser Gly Ser Gly Thr Asp Phe Thr Leu
                100                 105                 110
Thr Ile Ser Ser Leu Gln Pro Glu Asp Ile Ala Thr Tyr Phe Cys Gln
                115                 120                 125
Gln Gly Asn Thr Leu Pro Tyr Thr Phe Gly Gly Gly Thr Lys Leu Glu
                130                 135                 140
Ile Thr Gly Gly Gly Gly Ser Gly Gly Gly Gly Ser Gly Gly Gly Gly
145                 150                 155                 160
Ser Gln Val Gln Leu Gln Glu Ser Gly Pro Gly Leu Val Lys Pro Ser
                165                 170                 175
Gln Thr Leu Ser Val Thr Cys Thr Val Ser Gly Val Ser Leu Pro Asp
                180                 185                 190
Tyr Gly Val Ser Trp Ile Arg Gln Pro Pro Gly Lys Gly Leu Glu Trp
                195                 200                 205
Leu Gly Val Ile Trp Gly Ser Glu Thr Thr Tyr Tyr Asn Ser Ala Leu
                210                 215                 220
Lys Ser Arg Leu Thr Ile Ser Lys Asp Asn Ser Lys Ser Gln Val Ser
225                 230                 235                 240
Leu Lys Leu Ser Ser Val Thr Ala Ala Asp Thr Ala Val Tyr Tyr Cys
                245                 250                 255
Ala Lys His Tyr Tyr Tyr Gly Gly Ser Tyr Ala Met Asp Tyr Trp Gly
                260                 265                 270
Gln Gly Thr Ser Val Thr Val Ser Ser Thr Thr Thr Pro Ala Pro Arg
                275                 280                 285
Pro Pro Thr Pro Ala Pro Thr Ile Ala Ser Gln Pro Leu Ser Leu Arg
                290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
                325                 330                 335
Cys Gly Val Leu Leu Leu Ser Leu Val Ile Thr Leu Tyr Cys Arg Arg
                340                 345                 350
Asp Gln Arg Leu Pro Pro Asp Ala His Lys Pro Pro Gly Gly Gly Ser
                355                 360                 365
Phe Arg Thr Pro Ile Gln Glu Glu Gln Ala Asp Ala His Ser Thr Leu
                370                 375                 380
Ala Lys Ile Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
                405                 410                 415
Glu Glu Tyr Asp Val Leu Asp Lys Arg Arg Gly Arg Asp Pro Glu Met
                420                 425                 430
Gly Gly Lys Pro Arg Arg Lys Asn Pro Gln Glu Gly Leu Tyr Asn Glu
                435                 440                 445
```

```
Leu Gln Lys Asp Lys Met Ala Glu Ala Tyr Ser Glu Ile Gly Met Lys
    450                 455                 460
Gly Glu Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                485                 490                 495
Pro Pro Arg Gly Ser Gly Glu Gly Arg Gly Ser Leu Leu Thr Cys Gly
            500                 505                 510
Asp Val Glu Glu Asn Pro Gly Pro Met Ala Leu Pro Val Thr Ala Leu
        515                 520                 525
Leu Leu Pro Leu Ala Leu Leu Leu His Ala Ala Arg Pro Asn Trp Val
    530                 535                 540
Asn Val Ile Ser Asp Leu Lys Lys Ile Glu Asp Leu Ile Gln Ser Met
545                 550                 555                 560
His Ile Asp Ala Thr Leu Tyr Thr Glu Ser Asp Val His Pro Ser Cys
                565                 570                 575
Lys Val Thr Ala Met Lys Cys Phe Leu Leu Glu Leu Gln Val Ile Ser
            580                 585                 590
Leu Glu Ser Gly Asp Ala Ser Ile His Asp Thr Val Glu Asn Leu Ile
    595                 600                 605
Ile Leu Ala Asn Asn Ser Leu Ser Ser Asn Gly Asn Val Thr Glu Ser
610                 615                 620
Gly Cys Lys Glu Cys Glu Glu Leu Glu Glu Lys Asn Ile Lys Glu Phe
                630                 635                 640
625
Leu Gln Ser Phe Val His Ile Val Gln Met Phe Ile Asn Thr Ser Thr
                645                 650                 655
Thr Thr Pro Ala Pro Arg Pro Pro Thr Pro Ala Pro Thr Ile Ala Ser
            660                 665                 670
Gln Pro Leu Ser Leu Arg Pro Glu Ala Cys Arg Pro Ala Ala Gly Gly
        675                 680                 685
Ala Val His Thr Arg Gly Leu Asp Phe Ala Cys Asp Ile Tyr Ile Trp
    690                 695                 700
Ala Pro Leu Ala Gly Thr Cys Gly Val Leu Leu Leu Ser Leu Val Ile
705                 710                 715                 720
Thr Leu Tyr Cys

<210> SEQ ID NO 176
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-9

<400> SEQUENCE: 176
gaattcgccg ccaccatggc cttaccagtg accgccttgc tcctgccgct ggccttgctg      60
ctccacgccg ccaggccgga ctacaaagac gatgacgata aggcggtggt ggctctggt     120
ggtggcggca gcgacatcca gatgacacag agcccgtcct ccctgtctgc ctctgtggga     180
gacagagtca ccatcacctg cagggcaagt caggacatta gtaaatattt aaattggtat     240
cagcagaaac cagacggaac tgttaaactc ctgatctacc atacatcaag attacactca     300
ggagtcccat caaggttcag tggcagtggg tctggaacag attacaccct caccattagc     360
agcctgcaac cggaagatat tgccacttac ttctgccaac agggtaatac gcttccgtac     420
```

```
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccgtgac atgcactgtc tcagggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcaccottt actgccggag ggaccagagg   1080
ctgccccccg atgcccacaa gcccctgggg ggaggcagtt ccggacccc catccaagag   1140
gagcaggcca cgcccactc cacccctggcc aagatcagag tgaagttcag caggagcgca   1200
gacgcccccg cgtaccagca gggccagaac cagctctata cgagctcaa tctaggacga   1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt cgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                   2204
```

<210> SEQ ID NO 177
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-9

<400> SEQUENCE: 177

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
                20                  25                  30

Gly Ser Gly Gly Gly Gly Ser Asp Ile Gln Met Thr Gln Ser Pro Ser
        35                  40                  45

```
Ser Leu Ser Ala Ser Val Gly Asp Arg Val Thr Ile Thr Cys Arg Ala
 50                  55                  60

Ser Gln Asp Ile Ser Lys Tyr Leu Asn Trp Tyr Gln Gln Lys Pro Asp
 65                  70                  75                  80

Gly Thr Val Lys Leu Leu Ile Tyr His Thr Ser Arg Leu His Ser Gly
                 85                  90                  95

Val Pro Ser Arg Phe Ser Gly Ser Gly Ser Gly Thr Asp Tyr Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460
```

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys

<210> SEQ ID NO 178
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-10

<400> SEQUENCE: 178
gaattcgccg ccaccatggc cttaccagtg accgccttgc tcctgccgct ggccttgctg      60
ctccacgccg ccaggccgga ctacaaagac gatgacgata aggcggtggt ggctctggtt     120
ggtggcggca gcgatattca gatgacccag agcccgagca gcctgagcgc gagcgtgggc     180
gatcgcgtga ccattacctg ccgcgcgagc caggatatta gcaaatatct gaactggtat     240
cagcagaaac cgggcggcac cgtgaaactg ctgatttatc ataccagccg cctgcatagc     300
ggcgtgccga ccgctttag cggcagcggc agcggcaccg attttaccct gaccattagc      360
agcctgcagc cggaagatat tgcgacctat tattgccagc agggcaacac cctgccgtat     420
acctttggcg gcggcaccaa actggaaatt accggtggcg gtggctcggg cggtggtggg     480
tcgggtggcg gcggatctca ggtgcagctg caggaaagcg gcccgggcct ggtgaaaccg     540

|   |   |   |
|---|---|---|
| agccagaccc tgagcgtgac ctgcaccgtg agcggcgtga gcctgccgga ttatggcgtg | 600 |
| agctggattc gccagccgcc gcgcaaaggc ctggaatggc tgggcgtgat ttggggcagc | 660 |
| gaaaccacct attataacag cgcgctgaaa agccgcctga ccattagcaa agataacagc | 720 |
| aaaagccagg tgagcctgaa aatgagcagc gtgaccgcgg cggataccgc gatttattat | 780 |
| tgcgcgaaac attattatta tggcggcagc tatgcgatgg attattgggg ccagggcacc | 840 |
| agcgtgaccg tgagcagcac cacgacgcca gcgccgcgac caccaacacc ggcgcccacc | 900 |
| atcgcgtcgc agcccctgtc cctgcgccca gaggcgtgcc ggccagcggc ggggggcgca | 960 |
| gtgcacacga gggggctgga cttcgcctgt gatatctaca tctgggcgcc cttggccggg | 1020 |
| acttgtgggg tccttctcct gtcactggtt atcacccttt actgccggag ggaccagagg | 1080 |
| ctgcccccg atgcccacaa gcccctggg ggaggcagtt tccggacccc catccaagag | 1140 |
| gagcaggccg acgcccactc caccctggcc aagatcagag tgaagttcag caggagcgca | 1200 |
| gacgcccccg cgtaccagca gggccagaac cagctctata acgagctcaa tctaggacga | 1260 |
| agagaggagt acgatgtttt ggacaagaga cgtggccggg accctgagat ggggggaaag | 1320 |
| ccgagaagga agaaccctca ggaaggcctg tacaatgaac tgcagaaaga taagatggcg | 1380 |
| gaggcctaca gtgagattgg gatgaaaggc gagcgccgga ggggcaaggg cacgatggc | 1440 |
| ctttaccagg gtctcagtac agccaccaag gacacctacg acgcccttca catgcaggcc | 1500 |
| ctgccccctc gcggctctgg cgaggaaagg ggttccctgc ttacttgcgg cgacgtcgaa | 1560 |
| gagaatcccg gtccgatggc cctcccagta actgccctcc ttttgcccct cgcactcctt | 1620 |
| cttcatgccc ctcgccccaa ctgggtcaac gtgattagcg atttgaagaa atcgaggac | 1680 |
| cttatacagt ctatgcatat tgacgctaca ctgtatactg agagtgatgt acacccgtcc | 1740 |
| tgtaaggtaa cggccatgaa atgctttctt ctggagctcc aggtcatcag cttggagtct | 1800 |
| ggggacgcaa gcatccacga tacggttgaa aacctcatca tccttgcgaa caactctctc | 1860 |
| tcatctaatg gaaacgttac agagagtggg tgtaaggagt gcgaagagtt ggaagaaaaa | 1920 |
| aacatcaaag aatttcttca atccttcgtt cacatagtgc aaatgttcat taacacgtcc | 1980 |
| actaccacac ccgccccgag gccacctacg ccggcaccga ctatcgccag tcaacccctc | 2040 |
| tctctgcgcc ccgaggcttg ccggcctgcg gctggtgggg cggtccacac ccggggcctg | 2100 |
| gattttgcgt gcgatatata catctgggca cctcttgccg gcacctgcgg agtgctgctt | 2160 |
| ctctcactcg ttattacgct gtactgctaa gcggccgcgt cgac | 2204 |

<210> SEQ ID NO 179
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-10

<400> SEQUENCE: 179

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

-continued

```
Ser Gln Asp Ile Ser Lys Tyr Leu Asn Trp Tyr Gln Gln Lys Pro Gly
 65                  70                  75                  80

Gly Thr Val Lys Leu Leu Ile Tyr His Thr Ser Arg Leu His Ser Gly
                 85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Met Ser Ser Val Thr Ala Ala Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
```

| | | | | | 485 | | | | 490 | | | | 495 | | |
|---|---|---|---|---|---|---|---|---|---|---|---|---|---|---|---|
Pro Pro Arg Gly Ser Gly Glu Gly Arg Gly Ser Leu Leu Thr Cys Gly
500                     505                     510

Asp Val Glu Glu Asn Pro Gly Pro Met Ala Leu Pro Val Thr Ala Leu
        515                     520                     525

Leu Leu Pro Leu Ala Leu Leu Leu His Ala Ala Arg Pro Asn Trp Val
530                     535                     540

Asn Val Ile Ser Asp Leu Lys Lys Ile Glu Asp Leu Ile Gln Ser Met
545                     550                     555                 560

His Ile Asp Ala Thr Leu Tyr Thr Glu Ser Asp Val His Pro Ser Cys
                565                     570                     575

Lys Val Thr Ala Met Lys Cys Phe Leu Leu Glu Leu Gln Val Ile Ser
                580                     585                     590

Leu Glu Ser Gly Asp Ala Ser Ile His Asp Thr Val Glu Asn Leu Ile
        595                     600                     605

Ile Leu Ala Asn Asn Ser Leu Ser Ser Asn Gly Asn Val Thr Glu Ser
        610                     615                     620

Gly Cys Lys Glu Cys Glu Glu Leu Glu Glu Lys Asn Ile Lys Glu Phe
625                     630                     635                 640

Leu Gln Ser Phe Val His Ile Val Gln Met Phe Ile Asn Thr Ser Thr
                645                     650                     655

Thr Thr Pro Ala Pro Arg Pro Pro Thr Pro Ala Pro Thr Ile Ala Ser
                660                     665                     670

Gln Pro Leu Ser Leu Arg Pro Glu Ala Cys Arg Pro Ala Ala Gly Gly
        675                     680                     685

Ala Val His Thr Arg Gly Leu Asp Phe Ala Cys Asp Ile Tyr Ile Trp
        690                     695                     700

Ala Pro Leu Ala Gly Thr Cys Gly Val Leu Leu Leu Ser Leu Val Ile
705                     710                     715                 720

Thr Leu Tyr Cys

<210> SEQ ID NO 180
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-11

<400> SEQUENCE: 180

```
gaattcgccg ccaccatggc cttaccagtg accgccttgc tcctgccgct ggccttgctg      60
ctccacgccg ccaggccgga ctacaaagac gatgacgata aggcggtggt ggctctggt     120 ggtggcggca gcgatattca gatgacccag agcccgagca gcctgagcgc gagcgtgggc     180
gatcgcgtga ccattacctg ccgcgcgagc caggatatta gcaaatatct gaactggtat     240
cagcagaaac cgggcggcac cgtgaaactg ctgatttatc ataccagccg cctgcatagc     300
ggcgtgccga gccgctttag cggcagcggc agcggcaccg attttaccct gaccattagc     360
agcctgcagc cggaagatat tgcgacctat ttttgccagc agggcaacac cctgccgtat     420
acctttggcc gcggcaccaa actggaaatt accggtggcg gtggctcggg cggtggtggg     480
tcgggtggcg gcggatctca ggtgcagctg caggaaagcg gcccgggcct ggtgaaaccg     540
agccagaccc tgagcgtgac ctgcaccgtg agcggcgtga gcctgccgga ttatggcgtg     600
agctggattc gccagccgcc gcgcaaaggc ctggaatggc tgggcgtgat ttggggcagc     660
```

```
gaaaccacct attataacag cgcgctgaaa agccgcctga ccattagcaa agataacagc    720
aaaagccagg tgagcctgaa aatgagcagc gtgaccgcgg cggataccgc gatttattat    780
tgcgcgaaac attattatta tggcggcagc tatgcgatgg attattgggg ccagggcacc    840
agcgtgaccg tgagcagcac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttgccgggg   1020
acttgtgggg tccttctcct gtcactggtt atcacccttt actgccggag ggaccagagg   1080
ctgccccccg atgcccacaa gcccctgggg ggaggcagtt ccggacccc catccaagag    1140
gagcaggccg acgcccactc caccctggcc aagatcagag tgaagttcag caggagcgca   1200
gacgcccccg cgtaccagca gggccagaac cagctctata cgagctcaa tctaggacga    1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgccttca catgcaggcc    1500
ctgccccctc gcggctctgg cgaggaaggg ggttccctgc ttacttgcgg cgacgtcgaa   1560
gagaatcccg gtccgatggc cctcccagta actgccctcc ttttgcccct cgcactcctt   1620
cttcatgccc tcgccccaa ctgggtcaac gtgattagcg atttgaagaa aatcgaggac    1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 181
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-11

<400> SEQUENCE: 181

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
```

```
            85                  90                  95
Val Pro Ser Arg Phe Ser Gly Ser Gly Ser Gly Thr Asp Phe Thr Leu
            100                 105                 110
Thr Ile Ser Ser Leu Gln Pro Glu Asp Ile Ala Thr Tyr Phe Cys Gln
            115                 120                 125
Gln Gly Asn Thr Leu Pro Tyr Thr Phe Gly Gly Gly Thr Lys Leu Glu
            130                 135                 140
Ile Thr Gly Gly Gly Gly Ser Gly Gly Gly Ser Gly Gly Gly Gly
145                 150                 155                 160
Ser Gln Val Gln Leu Gln Glu Ser Gly Pro Gly Leu Val Lys Pro Ser
            165                 170                 175
Gln Thr Leu Ser Val Thr Cys Thr Val Ser Gly Val Ser Leu Pro Asp
            180                 185                 190
Tyr Gly Val Ser Trp Ile Arg Gln Pro Pro Arg Lys Gly Leu Glu Trp
            195                 200                 205
Leu Gly Val Ile Trp Gly Ser Glu Thr Thr Tyr Tyr Asn Ser Ala Leu
            210                 215                 220
Lys Ser Arg Leu Thr Ile Ser Lys Asp Asn Ser Lys Ser Gln Val Ser
225                 230                 235                 240
Leu Lys Met Ser Ser Val Thr Ala Ala Asp Thr Ala Ile Tyr Tyr Cys
            245                 250                 255
Ala Lys His Tyr Tyr Gly Gly Ser Tyr Ala Met Asp Tyr Trp Gly
            260                 265                 270
Gln Gly Thr Ser Val Thr Val Ser Ser Thr Thr Pro Ala Pro Arg
            275                 280                 285
Pro Pro Thr Pro Ala Pro Thr Ile Ala Ser Gln Pro Leu Ser Leu Arg
            290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
            325                 330                 335
Cys Gly Val Leu Leu Leu Ser Leu Val Ile Thr Leu Tyr Cys Arg Arg
            340                 345                 350
Asp Gln Arg Leu Pro Pro Asp Ala His Lys Pro Pro Gly Gly Gly Ser
            355                 360                 365
Phe Arg Thr Pro Ile Gln Glu Glu Gln Ala Asp Ala His Ser Thr Leu
            370                 375                 380
Ala Lys Ile Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
            405                 410                 415
Glu Glu Tyr Asp Val Leu Asp Lys Arg Arg Gly Arg Asp Pro Glu Met
            420                 425                 430
Gly Gly Lys Pro Arg Arg Lys Asn Pro Gln Glu Gly Leu Tyr Asn Glu
            435                 440                 445
Leu Gln Lys Asp Lys Met Ala Glu Ala Tyr Ser Glu Ile Gly Met Lys
            450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
            485                 490                 495
Pro Pro Arg Gly Ser Gly Glu Gly Arg Gly Ser Leu Leu Thr Cys Gly
            500                 505                 510
```

Asp Val Glu Glu Asn Pro Gly Pro Met Ala Leu Pro Val Thr Ala Leu
        515                 520                 525
Leu Leu Pro Leu Ala Leu Leu His Ala Ala Arg Pro Asn Trp Val
    530                 535                 540
Asn Val Ile Ser Asp Leu Lys Lys Ile Glu Asp Leu Ile Gln Ser Met
545                 550                 555                 560
His Ile Asp Ala Thr Leu Tyr Thr Glu Ser Asp Val His Pro Ser Cys
                565                 570                 575
Lys Val Thr Ala Met Lys Cys Phe Leu Leu Glu Leu Gln Val Ile Ser
            580                 585                 590
Leu Glu Ser Gly Asp Ala Ser Ile His Asp Thr Val Glu Asn Leu Ile
        595                 600                 605
Ile Leu Ala Asn Asn Ser Leu Ser Ser Asn Gly Asn Val Thr Glu Ser
    610                 615                 620
Gly Cys Lys Glu Cys Glu Glu Leu Glu Glu Lys Asn Ile Lys Glu Phe
625                 630                 635                 640
Leu Gln Ser Phe Val His Ile Val Gln Met Phe Ile Asn Thr Ser Thr
                645                 650                 655
Thr Thr Pro Ala Pro Arg Pro Pro Thr Pro Ala Pro Thr Ile Ala Ser
            660                 665                 670
Gln Pro Leu Ser Leu Arg Pro Glu Ala Cys Arg Pro Ala Ala Gly Gly
        675                 680                 685
Ala Val His Thr Arg Gly Leu Asp Phe Ala Cys Asp Ile Tyr Ile Trp
        690                 695                 700
Ala Pro Leu Ala Gly Thr Cys Gly Val Leu Leu Leu Ser Leu Val Ile
705                 710                 715                 720
Thr Leu Tyr Cys

<210> SEQ ID NO 182
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-12

<400> SEQUENCE: 182
gaattcgccg ccaccatggc cttaccagtg accgccttgc tcctgccgct ggccttgctg      60
ctccacgccg ccaggccgga ctacaaagac gatgacgata aggcggtggt ggctctggt     120 ggtggcggca gcgatattca gatgacccag agcccgagca gcctgagcgc gagcgtgggc     180
gatcgcgtga ccattacctg ccgcgcgagc caggatatta gcaaatatct gaactggtat     240
cagcagaaac cggatggcac cgtgaaactg ctgatttatc ataccagccg cctgcatagc     300
ggcgtgccga ccgctttag cggcagcggc agcggcaccg attataccct gaccattagc     360
agcctgcagc cggaagatat tgcgacctat ttttgccagc agggcaacac cctgccgtat     420
acctttggcg gcggcaccaa actggaaatt accgtggcg gtggctcggg cggtggtggg     480
tcgggtggcg gcggatctca ggtgcagctg caggaaagcg gcccgggcct ggtgaaaccg     540
agccagaccc tgagcgtgac ctgcaccgtg agcggcgtga gcctgccgga ttatggcgtg     600
agctggattc gccagccgcc gcgcaaaggc ctggaatggc tgggcgtgat tgggggcagc     660
gaaaccacct attataacag cgcgctgaaa agccgcctga ccattagcaa agataacagc     720
aaaagccagg tgagcctgaa aatgagcagc gtgaccgcgg cggataccgc gatttattat     780

```
tgcgcgaaac attattatta tggcggcagc tatgcgatgg attattgggg ccagggcacc      840
agcgtgaccg tgagcagcac cacgacgcca gcgccgcgac caccaacacc ggcgcccacc      900
atcgcgtcgc agcccctgtc cctgcgccca gaggcgtgcc ggccagcggc gggggcgca      960 gtgcacacga gggggctgga cttcgccgt gatatctaca tctgggcgcc cttggccggg    1020
acttgtgggg tccttctcct gtcactggtt atcacccttt actgccggag ggaccagagg     1080 ctgcccccg atgccacaa gcccctggg ggaggcagtt tccggacccc catccaagag        1140
gagcaggccg acgcccactc caccctggcc aagatcagag tgaagttcag caggagcgca    1200
gacgcccccg cgtaccagca gggccagaac cagctctata cgagctcaa tctaggacga     1260 agagaggagt acgatgtttt ggacaagaga cgtggccggg accctgagat ggggggaaag    1320
ccgagaagga agaaccctca ggaaggcctg tacaatgaac tgcagaaaga taagatggcg    1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc    1500
ctgccccctc gcggctctgg cgagggaagg ggttccctgc ttacttgcgg cgacgtcgaa    1560
gagaatcccg gtccgatggc cctcccagta actgccctcc ttttgcccct cgcactcctt    1620
cttcatgccc ctcgccccaa ctgggtcaac gtgattagcg atttgaagaa aatcgaggac    1680
cttatacagt ctatgcatat tgacgctaca ctgtatactg agagtgatgt acacccgtcc    1740
tgtaaggtaa cggccatgaa atgctttctt ctggagctcc aggtcatcag cttggagtct    1800
ggggacgcaa gcatccacga tacggttgaa aacctcatca tccttgcgaa caactctctc    1860
tcatctaatg gaaacgttac agagagtggg tgtaaggagt gcgaagagtt ggaagaaaaa    1920
aacatcaaag aatttcttca atccttcgtt cacatagtgc aaatgttcat taacacgtcc    1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg    2100
gattttgcgt gcgatatata catctgggca cctcttgccg gcacctgcgg agtgctgctt    2160
ctctcactcg ttattacgct gtactgctaa gcggccgcgt cgac                     2204
```

<210> SEQ ID NO 183
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-12

<400> SEQUENCE: 183

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Lys Gly Gly Gly Gly
                20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110
```

```
Thr Ile Ser Ser Leu Gln Pro Glu Asp Ile Ala Thr Tyr Phe Cys Gln
            115                 120                 125

Gln Gly Asn Thr Leu Pro Tyr Thr Phe Gly Gly Gly Thr Lys Leu Glu
        130                 135                 140

Ile Thr Gly Gly Gly Gly Ser Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Met Ser Ser Val Thr Ala Ala Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525
```

| | | | | | | | | | | | |
|---|---|---|---|---|---|---|---|---|---|---|---|
|Leu|Leu|Pro|Leu|Ala|Leu|Leu|Leu|His|Ala|Ala|Arg Pro Asn Trp Val|
| |530| | | |535| | | | |540| |

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
            565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
            595                 600                 605

Ile Leu Ala Asn Asn Ser Leu Ser Ser Asn Gly Asn Val Thr Glu Ser
610                 615                 620

Gly Cys Lys Glu Cys Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Gly Gly
            675                 680                 685

Ala Val His Thr Arg Gly Leu Asp Phe Ala Cys Asp Ile Tyr Ile Trp
690                 695                 700

Ala Pro Leu Ala Gly Thr Cys Gly Val Leu Leu Leu Ser Leu Val Ile
705                 710                 715                 720

Thr Leu Tyr Cys

```
<210> SEQ ID NO 184
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-1

<400> SEQUENCE: 184
gaattcgccg ccaccatggc cttaccagtg accgccttgc tcctgccgct ggccttgctg     60
ctccacgccg ccaggccgga tattcagatg acccagagcc cgagcagcct gagcgcgagc    120
gtgggcgatc gcgtgaccat tacctgccgc gcgagccagg atattagcaa atatctgaac    180
tggtatcagc agaaaccggg cggcaccgtg aaactgctga tttatcatac cagccgcctg    240
catagcggcg tgccgagccg ctttagcggc agcggcagcg gcaccgattt tacccctgacc    300 attagcagcc tgcagccgga agatattgcg acctattatt gccagcaggg caacacccctg    360 ccgtatacct tggcggcggg caccaaactg gaaattaccg gtggcggtgg ctcgggcggt    420
ggtgggtcgg gtggcggcgg atctcaggtg cagctgcagg aaagcggccc gggcctggtg    480
aaaccgagcc agaccctgag cctgacctgc accgtgagcg gcgtgagcct gccggattat    540
ggcgtgagct ggattcgcca gccgccgggc aaaggcctgg aatggattgg cgtgatttgg    600
ggcagcgaaa ccacctatta taacagcgcg ctgaaaagcc gcctgaccat tagcaaagat    660
aacagcaaaa accaggtgag cctgaaactg agcagcgtga ccgcggcgga taccgcggtg    720
tattattgcg cgaaacatta ttattatggc ggcagctatg cgatggatta ttggggccag    780
ggcaccagcg tgaccgtgag cagcaccacg acgccagcgc cgcgaccacc aacaccggcg    840
cccaccatcg cgtcgcagcc cctgtccctg cgcccagagg cgtgccggcc agcggcgggg    900
```

```
ggcgcagtgc acacgagggg gctggacttc gcctgtgata tctacatctg ggcgcccttg      960
gccgggactt gtggggtcct tctcctgtca ctggttatca cccttttactg ccggagggac    1020 cagaggctgc ccccgatgc ccacaagccc cctgggggag gcagtttccg gacccccatc     1080
caagaggagc aggccgacgc ccactccacc ctggccaaga tcagagtgaa gttcagcagg    1140
agcgcagacg ccccgcgta ccagcagggc cagaaccagc tctataacga gctcaatcta     1200
ggacgaagag aggagtacga tgttttggac aagagacgtg gccgggaccc tgagatgggg    1260
ggaaagccga gaaggaagaa ccctcaggaa ggcctgtaca tgaactgca gaaagataag     1320 atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcgg ctctggcgag ggaaggggtt ccctgcttac ttgcggcgac     1500
gtcgaagaga atcccggtcc gatggccctc ccagtaactg ccctccttttt gccccctcgca 1560 ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860 gaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980 ccctctctc tgcgccccga ggcttgccgg cctgcggctg gtggggcggt ccacacccgg    2040
ggcctggatt ttgcgtgcga tatatacatc tgggcacctc ttgccggcac ctgcggagtg    2100
ctgcttctct cactcgttat tacgctgtac tgctaagcgg ccgcgtcgac              2150
```

<210> SEQ ID NO 185
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-1

<400> SEQUENCE: 185

```
Met Ala Leu Pro Val Thr Ala Leu Leu Leu Pro Leu Ala Leu Leu Leu
1               5                  10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Gln
    130                 135                 140
```

-continued

```
Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560
```

```
Thr Ala Met Lys Cys Phe Leu Leu Glu Leu Gln Val Ile Ser Leu Glu
            565                 570                 575
Ser Gly Asp Ala Ser Ile His Asp Thr Val Glu Asn Leu Ile Ile Leu
        580                 585                 590
Ala Asn Asn Ser Leu Ser Ser Asn Gly Asn Val Thr Glu Ser Gly Cys
            595                 600                 605
Lys Glu Cys Glu Glu Leu Glu Glu Lys Asn Ile Lys Glu Phe Leu Gln
        610                 615                 620
Ser Phe Val His Ile Val Gln Met Phe Ile Asn Thr Ser Thr Thr Thr
625                 630                 635                 640
Pro Ala Pro Arg Pro Pro Thr Pro Ala Pro Thr Ile Ala Ser Gln Pro
                645                 650                 655
Leu Ser Leu Arg Pro Glu Ala Cys Arg Pro Ala Ala Gly Gly Ala Val
            660                 665                 670
His Thr Arg Gly Leu Asp Phe Ala Cys Asp Ile Tyr Ile Trp Ala Pro
        675                 680                 685
Leu Ala Gly Thr Cys Gly Val Leu Leu Leu Ser Leu Val Ile Thr Leu
            690                 695                 700
Tyr Cys
705
```

<210> SEQ ID NO 186
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-2

<400> SEQUENCE: 186

```
gaattcgccg ccaccatggc cttaccagtg accgccttgc tcctgccgct ggccttgctg    60
ctccacgccg ccaggccgga tattcagatg acccagagcc cgagcagcct gagcgcgagc   120
gtgggcgatc gcgtgaccat tacctgccgc gcgagccagg atattagcaa atatctgaac   180
tggtatcagc agaaaccggg cggcaccgtg aaactgctga tttatcatac cagccgcctg   240
catagcggcg tgccgagccg ctttagcggc agcggcagcg gcaccgattt tacccctgac   300
attagcagcc tgcagccgga agatattgcg acctattttt gccagcaggg caacaccctg   360
ccgtatacct ttggcggcgg caccaaactg gaaattaccg gtggcggtgg ctcgggcggt   420
ggtgggtcgg gtggcggcgg atctcaggtg cagctgcagg aaagcggccc gggcctggtg   480
aaaccgagcc agaccctgag cctgacctgc accgtgagcg gcgtgagcct gccggattat   540
ggcgtgagct ggattcgcca gccgccgggc aaaggcctgg aatggattgg cgtgatttgg   600
ggcagcgaaa ccacctatta taacagcgcg ctgaaaagcc gcctgaccat tagcaaagat   660
aacagcaaaa accaggtgag cctgaaactg agcagcgtga ccgcggcgga taccgcggtg   720
tattattgcg cgaaacatta ttattatggc ggcagctatg cgatggatta ttggggccag   780
ggcaccagcg tgaccgtgag cagcaccacg acgccagcgc cgcgaccacc aacaccggcg   840
cccaccatcg cgtcgcagcc cctgtccctg cgcccagagg cgtgccggcc agcggcgggg   900
ggcgcagtgc acacgagggg gctggacttc gcctgtgata tctacatctg ggcgcccttg   960
gccgggactt gtggggtcct tctcctgtca ctggttatca ccctttactg ccggagggac  1020
cagaggctgc cccccgatgc ccacaagccc cctgggggag cagtttccg gacccccatc  1080
caagaggagc aggccgacgc ccactccacc ctggccaaga tcagagtgaa gttcagcagg  1140
```

-continued

```
agcgcagacg ccccccgcgta ccagcagggc cagaaccagc tctataacga gctcaatcta    1200
ggacgaagag aggagtacga tgttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg ctctggcgag ggaaggggtt ccctgcttac ttgcggcgac    1500
gtcgaagaga atcccggtcc gatggccctc ccagtaactg ccctccttttt gcccctcgca    1560 ctccttcttc atgccgctcg ccccaactgg gtcaacgtga ttagcgattt gaagaaaatc    1620 gaggaccta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtgggcggt ccacacccgg    2040 ggcctggatt ttgcgtgcga tatatacatc tgggcacctc ttgccggcac ctgcggagtg    2100
ctgcttctct cactcgttat tacgctgtac tgctaagcgg ccgcgtcgac    2150
```

<210> SEQ ID NO 187
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-2

<400> SEQUENCE: 187

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
```

-continued

```
                180                 185                 190
Val Ile Trp Gly Ser Glu Thr Thr Tyr Tyr Asn Ser Ala Leu Lys Ser
            195                 200                 205

Arg Leu Thr Ile Ser Lys Asp Asn Ser Lys Asn Gln Val Ser Leu Lys
        210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
            325                 330                 335

Arg Leu Pro Pro Asp Ala His Lys Pro Gly Gly Gly Ser Phe Arg
        340                 345                 350

Thr Pro Ile Gln Glu Glu Gln Ala Asp Ala His Ser Thr Leu Ala Lys
            355                 360                 365

Ile Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
            405                 410                 415

Lys Pro Arg Arg Lys Asn Pro Gln Glu Gly Leu Tyr Asn Glu Leu Gln
        420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
            485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
        530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
            565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605
```

-continued

```
Lys Glu Cys Glu Glu Leu Glu Glu Lys Asn Ile Lys Glu Phe Leu Gln
        610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
                660                 665                 670

His Thr Arg Gly Leu Asp Phe Ala Cys Asp Ile Tyr Ile Trp Ala Pro
            675                 680                 685

Leu Ala Gly Thr Cys Gly Val Leu Leu Leu Ser Leu Val Ile Thr Leu
            690                 695                 700

Tyr Cys
705

<210> SEQ ID NO 188
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-3

<400> SEQUENCE: 188
gaattcgccg ccaccatggc cttaccagtg accgccttgc tcctgccgct ggccttgctg      60
ctccacgccg ccaggccgga tattcagatg acccagagcc cgagcagcct gagcgcgagc     120
gtgggcgatc gcgtgaccat tacctgccgc gcgagccagg atattagcaa atatctgaac     180
tggtatcagc agaaaccgga tggcaccgtg aaactgctga tttatcatac cagccgcctg     240
catagcggcg tgccgagccg ctttagcggc agcggcagcg gcaccgatta cccctgacc      300 attagcagcc tgcagccgga agatattgcg acctattttt gccagcaggg caacaccctg     360
ccgtatacct ttggcggcgg caccaaactg gaaattaccg gtggcggtgg ctcgggcggt     420
ggtgggtcgg gtggcggcgg atctcaggtg cagctgcagg aaagcggccc gggcctggtg     480
aaaccgagcc agaccctgag cctgacctgc accgtgagcg gcgtgagcct gccggattat     540
ggcgtgagct ggattcgcca gccgccgggc aaaggcctgg aatggattgg cgtgatttgg     600
ggcagcgaaa ccacctatta taacagcgcg ctgaaaagcc gcctgaccat tagcaaagat     660
aacagcaaaa accaggtgag cctgaaactg agcagcgtga ccgcggcgga taccgcggtg     720
tattattgcg cgaaacatta ttattatggc ggcagctatg cgatggatta ttggggccag     780
ggcaccagcg tgaccgtgag cagcaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca cccttactgc cggagggac    1020 cagaggctgc ccccgatgc ccacaagccc cctggggag gcagtttccg accccccatc     1080
caagaggagc aggccgacgc ccactccacc ctggccaaga tcagagtgaa gttcagcagg    1140
agcgcagacg ccccgcgta ccagcagggc cagaaccagc tctataacga gctcaatcta     1200
ggacgaagag aggagtacga tgttttggac aagagacgtg gccgggaccc tgagatgggg     1260
ggaaagccga aaggaagaa ccctcaggaa ggcctgtaca atgaactgca gaaagataag     1320
atggcggagg cctacagtga gattgggatg aaaggcgagc gccggagggg caaggggcac    1380
```

-continued

```
gatggccttt accagggtct cagtacagcc accaaggaca cctacgacgc ccttcacatg    1440
caggccctgc cccctcgcgg ctctggcgag ggaaggggtt ccctgcttac ttgcggcgac    1500
gtcgaagaga atcccggtcc gatggccctc ccagtaactg ccctccttt gcccctcgca     1560 ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtgggcggt ccacacccgg      2040 ggcctggatt ttgcgtgcga tatatacatc tgggcacctc ttgccggcac ctgcggagtg    2100
ctgcttctct cactcgttat tacgctgtac tgctaagcgg ccgcgtcgac                 2150
```

<210> SEQ ID NO 189
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-3

<400> SEQUENCE: 189

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
    210                 215                 220
```

-continued

```
Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
        260                 265                 270

Thr Pro Ala Pro Thr Ile Ala Ser Gln Pro Leu Ser Leu Arg Pro Glu
    275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
            325                 330                 335

Arg Leu Pro Pro Asp Ala His Lys Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
            485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
            515                 520                 525

Ile Ser Asp Leu Lys Lys Ile Glu Asp Leu Ile Gln Ser Met His Ile
530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
            565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
            595                 600                 605

Lys Glu Cys Glu Glu Leu Glu Glu Lys Asn Ile Lys Glu Phe Leu Gln
            610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
```

```
              645                 650                 655
Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
            675                 680                 685

Leu Ala Gly Thr Cys Gly Val Leu Leu Leu Ser Leu Val Ile Thr Leu
            690                 695                 700

Tyr Cys
705

<210> SEQ ID NO 190
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-4

<400> SEQUENCE: 190
gaattcgccg ccaccatggc cttaccagtg accgccttgc tcctgccgct ggccttgctg      60
ctccacgccg ccaggccgga tattcagatg acccagagcc cgagcagcct gagcgcgagc     120
gtgggcgatc gcgtgaccat tacctgccgc gcgagccagg atattagcaa atatctgaac     180
tggtatcagc agaaaccggg cggcaccgtg aaactgctga tttatcatac cagccgcctg     240
catagcggcg tgccgagccg ctttagcggc agcggcagcg gcaccgattt taccctgacc     300
attagcagcc tgcagccgga agatattgcg acctattatt gccagcaggg caacaccctg     360
ccgtatacct ttggcggcgg caccaaactg gaaattaccg gtggcggtgg ctcgggcggt     420
ggtgggtcgg gtggcggcgg atctcaggtg cagctgcagg aaagcggccc gggcctggtg     480
aaaccgagcc agaccctgag cctgacctgc accgtgagcg gcgtgagcct gccggattat     540
ggcgtgagct ggattcgcca gccgccgggc aaaggcctgg aatggctggg cgtgatttgg     600
ggcagcgaaa ccacctatta taacagcgcg ctgaaaagcc gcctgaccat tagcaaagat     660
aacagcaaaa gccaggtgag cctgaaactg agcagcgtga ccgcggcgga taccgcggtg     720
tattattgcg cgaaacatta ttattatggc ggcagctatg cgatggatta ttggggccag     780
ggcaccagcg tgaccgtgag cagcaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca cccttttactg ccggagggac    1020 cagaggctgc cccccgatgc cacaagccc ctgggggag cagtttccg accccccatc    1080 caagaggagc aggccgacgc ccactccacc ctggccaaga tcagagtgaa gttcagcagg    1140
agcgcagacg ccccccgcgta ccagcagggc cagaaccagc tctataacga gctcaatcta    1200
ggacgaagag aggagtacga tgttttggac aagagacgtg gccgggaccc tgagatgggg    1260
ggaaagccga aaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcgg ctctggcgag ggaaggggtt ccctgcttac ttgcggcgac    1500
gtcgaagaga atcccggtcc gatggccctc cagtaactg ccctcctttt gcccctcgca    1560
ctccttcttc atgccgctcg ccccaactgg gtcaacgtga ttagcgattt gaagaaaatc    1620
```

-continued

```
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacccccgc cccgaggcca cctacgccgg caccgactat cgccagtcaa    1980
cccctctctc tgcgccccga ggcttgccgg cctgcggctg gtggggcggt ccacacccgg    2040
ggcctggatt ttgcgtgcga tatatacatc tgggcacctc ttgccggcac ctgcggagtg    2100
ctgcttctct cactcgttat tacgctgtac tgctaagcgg ccgcgtcgac               2150
```

<210> SEQ ID NO 191
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-4

<400> SEQUENCE: 191

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270
```

```
Thr Pro Ala Pro Thr Ile Ala Ser Gln Pro Leu Ser Leu Arg Pro Glu
        275                 280                 285

Ala Cys Arg Pro Ala Ala Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685
```

Leu Ala Gly Thr Cys Gly Val Leu Leu Ser Leu Val Ile Thr Leu
690                 695                 700

Tyr Cys
705

<210> SEQ ID NO 192
<211> LENGTH: 2153
<212> TYPE: DNA
<213> ORGANISM: Homo sapiens
<220> FEATURE:
<221> NAME/KEY: misc_feature
<223> OTHER INFORMATION: DNA NK19H-NF-5

<400> SEQUENCE: 192

| | | | | | |
|---|---|---|---|---|---|
| gaattcgccg | ccaccatggc | cttaccagtg | accgccttgc | tcctgccgct | ggccttgctg | 60 |
| ctccacgccg | ccaggccgga | tattcagatg | acccagagcc | cgagcagcct | gagcgcgagc | 120 |
| gtgggcgatc | gcgtgaccat | tacctgccgc | gcgagccagg | atattagcaa | atatctgaac | 180 |
| tggtatcagc | agaaaccggg | cggcaccgtg | aaactgctga | tttatcatac | cagccgcctg | 240 |
| catagcggcg | tgccgagccg | ctttagcggc | agcggcagcg | gcaccgattt | taccctgacc | 300 |
| attagcagcc | tgcagccgga | agatattgcg | acctattttt | gccagcaggg | caacaccctg | 360 |
| ccgtatacct | ttggcggcgg | caccaaactg | gaaattaccg | gtggcggtgg | ctcgggcggt | 420 |
| ggtgggtcgg | gtggcggcgg | atctcaggtg | cagctgcagg | agtcaggacc | tggcctggtg | 480 |
| aaaccctcac | agactctgtc | cctgacatgc | actgtctcag | gggtctcatt | acccgactat | 540 |
| ggtgtaagct | ggattcgcca | gcctccaggt | aagggtctgg | agtggctggg | agtaatatgg | 600 |
| ggtagtgaaa | ccacatacta | taattcagct | ctcaaatcca | gactgaccat | ctccaaggac | 660 |
| aactccaaga | gccaagtttc | cttaaaatta | agtagtgtta | ctgctgctga | cacagccgtc | 720 |
| tactactgtg | ccaaacatta | ttactacggt | ggtagctatg | ctatggacta | ctggggccaa | 780 |
| ggaacctcag | tcaccgtctc | ctcaaccacg | acgccagcgc | cgcgaccacc | aacaccggcg | 840 |
| cccaccatcg | cgtcgcagcc | cctgtccctg | cgcccagagg | cgtgccggcc | agcggcgggg | 900 |
| ggcgcagtgc | acacgagggg | gctggacttc | gcctgtgata | tctacatctg | ggcgcccttg | 960 |
| gccgggactt | gtgggtcct | tctcctgtca | ctggttatca | ccctttactg | ccggaggac | 1020 |
| cagaggctgc | cccccgatgc | ccacaagccc | ctggggggag | cagtttccg | acccccatc | 1080 |
| caagaggagc | aggccgacgc | ccactccacc | ctggccaaga | tcagagtgaa | gttcagcaga | 1140 |
| tctagcgcag | acgcccccgc | gtaccagcag | ggccagaacc | agctctataa | cgagctcaat | 1200 |
| ctaggacgaa | gagaggagta | cgatgttttg | gacaagagac | gtggccggga | ccctgagatg | 1260 |
| ggggaaagc | cgagaaggaa | gaaccctcag | gaaggcctgt | acaatgaact | gcagaaagat | 1320 |
| aagatggcgg | aggcctacag | tgagattggg | atgaaaggcg | agcgccggag | gggcaagggg | 1380 |
| cacgatggcc | tttaccaggg | tctcagtaca | gccaccaagg | acacctacga | cgcccttcac | 1440 |
| atgcaggccc | tgcccctcg | cggctctggc | gaggaaggg | gttccctgct | tacttgcggc | 1500 |
| gacgtcgaag | agaatcccgg | tccgatggcc | ctcccagtaa | ctgccctcct | tttgccctc | 1560 |
| gcactccttc | ttcatgccgc | tcgccccaac | tgggtcaacg | tgattagcga | tttgaagaaa | 1620 |
| atcgaggacc | ttatacagtc | tatgcatatt | gacgctacac | tgtatactga | gagtgatgta | 1680 |
| cacccgtcct | gtaaggtaac | ggccatgaaa | tgctttcttc | tggagctcca | ggtcatcagc | 1740 |
| ttggagtctg | gggacgcaag | catccacgat | acgttgaaa | acctcatcat | ccttgcgaac | 1800 |
| aactctctct | catctaatgg | aaacgttaca | gagagtgggt | gtaaggagtg | cgaagagttg | 1860 |

-continued

```
gaagaaaaaa acatcaaaga atttcttcaa tccttcgttc acatagtgca aatgttcatt    1920
aacacgtcca ctaccacacc cgccccgagg ccacctacgc cggcaccgac tatcgccagt    1980 caaccectct ctctgcgccc cgaggcttgc cggcctgcgg ctggtggggc ggtccacacc    2040
cggggcctgg attttgcgtg cgatatatac atctgggcac ctcttgccgg cacctgcgga    2100
gtgctgcttc tctcactcgt tattacgctg tactgctaag cggccgcgtc gac          2153
```

<210> SEQ ID NO 193
<211> LENGTH: 707
<212> TYPE: PRT
<213> ORGANISM: Homo sapiens
<220> FEATURE:
<221> NAME/KEY: MISC_FEATURE
<223> OTHER INFORMATION: AA NK19H-NF-5

<400> SEQUENCE: 193

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
```

```
            305                 310                 315                 320
        Val Leu Leu Leu Ser Leu Val Ile Thr Leu Tyr Cys Arg Arg Asp Gln
                            325                 330                 335

Arg Leu Pro Pro Asp Ala His Lys Pro Pro Gly Gly Ser Phe Arg
                        340                 345                 350

Thr Pro Ile Gln Glu Glu Gln Ala Asp Ala His Ser Thr Leu Ala Lys
                            355                 360                 365

Ile Arg Val Lys Phe Ser Arg Ser Ser Ala Asp Ala Pro Ala Tyr Gln
                        370                 375                 380

Gln Gly Gln Asn Gln Leu Tyr Asn Glu Leu Asn Leu Gly Arg Arg Glu
        385                 390                 395                 400

Glu Tyr Asp Val Leu Asp Lys Arg Arg Gly Arg Asp Pro Glu Met Gly
                        405                 410                 415

Gly Lys Pro Arg Arg Lys Asn Pro Gln Glu Gly Leu Tyr Asn Glu Leu
                        420                 425                 430

Gln Lys Asp Lys Met Ala Glu Ala Tyr Ser Glu Ile Gly Met Lys Gly
                        435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
        465                 470                 475                 480

Pro Arg Gly Ser Gly Glu Gly Arg Gly Ser Leu Leu Thr Cys Gly Asp
                            485                 490                 495

Val Glu Glu Asn Pro Gly Pro Met Ala Leu Pro Val Thr Ala Leu Leu
                        500                 505                 510

Leu Pro Leu Ala Leu Leu Leu His Ala Ala Arg Pro Asn Trp Val Asn
                    515                 520                 525

Val Ile Ser Asp Leu Lys Lys Ile Glu Asp Leu Ile Gln Ser Met His
                    530                 535                 540

Ile Asp Ala Thr Leu Tyr Thr Glu Ser Asp Val His Pro Ser Cys Lys
        545                 550                 555                 560

Val Thr Ala Met Lys Cys Phe Leu Leu Glu Leu Gln Val Ile Ser Leu
                            565                 570                 575

Glu Ser Gly Asp Ala Ser Ile His Asp Thr Val Glu Asn Leu Ile Ile
                        580                 585                 590

Leu Ala Asn Asn Ser Leu Ser Ser Asn Gly Asn Val Thr Glu Ser Gly
                    595                 600                 605

Cys Lys Glu Cys Glu Glu Leu Glu Glu Lys Asn Ile Lys Glu Phe Leu
            610                 615                 620

Gln Ser Phe Val His Ile Val Gln Met Phe Ile Asn Thr Ser Thr Thr
        625                 630                 635                 640

Thr Pro Ala Pro Arg Pro Pro Thr Pro Ala Pro Thr Ile Ala Ser Gln
                            645                 650                 655

Pro Leu Ser Leu Arg Pro Glu Ala Cys Arg Pro Ala Ala Gly Gly Ala
                        660                 665                 670

Val His Thr Arg Gly Leu Asp Phe Ala Cys Asp Ile Tyr Ile Trp Ala
                    675                 680                 685

Pro Leu Ala Gly Thr Cys Gly Val Leu Leu Leu Ser Leu Val Ile Thr
                    690                 695                 700

Leu Tyr Cys
        705

<210> SEQ ID NO 194
```

<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-6

<400> SEQUENCE: 194

| | | | | | |
|---|---|---|---|---|---|
| gaattcgccg | ccaccatggc | cttaccagtg | accgccttgc | tcctgccgct | ggccttgctg | 60 |
| ctccacgccg | ccaggccgga | catccagatg | acacagagcc | cgtcctccct | gtctgcctct | 120 |
| gtgggagaca | gagtcaccat | cacctgcagg | gcaagtcagg | acattagtaa | atatttaaat | 180 |
| tggtatcagc | agaaaccaga | cggaactgtt | aaactcctga | tctaccatac | atcaagatta | 240 |
| cactcaggag | tcccatcaag | gttcagtggc | agtgggtctg | gaacagatta | caccctcacc | 300 |
| attagcagcc | tgcaaccgga | agatattgcc | acttacttct | gccaacaggg | taatacgctt | 360 |
| ccgtacacgt | tcggaggggg | gaccaagctg | gagatcacag | gtggcggtgg | ctcgggcggt | 420 |
| ggtgggtcgg | gtggcggcgg | atctcaggtg | cagctgcagg | agtcaggacc | tggcctggtg | 480 |
| aaaccctcac | agactctgtc | cctgacatgc | actgtctcag | gggtctcatt | acccgactat | 540 |
| ggtgtaagct | ggattcgcca | gcctccaggt | aagggtctgg | agtggctggg | agtaatatgg | 600 |
| ggtagtgaaa | ccacatacta | taattcagct | ctcaaatcca | gactgaccat | ctccaaggac | 660 |
| aactccaaga | gccaagtttc | cttaaaatta | agtagtgtta | ctgctgctga | cacagccgtc | 720 |
| tactactgtg | ccaaacatta | ttactacggt | ggtagctatg | ctatggacta | ctggggccaa | 780 |
| ggaacctcag | tcaccgtctc | ctcaaccacg | acgccagcgc | cgcgaccacc | aacaccggcg | 840 |
| cccaccatcg | cgtcgcagcc | cctgtccctg | cgcccagagg | cgtgccggcc | agcggcgggg | 900 |
| ggcgcagtgc | acacgagggg | gctggacttc | gcctgtgata | tctacatctg | gcgcccttg | 960 |
| gccgggactt | gtgggtcct | tctcctgtca | ctggttatca | ccctttactg | ccggagggac | 1020 |
| cagaggctgc | cccccgatgc | ccacaagccc | cctggggggag | gcagtttccg | gaccccatc | 1080 |
| caagaggagc | aggccgacgc | ccactccacc | ctggccaaga | tcagagtgaa | gttcagcagg | 1140 |
| agcgcagacg | ccccgcgta | ccagcagggc | cagaaccagc | tctataacga | gctcaatcta | 1200 |
| ggacgaagag | aggagtacga | tgtttttggac | aagagacgtg | gccgggaccc | tgagatgggg | 1260 |
| ggaaagccga | aaggaagaa | ccctcaggaa | ggcctgtaca | atgaactgca | gaaagataag | 1320 |
| atggcggagg | cctacagtga | gattgggatg | aaaggcgagc | gccggagggg | caaggggcac | 1380 |
| gatggccttt | accagggtct | cagtacagcc | accaaggaca | cctacgacgc | cttcacatg | 1440 |
| caggccctgc | cccctcgcgg | ctctggcgag | ggaaggggtt | ccctgcttac | ttgcggcgac | 1500 |
| gtcgaagaga | atcccggtcc | gatggccctc | ccagtaactg | ccctcctttt | gccctcgca | 1560 |
| ctccttcttc | atgccgctcg | ccccaactgg | gtcaacgtga | ttagcgattt | gaagaaaatc | 1620 |
| gaggacctta | tacagtctat | gcatattgac | gctacactgt | atactgagag | tgatgtacac | 1680 |
| ccgtcctgta | aggtaacggc | catgaaatgc | tttcttctgg | agctccaggt | catcagcttg | 1740 |
| gagtctgggg | acgcaagcat | ccacgatacg | gttgaaaacc | tcatcatcct | tgcgaacaac | 1800 |
| tctctctcat | ctaatggaaa | cgttacagag | agtgggtgta | aggagtgcga | agagttggaa | 1860 |
| gaaaaaaaca | tcaaagaatt | tcttcaatcc | ttcgttcaca | tagtgcaaat | gttcattaac | 1920 |
| acgtccacta | ccacacccgc | cccgaggcca | cctacgccgg | caccgactat | cgccagtcaa | 1980 |
| cccctctctc | tgcgccccga | ggcttgccgg | cctcgcgctg | gtgggcggt | ccacacccgg | 2040 |
| ggcctggatt | ttgcgtgcga | tatatacatc | tgggcacctc | ttgccggcac | ctgcggagtg | 2100 |

```
ctgcttctct cactcgttat tacgctgtac tgctaagcgg ccgcgtcgac            2150
```

<210> SEQ ID NO 195
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-6

<400> SEQUENCE: 195

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

```
Thr Pro Ile Gln Glu Glu Gln Ala Asp Ala His Ser Thr Leu Ala Lys
            355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
                500                 505                 510

Pro Leu Ala Leu Leu Leu His Ala Ala Arg Pro Asn Trp Val Asn Val
    515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
                580                 585                 590

Ala Asn Asn Ser Leu Ser Ser Asn Gly Asn Val Thr Glu Ser Gly Cys
    595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
                660                 665                 670

His Thr Arg Gly Leu Asp Phe Ala Cys Asp Ile Tyr Ile Trp Ala Pro
    675                 680                 685

Leu Ala Gly Thr Cys Gly Val Leu Leu Leu Ser Leu Val Ile Thr Leu
    690                 695                 700

Tyr Cys
705

<210> SEQ ID NO 196
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-7

<400> SEQUENCE: 196
```

```
gaattcgccg ccaccatggc cttaccagtg accgccttgc tcctgccgct ggccttgctg      60
ctccacgccg ccaggccgga catccagatg acacagagcc cgtcctccct gtctgcctct     120
gtgggagaca gagtcaccat cacctgcagg gcaagtcagg acattagtaa atatttaaat     180
tggtatcagc agaaaccagg tggaactgtt aaactcctga tctaccatac atcaagatta     240
cactcaggag tcccatcaag gttcagtggc agtgggtctg gaacagattt caccctcacc     300
attagcagcc tgcaaccgga agatattgcc acttactact gccaacaggg taatacgctt     360
ccgtacacgt tcggagggg gaccaagctg gagatcacag gtggcggtgg ctcgggcggt     420
ggtgggtcgg gtggcggcgg atctcaggtg cagctgcagg agtcaggacc tggcctggtg     480
aaaccctcac agactctgtc cgtgacatgc actgtctcag gggtctcatt acccgactat     540
ggtgtaagct ggattcgcca gcctccaggt aagggtctgg agtggctggg agtaatatgg     600
ggtagtgaaa ccacatacta taattcagct ctcaaatcca gactgaccat ctccaaggac     660
aactccaaga gccaagtttc cttaaaatta agtagtgtta ctgctgctga cacagccgtc     720
tactactgtg ccaaacatta ttactacggt ggtagctatg ctatggacta ctggggccaa     780
ggaacctcag tcaccgtctc ctcaaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg gcgcccttg      960
gccgggactt gtggggtcct tctcctgtca ctggttatca ccctttactg ccggagggac    1020
cagaggctgc cccccgatgc ccacaagccc cctgggggag gcagtttccg gacccccatc    1080
caagaggagc aggccgacgc ccactccacc ctggccaaga tcagagtgaa gttcagcagg    1140
agcgcagacg cccccgcgta ccagcagggc cagaaccagc tctataacga gctcaatcta    1200
ggacgaagag aggagtacga tgttttggac aagagacgtg gccgggaccc tgagatgggg    1260
ggaaagccga aaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg ctctggcgag ggaagggggtt ccctgcttac ttgcggcgac    1500
gtcgaagaga atcccggtcc gatggccctc ccagtaactg ccctccttt gccctcgca    1560
ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct gcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtgggcggt ccacacccgg    2040
ggcctggatt ttgcgtgcga tatatacatc tgggcacctc ttgccggcac ctgcggagtg    2100
ctgcttctct cactcgttat tacgctgtac tgctaagcgg ccgcgtcgac             2150
```

<210> SEQ ID NO 197
<211> LENGTH: 706
<212> TYPE: PRT
<213> ORGANISM: Homo sapiens
<220> FEATURE:

```
<221> NAME/KEY: MISC_FEATURE
<223> OTHER INFORMATION: AA NK19H-NF-7

<400> SEQUENCE: 197

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400
```

Tyr Asp Val Leu Asp Lys Arg Arg Gly Arg Asp Pro Glu Met Gly Gly
                405                 410                 415
Lys Pro Arg Arg Lys Asn Pro Gln Glu Gly Leu Tyr Asn Glu Leu Gln
            420                 425                 430
Lys Asp Lys Met Ala Glu Ala Tyr Ser Glu Ile Gly Met Lys Gly Glu
        435                 440                 445
Arg Arg Arg Gly Lys Gly His Asp Gly Leu Tyr Gln Gly Leu Ser Thr
    450                 455                 460
Ala Thr Lys Asp Thr Tyr Asp Ala Leu His Met Gln Ala Leu Pro Pro
465                 470                 475                 480
Arg Gly Ser Gly Glu Gly Arg Gly Ser Leu Leu Thr Cys Gly Asp Val
                485                 490                 495
Glu Glu Asn Pro Gly Pro Met Ala Leu Pro Val Thr Ala Leu Leu Leu
            500                 505                 510
Pro Leu Ala Leu Leu Leu His Ala Ala Arg Pro Asn Trp Val Asn Val
        515                 520                 525
Ile Ser Asp Leu Lys Lys Ile Glu Asp Leu Ile Gln Ser Met His Ile
    530                 535                 540
Asp Ala Thr Leu Tyr Thr Glu Ser Asp Val His Pro Ser Cys Lys Val
545                 550                 555                 560
Thr Ala Met Lys Cys Phe Leu Leu Glu Leu Gln Val Ile Ser Leu Glu
                565                 570                 575
Ser Gly Asp Ala Ser Ile His Asp Thr Val Glu Asn Leu Ile Ile Leu
            580                 585                 590
Ala Asn Asn Ser Leu Ser Ser Asn Gly Asn Val Thr Glu Ser Gly Cys
        595                 600                 605
Lys Glu Cys Glu Glu Leu Glu Glu Lys Asn Ile Lys Glu Phe Leu Gln
    610                 615                 620
Ser Phe Val His Ile Val Gln Met Phe Ile Asn Thr Ser Thr Thr Thr
625                 630                 635                 640
Pro Ala Pro Arg Pro Pro Thr Pro Ala Pro Thr Ile Ala Ser Gln Pro
                645                 650                 655
Leu Ser Leu Arg Pro Glu Ala Cys Arg Pro Ala Ala Gly Gly Ala Val
            660                 665                 670
His Thr Arg Gly Leu Asp Phe Ala Cys Asp Ile Tyr Ile Trp Ala Pro
        675                 680                 685
Leu Ala Gly Thr Cys Gly Val Leu Leu Leu Ser Leu Val Ile Thr Leu
    690                 695                 700
Tyr Cys
705

<210> SEQ ID NO 198
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-8

<400> SEQUENCE: 198
gaattcgccg ccaccatggc cttaccagtg accgccttgc tcctgccgct ggccttgctg         60
ctccacgccg ccaggccgga catccagatg acacagagcc cgtcctccct gtctgcctct        120
gtgggagaca gagtcaccat cacctgcagg gcaagtcagg acattagtaa atatttaaat        180
tggtatcagc agaaaccagg tgaactgtt aaactcctga tctaccatac atcaagatta        240

```
cactcaggag tcccatcaag gttcagtggc agtgggtctg gaacagattt caccctcacc    300
attagcagcc tgcaaccgga agatattgcc acttacttct gccaacaggg taatacgctt    360
ccgtacacgt tcggaggggg gaccaagctg gagatcacag gtggcggtgg ctcgggcggt    420
ggtgggtcgg gtggcggcgg atctcaggtg cagctgcagg agtcaggacc tggcctggtg    480
aaaccctcac agactctgtc cgtgacatgc actgtctcag ggtctcatt acccgactat    540 ggtgtaagct ggattcgcca gcctccaggt aagggtctgg agtggctggg agtaatatgg    600
ggtagtgaaa ccacatacta taattcagct ctcaaatcca gactgaccat ctccaaggac    660
aactccaaga gccaagtttc cttaaaatta agtagtgtta ctgctgctga cacagccgtc    720
tactactgtg ccaaacatta ttactacggt ggtagctatg ctatggacta ctggggccaa    780
ggaacctcag tcaccgtctc ctcaaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg gcgcccttg    960 gccgggactt gtggggtcct tctcctgtca ctggttatca ccctttactg ccggagggac    1020
cagaggctgc ccccgatgc ccacaagccc ctgggggag gcagtttccg gacccccatc    1080
caagaggagc aggccgacgc ccactccacc ctggccaaga tcagagtgaa gttcagcagg    1140
agcgcagacg ccccgcgta ccagcagggc cagaaccagc tctataacga gctcaatcta    1200
ggacgaagag aggagtacga tgttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg ctctggcgag ggaaggggtt ccctgcttac ttgcggcgac    1500
gtcgaagaga atcccggtcc gatggccctc ccagtaactg ccctccttt gcccctcgca    1560 ctccttcttc atgccgctcg ccccaactgg gtcaacgtga ttagcgattt gaagaaaatc    1620 gaggaccta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtgggcggt ccacacccgg    2040 ggcctggatt ttgcgtgcga tatatacatc tgggcacctc ttgccggcac ctgcggagtg    2100
ctgcttctct cactcgttat tacgctgtac tgctaagcgg ccgcgtcgac    2150
```

<210> SEQ ID NO 199
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-8

<400> SEQUENCE: 199

```
Met Ala Leu Pro Val Thr Ala Leu Leu Leu Pro Leu Ala Leu Leu Leu
1               5                   10                  15
```

```
His Ala Ala Arg Pro Asp Ile Gln Met Thr Gln Ser Pro Ser Ser Leu
             20                  25                  30
Ser Ala Ser Val Gly Asp Arg Val Thr Ile Thr Cys Arg Ala Ser Gln
         35                  40                  45
Asp Ile Ser Lys Tyr Leu Asn Trp Tyr Gln Gln Lys Pro Gly Gly Thr
     50                  55                  60
Val Lys Leu Leu Ile Tyr His Thr Ser Arg Leu His Ser Gly Val Pro
 65                  70                  75                  80
Ser Arg Phe Ser Gly Ser Gly Ser Gly Thr Asp Phe Thr Leu Thr Ile
                 85                  90                  95
Ser Ser Leu Gln Pro Glu Asp Ile Ala Thr Tyr Phe Cys Gln Gln Gly
             100                 105                 110
Asn Thr Leu Pro Tyr Thr Phe Gly Gly Gly Thr Lys Leu Glu Ile Thr
         115                 120                 125
Gly Gly Gly Gly Ser Gly Gly Gly Ser Gly Gly Gly Ser Gln
     130                 135                 140
Val Gln Leu Gln Glu Ser Gly Pro Gly Leu Val Lys Pro Ser Gln Thr
145                 150                 155                 160
Leu Ser Val Thr Cys Thr Val Ser Gly Val Ser Leu Pro Asp Tyr Gly
                 165                 170                 175
Val Ser Trp Ile Arg Gln Pro Pro Gly Lys Gly Leu Glu Trp Leu Gly
             180                 185                 190
Val Ile Trp Gly Ser Glu Thr Thr Tyr Tyr Asn Ser Ala Leu Lys Ser
         195                 200                 205
Arg Leu Thr Ile Ser Lys Asp Asn Ser Lys Ser Gln Val Ser Leu Lys
210                 215                 220
Leu Ser Ser Val Thr Ala Ala Asp Thr Ala Val Tyr Tyr Cys Ala Lys
225                 230                 235                 240
His Tyr Tyr Tyr Gly Gly Ser Tyr Ala Met Asp Tyr Trp Gly Gln Gly
                 245                 250                 255
Thr Ser Val Thr Val Ser Ser Thr Thr Thr Pro Ala Pro Arg Pro Pro
             260                 265                 270
Thr Pro Ala Pro Thr Ile Ala Ser Gln Pro Leu Ser Leu Arg Pro Glu
         275                 280                 285
Ala Cys Arg Pro Ala Ala Gly Gly Ala Val His Thr Arg Gly Leu Asp
         290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Arg Arg Asp Gln
                 325                 330                 335
Arg Leu Pro Pro Asp Ala His Lys Pro Pro Gly Gly Gly Ser Phe Arg
             340                 345                 350
Thr Pro Ile Gln Glu Glu Gln Ala Asp Ala His Ser Thr Leu Ala Lys
         355                 360                 365
Ile Arg Val Lys Phe Ser Arg Ser Ala Asp Ala Pro Ala Tyr Gln Gln
     370                 375                 380
Gly Gln Asn Gln Leu Tyr Asn Glu Leu Asn Leu Gly Arg Arg Glu Glu
385                 390                 395                 400
Tyr Asp Val Leu Asp Lys Arg Arg Gly Arg Asp Pro Glu Met Gly Gly
                 405                 410                 415
Lys Pro Arg Arg Lys Asn Pro Gln Glu Gly Leu Tyr Asn Glu Leu Gln
             420                 425                 430
Lys Asp Lys Met Ala Glu Ala Tyr Ser Glu Ile Gly Met Lys Gly Glu
```

```
            435                 440                 445
Arg Arg Arg Gly Lys Gly His Asp Gly Leu Tyr Gln Gly Leu Ser Thr
450                 455                 460
Ala Thr Lys Asp Thr Tyr Asp Ala Leu His Met Gln Ala Leu Pro Pro
465                 470                 475                 480
Arg Gly Ser Gly Glu Gly Arg Gly Ser Leu Leu Thr Cys Gly Asp Val
                485                 490                 495
Glu Glu Asn Pro Gly Pro Met Ala Leu Pro Val Thr Ala Leu Leu Leu
                500                 505                 510
Pro Leu Ala Leu Leu Leu His Ala Ala Arg Pro Asn Trp Val Asn Val
            515                 520                 525
Ile Ser Asp Leu Lys Lys Ile Glu Asp Leu Ile Gln Ser Met His Ile
            530                 535                 540
Asp Ala Thr Leu Tyr Thr Glu Ser Asp Val His Pro Ser Cys Lys Val
545                 550                 555                 560
Thr Ala Met Lys Cys Phe Leu Leu Glu Leu Gln Val Ile Ser Leu Glu
                565                 570                 575
Ser Gly Asp Ala Ser Ile His Asp Thr Val Glu Asn Leu Ile Ile Leu
                580                 585                 590
Ala Asn Asn Ser Leu Ser Ser Asn Gly Asn Val Thr Glu Ser Gly Cys
            595                 600                 605
Lys Glu Cys Glu Glu Leu Glu Glu Lys Asn Ile Lys Glu Phe Leu Gln
610                 615                 620
Ser Phe Val His Ile Val Gln Met Phe Ile Asn Thr Ser Thr Thr Thr
625                 630                 635                 640
Pro Ala Pro Arg Pro Thr Pro Ala Pro Thr Ile Ala Ser Gln Pro
                645                 650                 655
Leu Ser Leu Arg Pro Glu Ala Cys Arg Pro Ala Ala Gly Gly Ala Val
                660                 665                 670
His Thr Arg Gly Leu Asp Phe Ala Cys Asp Ile Tyr Ile Trp Ala Pro
            675                 680                 685
Leu Ala Gly Thr Cys Gly Val Leu Leu Leu Ser Leu Val Ile Thr Leu
            690                 695                 700
Tyr Cys
705

<210> SEQ ID NO 200
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-9

<400> SEQUENCE: 200
gaattcgccg ccaccatggc cttaccagtg accgccttgc tcctgccgct ggccttgctg      60
ctccacgccg ccaggccgga catccagatg acacagagcc cgtcctccct gtctgcctct     120
gtgggagaca gagtcaccat cacctgcagg gcaagtcagg acattagtaa atatttaaat     180
tggtatcagc agaaaccaga cggaactgtt aaactcctga tctaccatac atcaagatta     240
cactcaggag tcccatcaag gttcagtggc agtgggtctg gaacagatta cacctcacc      300 attagcagcc tgcaaccgga agatattgcc acttacttct gccaacaggg taatacgctt     360
ccgtacacgt tcggagggg gaccaagctg gagatcacag gtggcggtgg ctcgggcggt     420
ggtgggtcgg gtggcggcgg atctcaggtg cagctgcagg agtcaggacc tggcctggtg     480
```

-continued

```
aaaccctcac agactctgtc cgtgacatgc actgtctcag gggtctcatt acccgactat     540
ggtgtaagct ggattcgcca gcctccaggt aagggtctgg agtggctggg agtaatatgg     600
ggtagtgaaa ccacatacta taattcagct ctcaaatcca gactgaccat ctccaaggac     660
aactccaaga gccaagtttc cttaaaatta agtagtgtta ctgctgctga cacagccgtc     720
tactactgtg ccaaacatta ttactacggt ggtagctatg ctatggacta ctggggccaa     780
ggaacctcag tcaccgtctc ctcaaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca ccctttactg ccggagggac    1020
cagaggctgc cccccgatgc ccacaagccc ctgggggag gcagtttccg gacccccatc     1080
caagaggagc aggccgacgc ccactccacc ctggccaaga tcagagtgaa gttcagcagg    1140
agcgcagacg cccccgcgta ccagcagggc cagaaccagc tctataacga gctcaatcta    1200
ggacgaagag aggagtacga tgttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg ctctggcgag gaaggggtt ccctgcttac ttgcggcgac     1500
gtcgaagaga atcccggtcc gatggccctc ccagtaactg ccctccttt gcccctcgca    1560
ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtggggcggt ccacacccgg    2040
ggcctggatt ttgcgtgcga tatatacatc tgggcacctc ttgccggcac ctgcggagtg    2100
ctgcttctct cactcgttat tacgctgtac tgctaagcgg ccgcgtcgac              2150
```

<210> SEQ ID NO 201
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-9

<400> SEQUENCE: 201

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60
```

-continued

```
Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Thr Leu Thr Ile
                 85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Ser Gln
130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
            355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480
```

```
Arg Gly Ser Gly Glu Gly Arg Gly Ser Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
            515                 520                 525

Ile Ser Asp Leu Lys Lys Ile Glu Asp Leu Ile Gln Ser Met His Ile
            530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
            595                 600                 605

Lys Glu Cys Glu Glu Leu Glu Glu Lys Asn Ile Lys Glu Phe Leu Gln
610                 615                 620

Ser Phe Val His Ile Val Gln Met Phe Ile Asn Thr Ser Thr Thr Thr
625                 630                 635                 640

Pro Ala Pro Arg Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
                660                 665                 670

His Thr Arg Gly Leu Asp Phe Ala Cys Asp Ile Tyr Ile Trp Ala Pro
            675                 680                 685

Leu Ala Gly Thr Cys Gly Val Leu Leu Leu Ser Leu Val Ile Thr Leu
            690                 695                 700

Tyr Cys
705

<210> SEQ ID NO 202
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-10

<400> SEQUENCE: 202
gaattcgccg ccaccatggc cttaccagtg accgccttgc tcctgccgct ggccttgctg     60
ctccacgccg ccaggccgga tattcagatg acccagagcc cgagcagcct gagcgcgagc    120
gtgggcgatc gcgtgaccat tacctgccgc gcgagccagg atattagcaa atatctgaac    180
tggtatcagc agaaaccggg cggcaccgtg aaactgctga tttatcatac cagccgcctg    240
catagcggcg tgccgagccg ctttagcggc agcggcagcg gcaccgattt tacccttgacc    300 attagcagcc tgcagccgga agatattgcg acctattatt gccagcaggg caacaccctg    360
ccgtatacct ttggcggcgg caccaaactg gaaattaccg tggcggtgg ctcgggcggt    420 ggtgggtcgg gtgcggcgg atctcaggtg cagctgcagg aaagcggccc gggcctggtg    480
aaaccgagcc agaccctgag cgtgacctgc accgtgagcg gcgtgagcct gccggattat    540
ggcgtgagct ggattcgcca gccgccgcgc aaaggcctgg aatggctggg cgtgatttgg    600
ggcagcgaaa ccacctatta taacagcgcg ctgaaaagcc gcctgaccat tagcaaagat    660
aacagcaaaa gccaggtgag cctgaaaatg agcagcgtga ccgcggcgga taccgcgatt    720
```

-continued

```
tattattgcg cgaaacatta ttattatggc ggcagctatg cgatggatta ttggggccag    780
ggcaccagcg tgaccgtgag cagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca ccctttactg ccggagggac   1020
cagaggctgc ccccgatgc ccacaagccc cctgggggag gcagtttccg gaccccatc    1080
caagaggagc aggccgacgc ccactccacc ctggccaaga tcagagtgaa gttcagcagg   1140
agcgcagacg ccccgcgta ccagcagggc cagaaccagc tctataacga gctcaatcta   1200
ggacgaagag aggagtacga tgttttggac aagagacgtg gccgggaccc tgagatgggg   1260
ggaaagccga aaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cctcgcgg ctctggcgag ggaagggggtt ccctgcttac ttgcggcgac   1500
gtcgaagaga tcccggtcc gatggcctc ccagtaactg ccctccttttt gccctcgca    1560
ctccttcttc atgccgctcg ccccaactgg gtcaacgtga ttagcgattt gaagaaaatc   1620
gaggacctta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860
gaaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
ccctctctc tgcgccccga ggcttgccgg cctgcggctg gtggcggt ccacacccgg    2040
ggcctggatt ttgcgtgcga tatatacatc tgggcacctc ttgccggcac ctgcggagtg   2100
ctgcttctct cactcgttat tacgctgtac tgctaagcgg ccgcgtcgac              2150
```

<210> SEQ ID NO 203
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-10

<400> SEQUENCE: 203

| Met | Ala | Leu | Pro | Val | Thr | Ala | Leu | Leu | Leu | Pro | Leu | Ala | Leu | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| His | Ala | Ala | Arg | Pro | Asp | Ile | Gln | Met | Thr | Gln | Ser | Pro | Ser | Ser | Leu |
|     |     |     | 20  |     |     |     |     | 25  |     |     |     |     | 30  |     |     |

| Ser | Ala | Ser | Val | Gly | Asp | Arg | Val | Thr | Ile | Thr | Cys | Arg | Ala | Ser | Gln |
|     |     | 35  |     |     |     |     | 40  |     |     |     |     | 45  |     |     |     |

| Asp | Ile | Ser | Lys | Tyr | Leu | Asn | Trp | Tyr | Gln | Gln | Lys | Pro | Gly | Gly | Thr |
|     | 50  |     |     |     |     | 55  |     |     |     |     | 60  |     |     |     |     |

| Val | Lys | Leu | Leu | Ile | Tyr | His | Thr | Ser | Arg | Leu | His | Ser | Gly | Val | Pro |
| 65  |     |     |     |     | 70  |     |     |     |     | 75  |     |     |     |     | 80  |

| Ser | Arg | Phe | Ser | Gly | Ser | Gly | Ser | Gly | Thr | Asp | Phe | Thr | Leu | Thr | Ile |
|     |     |     |     | 85  |     |     |     |     | 90  |     |     |     |     | 95  |     |

| Ser | Ser | Leu | Gln | Pro | Glu | Asp | Ile | Ala | Thr | Tyr | Tyr | Cys | Gln | Gln | Gly |

```
                100                 105                 110
Asn Thr Leu Pro Tyr Thr Phe Gly Gly Gly Thr Lys Leu Glu Ile Thr
            115                 120                 125
Gly Gly Gly Gly Ser Gly Gly Gly Ser Gly Gly Gly Ser Gln
        130                 135             140
Val Gln Leu Gln Glu Ser Gly Pro Gly Leu Val Lys Pro Ser Gln Thr
145                 150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
            180                 185                 190
Val Ile Trp Gly Ser Glu Thr Thr Tyr Tyr Asn Ser Ala Leu Lys Ser
            195                 200                 205
Arg Leu Thr Ile Ser Lys Asp Asn Ser Lys Ser Gln Val Ser Leu Lys
        210                 215                 220
Met Ser Ser Val Thr Ala Ala Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Ser Val Thr Val Ser Ser Thr Thr Thr Pro Ala Pro Arg Pro Pro
            260                 265                 270
Thr Pro Ala Pro Thr Ile Ala Ser Gln Pro Leu Ser Leu Arg Pro Glu
        275                 280                 285
Ala Cys Arg Pro Ala Ala Gly Gly Ala Val His Thr Arg Gly Leu Asp
        290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Arg Arg Asp Gln
                325                 330                 335
Arg Leu Pro Pro Asp Ala His Lys Pro Pro Gly Gly Gly Ser Phe Arg
            340                 345                 350
Thr Pro Ile Gln Glu Glu Gln Ala Asp Ala His Ser Thr Leu Ala Lys
            355                 360                 365
Ile Arg Val Lys Phe Ser Arg Ser Ala Asp Ala Pro Ala Tyr Gln Gln
        370                 375                 380
Gly Gln Asn Gln Leu Tyr Asn Glu Leu Asn Leu Gly Arg Arg Glu Glu
385                 390                 395                 400
Tyr Asp Val Leu Asp Lys Arg Gly Arg Asp Pro Glu Met Gly Gly
                405                 410                 415
Lys Pro Arg Arg Lys Asn Pro Gln Glu Gly Leu Tyr Asn Glu Leu Gln
            420                 425                 430
Lys Asp Lys Met Ala Glu Ala Tyr Ser Glu Ile Gly Met Lys Gly Glu
            435                 440                 445
Arg Arg Arg Gly Lys Gly His Asp Gly Leu Tyr Gln Gly Leu Ser Thr
        450                 455                 460
Ala Thr Lys Asp Thr Tyr Asp Ala Leu His Met Gln Ala Leu Pro Pro
465                 470                 475                 480
Arg Gly Ser Gly Glu Gly Arg Gly Ser Leu Leu Thr Cys Gly Asp Val
                485                 490                 495
Glu Glu Asn Pro Gly Pro Met Ala Leu Pro Val Thr Ala Leu Leu Leu
            500                 505                 510
Pro Leu Ala Leu Leu Leu His Ala Ala Arg Pro Asn Trp Val Asn Val
            515                 520                 525
```

```
Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705

<210> SEQ ID NO 204
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-11

<400> SEQUENCE: 204
gaattcgccg ccaccatggc cttaccagtg accgccttgc tcctgccgct ggccttgctg      60
ctccacgccg ccaggccgga tattcagatg acccagagcc cgagcagcct gagcgcgagc     120
gtgggcgatc gcgtgaccat tacctgccgc gcgagccagg atattagcaa atatctgaac     180
tggtatcagc agaaaccggg cggcaccgtg aaactgctga tttatcatac cagccgcctg     240
catagcggcg tgccgagccg ctttagcggc agcggcagcg gcaccgattt tacccctgacc     300 attagcagcc tgcagccgga agatattgcg acctattttt gccagcaggg caacaccctg     360
ccgtataccc ttggcggcgg caccaaactg gaaattaccg gtggcggtgg ctcgggcggt     420
ggtgggtcgg gtggcggcgg atctcaggtg cagctgcagg aaagcggccc gggcctggtg     480
aaaccgagcc agaccctgag cgtgacctgc accgtgagcg gcgtgagcct gccggattat     540
ggcgtgagct ggattcgcca gccgccgcgc aaaggcctgg aatggctggg cgtgatttgg     600
ggcagcgaaa ccacctatta taacagcgcg ctgaaaagcc gcctgaccat tagcaaagat     660
aacagcaaaa gccaggtgag cctgaaaatg agcagcgtga ccgcggcgga taccgcgatt     720
tattattgcg cgaaacatta ttattatggc ggcagctatg cgatggatta ttggggccag     780
ggcaccagcg tgaccgtgag cagcaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
```

```
gccgggactt gtggggtcct tctcctgtca ctggttatca cccttactg ccggagggac   1020 cagaggctgc cccccgatgc ccacaagccc cctgggggag gcagtttccg gaccccatc   1080 caagaggagc aggccgacgc ccactccacc ctggccaaga tcagagtgaa gttcagcagg   1140
agcgcagacg ccccgcgta ccagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc ccctcgcgg ctctggcgag gaaggggtt ccctgcttac ttgcggcgac   1500
gtcgaagaga atcccggtcc gatggccctc ccagtaactg ccctcctttt gcccctcgca   1560
ctccttcttc atgccgctcg ccccaactgg gtcaacgtga ttagcgattt gaagaaaatc   1620 gaggaccta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860 gaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
cccctctctc tgcgccccga ggcttgccgg cctgcggctg gtggggcggt ccacacccgg   2040
ggcctggatt ttgcgtgcga tatatacatc tgggcacctc ttgccggcac ctgcggagtg   2100
ctgcttctct cactcgttat tacgctgtac tgctaagcgg ccgcgtcgac              2150
```

```
<210> SEQ ID NO 205
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-11

<400> SEQUENCE: 205

Met Ala Leu Pro Val Thr Ala Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Asp Ile Ser Lys Tyr Leu Asn Trp Tyr Gln Gln Lys Pro Gly Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Gln
        130                 135                 140
```

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
            165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ser Lys Asp Asn Ser Lys Ser Gln Val Ser Leu Lys
            210                 215                 220

Met Ser Ser Val Thr Ala Ala Asp Thr Ala Ile Tyr Tyr Cys Ala Lys
225                 230                 235                 240

His Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
            325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
            355                 360                 365

Ile Arg Val Lys Phe Ser Arg Ser Ala Asp Ala Pro Ala Tyr Gln Gln
            370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
            485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
            515                 520                 525

Ile Ser Asp Leu Lys Lys Ile Glu Asp Leu Ile Gln Ser Met His Ile
            530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu

```
                565                   570                     575
Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
            595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
        690                 695                 700

Tyr Cys
705

<210> SEQ ID NO 206
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-12

<400> SEQUENCE: 206
gaattcgccg ccaccatggc cttaccagtg accgccttgc tcctgccgct ggccttgctg      60
ctccacgccg ccaggccgga tattcagatg acccagagcc cgagcagcct gagcgcgagc     120
gtgggcgatc gcgtgaccat tacctgccgc gcgagccagg atattagcaa atatctgaac     180
tggtatcagc agaaaccgga tggcaccgtg aaactgctga tttatcatac cagccgcctg     240
catagcggcg tgccgagccg ctttagcggc agcggcagcg gcaccgatta taccctgacc     300
attagcagcc tgcagccgga agatattgcg acctattttt gccagcaggg caacacccct    360
ccgtatacct ttggcggcgg caccaaactg gaaattaccg gtggcggtgg ctcgggcggt     420
ggtgggtcgg gtggcggcgg atctcaggtg cagctgcagg aaagcggccc gggcctggtg     480
aaaccgagcc agaccctgag cgtgacctgc accgtgagcg gcgtgagcct gccggattat     540
ggcgtgagct ggattcgcca gccgccgcgc aaaggcctgg aatggctggg cgtgatttgg     600
ggcagcgaaa ccacctatta taacagcgcg ctgaaaagcc gcctgaccat tagcaaagat     660
aacagcaaaa gccaggtgag cctgaaaatg agcagcgtga ccgcggcgga taccgcgatt     720
tattattgcg cgaaacatta ttattatggc ggcagctatg cgatggatta ttggggccag     780
ggcaccagcg tgaccgtgag cagcaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtggggtcct tctcctgtca ctggttatca cccttactgc cggagggac    1020 cagaggctgc cccccgatgc ccacaagccc ctgggggag gcagtttccg gacccccatc    1080
caagaggagc aggccgacgc ccactccacc ctggccaaga tcagagtgaa gttcagcagg    1140
agcgcagacg ccccccgcgta ccagcagggc cagaaccagc tctataacga gctcaatcta    1200
```

```
ggacgaagag aggagtacga tgttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcgg ctctggcgag ggaaggggtt ccctgcttac ttgcggcgac     1500
gtcgaagaga atcccggtcc gatggccctc ccagtaactg ccctcctttt gcccctcgca    1560
ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtgggcggt ccacacccgg     2040 ggcctggatt ttgcgtgcga tatatacatc tgggcacctc ttgccggcac ctgcggagtg    2100
ctgcttctct cactcgttat tacgctgtac tgctaagcgg ccgcgtcgac                2150

<210> SEQ ID NO 207
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-12

<400> SEQUENCE: 207

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190
```

-continued

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

-continued

```
Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                     630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
                660                 665                 670

His Thr Arg Gly Leu Asp Phe Ala Cys Asp Ile Tyr Ile Trp Ala Pro
                675                 680                 685

Leu Ala Gly Thr Cys Gly Val Leu Leu Leu Ser Leu Val Ile Thr Leu
                690                 695             700

Tyr Cys
705
```

US 11,253,547 B2

CD19-DIRECTED CHIMERIC ANTIGEN RECEPTORS AND USES THEREOF IN IMMUNOTHERAPY

RELATED CASES

This application is a continuation of International Patent Application No. PCT/US2020/020824, filed Mar. 3, 2020, which claims the priority to U.S. Provisional Patent Application Nos. 62/814,180, filed Mar. 5, 2019, 62/895,910, filed Sep. 4, 2019, and 62/932,165, filed Nov. 7, 2019, the entire contents of each of which is incorporated by reference herein.

FIELD

Some embodiments of the methods and compositions provided herein relate to CD19-directed receptors. In some, embodiments the receptors are chimeric. Some embodiments include methods of use of the chimeric receptors in immunotherapy.

BACKGROUND

As further knowledge is gained about various cancers and what characteristics a cancerous cell has that can be used to specifically distinguish that cell from a healthy cell, therapeutics are under development that leverage the distinct features of a cancerous cell. Immunotherapies that employ engineered immune cells are one approach to treating cancers.

INCORPORATION BY REFERENCE OF MATERIAL IN ASCII TEXT FILE

This application incorporates by reference the Sequence Listing contained in the following ASCII text file being submitted concurrently herewith: File Name: NKT033C1_ST25.txt; created Nov. 3, 2020, 434 KB in size.

SUMMARY

Immunotherapy presents a new technological advancement in the treatment of disease, wherein immune cells are engineered to express certain targeting and/or effector molecules that specifically identify and react to diseased or damaged cells. This represents a promising advance due, at least in part, to the potential for specifically targeting diseased or damaged cells, as opposed to more traditional approaches, such as chemotherapy, where all cells are impacted, and the desired outcome is that sufficient healthy cells survive to allow the patient to live. One immunotherapy approach is the recombinant expression of chimeric receptors in immune cells to achieve the targeted recognition and destruction of aberrant cells of interest.

In several embodiments, there is provided herein an immune cell, and also populations of immune cells, that expresses a CD19-directed chimeric receptor, the chimeric receptor comprising an extracellular anti-CD19 binding moiety, a hinge and/or transmembrane domain, and an intracellular signaling domain. Also provided for herein are polynucleotides (as well as vectors for transfecting cells with the same) encoding a CD19-directed chimeric antigen receptor, the chimeric antigen receptor comprising an extracellular anti-CD19 binding moiety, a hinge and/or transmembrane domain, and an intracellular signaling domain.

In several embodiments, there is provided a polynucleotide encoding a CD19-directed chimeric antigen receptor, the chimeric antigen receptor comprising an extracellular anti-CD19 binding moiety, wherein the anti-CD19 binding moiety comprises a variable heavy (VH) domain of a single chain Fragment variable (scFv) and a variable light (VL) domain of a scFv, a hinge, a transmembrane domain, and an intracellular signaling domain, and wherein the intracellular signaling domain comprises an OX40 subdomain, a CD3 zeta subdomain.

In several embodiments, there is provided a polynucleotide encoding a CD19-directed chimeric antigen receptor, the chimeric antigen receptor comprising an extracellular anti-CD19 binding moiety, wherein the anti-CD19 binding moiety comprises a variable heavy (VH) domain of a single chain Fragment variable (scFv) and a variable light (VL) domain of a scFv, wherein the encoded VH domain comprises at least one heavy chain complementarity determining region (CDR) selected from the group consisting of SEQ ID NO: 133, SEQ ID NO: 134, and SEQ ID NO: 135, wherein the encoded VL domain comprises at least one light chain complementarity determining region (CDR) selected from the group consisting of SEQ ID NO: 127, SEQ ID NO: 128, and SEQ ID NO: 129, a hinge domain, a transmembrane domain, an intracellular signaling domain, and wherein the intracellular signaling domain comprises an OX40 subdomain and a CD3 zeta subdomain.

In several embodiments, the polynucleotide also encodes membrane-bound interleukin-15 (mbIL15). However, in some embodiments, a separate polynucleotide is used to encode the mbIL15. In several embodiments, the transmembrane domain is derived from or comprises a CD8 alpha transmembrane domain. In several embodiments, the CD8 alpha transmembrane domain is encoded by SEQ ID NO: 3. In several embodiments, the hinge is derived from or comprises a CD8 alpha hinge. In several embodiments, the CD8 alpha hinge is encoded by SEQ ID NO: 1. In several embodiments, the OX40 subdomain is encoded by a sequence having at least 90% (e.g., 90-95%, 95%, 96%, 97%, 98%, or 99%) sequence identity to SEQ ID NO: 5. In several embodiments, the CD3 zeta subdomain is encoded by a sequence having at least 90% (e.g., 90-95%, 95%, 96%, 97%, 98%, or 99%) sequence identity to SEQ ID NO: 7. In several embodiments, the mbIL15 is encoded by a sequence having at least 90% (e.g., 90-95%, 95%, 96%, 97%, 98%, or 99%) sequence identity to SEQ ID NO. 11. In several embodiments, the OX40 domain is encoded by SEQ ID NO: 5, the CD3 zeta subdomain is encoded by SEQ ID NO. 7 and/or mbIL15 (whether encoded separately or bicistronically) is encoded by SEQ ID NO: 11. In several embodiments, the encoded OX40 subdomain comprises the amino acid sequence of SEQ ID NO: 6, the encoded CD3 zeta subdomain comprises the amino acid sequence of SEQ ID NO: 8, and/or the encoded mbIL15 (whether encoded separately or bicistronically) comprises the amino acid sequence of SEQ ID NO: 12.

In several embodiments, the VH domain comprises a VH domain selected from SEQ ID NO: 120, SEQ ID NO: 121, SEQ ID NO: 122, and SEQ ID NO: 123, and wherein the VL domain comprises a VL domain selected from SEQ ID NO: 117, SEQ ID NO: 118, and SEQ ID NO: 119. In several embodiments, the polynucleotide encodes a VL domain comprising at least one light chain complementarity determining region (CDR) selected from the group consisting of SEQ ID NO: 127, SEQ ID NO: 128, and SEQ ID NO: 129. In several embodiments, the polynucleotide encodes a VH domain comprising at least one heavy chain complementarity determining region (CDR) selected from the group consisting of SEQ ID NO: 133, SEQ ID NO: 134, and SEQ ID NO: 135. In several embodiments, the polynucleotide is designed (e.g., engineered) to reduce potential antigenicity of the encoded protein and/or enhance one or more characteristics of the encoded protein (e.g., target recognition and/or binding characteristics) Thus, according to several embodiments, the anti-CD19 binding moiety does not comprise certain sequences. For example, according to several embodiments the polynucleotide does not encode one or more of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52. SEQ ID NO: 53, SEQ ID NO: 54, or SEQ ID NO: 55. In several embodiments, the encoded VH domain comprises an amino acid sequence at having at least 90% (e.g., 90-95%, 95%, 96%, 97%, 98%, or 99%) sequence identity to SEQ ID NO: 120. In several embodiments, the encoded VH domain comprises the amino acid sequence of SEQ ID NO: 120. In several embodiments, the encoded VL domain comprises an amino acid sequence at having at least 90% (e.g., 90-95%, 95%, 96%, 97%, 98%, or 99%) sequence identity to SEQ ID NO: 118. In several embodiments, the encoded VL domain comprises the amino acid sequence of SEQ ID NO: 118. In several embodiments, VH domain is derived from a parent amino acid sequence and is modified from the parent sequence. For example, mutations, truncations, extensions, conservative substitutions, or other modifications are introduced to increase the affinity of the domain for its target, increase the avidity for the target, and/or reduce potential antigenicity of the sequence. In several embodiments, the VH domain results from humanization of the VH domain amino acid sequence set forth in SEQ ID NO: 33. Likewise, in several embodiments, the VL domain results from humanization of the VL domain amino acid sequence set forth in SEQ ID NO: 32. In several embodiments, the polynucleotide encodes a CD19-directed chimeric antigen receptor having at least is encoded by a sequence having at least 90% (e.g., 90-95%, 95%, 96%, 97%, 98%, or 99%) sequence identity to the amino acid sequence set forth in SEQ ID NO: 187. In several embodiments, the polynucleotide encodes a CD19-directed chimeric antigen receptor comprising the amino acid sequence set forth in SEQ ID NO: 187.

In several embodiments, the polynucleotide does not encode or otherwise comprise a DAP10 domain. In several embodiments, the polynucleotide does not encode or otherwise comprise a DAP12 domain. In several embodiments, the intracellular signaling domain comprises additional subdomains, that advantageously enhance generation of cytotoxic signals by cells expressing the constructs. In several embodiments, the polynucleotide further encodes one or more of CD44 and CD27 as signaling subdomains. In several embodiments, the polynucleotide optionally further encodes a detection tag or other moiety (e.g., marker) that allows for detection of expression of the protein(s) encoded by the polynucleotide by host cells.

There are also provided for herein uses of the disclosed polynucleotides in the manufacture of a medicament for enhancing NK cell cytotoxicity in a mammal in need thereof, in the manufacture of a medicament for treating cancer in a mammal in need thereof and/or for the treatment of cancer in a mammal in need thereof.

There are also provided for herein engineered immune cells that express the CD19-directed chimeric antigen receptors encoded by the polynucleotides disclosed herein. In several embodiments, the engineered immune cells are natural killer (NK) cell. In some embodiments, the engineered cells are T cells, though combinations of NK cell and T cells (and optionally other immune cell types) are used in some embodiments. In several embodiments, the immune cells are allogeneic with respect to a subject receiving the cells. There are also provided for herein the use of immune cells that express the CD19-directed chimeric antigen receptors encoded by the polynucleotides disclosed herein for the treatment of cancer in a mammal in need thereof. There are also provided for herein the use of immune cells that express the CD19-directed chimeric antigen receptors encoded by the polynucleotides disclosed herein for the manufacture of a medicament for the treatment of cancer in a mammal in need thereof.

In several embodiments, there are provided methods for treating cancer using the polynucleotides disclosed herein. For example, in several embodiments the methods comprise administering to a subject having a cancer a composition comprising a population of immune cells expressing CD19-directed chimeric antigen receptors as disclosed herein. In several embodiments, the CAR comprises an extracellular anti-CD19 binding moiety, wherein the anti-CD19 binding moiety comprises a variable heavy (VH) domain of a single chain Fragment variable (scFv) and a variable light (VL) domain of a scFv, a hinge, such as a CD8 alpha hinge, a transmembrane domain, such as a CD8 alpha transmembrane domain; and an intracellular signaling domain comprising an OX40 subdomain and a CD3 zeta subdomain, and wherein the cell also expresses membrane-bound interleukin-15 (mbIL15). In several embodiments, the OX40 subdomain is encoded by a sequence having at least 95% sequence identity to SEQ ID NO. 5, the CD3 zeta subdomain is encoded by a sequence having at least 95% sequence identity to SEQ ID NO. 7, and/or the mbIL15 is encoded by a sequence having at least 95% sequence identity to SEQ ID NO. 11. In several embodiments, the encoded VH domain comprises an amino acid sequence having at least 95% sequence identity to SEQ ID NO: 120, wherein the encoded VL domain comprises an amino acid sequence having at least 95% sequence identity to SEQ ID NO: 118. In several embodiments, the polynucleotide encodes a CD19-directed chimeric antigen receptor having at least 95% sequence identity to the amino acid sequence set forth in SEQ ID NO: 187. As discussed above, in several embodiments, the immune cells expressing such CD19 CAR constructs are natural killer (NK) cells. In some embodiments, the immune cells are T cells. In several embodiments, combinations of NK and T cells (and optionally other immune cells) are used. In several embodiments, the cells are allogeneic cells originating from a donor that is not the subject. In several embodiments, the cells are autologous cells originating the subject. Mixtures of allogeneic and autologous cells may also be used, in some embodiments. In several embodiments, the administered population comprises about $2 \times 10^6$ cells per kilogram of body weight of the subject. In several embodiments, the administration is intravenous. In several embodiments, the method further comprises administering one or more doses of interleukin 2 to the subject. In several embodiments, the methods also involve the administration of another therapy to the subject. For example, in several embodiments, the methods involve administering a chemotherapy treatment to the subject prior to the administration of the cells. In several embodiments, the chemotherapy treatment induces lymphodepletion in the subject. In some embodiments, the subject is administered a combination of cyclophosphamide and fludarabine prior to administration of the cells. In several embodiments, the cyclophosphamide is administered in a dose between about 400 and about 600 mg/m². In several embodiments, the fludarabine is administered in a dose between about 25 and 25 mg/m². In several embodiments, the lymphodepleting chemotherapy is administered several days prior to administration of engineered immune cells and optionally administered multiple times. For example, in several embodiments the lymphodepleting chemotherapy is administered on at least the fifth, fourth, and/or third day prior to administration of engineered immune cells disclosed herein.

In several embodiments there is provided a polynucleotide encoding a humanized CD19-directed chimeric antigen receptor, the chimeric antigen receptor comprising a humanized anti-CD19 binding moiety, a co-stimulatory domain, and a signaling domain. In several embodiments, the co-stimulatory domain comprises OX40. In several embodiments, the humanized anti-CD19-binding moiety comprises a humanized scFv, wherein one or more of the heavy and light chains have been humanized. In several embodiments, one or more of the CDRs on the heavy and/or light chains have been humanized. For example, in several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain selected from SEQ ID NO: 120, SEQ ID NO: 121, SEQ ID NO: 122, and SEQ ID NO: 123 and the VL domain comprising a VL domain selected from SEQ ID NO: 117, SEQ ID NO: 118, and SEQ ID NO: 119, a hinge and/or transmembrane domain, an intracellular signaling domain.

In several embodiments, there is provided a polynucleotide encoding a humanized chimeric antigen receptor (CAR), wherein the CAR comprises a single chain antibody or single chain antibody fragment which comprises a humanized anti-CD19 binding domain, a transmembrane domain, a primary intracellular signaling domain comprising a native intracellular signaling domain of CD3-zeta, or a functional fragment thereof, and a costimulatory domain comprising a native intracellular signaling domain of a protein selected from the group consisting of OX40, CD27, CD28, ICOS, and 4-1 BB, or a functional fragment thereof, wherein said anti-CD19 binding domain comprises a light chain complementary determining region 1 (LC CDR1) of SEQ ID NO: 124, 127, or 130, a light chain complementary determining region 2 (LC CDR2) of SEQ ID NO: 125, 128, or 131, and a light chain complementary determining region 3 (LC CDR3) of SEQ ID NO: 126, 129, or 132, and a heavy chain complementary determining region 1 (HC CDR1) of SEQ ID NO: 133, 136, 139, or 142, a heavy chain complementary determining region 2 (HC CDR2) of SEQ ID NO: 134, 137, 140, or 143, and a heavy chain complementary determining region 3 (HC CDR3) of SEQ ID NO: 135, 138, 141, or 144.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 117, a hinge and/or transmembrane domain, and an intracellular signaling domain. In several embodiments, the polynucleotide encodes the humanized chimeric antigen receptor of SEQ ID NO: 161, SEQ ID NO: 167, SEQ ID NO: 173, SEQ ID NO: 179, SEQ ID NO: 185, SEQ ID NO: 191, SEQ ID NO: 197, or SEQ ID NO: 203.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 118, a hinge and/or transmembrane domain, and an intracellular signaling domain. In several embodiments, the polynucleotide encodes the humanized chimeric antigen receptor of SEQ ID NO: 163, SEQ ID NO: 169, SEQ ID NO: 175, SEQ ID NO: 181, SEQ ID NO: 187, SEQ ID NO: 193, SEQ ID NO: 199, or SEQ ID NO: 205.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 119, a hinge and/or transmembrane domain, and an intracellular signaling domain. In several embodiments, the polynucleotide encodes the humanized chimeric antigen receptor of SEQ ID NO: 165, SEQ ID NO: 171, SEQ ID NO: 177, SEQ ID NO: 183, SEQ ID NO: 189, SEQ ID NO: 195, SEQ ID NO: 201, or SEQ ID NO: 207.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 120, a hinge and/or transmembrane domain, and an intracellular signaling domain. In several embodiments, the polynucleotide encodes the humanized chimeric antigen receptor of SEQ ID NO: 161, SEQ ID NO: 163, SEQ ID NO: 165, SEQ ID NO: 185, SEQ ID NO: 187, or SEQ ID NO: 189.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 121, a hinge and/or transmembrane domain, and an intracellular signaling domain. In several embodiments, the polynucleotide encodes the humanized chimeric antigen receptor of SEQ ID NO: 167, SEQ ID NO: 169, SEQ ID NO: 171, SEQ ID NO: 191, SEQ ID NO: 193, or SEQ ID NO: 195.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 122, a hinge and/or transmembrane domain, and an intracellular signaling domain. In several embodiments, the polynucleotide encodes the humanized chimeric antigen receptor of SEQ ID NO: 173, SEQ ID NO: 175, SEQ ID NO: 177, SEQ ID NO: 197, SEQ ID NO: 199, or SEQ ID NO: 201.

In several embodiments, there is provided a polynucleotide encoding a humanized CD19-directed chimeric antigen receptor, the chimeric antigen receptor comprising an extracellular anti-CD19 binding moiety, wherein the anti- CD19 binding moiety comprises a humanized scFv sequence comprising a variable heavy (VH) domain of SEQ ID NO: 123, a hinge and/or transmembrane domain, and an intracellular signaling domain. In several embodiments, the polynucleotide encodes the humanized chimeric antigen receptor of SEQ ID NO: 179, SEQ ID NO: 181, SEQ ID NO: 183, SEQ ID NO: 203, SEQ ID NO: 205, or SEQ ID NO: 207.

In several embodiments, the provided polynucleotides also encode membrane-bound interleukin-15 (mbIL15).

In several embodiments, the intracellular signaling domain comprises an OX40 subdomain. However, in several embodiments the intracellular signaling domain comprises one or more of an OX40 subdomain, a CD28 subdomain, an iCOS subdomain, a CD28-41 BB subdomain, a CD27 subdomain, a CD44 subdomain, or combinations thereof.

In several embodiments, the chimeric antigen receptor comprises a hinge and a transmembrane domain, wherein the hinge is a CD8 alpha hinge, wherein the transmembrane domain is either a CD8 alpha or an NKG2D transmembrane domain. In several embodiments, the intracellular signaling domain comprises a CD3zeta domain.

In several embodiments, the polynucleotide does not encode SEQ ID NO: 112, 113, or 114. In several embodiments the polynucleotide does not encode SEQ ID NO: 116.

In several embodiments, there are provided engineered NK cells, engineered T cells, and/or mixed populations of NK cells and T cells that express one or more of the humanized CD19-directed chimeric antigen receptors provided for herein.

Also provided are methods for treating cancer in a subject comprising administering to a subject having cancer the engineered NK and/or T cells expressing chimeric antigen receptors as disclosed herein. Also provided for are the use of the polynucleotides provided for herein for the treatment of cancer as well as use of the polynucleotides provided for herein in the manufacture of a medicament for the treatment of cancer.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a scFv, a transmembrane domain, and an intracellular signaling domain, wherein the intracellular signaling domain comprises a CD28 co-stimulatory domain and a CD3 zeta signaling domain.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a scFv, a hinge, wherein the hinge is a CD8 alpha hinge, a transmembrane domain, and an intracellular signaling domain, wherein the intracellular signaling domain comprises a CD3 zeta ITAM.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a variable heavy chain of a scFv or a variable light chain of a scFv, a hinge, wherein the hinge is a CD8 alpha hinge, a transmembrane domain, wherein the transmembrane domain comprises a CD8 alpha transmembrane domain, and an intracellular signaling domain, wherein the intracellular signaling domain comprises a CD3 zeta ITAM.

In several embodiments, the transmembrane domain comprises a CD8 alpha transmembrane domain. In several embodiments, the transmembrane domain comprises an NKG2D transmembrane domain. In several embodiments, the transmembrane domain comprises a CD28 transmembrane domain.

In several embodiments the intracellular signaling domain comprises or further comprises a CD28 signaling domain. In several embodiments, the intracellular signaling domain comprises or further comprises a 4-1 BB signaling domain. In several embodiments, the intracellular signaling domain comprises an or further comprises OX40 domain. In several embodiments, the intracellular signaling domain comprises or further comprises a 4-1 BB signaling domain. In several embodiments, the intracellular signaling domain comprises or further comprises a domain selected from ICOS, CD70, CD161, CD40L, CD44, and combinations thereof.

In several embodiments, the polynucleotide also encodes a truncated epidermal growth factor receptor (EGFRt). In several embodiments, the EGFRt is expressed in a cell as a soluble factor. In several embodiments, the EGFRt is expressed in a membrane bound form. In several embodiments, the EGFRt operates to provide a "suicide switch" function in the engineered NK cells. In several embodiments, the polynucleotide also encodes membrane-bound interleukin-15 (mbIL15). Also provided for herein are engineered immune cells (e.g., NK or T cells, or mixtures thereof) that express a CD19-directed chimeric antigen receptor encoded by a polynucleotide disclosed herein. Further provided are methods for treating cancer in a subject comprising administering to a subject having cancer engineered immune cells expressing the chimeric antigen receptors disclosed herein. In several embodiments, there is provided the use of the polynucleotides disclosed herein in the treatment of cancer and/or in the manufacture of a medicament for the treatment of cancer.

In several embodiments, the anti-CD19 binding moiety comprises a heavy chain variable (VH) domain and a light chain variable (VL) domain. In several embodiments, the VH domain has at least 95% (e.g., 95, 96, 97, 98, or 99%) identity to the VH domain amino acid sequence set forth in SEQ ID NO: 33. In several embodiments, the VL domain has at least 95% (e.g., 95, 96, 97, 98, or 99%) identity to the VL domain amino acid sequence set forth in SEQ ID NO: 32. In several embodiments, the anti-CD19 binding moiety is derived from the VH and/or VL sequences of SEQ ID NO: 33 or 32. For example, in several embodiments, the VH and VL sequences for SEQ ID NO: 33 and/or 32 are subject to a humanization campaign and therefore are expressed more readily and/or less immunogenic when administered to human subjects. Thus, in several embodiments, the anti-CD19 binding moiety does not comprise SEQ ID NO: 32 and/or SEQ ID NO: 33. In several embodiments, the anti-CD19 binding moiety comprises a scFv that targets CD19 wherein the scFv comprises a heavy chain variable region comprising the sequence of SEQ ID NO. 35 or a sequence at least 95% (e.g., 95, 96, 97, 98, or 99%) identical to SEQ ID NO: 35. In several embodiments, the anti-CD19 binding moiety comprises an scFv that targets CD19 comprises a light chain variable region comprising the sequence of SEQ ID NO. 36 or a sequence at least 95% identical (e.g., 95, 96, 97, 98, or 99%) to SEQ ID NO: 36. In several embodiments, the anti-CD19 binding moiety comprises a light chain CDR comprising a first, second and third complementarity determining region (LC CDR1, LC CDR2, and LC CDR3, respectively) and/or a heavy chain CDR comprising a first, second and third complementarity determining region (HC CDR1, HC CDR2, and HC CDR3, respectively). Depending on the embodiment, various combinations of the LC CDRs and HC CDRs are used. For example, in one embodiment the anti-CD19 binding moiety comprises LC CDR1, LC CDR3, HC CD2, and HC, CDR3. Other combinations are used in some embodiments. In several embodiments, the LC CDR1 comprises the sequence of SEQ ID NO. 37 or a sequence at least about 95% homologous to the sequence of SEQ NO. 37. In several embodiments, the LC CDR2 comprises the sequence of SEQ ID NO. 38 or a or a sequence at least about 95% (e.g., 96, 97, 98, or 99%) homologous to the sequence of SEQ NO. 38. In several embodiments, the LC CDR3 comprises the sequence of SEQ ID NO. 39 or a sequence at least about 95% homologous to the sequence of SEQ NO. 39. In several embodiments, the HC CDR1 comprises the sequence of SEQ ID NO. 40 or a sequence at least about 95% homologous to the sequence of SEQ NO. 40. In several embodiments, the HC CDR2 comprises the sequence of SEQ ID NO. 41, 42, or 43 or a sequence at least about 95% homologous to the sequence of SEQ NO. 41, 42, or 43. In several embodiments, the HC CDR3 comprises the sequence of SEQ ID NO. 44 or a sequence at least about 95% (e.g., 96, 97, 98, 99 or 99%) homologous to the sequence of SEQ NO. 44.

In several embodiments, there is also provided an anti-CD19 binding moiety that comprises a light chain variable region (VL) and a heavy chain variable region (HL), the VL region comprising a first, second and third complementarity determining region (VL CDR1, VL CDR2, and VL CDR3, respectively and the VH region comprising a first, second and third complementarity determining region (VH CDR1, VH CDR2, and VH CDR3, respectively. In several embodiments, the VL region comprises the sequence of SEQ ID NO. 45, 46, 47, or 48 or a sequence at least about 95% (e.g., 96, 97, 98, 99 or 99%) homologous to the sequence of SEQ NO. 45, 46, 47, or 48. In several embodiments, the VH region comprises the sequence of SEQ ID NO. 49, 50, 51 or 52 or a sequence at least about 95% (e.g., 96, 97, 98, 99 or 99%) homologous to the sequence of SEQ NO. 49, 50, 51 or 52.

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 53 or a sequence at least about 95% homologous to the sequence of SEQ NO. 53. In several embodiments, the LC CDR2 comprises the sequence of SEQ ID NO. 54 or a sequence at least about 95% homologous to the sequence of SEQ NO. 54. In several embodiments, the LC CDR3 comprises the sequence of SEQ ID NO. 55 or a sequence at least about 95% homologous to the sequence of SEQ NO. 55. In several embodiments, the HC CDR1 comprises the sequence of SEQ ID NO. 56 or a sequence at least about 95% homologous to the sequence of SEQ NO. 56. In several embodiments, the HC CDR2 comprises the sequence of SEQ ID NO. 57 or a sequence at least about 95% homologous to the sequence of SEQ NO. 57. In several embodiments, the HC CDR3 comprises the sequence of SEQ ID NO. 58 or a sequence at least about 95% homologous to the sequence of SEQ NO. 58. In several embodiments, the anti-CD19 binding moiety (and thus the resultant CAR) is engineered to not include certain sequences, such as, for example, those that may cause increased risk of immunogenicity and/or side effects, such as cytokine release syndrome. Thus, according to several embodiments, the anti-CD19 binding moiety does not comprise one or more of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52. SEQ ID NO: 53, SEQ ID NO: 54, SEQ ID NO: 55, SEQ ID NO: 32, or SEQ ID NO: 33.

In several embodiments, the intracellular signaling domain of the chimeric receptor comprises an OX40 subdomain. In several embodiments, the intracellular signaling domain further comprises a CD3zeta subdomain. In several embodiments, the OX40 subdomain comprises the amino acid sequence of SEQ ID NO: 16 (or a sequence at least about 95% homologous to the sequence of SEQ ID NO. 16) and the CD3zeta subdomain comprises the amino acid sequence of SEQ ID NO: 8 (or a sequence at least about 95% homologous to the sequence of SEQ ID NO: 8).

In several embodiments, the hinge domain comprises a CD8a hinge domain. In several embodiments, the CD8a hinge domain, comprises the amino acid sequence of SEQ ID NO: 2 or a sequence at least about 95% homologous to the sequence of SEQ ID NO: 2).

In several embodiments, the immune cell also expresses membrane-bound interleukin-15 (mbIL15). In several embodiments, the mbIL15 comprises the amino acid sequence of SEQ ID NO: 12 or a sequence at least about 95% homologous to the sequence of SEQ ID NO: 12.

In several embodiments, wherein the chimeric receptor further comprises an extracellular domain of an NKG2D receptor. In several embodiments, the immune cell expresses a second chimeric receptor comprising an extracellular domain of an NKG2D receptor, a transmembrane domain, a cytotoxic signaling complex and optionally, mbIL15. In several embodiments, the extracellular domain of the NKG2D receptor comprises a functional fragment of NKG2D comprising the amino acid sequence of SEQ ID NO: 26 or a sequence at least about 95% homologous to the sequence of SEQ ID NO: 26. In various embodiments, the immune cell engineered to express the chimeric antigen receptor and/or chimeric receptors disclosed herein is an NK cell. In some embodiments, T cells are used. In several embodiments, combinations of NK and T cells (and/or other immune cells) are used.

In several embodiments, there are provided herein methods of treating cancer in a subject comprising administering to the subject having an engineered immune cell targeting CD19 as disclosed herein. Also provided for herein is the use of an immune cell targeting CD19 as disclosed herein for the treatment of cancer. Likewise, there is provided for herein the use of an immune cell targeting CD19 as disclosed herein in the preparation of a medicament for the treatment of cancer. In several embodiments, the cancer treated is acute lymphocytic leukemia.

Some embodiments of the methods and compositions described herein relate to an immune cell. In some embodiments, the immune cell expresses a CD19-directed chimeric receptor comprising an extracellular anti-CD19 moiety, a hinge and/or transmembrane domain, and/or an intracellular signaling domain. In some embodiments, the immune cell is a natural killer (NK) cell. In some embodiments, the immune cell is a T cell.

In some embodiments, the hinge domain comprises a CD8a hinge domain. In some embodiments, the hinge domain comprises an Ig4 SH domain.

In some embodiments, the transmembrane domain comprises a CD8a transmembrane domain. In some embodiments, the transmembrane domain comprises a CD28 transmembrane domain. In some embodiments, the transmembrane domain comprises a CD3 transmembrane domain.

In some embodiments, the signaling domain comprises an OX40 signaling domain. In some embodiments, the signaling domain comprises a 4-1 BB signaling domain. In some embodiments, the signaling domain comprises a CD28 signaling domain. In some embodiments, the signaling domain comprises an NKp80 signaling domain. In some embodiments, the signaling domain comprises a CD16 IC signaling domain. In some embodiments, the signaling domain comprises a CD3zeta or CD3ζ ITAM signaling domain. In some embodiments, the signaling domain comprises an mbIL-15 signaling domain. In some embodiments, the signaling domain comprises a 2A cleavage domain. In some embodiments, the mIL-15 signaling domain is separated from the rest or another portion of the CD19-directed chimeric receptor by a 2A cleavage domain.

Some embodiments relate to a method comprising administering an immune cell as described herein to a subject in need. In some embodiments, the subject has cancer. In some embodiments, the administration treats, inhibits, or prevents progression of the cancer.

BRIEF DESCRIPTION OF THE DRAWINGS

Figure 1A:
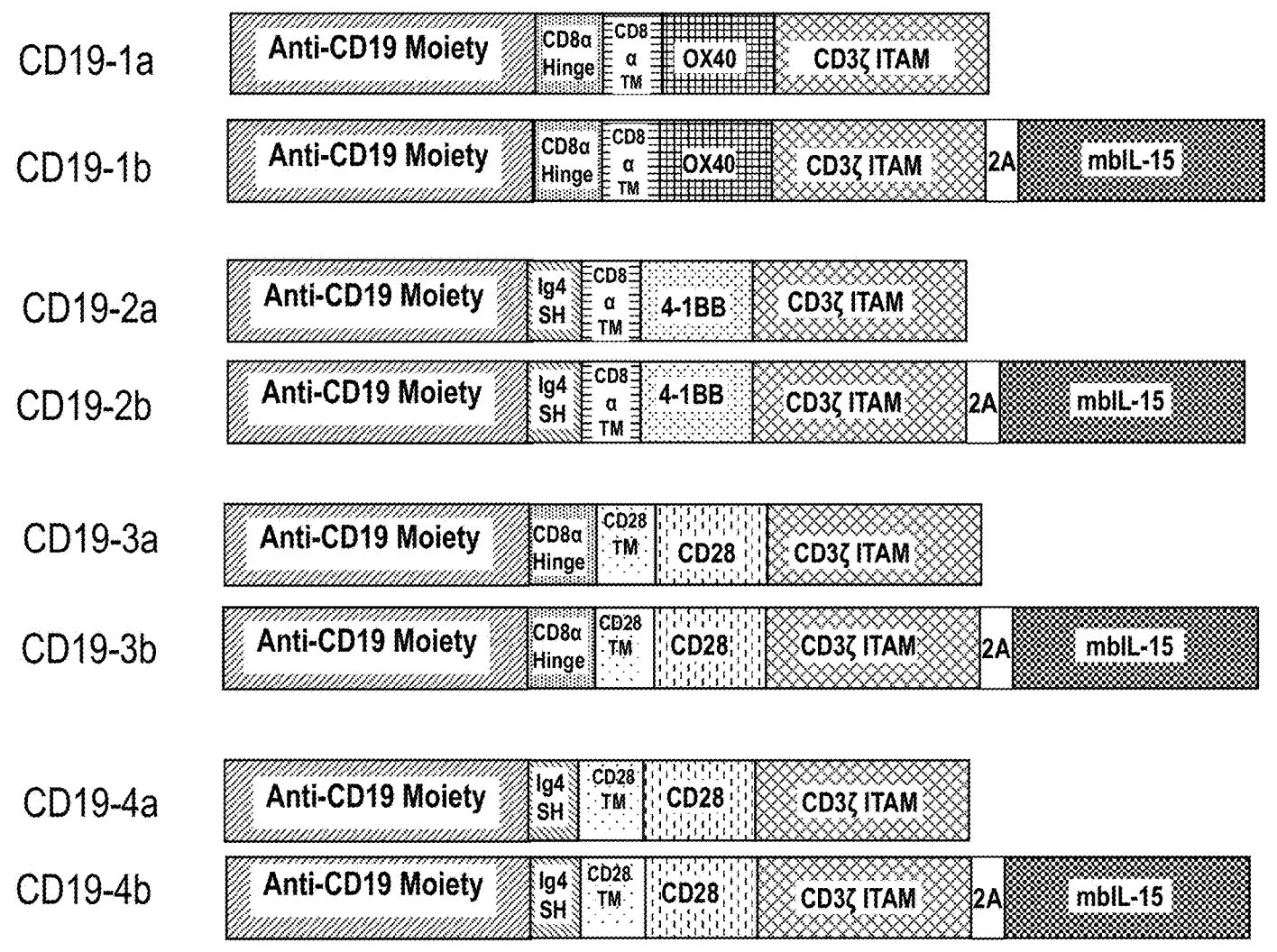

FIG. 1A includes depictions of non-limiting examples of CD19-directed chimeric receptors.

FIG. 3A also includes depictions of non-limiting examples of CD19-directed chimeric receptors.

FIG. 3B also includes depictions of non-limiting examples of CD19-directed chimeric receptors.

FIG. 3C also includes depictions of non-limiting examples of CD19-directed chimeric receptors.

FIG. 3D also includes depictions of non-limiting examples of CD19-directed chimeric receptors comprising humanized CD19 binding domains.

FIG. 3F also includes depictions of non-limiting examples of CD19-directed chimeric receptors comprising humanized CD19 binding domains.

FIG. 3G also includes depictions of non-limiting examples of CD19-directed chimeric receptors comprising humanized CD19 binding domains without a tag sequence.

FIG. 3H also includes depictions of non-limiting examples of CD19-directed chimeric receptors comprising humanized CD19 binding domains without a tag sequence.

FIG. 3I also includes depictions of non-limiting examples of CD19-directed chimeric receptors comprising humanized CD19 binding domains without a tag sequence.

FIGS. 11A-11E depict data related to cytokine release by NK cells expressing various CD19-directed chimeric receptors when co-cultured with Nalm6 cells. FIG. 11A depicts Granzyme B release. FIG. 11B depicts perforin release. FIG. 11C depicts TNF-alpha release. FIG. 11D depicts GM-CSF release. FIG. 11E depicts interferon gamma release.

FIGS. 12A-12E depict data related to cytokine release by NK cells expressing various CD19-directed chimeric receptors when co-cultured with Raji cells. FIG. 12A depicts Granzyme B release. FIG. 12B depicts perforin release. FIG. 12C depicts TNF-alpha release. FIG. 12D depicts GM-CSF release. FIG. 12E depicts interferon gamma release.

FIG. 15 depicts data related to selected functional characteristics of selected humanized anti-CD19 CAR constructs.

FIGS. 17A-17E show cytotoxicity data. 17A shows data related to the cytotoxicity of NK cells from a first donor engineered to express selected humanized CD19 CAR constructs disclosed herein against Nalm6 cells. 17A shows data related to the cytotoxicity of NK cells from a first donor engineered to express selected humanized CD19 CAR constructs disclosed herein against Raji cells. 17C shows data related to the cytotoxicity of NK cells from a second donor engineered to express selected humanized CD19 CAR constructs disclosed herein against Nalm6 cells. 17D shows data related to the cytotoxicity of NK cells from a third donor engineered to express selected humanized CD19 CAR constructs disclosed herein against Raji cells. 17E shows data related to the cytotoxicity of NK cells from a third donor engineered to express selected humanized CD19 CAR constructs disclosed herein against Nalm6 cells.

FIG. 19A shows data related to the cytotoxicity of NK cells from a first donor engineered to express selected humanized CD19 CAR constructs disclosed herein against Raji cells with addition of the Raji cells to the NK cell culture at day 7 and again at day 14. FIG. 19B shows data related to the cytotoxicity of NK cells from a first donor engineered to express selected humanized CD19 CAR constructs disclosed herein against Nalm6 cells with addition of the Nalm6 cells to the NK cell culture at day 7 and again at day 14. FIG. 19C shows data related to the cytotoxicity of NK cells from a second donor engineered to express selected humanized CD19 CAR constructs disclosed herein against Raji cells with addition of the Raji cells to the NK cell culture at day 7 and again at day 14. FIG. 19D shows data related to the cytotoxicity of NK cells from a second donor engineered to express selected humanized CD19 CAR constructs disclosed herein against Nalm6 cells with addition of the Nalm6 cells to the NK cell culture at day 7 and again at day 14.

FIG. 20A shows fluorescence data from expression of non-limiting examples of humanized anti-CD19 CAR constructs from two donors 10 days post-transduction. FIG. 20B shows data related to the percentage of cells expressing CD19 (indicative of the efficiency of expression of the given anti-CD19 CAR.

FIG. 21A shows data related to the cytotoxicity of NK cells (from the first of the two donors of FIG. 20) engineered to express selected humanized CD19 CAR constructs disclosed herein against Raji cells with addition of the Raji cells to the NK cell culture at day 7 and again at day 14. FIG. 21B shows data related to the cytotoxicity of NK cells (from the second of the two donors of FIG. 20) engineered to express selected humanized CD19 CAR constructs disclosed herein against Raji cells with addition of the Raji cells to the NK cell culture at day 7 and again at day 14.

FIG. 22A shows interferon gamma release. FIG. 22B shows GM-CSF release. FIG. 22C shows tumor necrosis factor release. FIG. 22D shows perforin release. FIG. 22E shows granzyme release.

FIG. 23A shows the analysis of survival of NK cells from a first donor engineered to express the indicated non-limiting embodiments of anti-CD19 CAR constructs at days 7, 13, 19, and 26 post-transduction. FIG. 23B shows the analysis of survival of NK cells from a second donor engineered to express the indicated non-limiting embodiments of anti-CD19 CAR constructs at days 7, 13, 19, and 26 post-transduction. FIG. 23C shows the analysis of survival of NK cells from a third donor engineered to express the indicated non-limiting embodiments of anti-CD19 CAR constructs at days 11, 19, and 26 post-transduction. FIG. 23D shows the analysis of survival of NK cells from a fourth donor engineered to express the indicated non-limiting embodiments of anti-CD19 CAR constructs at days 11, 19, and 26 post-transduction. For each experiment, media was changed twice per week.

FIG. 25A shows GFP transduced NK cells as a control. FIG. 25B shows CD19 expression in NK cells transduced with NK19-1. FIG. 25C shows CD19 expression in NK cells transduced with NK19H-1. FIG. 25D shows CD19 expression in NK cells transduced with NK19H-2. FIG. 25E shows CD19 expression in NK cells transduced with NK19H-3. FIG. 25F shows CD19 expression in NK cells transduced with NK19H-4. FIG. 25G shows CD19 expression in NK cells transduced with NK19H-5. FIG. 25H shows CD19 expression in NK cells transduced with NK19H-11. FIG. 25I shows CD19 expression in NK cells transduced with NK19H-12.

FIG. 26A shows data related to the cytotoxicity of NK cells (from a first donor) engineered to express selected humanized CD19 CAR constructs disclosed herein against Raji cells with addition of the Raji cells to the NK cell culture at day 7 and again at day 14. FIG. 26B shows data related to the cytotoxicity of NK cells (from the first donor) engineered to express selected humanized CD19 CAR constructs disclosed herein against Nalm6 cells with addition of the Nalm6 cells to the NK cell culture at day 7 and again at day 14. FIG. 26C shows data related to the cytotoxicity of NK cells (from a second donor) engineered to express selected humanized CD19 CAR constructs disclosed herein against Raji cells with addition of the Raji cells to the NK cell culture at day 7 and again at day 14. FIG. 26D shows data related to the cytotoxicity of NK cells (from the second donor) engineered to express selected humanized CD19 CAR constructs disclosed herein against Nalm6 cells with addition of the Nalm6 cells to the NK cell culture at day 7 and again at day 14.

FIG. 27A shows flow cytometry data for NK cells from a donor that were engineered to express various non-limiting anti-CD19 CAR constructs disclosed herein. FIG. 27B shows corresponding data from NK cells isolated from an additional donor.

FIGS. 28A-28B show cytotoxicity data. FIG. 28A shows the Raji cell count over time when exposed (at 1:1 E:T ratio) to NK cells (from the first donor of FIG. 27) expressing the non-limiting examples of anti-CD19 CAR constructs indicated. FIG. 28B shows the Raji cell count over time when exposed (at 1:1 E:T ratio) to NK cells (from the second donor of FIG. 27) expressing the non-limiting examples of anti-CD19 CAR constructs indicated.

FIG. 29A shows a schematic depiction of an experimental protocol for assessing the effectiveness of CD19-directed CAR constructs in vivo. FIG. 29B shows in vivo bioluminescent imaging of mice having been administered NALM6 tumor cells and treated with the indicated construct. FIG. 29C shows a line graph of the bioluminescent data collected from FIG. 29B. FIG. 29D is a survival curve showing the days that animals in each treatment group survived. FIG. 29E shows the relative expression level of the indicated constructs by NK cells, as measured by the MFI of a tag included in the CD19 CAR construct.

FIG. 30A shows data related to the expression of the indicated constructs as a percentage of all CD56 positive cells in a blood sample from mice 15 days post-NK cell administration (e.g., as per the schematic in FIG. 29A). FIG. 30B shows data related to expression of the indicated constructs as a percentage of cells that are both CD56 positive and express a Flag tag (as part of the CD19 CAR construct), also at 15 days post-NK cell administration. FIG. 30C shows data related to detection of GFP+ tumor cells in samples from animals treated with the indicated constructs, also at day 15 post-NK cell administration. FIGS. 30D, 30E, and 30F show corresponding data at 32 days post-NK cell administration.

FIG. 31A shows data related to the expressing of selected non-flag tagged humanized anti CD19 CAR constructs over time. FIG. 31B shows corresponding data in terms of the detected mean fluorescent intensity for the indicated constructs.

FIG. 32A shows data at 10 days after inception of co-culture with Raji cells. FIG. 32B shows data related to Raji at the final time point, 14 days. FIG. 32C shows data related to Nalm6 cells at 10 days. FIG. 32D shows data related to Nalm6 cells at 14 days.

FIG. 33A shows expression of interferon gamma by NK cells expressing the indicated constructs after co-culturing with Raji cells. FIG. 33B shows expression of GM-CSF by NK cells expressing the indicated constructs after co-culturing with Raji cells. FIG. 33C shows expression of tumor necrosis factor alpha by NK cells expressing the indicated constructs after co-culturing with Raji cells. FIG. 33D shows expression of perforin by NK cells expressing the indicated constructs after co-culturing with Raji cells. FIG. 33E shows expression of granzyme B by NK cells expressing the indicated constructs after co-culturing with Raji cells. FIG. 33F shows expression of interferon gamma by NK cells expressing the indicated constructs after co-culturing with Nalm6 cells. FIG. 33G shows expression of GM-CSF by NK cells expressing the indicated constructs after co-culturing with Nalm6cells. FIG. 33H shows expression of tumor necrosis factor alpha by NK cells expressing the indicated constructs after co-culturing with Nalm6cells. FIG. 33I shows expression of perforin by NK cells expressing the indicated constructs after co-culturing with Nalm6 cells. FIG. 33J shows expression of granzyme B by NK cells expressing the indicated constructs after co-culturing with Nalm6 cells.

FIG. 35A shows a schematic depiction of an experimental protocol for assessing the effectiveness of humanized, non-tagged, CD19-directed CAR constructs in vivo. FIG. 35B shows in vivo bioluminescent imaging of mice having been administered NALM6 tumor cells and treated with the indicated construct. FIG. 35C shows a line graph of the bioluminescent data collected from FIG. 35B. FIG. 35D shows the relative expression level of the indicated constructs by NK cells, as measured by detection of a CD19-Fc fusion protein that binds to the CD19 CAR construct.

FIG. 36A shows data related to the expression of the indicated constructs as a percentage of all CD56 positive cells in a blood sample from mice 13 days post-NK cell administration (e.g., as per the schematic in FIG. 35A). FIG. 36B shows data related to detection of CD19+ tumor cells in samples from animals treated with the indicated constructs, also at 13 days post-NK cell administration. FIG. 36C shows data related to detection of GFP+ tumor cells in samples from animals treated with the indicated constructs, also at 13 days post-NK cell administration. FIGS. 36D, 36E, and 36F show corresponding data at 27 days post-NK cell administration.

FIG. 37A shows a schematic depiction of an experimental protocol for assessing the effectiveness of humanized, NK cells expressing various CD19-directed CAR constructs in vivo. The various experimental groups tested are as indicated. For cells with an "IL12/IL18" designation, the cells were expanded in the presence of soluble IL12 and/or IL18, as described in in U.S. Provisional Patent Application No. 62/881,311, filed Jul. 31, 2019 and Application No. 62/932,342, filed Nov. 7, 2019, each of which is incorporated in its entirety by reference herein. FIGS. 37B and 37C show bioluminescence data from animals dosed with Nalm6 tumor cells and treated with the indicated construct.

FIG. 38A shows bioluminescence (as photon/second flux) from animals receiving untransduced NK cells. FIG. 38B shows flux measured in animals receiving PBS as a vehicle. FIG. 38C shows flux measured in animals receiving previously frozen NK cells expressing the NK19 NF2 CAR (as a non-limiting example of a CAR). FIG. 38D shows flux measured in animals receiving previously frozen NK cells expressing the NK19 NF2 CAR (as a non-limiting example of a CAR) expanded using IL12 and/or IL18. FIG. 38E and FIG. 38F show flux measured in animals receiving fresh NK cells expressing the NK19 NF2 CAR (as a non-limiting example of a CAR). FIG. 38G and FIG. 38H show flux measured in animals receiving previously fresh NK cells expressing the NK19 NF2 CAR (as a non-limiting example of a CAR) expanded using IL12 and/or IL18. FIG. 38I shows a line graph depicting the bioluminescence measured in the various groups over the first 30 days post-tumor inoculation. FIG. 38J shows a line graph depicting the bioluminescence measured in the various groups over the first 56 days post-tumor inoculation.

DETAILED DESCRIPTION

Figure 1B:
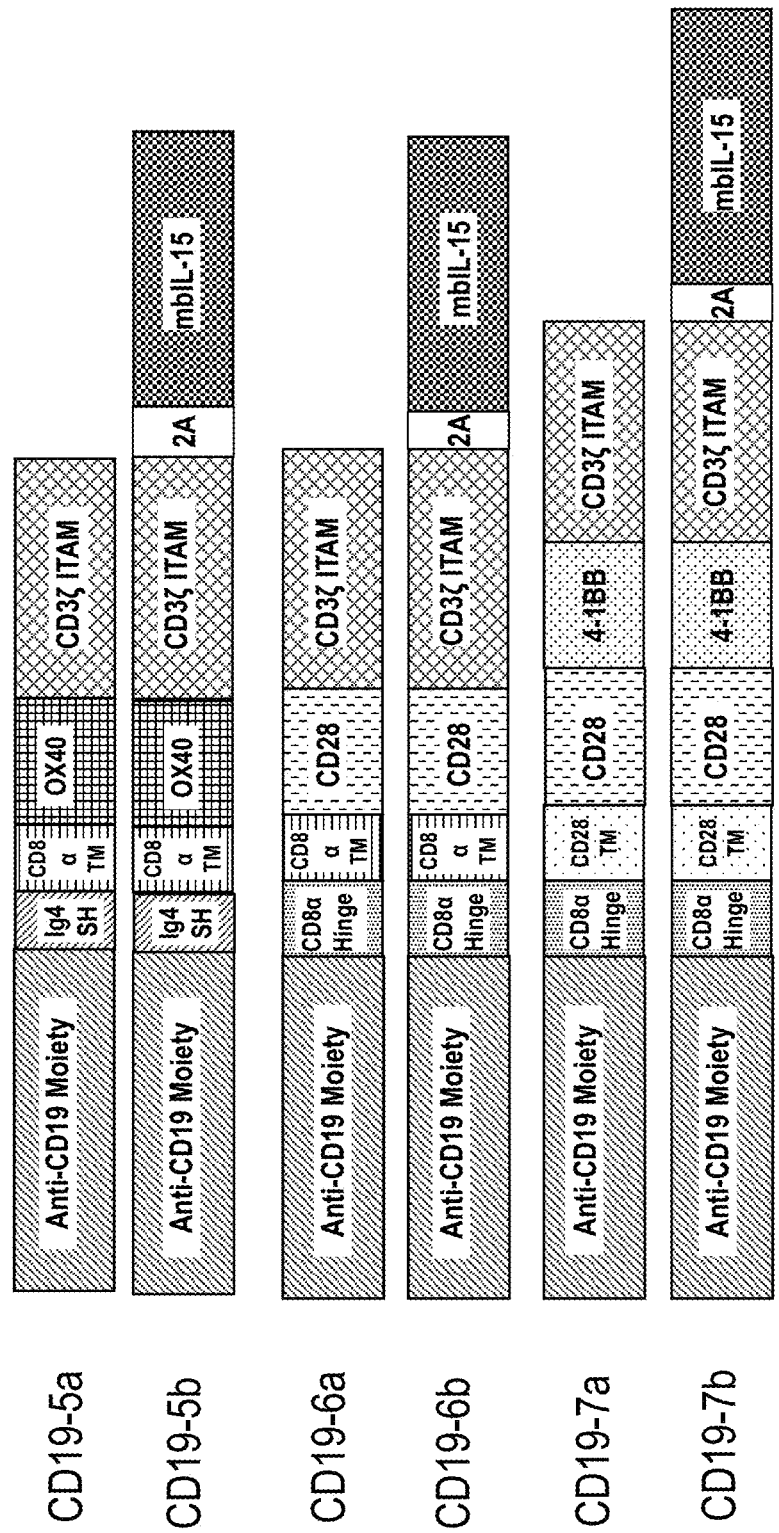
FIG. 1B includes depictions of additional non-limiting examples of CD19-directed chimeric receptors.

Some embodiments of the methods and compositions provided herein relate to CD19-directed chimeric receptors. In some embodiments, the receptors are expressed on a cell as described herein. Some embodiments include methods of use of the compositions or cells in immunotherapy.

The term "anticancer effect" refers to a biological effect which can be manifested by various means, including but not limited to, a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anticancer effect" can also be manifested by the ability of the SIRs in prevention of the occurrence of cancer in the first place.

Cell Types

Some embodiments of the methods and compositions provided herein relate to a cell such as an immune cell. For example, an immune cell may be engineered to include a chimeric receptor such as a CD19-directed chimeric receptor, or engineered to include a nucleic acid encoding said chimeric receptor as described herein.

Traditional anti-cancer therapies relied on a surgical approach, radiation therapy, chemotherapy, or combinations of these methods. As research led to a greater understanding of some of the mechanisms of certain cancers, this knowledge was leveraged to develop targeted cancer therapies. Targeted therapy is a cancer treatment that employs certain drugs that target specific genes or proteins found in cancer cells or cells supporting cancer growth, (like blood vessel cells) to reduce or arrest cancer cell growth. More recently, genetic engineering has enabled approaches to be developed that harness certain aspects of the immune system to fight cancers. In some cases, a patient's own immune cells are modified to specifically eradicate that patient's type of cancer. Various types of immune cells can be used, such as T cells or Natural Killer (NK cells), as described in more detail below.

To facilitate cancer immunotherapies, there are provided for herein polynucleotides, polypeptides, and vectors that encode chimeric antigen receptors (CAR) that comprise a target binding moiety (e.g., an extracellular binder of a ligand, or a CD19-directed chimeric receptor, expressed by a cancer cell) and a cytotoxic signaling complex. For example, some embodiments include a polynucleotide, polypeptide, or vector that encodes a CD19-directed chimeric receptor to facilitate targeting of an immune cell to a cancer and exerting cytotoxic effects on the cancer cell. Also provided are engineered immune cells (e.g., T cells or NK cells) expressing such CARs. There are also provided herein, in several embodiments, polynucleotides, polypeptides, and vectors that encode a construct comprising an extracellular domain comprising two or more subdomains, e.g., first CD19-targetingn subdomain comprising a CD19 binding moiety as disclosed herein and a second subdomain comprising a C-type lectin-like receptor and a cytotoxic signaling complex. Also provided are engineered immune cells (e.g., T cells or NK cells) expressing such bi-specific constructs. Engineered immune cells (e.g., T cells or NK cells) expressing multi-specific constructs and/or having the ability to bind a plurality of target markers are also provided. Methods of treating cancer and other uses of such cells for cancer immunotherapy are also provided for herein.

Engineered Cells for Immunotherapy

In several embodiments, cells of the immune system are engineered to have enhanced cytotoxic effects against target cells, such as tumor cells. For example, a cell of the immune system may be engineered to include a CD19-directed chimeric receptor as described herein. In several embodiments, white blood cells or leukocytes, are used, since their native function is to defend the body against growth of abnormal cells and infectious disease. There are a variety of types of white bloods cells that serve specific roles in the human immune system, and are therefore a preferred starting point for the engineering of cells disclosed herein. White blood cells include granulocytes and agranulocytes (presence or absence of granules in the cytoplasm, respectively). Granulocytes include basophils, eosinophils, neutrophils, and mast cells. Agranulocytes include lymphocytes and monocytes. Cells such as those that follow or are otherwise described herein may be engineered to include a chimeric receptor such as a CD19-directed chimeric receptor, or a nucleic acid encoding the chimeric receptor and/or engineered to co-express a membrane-bound interleukin 15 (mbIL15) co-stimulatory domain.

Monocytes for Immunotherapy

Monocytes are a subtype of leukocyte. Monocytes can differentiate into macrophages and myeloid lineage dendritic cells. Monocytes are associated with the adaptive immune system and serve the main functions of phagocytosis, antigen presentation, and cytokine production. Phagocytosis is the process of uptake cellular material, or entire cells, followed by digestion and destruction of the engulfed cellular material. In several embodiments, monocytes are used in connection with one or more additional engineered cells as disclosed herein. Some embodiments of the methods and compositions described herein relate to a monocyte that includes a CD19-directed chimeric receptor, or a nucleic acid encoding the CD19-directed chimeric receptor. Several embodiments of the methods and compositions disclosed herein relate to monocytes engineered to express a CD19-directed chimeric receptor and a membrane-bound interleukin 15 (mbIL15) co-stimulatory domain.

Lymphocytes for Immunotherapy

Lymphocytes, the other primary sub-type of leukocyte include T cells (cell-mediated, cytotoxic adaptive immunity), natural killer cells (cell-mediated, cytotoxic innate immunity), and B cells (humoral, antibody-driven adaptive immunity). While B cells are engineered according to several embodiments, disclosed herein, several embodiments also relate to engineered T cells or engineered NK cells (mixtures of T cells and NK cells are used in some embodiments). Some embodiments of the methods and compositions described herein relate to a lymphocyte that includes a CD19-directed chimeric receptor, or a nucleic acid encoding the CD19-directed chimeric receptor. Several embodiments of the methods and compositions disclosed herein relate to lymphocytes engineered to express a CD19-directed chimeric receptor and a membrane-bound interleukin 15 (mbIL15) co-stimulatory domain.

T Cells for Immunotherapy

T cells are distinguishable from other lymphocytes subtypes (e.g., B cells or NK cells) based on the presence of a T-cell receptor on the cell surface. T cells can be divided into various different subtypes, including effector T cells, helper T cells, cytotoxic T cells, memory T cells, regulatory T cells, natural killer T cell, mucosal associated invariant T cells and gamma delta T cells. In some embodiments, a specific subtype of T cell is engineered. In some embodiments, a mixed pool of T cell subtypes is engineered. In some embodiments, there is no specific selection of a type of T cells to be engineered to express the cytotoxic receptor complexes disclosed herein. In several embodiments, specific techniques, such as use of cytokine stimulation are used to enhance expansion/collection of T cells with a specific marker profile. For example, in several embodiments, activation of certain human T cells, e.g. CD4+ T cells, CD8+ T cells is achieved through use of CD3 and/or CD28 as stimulatory molecules. In several embodiments, there is provided a method of treating or preventing cancer or an infectious disease, comprising administering a therapeutically effective amount of T cells expressing the cytotoxic receptor complex and/or a homing moiety as described herein. In several embodiments, the engineered T cells are autologous cells, while in some embodiments, the T cells are allogeneic cells. Some embodiments of the methods and compositions described herein relate to a T cell that includes a CD19-directed chimeric receptor, or a nucleic acid encoding the CD19-directed chimeric receptor. Several embodiments of the methods and compositions disclosed herein relate to T-cells engineered to express a CD19-directed chimeric receptor and a membrane-bound interleukin 15 (mbIL15) co-stimulatory domain.

NK Cells for Immunotherapy

In several embodiments, there is provided a method of treating or preventing cancer or an infectious disease, comprising administering a therapeutically effective amount of natural killer (NK) cells expressing the cytotoxic receptor complex and/or a homing moiety as described herein. In several embodiments, the engineered NK cells are autologous cells, while in some embodiments, the NK cells are allogeneic cells. In several embodiments, NK cells are preferred because the natural cytotoxic potential of NK cells is relatively high. In several embodiments, it is unexpectedly beneficial that the engineered cells disclosed herein can further upregulate the cytotoxic activity of NK cells, leading to an even more effective activity against target cells (e.g., tumor or other diseased cells). Some embodiments of the methods and compositions described herein relate to an NK that includes a CD19-directed chimeric receptor, or a nucleic acid encoding the CD19-directed chimeric receptor. Several embodiments of the methods and compositions disclosed herein relate to NK cells engineered to express a CD19-directed chimeric receptor and a membrane-bound interleukin 15 (mbIL15) co-stimulatory domain.

Hematopoietic Stem Cells for Cancer Immunotherapy

In some embodiments, hematopoietic stem cells (HSCs) are used in the methods of immunotherapy disclosed herein. In several embodiments, the cells are engineered to express a homing moiety and/or a cytotoxic receptor complex. HSCs are used, in several embodiments, to leverage their ability to engraft for long-term blood cell production, which could result in a sustained source of targeted anti-cancer effector cells, for example to combat cancer remissions. In several embodiments, this ongoing production helps to offset anergy or exhaustion of other cell types, for example due to the tumor microenvironment. In several embodiments allogeneic HSCs are used, while in some embodiments, autologous HSCs are used. In several embodiments, HSCs are used in combination with one or more additional engineered cell type disclosed herein. Some embodiments of the methods and compositions described herein relate to a stem cell, such as a hematopoietic stem cell, that includes a CD19-directed chimeric receptor, or a nucleic acid encoding the CD19-directed chimeric receptor. Several embodiments of the methods and compositions disclosed herein relate to stem cells, such as hematopoietic stem cells that are engineered to express a CD19-directed chimeric receptor and a membrane-bound interleukin 15 (mbIL15) co-stimulatory domain.

Extracellular Domains (Tumor Binder)

Some embodiments of the compositions and methods described herein relate to a chimeric receptor, such as a CD19-directed chimeric receptor, that includes an extracellular domain. In some embodiments, the extracellular domain comprises a tumor-binding domain (also referred to as an antigen-binding protein or antigen-binding domain) as described herein. In some embodiments, the antigen-binding domain is derived from or comprises wild-type or non-wild-type sequence of an antibody, an antibody fragment, an scFv, a Fv, a Fab, a (Fab')2, a single domain antibody (SDAB), a vH or vL domain, a camelid VHH domain, or a non-immunoglobulin scaffold such as a DARPIN, an affibody, an affilin, an adnectin, an affitin, a repebody, a fynomer, an alphabody, an avimer, an atrimer, a centyrin, a pronectin, an anticalin, a kunitz domain, an Armadillo repeat protein, an autoantigen, a receptor or a ligand. In some embodiments, the tumor-binding domain contains more than one antigen binding domain. In embodiments, the antigen-binding domain is operably linked directly or via an optional linker to the NH2-terminal end of a TCR domain (e.g. constant chains of TCR-alpha, TCR-beta1, TCR-beta2, preTCR-alpha, pre-TCR-alpha-Del48, TCR-gamma, or TCR-delta)

Antigen-Binding Proteins

There are provided, in several embodiments, antigen-binding proteins. As used herein, the term "antigen-binding protein" shall be given its ordinary meaning, and shall also refer to a protein comprising an antigen-binding fragment that binds to an antigen and, optionally, a scaffold or framework portion that allows the antigen-binding fragment to adopt a conformation that promotes binding of the antigen-binding protein to the antigen. In some embodiments, the antigen is a cancer antigen (e.g., CD19) or a fragment thereof. In some embodiments, the antigen-binding fragment comprises at least one CDR from an antibody that binds to the antigen. In some embodiments, the antigen-binding fragment comprises all three CDRs from the heavy chain of an antibody that binds to the antigen or from the light chain of an antibody that binds to the antigen. In still some embodiments, the antigen-binding fragment comprises all six CDRs from an antibody that binds to the antigen (three from the heavy chain and three from the light chain). In several embodiments, the antigen-binding fragment comprises one, two, three, four, five, or six CDRs from an antibody that binds to the antigen, and in several embodiments, the CDRs can be any combination of heavy and/or light chain CDRs. The antigen-binding fragment in some embodiments is an antibody fragment.

Nonlimiting examples of antigen-binding proteins include antibodies, antibody fragments (e.g., an antigen-binding fragment of an antibody), antibody derivatives, and antibody analogs. Further specific examples include, but are not limited to, a single-chain variable fragment (scFv), a nanobody (e.g. VH domain of camelid heavy chain antibodies; VHH fragment), a Fab fragment, a Fab' fragment, a F(ab')2 fragment, a Fv fragment, a Fd fragment, and a complementarity determining region (CDR) fragment. These molecules can be derived from any mammalian source, such as human, mouse, rat, rabbit, or pig, dog, or camelid. Antibody fragments may compete for binding of a target antigen with an intact (e.g., native) antibody and the fragments may be produced by the modification of intact antibodies (e.g. enzymatic or chemical cleavage) or synthesized de novo using recombinant DNA technologies or peptide synthesis. The antigen-binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen-binding protein as well as wholly synthetic scaffolds comprising, for example, a biocompatible polymer. In addition, peptide antibody mimetics ("PAMs") can be used, as well as scaffolds based on antibody mimetics utilizing fibronectin components as a scaffold.

In some embodiments, the antigen-binding protein comprises one or more antibody fragments incorporated into a single polypeptide chain or into multiple polypeptide chains. For instance, antigen-binding proteins can include, but are not limited to, a diabody; an intrabody; a domain antibody (single VL or VH domain or two or more VH domains joined by a peptide linker); a maxibody (2 scFvs fused to Fc region); a triabody; a tetrabody; a minibody (scFv fused to CH3 domain); a peptibody (one or more peptides attached to an Fc region); a linear antibody (a pair of tandem Fd segments (VH-CH1-VH-CH1) which, together with complementary light chain polypeptides, form a pair of antigen binding regions); a small modular immunopharmaceutical; and immunoglobulin fusion proteins (e.g. IgG-scFv, IgG-Fab, 2scFv-IgG, 4scFv-IgG, VH-IgG, IgG-VH, and Fab-scFv-Fc).

In some embodiments, the antigen-binding protein has the structure of an immunoglobulin. As used herein, the term "immunoglobulin" shall be given its ordinary meaning, and shall also refer to a tetrameric molecule, with each tetramer comprising two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Within light and heavy chains, the variable (V) and constant regions (C) are joined by a "J" region of about 12 or more amino acids, with the heavy chain also including a "D" region of about 10 more amino acids. The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

Human light chains are classified as kappa and lambda light chains. An antibody "light chain", refers to the smaller of the two types of polypeptide chains present in antibody molecules in their naturally occurring conformations. Kappa (κ) and lambda (λ) light chains refer to the two major antibody light chain isotypes. A light chain may include a polypeptide comprising, from amino terminus to carboxyl terminus, a single immunoglobulin light chain variable region (VL) and a single immunoglobulin light chain constant domain (CL).

Heavy chains are classified as mu (μ), delta (Δ), gamma (γ), alpha (α), and epsilon (ε), and define the antibody's isotype as IgM, IgD, IgG, IgA, and IgE, respectively. An antibody "heavy chain" refers to the larger of the two types of polypeptide chains present in antibody molecules in their naturally occurring conformations, and which normally determines the class to which the antibody belongs. A heavy chain may include a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4).

The IgG-class is further divided into subclasses, namely, IgG1, IgG2, IgG3, and IgG4. The IgA-class is further divided into subclasses, namely IgA1 and IgA2. The IgM has subclasses including, but not limited to, IgM1 and IgM2. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (e.g., between the light and heavy chain) and between the hinge regions of the antibody heavy chains.

In some embodiments, the antigen-binding protein is an antibody. The term "antibody", as used herein, refers to a protein, or polypeptide sequence derived from an immunoglobulin molecule which specifically binds with an antigen. Antibodies can be monoclonal, or polyclonal, multiple or single chain, or intact immunoglobulins, and may be derived from natural sources or from recombinant sources. Antibodies can be tetramers of immunoglobulin molecules. The antibody may be "humanized", "chimeric" or non-human. An antibody may include an intact immunoglobulin of any isotype, and includes, for instance, chimeric, humanized, human, and bispecific antibodies. An intact antibody will generally comprise at least two full-length heavy chains and two full-length light chains. Antibody sequences can be derived solely from a single species, or can be "chimeric," that is, different portions of the antibody can be derived from two different species as described further below. Unless otherwise indicated, the term "antibody" also includes antibodies comprising two substantially full-length heavy chains and two substantially full-length light chains provided the antibodies retain the same or similar binding and/or function as the antibody comprised of two full length light and heavy chains. For example, antibodies having 1, 2, 3, 4, or 5 amino acid residue substitutions, insertions or deletions at the N-terminus and/or C-terminus of the heavy and/or light chains are included in the definition provided that the antibodies retain the same or similar binding and/or function as the antibodies comprising two full length heavy chains and two full length light chains. Examples of antibodies include monoclonal antibodies, polyclonal antibodies, chimeric antibodies, humanized antibodies, human antibodies, bispecific antibodies, and synthetic antibodies. There is provided, in some embodiments, monoclonal and polyclonal antibodies. As used herein, the term "polyclonal antibody" shall be given its ordinary meaning, and shall also refer to a population of antibodies that are typically widely varied in composition and binding specificity. As used herein, the term "monoclonal antibody" ("mAb") shall be given its ordinary meaning, and shall also refer to one or more of a population of antibodies having identical sequences. Monoclonal antibodies bind to the antigen at a particular epitope on the antigen.

In some embodiments, the antigen-binding protein is a fragment or antigen-binding fragment of an antibody. The term "antibody fragment" refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CHI domains, linear antibodies, single domain antibodies such as sdAb (either vL or vH), camelid vHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23: 1126-1136, 2005). Antigen binding fragments can also be grafted into scaffolds based on polypeptides such as a fibronectin type III (Fn3)(see U.S. Pat. No. 6,703,199, which describes fibronectin polypeptide mini bodies). An antibody fragment may include a Fab, Fab', F(ab')2, and/or Fv fragment that contains at least one CDR of an immunoglobulin that is sufficient to confer specific antigen binding to a cancer antigen (e.g., CD19). Antibody fragments may be produced by recombinant DNA techniques or by enzymatic or chemical cleavage of intact antibodies.

In some embodiments, Fab fragments are provided. A Fab fragment is a monovalent fragment having the VL, VH, CL and CH1 domains; a F(ab')2 fragment is a bivalent fragment having two Fab fragments linked by a disulfide bridge at the hinge region; a Fd fragment has the VH and CH1 domains; an Fv fragment has the VL and VH domains of a single arm of an antibody; and a dAb fragment has a VH domain, a VL domain, or an antigen-binding fragment of a VH or VL domain. In some embodiments, these antibody fragments can be incorporated into single domain antibodies, single-chain antibodies, maxibodies, minibodies, intrabodies, diabodies, triabodies, tetrabodies, v-NAR and bis-scFv. In some embodiments, the antibodies comprise at least one CDR as described herein.

There is also provided for herein, in several embodiments, single-chain variable fragments. As used herein, the term "single-chain variable fragment" ("scFv") shall be given its ordinary meaning, and shall also refer to a fusion protein in which a VL and a VH region are joined via a linker (e.g., a synthetic sequence of amino acid residues) to form a continuous protein chain wherein the linker is long enough to allow the protein chain to fold back on itself and form a monovalent antigen binding site). For the sake of clarity, unless otherwise indicated as such, a "single-chain variable fragment" is not an antibody or an antibody fragment as defined herein. Diabodies are bivalent antibodies comprising two polypeptide chains, wherein each polypeptide chain comprises VH and VL domains joined by a linker that is configured to reduce or not allow for pairing between two domains on the same chain, thus allowing each domain to pair with a complementary domain on another polypeptide chain. According to several embodiments, if the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

In several embodiments, the antigen-binding protein comprises one or more CDRs. As used herein, the term "CDR" shall be given its ordinary meaning, and shall also refer to the complementarity determining region (also termed "minimal recognition units" or "hypervariable region") within antibody variable sequences. The CDRs permit the antigen-binding protein to specifically bind to a particular antigen of interest. There are three heavy chain variable region CDRs (CDRH1, CDRH2 and CDRH3) and three light chain variable region CDRs (CDRL1, CDRL2 and CDRL3). The CDRs in each of the two chains typically are aligned by the framework regions to form a structure that binds specifically to a specific epitope or domain on the target protein. From N-terminus to C-terminus, naturally-occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883. Complementarity determining regions (CDRs) and framework regions (FR) of a given antibody may be identified using this system. Other numbering systems for the amino acids in immunoglobulin chains include IMGT® (the international ImMunoGeneTics information system; Lefranc et al, Dev. Comp. Immunol. 29:185-203; 2005) and AHo (Honegger and Pluckthun, J. Mol. Biol. 309(3):657-670; 2001). One or more CDRs may be incorporated into a molecule either covalently or noncovalently to make it an antigen-binding protein. In several embodiments, the antigen-binding proteins provided herein comprise a heavy chain variable region selected from SEQ ID NO: 104 and SEQ ID NO: 106. In several embodiments, the antigen-binding proteins provided herein comprise a light chain variable region selected from SEQ ID NO: 105 and SEQ ID NO: 107.

In several embodiments, the antigen-binding protein has been modified from its original sequence, for example for purposes of improving expression, function, or reducing a potential immune response to the antigen-binding protein by a host. In several embodiments, the antigen-binding protein comprises a light chain variable region selected from SEQ ID NO: 117, SEQ ID NO: 118, and SEQ ID NO: 119 and/or sequences having at least 90% identity and/or homology (e.g., 90-95%, 95%, 96%, 97%, 98%, 99%). In several embodiments, the light chain variable region differs in sequence from SEQ ID NO: 117, SEQ ID NO: 118, or SEQ ID NO: 119 by more than 5% (e.g., by 5-7%, 5-10%, 10-20% or higher) with ligand-binding function (or other functionality) being similar, substantially similar or the same as SEQ ID NO: 117, SEQ ID NO: 118, or SEQ ID NO: 119.

In several embodiments, the antigen-binding protein comprises a heavy chain variable region selected from SEQ ID NO: 120, SEQ ID NO: 121, SEQ ID NO: 122, and SEQ ID NO: 123 and/or sequences having at least 90% identity and/or homology (e.g., 90-95%, 95%, 96%, 97%, 98%, 99%). In several embodiments, the heavy chain variable region differs in sequence from SEQ ID NO: 120, SEQ ID NO: 121, SEQ ID NO: 122, or SEQ ID NO: 123 by more than 5% (e.g., by 5-7%, 5-10%, 10-20% or higher) with ligand-binding function (or other functionality) being similar, substantially similar or the same as SEQ ID NO: 120, SEQ ID NO: 121, SEQ ID NO: 122, or SEQ ID NO: 123. Depending on the embodiment, any combination of heavy and light chain regions may be used (e.g., in assembling a scFv). In several embodiments, the antigen-binding protein comprises one or more CDRs selected from SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 134, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, and SEQ ID NO: 144.

In additional embodiments, the CDRs are selected from SEQ ID NO: 108, SEQ ID NO: 109, SEQ ID NO: 110, SEQ ID NO: 111, SEQ ID NO: 112, SEQ ID NO: 113, SEQ ID NO: 114, and SEQ ID NO: 115, in any combination. In one embodiment, the CDRs are assembled to generate a CAR directed to CD19 and comprising SEQ ID NO: 116.

In several embodiments, the antigen-binding protein comprises a heavy chain having the sequence of SEQ ID NO: 88. In several embodiments, that heavy chain is coupled with (e.g., as an scFv), one of the light chains of SEQ ID NO: 89, SEQ ID NO: 90, and/or SEQ ID NO: 91. In several embodiments, the antigen-binding protein comprises one of more CDRs selected from SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, and SEQ ID NO: 100.

In several embodiments, the antigen-binding protein comprises a light chain region of an FMC63 antibody that has the sequence of SEQ ID NO: 150. In several embodiments, the antigen-binding protein comprises a light chain region of an FMC63 antibody that has the sequence of SEQ ID NO: 148. In several embodiments, linkers are used between heavy and light chains, and in some embodiments, the linker comprises the sequence of SEQ ID NO: 149. In several embodiments, such heavy and light chains are used in conjunction with a CD28 co-stimulatory domain, such as that of SEQ ID NO: 153. Often a spacer is used to separate component parts of a CAR. For example, in several embodiments, a spacer is used comprising the sequence of SEQ ID NO: 151. In several embodiments, a transmembrane domain having the sequence of SEQ ID NO: 152 is used. In several embodiments, the CAR comprises a nucleic acid sequence that shares at least about 90%, at least about 94%, at least about 95%, at least about 96%, at least about 97%, at least about 98%, or at least about 99%, sequence identity, homology and/or functional equivalence with SEQ ID NO: 147.

In some embodiments, the antigen-binding proteins provided herein comprise one or more CDR(s) as part of a larger polypeptide chain. In some embodiments, the antigen-binding proteins covalently link the one or more CDR(s) to another polypeptide chain. In some embodiments, the antigen-binding proteins incorporate the one or more CDR(s) noncovalently. In some embodiments, the antigen-binding proteins may comprise at least one of the CDRs described herein incorporated into a biocompatible framework structure. In some embodiments, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions and/or substitutions of amino acids, relative to a naturally occurring polypeptide or fold. Depending on the embodiment, the scaffolds can be derived from a polypeptide of a variety of different species (or of more than one species), such as a human, a non-human primate or other mammal, other vertebrate, invertebrate, plant, bacteria or virus.

Depending on the embodiment, the biocompatible framework structures are based on protein scaffolds or skeletons other than immunoglobulin domains. In some such embodiments, those framework structures are based on fibronectin, ankyrin, lipocalin, neocarzinostain, cytochrome b, CP1 zinc finger, PST1, coiled coil, LACI-D1, Z domain and/or tendamistat domains.

There is also provided, in some embodiments, antigen-binding proteins with more than one binding site. In several embodiments, the binding sites are identical to one another while in some embodiments the binding sites are different from one another. For example, an antibody typically has two identical binding sites, while a "bispecific" or "bifunctional" antibody has two different binding sites. The two binding sites of a bispecific antigen-binding protein or antibody will bind to two different epitopes, which can reside on the same or different protein targets. In several embodiments, this is particularly advantageous, as a bispecific chimeric antigen receptor can impart to an engineered cell the ability to target multiple tumor markers. For example, CD19 and an additional tumor marker, such as CD123, NKG2D or any other marker disclosed herein or appreciated in the art as a tumor specific antigen or tumor associated antigen.

As used herein, the term "chimeric antibody" shall be given its ordinary meaning, and shall also refer to an antibody that contains one or more regions from one antibody and one or more regions from one or more other antibodies. In some embodiments, one or more of the CDRs are derived from an anti-cancer antigen (e.g., CD19) antibody. In several embodiments, all of the CDRs are derived from an anti-cancer antigen antibody (such as an anti-CD19 antibody). In some embodiments, the CDRs from more than one anti-cancer antigen antibodies are mixed and matched in a chimeric antibody. For instance, a chimeric antibody may comprise a CDR1 from the light chain of a first anti-cancer antigen antibody, a CDR2 and a CDR3 from the light chain of a second anti-cancer antigen antibody, and the CDRs from the heavy chain from a third anti-cancer antigen antibody. Further, the framework regions of antigen-binding proteins disclosed herein may be derived from one of the same anti-cancer antigen (e.g., CD19) antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also provided herein are fragments of such antibodies that exhibit the desired biological activity.

In some embodiments, an antigen-binding protein is provided comprising a heavy chain variable domain having at least 90% identity to the VH domain amino acid sequence set forth in SEQ ID NO: 33. In some embodiments, the antigen-binding protein comprises a heavy chain variable domain having at least 95% identity to the VH domain amino acid sequence set forth in SEQ ID NO: 33. In some embodiments, the antigen-binding protein comprises a heavy chain variable domain having at least 96, 97, 98, or 99% identity to the VH domain amino acid sequence set forth in SEQ ID NO: 33. In several embodiments, the heavy chain variable domain may have one or more additional mutations (e.g., for purposes of humanization) in the VH domain amino acid sequence set forth in SEQ ID NO: 33, but retains specific binding to a cancer antigen (e.g., CD19). In several embodiments, the heavy chain variable domain may have one or more additional mutations in the VH domain amino acid sequence set forth in SEQ ID NO: 33, but has improved specific binding to a cancer antigen (e.g., CD19).

In some embodiments, the antigen-binding protein comprises a light chain variable domain having at least 90% identity to the VL domain amino acid sequence set forth in SEQ ID NO: 32. In some embodiments, the antigen-binding protein comprises a light chain variable domain having at least 95% identity to the VL domain amino acid sequence set forth in SEQ ID NO: 32. In some embodiments, the antigen-binding protein comprises a light chain variable domain having at least 96, 97, 98, or 99% identity to the VL domain amino acid sequence set forth in SEQ ID NO: 32. In several embodiments, the light chain variable domain may have one or more additional mutations (e.g., for purposes of humanization) in the VL domain amino acid sequence set forth in SEQ ID NO: 32, but retains specific binding to a cancer antigen (e.g., CD19). In several embodiments, the light chain variable domain may have one or more additional mutations in the VL domain amino acid sequence set forth in SEQ ID NO: 32, but has improved specific binding to a cancer antigen (e.g., CD19).

In some embodiments, the antigen-binding protein comprises a heavy chain variable domain having at least 90% identity to the VH domain amino acid sequence set forth in SEQ ID NO: 33, and a light chain variable domain having at least 90% identity to the VL domain amino acid sequence set forth in SEQ ID NO: 32. In some embodiments, the antigen-binding protein comprises a heavy chain variable domain having at least 95% identity to the VH domain amino acid sequence set forth in SEQ ID NO: 33, and a light chain variable domain having at least 95% identity to the VL domain amino acid sequence set forth in SEQ ID NO: 32. In some embodiments, the antigen-binding protein comprises a heavy chain variable domain having at least 96, 97, 98, or 99% identity to the VH domain amino acid sequence set forth in SEQ ID NO: 33, and a light chain variable domain having at least 96, 97, 98, or 99% identity to the VL domain amino acid sequence set forth in SEQ ID NO: 32.

In some embodiments, the antigen-binding protein comprises a heavy chain variable domain having the VH domain amino acid sequence set forth in SEQ ID NO: 33, and a light chain variable domain having the VL domain amino acid sequence set forth in SEQ ID NO: 32. In some embodiments, the light-chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a light chain variable domain of SEQ ID NO: 32. In some embodiments, the light-chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a heavy chain variable domain in accordance with SEQ ID NO: 33.

In some embodiments, the light chain variable domain comprises a sequence of amino acids that is encoded by a nucleotide sequence that is at least 70%, 75%, 80%, 85%, 90%, 91%, 92%, 93%, 94%, 95%, 96%, 97%, 98%, 99% or 100% identical to the polynucleotide sequence SEQ ID NO: 32. In some embodiments, the light chain variable domain comprises a sequence of amino acids that is encoded by a polynucleotide that hybridizes under moderately stringent conditions to the complement of a polynucleotide that encodes a light chain variable domain in accordance with the sequence in SEQ ID NO: 32. In some embodiments, the light chain variable domain comprises a sequence of amino acids that is encoded by a polynucleotide that hybridizes under stringent conditions to the complement of a polynucleotide that encodes a light chain variable domain in accordance with the sequence in SEQ ID NO: 32.

In some embodiments, the heavy chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a heavy chain variable domain in accordance with the sequence of SEQ ID NO: 33. In some embodiments, the heavy chain variable domain comprises a sequence of amino acids that is encoded by a polynucleotide that hybridizes under moderately stringent conditions to the complement of a polynucleotide that encodes a heavy chain variable domain in accordance with the sequence of SEQ ID NO: 33. In some embodiments, the heavy chain variable domain comprises a sequence of amino acids that is encoded by a polynucleotide that hybridizes under stringent conditions to the complement of a polynucleotide that encodes a heavy chain variable domain in accordance with the sequence of SEQ ID NO: 33.

In several embodiments, additional anti-CD19 binding constructs are provided. For example, in several embodiments, there is provided an scFv that targets CD19 wherein the scFv comprises a heavy chain variable region comprising the sequence of SEQ ID NO. 35. In some embodiments, the antigen-binding protein comprises a heavy chain variable domain having at least 95% identity to the HCV domain amino acid sequence set forth in SEQ ID NO: 35. In some embodiments, the antigen-binding protein comprises a heavy chain variable domain having at least 96, 97, 98, or 99% identity to the HCV domain amino acid sequence set forth in SEQ ID NO: 35. In several embodiments, the heavy chain variable domain may have one or more additional mutations (e.g., for purposes of humanization) in the HCV domain amino acid sequence set forth in SEQ ID NO: 35, but retains specific binding to a cancer antigen (e.g., CD19). In several embodiments, the heavy chain variable domain may have one or more additional mutations in the HCV domain amino acid sequence set forth in SEQ ID NO: 35, but has improved specific binding to a cancer antigen (e.g., CD19).

Additionally, in several embodiments, an scFv that targets CD19 comprises a light chain variable region comprising the sequence of SEQ ID NO. 36. In some embodiments, the antigen-binding protein comprises a light chain variable domain having at least 95% identity to the LCV domain amino acid sequence set forth in SEQ ID NO: 36. In some embodiments, the antigen-binding protein comprises a light chain variable domain having at least 96, 97, 98, or 99% identity to the LCV domain amino acid sequence set forth in SEQ ID NO: 36. In several embodiments, the light chain variable domain may have one or more additional mutations (e.g., for purposes of humanization) in the LCV domain amino acid sequence set forth in SEQ ID NO: 36, but retains specific binding to a cancer antigen (e.g., CD19). In several embodiments, the light chain variable domain may have one or more additional mutations in the LCV domain amino acid sequence set forth in SEQ ID NO: 36, but has improved specific binding to a cancer antigen (e.g., CD19).

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 37. In several embodiments, the LC CDR1 comprises an amino acid sequence with at least about 85%, about 90%, about 95%, or about 98% homology to the sequence of SEQ NO. 37. In several embodiments, the LC CDR2 comprises the sequence of SEQ ID NO. 38. In several embodiments, the LC CDR2 comprises an amino acid sequence with at least about 85%, about 90%, about 95%, or about 98% homology to the sequence of SEQ NO. 38. In several embodiments, the LC CDR3 comprises the sequence of SEQ ID NO. 39. In several embodiments, the LC CDR3 comprises an amino acid sequence with at least about 85%, about 90%, about 95%, or about 98% homology to the sequence of SEQ NO. 39. In several embodiments, the HC CDR1 comprises the sequence of SEQ ID NO. 40. In several embodiments, the HC CDR1 comprises an amino acid sequence with at least about 85%, about 90%, about 95%, or about 98% homology to the sequence of SEQ NO. 40. In several embodiments, the HC CDR2 comprises the sequence of SEQ ID NO. 41, 42, or 43. In several embodiments, the HC CDR2 comprises an amino acid sequence with at least about 85%, about 90%, about 95%, or about 98% homology to the sequence of SEQ NO. 41, 42, or 43. In several embodiments, the HC CDR3 comprises the sequence of SEQ ID NO. 44. In several embodiments, the HC CDR3 comprises an amino acid sequence with at least about 85%, about 90%, about 95%, or about 98% homology to the sequence of SEQ NO. 44.

In several embodiments, there is also provided an anti-CD19 binding moiety that comprises a light chain variable region (VL) and a heavy chain variable region (HL), the VL region comprising a first, second and third complementarity determining region (VL CDR1, VL CDR2, and VL CDR3, respectively and the VH region comprising a first, second and third complementarity determining region (VH CDR1, VH CDR2, and VH CDR3, respectively. In several embodiments, the VL region comprises the sequence of SEQ ID NO. 45, 46, 47, or 48. In several embodiments, the VL region comprises an amino acid sequence with at least about 85%, about 90%, about 95%, or about 98% homology to the sequence of SEQ NO. 45, 46, 47, or 48. In several embodiments, the VH region comprises the sequence of SEQ ID NO. 49, 50, 51 or 52. In several embodiments, the VH region comprises an amino acid sequence with at least about 85%, about 90%, about 95%, or about 98% homology to the sequence of SEQ NO. 49, 50, 51 or 52.

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 53. In several embodiments, the LC CDR1 comprises an amino acid sequence with at least about 85%, about 90%, about 95%, or about 98% homology to the sequence of SEQ NO. 53. In several embodiments, the LC CDR2 comprises the sequence of SEQ ID NO. 54. In several embodiments, the LC CDR2 comprises an amino acid sequence with at least about 85%, about 90%, about 95%, or about 98% homology to the sequence of SEQ NO. 54. In several embodiments, the LC CDR3 comprises the sequence of SEQ ID NO. 55. In several embodiments, the LC CDR3 comprises an amino acid sequence with at least about 85%, about 90%, about 95%, or about 98% homology to the sequence of SEQ NO. 55. In several embodiments, the HC CDR1 comprises the sequence of SEQ ID NO. 56. In several embodiments, the HC CDR1 comprises an amino acid sequence with at least about 85%, about 90%, about 95%, or about 98% homology to the sequence of SEQ NO. 56. In several embodiments, the HC CDR2 comprises the sequence of SEQ ID NO. 57. In several embodiments, the HC CDR2 comprises an amino acid sequence with at least about 85%, about 90%, about 95%, or about 98% homology to the sequence of SEQ NO. 57. In several embodiments, the HC CDR3 comprises the sequence of SEQ ID NO. 58. In several embodiments, the HC CDR3 comprises an amino acid sequence with at least about 85%, about 90%, about 95%, or about 98% homology to the sequence of SEQ NO. 58.

Additional anti-CD19 binding moieties are known in the art, such as those disclosed in, for example, U.S. Pat. No. 8,399,645, US Patent Publication No. 2018/0153977, US Patent Publication No. 2014/0271635, US Patent Publication No. 2018/0251514, and US Patent Publication No. 2018/0312588, the entirety of each of which is incorporated by reference herein.

Natural Killer Group Domains that Bind Tumor Ligands

In several embodiments, engineered immune cells such as NK cells are leveraged for their ability to recognize and destroy tumor cells. For example, an engineered NK cell may include a CD19-directed chimeric receptor or a nucleic acid encoding said chimeric receptor. NK cells express both inhibitory and activating receptors on the cell surface. Inhibitory receptors bind self-molecules expressed on the surface of healthy cells (thus preventing immune responses against "self" cells), while the activating receptors bind ligands expressed on abnormal cells, such as tumor cells. When the balance between inhibitory and activating receptor activation is in favor of activating receptors, NK cell activation occurs and target (e.g., tumor) cells are lysed.

Natural killer Group 2 member D (NKG2D) is an NK cell activating receptor that recognizes a variety of ligands expressed on cells. The surface expression of various NKG2D ligands is generally low in healthy cells but is upregulated upon, for example, malignant transformation. Non-limiting examples of ligands recognized by NKG2D include, but are not limited to, MICA, MICB, ULBP1, ULBP2, ULBP3, ULBP4, ULBP5, and ULBP6, as well as other molecules expressed on target cells that control the cytolytic or cytotoxic function of NK cells. In several embodiments, T cells are engineered to express an extracellular domain to binds to one or more tumor ligands and activate the T cell. For example, in several embodiments, T cells are engineered to express an NKG2D receptor as the binder/activation moiety. In several embodiments, engineered cells as disclosed herein are engineered to express another member of the NKG2 family, e.g., NKG2A, NKG2C, and/or NKG2E. Combinations of such receptors are engineered in some embodiments. Moreover, in several embodiments, other receptors are expressed, such as the Killer-cell immunoglobulin-like receptors (KIRs).

In several embodiments, cells are engineered to express a cytotoxic receptor complex comprising a full length NKG2D as an extracellular component to recognize ligands on the surface of tumor cells (e.g., liver cells). In one embodiment, full length NKG2D has the nucleic acid sequence of SEQ ID NO: 27. In several embodiments, the full length NKG2D, or functional fragment thereof is human NKG2D.

In several embodiments, cells are engineered to express a cytotoxic receptor complex comprising a functional fragment of NKG2D as an extracellular component to recognize ligands on the surface of tumor cells or other diseased cells. In one embodiment, the functional fragment of NKG2D has the nucleic acid sequence of SEQ ID NO: 25. In several embodiments, the fragment of NKG2D is at least 70%, at least 75%, at least 80%, at least 85%, at least 90%, or at least 95% homologous with full-length wild-type NKG2D. In several embodiments, the fragment may have one or more additional mutations from SEQ ID NO: 25, but retains, or in some embodiments, has enhanced, ligand-binding function. In several embodiments, the functional fragment of NKG2D comprises the amino acid sequence of SEQ ID NO: 26. In several embodiments, the NKG2D fragment is provided as a dimer, trimer, or other concatameric format, such embodiments providing enhanced ligand-binding activity. In several embodiments, the sequence encoding the NKG2D fragment is optionally fully or partially codon optimized. In one embodiment, a sequence encoding a codon optimized NKG2D fragment comprises the sequence of SEQ ID NO: 28.

Advantageously, according to several embodiments, the functional fragment lacks its native transmembrane or intracellular domains but retains its ability to bind ligands of NKG2D as well as transduce activation signals upon ligand binding. A further advantage of such fragments is that expression of DAP10 to localize NKG2D to the cell membrane is not required. Thus, in several embodiments, the cytotoxic receptor complex encoded by the polypeptides disclosed herein does not comprise DAP10. In several embodiments, immune cells, such as NK or T cells, are engineered to express one or more chimeric receptors that target CD19 and an NGG2D ligand. Such cells, in several embodiments, also co-express mbIL15.

In several embodiments, the cytotoxic receptor complexes are configured to dimerize. Dimerization may comprise homodimers or heterodimers, depending on the embodiment. In several embodiments, dimerization results in improved ligand recognition by the cytotoxic receptor complexes (and hence the NK cells expressing the receptor), resulting in a reduction in (or lack) of adverse toxic effects. In several embodiments, the cytotoxic receptor complexes employ internal dimers, or repeats of one or more component subunits. For example, in several embodiments, the cytotoxic receptor complexes may optionally comprise a first NKG2D extracellular domain coupled to a second NKG2D extracellular domain, and a transmembrane/signaling region (or a separate transmembrane region along with a separate signaling region).

In several embodiments, the various domains/subdomains are separated by a linker such as, a GS3 linker (SEQ ID NO: 15 and 16, nucleotide and protein, respectively) is used (or a GSn linker). Other linkers used according to various embodiments disclosed herein include, but are not limited to those encoded by SEQ ID NO: 17, 19, 21 or 23. This provides the potential to separate the various component parts of the receptor complex along the polynucleotide, which can enhance expression, stability, and/or functionality of the receptor complex.

Cytotoxic Signaling Complex

Some embodiments of the compositions and methods described herein relate to a chimeric receptor, such as a CD19-directed chimeric receptor, that includes a cytotoxic signaling complex. As disclosed herein, according to several embodiments, the provided cytotoxic receptor complexes comprise one or more transmembrane and/or intracellular domains that initiate cytotoxic signaling cascades upon the extracellular domain(s) binding to ligands on the surface of target cells. Certain embodiments disclosed herein relate to chimeric antigen receptor constructs wherein the tumor-targeting domain (or CD19-directed domain) is coupled to a cytotoxic signaling complex.

In several embodiments, the cytotoxic signaling complex comprises at least one transmembrane domain, at least one co-stimulatory domain, and/or at least one signaling domain. In some embodiments, more than one component part makes up a given domain—e.g., a co-stimulatory domain may comprise two subdomains. Moreover, in some embodiments, a domain may serve multiple functions, for example, a transmembrane domain may also serve to provide signaling function.

Transmembrane Domains

Some embodiments of the compositions and methods described herein relate to a chimeric receptor, such as a CD19-directed chimeric receptor, that includes a transmembrane domain. Some embodiments include a transmembrane domain from NKG2D or another transmembrane protein. In several embodiments in which a transmembrane domain is employed, the portion of the transmembrane protein employed retains at least a portion of its normal transmembrane domain.

In several embodiments, however, the transmembrane domain comprises at least a portion of CD8, a transmembrane glycoprotein normally expressed on both T cells and NK cells. In several embodiments, the transmembrane domain comprises CD8α. In several embodiments, the transmembrane domain is referred to as a "hinge". In several embodiments, the "hinge" of CD8α has the nucleic acid sequence of SEQ ID NO: 1. In several embodiments, the CD8α hinge is truncated or modified and is at least 70%, at least 75%, at least 80%, at least 85%, at least 90%, at least 95% homologous with the CD8α having the sequence of SEQ ID NO: 1. In several embodiments, the "hinge" of CD8α comprises the amino acid sequence of SEQ ID NO: 2. In several embodiments, the CD8α can be truncated or modified, such that it is at least 70%, at least 75%, at least 80%, at least 85%, at least 90%, at least 95% homologous with the sequence of SEQ ID NO: 2.

In several embodiments, the transmembrane domain comprises a CD8α transmembrane region. In several embodiments, the CD8α transmembrane domain has the nucleic acid sequence of SEQ ID NO: 3. In several embodiments, the CD8α hinge is truncated or modified and is at least 70%, at least 75%, at least 80%, at least 85%, at least 90%, at least 95% homologous with the CD8α having the sequence of SEQ ID NO: 3. In several embodiments, the CD8α transmembrane domain comprises the amino acid sequence of SEQ ID NO: 4. In several embodiments, the CD8α hinge is truncated or modified and is at least 70%, at least 75%, at least 80%, at least 85%, at least 90%, at least 95% homologous with the CD8α having the sequence of SEQ ID NO: 4.

Taken together in several embodiments, the CD8 hinge/transmembrane complex is encoded by the nucleic acid sequence of SEQ ID NO: 13. In several embodiments, the CD8 hinge/transmembrane complex is truncated or modified and is at least 70%, at least 75%, at least 80%, at least 85%, at least 90%, at least 95% homologous with the CD8 hinge/transmembrane complex having the sequence of SEQ ID NO: 13. In several embodiments, the CD8 hinge/transmembrane complex comprises the amino acid sequence of SEQ ID NO: 14. In several embodiments, the CD8 hinge/transmembrane complex hinge is truncated or modified and is at least 70%, at least 75%, at least 80%, at least 85%, at least 90%, at least 95% homologous with the CD8 hinge/transmembrane complex having the sequence of SEQ ID NO: 14.

In some embodiments, the transmembrane domain comprises a CD28 transmembrane domain or a fragment thereof. In several embodiments, the CD28 transmembrane domain comprises the amino acid sequence of SEQ ID NO: 30. In several embodiments, the CD28 transmembrane domain complex hinge is truncated or modified and is at least 70%, at least 75%, at least 80%, at least 85%, at least 90%, at least 95% homologous with the CD28 transmembrane domain having the sequence of SEQ ID NO: 30.

Co-Stimulatory Domains

Some embodiments of the compositions and methods described herein relate to a chimeric receptor, such as a CD19-directed chimeric receptor, that includes a co-stimulatory domain. In addition the various the transmembrane domains and signaling domain (and the combination transmembrane/signaling domains), additional co-activating molecules can be provided, in several embodiments. These can be certain molecules that, for example, further enhance activity of the immune cells. Cytokines may be used in some embodiments. For example, certain interleukins, such as IL-2 and/or IL-15 as non-limiting examples, are used. In some embodiments, the immune cells for therapy are engineered to express such molecules as a secreted form. In additional embodiments, such co-stimulatory domains are engineered to be membrane bound, acting as autocrine stimulatory molecules (or even as paracrine stimulators to neighboring cells delivered). In several embodiments, NK cells are engineered to express membrane-bound interleukin 15 (mbIL15). In such embodiments, mbIL15 expression on the NK enhances the cytotoxic effects of the engineered NK cell by enhancing the proliferation and/or longevity of the NK cells. In several embodiments, mbIL15 has the nucleic acid sequence of SEQ ID NO: 11. In several embodiments, mbIL15 can be truncated or modified, such that it is at least 70%, at least 75%, at least 80%, at least 85%, at least 90%, at least 95% homologous with the sequence of SEQ ID NO: 11. In several embodiments, the mbIL15 comprises the amino acid sequence of SEQ ID NO: 12. In several embodiments, the mbIL15 is truncated or modified and is at least 70%, at least 75%, at least 80%, at least 85%, at least 90%, at least 95% homologous with the mbIL15 having the sequence of SEQ ID NO: 12.

In some embodiments, the CD19-directed chimeric receptor or engineered cytotoxic receptor complex is encoded by a polynucleotide that includes one or more cytosolic protease cleavage sites, for example a T2A cleavage site, a P2A cleavage site, an E2A cleavage site, and/or a F2A cleavage site. Such sites are recognized and cleaved by a cytosolic protease, which can result in separation (and separate expression) of the various component parts of the receptor encoded by the polynucleotide. As a result, depending on the embodiment, the various constituent parts of a CD19-directed chimeric receptor or engineered cytotoxic receptor complex can be delivered to an NK cell or T cell in a single vector or by multiple vectors. Thus, as shown schematically, in the Figures, a construct can be encoded by a single polynucleotide, but also include a cleavage site, such that downstream elements of the constructs are expressed by the cells as a separate protein (as is the case in some embodiments with IL-15). In several embodiments, a T2A cleavage site is used. In several embodiments, a T2A cleavage site has the nucleic acid sequence of SEQ ID NO: 9. In several embodiments, T2A cleavage site can be truncated or modified, such that it is at least 70%, at least 75%, at least 80%, at least 85%, at least 90%, at least 95% homologous with the sequence of SEQ ID NO: 9. In several embodiments, the T2A cleavage site comprises the amino acid sequence of SEQ ID NO: 10. In several embodiments, the T2A cleavage site is truncated or modified and is at least 70%, at least 75%, at least 80%, at least 85%, at least 90%, at least 95% homologous with the T2A cleavage site having the sequence of SEQ ID NO: 10.

Signaling Domains

Some embodiments of the compositions and methods described herein relate to a chimeric receptor, such as a CD19-directed chimeric receptor, that includes a signaling domain. For example, immune cells engineered according to several embodiments disclosed herein may comprise at least one subunit of the CD3 T cell receptor complex (or a fragment thereof). In several embodiments, the signaling domain comprises the CD3 zeta subunit. In several embodiments, the CD3 zeta is encoded by the nucleic acid sequence of SEQ ID NO: 7. In several embodiments, the CD3 zeta can be truncated or modified, such that it is at least 70%, at least 75%, at least 80%, at least 85%, at least 90%, at least 95% homologous with the CD3 zeta having the sequence of SEQ ID NO: 7. In several embodiments, the CD3 zeta domain comprises the amino acid sequence of SEQ ID NO: 8. In several embodiments, the CD3 zeta domain is truncated or modified and is at least 70%, at least 75%, at least 80%, at least 85%, at least 90%, at least 95% homologous with the CD3 zeta domain having the sequence of SEQ ID NO: 8.

In several embodiments, unexpectedly enhanced signaling is achieved through the use of multiple signaling domains whose activities act synergistically. For example, in several embodiments, the signaling domain further comprises an OX40 domain. In several embodiments, the OX40 domain is an intracellular signaling domain. In several embodiments, the OX40 intracellular signaling domain has the nucleic acid sequence of SEQ ID NO: 5. In several embodiments, the OX40 intracellular signaling domain can be truncated or modified, such that it is at least 70%, at least 75%, at least 80%, at least 85%, at least 90%, at least 95% homologous with the OX40 having the sequence of SEQ ID NO: 5. In several embodiments, the OX40 intracellular signaling domain comprises the amino acid sequence of SEQ ID NO: 16. In several embodiments, the OX40 intracellular signaling domain is truncated or modified and is at least 70%, at least 75%, at least 80%, at least 85%, at least 90%, at least 95% homologous with the OX40 intracellular signaling domain having the sequence of SEQ ID NO: 6. In several embodiments, OX40 is used as the sole transmembrane/signaling domain in the construct, however, in several embodiments, OX40 can be used with one or more other domains. For example, combinations of OX40 and CD3zeta are used in some embodiments. By way of further example, combinations of CD28, OX40, 4-1 BB, and/or CD3zeta are used in some embodiments.

In several embodiments, the signaling domain comprises a 4-1BB domain. In several embodiments, the 4-1 BB domain is an intracellular signaling domain. In several embodiments, the 4-1 BB intracellular signaling domain comprises the amino acid sequence of SEQ ID NO: 29. In several embodiments, the 4-1 BB intracellular signaling domain is truncated or modified and is at least 70%, at least 75%, at least 80%, at least 85%, at least 90%, at least 95% homologous with the 4-1BB intracellular signaling domain having the sequence of SEQ ID NO: 29. In several embodiments, 4-1 BB is used as the sole transmembrane/signaling domain in the construct, however, in several embodiments, 4-1BB can be used with one or more other domains. For example, combinations of 4-1 BB and CD3zeta are used in some embodiments. By way of further example, combinations of CD28, OX40, 4-1 BB, and/or CD3zeta are used in some embodiments.

In several embodiments, the signaling domain comprises a CD28 domain. In several embodiments the CD28 domain is an intracellular signaling domain. In several embodiments, the CD28 intracellular signaling domain comprises the amino acid sequence of SEQ ID NO: 31. In several embodiments, the CD28 intracellular signaling domain is truncated or modified and is at least 70%, at least 75%, at least 80%, at least 85%, at least 90%, at least 95% homologous with the CD28 intracellular signaling domain having the sequence of SEQ ID NO: 31. In several embodiments, CD28 is used as the sole transmembrane/signaling domain in the construct, however, in several embodiments, CD28 can be used with one or more other domains. For example, combinations of CD28 and CD3zeta are used in some embodiments. By way of further example, combinations of CD28, OX40, 4-1 BB, and/or CD3zeta are used in some embodiments.

Cytotoxic Receptor Complex Constructs

Some embodiments of the compositions and methods described herein relate to a chimeric receptor, such as a CD19-directed chimeric receptor, that comprises a cytotoxic receptor complex or cytotoxic receptor complex construct. In line with the above, a variety of cytotoxic receptor complexes (also referred to as cytotoxic receptors) are provided for herein. The expression of these complexes in immune cells, such as T cells and/or NK cells, allows the targeting and destruction of particular target cells, such as cancerous cells. Non-limiting examples of such cytotoxic receptor complexes are discussed in more detail below.

Chimeric Antigen Receptor Cytotoxic Receptor Complex Constructs

Figure 2:
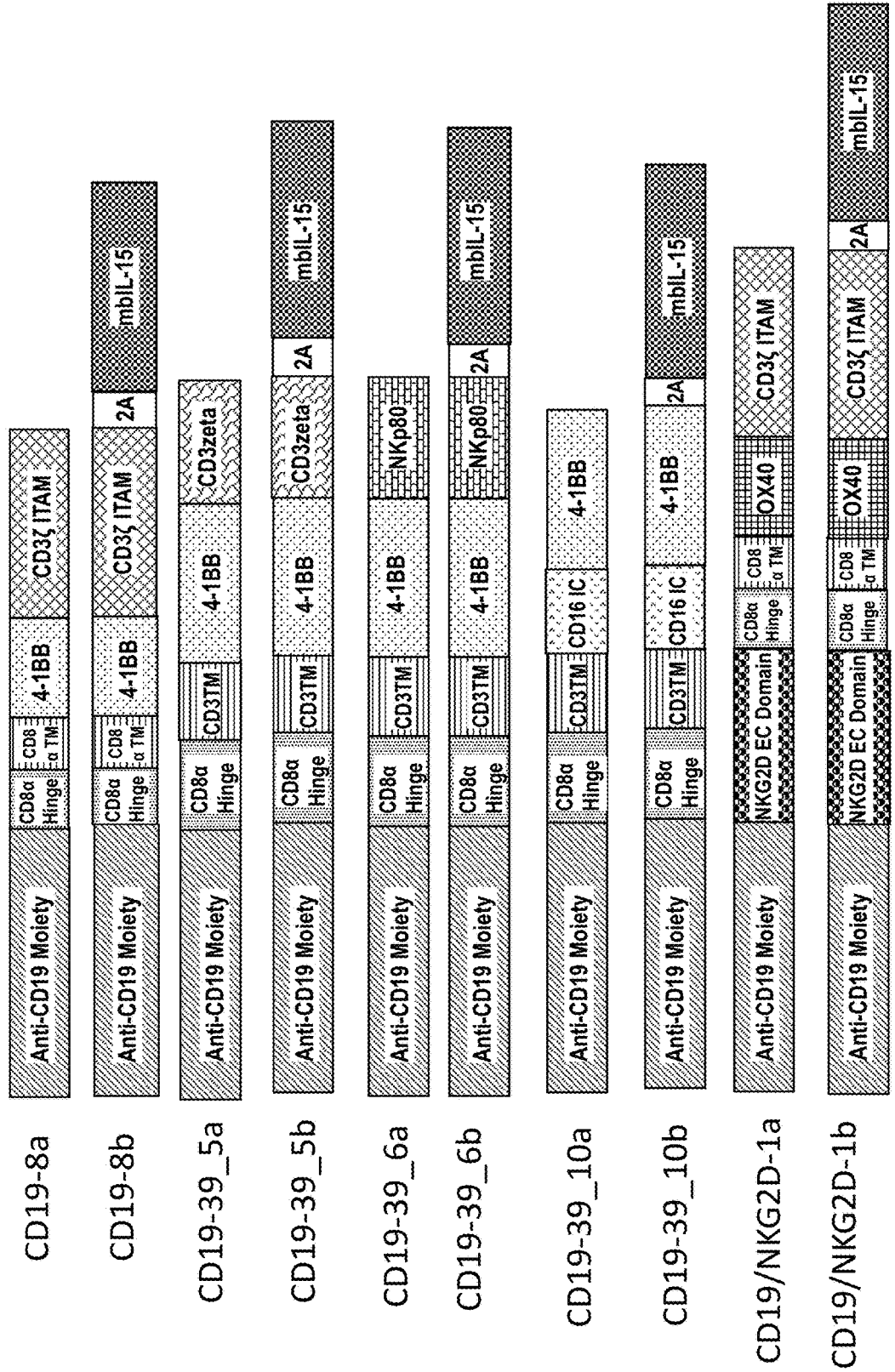
FIG. 2 also includes depictions of non-limiting examples of CD19-directed chimeric receptors.

In several embodiments, there are provided for herein a variety of cytotoxic receptor complexes (also referred to as cytotoxic receptors) are provided for herein with the general structure of a chimeric antigen receptor. FIGS. 1A, 1B, and 2 schematically depict non-limiting schematics of constructs that include an anti-CD19 moiety that binds to tumor antigens or tumor-associated antigens expressed on the surface of cancer cells and activates the engineered cell expressing the chimeric antigen receptor. As shown in the figures, several embodiments of the chimeric receptor include an anti-CD19 moiety, a CD8a hinge domain, an Ig4 SH domain (or hinge), a CD8a transmembrane domain, a CD28 transmembrane domain, an OX40 domain, a 4-1BB domain, a CD28 domain, a CD3 ITAM domain or subdomain, a CD3zeta domain, an NKp80 domain, a CD16 IC domain, a 2A cleavage site, and a membrane-bound IL-15 domain (though, as above, in several embodiments soluble IL-15 is used). In several embodiments, the binding and activation functions are engineered to be performed by separate domains. Several embodiments relate to complexes with more than one anti-CD19 moiety or other binder/activation moiety. In some embodiments, the binder/activation moiety targets other markers besides CD19, such as a cancer target described herein. In several embodiments, the general structure of the chimeric antigen receptor construct includes a hinge and/or transmembrane domain. These may, in some embodiments, be fulfilled by a single domain, or a plurality of subdomains may be used, in several embodiments. The receptor complex further comprises a signaling domain, which transduces signals after binding of the homing moiety to the target cell, ultimately leading to the cytotoxic effects on the target cell. In several embodiments, the complex further comprises a co-stimulatory domain, which operates, synergistically, in several embodiments, to enhance the function of the signaling domain. Expression of these complexes in immune cells, such as T cells and/or NK cells, allows the targeting and destruction of particular target cells, such as cancerous cells that express CD19. Some such receptor complexes comprise an extracellular domain comprising an anti-CD19 moiety, or CD19-binding moiety, that binds CD19 on the surface of target cells and activates the engineered cell. The CD3zeta ITAM subdomain may act in concert as a signaling domain. The IL-15 domain, e.g., mbIL-15 domain, may acting as a co-stimulatory domain. The IL-15 domain, e.g. mbIL-15 domain, may render immune cells (e.g., NK or T cells) expressing it particularly efficacious against target tumor cells. It shall be appreciated that the IL-15 domain, such as an mbIL-15 domain, can, in accordance with several embodiments, be encoded on a separate construct. Additionally, each of the components may be encoded in one or more separate constructs. In some embodiments, the cytotoxic receptor or CD19-directed receptor comprises a sequence of amino acids that is at least 70%, 75%, 80%, 85%, 90%, 91%, 92%, 93%, 94%, 95%, 96%, 97%, 98%, 99% or 100%, or a range defined by any two of the aforementioned percentages, identical to the sequence of SEQ ID NO: 34.

In one embodiment, there is provided a polynucleotide encoding an anti-CD19moiety/CD8hinge-CD8TM/OX40/CD3zeta chimeric antigen receptor complex (see FIG. 1A, CD19-1a). The polynucleotide comprises or is composed of an anti-CD19 moiety, a CD8a hinge, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD8TM/

OX40/CD3zeta/2A/mIL-15 chimeric antigen receptor complex (see FIG. 1A, CD19-1b). The polynucleotide comprises or is composed of an anti-CD19 moiety, a CD8a hinge, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/4-1BB/CD3zeta chimeric antigen receptor complex (see FIG. 1A, CD19-2a). The polynucleotide comprises or is composed of an anti-CD19 moiety, a Ig4 SH domain, a CD8a transmembrane domain, a 4-1BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/4-1BB/CD3zeta/2A/mIL-15 chimeric antigen receptor complex (see FIG. 1A, CD19-2b). The polynucleotide comprises or is composed of an anti-CD19 moiety, a Ig4 SH domain, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/CD3zeta chimeric antigen receptor complex (see FIG. 1A, CD19-3a). The polynucleotide comprises or is composed of an anti-CD19 moiety, a CD8a hinge, a CD28 transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/CD3zeta/2A/mIL-15 chimeric antigen receptor complex (see FIG. 1A, CD19-3b). The polynucleotide comprises or is composed of an anti-CD19 moiety, a CD8a hinge, a CD28 transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD28TM/CD28/CD3zeta chimeric antigen receptor complex (see FIG. 1A, CD19-4a). The polynucleotide comprises or is composed of an anti-CD19 moiety, an Ig4 SH domain, a CD28 transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD28TM/ CD28/CD3zeta/2A/mIL-15 chimeric antigen receptor complex (see FIG. 1A, CD19-4b). The polynucleotide comprises or is composed of an anti-CD19 moiety, an Ig4 SH domain, a CD28 transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/OX40/ CD3zeta chimeric antigen receptor complex (see FIG. 2A, CD19-5a). The polynucleotide comprises or is composed of an anti-CD19 moiety, a Ig4 SH domain, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/OX40/ CD3zeta/2A/mIL-15 chimeric antigen receptor complex (see FIG. 2A, CD19-5b). The polynucleotide comprises or is composed of an anti-CD19 moiety, a Ig4 SH domain, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD3αTM/ CD28/CD3zeta chimeric antigen receptor complex (see FIG. 1B, CD19-6a). The polynucleotide comprises or is composed of an anti-CD19 moiety, a CD8a hinge, a CD3α transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD3αTM/ CD28/CD3zeta/2A/mIL-15 chimeric antigen receptor complex (see FIG. 1B, CD19-6b). The polynucleotide comprises or is composed of an anti-CD19 moiety, a CD8a hinge, a CD3α transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/ CD28/4-1BB/CD3zeta chimeric antigen receptor complex (see FIG. 1B, CD19-7a). The polynucleotide comprises or is composed of an anti-CD19 moiety, a CD8a hinge, a CD28 transmembrane domain, a CD28 domain, a 4-1 BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/4-1BB/CD3zeta/2A/mIL-15 chimeric antigen receptor complex (see FIG. 1B, CD19-7b). The polynucleotide comprises or is composed of an anti-CD19 moiety, a CD8a hinge, a CD28 transmembrane domain, a CD28 domain, a 4-1BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD8 alpha TM/4-1BB/CD3zeta chimeric antigen receptor complex (see FIG. 2, CD19-8a). The polynucleotide comprises or is composed of an anti-CD19 moiety, a CD8a hinge, a CD8a transmembrane domain, a 4-1 BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD8 alpha TM/4-1BB/CD3zeta/2A/mIL-15 chimeric antigen receptor complex (see FIG. 2, CD19-8b). The polynucleotide comprises or is composed of an anti-CD19 moiety, a CD8a hinge, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1 BB/CD3zeta chimeric antigen receptor complex (see FIG. 2, CD19-39_5a). The polynucleotide comprises or is composed of an anti-CD19 moiety, a CD8a hinge, a CD3 transmembrane domain, a 4-1BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/CD3zeta/2A/mIL-15 chimeric antigen receptor complex (see FIG. 2, CD19-39_5b). The polynucleotide comprises or is composed of an anti-CD19 moiety, a CD8a hinge, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/NKp80 chimeric antigen receptor complex (see FIG. 2, CD19-39_6a). The polynucleotide comprises or is composed of an anti-CD19 moiety, a CD8a hinge, a CD3 transmembrane domain, a 4-1BB domain, and an NKp80 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/NKp80/2A/mIL-15 chimeric antigen receptor complex (see FIG. 2, CD19-39_6b). The polynucleotide comprises or is composed of an anti-CD19 moiety, a CD8a hinge, a CD8a transmembrane domain, a 4-1 BB domain, an NKp80 domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/CD16 intracellular domain/4-1BB chimeric antigen receptor complex (see FIG. 2, CD19-39_10a). The polynucleotide comprises or is composed of an anti-CD19 moiety, a CD8a hinge, a CD3 transmembrane domain, CD16 intracellular domain, and a 4-1 BB domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/CD16/4-1BB/2A/mIL-15 chimeric antigen receptor complex (see FIG. 2, CD19-39_10b). The polynucleotide comprises or is composed of an anti-CD19 moiety, a CD8a hinge, a CD8a transmembrane domain, a CD16 intracellular domain, a 4-1 BB domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/NKG2D Extracellular Domain/CD8hinge-CD8TM/OX40/CD3zeta chimeric antigen receptor complex (see FIG. 2, CD19/NKG2D-1a). The polynucleotide comprises or is composed of an anti-CD19 moiety, an NKG2D extracellular domain (either full length or a fragment), a CD8a hinge, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/NKG2D EC Domain/CD8hinge-CD8TM/OX40/CD3zeta/2A/mIL-15 chimeric antigen receptor complex (see FIG. 2, CD19/NKG2D-1b). The polynucleotide comprises or is composed of an anti-CD19 moiety, an NKG2D extracellular domain (either full length or a fragment), a CD8a hinge, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge/CD8TM/4-1BB/CD3zeta/mbIL15 chimeric antigen receptor complex (see FIG. 3A, NK19). The polynucleotide comprises or is composed of an anti-CD19 scFv, a CD8a hinge, a CD8a transmembrane domain, a 4-1BB domain, and a CD3zeta domain. In several embodiments, this receptor complex is encoded by a nucleic acid molecule having the sequence of SEQ ID NO: 85. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 85. In several embodiments, the chimeric receptor comprises the amino acid sequence of SEQ ID NO: 86. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 86. Schematically depicted and used in several embodiments, there is provided an NK19 construct that lacks an mbIL15 domain (FIG. 3A, NK19 opt.)

In several embodiments, there is provided a polynucleotide encoding an anti-CD19moiety/CD8hinge/CD8TM/OX40/CD3zeta chimeric antigen receptor complex (see FIG. 3A, NK19-1a). The polynucleotide comprises or is composed of an anti-CD19 scFv, a CD8a hinge, a CD8a transmembrane domain, an OX40 domain, and a CD3zeta domain. In several embodiments, the chimeric antigen receptor further comprises mbIL15 (see FIG. 3A, NK19-1b). In such embodiments, the polynucleotide comprises or is composed of an anti-CD19 scFv, a CD8a hinge, a CD8a transmembrane domain, an OX40 domain, a CD3zeta domain, a 2A cleavage site, and an mbIL-15 domain as described herein. In several embodiments, this receptor complex is encoded by a nucleic acid molecule having the sequence of SEQ ID NO: 59. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 59. In several embodiments, the chimeric receptor comprises the amino acid sequence of SEQ ID NO: 60. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 60. In several embodiments, the CD19 scFv does not comprise a Flag tag.

In several embodiments, there is provided a polynucleotide encoding an anti-CD19moiety/CD8hinge/CD28TM/CD28/CD3zeta chimeric antigen receptor complex (see FIG. 3A, NK19-2a). The polynucleotide comprises or is composed of an anti-CD19 scFv, a CD8a hinge, a CD28 transmembrane domain, CD28 signaling domain, and a CD3zeta domain. In several embodiments, the chimeric antigen receptor further comprises mbIL15 (see FIG. 3A, NK19-2b). In such embodiments, the polynucleotide comprises or is composed of an anti-CD19 scFv, a CD8a hinge, a CD28 transmembrane domain, CD28 signaling domain, a CD3zeta domain a 2A cleavage site, and an mbIL-15 domain as described herein. In several embodiments, this receptor complex is encoded by a nucleic acid molecule having the sequence of SEQ ID NO: 61. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 61. In several embodiments, the chimeric receptor comprises the amino acid sequence of SEQ ID NO: 62. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 62. In several embodiments, the CD19 scFv does not comprise a Flag tag.

In several embodiments, there is provided a polynucleotide encoding an anti-CD19moiety/CD8hinge/CD8aTM/ICOS/CD3zeta chimeric antigen receptor complex (see FIG. 3A, NK19-3a). The polynucleotide comprises or is composed of an anti-CD19 scFv, a CD8a hinge, a CD8a transmembrane domain, inducible costimulator (ICOS) signaling domain, and a CD3zeta domain. In several embodiments, the chimeric antigen receptor further comprises mbIL15 (see FIG. 3A, NK19-3b). In such embodiments, the polynucleotide comprises or is composed of an anti-CD19 scFv, a CD8a hinge, a CD8a transmembrane domain, inducible costimulator (ICOS) signaling domain, a CD3zeta domain, a 2A cleavage site, and an mbIL-15 domain as described herein. In several embodiments, this receptor complex is encoded by a nucleic acid molecule having the sequence of SEQ ID NO: 63. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 63. In several embodiments, the chimeric receptor comprises the amino acid sequence of SEQ ID NO: 64. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 64. In several embodiments, the CD19 scFv does not comprise a Flag tag.

In several embodiments, there is provided a polynucleotide encoding an anti-CD19moiety/CD8hinge/CD8aTM/CD28/4-1BB/CD3zeta chimeric antigen receptor complex (see FIG. 3A, NK19-4a).

The polynucleotide comprises or is composed of an anti-CD19 scFv, a CD8a hinge, a CD8a transmembrane domain, a CD28 signaling domain, a 4-1 BB signaling domain, and a CD3zeta domain. In several embodiments, the chimeric antigen receptor further comprises mbIL15 (see FIG. 3A, NK19-4b). In such embodiments, the polynucleotide comprises or is composed of an anti-CD19 scFv, a CD8a hinge, a CD8a transmembrane domain, a CD28 signaling domain, a 4-1 BB signaling domain, a CD3zeta domain, a 2A cleavage site, and an mbIL-15 domain as described herein. In several embodiments, this receptor complex is encoded by a nucleic acid molecule having the sequence of SEQ ID NO: 65. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 65. In several embodiments, the chimeric receptor comprises the amino acid sequence of SEQ ID NO: 66. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 66. In several embodiments, the CD19 scFv does not comprise a Flag tag.

Figure 3B:
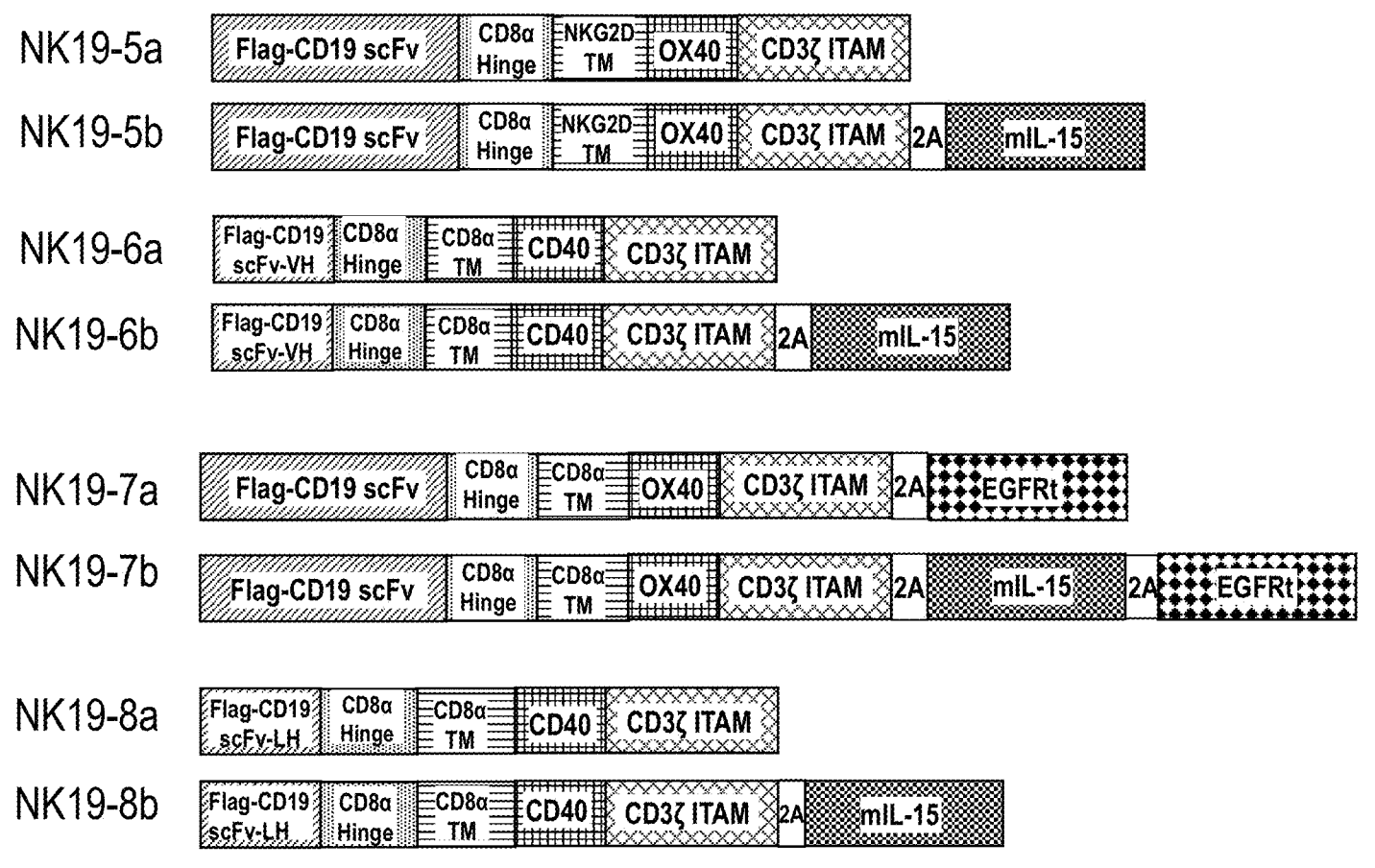

In several embodiments, there is provided a polynucleotide encoding an anti-CD19moiety/CD8hinge/NKG2DTM/OX40/CD3zeta chimeric antigen receptor complex (see FIG. 3B, NK19-5a). The polynucleotide comprises or is composed of an anti-CD19 scFv, a CD8a hinge, a NKG2D transmembrane domain, an OX40 signaling domain, and a CD3zeta domain. In several embodiments, the chimeric antigen receptor further comprises mbIL15 (see FIG. 3B, NK19-5b). In such embodiments, the polynucleotide comprises or is composed of an anti-CD19 scFv, a CD8a hinge, a NKG2D transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 67. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 67. In several embodiments, the chimeric receptor comprises the amino acid sequence of SEQ ID NO: 68. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 68. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-6a). The polynucleotide comprises or is composed of an anti-CD19 scFv variable heavy chain, a CD8a hinge, a CD8a transmembrane domain, a CD40 signaling domain, and a CD3zeta domain. In several embodiments, the chimeric antigen receptor further comprises mbIL15 (see FIG. 3B, NK19-6b). In such embodiments, the polynucleotide comprises or is composed of an anti-CD19 scFv variable heavy chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 69. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 69. In several embodiments, the chimeric receptor comprises the amino acid sequence of SEQ ID NO: 70. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 70. In several embodiments, the CD19 scFv does not comprise a Flag tag.

In several embodiments, there is provided a polynucleotide encoding an anti-CD19moiety/CD8hinge/CD8aTM/OX40/CD3zeta/2A/EGFRt chimeric antigen receptor complex (see FIG. 3B, NK19-7a). The polynucleotide comprises or is composed of an anti-CD19 scFv, a CD8a hinge, a CD8a transmembrane domain, an OX40 signaling domain, a CD3zeta domain, a 2A cleavage side, and a truncated version of the epidermal growth factor receptor (EGFRt). In several embodiments, the chimeric antigen receptor further comprises mbIL15 (see FIG. 3B, NK19-7b). In such embodiments, the polynucleotide comprises or is composed of an anti-CD19 scFv, a CD8a hinge, a CD8a transmembrane domain, an OX40 signaling domain, a CD3zeta domain, a 2A cleavage side, a truncated version of the epidermal growth factor receptor (EGFRt), an additional 2A cleavage site, and an mbIL-15 domain as described herein. In several embodiments, this receptor complex is encoded by a nucleic acid molecule having the sequence of SEQ ID NO: 71. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 71. In several embodiments, the chimeric receptor comprises the amino acid sequence of SEQ ID NO: 72. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 72. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-8a). The polynucleotide comprises or is composed of an anti-CD19 scFv variable light chain, a CD8a hinge, a CD8a transmembrane domain, a CD40 signaling domain, and a CD3zeta domain. In several embodiments, the chimeric antigen receptor further comprises mbIL15 (see FIG. 3B, NK19-7b). In such embodiments, the polynucleotide comprises or is composed of an anti-CD19 scFv variable light chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 73. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 73. In several embodiments, the chimeric receptor comprises the amino acid sequence of SEQ ID NO: 74. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 74. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-8a). The polynucleotide comprises or is composed of an anti-CD19 scFv variable light chain, a CD8a hinge, a CD8a transmembrane domain, a CD40 signaling domain, and a CD3zeta domain. In several embodiments, the chimeric antigen receptor further comprises mbIL15 (see FIG. 3B, NK19-7b). In such embodiments, the polynucleotide comprises or is composed of an anti-CD19 scFv variable light chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 73. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 73. In several embodiments, the chimeric receptor comprises the amino acid sequence of SEQ ID NO: 74. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 74. In several embodiments, the CD19 scFv does not comprise a Flag tag.

In several embodiments, there is provided a polynucleotide encoding an anti-CD19moiety/CD8hinge/CD8aTM/CD27/CD3zeta chimeric antigen receptor complex (see FIG. 3C, NK19-9a). The polynucleotide comprises or is composed of an anti-CD19 scFv, a CD8a hinge, a CD8a transmembrane domain, a CD27 signaling domain, and a CD3zeta domain. In several embodiments, the chimeric antigen receptor further comprises mbIL15 (see FIG. 3C, NK19-9b). In such embodiments, the polynucleotide comprises or is composed of an anti-CD19 scFv, a CD8a hinge, a CD8a transmembrane domain, a CD27 signaling domain, a CD3zeta domain, a 2A cleavage site, and an mbIL-15 domain as described herein. In several embodiments, this receptor complex is encoded by a nucleic acid molecule having the sequence of SEQ ID NO: 75. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 75. In several embodiments, the chimeric receptor comprises the amino acid sequence of SEQ ID NO: 76. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 76. In several embodiments, the CD19 scFv does not comprise a Flag tag.

In several embodiments, there is provided a polynucleotide encoding an anti-CD19moiety/CD8hinge/CD8aTM/CD70/CD3zeta chimeric antigen receptor complex (see FIG. 3C, NK19-10a). The polynucleotide comprises or is composed of an anti-CD19 scFv, a CD8a hinge, a CD8a transmembrane domain, a CD70 signaling domain, and a CD3zeta domain. In several embodiments, the chimeric antigen receptor further comprises mbIL15 (see FIG. 3C, NK19-10b). In such embodiments, the polynucleotide comprises or is composed of an anti-CD19 scFv, a CD8a hinge, a CD8a transmembrane domain, a CD70 signaling domain, a CD3zeta domain, a 2A cleavage site, and an mbIL-15 domain as described herein. In several embodiments, this receptor complex is encoded by a nucleic acid molecule having the sequence of SEQ ID NO: 77. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 77. In several embodiments, the chimeric receptor comprises the amino acid sequence of SEQ ID NO: 78. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 78. In several embodiments, the CD19 scFv does not comprise a Flag tag.

In several embodiments, there is provided a polynucleotide encoding an anti-CD19moiety/CD8hinge/CD8aTM/CD161/CD3zeta chimeric antigen receptor complex (see FIG. 3C, NK19-11a). The polynucleotide comprises or is composed of an anti-CD19 scFv, a CD8a hinge, a CD8a transmembrane domain, a CD161 signaling domain, and a CD3zeta domain. In several embodiments, the chimeric antigen receptor further comprises mbIL15 (see FIG. 3C, NK19-11b). In such embodiments, the polynucleotide comprises or is composed of an anti-CD19 scFv, a CD8a hinge, a CD8a transmembrane domain, a CD161 signaling domain, a CD3zeta domain, a 2A cleavage site, and an mbIL-15 domain as described herein. In several embodiments, this receptor complex is encoded by a nucleic acid molecule having the sequence of SEQ ID NO: 79. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 79. In several embodiments, the chimeric receptor comprises the amino acid sequence of SEQ ID NO: 80. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 80. In several embodiments, the CD19 scFv does not comprise a Flag tag.

In several embodiments, there is provided a polynucleotide encoding an anti-CD19moiety/CD8hinge/CD8aTM/

CD40L/CD3zeta chimeric antigen receptor complex (see FIG. 3C, NK19-12a). The polynucleotide comprises or is composed of an anti-CD19 scFv, a CD8a hinge, a CD8a transmembrane domain, a CD40L signaling domain, and a CD3zeta domain. In several embodiments, the chimeric antigen receptor further comprises mbIL15 (see FIG. 3C, NK19-12b). In such embodiments, the polynucleotide comprises or is composed of an anti-CD19 scFv, a CD8a hinge, a CD8a transmembrane domain, a CD40L signaling domain, a CD3zeta domain, a 2A cleavage site, and an mbIL-15 domain as described herein. In several embodiments, this receptor complex is encoded by a nucleic acid molecule having the sequence of SEQ ID NO: 81. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 81. In several embodiments, the chimeric receptor comprises the amino acid sequence of SEQ ID NO: 82. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 82. In several embodiments, the CD19 scFv does not comprise a Flag tag.

In several embodiments, there is provided a polynucleotide encoding an anti-CD19moiety/CD8hinge/CD8aTM/CD44/CD3zeta chimeric antigen receptor complex (see FIG. 3C, NK19-13). The polynucleotide comprises or is composed of an anti-CD19 scFv, a CD8a hinge, a CD8a transmembrane domain, a CD44 signaling domain, and a CD3zeta domain. In several embodiments, the chimeric antigen receptor further comprises mbIL15 (see FIG. 3C, NK19-13b). In such embodiments, the polynucleotide comprises or is composed of an anti-CD19 scFv, a CD8a hinge, a CD8a transmembrane domain, a CD44 signaling domain, a CD3zeta domain, a 2A cleavage site, and an mbIL-15 domain as described herein. In several embodiments, this receptor complex is encoded by a nucleic acid molecule having the sequence of SEQ ID NO: 83. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 83. In several embodiments, the chimeric receptor comprises the amino acid sequence of SEQ ID NO: 84. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 84. In several embodiments, the CD19 scFv does not comprise a Flag tag.

Figure 3D:
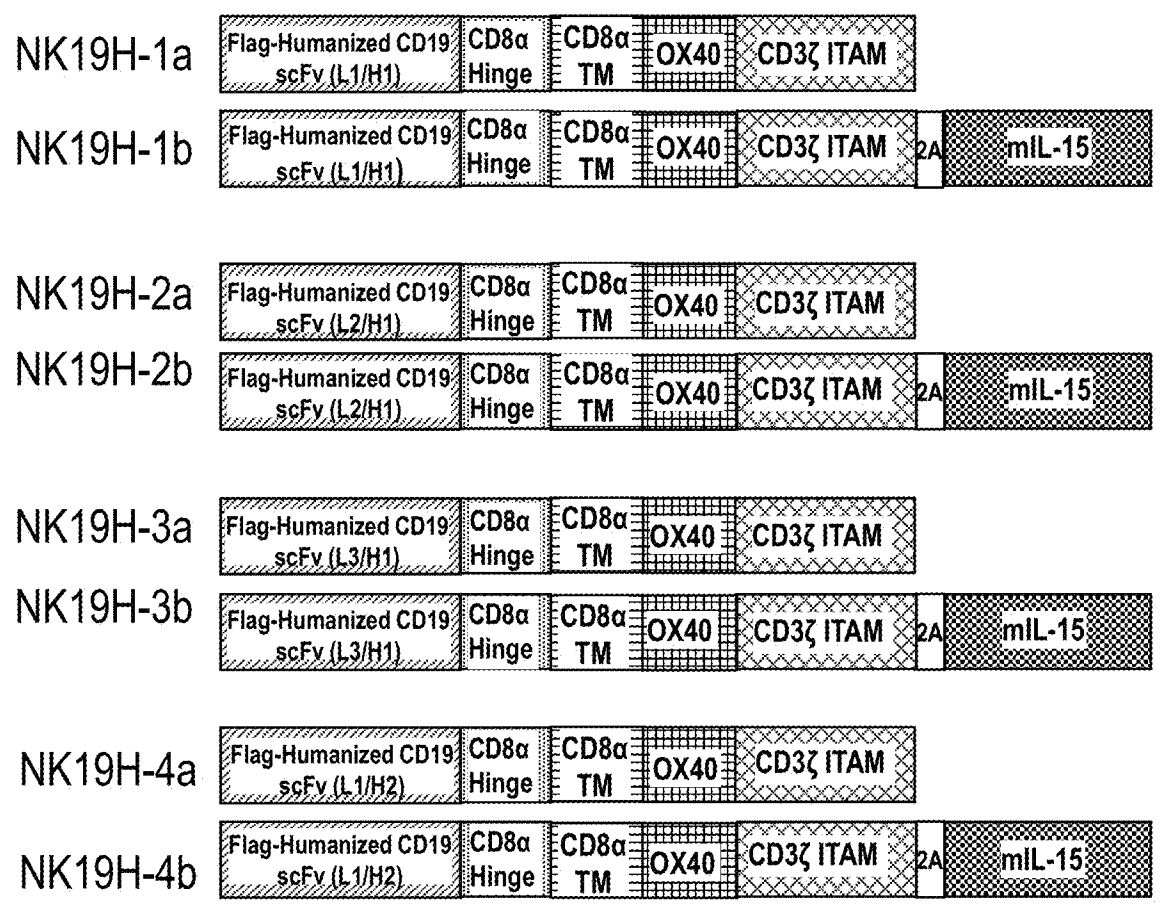

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-1a). The polynucleotide comprises or is composed of an anti-CD19 scFv that has been humanized and comprises a first humanized light chain and a first humanized heavy chain (L1/H1), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-1b). In such embodiments, the polynucleotide comprises or is composed of an anti-CD19 scFv that has been humanized and comprises a first humanized light chain and a first humanized heavy chain (L1/H1), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 160. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 160. In several embodiments, the chimeric receptor comprises the amino acid sequence of SEQ ID NO: 161. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 161.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-2a). The polynucleotide comprises or is composed of an anti-CD19 scFv that has been humanized, and comprises a second humanized light chain and a first humanized heavy chain (L2/H1), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-2b). In such embodiments, the polynucleotide comprises or is composed of an anti-CD19 scFv that has been humanized comprises a second humanized light chain and a first humanized heavy chain (L2/H1), and comprises a Flag tag, a CD8a hinge, a CD8a transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 162. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 162. In several embodiments, the chimeric receptor comprises the amino acid sequence of SEQ ID NO: 163. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 162.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-3a). The polynucleotide comprises or is composed of an anti-CD19 scFv that has been humanized and comprises a third humanized light chain and a first humanized heavy chain (L3/H1), and comprises a Flag tag, a CD8a hinge, a CD8a transmembrane domain, an OX40 signaling domain, and a CD3zeta domain.

In several embodiments, the chimeric antigen receptor further comprises mbIL15 (see FIG. 3D, NK19H-3b). In such embodiments, the polynucleotide comprises or is composed of an anti-CD19 scFv that has been humanized and comprises a third humanized light chain and a first humanized heavy chain (L3/H1), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 164. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 164. In several embodiments, the chimeric receptor comprises the amino acid sequence of SEQ ID NO: 165. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 165.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-4a). The polynucleotide comprises or is composed of an anti-CD19 scFv that has been humanized and comprises a first humanized light chain and a second humanized heavy chain (L1/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-4b). In such embodiments, the polynucleotide comprises or is composed of an anti-CD19 scFv that has been humanized and comprises a first humanized light chain and a second humanized heavy chain (L1/H2), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 166. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 166. In several embodiments, the chimeric receptor comprises the amino acid sequence of SEQ ID NO: 167. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 167.

Figure 3E:
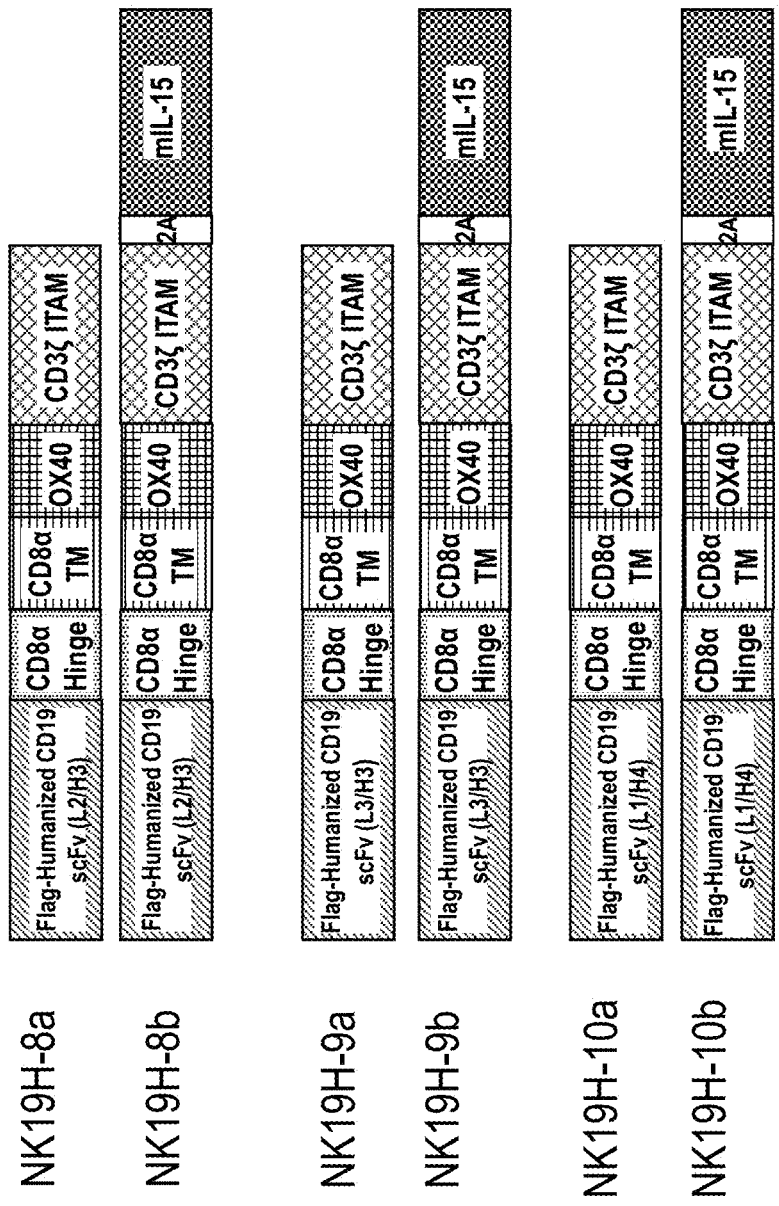
FIG. 3E also includes depictions of non-limiting examples of CD19-directed chimeric receptors comprising humanized CD19 binding domains.
Figure 4:
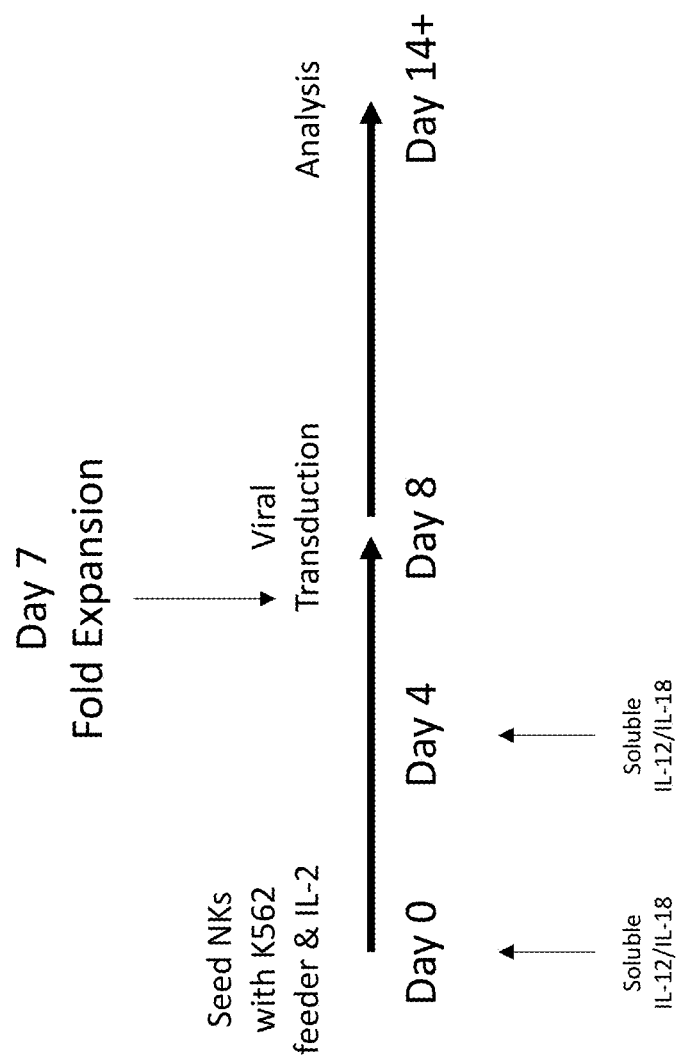
FIG. 4 depicts a schematic of a non-limiting NK cell expansion protocol.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-5a). The polynucleotide comprises or is composed of an anti-CD19 scFv that has been humanized and comprises a second humanized light chain and a second humanized heavy chain (L2/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-5b). In such embodiments, the polynucleotide comprises or is composed of an anti-CD19 scFv that has been humanized and comprises a second humanized light chain and a second humanized heavy chain (L2/H2), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 168. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 168. In several embodiments, the chimeric receptor comprises the amino acid sequence of SEQ ID NO: 169. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 169.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-6a). The polynucleotide comprises or is composed of an anti-CD19 scFv that has been humanized and comprises a third humanized light chain and a second humanized heavy chain (L3/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-6b). In such embodiments, the polynucleotide comprises or is composed of an anti-CD19 scFv that has been humanized and comprises a third humanized light chain and a second humanized heavy chain (L3/H2) and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 170. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 170. In several embodiments, the chimeric receptor comprises the amino acid sequence of SEQ ID NO: 171. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 171.

In several embodiments, there is provided a polynucleotide encoding an Flag-tag humanized anti-CD19moiety/CD8hinge/CD8TM/OX40/CD3zeta chimeric antigen receptor complex (see FIG. 3E, NK19H-7a). The polynucleotide comprises or is composed of an anti-CD19 scFv that has been humanized and comprises a first humanized light chain and a third humanized heavy chain (L1/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-7b). In such embodiments, the polynucleotide comprises or is composed of an anti-CD19 scFv that has been humanized and comprises a first humanized light chain and a third humanized heavy chain (L1/H3), and comprises a Flag tag, a CD8a hinge, a CD8a transmembrane domain, an OX40 signaling domain, and a CD3zeta domain, a 2A cleavage side, a truncated version of the epidermal growth factor receptor (EGFRt), an additional 2A cleavage site, and an mbIL-15 domain as described herein. In several embodiments, this receptor complex is encoded by a nucleic acid molecule having the sequence of SEQ ID NO: 172. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 172. In several embodiments, the chimeric receptor comprises the amino acid sequence of SEQ ID NO: 173. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 174.

In several embodiments, there is provided a polynucleotide encoding a Flag-tag humanized anti-CD19moiety/ CD8hinge/CD8TM/OX40/CD3zeta chimeric antigen receptor complex (see FIG. 3E, NK19H-8a). The polynucleotide comprises or is composed of an anti-CD19 scFv that has been humanized and comprises a second humanized light chain and a third humanized heavy chain (L2/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NKH19-8b). In such embodiments, the polynucleotide comprises or is composed of an anti-CD19 scFv that has been humanized and comprises a second humanized light chain and a third humanized heavy chain (L2/H3), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 174. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 174. In several embodiments, the chimeric receptor comprises the amino acid sequence of SEQ ID NO: 175. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 175.

In several embodiments, there is provided a polynucleotide encoding a Flag-tag humanized anti-CD19moiety/ CD8hinge/CD8TM/OX40/CD3zeta chimeric antigen receptor complex (see FIG. 3E, NK19H-9a). The polynucleotide comprises or is composed of an anti-CD19 scFv that has been humanized and comprises a third humanized light chain and a third humanized heavy chain (L3/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NKH19-9b). In such embodiments, the polynucleotide comprises or is composed of an anti-CD19 scFv that has been humanized and comprises a third humanized light chain and a third humanized heavy chain (L3/H3), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 176. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 176. In several embodiments, the chimeric receptor comprises the amino acid sequence of SEQ ID NO: 177. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 177.

In several embodiments, there is provided a polynucleotide encoding a Flag-tag humanized anti-CD19moiety/ CD8hinge/CD8TM/OX40/CD3zeta chimeric antigen receptor complex (see FIG. 3E, NKH19-10a). The polynucleotide comprises or is composed of an anti-CD19 scFv that has been humanized and comprises a first humanized light chain and a fourth humanized heavy chain (L1/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-10b). In such embodiments, the polynucleotide comprises or is composed of an anti-CD19 scFv that has been humanized and comprises a first humanized light chain and a fourth humanized heavy chain (L1/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 178. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 178. In several embodiments, the chimeric receptor comprises the amino acid sequence of SEQ ID NO: 179. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 179.

Figure 3F:
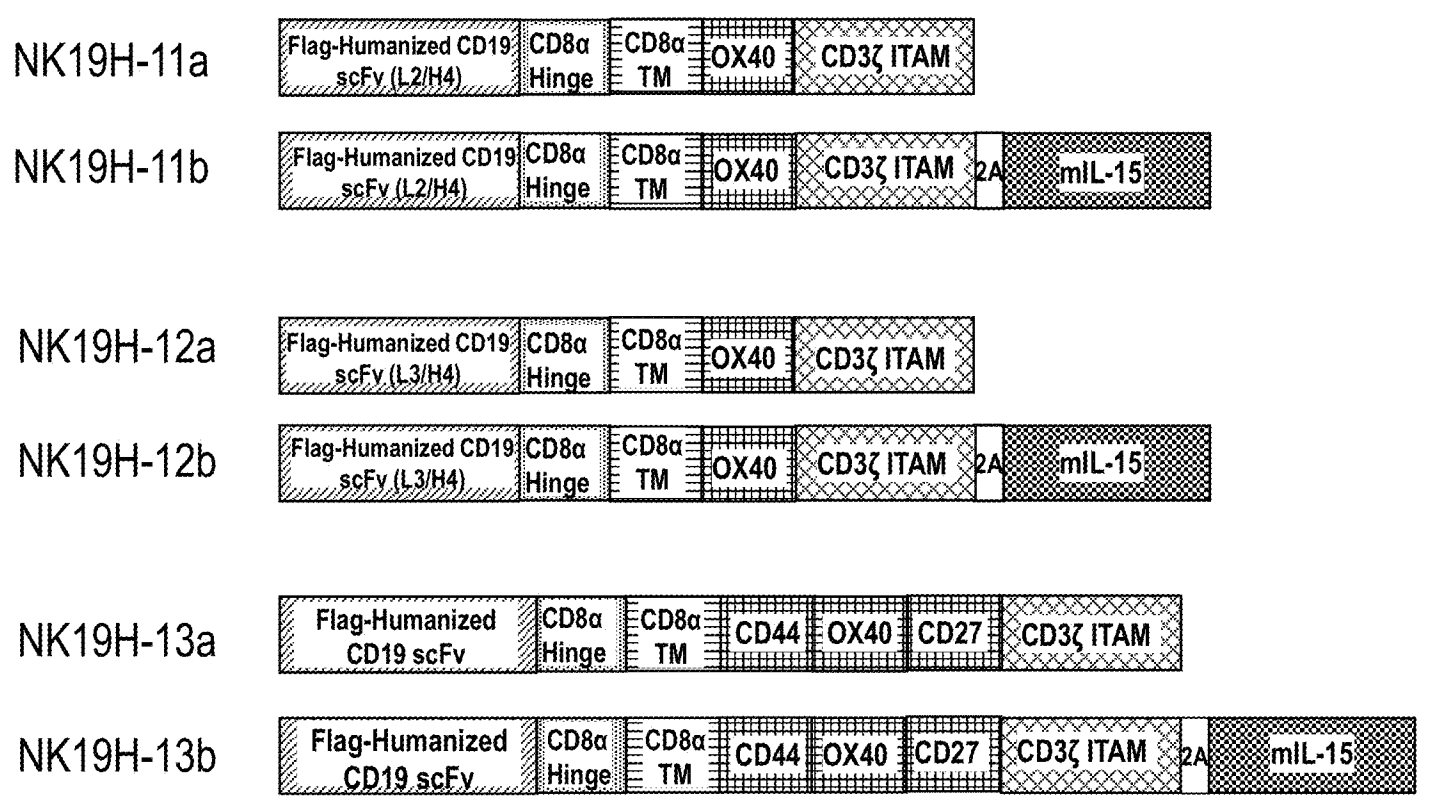

In several embodiments, there is provided a polynucleotide encoding a Flag-tag humanized anti-CD19moiety/ CD8hinge/CD8TM/OX40/CD3zeta chimeric antigen receptor complex (see FIG. 3F, NK19H-11a). The polynucleotide comprises or is composed of an anti-CD19 scFv that has been humanized and comprises a second humanized light chain and a fourth humanized heavy chain (L2/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3F, NK19H-11b). In such embodiments, the polynucleotide comprises or is composed of an anti-CD19 scFv that has been humanized and comprises a second humanized light chain and a fourth humanized heavy chain (L2/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 180. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 180. In several embodiments, the chimeric receptor comprises the amino acid sequence of SEQ ID NO: 181. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 181.

In several embodiments, there is provided a polynucleotide encoding a Flag-tag, humanized anti-CD19moiety/CD8hinge/CD8TM/OX40/CD3zeta chimeric antigen receptor complex (see FIG. 3F NK19H-12a). The polynucleotide comprises or is composed of an anti-CD19 scFv that has been humanized and comprises a third humanized light chain and a fourth humanized heavy chain (L3/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3F, NK19H-12b). In such embodiments, the polynucleotide comprises or is composed of an anti-CD19 scFv that has been humanized and comprises a third humanized light chain and a fourth humanized heavy chain (L3/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 182. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 182. In several embodiments, the chimeric receptor comprises the amino acid sequence of SEQ ID NO: 183. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 183.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3F, NK19H-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3F, NK19H-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

In several embodiments, there is provided a polynucleotide encoding a humanized anti-CD19moiety/CD8hinge/CD8TM/OX40/CD3zeta chimeric antigen receptor complex (see FIG. 3G, NK19H-NF-1a). The polynucleotide comprises or is composed of an anti-CD19 scFv that has been humanized and comprises a first humanized light chain and a first humanized heavy chain (L1/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-1b). In such embodiments, the polynucleotide comprises or is composed of an anti-CD19 scFv that has been humanized and comprises a first humanized light chain and a first humanized heavy chain (L1/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 184. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 184. In several embodiments, the chimeric receptor comprises the amino acid sequence of SEQ ID NO: 185. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 185.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-2a). The polynucleotide comprises or is composed of an anti-CD19 scFv that has been humanized and comprises a second humanized light chain and a first humanized heavy chain (L2/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-2b). In such embodiments, the polynucleotide comprises or is composed of an anti-CD19 scFv that has been humanized and comprises a second humanized light chain and a first humanized heavy chain (L2/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 186. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 186. In several embodiments, the chimeric receptor comprises the amino acid sequence of SEQ ID NO: 187. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 187.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-3a). The polynucleotide comprises or is composed of an anti-CD19 scFv that has been humanized and comprises a third humanized light chain and a first humanized heavy chain (L3/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-3b). In such embodiments, the polynucleotide comprises or is composed of an anti-CD19 scFv that has been humanized and comprises a third humanized light chain and a first humanized heavy chain (L3/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 188. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 188. In several embodiments, the chimeric receptor comprises the amino acid sequence of SEQ ID NO: 189. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 189.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-4a). The polynucleotide comprises or is composed of an anti-CD19 scFv that has been humanized and comprises a first humanized light chain and a second humanized heavy chain (L1/H2), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-4b). In such embodiments, the polynucleotide comprises or is composed of an anti-CD19 scFv that has been humanized and comprises a first humanized light chain and a second humanized heavy chain (L1/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 190. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 190. In several embodiments, the chimeric receptor comprises the amino acid sequence of SEQ ID NO: 191. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 191.

Figure 3H:
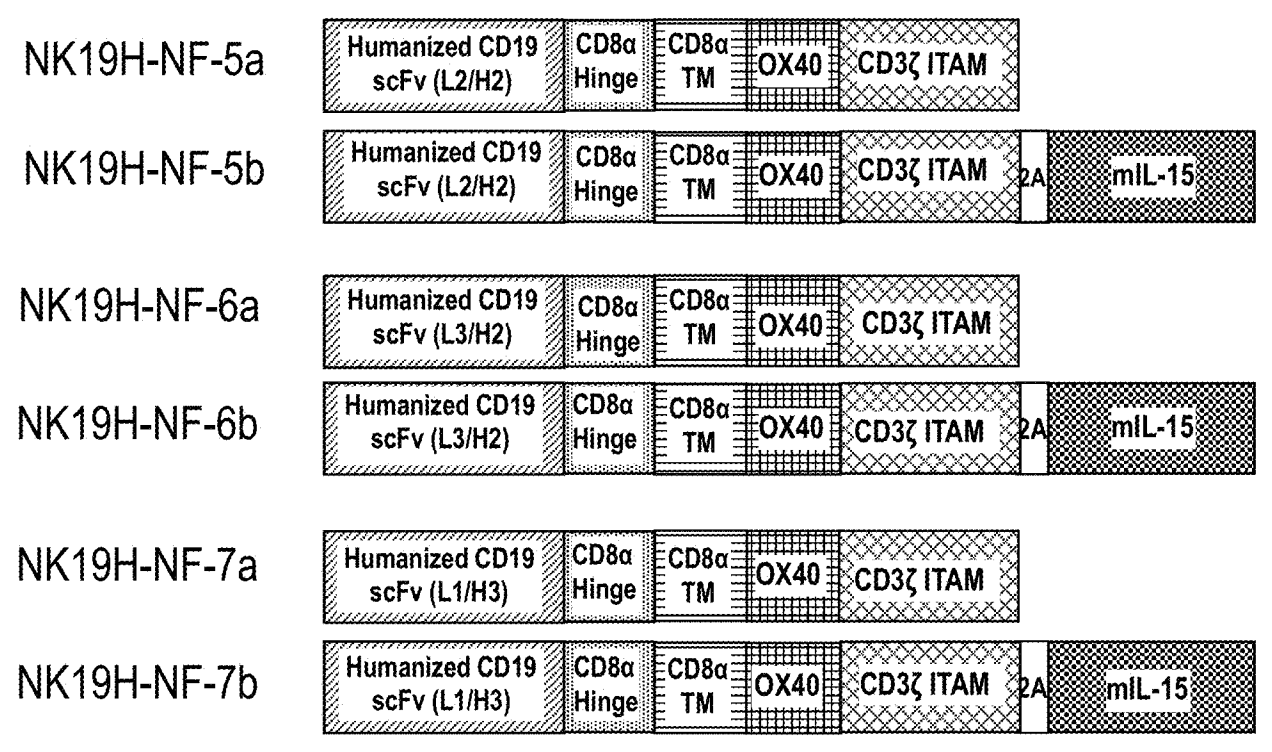

In several embodiments, there is provided a polynucleotide encoding a humanized anti-CD19moiety/CD8hinge/CD8TM/OX40/CD3zeta chimeric antigen receptor complex (see FIG. 3H, NK19H-NF-5a). The polynucleotide comprises or is composed of an anti-CD19 scFv that has been humanized and comprises a second humanized light chain and a second humanized heavy chain (L2/H2), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-5b). In such embodiments, the polynucleotide comprises or is composed of an anti-CD19 scFv that has been humanized and comprises a second humanized light chain and a second humanized heavy chain (L2/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 192. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 192. In several embodiments, the chimeric receptor comprises the amino acid sequence of SEQ ID NO: 193. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 193.

In several embodiments, there is provided a polynucleotide encoding a humanized anti-CD19moiety/CD8hinge/CD8TM/OX40/CD3zeta chimeric antigen receptor complex (see FIG. 3H, NK19H-NF-6a). The polynucleotide comprises or is composed of an anti-CD19 scFv that has been humanized and comprises a third humanized light chain and a second humanized heavy chain (L3/H2), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-6b). In such embodiments, the polynucleotide comprises or is composed of an anti-CD19 scFv that has been humanized and comprises a third humanized light chain and a second humanized heavy chain (L3/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 194. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 194. In several embodiments, the chimeric receptor comprises the amino acid sequence of SEQ ID NO: 195. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 195.

In several embodiments, there is provided a polynucleotide encoding a humanized anti-CD19moiety/CD8hinge/CD8TM/OX40/CD3zeta chimeric antigen receptor complex (see FIG. 3G, NK19H-NF-7a). The polynucleotide comprises or is composed of an anti-CD19 scFv that has been humanized and comprises a first humanized light chain and a third humanized heavy chain (L1/H3), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-7b). In such embodiments, the polynucleotide comprises or is composed of an anti-CD19 scFv that has been humanized and comprises a first humanized light chain and a third humanized heavy chain (L1/H3), a CD8a hinge, a CD8a transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 196. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 196. In several embodiments, the chimeric receptor comprises the amino acid sequence of SEQ ID NO: 197. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 197.

In several embodiments, there is provided a polynucleotide encoding a humanized anti-CD19moiety/CD8hinge/CD8TM/OX40/CD3zeta chimeric antigen receptor complex (see FIG. 3H, NK19H-NF-8a). The polynucleotide comprises or is composed of an anti-CD19 scFv that has been humanized and comprises a second humanized light chain and a third humanized heavy chain (L2/H3), a CD8a hinge, a CD8a transmembrane domain, an OX40 signaling domain, and a CD3zeta domain. In several embodiments, the chimeric antigen receptor further comprises mbIL15 (see FIG. 3H, NKH19-NF-8b). In such embodiments, the polynucleotide comprises or is composed of an anti-CD19 scFv variable light chain that has been humanized and comprises a second humanized light chain and a third humanized heavy chain (L2/H3), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 198. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 198. In several embodiments, the chimeric receptor comprises the amino acid sequence of SEQ ID NO: 199. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 199.

In several embodiments, there is provided a polynucleotide encoding a humanized anti-anti-CD19moiety/CD8hinge/CD8TM/OX40/CD3zeta chimeric antigen receptor complex (see FIG. 3H, NK19H-NF-9a). The polynucleotide comprises or is composed of an anti-CD19 scFv that has been humanized and comprises a third humanized light chain and a third humanized heavy chain (L3/H3), a CD8a hinge, a CD8a transmembrane domain, an OX40 signaling domain, and a CD3zeta domain. In several embodiments, the chimeric antigen receptor further comprises mbIL15 (see FIG. 3H, NKH19-NF-9b). In such embodiments, the polynucleotide comprises or is composed of an anti-CD19 scFv that has been humanized and comprises a third humanized light chain and a third humanized heavy chain (L3/H3), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 200. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 200. In several embodiments, the chimeric receptor comprises the amino acid sequence of SEQ ID NO: 201. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 201.

In several embodiments, there is provided a polynucleotide encoding a humanized anti-CD19moiety/CD8hinge/CD8TM/OX40/CD3zeta chimeric antigen receptor complex (see FIG. 3H, NKH19-NF-10a). The polynucleotide comprises or is composed of an anti-CD19 scFv that has been humanized and comprises a first humanized light chain and a fourth humanized heavy chain (L1/H4), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-10b). In such embodiments, the polynucleotide comprises or is composed of an anti-CD19 scFv that has been humanized and comprises a first humanized light chain and a fourth humanized heavy chain (L1/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 202. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 202. In several embodiments, the chimeric receptor comprises the amino acid sequence of SEQ ID NO: 203. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 203.

In several embodiments, there is provided a polynucleotide encoding a humanized anti-CD19moiety/CD8hinge/CD8TM/OX40/CD3zeta chimeric antigen receptor complex (see FIG. 3I, NK19H-NF-11a). The polynucleotide comprises or is composed of an anti-CD19 scFv that has been humanized and comprises a second humanized light chain and a fourth humanized heavy chain (L2/H4), a CD8a hinge, a CD8a transmembrane domain, an OX40 signaling domain, and a CD3zeta domain. In several embodiments, the chimeric antigen receptor further comprises mbIL15 (see FIG. 3I, NK19H-NF-11b). In such embodiments, the polynucleotide comprises or is composed of an anti-CD19 scFv that has been humanized, and comprises a second humanized light chain and a fourth humanized heavy chain (L2/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 204. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 204. In several embodiments, the chimeric receptor comprises the amino acid sequence of SEQ ID NO: 205. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 205.

In several embodiments, there is provided a polynucleotide encoding a humanized anti-CD19moiety/CD8hinge/CD8TM/OX40/CD3zeta chimeric antigen receptor complex (see FIG. 3I NK19H-12a). The polynucleotide comprises or is composed of an anti-CD19 scFv that has been humanized and comprises a third humanized light chain and a fourth humanized heavy chain (L3/H4), a CD8a hinge, a CD8a transmembrane domain, an OX40 signaling domain, and a CD3zeta domain. In several embodiments, the chimeric antigen receptor further comprises mbIL15 (see FIG. 3I, NK19H-NF-12b). In such embodiments, the polynucleotide comprises or is composed of an anti-CD19 scFv that has been humanized and comprises a third humanized light chain and a fourth humanized heavy chain (L3/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 206. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 206. In several embodiments, the chimeric receptor comprises the amino acid sequence of SEQ ID NO: 207. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 207.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3I, NK19H-NF-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3I, NK19H-NF-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3F, NK19H-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3F, NK19H-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

It shall be appreciated that, for any receptor construct described herein, certain sequence variability, extensions, and/or truncations of the disclosed sequences may result when combining sequences, as a result of, for example, ease or efficiency in cloning (e.g., for creation of a restriction site).

Methods of Treatment

Some embodiments relate to a method of treating, ameliorating, inhibiting, or preventing cancer with a cell or immune cell comprising a chimeric receptor such as a CD19-directed chimeric receptor. In some embodiments, the method includes treating or preventing cancer. In some embodiments, the method includes administering a therapeutically effective amount of immune cells expressing a CD19-directed chimeric receptor as described herein. Examples of types of cancer that may be treated as such are described herein.

In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intra-arterial, subcutaneous, intramuscular, intrahepatic, intraperitoneal and/or local delivery to an affected tissue.

Administration and Dosing

Further provided herein are methods of treating a subject having cancer, comprising administering to the subject a composition comprising immune cells (such as NK and/or T cells) engineered to express a cytotoxic receptor complex as disclosed herein. For example, some embodiments of the compositions and methods described herein relate to use of a CD19-directed chimeric receptor, or use of cells expressing the CD19-directed chimeric receptor, for treating a cancer patient. Uses of such engineered immune cells for treating cancer are also provided.

In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Each of these comparisons are versus, for example, a different therapy for a disease, which includes a cell-based immunotherapy for a disease using cells that do not express the constructs disclosed herein.

Administration can be by a variety of routes, including, without limitation, intravenous, intra-arterial, subcutaneous, intramuscular, intrahepatic, intraperitoneal and/or local delivery to an affected tissue. Doses of immune cells such as NK and/or T cells can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In one embodiment, a dose escalation regimen is used. In several embodiments, a range of immune cells such as NK and/or T cells is administered, for example between about $1\times10^6$ cells/kg to about $1\times10^8$ cells/kg. In several embodiments, the dosage ranges from about $2\times10^5$ cells/kg to about $2\times10^8$ cells/kg, including about $2\times10^6$ and $2\times10^7$ cells/kg. In several embodiments, a dose is determined by the maximum number of viable engineered cells at the time of dosing. For example, in some embodiments, a single dose comprises a maximum of between about $2\times10^5$ and about $2\times10^9$ viable engineered cells, including about $2\times10^6$, about $2\times10^7$, or about $2\times10^8$ viable engineered cells. Depending on the embodiment, various types of cancer can be treated. In several embodiments, hepatocellular carcinoma is treated. Additional embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, glioblastoma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

In some embodiments, also provided herein are nucleic acid and amino acid sequences that have sequence identity or homology of at least 80%, 85%, 90%, 95%, 96%, 97%, 98%, 99% (and ranges therein) as compared with the respective nucleic acid or amino acid sequences of SEQ ID NOS. 1-207 (or combinations of two or more of SEQ ID NOS: 1-207) and that also exhibit one or more of the functions as compared with the respective SEQ ID NOS. 1-207 (or combinations of two or more of SEQ ID NOS: 1-207) including but not limited to, (i) enhanced proliferation, (ii) enhanced activation, (iii) enhanced cytotoxic activity against cells presenting ligands to which NK cells harboring receptors encoded by the nucleic acid and amino acid sequences bind, (iv) enhanced homing to tumor or infected sites, (v) reduced off target cytotoxic effects, (vi) enhanced secretion of immunostimulatory cytokines and chemokines (including, but not limited to IFNg, TNFa, IL-22, CCL3, CCL4, and CCL5), (vii) enhanced ability to stimulate further innate and adaptive immune responses, and (viii) combinations thereof.

Additionally, in several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

In several embodiments, polynucleotides encoding the disclosed cytotoxic receptor complexes or CD19-directed chimeric receptors are mRNA. In some embodiments, the polynucleotide is DNA. In some embodiments, the polynucleotide is operably linked to at least one regulatory element for the expression of the cytotoxic receptor complex.

Additionally provided, according to several embodiments, is a vector comprising the polynucleotide encoding any of the polynucleotides provided for herein, wherein the polynucleotides are optionally operatively linked to at least one regulatory element for expression of a cytotoxic receptor complex. In several embodiments, the vector is a retrovirus.

Further provided herein are engineered immune cells (such as NK and/or T cells) comprising the polynucleotide, vector, or cytotoxic receptor complexes as disclosed herein. Further provided herein are compositions comprising a mixture of engineered immune cells (such as NK cells and/or engineered T cells), each population comprising the polynucleotide, vector, or cytotoxic receptor complexes as disclosed herein.

Doses of immune cells such as NK cells or T cells can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In one embodiment, a dose escalation regimen is used. In several embodiments, a range of NK cells is administered, for example between about $1\times10^6$ cells/kg to about $1\times10^8$ cells/kg. Depending on the embodiment, various types of cancer or infection disease can be treated.

Cancer Types

Some embodiments of the compositions and methods described herein relate to administering immune cells comprising a chimeric receptor, such as a CD19-directed chimeric receptor, to a subject with cancer. Various embodiments provided for herein include treatment or prevention of the following non-limiting examples of cancers. Examples of cancer include, but are not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

Cancer Targets

Some embodiments of the compositions and methods described herein relate to immune cells comprising a chimeric receptor that targets a cancer antigen. Non-limiting examples of target antigens include: CD5, CD19; CD123; CD22; CD30; CD171; CS1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8)aNeu5Ac(2-3) bDGalp(I-4)bDGlcp(I-I)Cer); TNF receptor family member B cell maturation (BCMA); Tn antigen ((Tn Ag) or (GalN-Aca-Ser/Thr)); prostate-specific membrane antigen (PSMA); Receptor tyrosine kinase-like orphan receptor 1 (ROR1); Fms Like Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-IIRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha (FRa or FR1); Folate receptor beta (FRb); Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); sialyl Lewis adhesion molecule (sLe); ganglioside GM3 (aNeu5Ac(2-3)bD-CIalp(I-4)bDGlcp(I-I)Cer); transglutaminase 5 (TGS5); high molecular weight-melanoma associated antigen (HMWMAA); o-acetyl-GD2 ganglioside (OAcGD2); tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCT A-I or Galectin 8), melanoma antigen recognized by T cells 1 (MelanA or MARTI); Rat sarcoma (Ras) mutant; human Telomerase; reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin BI; v-myc avian myelocytomatosis viral oncogene neuroblastoma derived homolog (MYCN); Ras Homolog Family Member C (RhoC); Tyrosinase-related protein 2 (TRP-2); Cytochrome P450 IB 1 (CYPIB 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Gly cation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); and immunoglobulin lambda-like polypeptide 1 (IGLLI), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen); Fucosyl-GMI, PTK7, gpNMB, CDH1-CD324, DLL3, CD276/B7H3, ILI IRa, IL13Ra2, CD179b-IGLII, TCRgamma-delta, NKG2D, CD32 (FCGR2A), Tn ag, Timl-/HVCR1, CSF2RA (GM-CSFR-alpha), TGF-betaR2, Lews Ag, TCR-betal chain, TCR-beta2 chain, TCR-gamma chain, TCR-delta chain, FITC, Luteinizing hormone receptor (LHR), Follicle stimulating hormone receptor (FSHR), Gonadotropin Hormone receptor (CGHR or GR), CCR4, GD3, SLAMF6, SLAMF4, HIV1 envelope glycoprotein, HTLVI-Tax, CMV pp65, EBV-EBNA3c, KSHV K8.1, KSHV-gH, influenza A hemagglutinin (HA), GAD, PDL1, Guanylyl cyclase C (GCC), auto antibody to desmoglein 3 (Dsg3), auto antibody to desmoglein 1 (Dsgl), HLA, HLA-A, HLA-A2, HLA-B, HLA-C, HLA-DP, HLA-DM, HLA-DOA, HLA-DOB, HLA-DQ, HLA-DR, HLA-G, IgE, CD99, Ras G12V, Tissue Factor 1 (TF1), AFP, GPRC5D, Claudin 18.2 (CLD18A2 or CLDN18A.2)), P-glycoprotein, STEAP1, Livl, Nectin-4, Cripto, gpA33, BST1/CD157, low conductance chloride channel, and the antigen recognized by TNT antibody.

Additionally, in several embodiments there is provided an immune cell that expresses a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain having at least 95% identity to the VH domain amino acid sequence set forth in SEQ ID NO: 33, the VL domain having at least 95% identity to the VL domain amino acid sequence set forth in SEQ ID NO: 32, a hinge and/or transmembrane domain, an intracellular signaling domain, wherein the intracellular signaling domain comprises an OX40 subdomain, and wherein the cell also expresses membrane-bound interleukin-15 (mbIL15). In several embodiments, the intracellular signaling domain further comprises a CD3zeta subdomain. In several embodiments, the OX40 subdomain comprises the amino acid sequence of SEQ ID NO: 6 and the CD3zeta subdomain comprises the amino acid sequence of SEQ ID NO: 7. In several embodiments, the hinge domain comprises a CD8a hinge domain. In several embodiments, the CD8a hinge domain, comprises the amino acid sequence of SEQ ID NO: 2. In several embodiments, the mbIL15 comprises the amino acid sequence of SEQ ID NO: 12. In several embodiments, the chimeric receptor further comprises an extracellular domain of an NKG2D receptor. In several embodiments, the extracellular domain of the NKG2D receptor comprises a functional fragment of NKG2D comprising the amino acid sequence of SEQ ID NO: 26. In several embodiments, the immune cell is a natural killer (NK) cell. In several embodiments, the immune cell is a T cell. In several embodiments, the such immune cells are administered to a subject in a method of treating cancer, or are otherwise used to the treatment of cancer, such as in the preparation of a medicament for the treatment of cancer. In several embodiments, the cancer is acute lymphocytic leukemia.

In several embodiments there is provided a polynucleotide encoding a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain having at least 95% identity to the VH domain amino acid sequence set forth in SEQ ID NO: 33, the VL domain having at least 95% identity to the VL domain amino acid sequence set forth in SEQ ID NO: 32, a hinge and/or transmembrane domain, an intracellular signaling domain, wherein the intracellular signaling domain comprises an OX40 subdomain, and wherein the polynucleotide also encodes membrane-bound interleukin-15 (mbIL15). In several embodiments, the intracellular signaling domain further comprises a CD3zeta subdomain. In several embodiments, the encoded OX40 subdomain comprises the amino acid sequence of SEQ ID NO: 16 and the encoded CD3zeta subdomain comprises the amino acid sequence of SEQ ID NO: 8. In several embodiments, the hinge domain comprises a CD8a hinge domain and comprises the amino acid sequence of SEQ ID NO: 2. In several embodiments, the encoded mbIL15 comprises the amino acid sequence of SEQ ID NO: 12. In several embodiments, the chimeric receptor further comprises an extracellular domain of an NKG2D receptor.

In several embodiments, the encoded extracellular domain of the NKG2D receptor comprises a functional fragment of NKG2D comprising the amino acid sequence of SEQ ID NO: 26.

Also provided herein is an immune cell that expresses a CD19-directed chimeric receptor comprising an extracellular anti-CD19 moiety, a hinge and/or transmembrane domain, and an intracellular signaling domain. In several embodiments, the immune cell is an NK cell. In several embodiments, the immune cell is a T cell. In several embodiments, the hinge domain comprises a CD8a hinge domain or an Ig4 SH domain. In several embodiments, the transmembrane domain comprises a CD8a transmembrane domain, a CD28 transmembrane domain and/or a CD3 transmembrane domain. In several embodiments, the signaling domain comprises an OX40 signaling domain, a 4-1 BB signaling domain, a CD28 signaling domain, an NKp80 signaling domain, a CD16 IC signaling domain, a CD3zeta or CD3 ITAM signaling domain, and/or a mIL-15 signaling domain. In several embodiments, the signaling domain comprises a 2A cleavage domain. In several embodiments, the mIL-15 signaling domain is separated from the rest or another portion of the CD19-directed chimeric receptor by a 2A cleavage domain. In several embodiments, such immune cells are administered to a subject having cancer in order to treat, inhibit or prevent progression of the cancer.

Provided herein is also an engineered NK or T cell that expresses a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain resulting from humanization of the VH domain amino acid sequence set forth in SEQ ID NO: 33, the VL domain comprising a VL domain resulting from humanization the VL domain amino acid sequence set forth in SEQ ID NO: 32, a hinge and/or transmembrane domain, an intracellular signaling domain, wherein the intracellular signaling domain comprises an OX40 subdomain, and wherein the cell also expresses membrane-bound interleukin-15 (mbIL15).

Provided herein is a polynucleotide encoding a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain resulting from humanization of the VH domain amino acid sequence set forth in SEQ ID NO: 33, the VL domain comprising a VL domain resulting from humanization the VL domain amino acid sequence set forth in SEQ ID NO: 32; a hinge and/or transmembrane domain, an intracellular signaling domain, wherein the intracellular signaling domain comprises an OX40 subdomain, and wherein the polynucleotide also encodes membrane-bound interleukin-15 (mbIL15).

Provided here is a polynucleotide encoding a CD19-directed chimeric antigen receptor, the chimeric antigen receptor comprising an extracellular anti-CD19 binding moiety, wherein the anti-CD19 binding moiety comprises a scFv; a hinge, wherein the hinge is a CD8 alpha hinge; a transmembrane domain; and an intracellular signaling domain, wherein the intracellular signaling domain comprises a CD3 zeta ITAM. In several embodiments, the transmembrane domain comprises a CD8 alpha transmembrane domain, an NKG2D transmembrane domain, and/or a CD28 transmembrane domain. In several embodiments, the intracellular signaling domain comprises a CD28 signaling domain, a 4-1 BB signaling domain, and/or an OX40 domain. In several embodiments, the intracellular signaling domain may also comprise a domain selected from ICOS, CD70, CD161, CD40L, CD44, and combinations thereof.

Provided herein is a polynucleotide encoding a CD19-directed chimeric antigen receptor, the chimeric antigen receptor comprising an extracellular anti-CD19 binding moiety, wherein the anti-CD19 binding moiety comprises a variable heavy chain of a scFv or a variable light chain of a scFv; a hinge, wherein the hinge is a CD8 alpha hinge; a transmembrane domain, wherein the transmembrane domain comprises a CD8 alpha transmembrane domain; and an intracellular signaling domain, wherein the intracellular signaling domain comprises a CD3 zeta ITAM. In several embodiments, the polynucleotide also encodes a truncated epidermal growth factor receptor (EGFRt). In several embodiments, the polynucleotide also encodes membrane-bound interleukin-15 (mbIL15). Provided herein is an engineered NK or T cell that expresses such a CD19-directed chimeric antigen, as well as methods of treating cancer by administering such an NK cell or T cell. Also provided for is the use of such polynucleotides in the treatment of cancer, for example, in the manufacture of a medicament for the treatment of cancer.

Provided herein is a polynucleotide encoding a humanized CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain selected from SEQ ID NO: 120, SEQ ID NO: 121, SEQ ID NO: 122, and SEQ ID NO: 123, the VL domain comprising a VL domain selected from SEQ ID NO: 117, SEQ ID NO: 118, and SEQ ID NO: 119; a hinge and/or transmembrane domain, an intracellular signaling domain, and wherein the polynucleotide also encodes membrane-bound interleukin-15 (mbIL15). In several embodiments, the intracellular signaling domain comprises an OX40 subdomain, a CD28 subdomain, an iCOS subdomain, a CD28-41 BB subdomain, a CD27 subdomain, a CD44 subdomain, or combinations thereof. In several embodiments, the chimeric antigen receptor comprises a hinge and a transmembrane domain, wherein the hinge is a CD8 alpha hinge, wherein the transmembrane domain is either a CD8 alpha or an NKG2D transmembrane domain. In several embodiments, the intracellular signaling domain comprises a CD3zeta domain.

Provided for herein is a polynucleotide encoding a humanized chimeric antigen receptor (CAR), wherein the CAR comprises a single chain antibody or single chain antibody fragment which comprises a humanized anti-CD19 binding domain, a transmembrane domain, a primary intracellular signaling domain comprising a native intracellular signaling domain of CD3-zeta, or a functional fragment thereof, and a costimulatory domain comprising a native intracellular signaling domain of a protein selected from the group consisting of OX40, CD27, CD28, ICOS, and 4-1BB, or a functional fragment thereof, wherein said anti-CD19 binding domain comprises a light chain complementary determining region 1 (LC CDR1) of SEQ ID NO: 124, 127, or 130, a light chain complementary determining region 2 (LC CDR2) of SEQ ID NO: 125, 128, or 131, and a light chain complementary determining region 3 (LC CDR3) of SEQ ID NO: 126, 129, or 132, and a heavy chain complementary determining region 1 (HC CDR1) of SEQ ID NO: 133, 136, 139, or 142, a heavy chain complementary determining region 2 (HC CDR2) of SEQ ID NO: 134, 137, 140, or 143, and a heavy chain complementary determining region 3 (HC CDR3) of SEQ ID NO: 135, 138, 141, or 144. In several embodiments, the polynucleotide further comprises a region encoding membrane-bound interleukin 15 (mbIL15).

Provided for herein is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 117, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 161, SEQ ID NO: 167, SEQ ID NO: 173, SEQ ID NO: 179, SEQ ID NO: 185, SEQ ID NO: 191, SEQ ID NO: 197, or SEQ ID NO: 203.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 118, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 163, SEQ ID NO: 169, SEQ ID NO: 175, SEQ ID NO: 181, SEQ ID NO: 187, SEQ ID NO: 193, SEQ ID NO: 199, or SEQ ID NO: 205.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 119, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 165, SEQ ID NO: 171, SEQ ID NO: 177, SEQ ID NO: 183, SEQ ID NO: 189, SEQ ID NO: 195, SEQ ID NO: 201, or SEQ ID NO: 207.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 120, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 161, SEQ ID NO: 163, SEQ ID NO: 165, SEQ ID NO: 185, SEQ ID NO: 187, or SEQ ID NO: 189.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 121, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 167, SEQ ID NO: 169, SEQ ID NO: 171, SEQ ID NO: 191, SEQ ID NO: 193, or SEQ ID NO: 195.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 122, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 173, SEQ ID NO: 175, SEQ ID NO: 177, SEQ ID NO: 197, SEQ ID NO: 199, or SEQ ID NO: 201.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 123, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 179, SEQ ID NO: 181, SEQ ID NO: 183, SEQ ID NO: 203, SEQ ID NO: 205, or SEQ ID NO: 207.

In several embodiments, the provided for polynucleotides do not encode SEQ ID NO: 112, 113, 114, or 116.

Provided for is a polynucleotide encoding a humanized CD19-directed chimeric antigen receptor, the chimeric antigen receptor comprising an extracellular anti-CD19 binding moiety; a hinge and/or transmembrane domain; an intracellular signaling domain, and wherein the polynucleotide also encodes membrane-bound interleukin-15 (mbIL15), and wherein the polynucleotide is selected from the group consisting of polynucleotides having at least 95% identity to SEQ ID NO: 184, SEQ ID NO: 186, SEQ ID NO: 192, or SEQ ID NO: 200. In several embodiments, the polynucleotide has the sequence of SEQ ID NO: 184, SEQ ID NO: 186, SEQ ID NO: 192, or SEQ ID NO: 200. In several embodiments, there are provided engineered NK or T cells that express such a humanized CD19-directed chimeric antigen receptor. Also provided for is a method of treating cancer in a subject comprising administering to a subject having cancer such engineered NK or T cells. Also provided is the use of such polynucleotides in the treatment of cancer, such as in the manufacture of a medicament for the treatment of cancer.

EXAMPLES

The materials and methods disclosed herein are non-limiting examples that are employed according to certain embodiments disclosed herein.

According to several embodiments, NK cells are isolated from peripheral blood mononuclear cells and expanded through the use of a feeder cell line. As discussed in more detail below, in several embodiments, the feeder cells are engineered to express certain stimulatory molecules (e.g. interleukins, CD3, 4-1 BBL, etc.) to promote immune cell expansion and activation. Engineered feeder cells are disclosed in, for example, International Patent Application PCT/SG2018/050138, which is incorporated in its entirety by reference herein. In several embodiments, the stimulatory molecules, such as interleukin 12, 18, and/or 21 are separately added to the co-culture media, for example at defined times and in particular amounts, to effect an enhanced expansion of a desired sub-population(s) of immune cells.

NK cells isolated from PBMC were cocultured with K562 cells expressing membrane-bound IL15 and 4-1 BBL, with the media being supplemented with IL2. For one group of engineered NK cells, they were expanded in media was supplemented (at Day 0) with a combination of soluble IL12 and soluble IL18. The media was refreshed with additional soluble IL12 and soluble IL18 at Day 4. Additional details on embodiments of such culture methodology is disclosed in U.S. Provisional Patent Application No. 62/881,311, filed Jul. 31, 2019 and incorporated in its entirety by reference here. Viral transduction, with a CD19-directed chimeric receptor construct, was performed at Day 7. The resultant engineered NK cells were evaluated at 14, or more, days of total culture time.

Example 1

Figure 5:
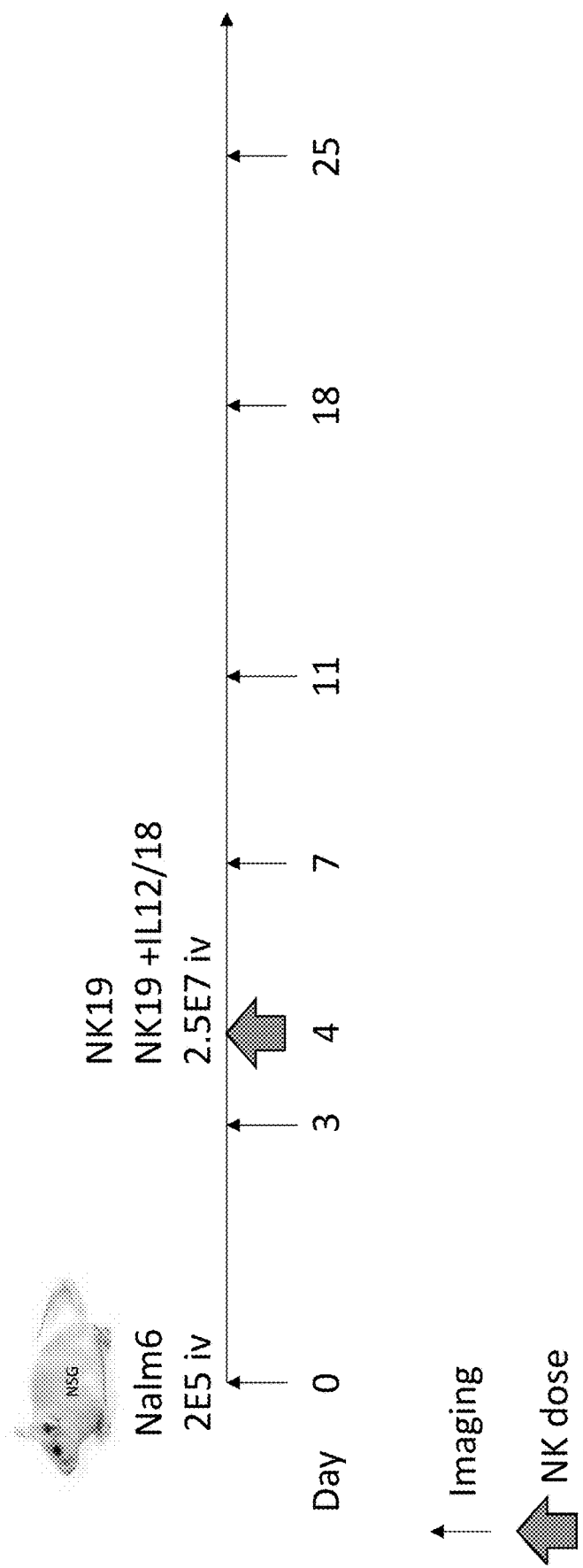
FIG. 5 shows a schematic of an experimental protocol assessing the effectiveness of a CD19-directed chimeric antigen receptor in accordance with several embodiments disclosed herein.
Figure 6A:
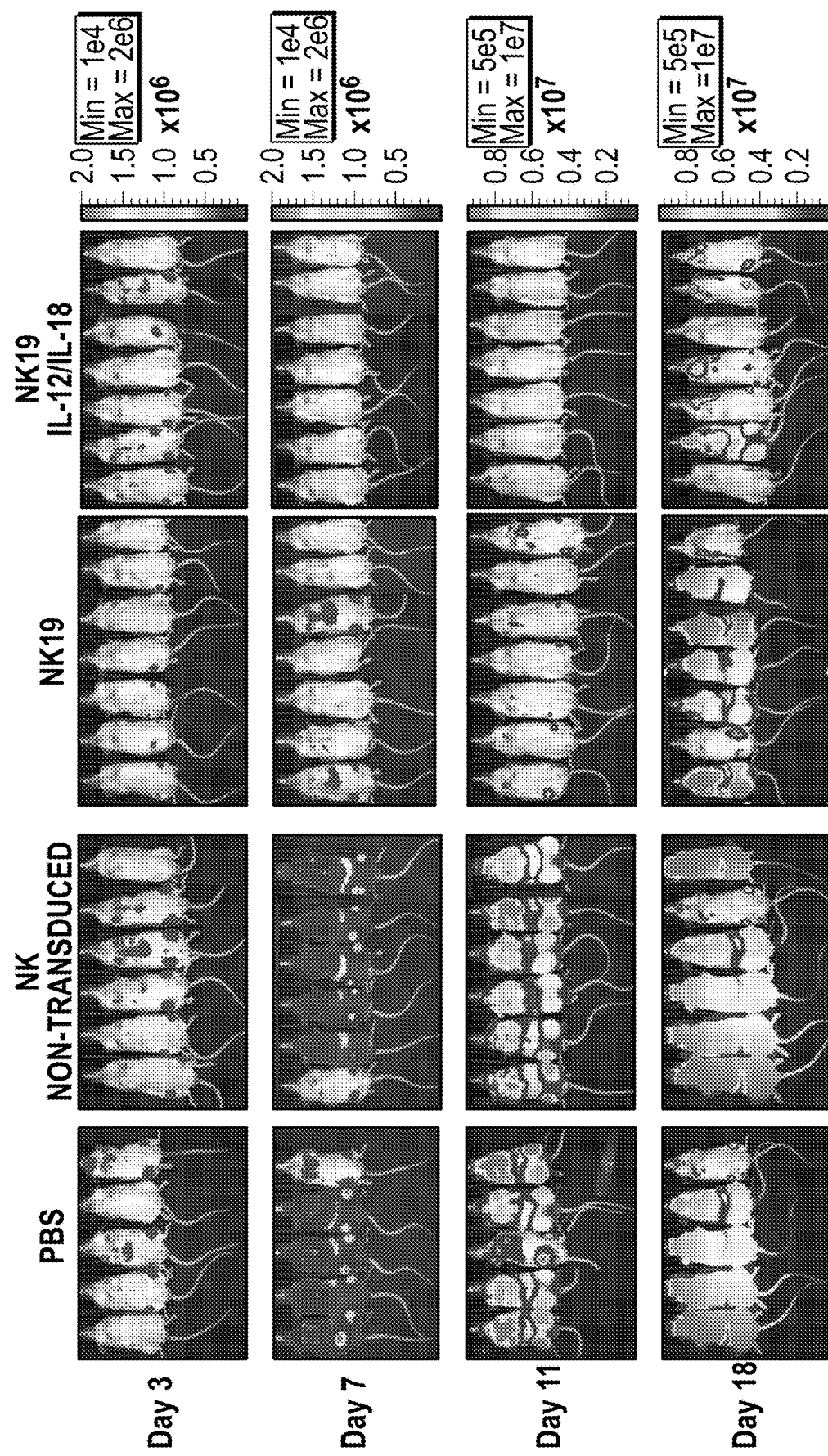
FIG. 6A depicts in vivo data related to the anti-tumor effect of various non-limiting CD19-directed chimeric receptors.
Figure 6B:
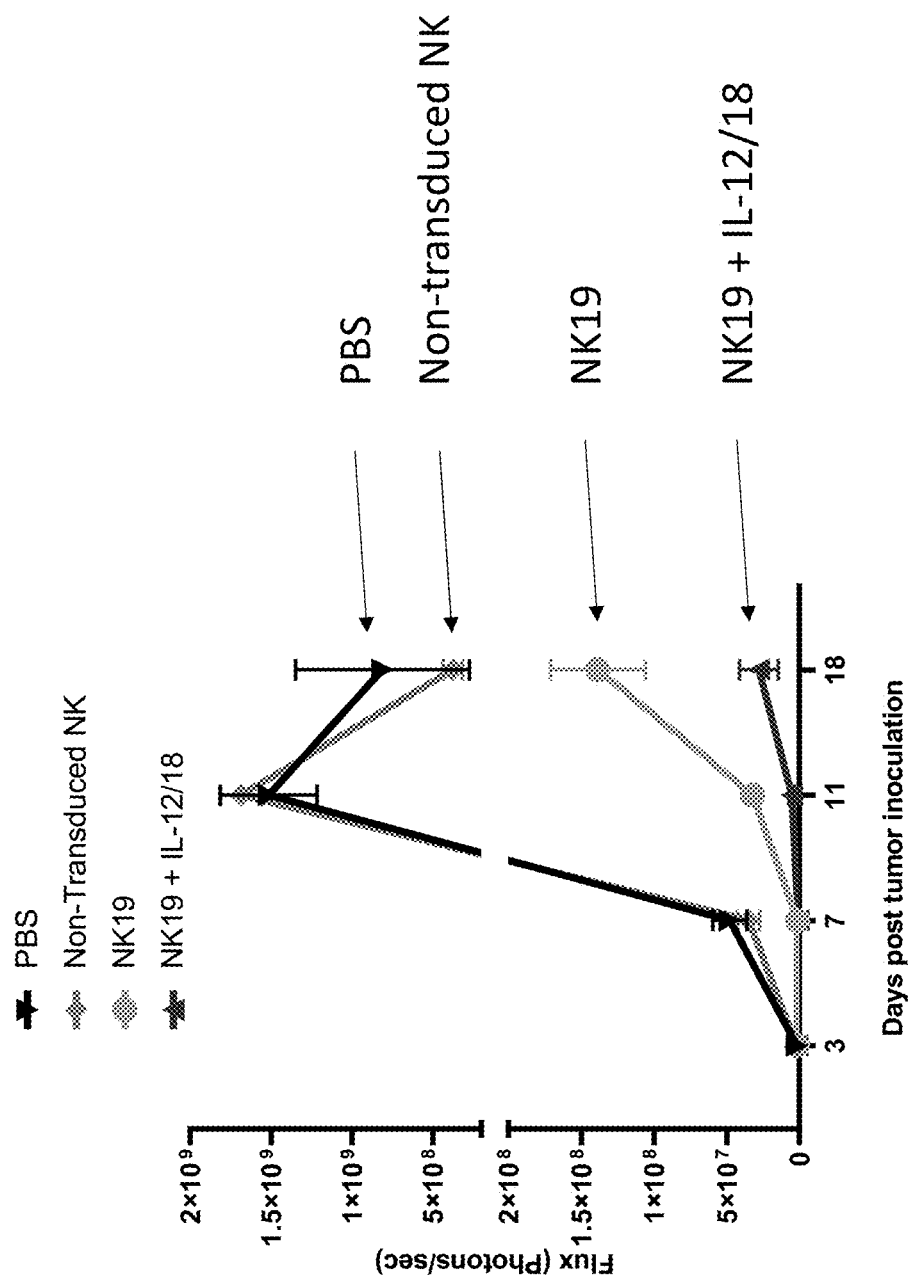
FIG. 6B depicts summary data related to the anti-tumor effect of various non-limiting CD19-directed chimeric receptors.

FIG. 5 depicts a schematic experimental model for evaluating the anti-tumor efficacy of engineered NK cells generated according to methods disclosed herein. NOD-scid IL2Rgamma$^{null}$ mice were administered $2 \times 10^5$ Nalm6 cells (B cell precursor leukemia cell line) intravenously at Day 0. At Day 4, one group of mice received $2.7 \times 10^7$ NK cells expressing an NK19 CAR (see FIG. 3A, though it shall be appreciated that other CD19-directed chimeric receptors could be used) while another group received NK cells that had been expanded using soluble IL12/1L18 (identified as NK19-IL12/18 cells). Leukemic tumor burden was assessed by fluorescent imaging performed at Days 3, 7, 11, 18, and 25. FIG. 6A shows the imaging results from Days 3, 7, 11, and 18. As can be seen, mice receiving either NK19 or NK19 IL12/18 had significantly less tumor burden than mice receiving either non-transduced NK cells or PBS as a control. FIG. 6B shows a summary of the imaging data in a line graph (greater values of Flux (photons/second) indicates more fluorescent signal detection and greater tumor burden). Both NK19 and NK19 IL12/18 groups have less tumor burden as early as Day 7 post-injection of the Nalm6 leukemia cells. This difference is even more pronounced at Day 11, when the PBS and NT NK cell groups are exhibiting large amounts of tumor growth. Even as far out as Day 18, when tumor burden in the PBS and NT NK groups is extensive, the NK19 and NK19 IL12/18 groups show much less tumor burden. Unexpectedly, the NK19 IL12/18 groups show less tumor burden than this receiving the NK19 construct. This is surprising not only because NK19 cells are quite efficacious at preventing leukemia cell growth, so the further enhancement of this effect is unexpected, but also because an upstream methodology of expanding the cells has not only impacted the cell number itself, but also the activity level of those expanded cells.

Example 2

Experiments were undertaken to determine if a given stimulatory domain (also referred to as co-stimulatory domains, given that many construct employ multiple "signaling" domains in tandem, triplet or other multiplex fashion) utilized in a CAR impacted expression (as well as activity). NK cells were generated by transduction with viruses encoding various CARs depicted in FIGS. 3A-3C (though other constructs are used, in several embodiments). By way of non-limiting example, NK cells were cells were generated by transduction with a bicistronic virus encoding an anti-CD19 scFv, an intracellular OX40 costimulatory domain, CD3ζ signaling domain, and membrane-bound IL-15 (see NK19, FIG. 3A) which supports prolonged cell survival and proliferation. The other CAR constructs tested, NK19-1, 2, 3, 4, 5, 8, 9, 10, 11, 12, and NK19-13, were transduced into NK cells in similar fashion. It shall be appreciated that, for those constructs that employ a Flag domain to determine expression, analogous constructs not including the Flag (or other tag domain) are provided for, in several embodiments.

Figure 7:
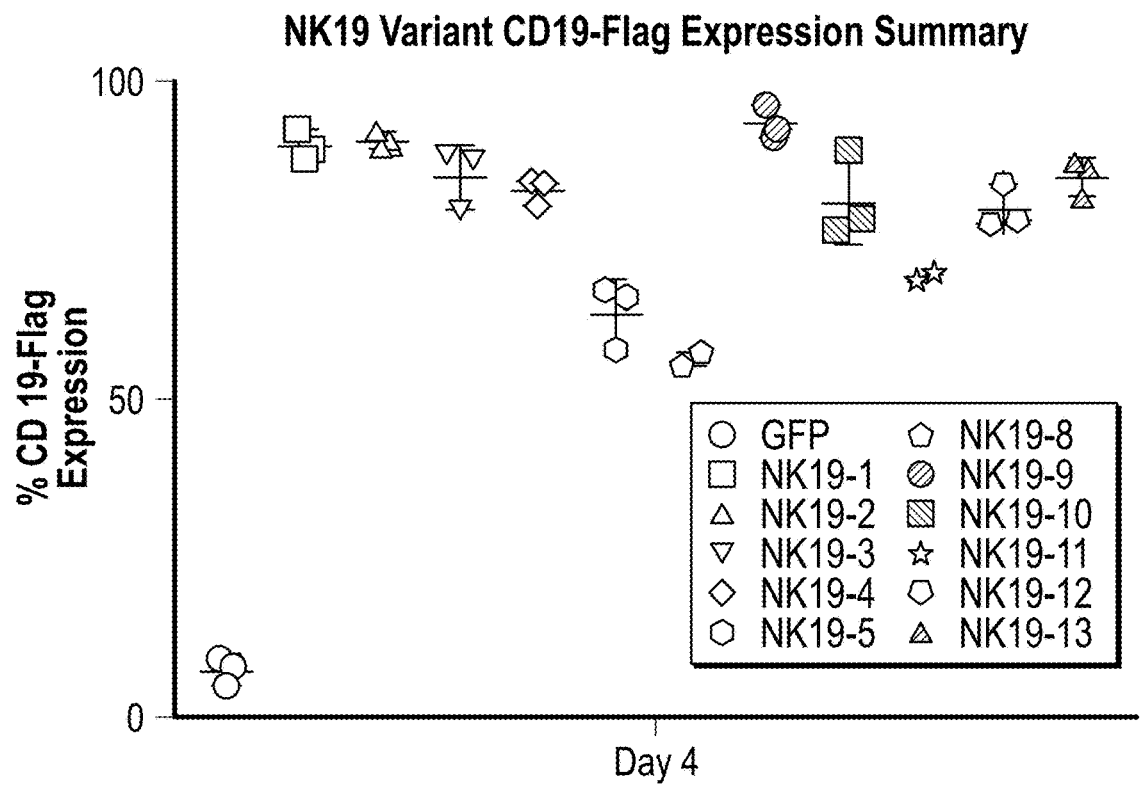
FIG. 7 depicts data related to the expression of various CD19-direcetd chimeric receptor constructs by NK cells.

FIG. 7 summarizes the expression data of NK 19-1 to NK5 and NK8 to NK19-13 as evidenced by detection of CD19Flag. Data are presented as percentage of NK cells expressing CD19-Flag relative to the total number of NK cells presented. The data were collected at 4 days after transduction with the relevant virus encoding the NK19-"X" CAR. As evidenced by the expression data, all constructs were expressed by at least 55% of the NK cells. In fact, for eight of the eleven constructs for which data was generated expression was detected in approximately 75% or more of the total number of NK cells, with several constructs expressed at over 80% efficiency. This expression data indicates that, according to several embodiments, selection of specific stimulatory domains can enable a more efficient expression of the CAR by the NK cell. This is advantageous, in several embodiments, because a greater portion of a given NK cell preparation is useful clinically (e.g., fewer input NK cells needed to generate a clinically relevant engineered NK cell dose).

Figure 8A:
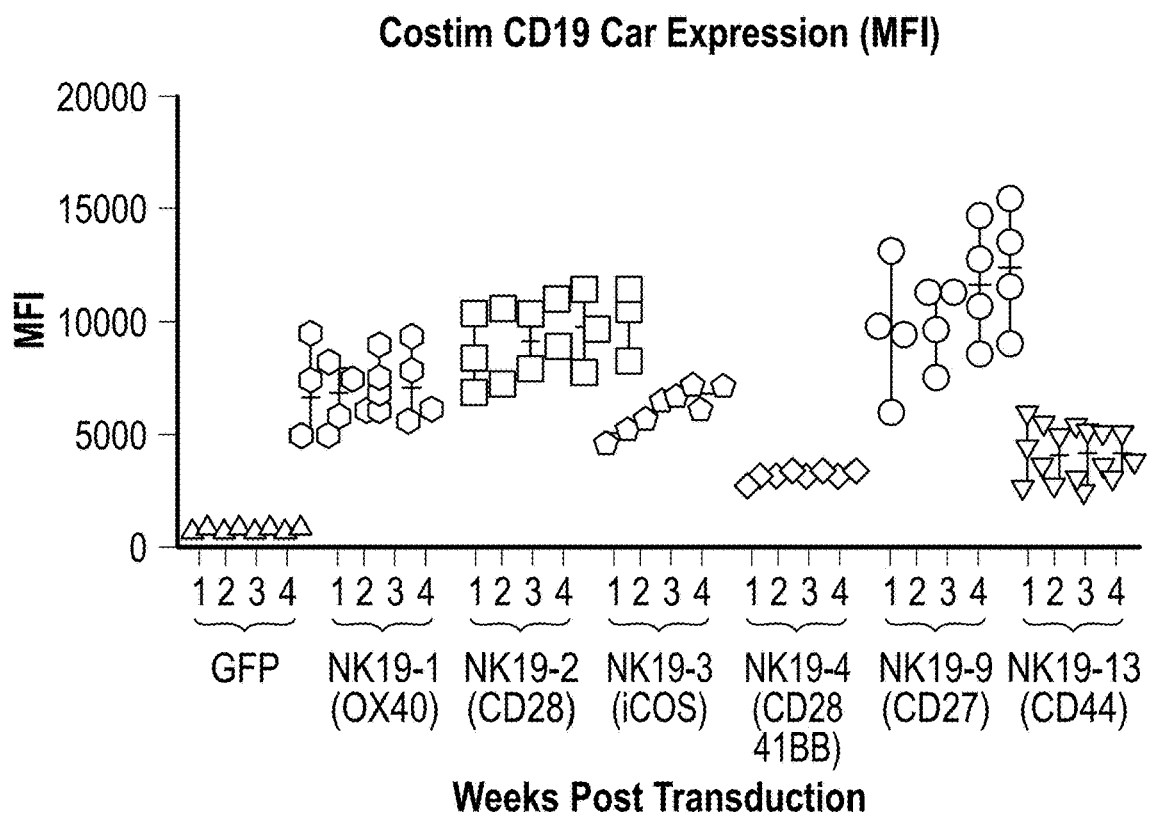
FIG. 8A depicts raw fluorescence data (mean fluorescence intensity, MFI) related to the expression of selected CD19-directed chimeric receptors.
Figure 8B:
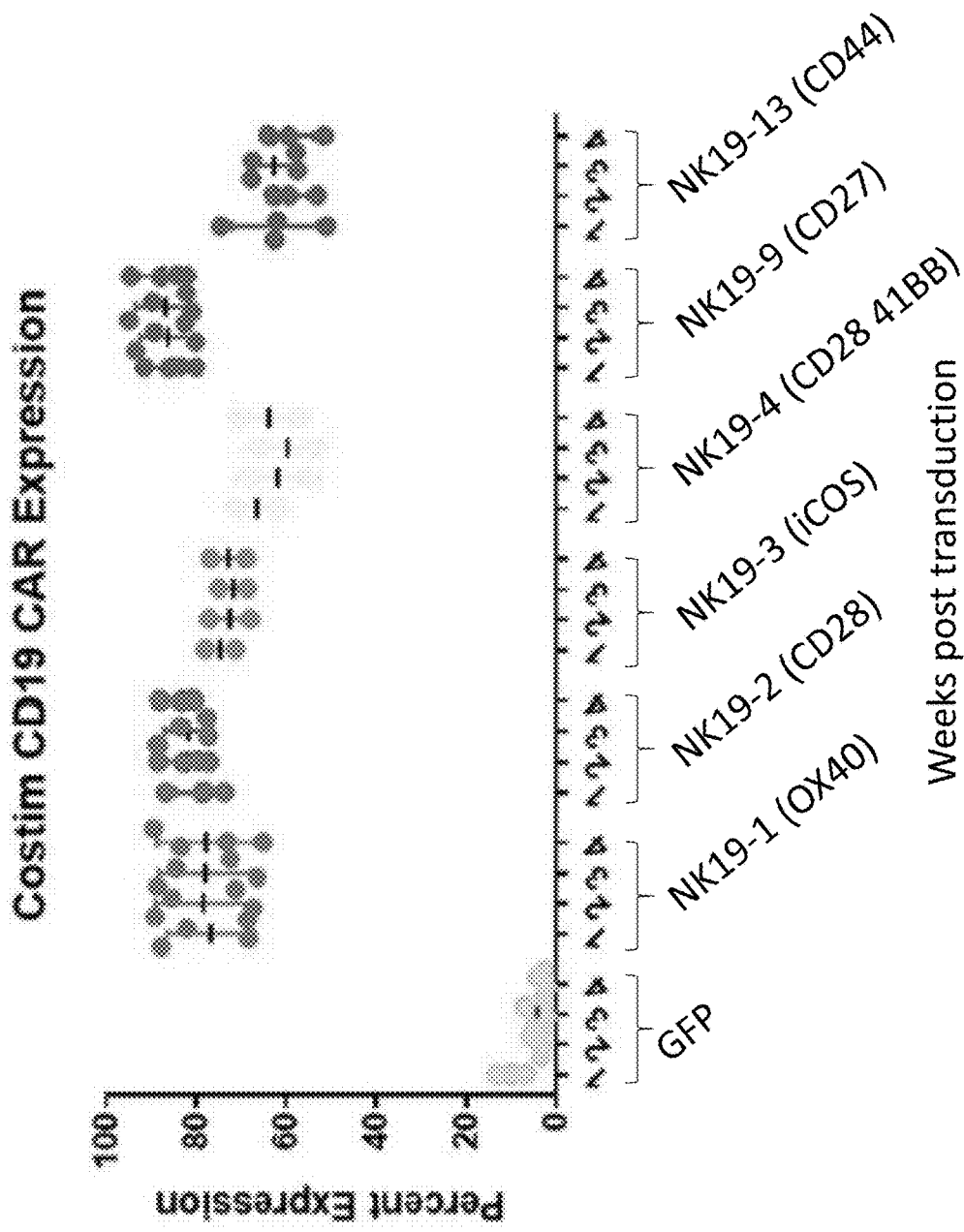
FIG. 8B depicts data related to the expression of selected CD19-directed chimeric receptors, displayed as percent of NK cells expressing the indicated receptor.

As discussed herein, various co-stimulatory domains can be employed in chimeric antigen receptors that Target CD19 (or other tumor markers). FIG. 8A depicts data related to the expression of CARs targeting CD19 using various co-stimulatory domains. By way of non-limiting example, co-stimulatory domains can include, but are not limited to, OX40, CD28, iCOS, CD28/41 BB, CS27, and CD44). FIG. 8A shows mean fluorescence intensity data representing expression of the indicated CAR constructs by NK cells. As evidenced by the low MFI detected for the GFP control, these data indicate that these construct (a) are expressed by NK cells, and (b) are expressed relatively stably by NK cells over a 4 week period post-transduction. FIG. 8B shows the efficiency of expression of the CARs with the indicated co-stimulatory domains. While there is some variability in efficiency of expression, ranging from about 60% to about 80% efficiency, each of the CARs with the indicated co-stimulatory domains expressed well, and also expressed relatively consistently over at least 4 weeks.

Figure 9A:
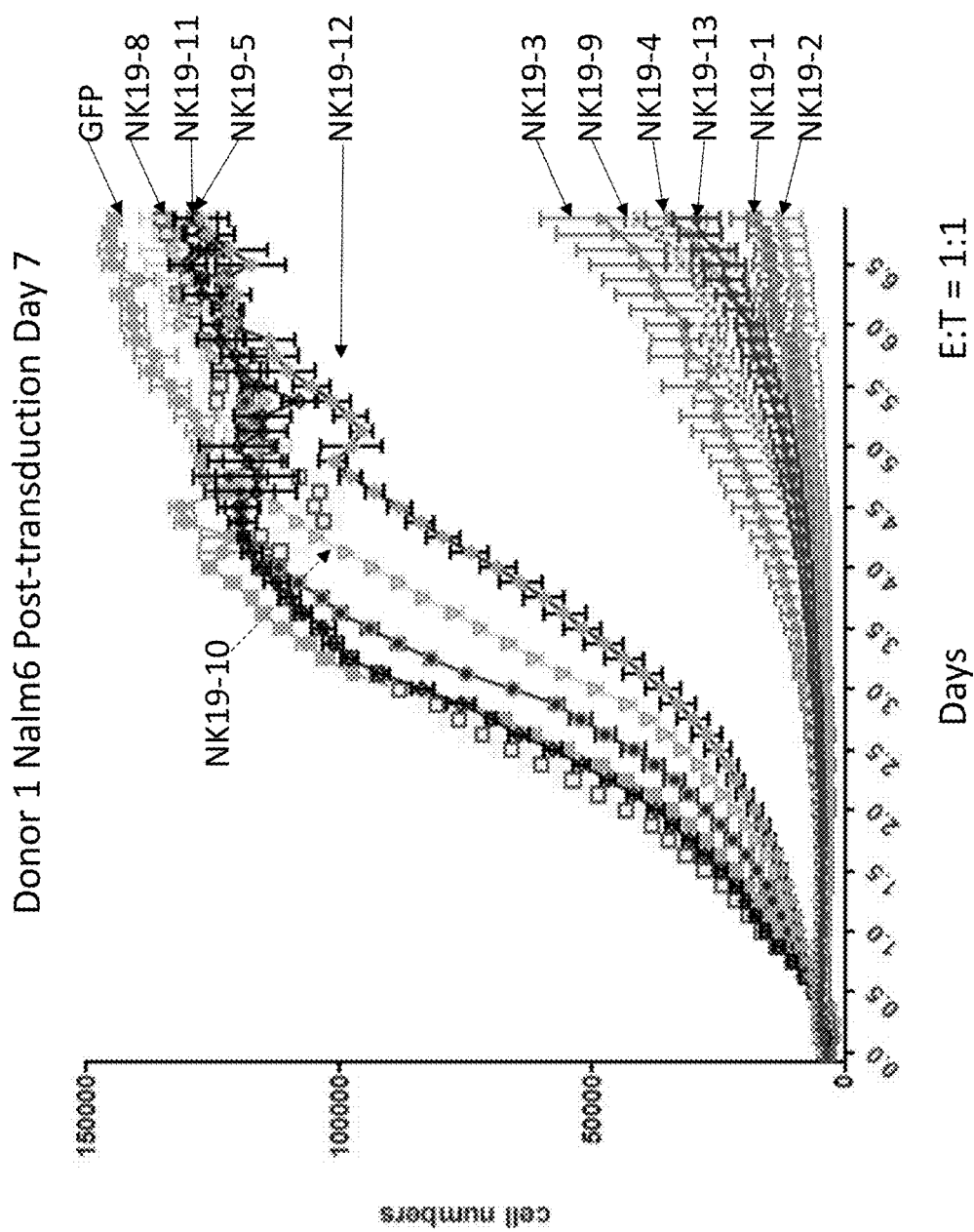
FIGS. 9A-9D depicts data related to the cytotoxicity (against Nalm6 or Raji cells) for the indicated CD19-directed chimeric receptors.

With respect to the cytotoxic efficacy of the NK cells expressing the CD19-directed CARs utilizing the various co-stimulatory domains, that data is shown in FIGS. 9A-9F. Cultured Nalm6 or Raji cells were exposed to engineered NK cells expressing the indicated NK19 constructs and co-cultured for the indicated number of days (X axis represents days) of exposure to NK19-X-expressing NK cells. FIG. 9A shows the cytotoxic effects of the indicated constructs against Nalm6 cells 7 days after NK cells from a first donor were transduced with the indicated construct. The effector cell to target cell ratio for this experiment was 1:1. As shown in the traces, each of NK19-10, NK19-8, NK-1911, NK19-5, and NK19-12 allowed increases in the number of Nalm6 cells detected, on par with that of NK cells expressing only GFP as a control. However, each of NK19-3, NK19-9, NK19-4, NK19-13, NK19-1 and NK19-2 showed significantly less increase in Nalm6 cell number (e.g., greater cytotoxicity). In several embodiments, such constructs are therefore expressed in NK cells and used in treating B cell leukemia (or other tumor types). In several embodiments, one or more of the stimulatory domains from one of the constructs is engineered into another construct with a different stimulatory domain, which advantageously results in synergistic signaling and further enhanced cytotoxicity. By way of non-limiting example, an NK19-1 construct with an OX40 stimulatory domain is, in several embodiments, further engineered to also express a CD44 stimulatory domain in addition to OX40. By way of further non-limiting example, an NK19-1 construct with an OX40 stimulatory domain is, in several embodiments, further engineered to also express a CD44 stimulatory domain and a CD17 stimulatory domain in addition to OX40.

Figure 9B:
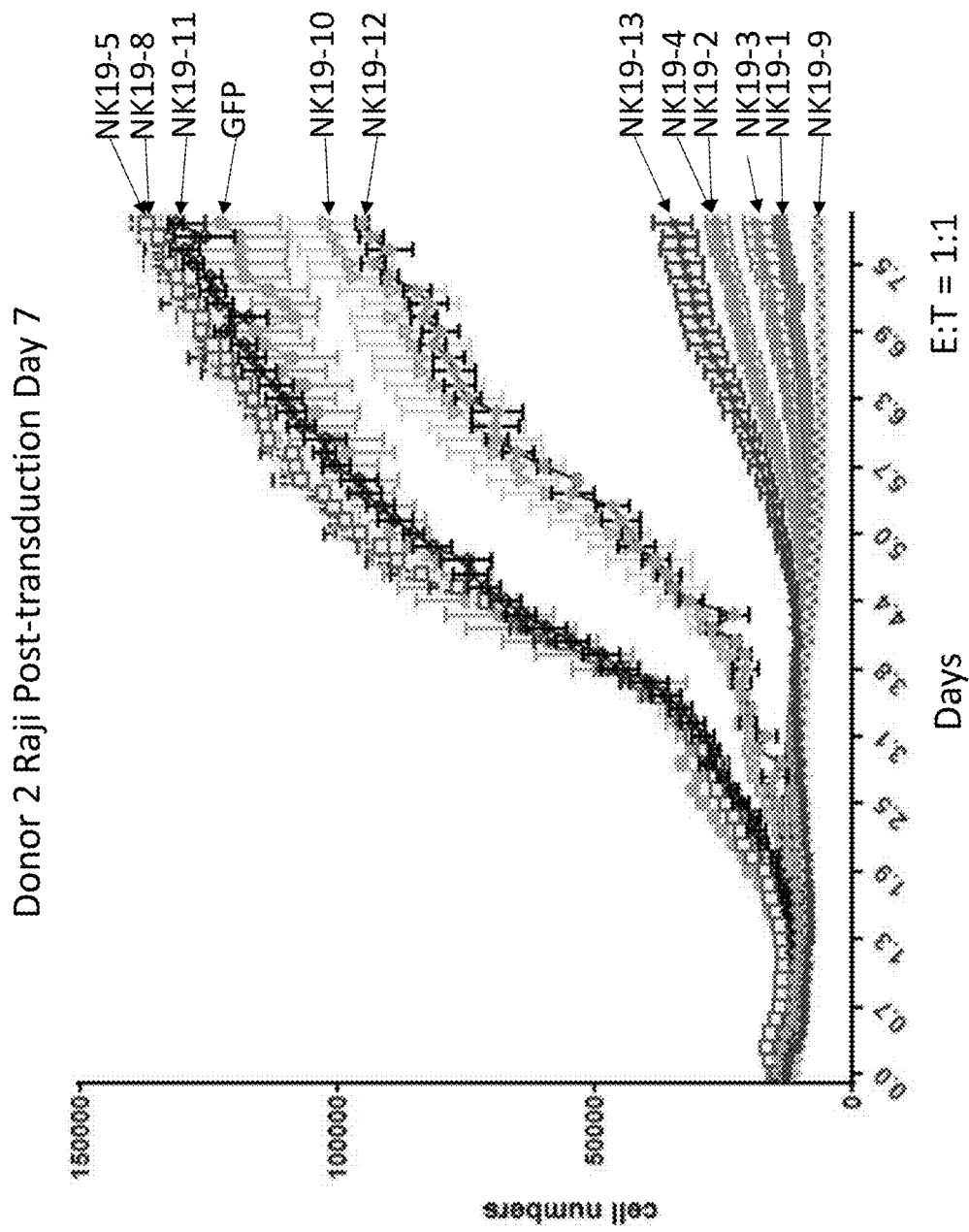

FIG. 9B shows corresponding cytotoxicity data for engineered NK cells from a second donor against Raji B-cell leukemia cells, 7 days post-transduction. The effector cell to target cell ratio here was also 1:1. As shown, similar to the engineered constructs activity against Nalm6 cells, several constructs allowed for increased Raji cell count. However, each of NK19-13, NK 19-4, NK19-2, NK19-3, NK19-1, and NK19-9 prevented Raji cell growth to a substantial degree, with several of the constructs resulting in nearly no Raji cell growth. In several embodiments, such constructs are therefore expressed in NK cells and used in treating B cell leukemia (or other tumor types).

Figure 9C:
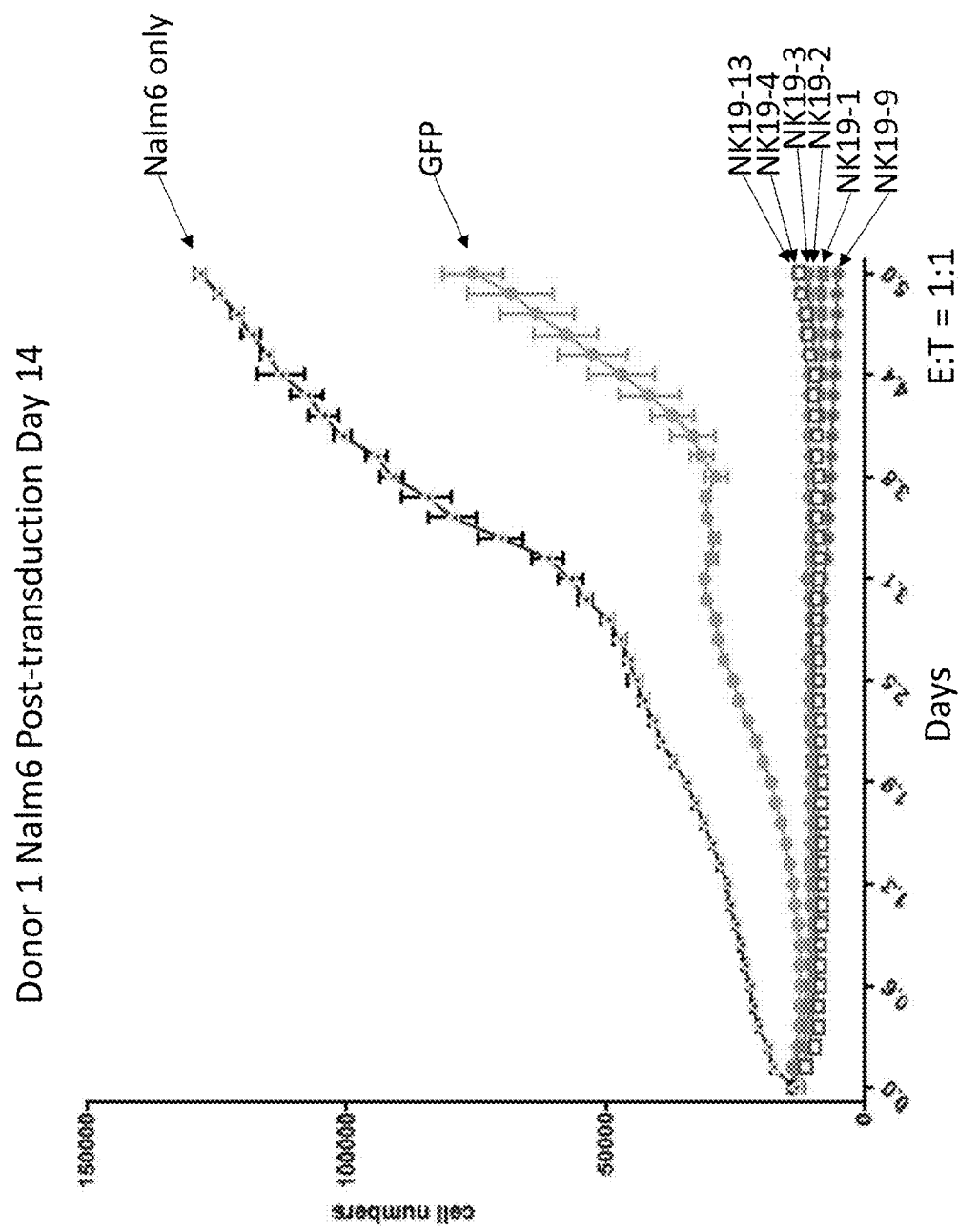

FIG. 9C shows data for NK cells from Donor 1 against Nalm6 cells 14 days post-transduction. The effector to target cell ratio is 1:1. As shown, even at two weeks post-transduction, the NK19-13, NK19-4, NK19-3, NK19-2, NK19-1, and NK19-9 expressing NK cells prevented virtually all Nalm6 cell growth, indicative of their highly cytotoxic effect against tumor cells. In several embodiments, such constructs are therefore expressed in NK cells and used in treating B cell leukemia (or other tumor types). As discussed above, in several embodiments, a construct is generated that employs a combination two, three, or more of the stimulatory domains, resulting in a synergistic NK cell stimulation and enhanced cytotoxicity.

Figure 9D:
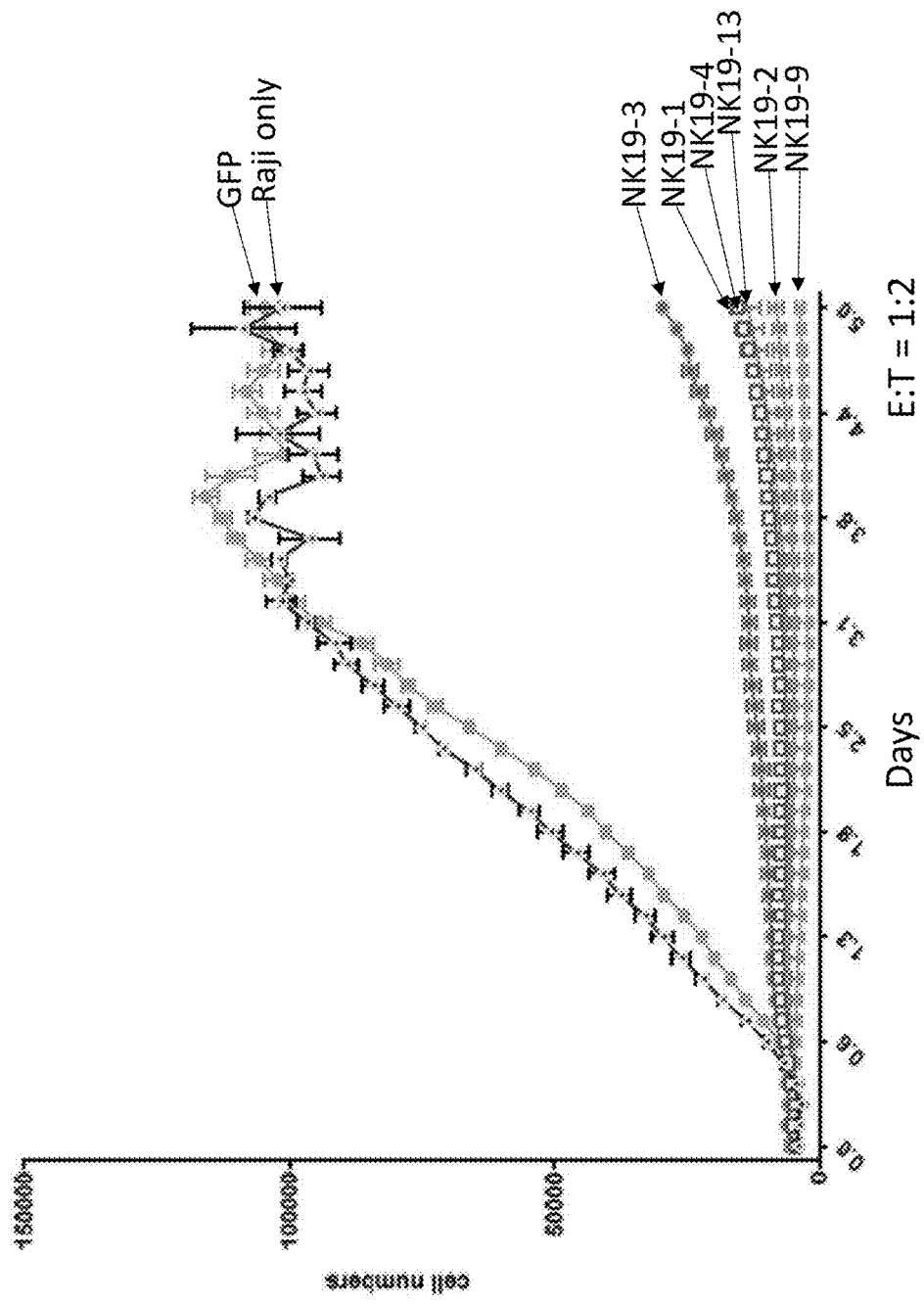

FIG. 9D shows data for NK cells from Donor 2 against Raji cells at 14 days post-transduction. The effector cell to target cell ratio was 1:2. As shown, NK cells expressing GFP only allowed growth of Raji cells essentially the same as untreated Raji cells. In contrast, each of NK19-3, NK19-1, NK19-4, NK19-13, NK19-2, and NK19-9 expressing NK cells significantly retarded the growth of Raji cells, with several of the constructs allowing little to no Raji cell growth. In several embodiments, such constructs are therefore expressed in NK cells and used in treating B cell leukemia (or other tumor types). As discussed above, in several embodiments, a construct is generated that employs a combination two, three, or more of the stimulatory domains, resulting in a synergistic NK cell stimulation and enhanced cytotoxicity.

Figure 9E:
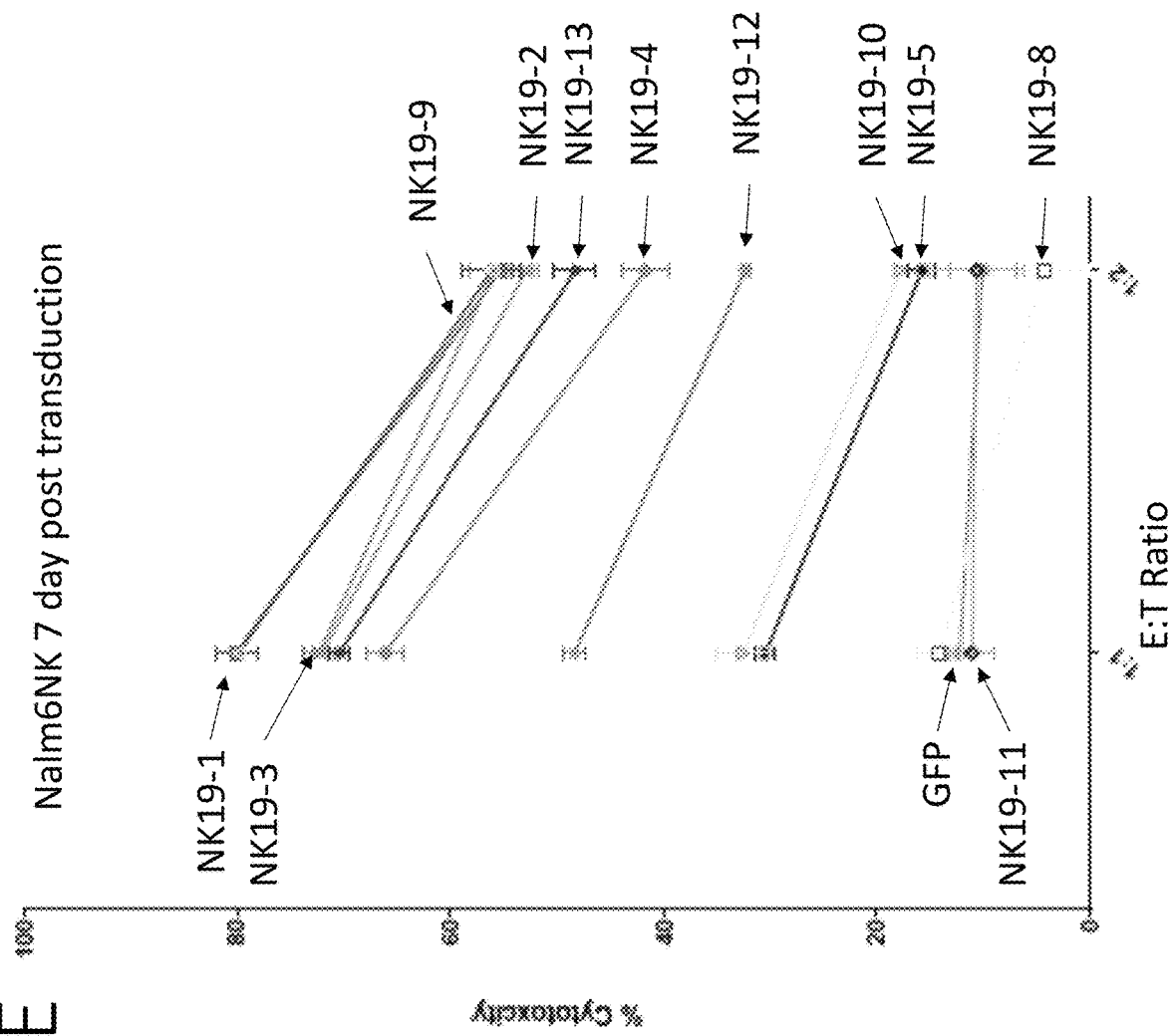
FIG. 9E depicts summary data related to the cytotoxicity (against Nalm6 cells) for the indicated CD19-directed chimeric receptors at various effector:target ratios.
Figure 9F:
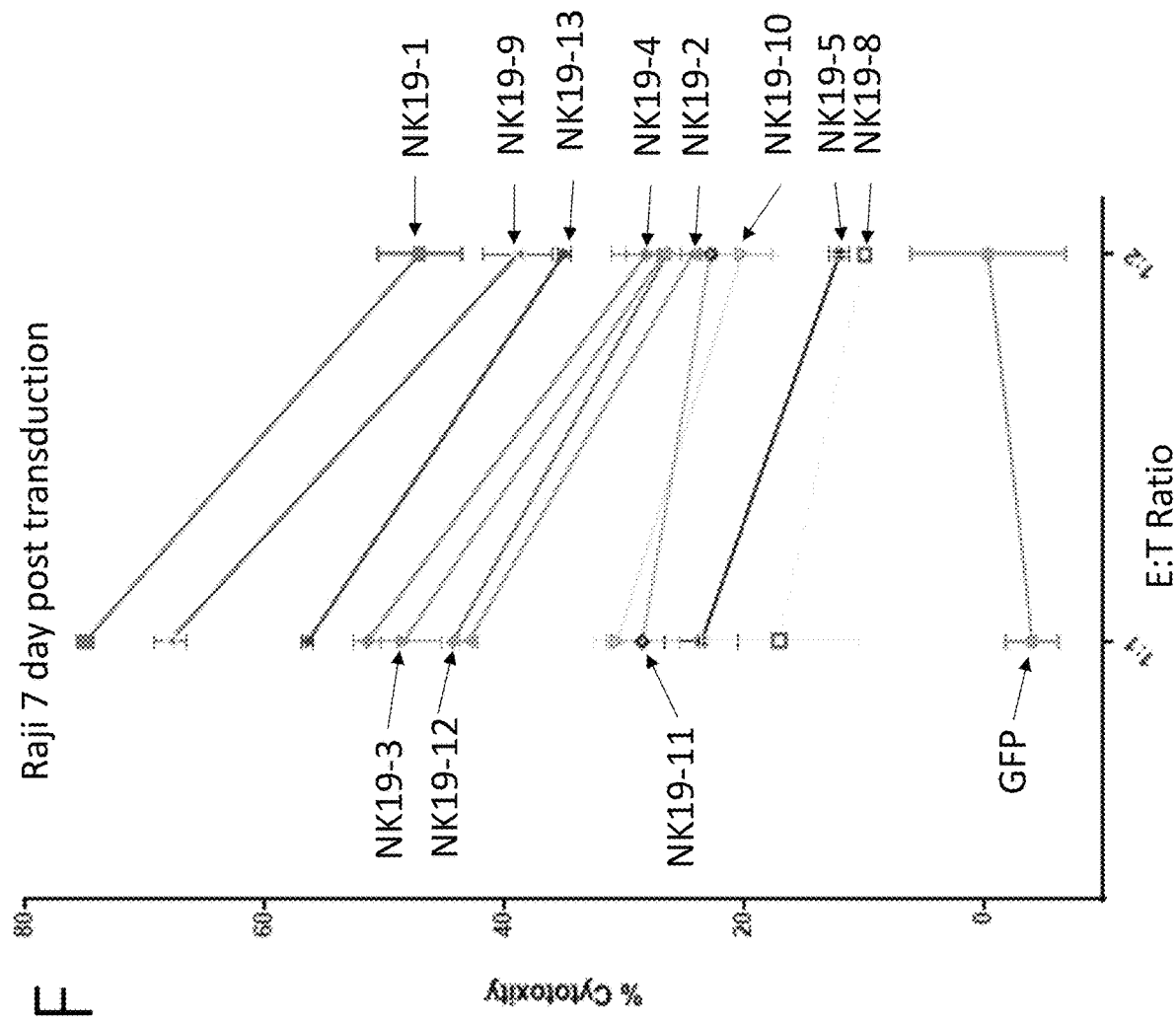
FIG. 9F depicts summary data related to the cytotoxicity (against Raji cells) for the indicated CD19-directed chimeric receptors at various effector:target ratios.

FIG. 9E shows summary data for cytotoxicity against Nalm6 cells at an E:T ratio of 1:1 and 1:2 at 7 days post-transduction. At an E:T ratio of 1:2, all but one of the NK19 constructs was equivalent to, or more, cytotoxic than NK cells expressing GFP alone. In fact, even while at a 1:2 ratio, six of the constructs achieved ~50% or greater cytotoxicity. When tested at an E:T of 1:1, seven of the constructs achieved ~50% or greater cytotoxicity, however, five of the constructs (NK19-13, NK19-2, NK19-9, NK19-3, and NK19-1) yielded cytotoxicity exceeding 70%. FIG. 9F shows the corresponding data for Raji cells. All constructs tested showed enhanced cytotoxicity over GFP-expressing NK cells at both 1:2 and 1:1 E:T ratios. At an E:T of 1:2, four of the constructs exceeded 40% cytotoxicity, while at 1:1, seven constructs exceeded that kill rate. Furthermore, at a 1:1 E:T, three constructs yielded cytotoxicity of 60% or more, with the most efficacious construct achieving nearly 90% cytotoxicity. Taken together, these data demonstrated that various CD19-directed CAR constructs can not only be expressed, but are stably expressed, and are also effective an inducing cytotoxicity in multiple cancer cell types, in some cases exceeding an 80% kill rate. According to additional embodiments, CD19-targeting constructs are generated that employ combinations of two, three or more stimulatory domains, which result in further enhancements in the cytotoxicity of the NK cells expressing them. In several embodiments, CD19-directed constructs can synergistically interact with NK cells expressing receptors directed against other tumor markers, such as ligands of NKG2D (such chimeric receptor bearing NK cells are described in PCT/US2018/024650, which is incorporated by reference herein in its entirety). For example, a chimeric receptor comprising an binding domain that binds ligands of NKG2D, an OX40 stimulatory domain, and a CD3zeta signaling domain could be used in conjunction with any of the CD19-targeting constructs disclosed herein. In several embodiments, such a chimeric receptor is at least 90% identical in sequence to the nucleic acid sequence of SEQ ID NO: 145. In several embodiments, such a chimeric receptor is at least 90% identical in sequence to the amino acid sequence of SEQ ID NO: 146.

Figure 10A:
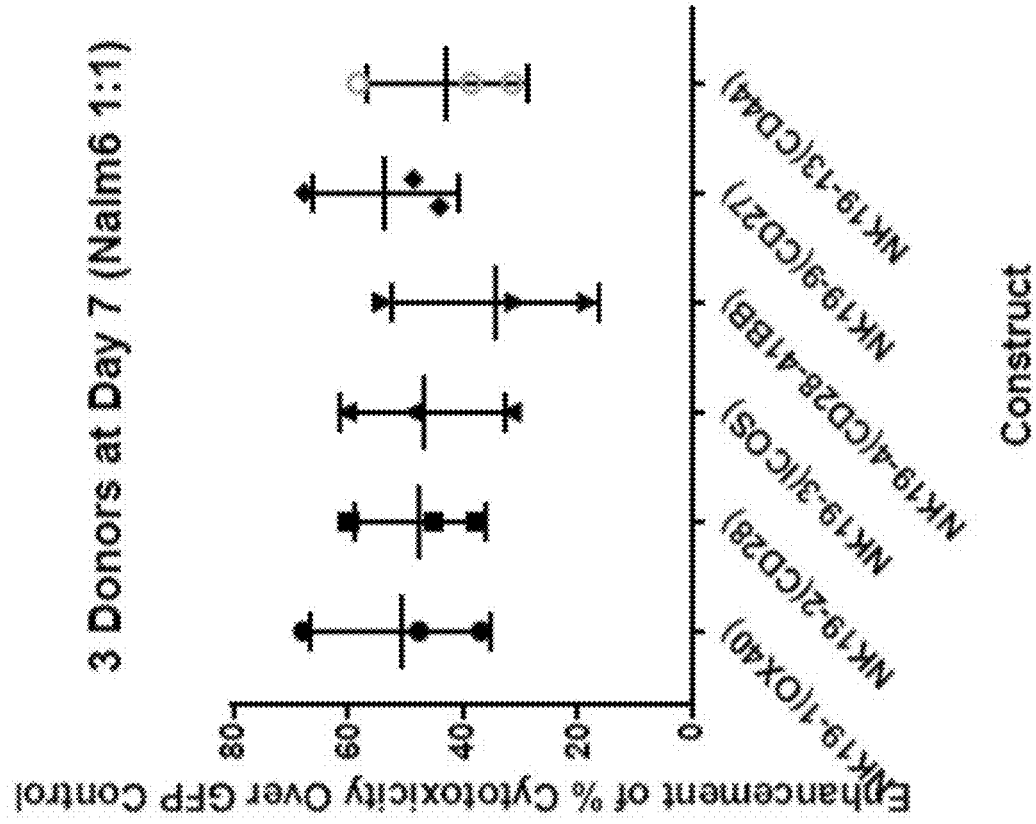
FIG. 10A depicts data related to the degree of enhanced cytotoxicity (against Nalm6 cells) for the indicated CD19-directed chimeric receptors at 7 days post transduction.
Figure 10B:
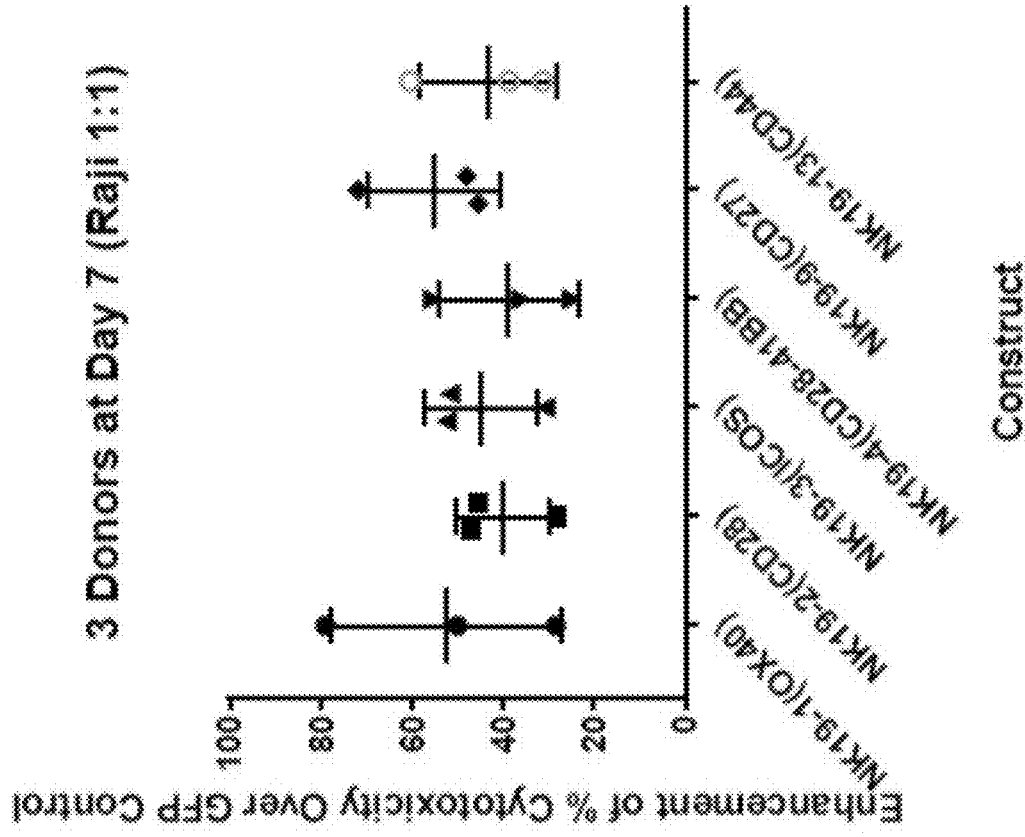
FIG. 10B depicts data related to the degree of enhanced cytotoxicity (against Raji cells) for the indicated CD19-directed chimeric receptors at 7 days post transduction.
Figure 10C:
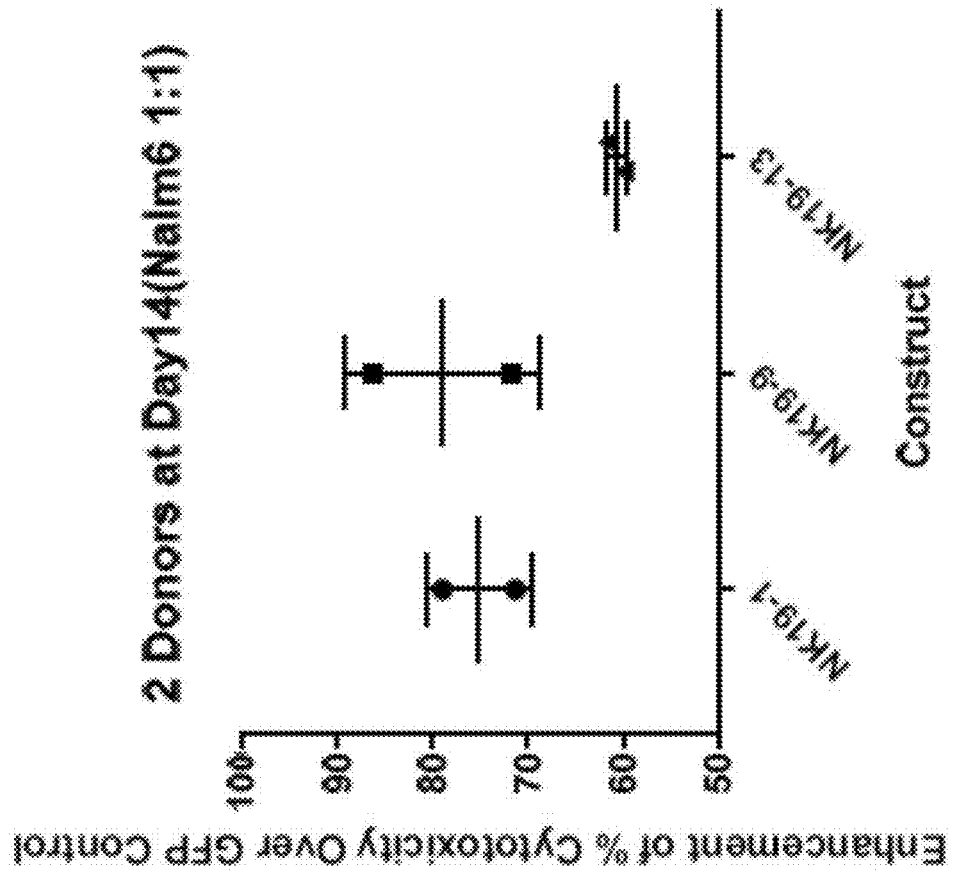
FIG. 10C depicts data related to the degree of enhanced cytotoxicity (against Nalm6 cells) for the indicated CD19-directed chimeric receptors at 14 days post transduction.
Figure 10D:
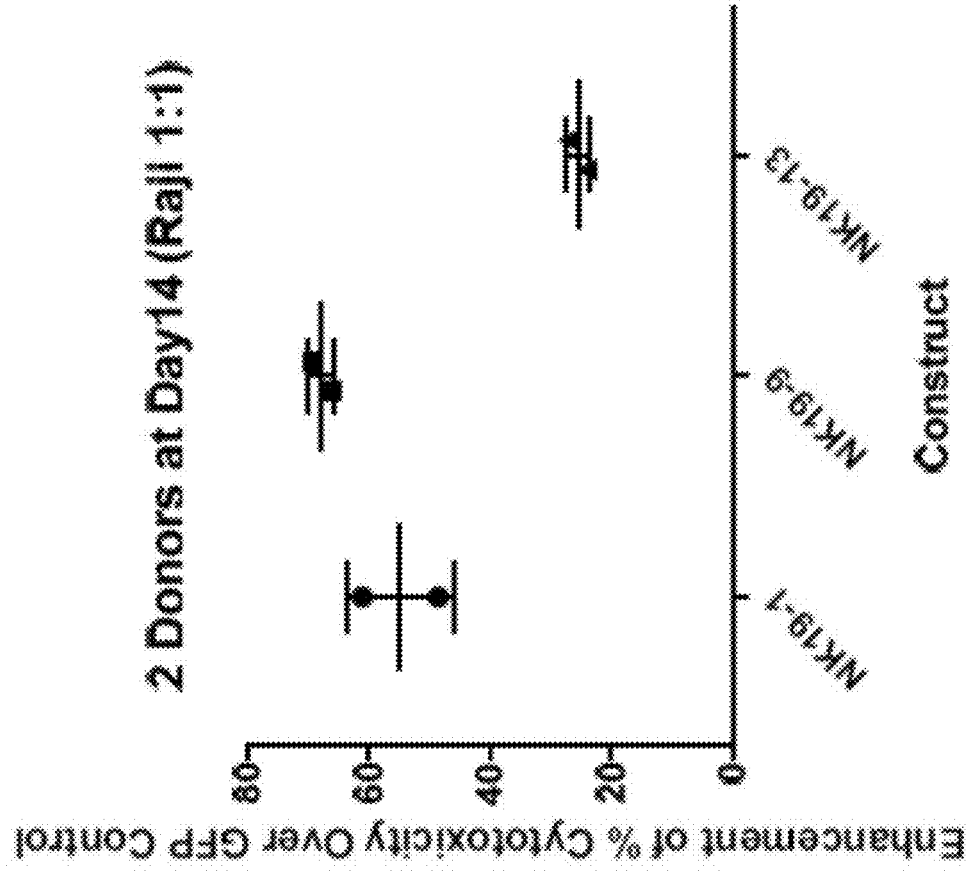
FIG. 10D depicts data related to the degree of enhanced cytotoxicity (against Raji cells) for the indicated CD19-directed chimeric receptors at 14 days post transduction.

Further experiments were performed to evaluate the cytotoxicity of selected CD19-directed CAR constructs. NK cells isolated from three different donors (two donors for 14 day experiment) were transduced with vectors encoding the indicated constructs, NK19-1 (OX40 co-stimulatory domain); NK19-2 (CD28 co-stimulatory domain); NK19-3 (ICOS co-stimulatory domain); NK19-4 (CD28-41BB co-stimulatory domain); NK19-9 (CD27 co-stimulatory domain); and NK19-13 (CD44 co-stimulatory domain). Seven (n=3) or 14 (n=2) days after transduction, those engineered NK cells were co-cultured with Nalm6 or Raji cells at an E:T ratio of 1:1. Results are shown in FIG. 10A (expressed as percent enhanced cytotoxicity over NK cells expressing GFP). Consistent with the data from FIG. 9, each of the constructs tested yielded enhanced cytotoxic effects against Nalm6 cells, ranging from a mean 40% increase with NK19-4 to an overall average of about 50% increase with the other 5 constructs. FIG. 10B shows the corresponding data against Raji cells. Again, each construct outperformed NK cells expressing only GFP, with mean increases in cytotoxicity over GFP NK cells ranging from about 40% increase to about 50% increase. Using cells from two donors at 14 days post-transduction, NK19-1, NK19-9 and NK19-13 were tested on Nalm6 and Raji cells. FIG. 10C shows the calculated enhanced cytotoxicity of these constructs over GFP-expressing NK cells, where average increases of nearly 80% were seen with NK19-9 expressing NK cells, about 75% with NK19-1 expressing cells and over 60% with NK19-13 expressing cells. Similar results were obtained against Raji cells—NK19-13 expressing cells showed over a 20% improvement in cytotoxicity, NK19-1 expressing cells exhibiting nearly 60% enhanced activity and NK19-9 expressing cells showing almost 70% more cytotoxic activity against Raji cells. These results further support the embodiments disclosed herein wherein engineered NK cells expressing CD19-directed CARs are provided, as are methods for their use in treating cancer immunotherapy results in enhanced cytotoxicity against target tumor cells.

Figure 11E:
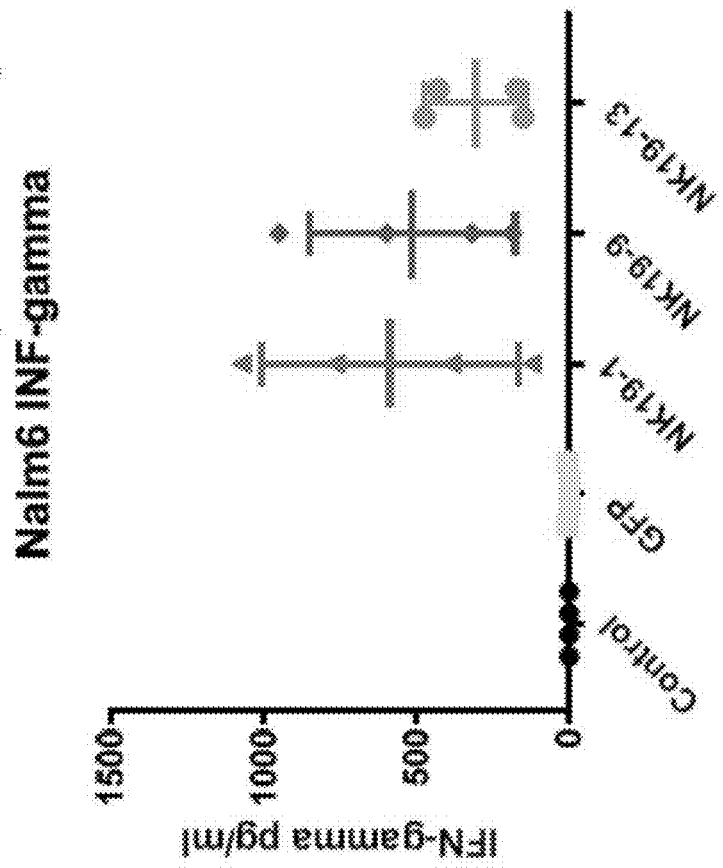
Figure 12E:
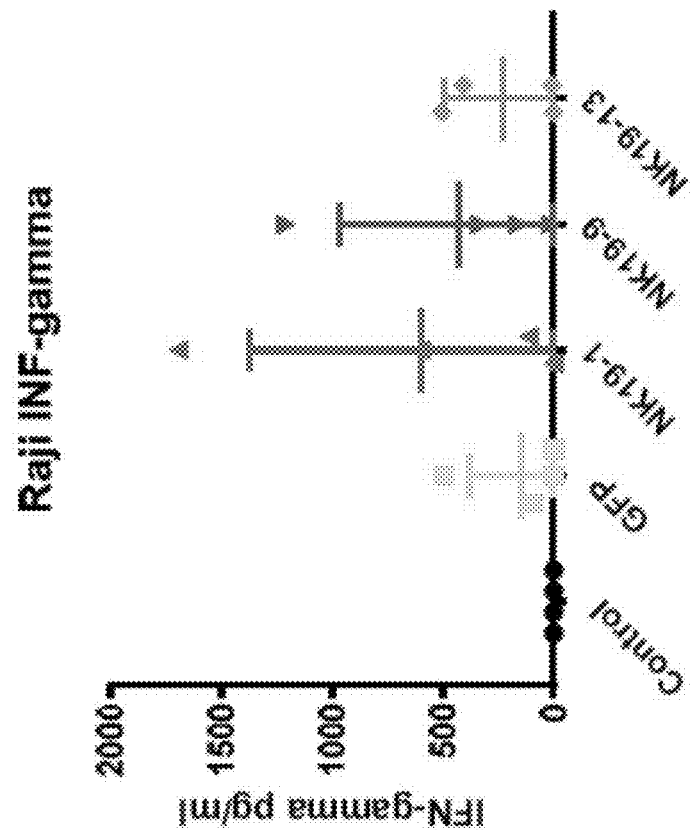

FIGS. 11A-11E depict data related to the cytokine release profiles from NK cells when cultured the Nalm6 cells, which ties into the mechanism by which NK cells control tumor and virus-infected cells—through releasing cytotoxic granules and proinflammatory cytokines. FIG. 11A shows that as compared to control, or even GFP-expressing NK cells, NK cells expressing NK19-1, NK19-9, or NK19-13 all express greater concentrations of the serine protease, Granzyme B, that is present in the granules released by NK cells. NK cells expressing these CD19-directed CARs released approximately 4 times more Granzyme B than control GFP-expressing NK cells. FIG. 11B shows data related to increased release of perforin by the engineered NK cells. Interestingly, perforin levels were not substantially elevated over the concentrations resulting from GFP-expressing NK cells (though perforin concentration was elevated over control. Perforins work in concert with Granzyme B (and other granzymes), with perforins functioning to generate pores through a cell membrane to allow granzymes to cross the membrane, then exert their protease effects on intracellular protein targets. The data raise the possibility that the perforin release while approximately the same, or reduced in connection with certain constructs, are actually more efficient at pore-formation, thus allowing the same degree of pore formation. Alternatively, if the perforins released from NK19 expressing NK cells are no more efficient at pore formation, this is offset by the elevated increase of granzyme B (and/or other granzymes). Thus, enhanced cytotoxicity is still achieved.

FIG. 11C shows that as compared to control, or even GFP-expressing NK cells, NK cells expressing NK19-1, NK19-9, or NK19-13 all release greater concentrations of the inflammatory cytokine TNF alpha. FIG. 11D shows similar data for GM-CSF release by NK19-expressing NK cells and FIG. 11E shows similar data for interferon gamma release. Likewise, when tested on Raji cells, similar patterns of release result, as shown in FIGS. 12A-12E. These data indicate that the NK19-epressing cells exert their cytotoxic effects, at least in part, through the increased release of inflammatory cytokines and/or cytotoxic granules. As mentioned above, in several embodiments, the engineered CARs are designed to have combinations of two, three or more co-stimulatory domains, with synergistically increased cytokine/granule release and cytotoxicity against target cancers.

Figure 13:
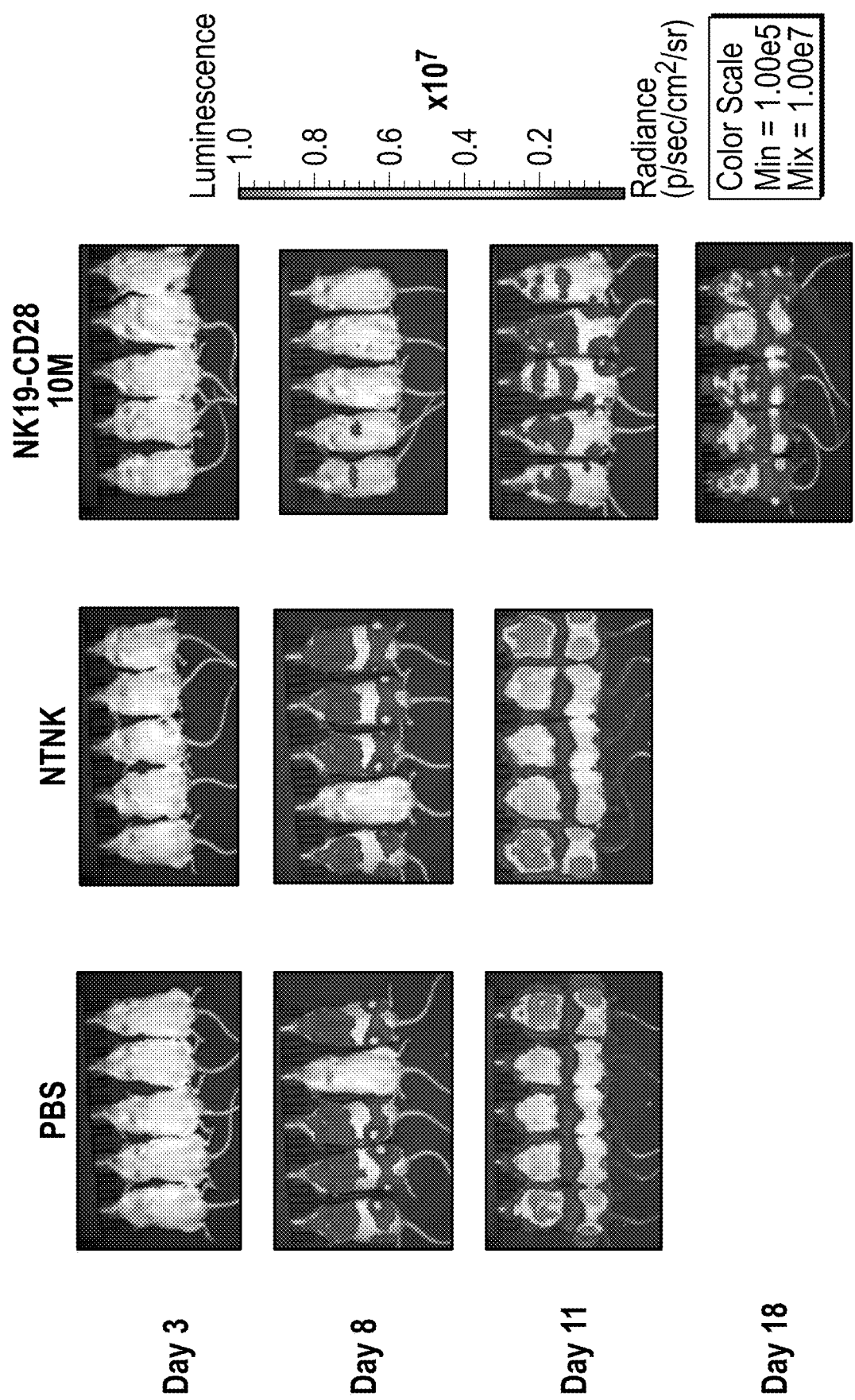
FIG. 13 depicts in vivo imaging data related to tumor burden over time in mice treated with PBS, non-transduced NK cells, or NK cells expressing the indicated CD19-directed chimeric receptors, with the indicated number of engineered NK cells administered (M=million cells).
Figure 13:
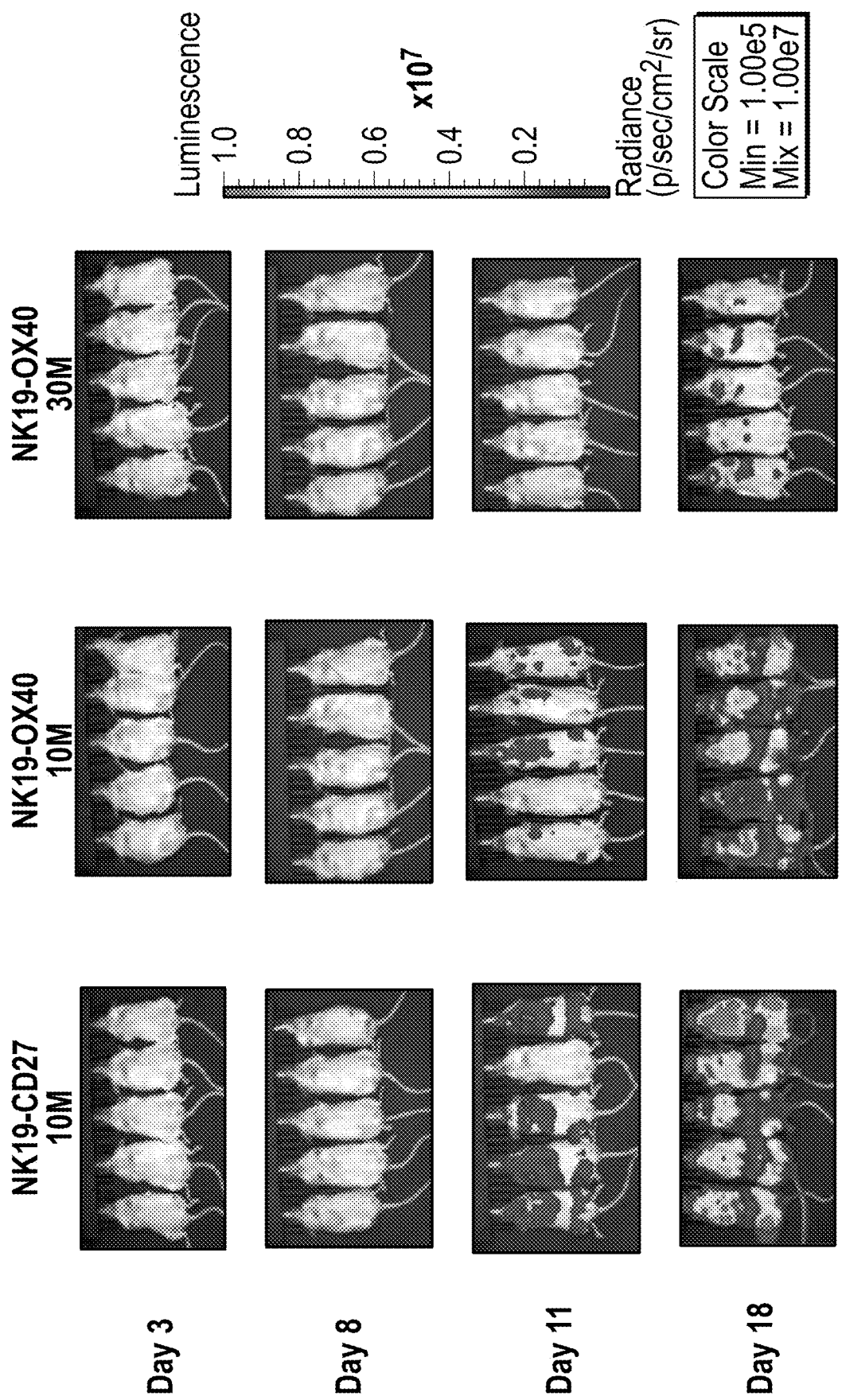

Further evidencing the enhanced effects of NK19 constructs on tumor progression, NSG mice were injected on Day 0 with $1\times10^5$ Nalm6 cells (expressing a fluorescent reporter) intravenously. At Day 3, mice received either a PBS control injection, non-transduced NK cells ("NTNK", 10M), NK19-2 expressing NK cells (10 million cells), NK19-9 expressing cells (10 million), NK19-1 expressing cells (10 million, or NK19-1 expressing cells (30 million). Fluorescent imaging to detect the Nalm6 cells was performed on Days 3, 8, 11, 18, and 25 (imaging data not shown). The data is shown in FIG. 13. As shown, the injection of NK cells expressing any NK19 variant resulted in a reduced progression of Nalm6 growth. NK19-2 expressing NK cells showed minor Nalm6 growth on Day 8, with more Nalm6 growth by Day 11, and substantial growth by Day 18 (though less than with NTNK cells). Neither NK19-9 or NK19-1 (at either dose) expressing NK cells showed detectable tumor burden on Day 8 by imaging. Mice receiving NK19-9 expressing NK cells did show some increase in Nalm6 cell growth by Day 11, with further progression by Day 18. At Day 11, mice receiving either dose of NK19-1 expressing cells did not exhibit Nalm6 cell growth. By day 18, mice receiving 10 million NK19-9 cells showed some tumor growth. However, with a 30 million cell dose, those mice receiving NK19-9 expressing NK cells showed only minor amounts of Nalm6 cell growth.

Figure 14A:
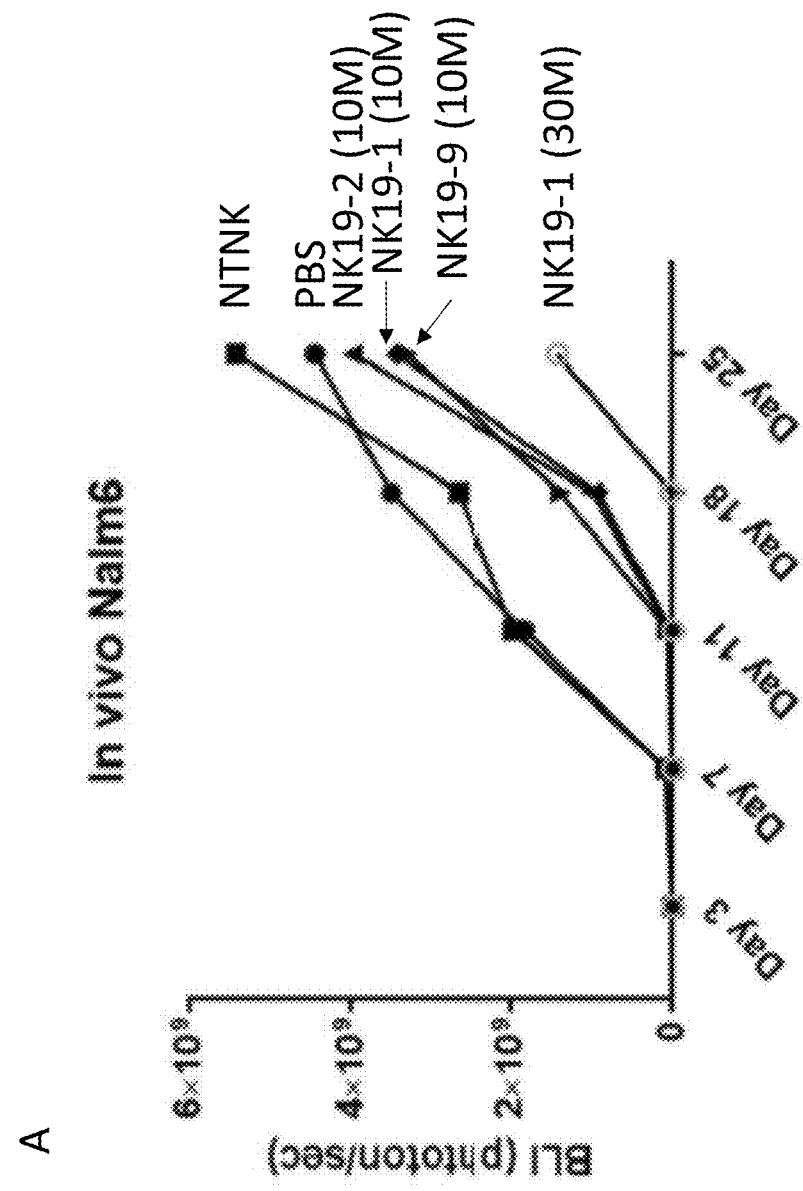
FIG. 14A shows raw data related to the detected fluorescent signal from the in vivo data shown in FIG. 13, with data being tracked for 25 days post-administration of Nalm6 cells.
Figure 14B:
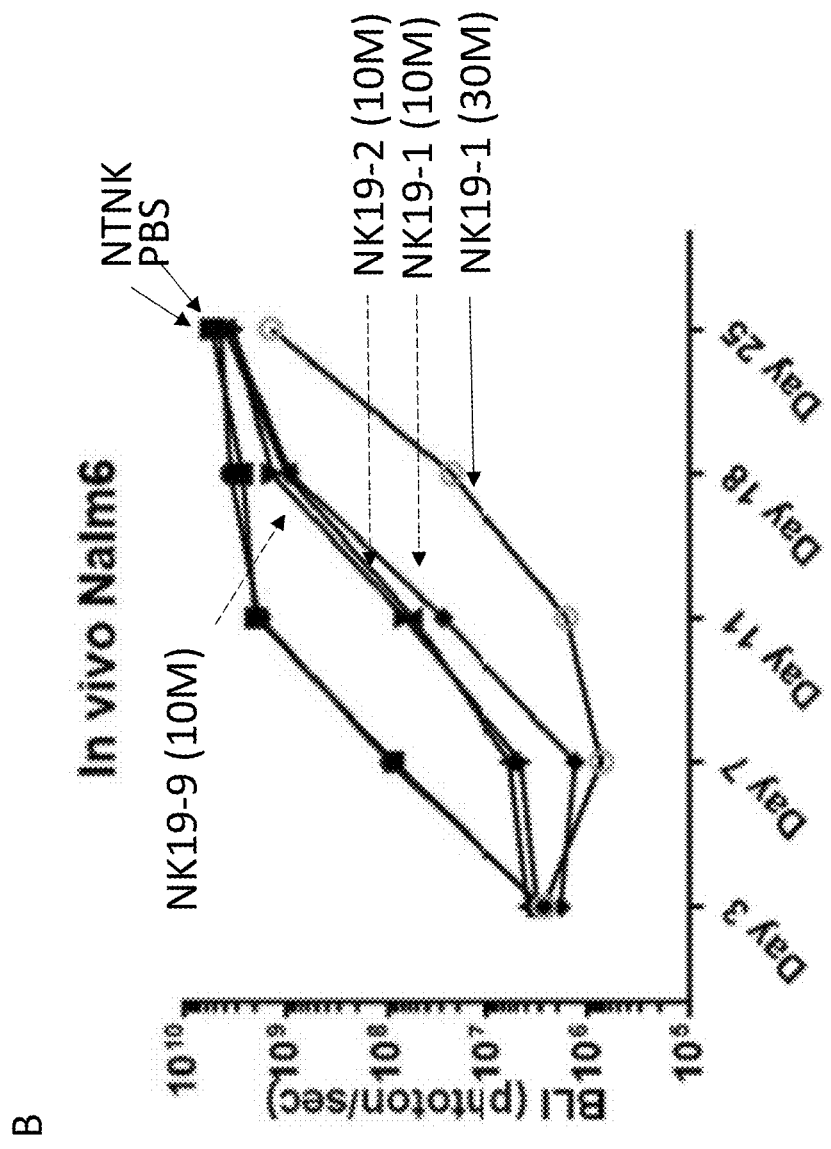
FIG. 14B shows the data from FIG. 14A on a logarithmic scale.
Figure 14C:
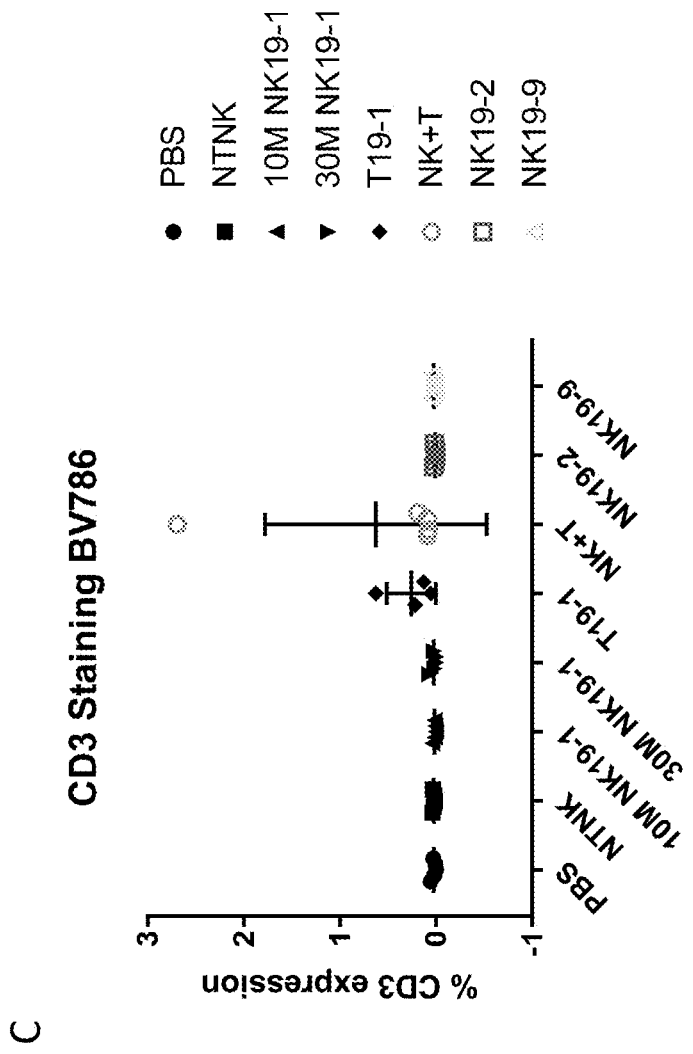
FIG. 14C shows data related to CD3 expression by the indicated cells expressing the indicated constructs.
Figure 14D:
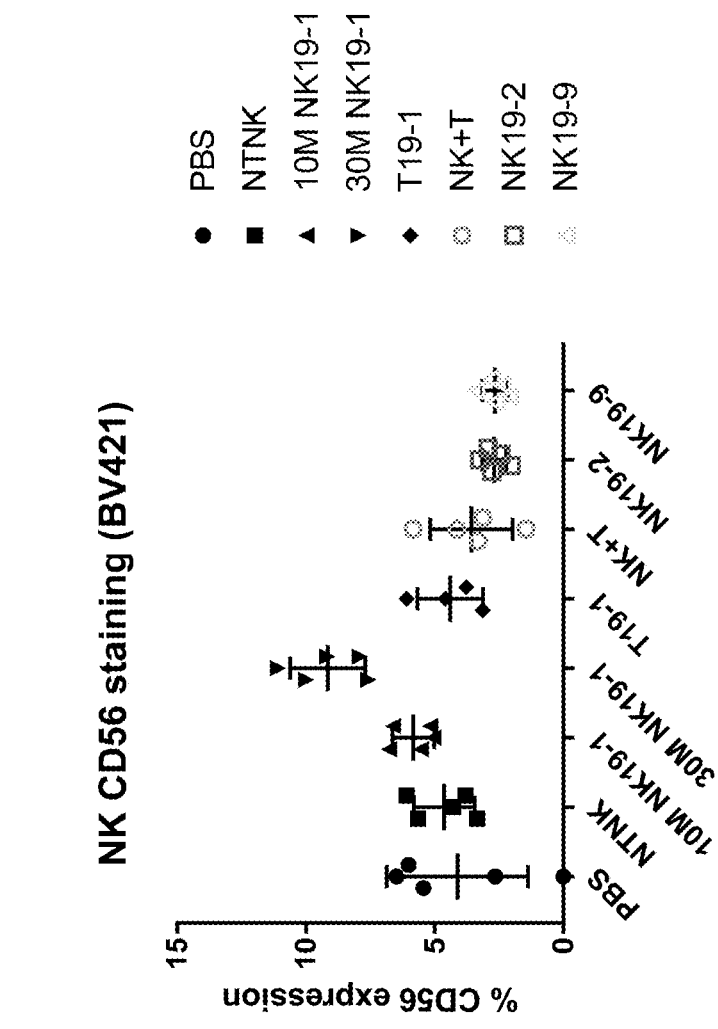
FIG. 14D shows data related to CD56 expression by the indicated cells expressing the indicated constructs.
Figure 14E:
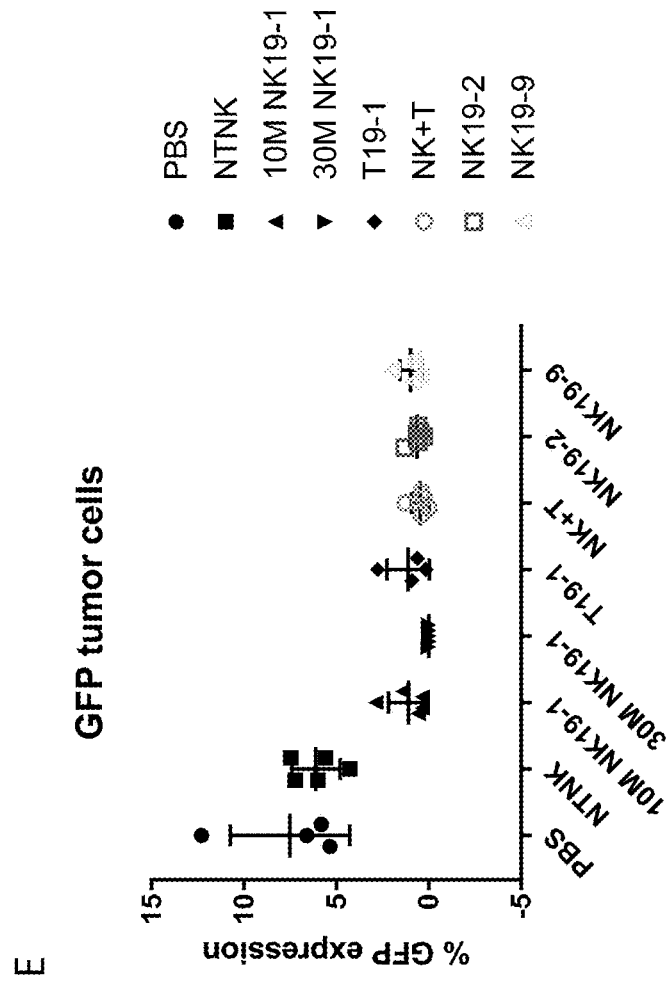
FIG. 14E shows data related to GFP-expressing tumor cells when contacted with the indicated cells expressing the indicated constructs.
Figure 14F:
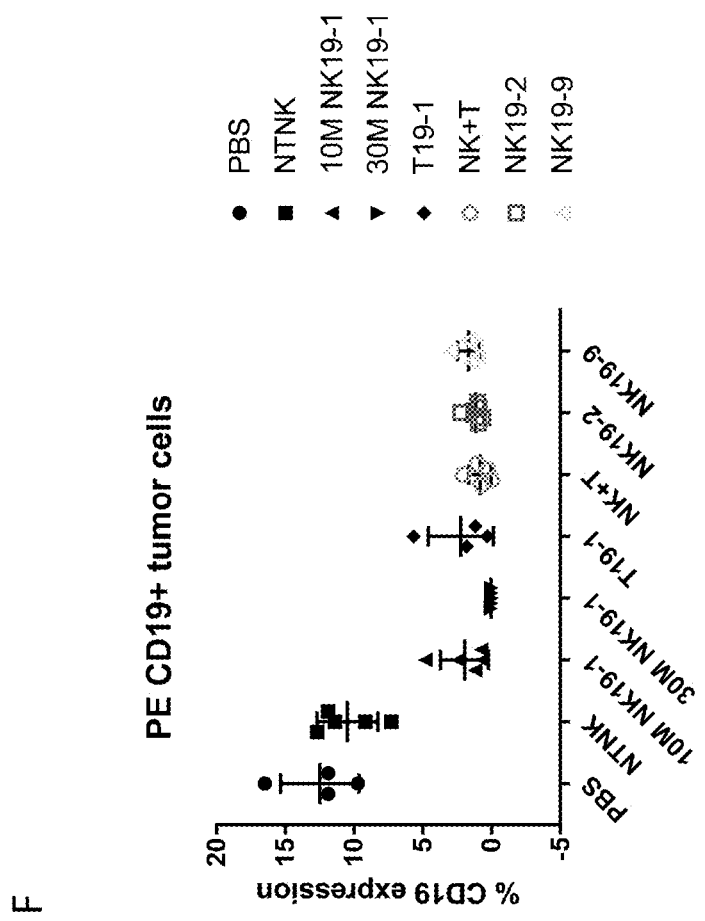
FIG. 14F shows the data related to CD19-expressing tumor cells when contacts with the indicated cells expressing the indicated constructs.

FIG. 14A depicts a line graph of the bioluminescence intensity shown detected in the mice (e.g., the fluorescent signal shown in FIG. 13, note that FIG. 13 does not show imaging data for Day 25). Consistent with the images of FIG. 13, the line graph of FIG. 14A shows increased Nalm6 cell count (as represented by increased BLI) for all groups at Day 25, with significant cell numbers detected in PBS and NTNK groups, and somewhat less for NK19-2, NK19-1 (10M) and NK19-9 groups. NK19-1 (30M) showed the smallest increase, representing that construct's ability to reduce the rate of Nalm6 progression due to cytotoxic effects on the Nalm6 cells. While each construct eventually allows some Nalm6 growth, even if modest, the tested NK19 constructs delayed the onset of that growth, as evidenced by the flat line through Day 11 for the NK19 curves. To better show that aspect, the data are replotted on a log scale Y-axis in FIG. 14B, which allows for curve separation. As displayed, the NTNK and PBS curves show an upward trend after Day 3, indicating nearly immediate Nalm6 growth. In contrast, the NK19-9, NK19-2 and both NK19-1 curves either drop, or only slightly trend upward through Day 7. At Day 11, consistent with the images in FIG. 13, Nalm6 cell growth is detected in the NK19-9, NK19-2 and NK19-1 (10M) groups. In contrast, the NK19-1 (30M) group is still approximately at baseline, reflecting the lack on any significant Nalm6 cell growth. Cell growth trends upward in the NK19-9 (30M group) on Day 18. While increases in tumor cell number occur, even with the NK19 constructs being administered, the delay of the growth onset could be advantageous in several embodiments. For example, this presents an opportunity to re-dose a patient with another dose of engineered NK cells expressing a CD19-directed construct. In several embodiments, a subsequent dose (as could the initial dose) may optionally comprise NK cells that have been edited to reduce allogenicty, for example by gene editing. Thus, in several embodiments, two, three, four or more doses of CD19-directed CAR expressing NK cells are administered. This delay in tumor cell growth presents an opportunity to dose, either serially (or concurrently) with an NK cell expressing a chimeric construct directed to a different tumor marker and/or some other variety of anti-cancer therapy (e.g., checkpoint inhibitor, antibody therapy, chemotherapy, etc.). FIG. 14C depicts data related to CD3 expression of cells transduced with the various constructs within blood samples taken from mice treated as indicated in the X axis. CD3 is a T cell marker. As indicated, but for T cells engineered to express the NK19-1 construct and a mixed population of NK cells and T cells, CD3 expression was essentially negligible. FIG. 14D depicts data related to CD56 expression, which is a marker for human NK cells. While there is some small amount of background staining, the blood samples from mice treated with NK cells expressing the indicated constructs is relatively low (as would be expected given that (i) the blood is a murine blood sample and murine cells would make the majority of the total, and (ii) CD56 is detecting only human NK cells (e.g., those administered). The data are consisting in that regard, with the 30M NK19-1 treatment group shoring markedly more CD56 expression than the other groups, and T cells/NK+ T cells groups expressing CD56 at background levels. FIG. 14E shows data related to the GFP expression by tumor cells. The blood samples were collected at ~3 weeks into the in vivo experiment. As shown (consistent with the images/BLI data), the control PBS and NTNK groups exhibit higher percentages of GFP expression (e.g., a greater percentage of the total of live blood cells in the sample is tumor cells). Each of the engineered constructs shows significantly less GFP expression, based on the engineered constructs controlling/reducing tumor cell growth. FIG. 14F shows similar data to FIG. 14D, but measures CD19 expression across all the live cells in a given murine blood sample. As with GFP, the PBS and NKNT groups show CD19 expression at approximately 10-12%, meaning 10-12% of the live cells in the blood sample are tumor cells, the remainder being murine blood cells. As shown in the other experimental group, CD19 expression is much lower, reflective of the engineered CAR constructs limiting the growth of the tumor cells. These data are in accordance with embodiments disclosed herein, wherein engineered NK cells expressing CD19-directed CARs are highly cytotoxic and allow for the treatment of cancerous tumors.

Further Evaluation of Humanized Constructs

As discussed in detail above, in several embodiments, several embodiments of the CARs disclosed herein involve the use of humanized sequences, such as in the extracellular binding moiety. In several embodiments, one or more aspects of that region is subjected to a humanization campaign. In several embodiments, one or more of the heavy and/or light chain of an antibody is humanized, which (as discussed above) can provide advantages including, but not limited to, reduced immunogenicity, increased stability, longer efficacy, increased potency, and the like.

Example 3

FIG. 15 shows a schematic of a series of humanized constructs according to several embodiments disclosed herein. Such constructs are designated by "H" in their identifier. By way of explanation, NK19H-1 is a humanized anti-CD19 CAR employing an scFv made up of a first light chain and a first heavy chain ('L1H1'), while NK19H-3 employs an scFv made up of a third light chain and the first heavy chain ('L3H1'). FIG. 15 also shows data related to the stability and aggregation of the various combinations of heavy and light chains following transient expression and secretion from 293T cells. Data are shown related to the mean fluorescence intensity detected by flow cytometry when each antibody was heated to 70° C. and then cooled back to room temperature ('Heating') vs. the same variant held on ice ('Unheating'). After heat treatment, the ScFv variants are used in a flow cytometry protocol at various concentrations (0.4, 0.25, and 0.125 ug/mL). Loss of fluorescence intensity indicates that the ScFv either lost structural integrity or aggregated through the heating process. ScFv's with the best thermal stability as indicated by comparable MFI under both conditions are favored for further development, according to some embodiments.

Figure 16:
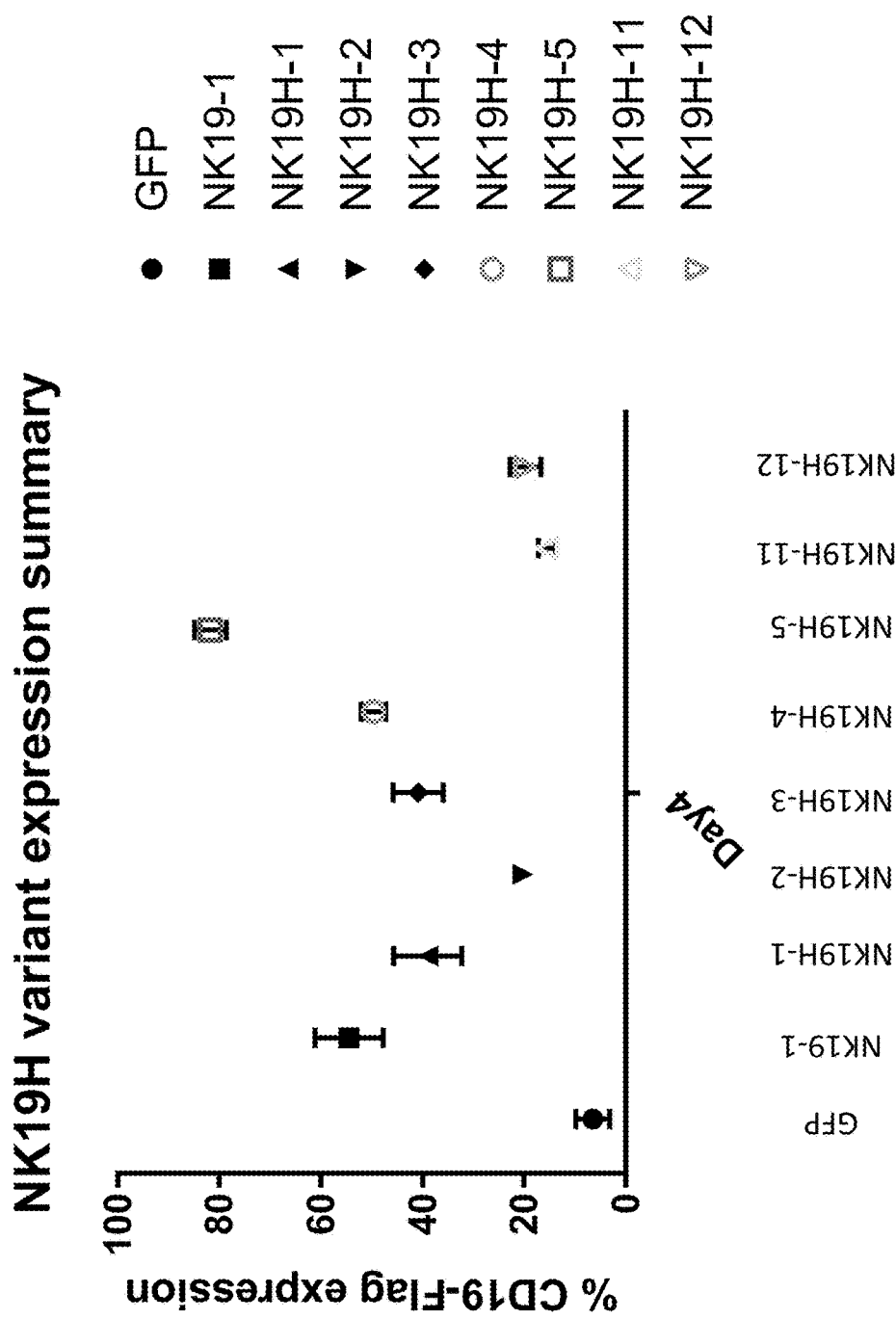
FIG. 16 depicts data related to the expression of various humanized anti-CD19 CAR constructs disclosed in embodiments herein.

After having assessed the stability of the constructs, selected anti-CD19 CAR constructs were further evaluated. FIG. 16 shows summary data of expression of the indicated constructs by the NK cells of 3 donors (#140, #9, and #20). As depicted in the Figure, expression is evaluated by detection of CD19Flag. Data are presented as percentage of NK cells expressing CD19-Flag relative to the total number of NK cells presented. The data were collected at 4 days after transduction with the relevant virus encoding the NK19H-"X" CAR. As evidenced by the expression data, each of the selected constructs were expressed by NK cells, to varying degrees. Expression levels ranged from expression by about 20% of the total NK cells with NK19H-2, NK19H-11 and NK19H-12. Most of the other constructs were successfully expression by ~40%-60% of the NK cells, which is on par with expression of the non-humanized NK19-1 construct. The NK19H-5 construct was expressed by over 80% of the NK cells. While certain constructs may be more efficiently expressed, those with lower expression levels were still evaluated because, as with several embodiments such constructs still exhibit significant cytotoxicity against target cells. According to several embodiments, however, those with higher expression efficiency can be advantageous, for example because a greater portion of a given NK cell preparation is useful clinically (e.g., fewer input NK cells needed to generate a clinically relevant engineered NK cell dose).

Figure 17A:
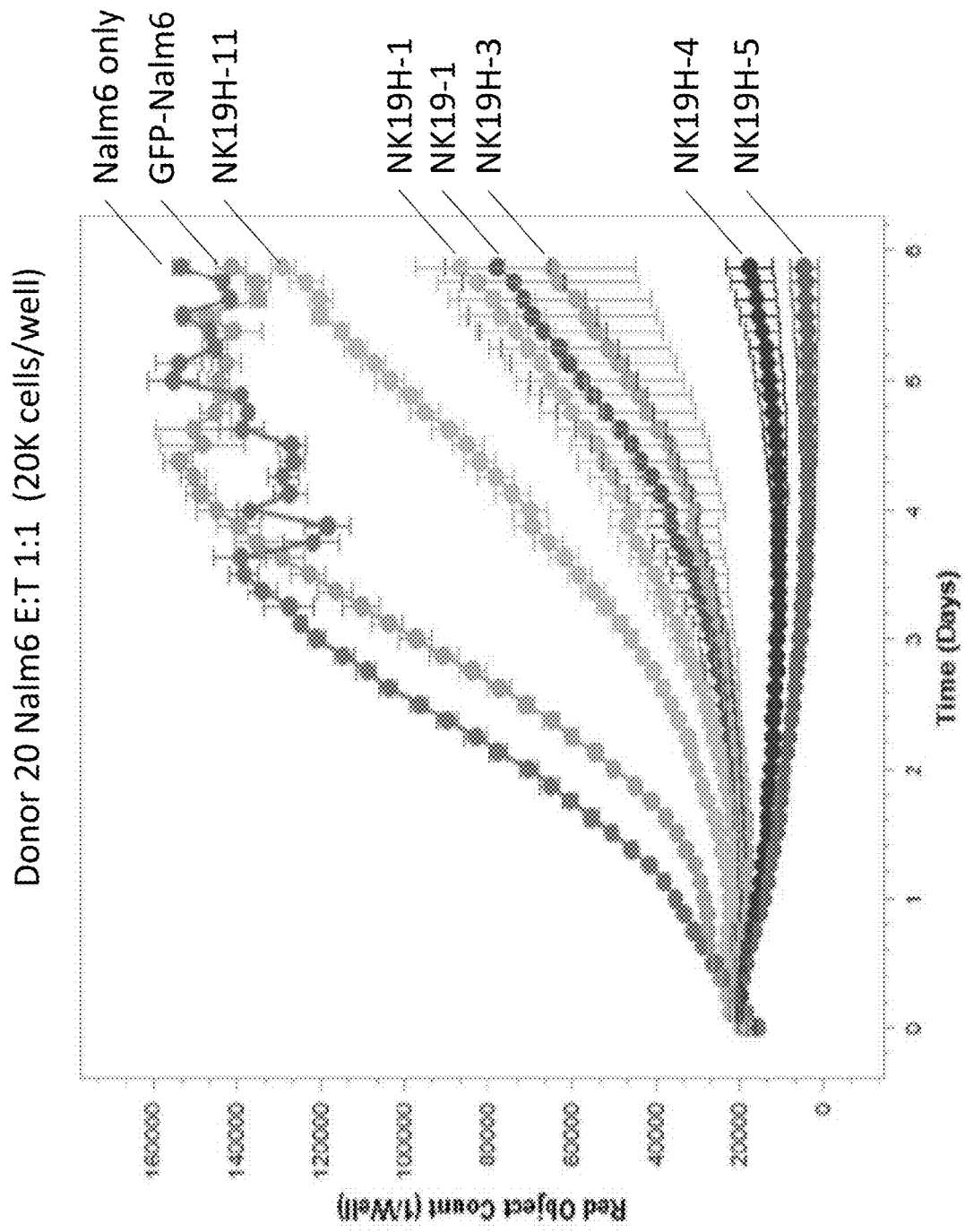

FIGS. 17A-17E depict such cytotoxicity data. FIG. 17A shows cytotoxicity of NK cells from Donor 20 and transduced with the indicated constructs against the CD19-positive Nalm6 leukemia cell line (at an E:T of 1:1; 20K cells per well). The data shows that, despite the varied expression levels, most of the NK19H constructs were able to exert cytotoxic effects against the Nalm6 target cells. NK19H-11 showed the least efficacy, allowing Nalm6 cell growth at levels just below the controls. In contrast, NK19H-1 and NK19H-3 showed cytotoxicity on par with the non-humanized NK19-1 construct, allowing for some cell growth at the later time points of co-culture. Notably NK19H-4 and NK19H-5 showed significant cytotoxicity, allowing only very limited Nalm6 growth throughout the experiment.

Figure 17B:
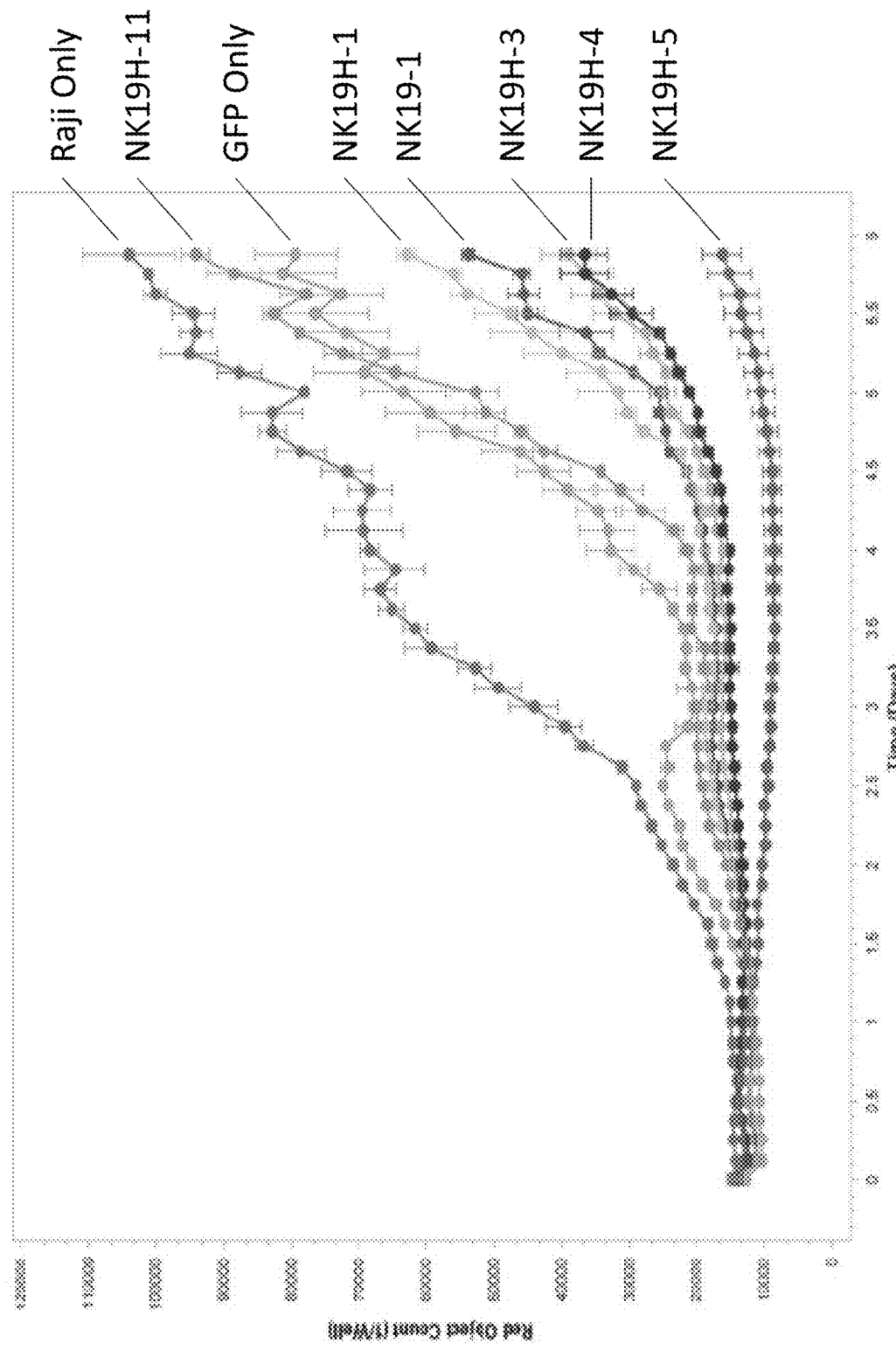
Figure 17D:
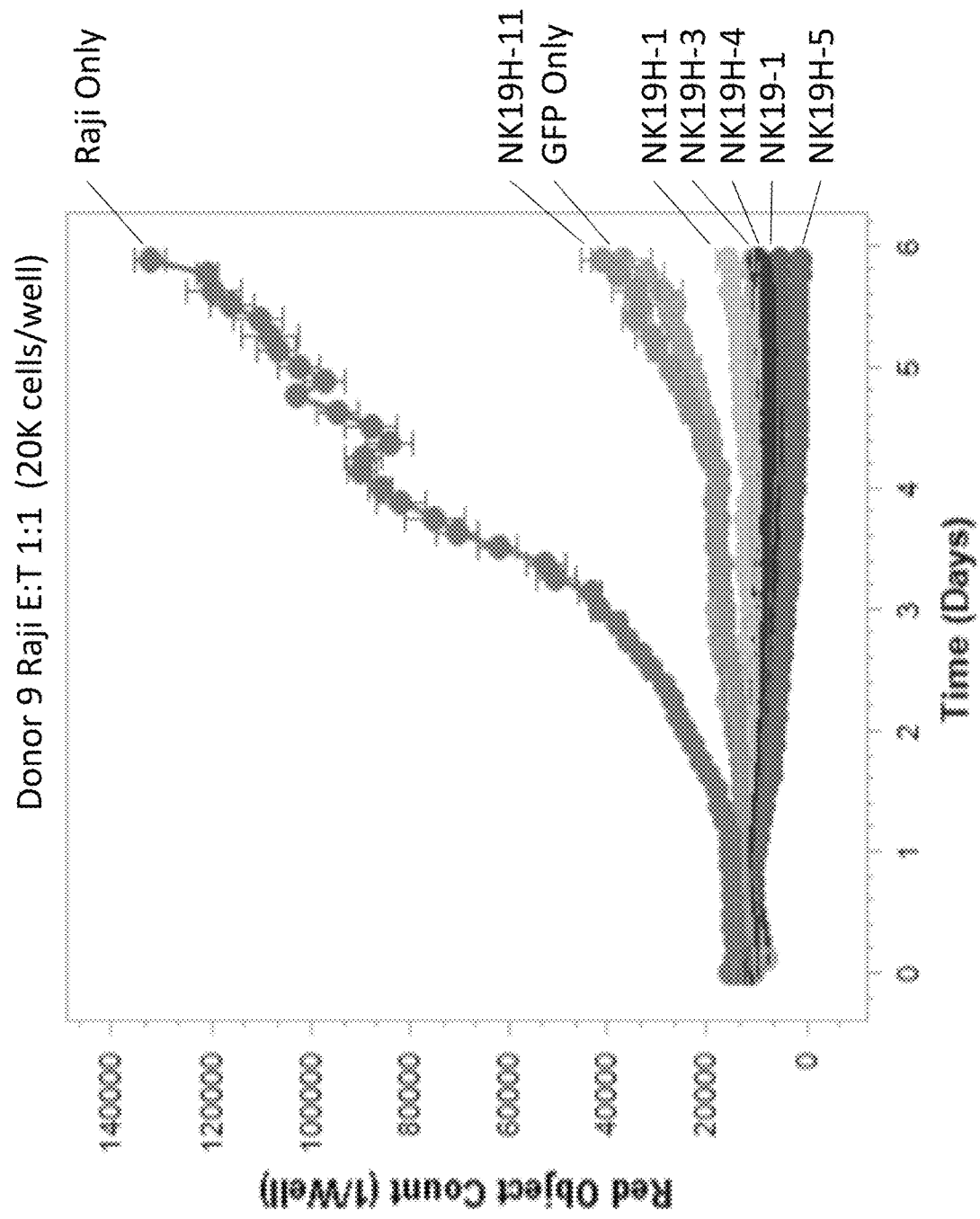
Figure 17E:
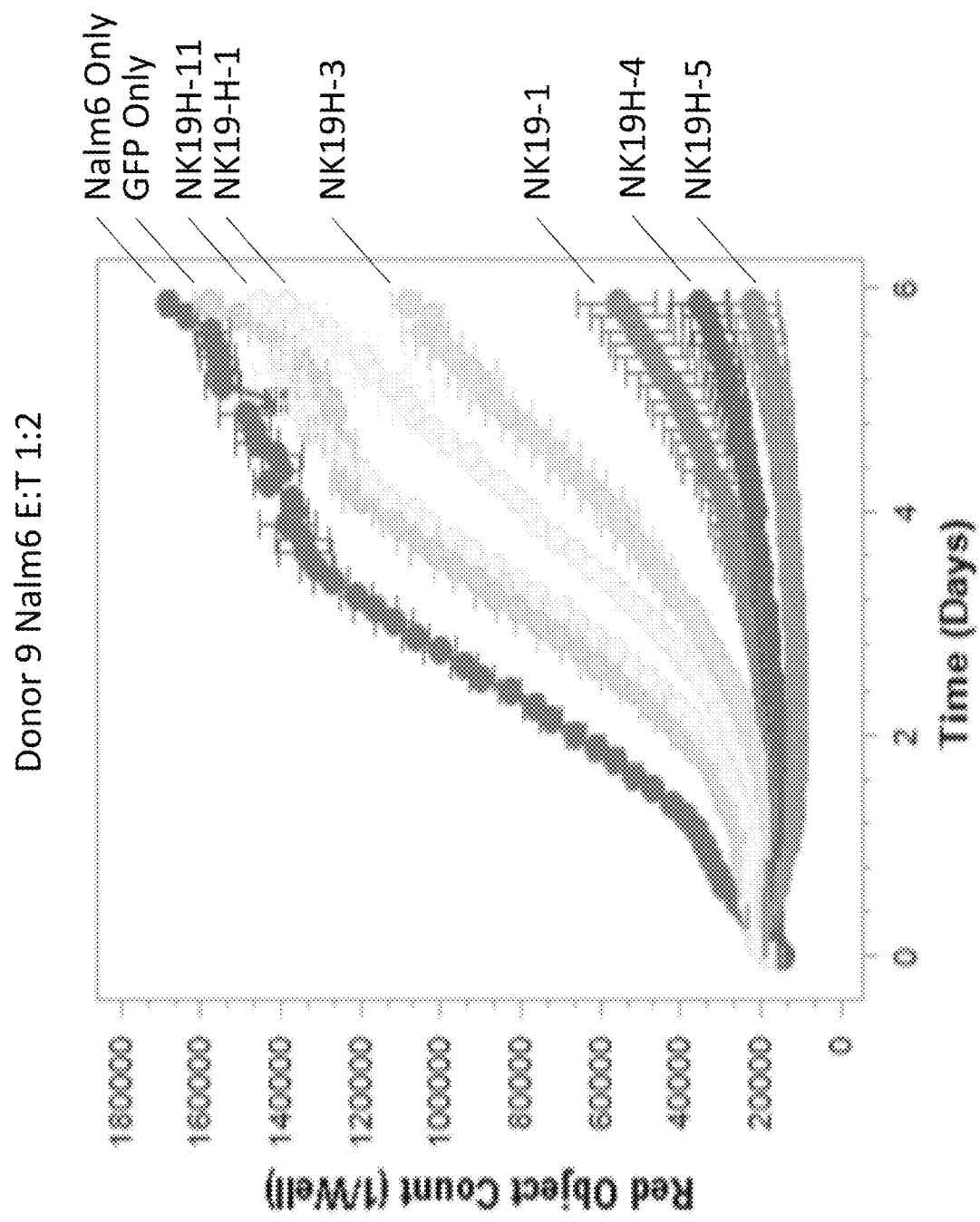

FIG. 17B shows NK cells from Donor 20 tested against the CD19-positive Burkitt's lymphoma cell line Raji. As with Nalm6 cells, the various humanized anti-CD19 constructs showed variable cytotoxicity against the target cells. Similar to the data of FIG. 17A, the NK19H-11 construct showed limited cytotoxicity, but all other constructs showed promising cytotoxicity against the target cells, with NK19H-1 performing on par with the non-humanized NK19-1 construct, and each of NK19H-3, 19H-4, and 19H-5 constructs inducing greater levels of cytotoxicity, limiting Raji growth until the later stages of the co-culture (with NK19H-5 allowing only very limited Raji cell growth). FIG. 17C shows corresponding Nalm6 data from Donor 140. Here, a similar pattern of efficacy was detected, with NK19H-11 allowing Nalm6 growth approximating negative controls. However, each of NK19H-1, 19H-3 and 19H-4 induced at least as much cytotoxicity as non-humanized NK19-1. Again, NK19H-5 showed significant cytotoxicity, limiting Nalm6 growth throughout the experiment. FIG. 17D shows data from Donor 9 against Raji cells. Only NK19H-11 allowed any substantial Raji cell growth. In contrast, NK cells from this donor expressed the non-humanized NK19-1 or any of the humanized NK19H-1, 19H-3, 19H-4, or 19H-5 constructs suppressed any Raji cell growth through the induced cytotoxic effects. FIG. 17E shows data for NK cells from Donor 9 against Nalm6 cells. In this experiment, the cytotoxicity of three of the humanized constructs (NK19H-11, 19H-1, and 19H-3) was limited. There is some donor to donor variability, as certain of these constructs induced cytotoxicity when expressed by NK cells of other donors. The NK19H-4 and 19H-5 constructs exhibited significant cytotoxic effects, nearly limiting Nalm6 growth to zero over the course of the experiment. Taken together, these data complement the expression data and show that, in accordance with several embodiments, humanized CAR constructs targeting CD19 are effective at killing tumor cells, even if they have variable expression efficiencies. Additionally, according to some embodiments, the expression efficiency is not correlated with cytotoxicity and even constructs with limited expression efficiency can demonstrate significant cytotoxicity.

Example 4

Figure 18:
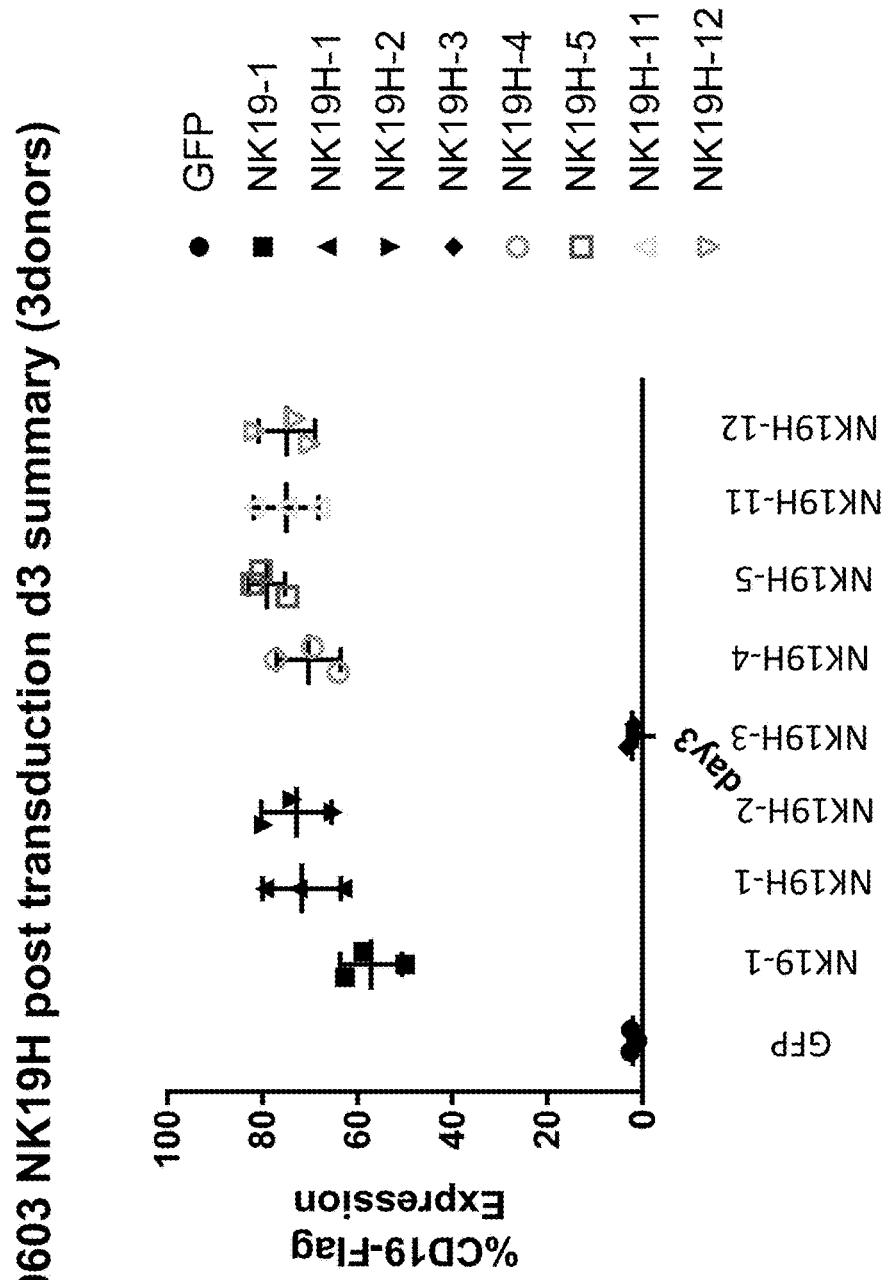
FIG. 18 shows summary (from 3 donors) expression data for NK cells expressing the indicated non-limiting anti-CD19 CAR constructs at 3 days post-transduction.
Figure 19A:
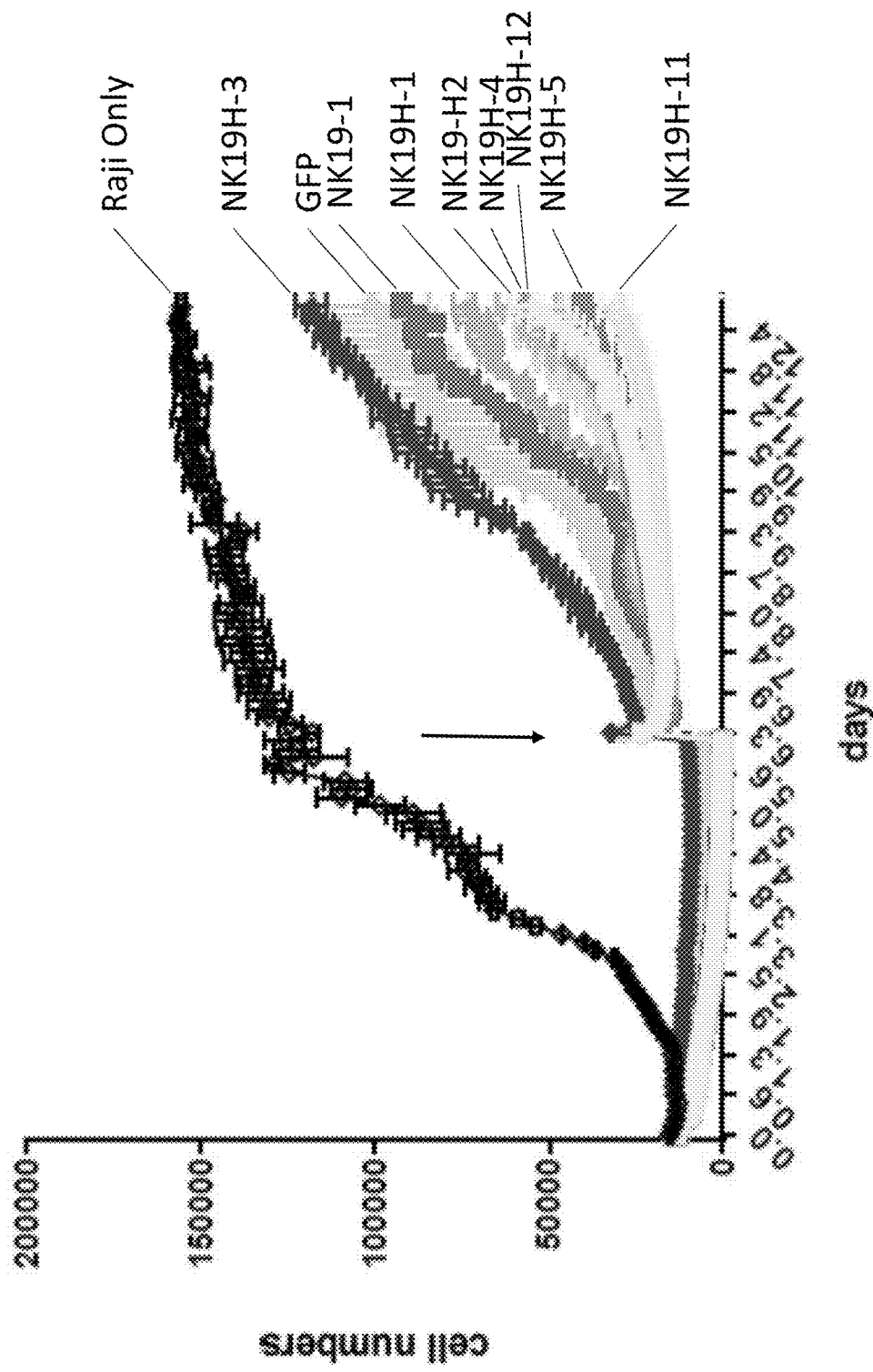
FIGS. 19A-19D show cytotoxicity rechallenge data.
Figure 19B:
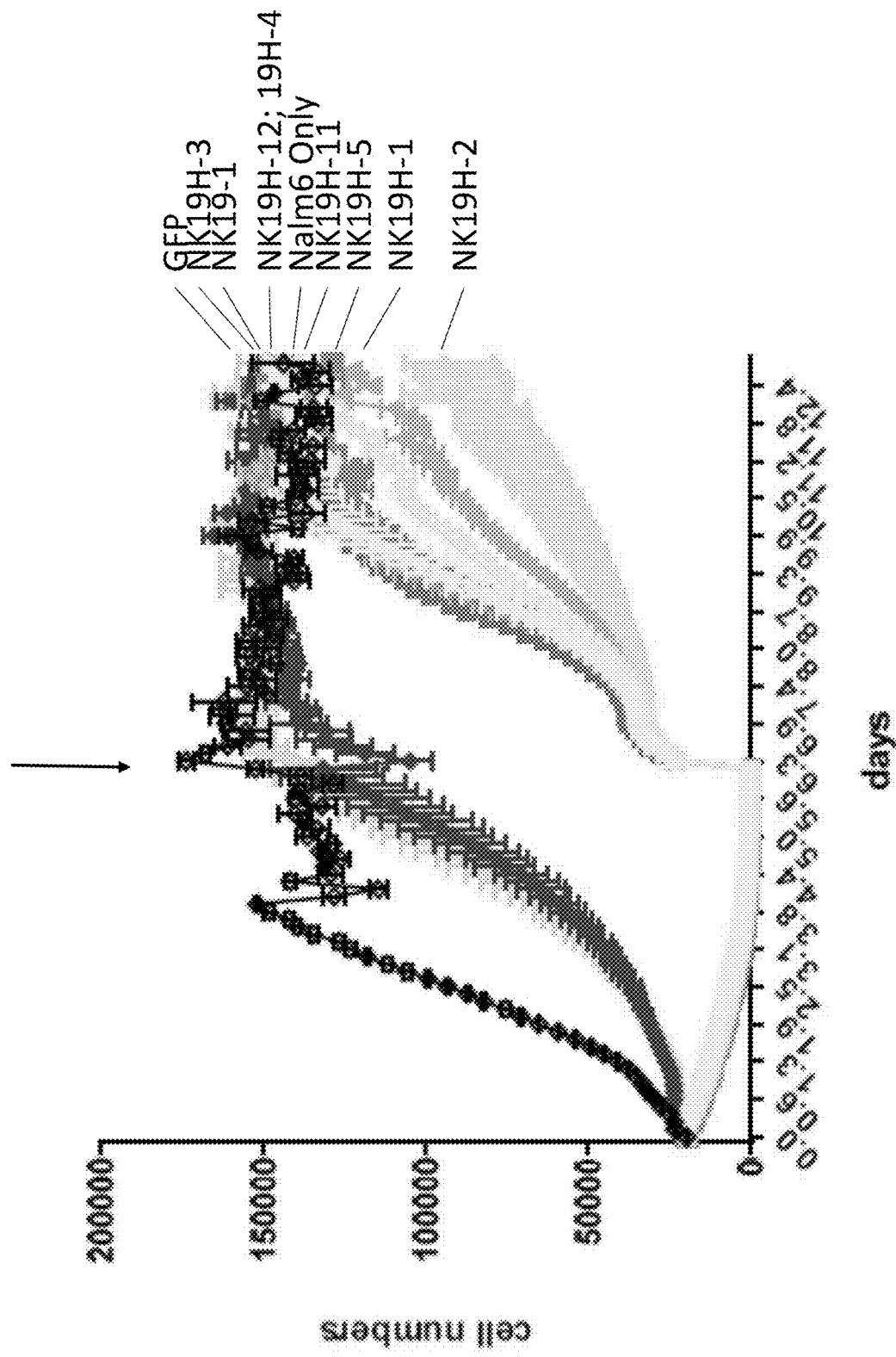
Figure 19C:
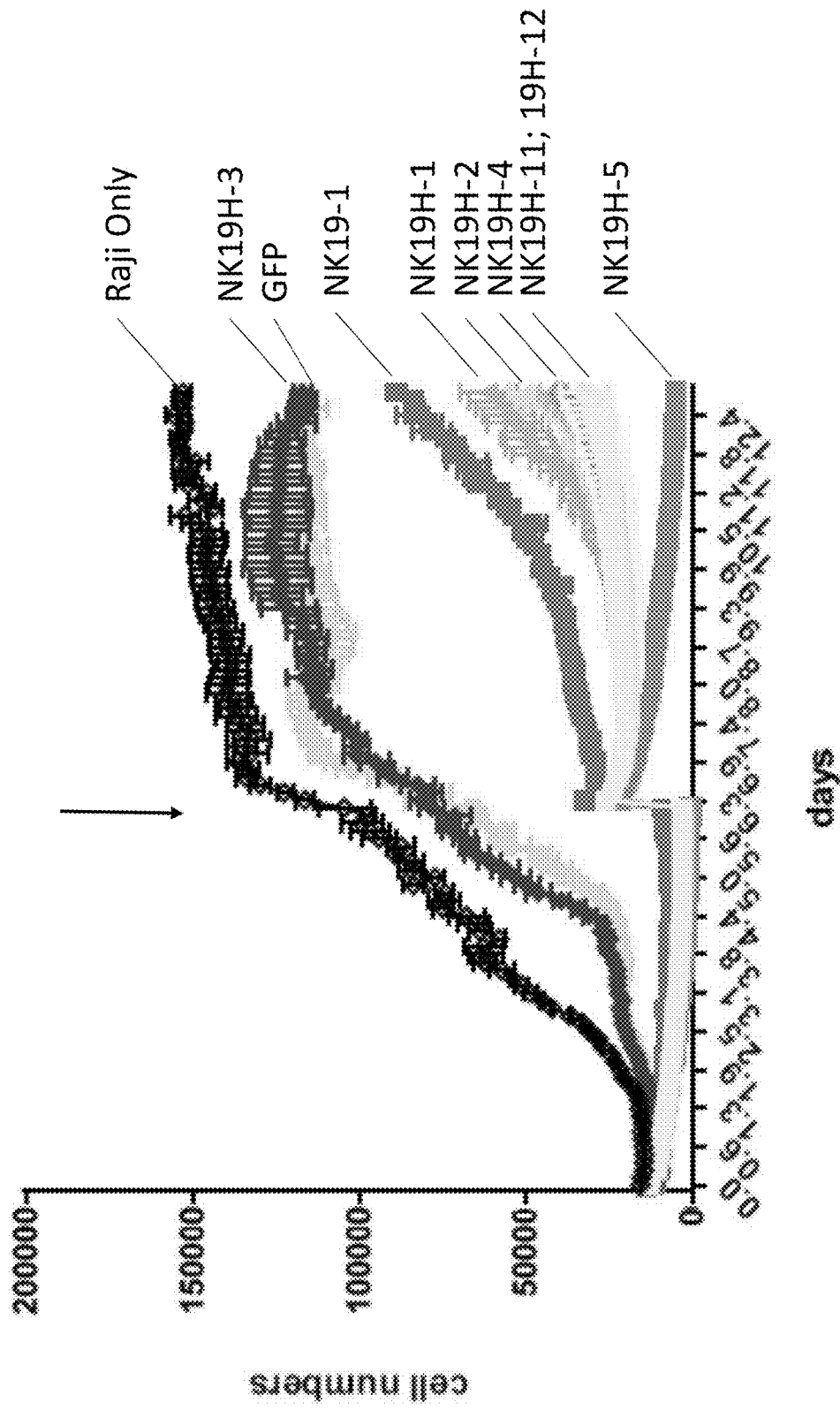
Figure 19D:
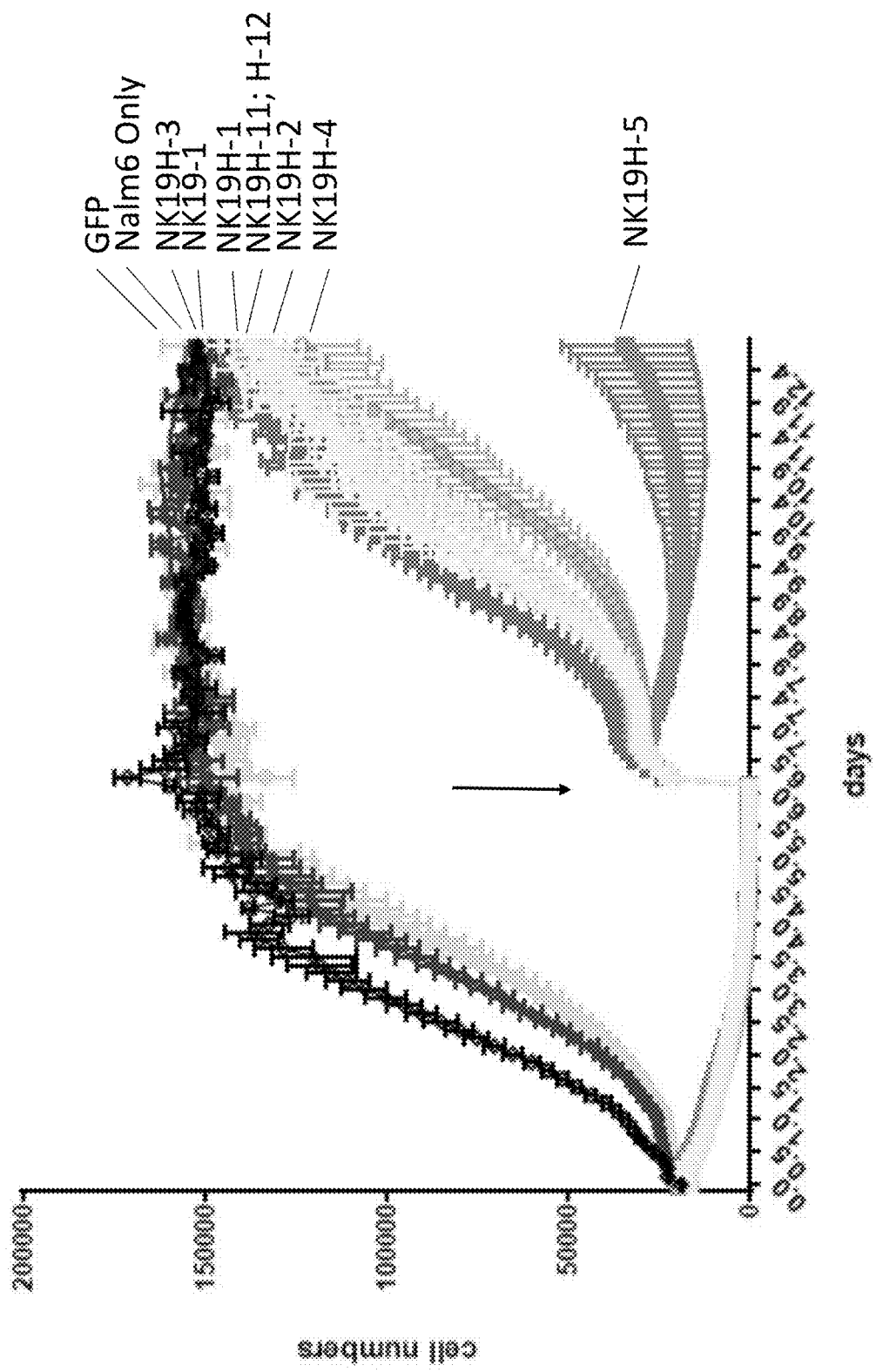

Further experiments paralleling those discussed above were performed using NK cells from additional donors. FIG. 18 shows construct expression efficiency for three donors (#945, 137 and 138) for the indicated constructs. As with the prior experiment the data presented represent the number of CD19-Flag positive cells out of the total number of NK cells evaluated. The data for these donors shows a higher overall efficiency of expression for all but one of the humanized constructs. Only NK19H-3 was expressed less than the non-humanized NK19-1 construct. With these donor NK cells, expression of the humanized constructs was detected on about 70% to 80% of the NK cells. As above, further to evaluation of expression, cytotoxicity against CD19 expression target cells was evaluated. FIG. 19A shows data related to NK cells from a donor (#137) expressing the indicated constructs and co-cultured with Raji cells. In this experiment, the engineered NK cells expressing the indicated constructs were exposed to the tumor cells at two time points, 7-days and an additional bolus of tumor cells was added at 14-days post-transduction. The arrow shows the second administration of tumor cells. As shown, untreated Raji cells expanded throughout the experiment. NK cells expressing GFP or non-humanized NK19-1 induced some cytotoxicity as shown by the reduced Raji cell growth as compared to control. NK cells expressing NKH19-3 (the humanized construct with the lowest expression efficiency) were also able to reduce Raji growth. Each of the other humanized NK constructs were able to reduce Raji cell growth compared to controls, even at 14 days post-transduction, which is indicative of the enhanced persistence of engineered NK cells disclosed herein. FIG. 19B shows corresponding data for Donor 137 NK cells against Nalm6 cells with engineered NK cells again being added at day 7 (day 0 of experiment) and day 14 post-transduction (~day 7 of experiment). Cytotoxicity of the indicated constructs was more variable in this particular experiment. However, several humanized anti-CD19 constructs were able to produce marked cytotoxicity and reduce Nalm6 cell growth as compared to controls. These data suggest that, according to several embodiments, a more frequent dosing schedule (e.g., every 2 days, every 3 days, every 4 days, every 5 days, etc.) would be beneficial for certain subjects. Advantageously, in several embodiments, engineered NK cells as disclosed herein are allogeneic and can be readily used in more frequent dosing regimens. FIG. 19C shows corresponding data for Donor 138 against Raji cells. Here, many of the humanized constructs still had significant cytotoxic effects on the Raji cells, even with the second dose of Raji cells at 14 days post-transduction. Six of the 7 humanized constructs showed this behavior, and outperformed the non-humanized NK19-1 construct. FIG. 19D shows the corresponding data for Donor 138 against Nalm6 cells. While the additional bolus of Nalm6 led to increased Nalm6 growth in the latter stages the experiment, nearly all of the humanized constructs performed better than controls. In fact, NK19H-5-bearing NK cells were able to limit Nalm6 growth until the final few days of the experiment (after the second dose). As above, these data show that humanized anti-CD19 CAR constructs can not only be expressed by NK cells, but can also exert cytotoxic activity against target cells, with an enhanced persistence. In several embodiments, this allows multiple dosing to be separated by longer periods of time, which could be advantageous for treating cancers, while limiting potential immunogenicity (at least in part due to the humanization and/or because of the reduced frequency of administration).

Example 5

Figures 20A, 20B:
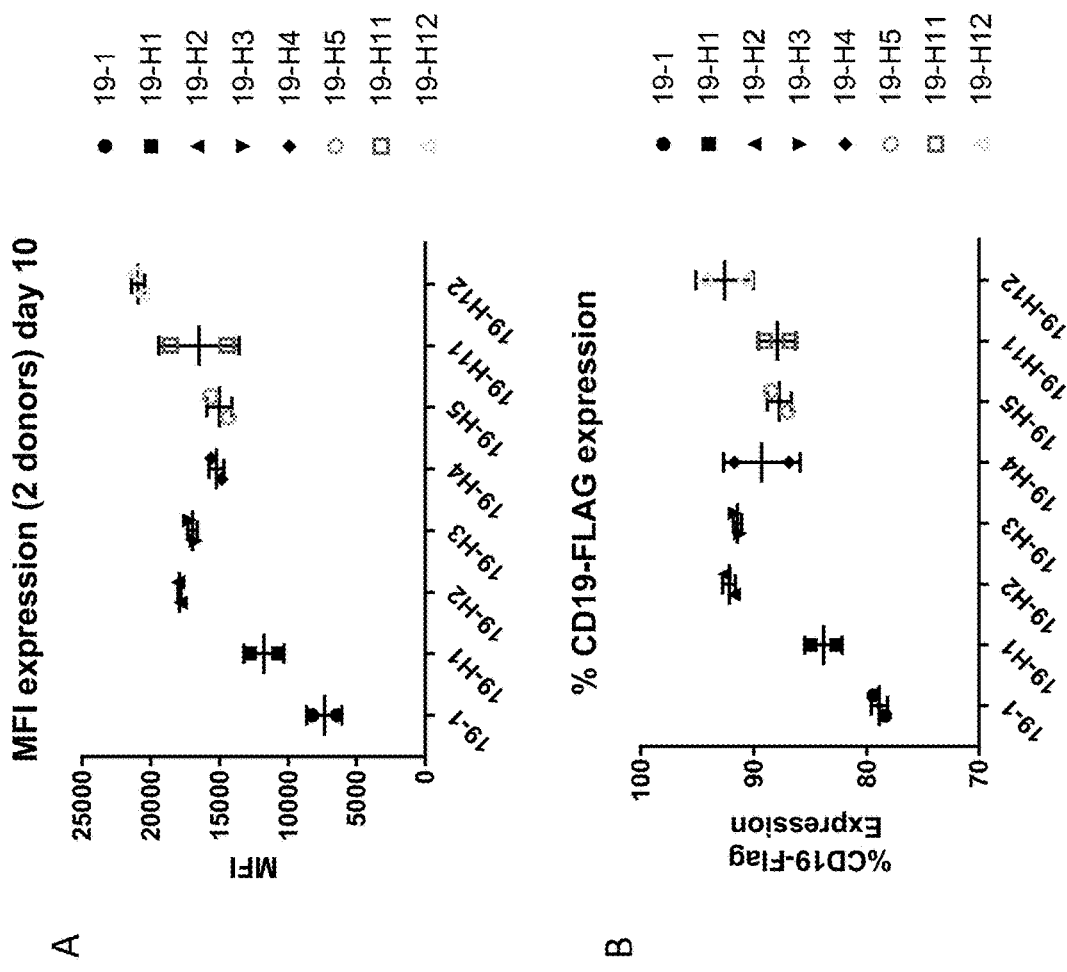
FIGS. 20A-20B show expression data.
Figure 21A:
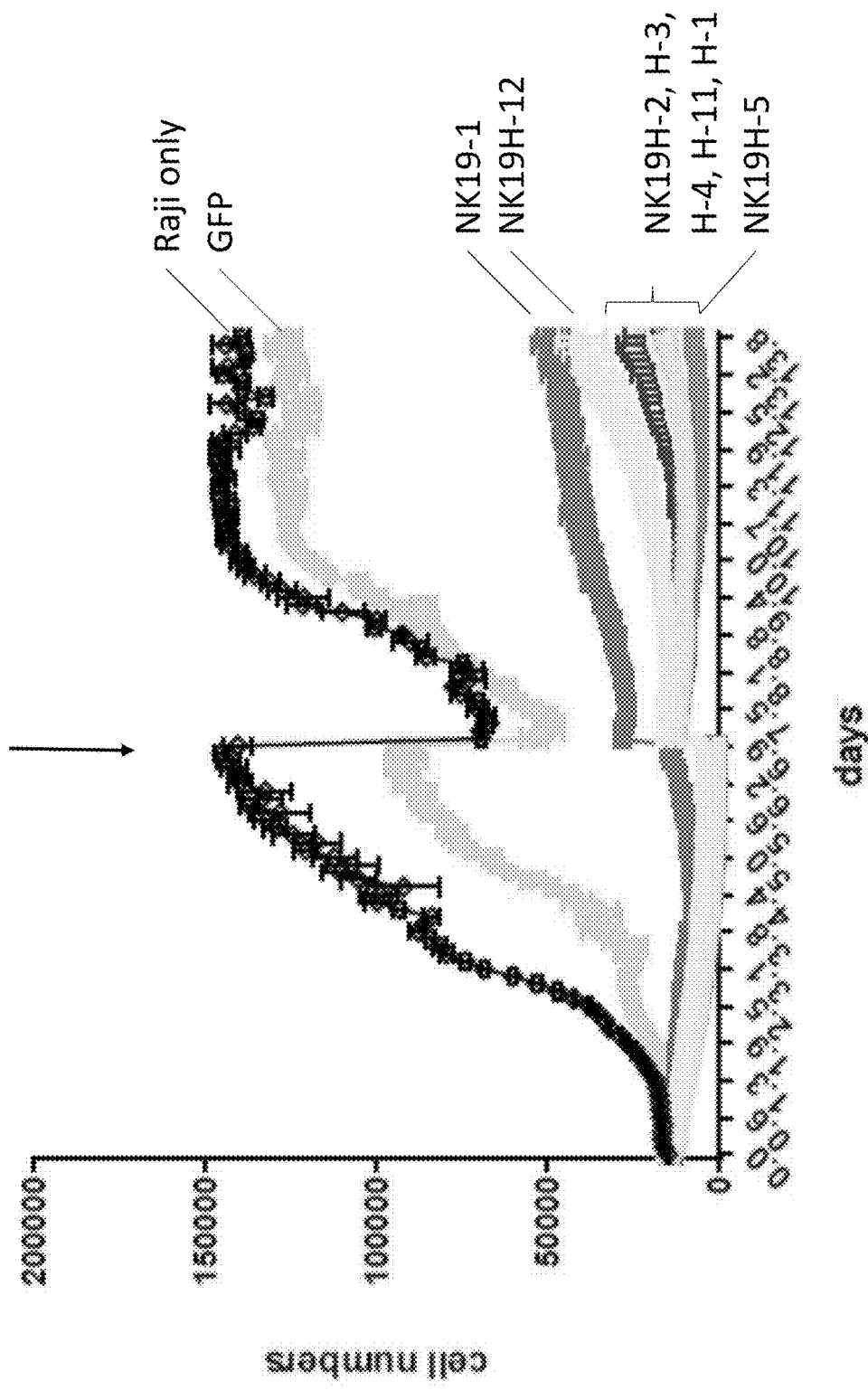
FIGS. 21A-21B show cytotoxicity data.
Figure 21B:
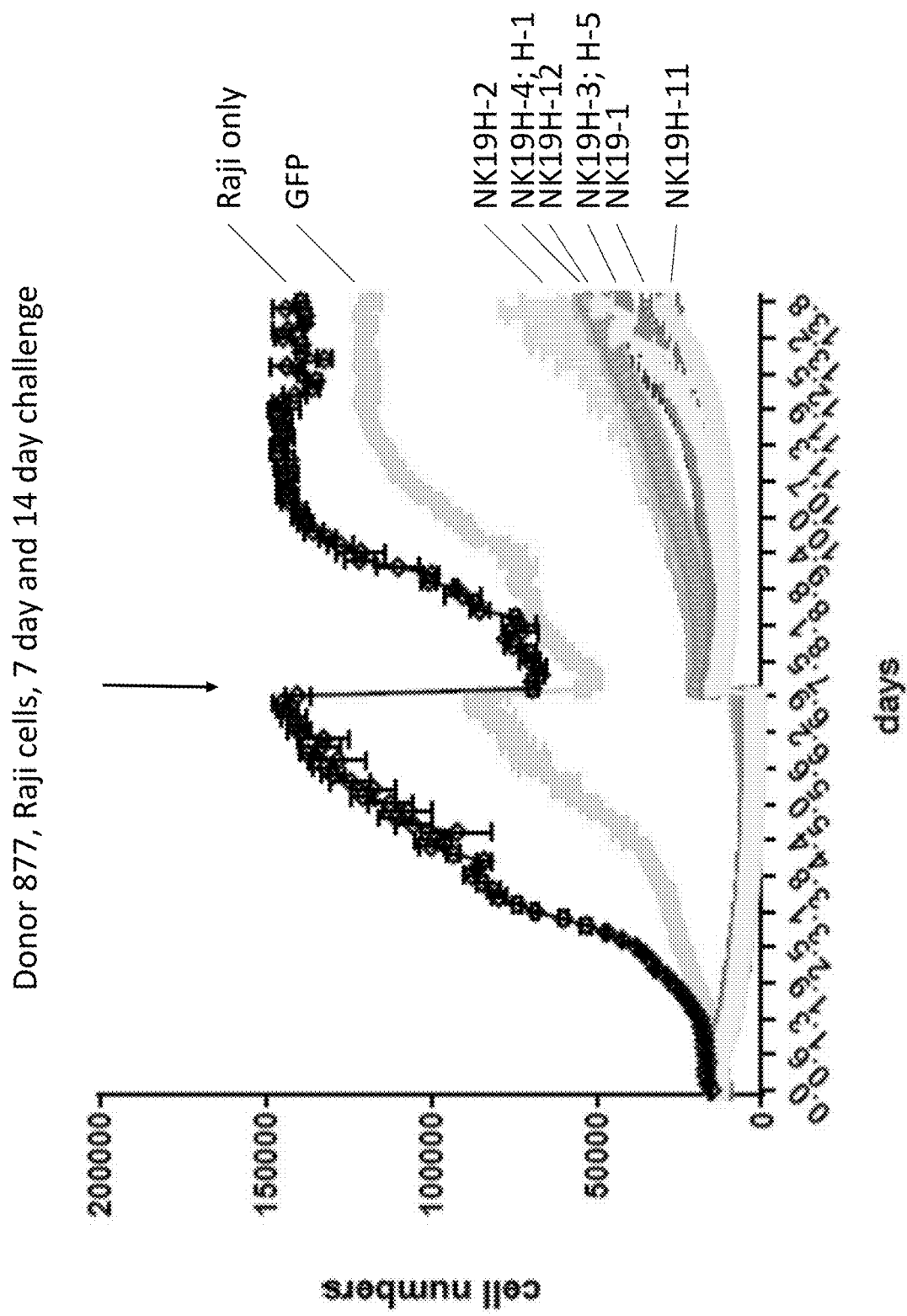

Further data for various humanized constructs in additional donors was collected. FIGS. 20A-20B show expression data for various anti-CD19 CAR constructs in NK cells from two additional donors. FIG. 20A shows the mean fluorescence intensity for NK cells at 10 days post-transduction. As indicated, as in accordance with several embodiments disclosed herein, each of the humanized anti-CD19 CAR constructs showed enhanced overall expression as compared to a non-humanized anti-CD19 CAR. FIG. 20B shows the expression data of CD19-Flag positive NK cells as a percentage of the total number of NK cells analyzed. As shown, each of the humanized anti-CD19 constructs were more efficiently expressed than the non-humanized construct (which was already expressed by almost 80% of the NK cells). The humanized CARs were expressed by approximately 85% to 95% of the NK cells, depending on the construct. FIG. 21A shows cytotoxicity data for engineered NK cells from Donor 703 (one of the two donors from FIG. 20) against Raji cells co-cultured with the NK cells at day 7 post-transduction and again at day 14 post-transduction. As shown in the Figure, Raji cells and NK cells expressing GFP alone grew robustly through day 7 and again through day 14. The non-humanized anti-CD19 CAR NK19-1 was able to suppress Raji cell growth through 7 days, and allowed relatively limited growth through 14 days. Each of the humanized anti-CD19 CAR constructs further suppressed Raji cell growth with several of the constructs nearly completely suppressing Raji cell growth. FIG. 21B shows corresponding data for cytotoxicity against Raji cells for NK cells isolated from Donor 877. These data show a similar trend to that from the prior donor. The two control groups allowed significant Raji cell growth, while each of the humanized anti-CD19 CAR constructs yielded significant cytotoxic effects.

Figures 22A, 22B:
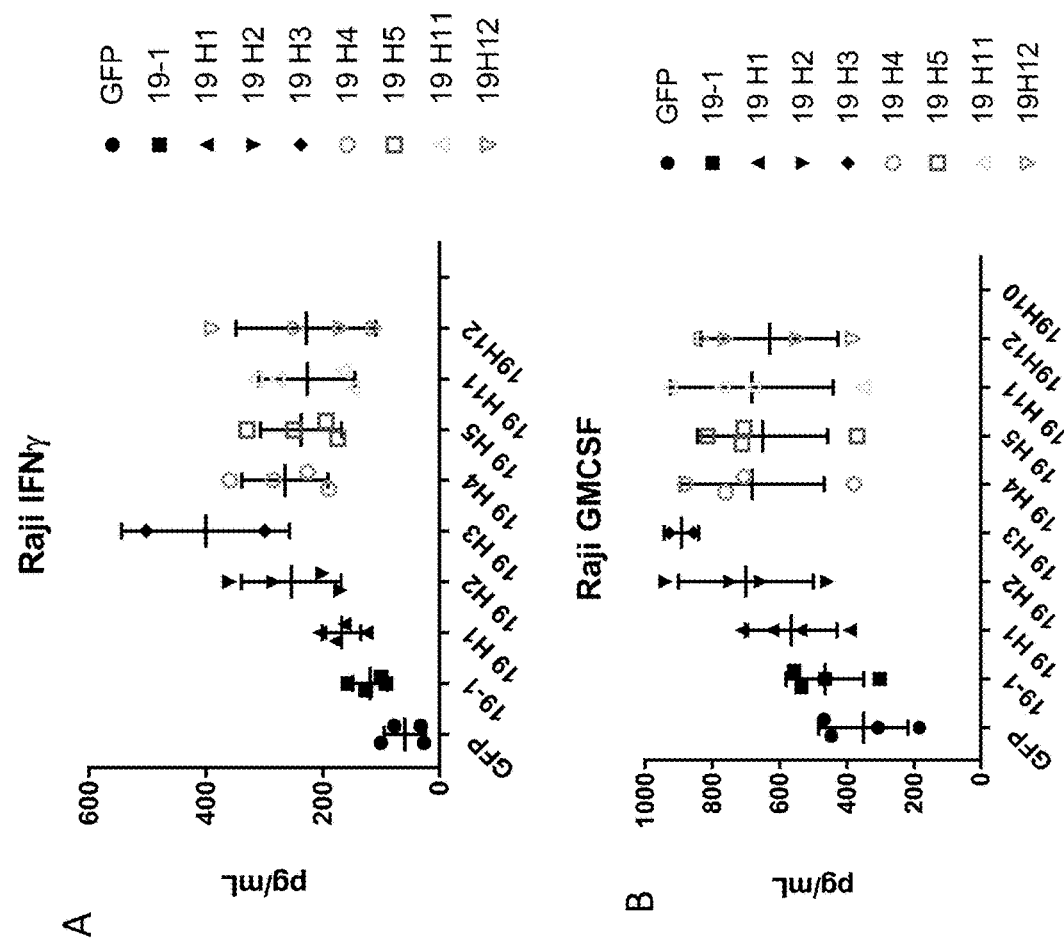
FIGS. 22A-22E show data related to cytokine release by NK cells expressing various CD19-directed chimeric receptors when co-cultured with Raji cells.
Figures 22C, 22D:
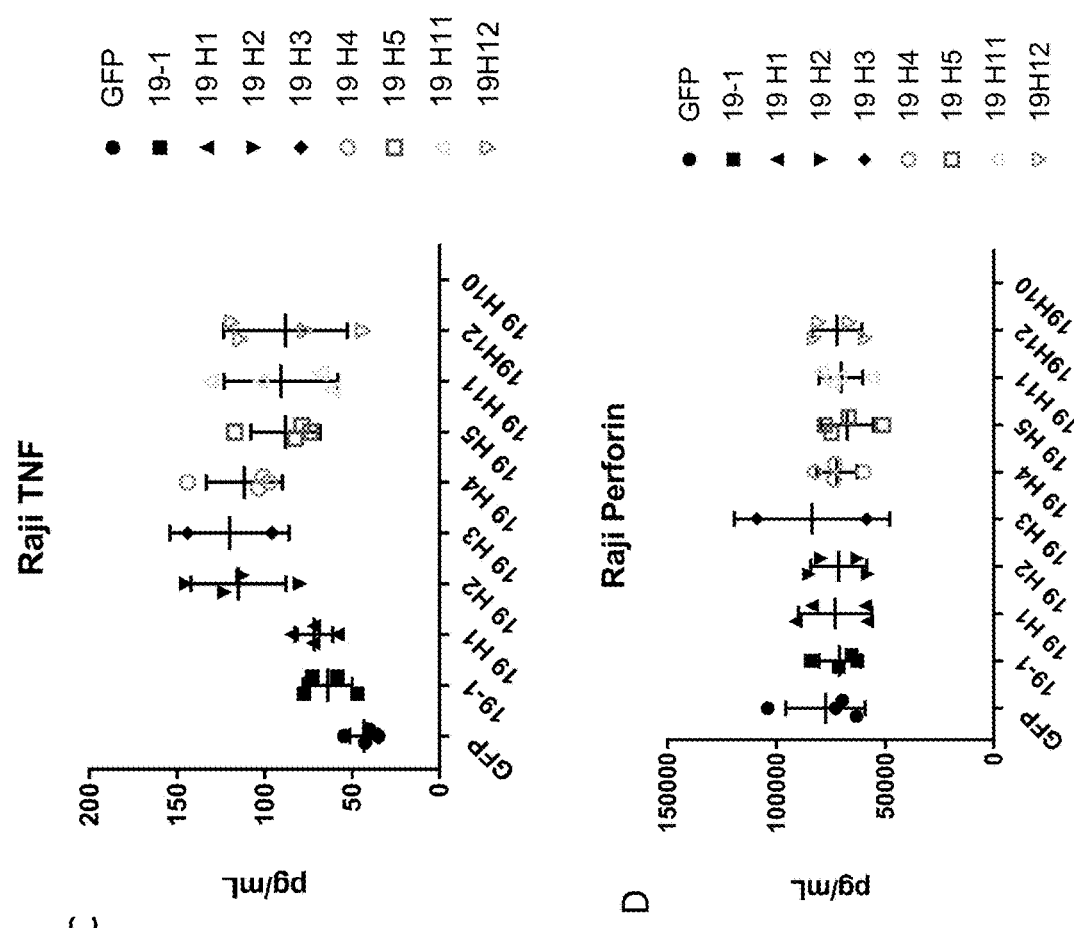
Figure 22E:
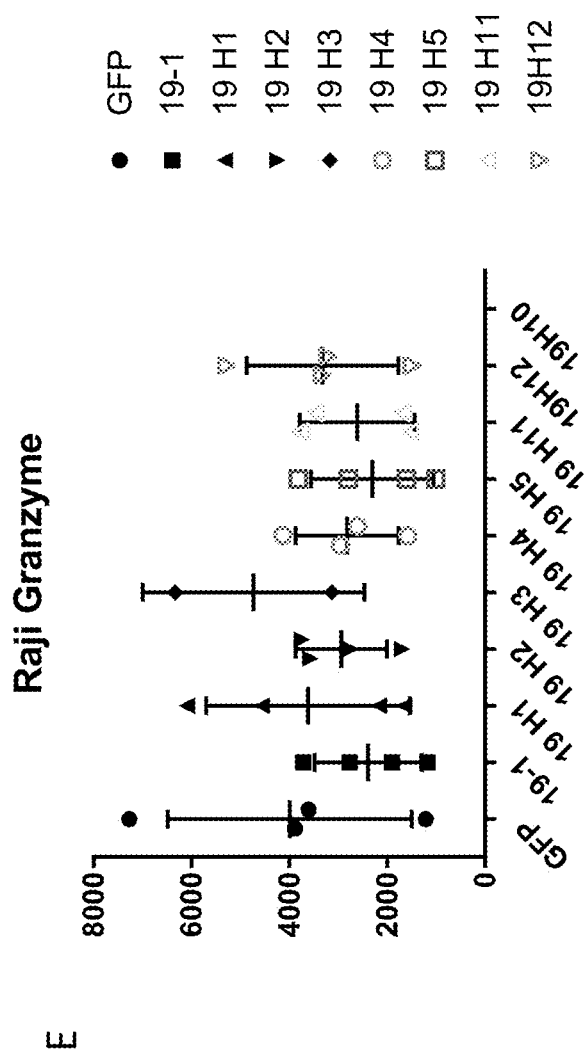

FIGS. 22A-22E show cytokine release profiles from Raji cells co-cultured with NK cells expressing the indicated constructs. FIG. 22A shows IFNg release by NK cells co-cultured with Raji cells. Each of the indicated humanized constructs resulted in increased IFNg release as compared to the non-humanized NK19-1 construct. Similarly, as shown in FIG. 22B, the humanized anti-CD19 constructs enabled the NK cells to release greater amounts of GM-CSF as compared to control NK cells. FIG. 22C show that humanized anti-CD19 CAR constructs induce elevated TNF release from the NK cells. Perforin levels were not significantly different across the constructs tested, as shown in FIG. 22D. Likewise Granzyme levels were relatively constant across the constructs. These data, taken together, indicate that according some embodiments, humanized anti-CD19 CAR constructs expressed on NK cells cause those NK cells to release greater amounts of one or more cytokines that lead to cytotoxic effects on target cells.

Example 6

Figure 23A:
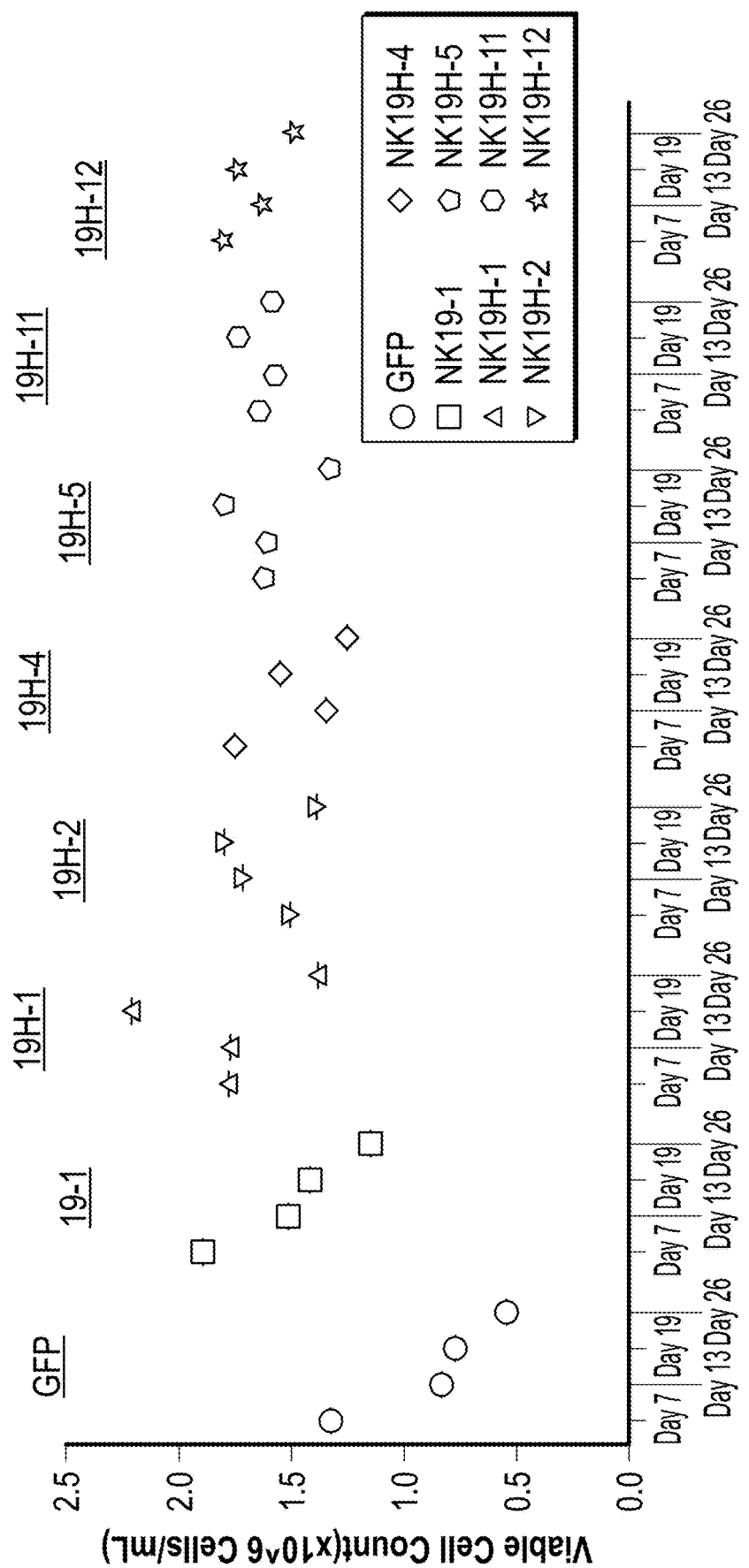
FIGS. 23A-23D show data related to NK cell survival.
Figure 23B:
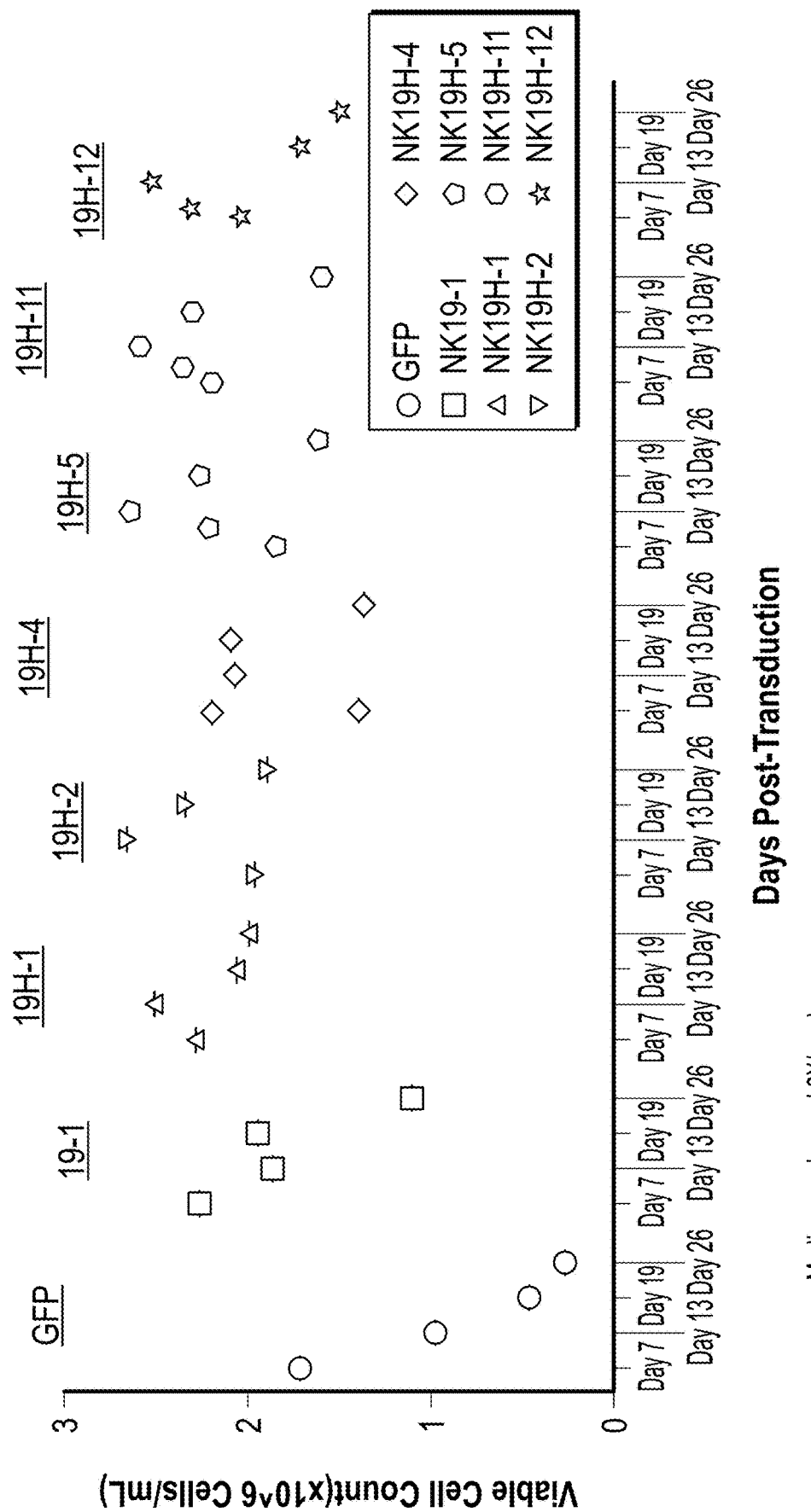
Figure 23C:
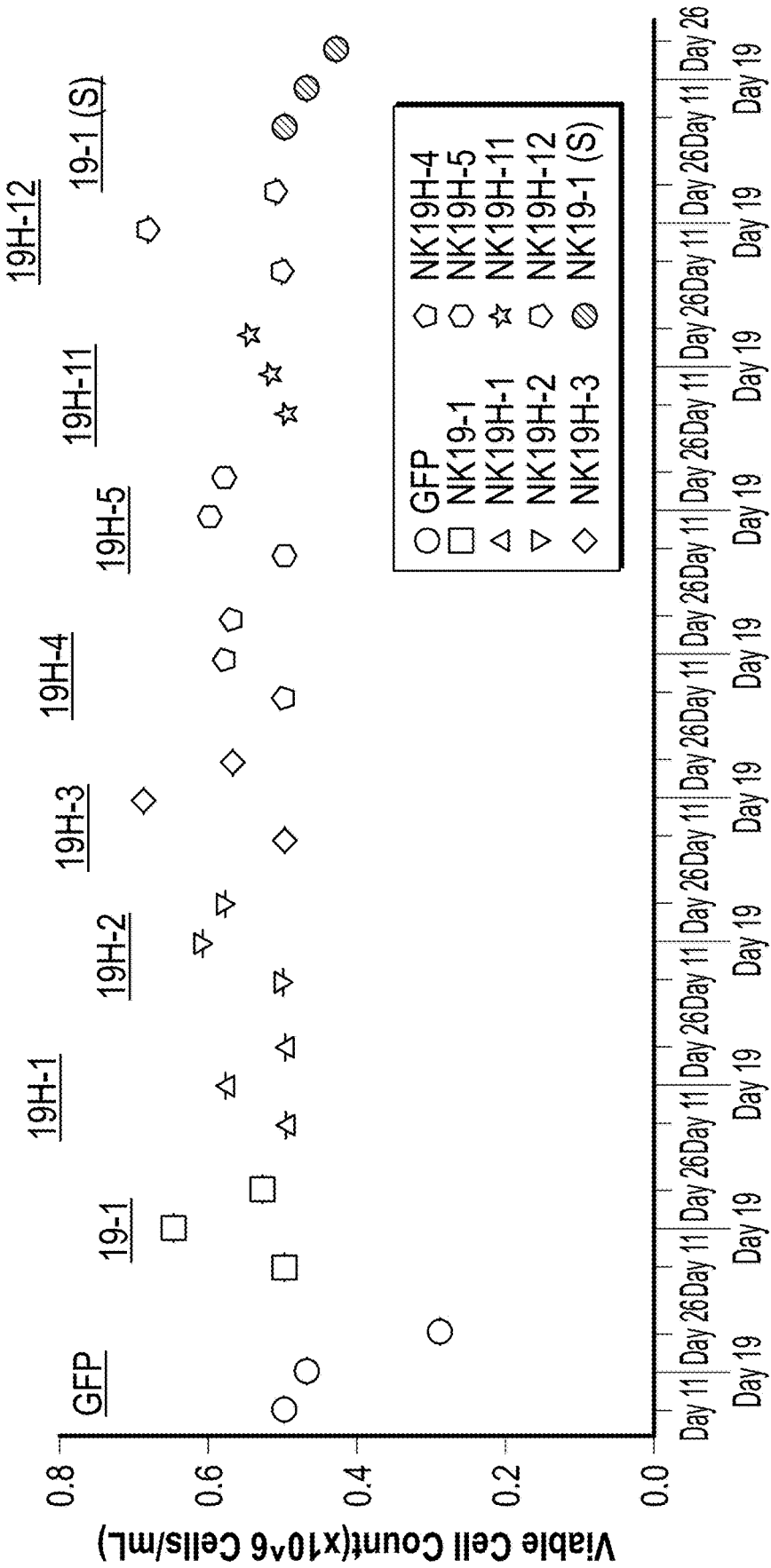
Figure 23D:
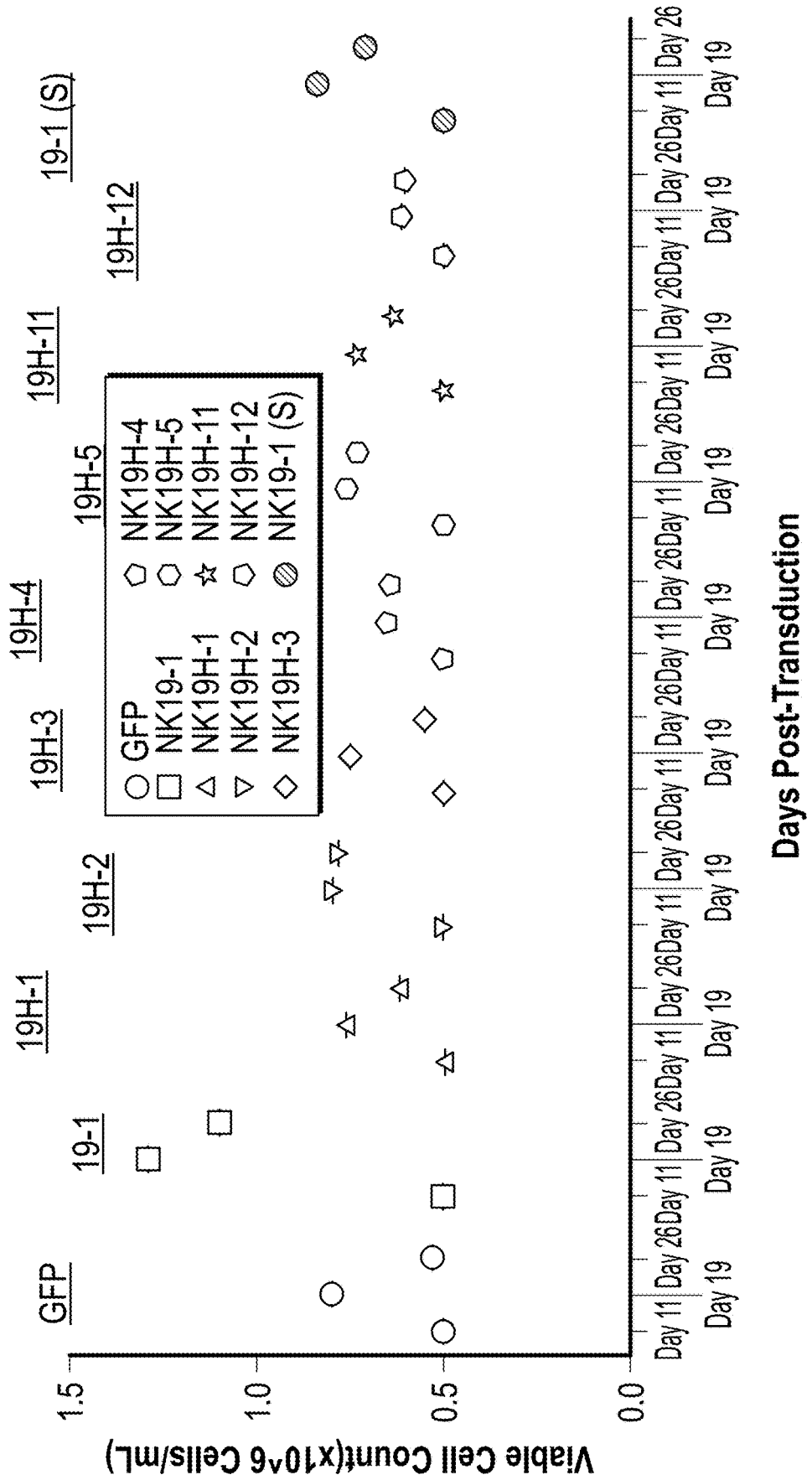

While the data presented above show that humanized anti-CD19 CARs can be expressed by NK cells and have cytotoxic effects on target tumor cells, additional experiments were performed to determine the longevity of the engineered NK cells. NK cells expressing the indicated anti-CD19 CAR constructs were cultured and the cell count was measured at various time points, out to 26 days post-transduction. FIG. 23A shows the survival data for NK cells from Donor 137. The data for the GFP-expressing NK cells show that the cell count at day 7 is higher than the cell count at any other time-point, suggesting that GFP has provided no additional longevity-inducing effects to the NK cells. Likewise, NK cells expressing non-humanized NK19-1 shows a fall off of cell number over time. While each of the humanized constructs shows some variability in terms of cell count, the trend of the data shows that expression of the humanized anti-CD19 constructs results in less NK cell death over time. A similar trend is shown in the data of FIG. 23B, which shows cell viability for NK cells from Donor 138. While the timing of analysis is modified, FIG. 23C shows data yielding a similar trend (for Donor 703), in that the expression of the humanized constructs results in longer NK cell survival over time in culture. FIG. 23D shows data for NK cells from Donor 877, where the expression of humanized anti-CD19 CAR constructs allows for reduced NK cell death over time in culture.

Figure 24:
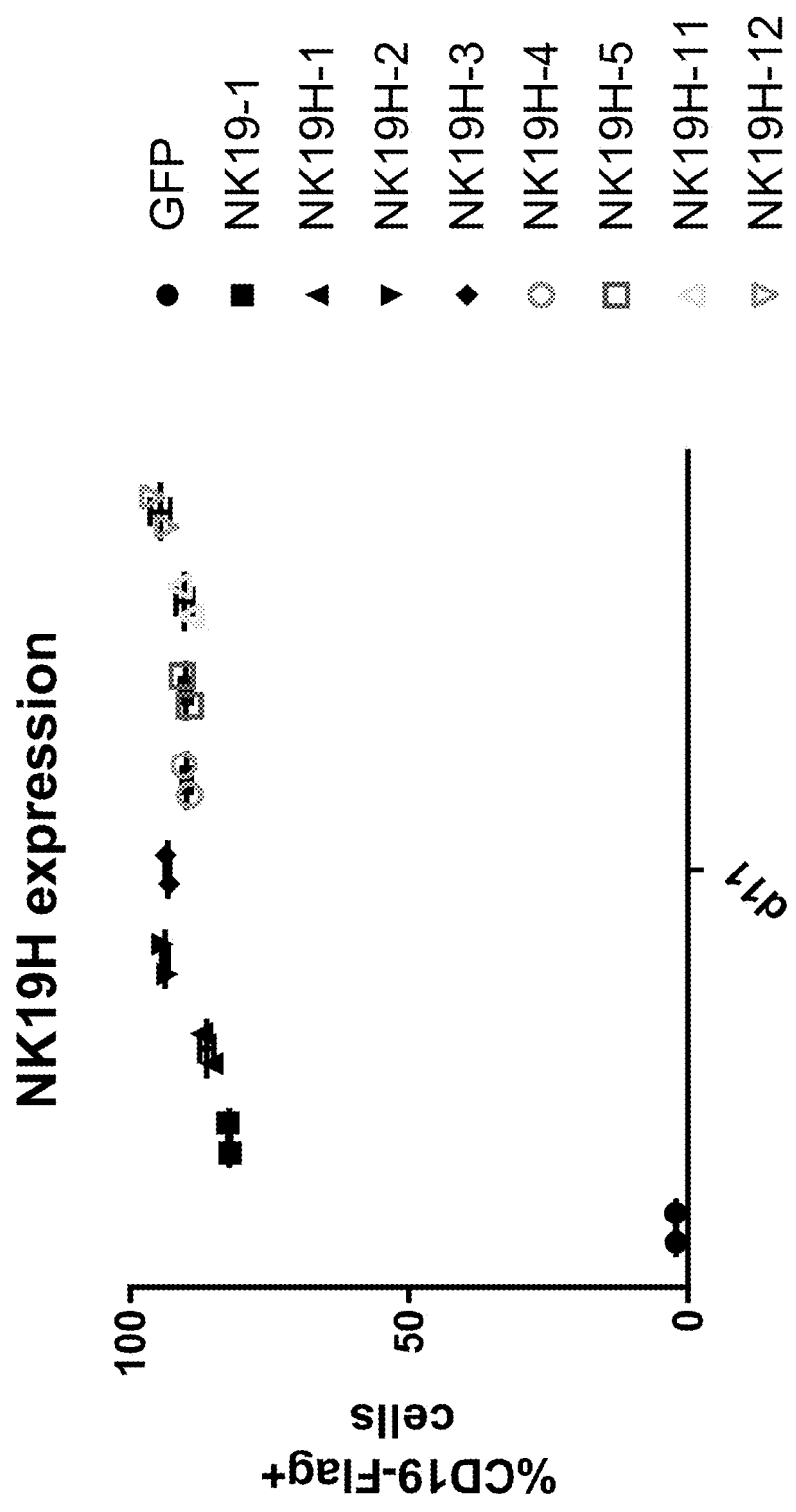
FIG. 24 shows data related to the percent of NK cells expressing the indicated non-limiting embodiments of anti-CD19 CAR constructs at 11 days post-transduction.

Summary data for the expression of the various anti-CD19 CAR constructs is shows in FIG. 24, which displays the expression efficiency of the indicated constructs at day 11 post-transduction. As anticipated, the GFP-transduced NK cells exhibit no CD19-Flag expression, serving as a negative control. Likewise, the non-humanized NK19-1 construct serves as a positive control. Each of the humanized constructs assessed showed enhanced expression efficiency as compared to NK19-1, with efficiencies ranging from about 85% to about 95% (e.g., 85%-95% of all the NK cells tested expressed the Flag-tagged CAR construct).

Figure 25A:
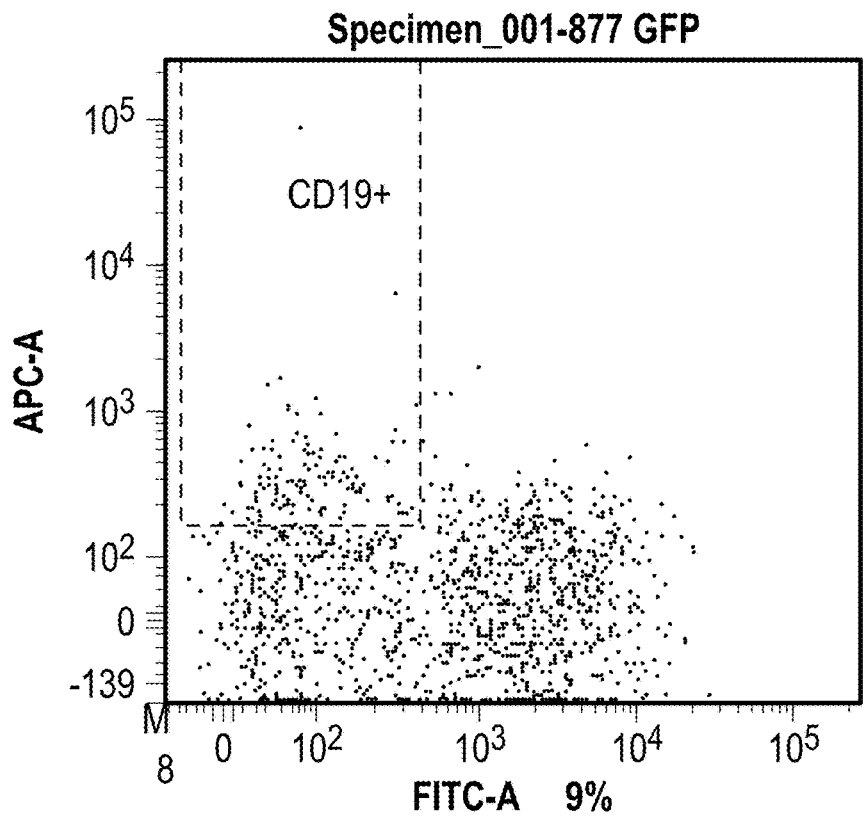
FIGS. 25A-25I show data related to the expression of CD19 by NK cells transduced with various non-limiting embodiments of anti-CD19 CAR constructs disclosed herein.
Figure 25B:
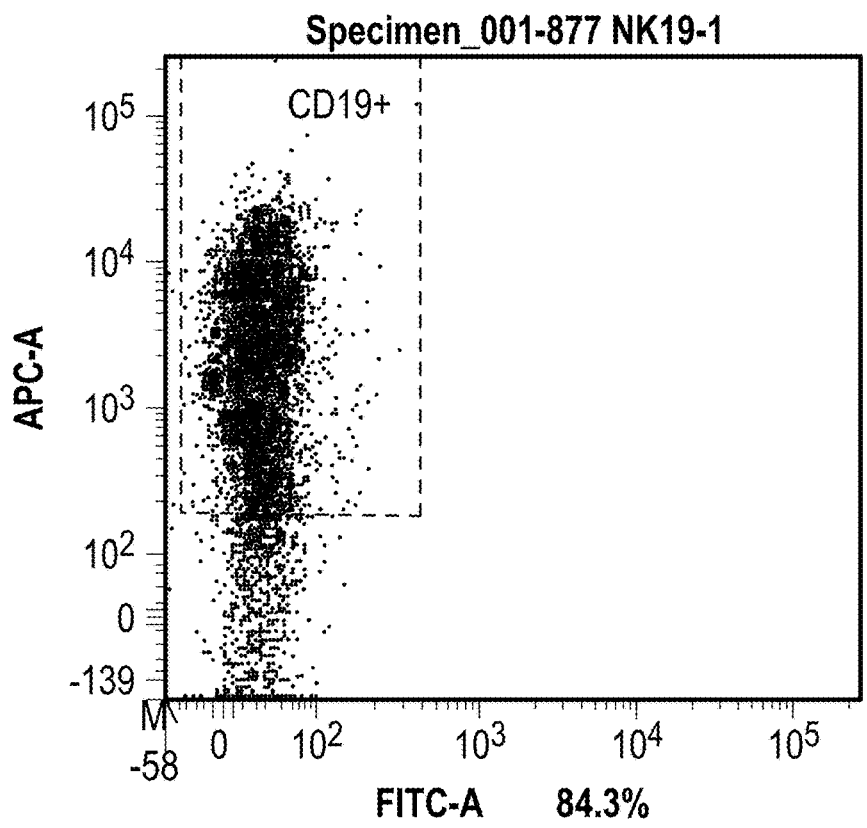
Figure 25C:
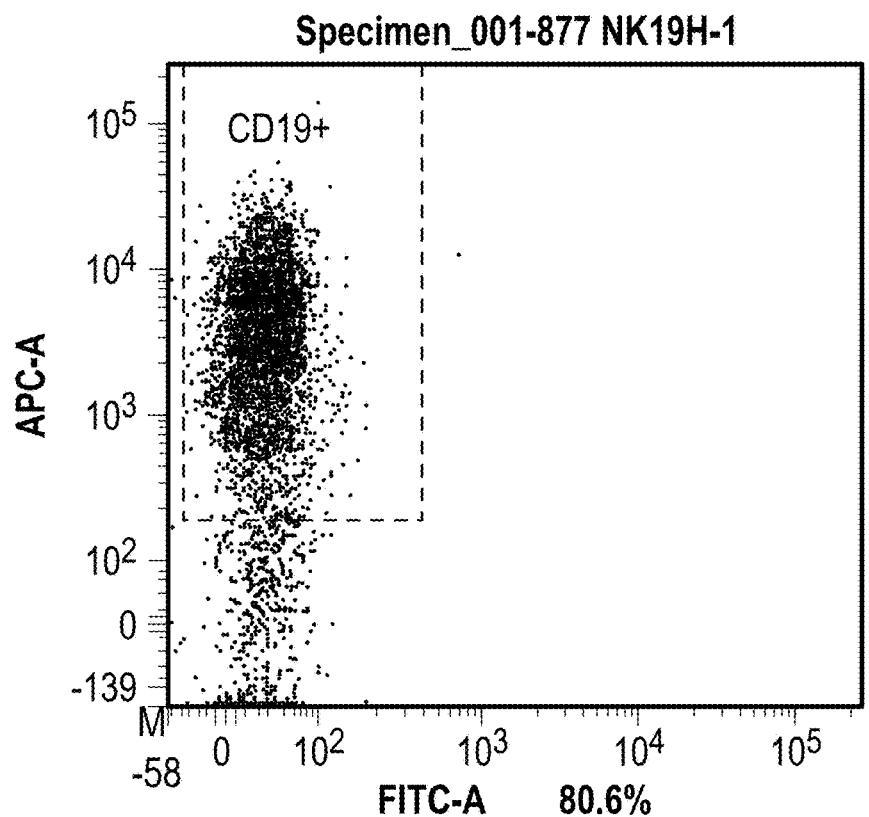
Figure 25D:
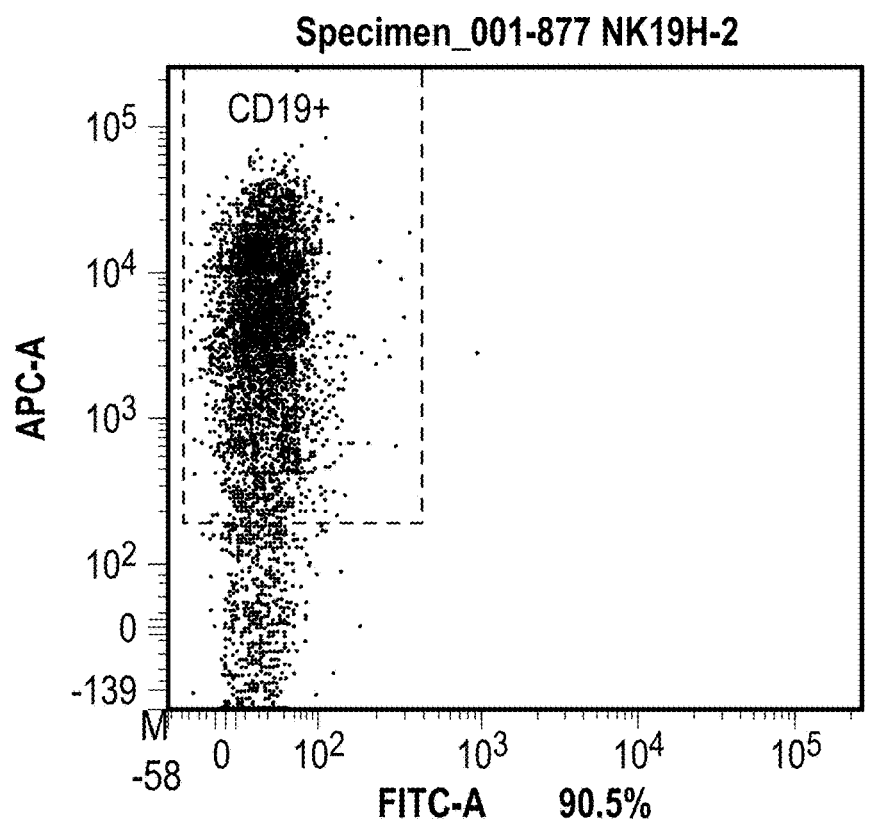
Figure 25E:
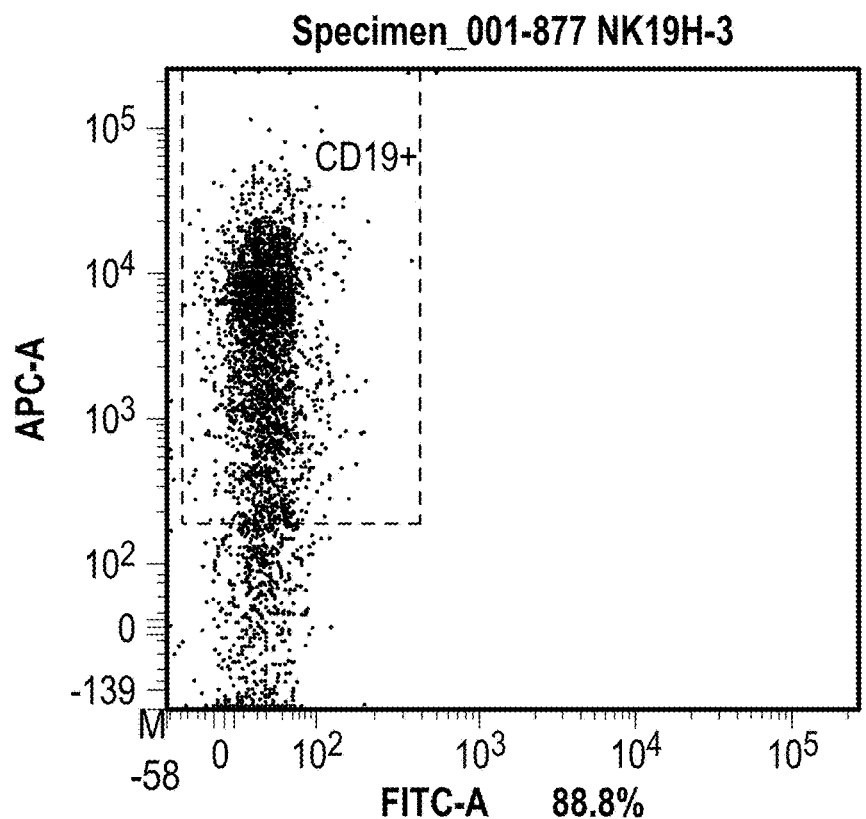
Figure 25F:
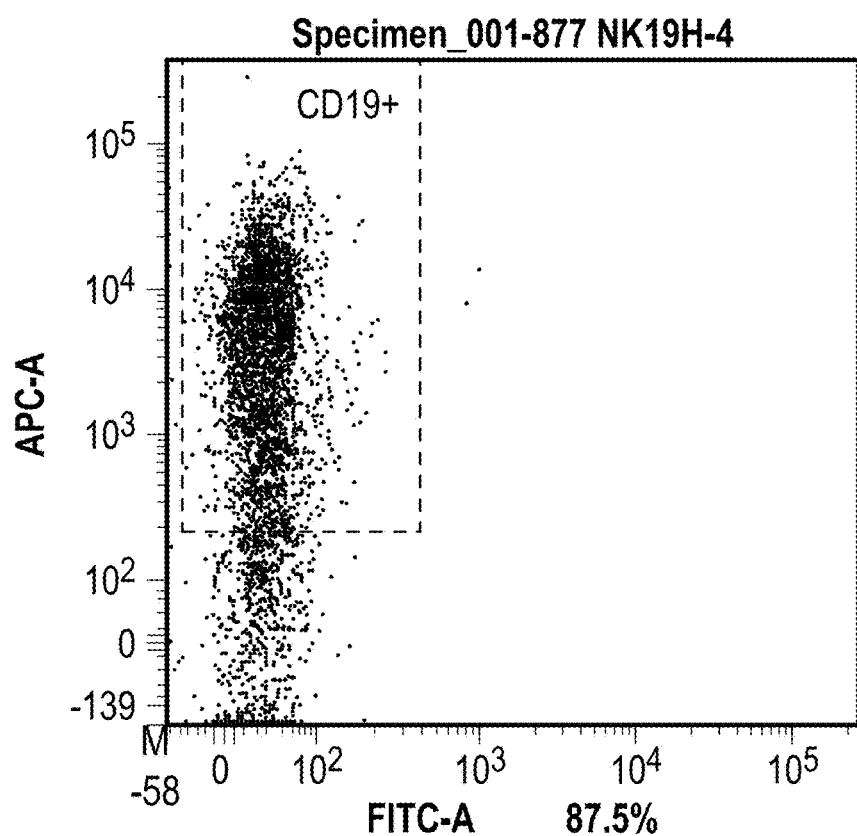
Figure 25G:
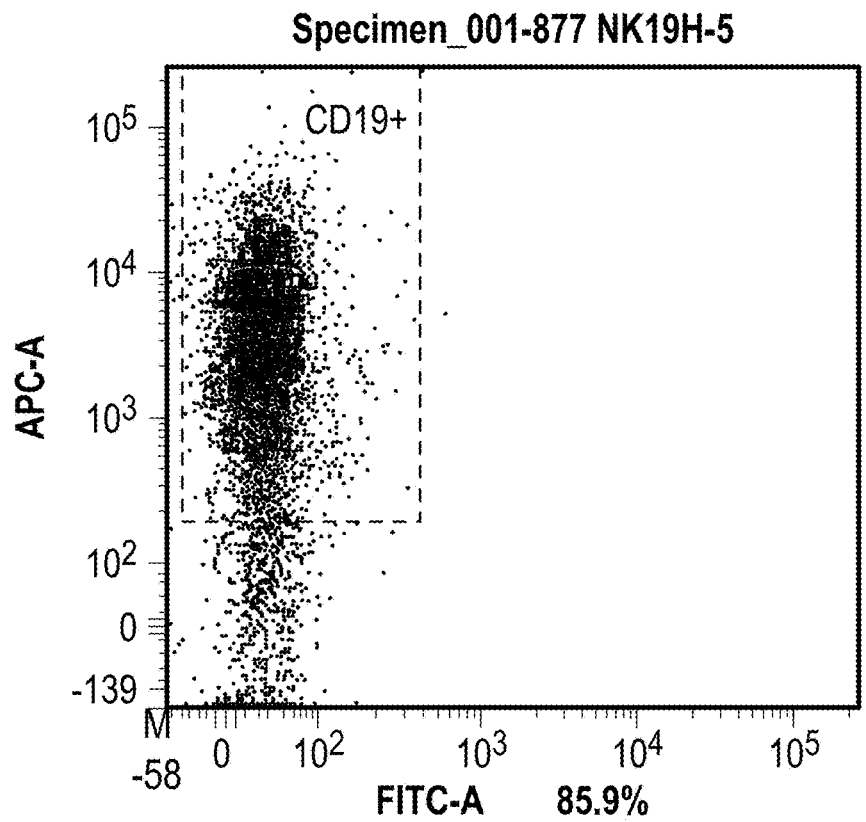
Figure 25H:
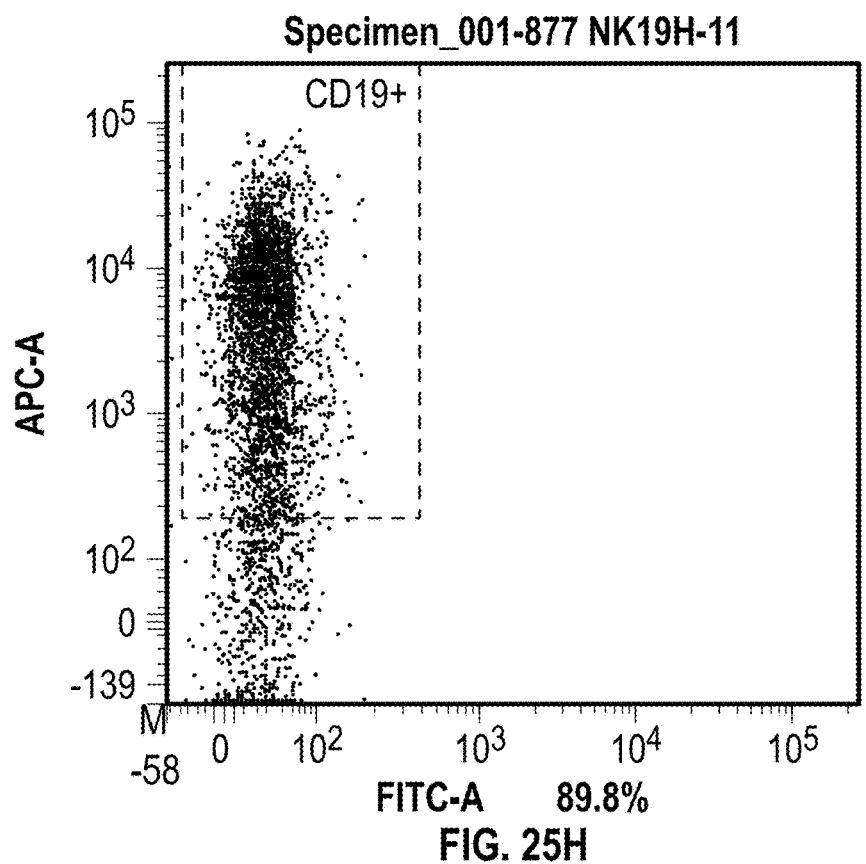
Figure 25I:
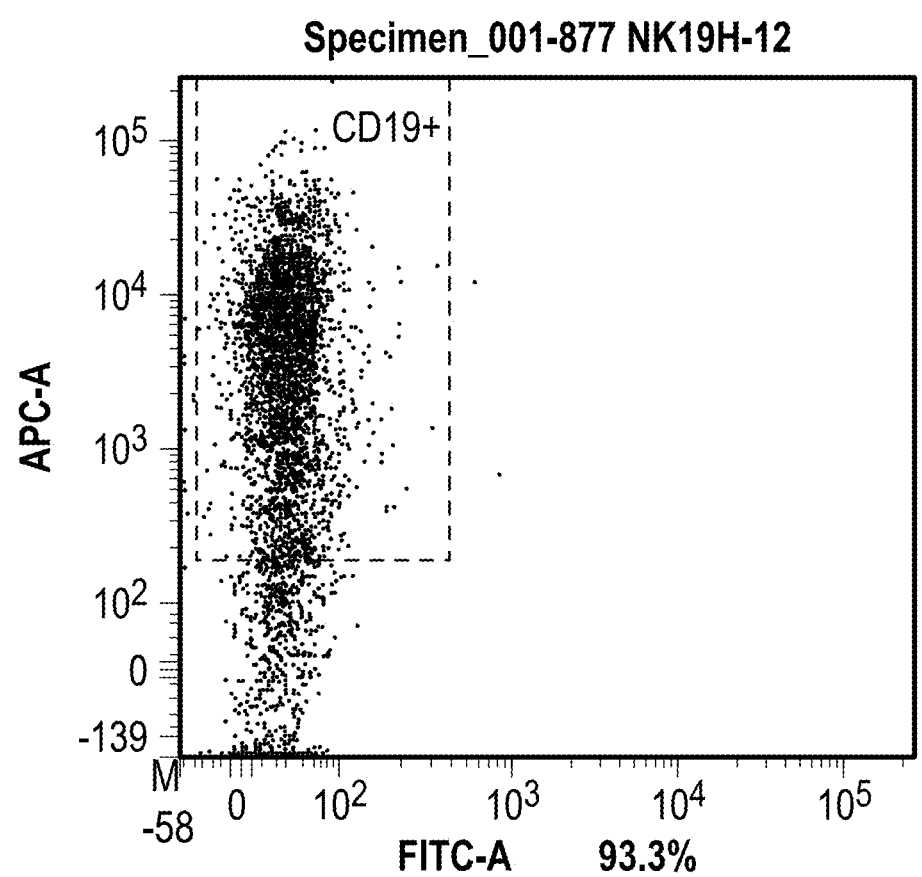

FIGS. 25A-25I show raw flow cytometry data for one donor wherein expression of CD19-Flag (indicative of CAR expression) is measured. FIG. 25A shows the GFP-control, with little to no Flag expression. FIG. 25B shows Flag detection with the NK19-1 positive control. FIGS. 25C-25I show the results of Flag detection for the indicated humanized anti-CD19 CAR constructs, with the percentage of cells expressing the constructs ranging from about 80% to about 95%. As with the experiments above, these data confirm that the humanized anti-CD19 CAR constructs can be robustly expressed by transduced NK cells.

Example 7

Figure 26A:
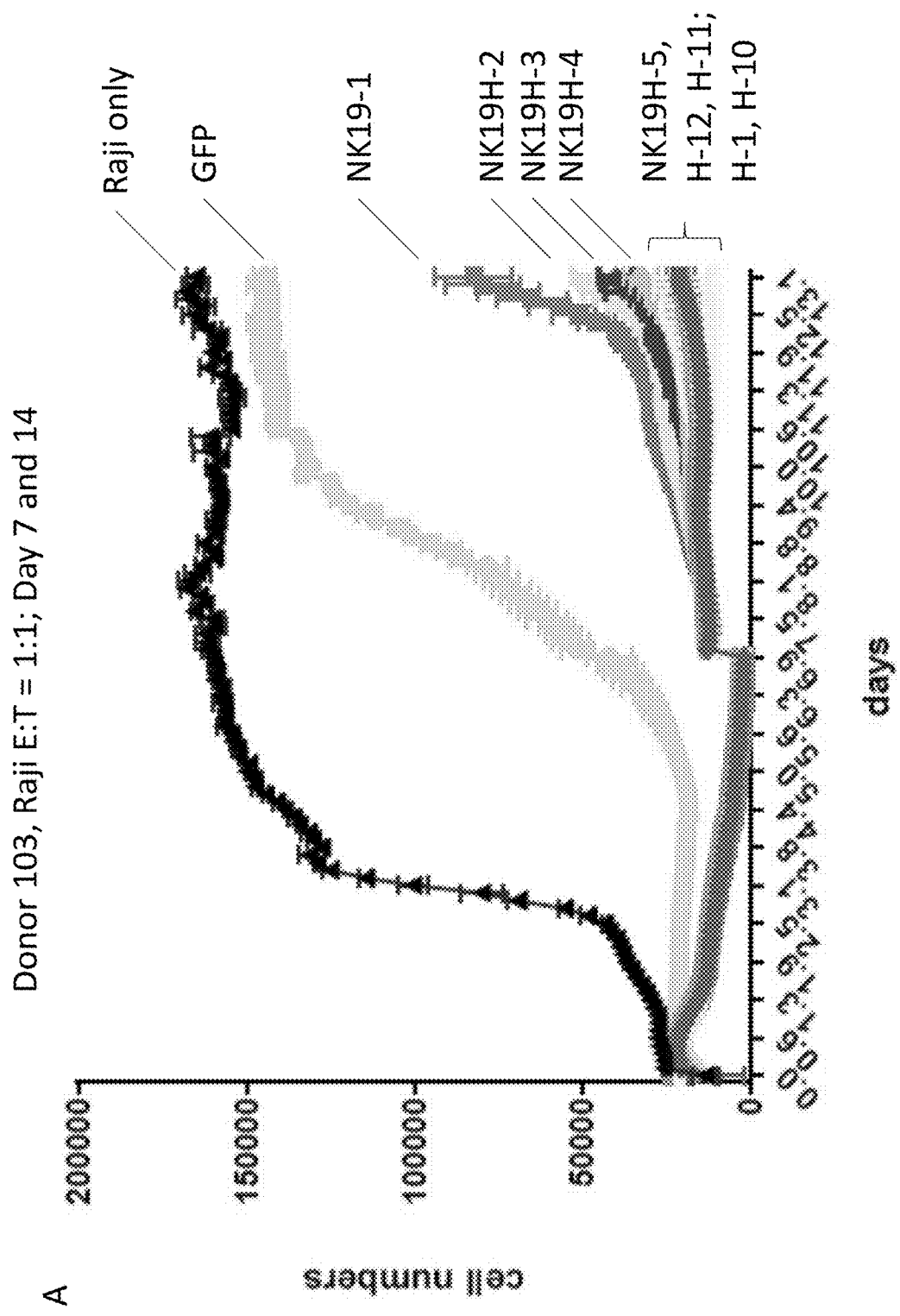
FIGS. 26A-26D show cytotoxicity data.
Figure 26B:
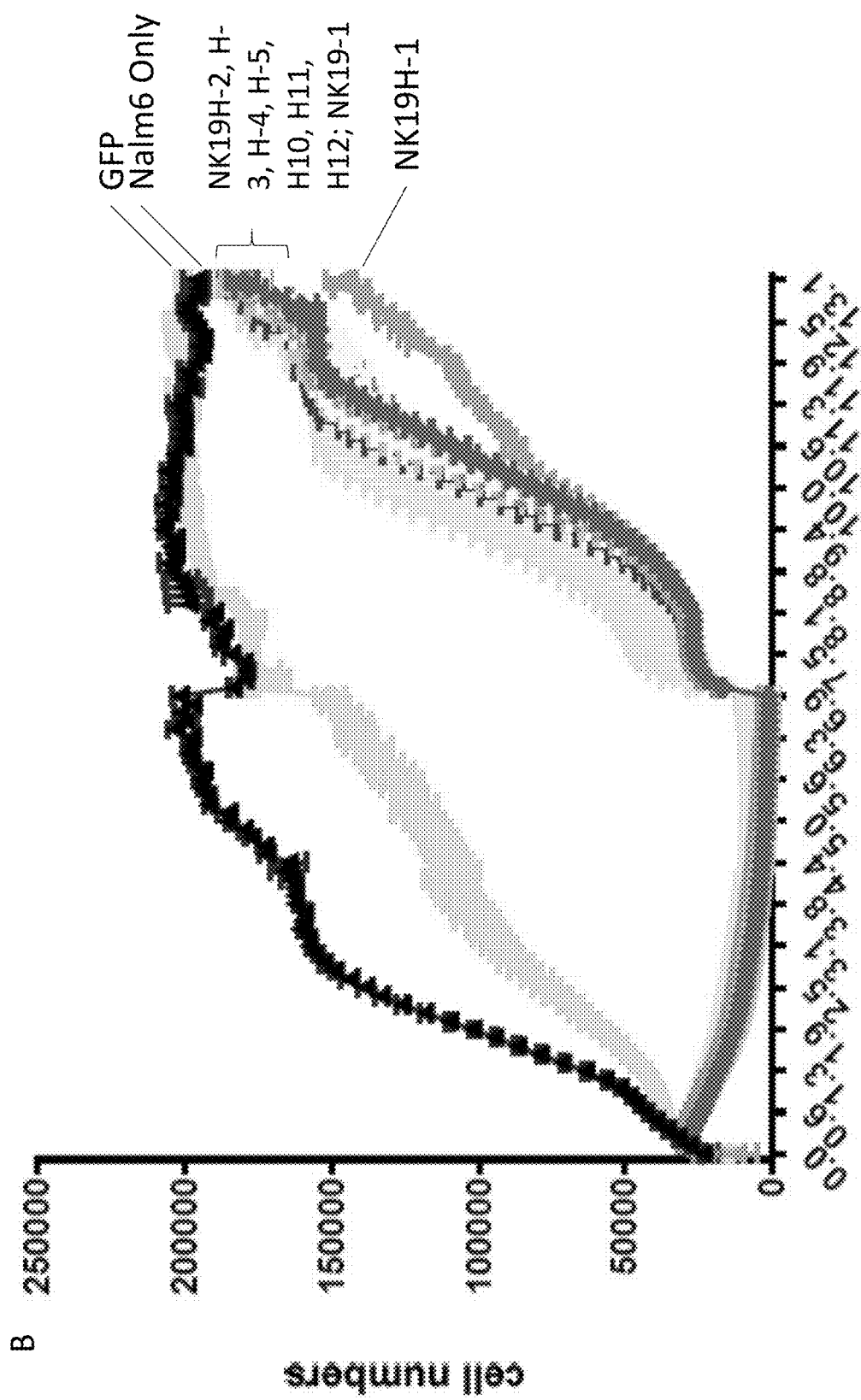

Similar to the experiments discussed above, Raji cells were exposed to NK cells from donor 103 which were transduced with the various constructs indicated (see FIG. 26A). Raji cells were co-cultured on day 7 post-transduction of the NK cells, and the NK cells were re-challenged again on day 14. As expected Raji cells alone exhibited continued growth, while GFP-transduced NK cells reduced that cell growth a small amount. In contrast, the positive control non-humanized NK19-1 construct reduced Raji cell growth until the very late stages of the experiment. Each of the humanized anti-CD19 CAR constructs yielded enhanced cytotoxicity against the Raji cells. Three of the constructs (NK19H-2, H-3, and H-4) allowed for minor Raji cell growth at the late stage of the experiment, while the other humanized constructs effectively eliminated Raji cell growth, even with the re-challenge at day 14. FIG. 26B shows corresponding data regarding the cytotoxicity of donor 103 NK cells against Nalm6 cells. As indicated in the Figure, all of the anti-CD19 CAR constructs (whether humanized or not) appeared exhibit significant cytotoxicity against the Nalm6 cells through 7 days of co-culture. However, Nalm6 growth increased for all groups with the day 14 re-challenge. While the growth curves initially were somewhat flat, Nlam6 growth later increased in rate. These data suggest that, according to some embodiments, a more frequent dosing strategy is employed to keep target cells from reaching a threshold growth rate. In several embodiments, a larger dose is given and/or a dose is given more frequently, to prevent target cell growth under a physiological equivalent context to a "re-challenge."

Figure 26C:
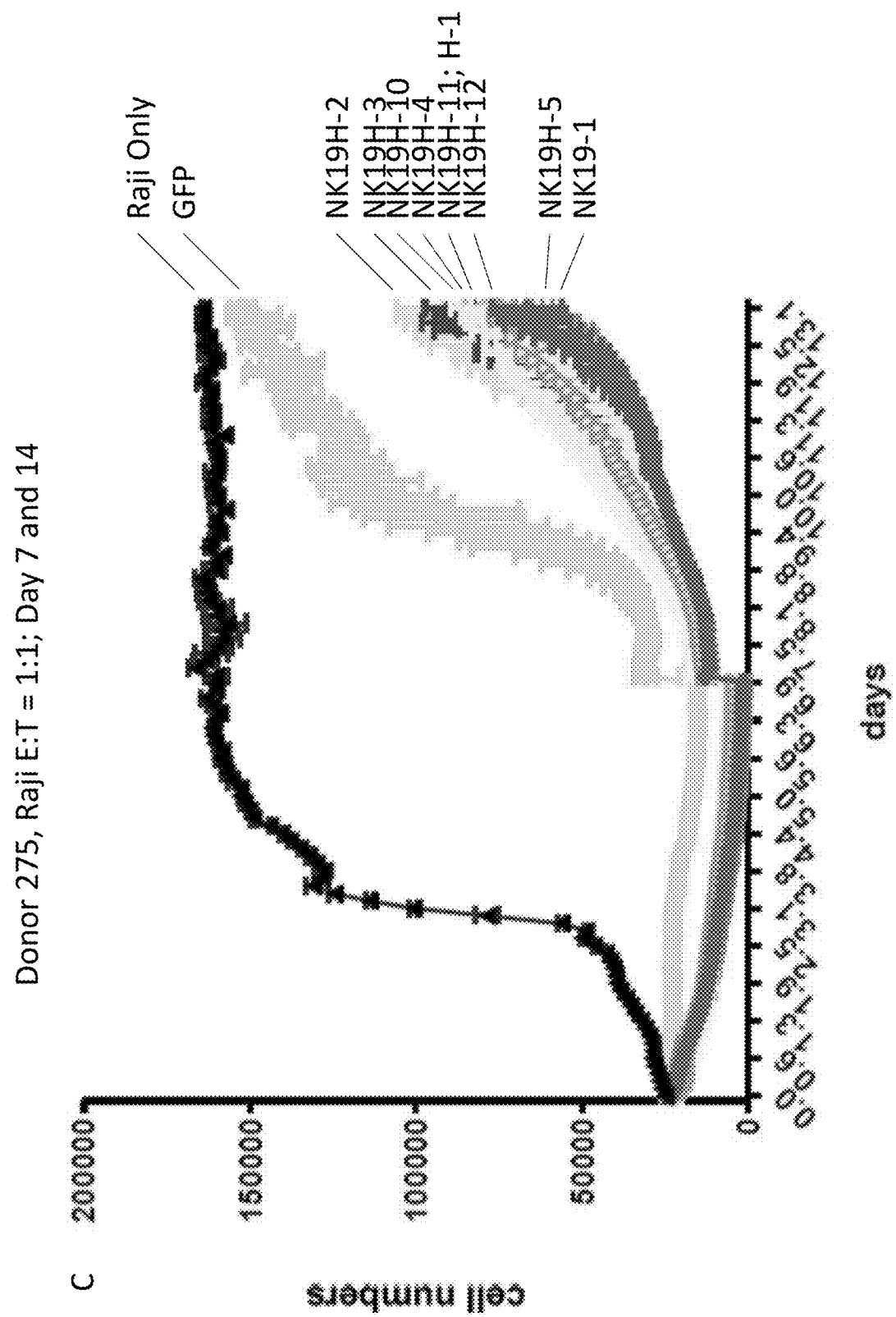
Figure 26D:
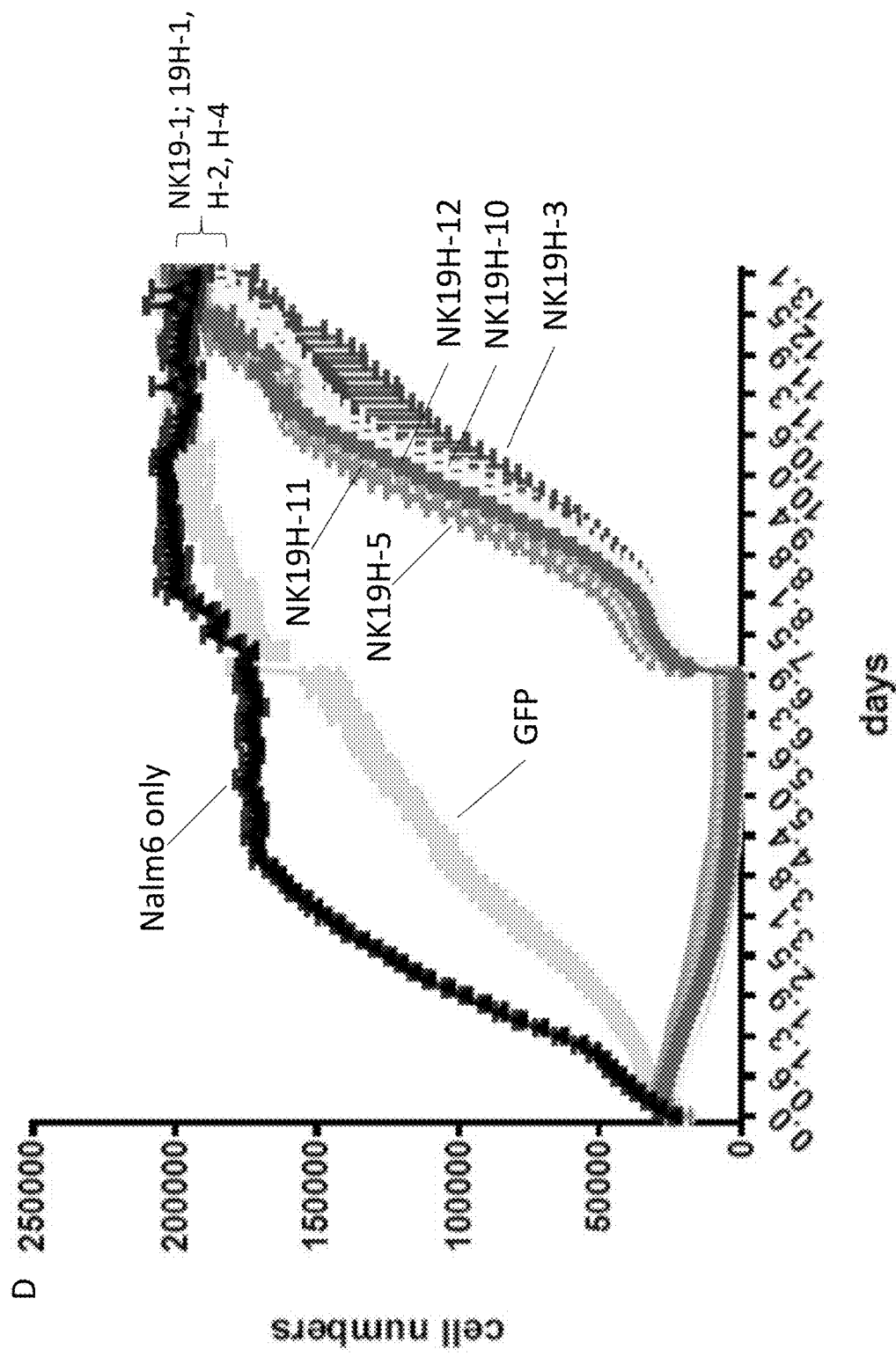

FIG. 26C shows data for Raji cells (as with FIG. 26A) with NK cells from donor 275. Similar to those of FIG. 26A, each of the anti-CD19 CAR constructs showed significant cytotoxicity against Raji cells, and allowing limited growth of the target cells, even with a re-challenge. FIG. 26D shows data for Nalm6 cells (as with FIG. 26B) with NK cells from donor 275. Results for this experiment were also similar to those for donor 103, with effective control of Nalm6 cells through 7 days, but reduced cytotoxicity after re-challenge. These data indicated that dosing strategies, depending on the embodiment, are developed for a specific donor and/or for a specific target tumor type. For example, while Nalm6 cells are CD19 positive, they may express less CD19 than, for example, Raji cells, thereby accounting for the reduced cytotoxicity of NK cells from donor 103 and 275 against the Nalm6 cell line. The efficacy of the transduced NK cells against the Raji cells indicates that the NK cells are capable of cytotoxicity, even showing persistence out to nearly two weeks post-transduction. Thus, according to several embodiments, an NK cell dose and/or dosing frequency can be tailored to a given patient's tumor type, native NK cell activity, and/or the aggressiveness/stage of a cancer to allow robust and ongoing cytotoxicity against the target cells and achieving control of tumor burden.

Figure 27A:
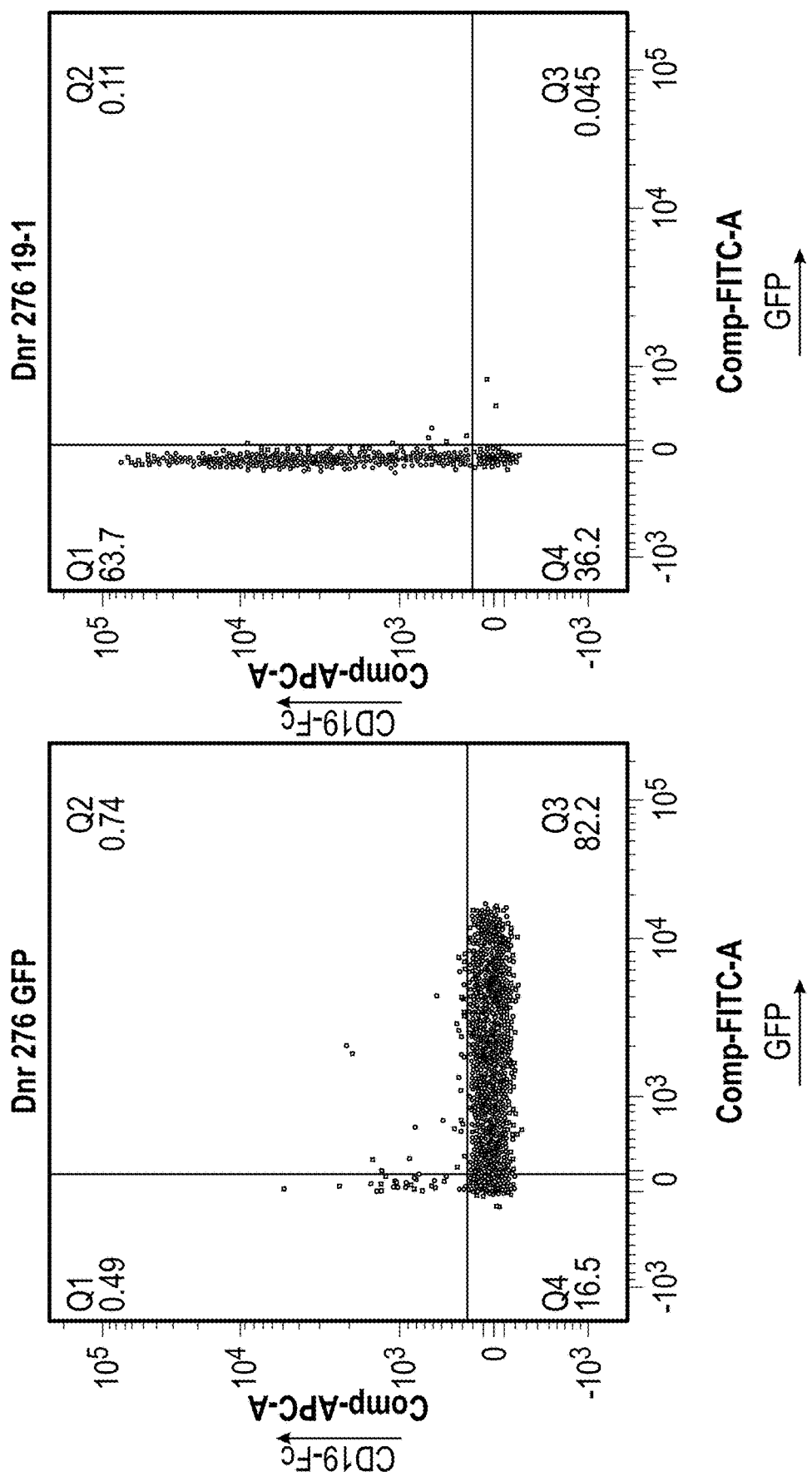
FIGS. 27A-27B show data related to CD19 expression by engineered NK cells.
Figure 27A:
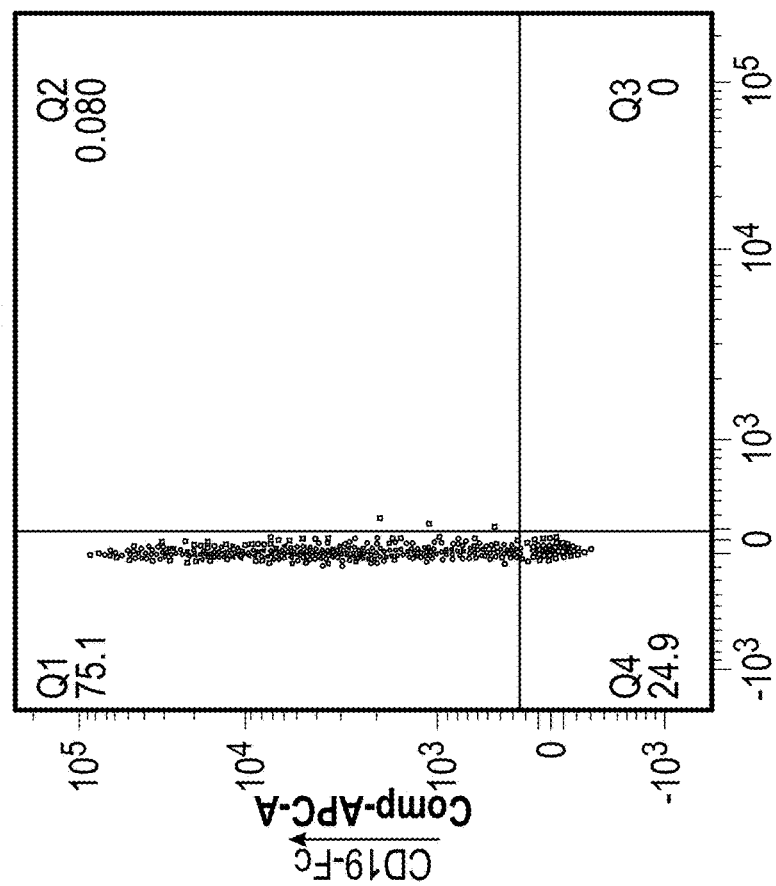
Figure 27A:
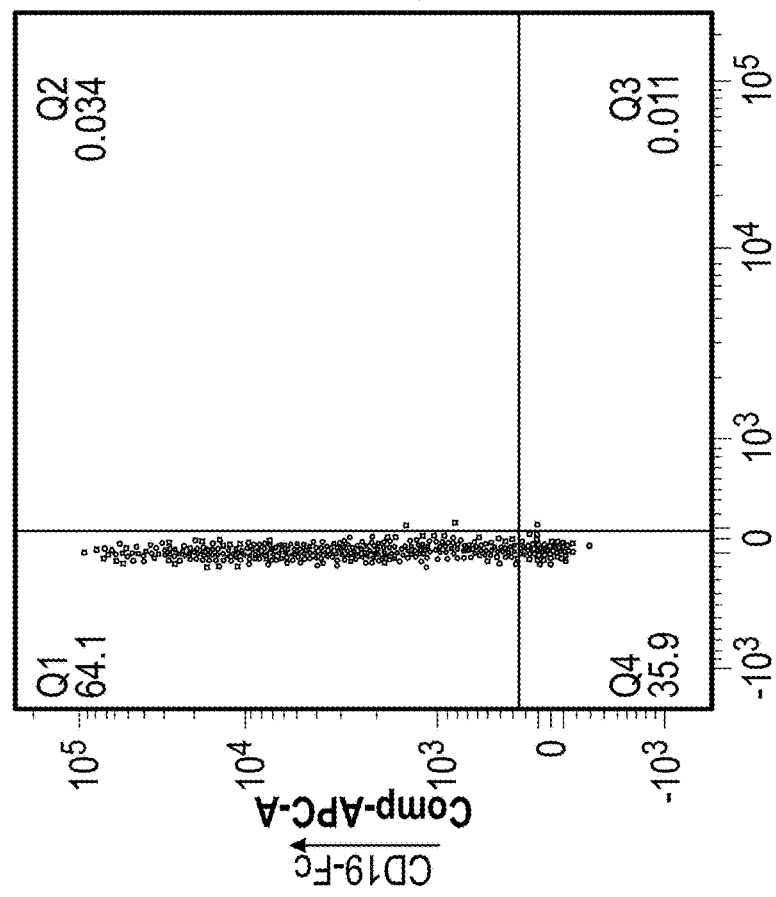
Figure 27A:
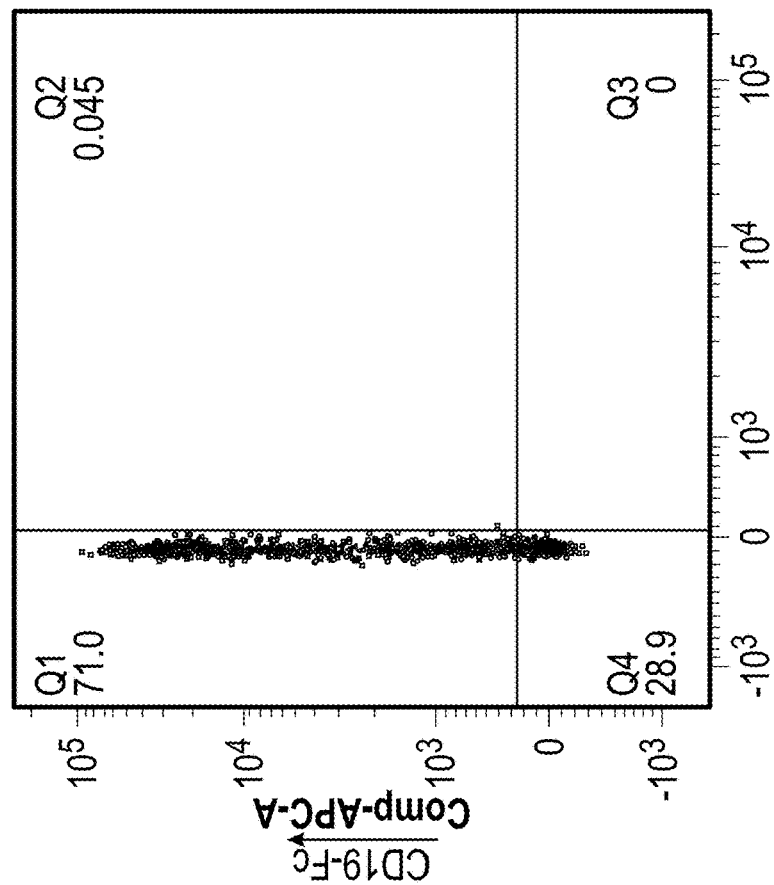
Figure 27A:
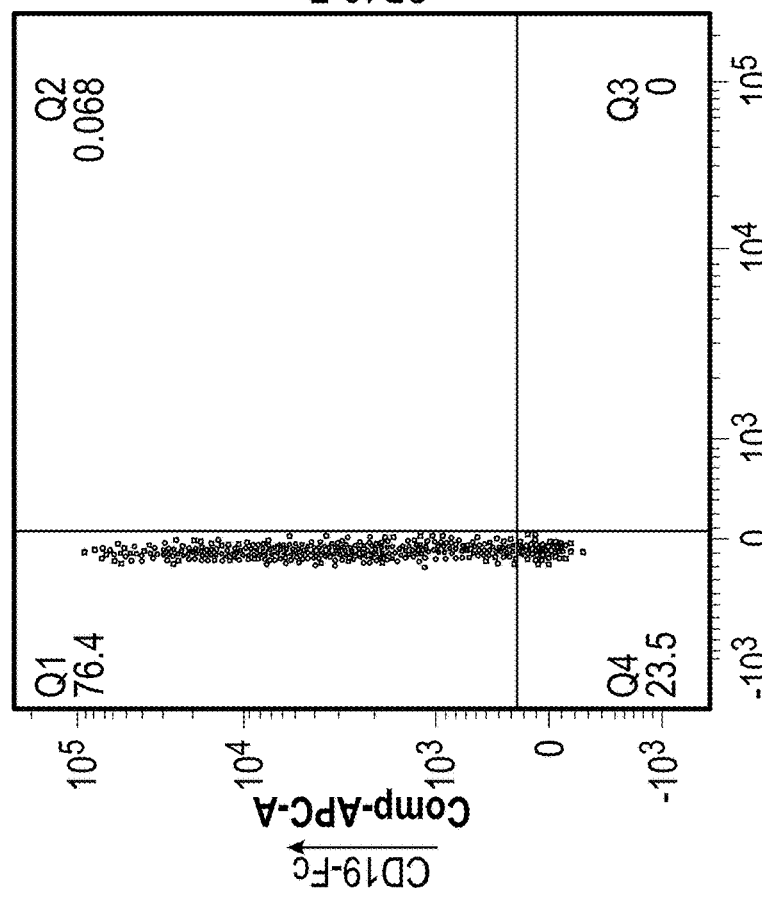
Figure 27B:
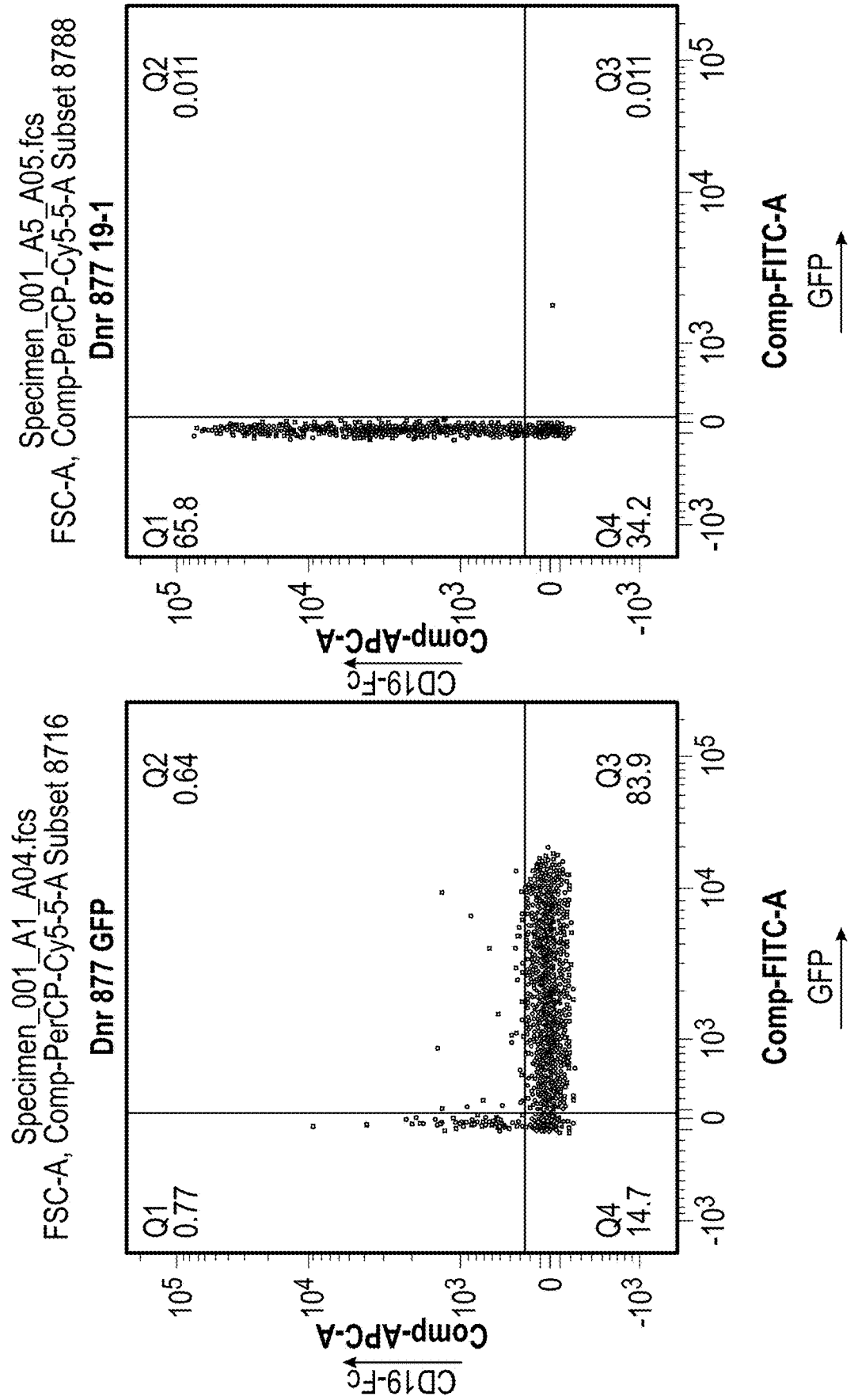
Figure 27B:
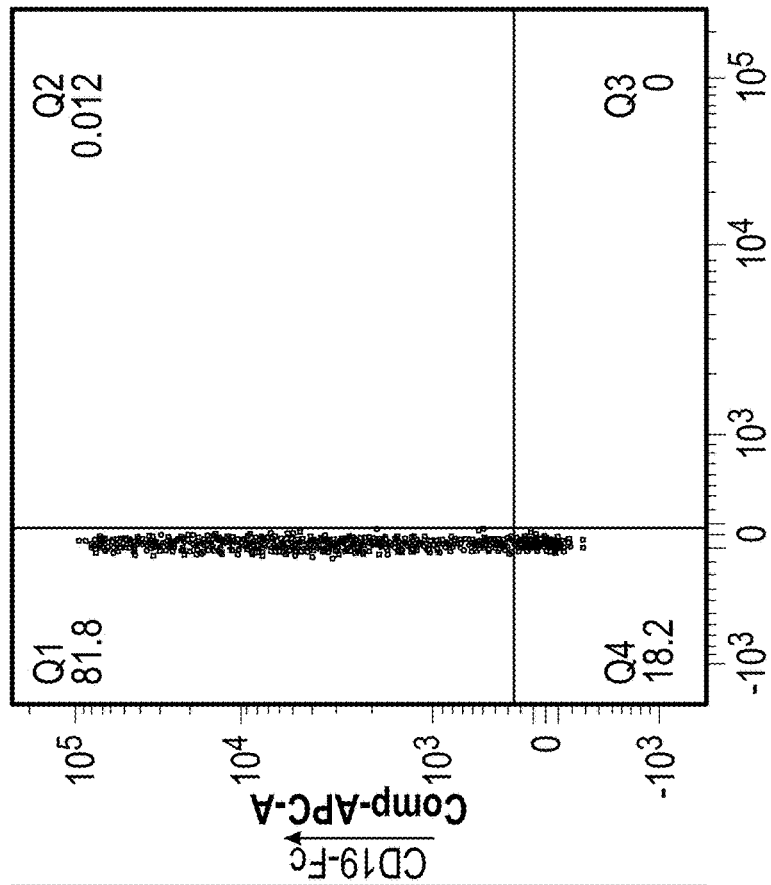
Figure 27B:
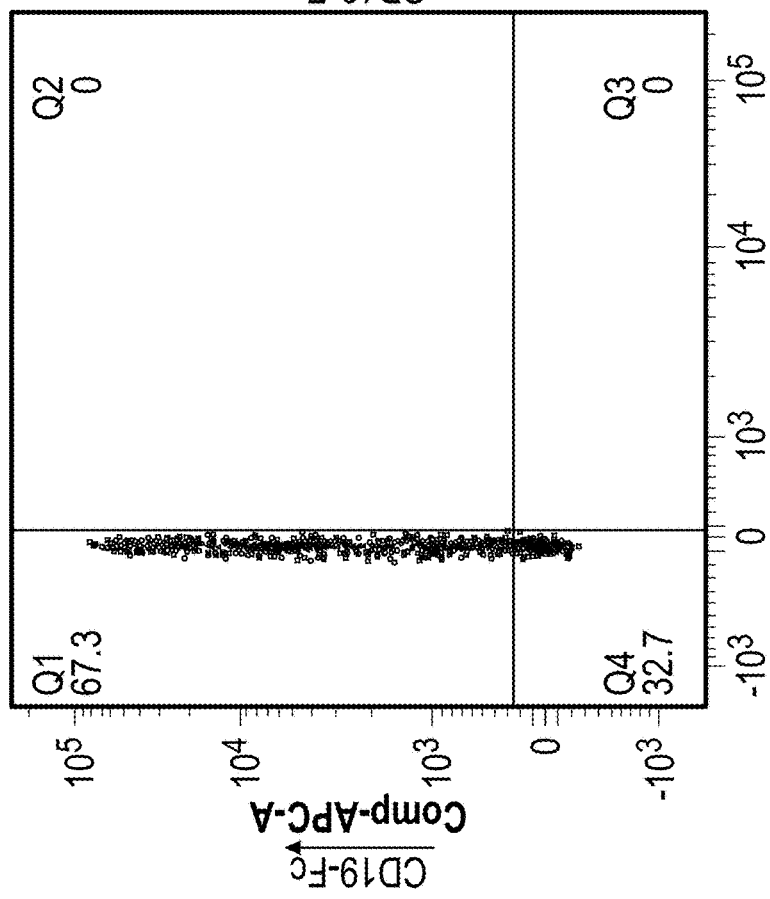
Figure 27B:
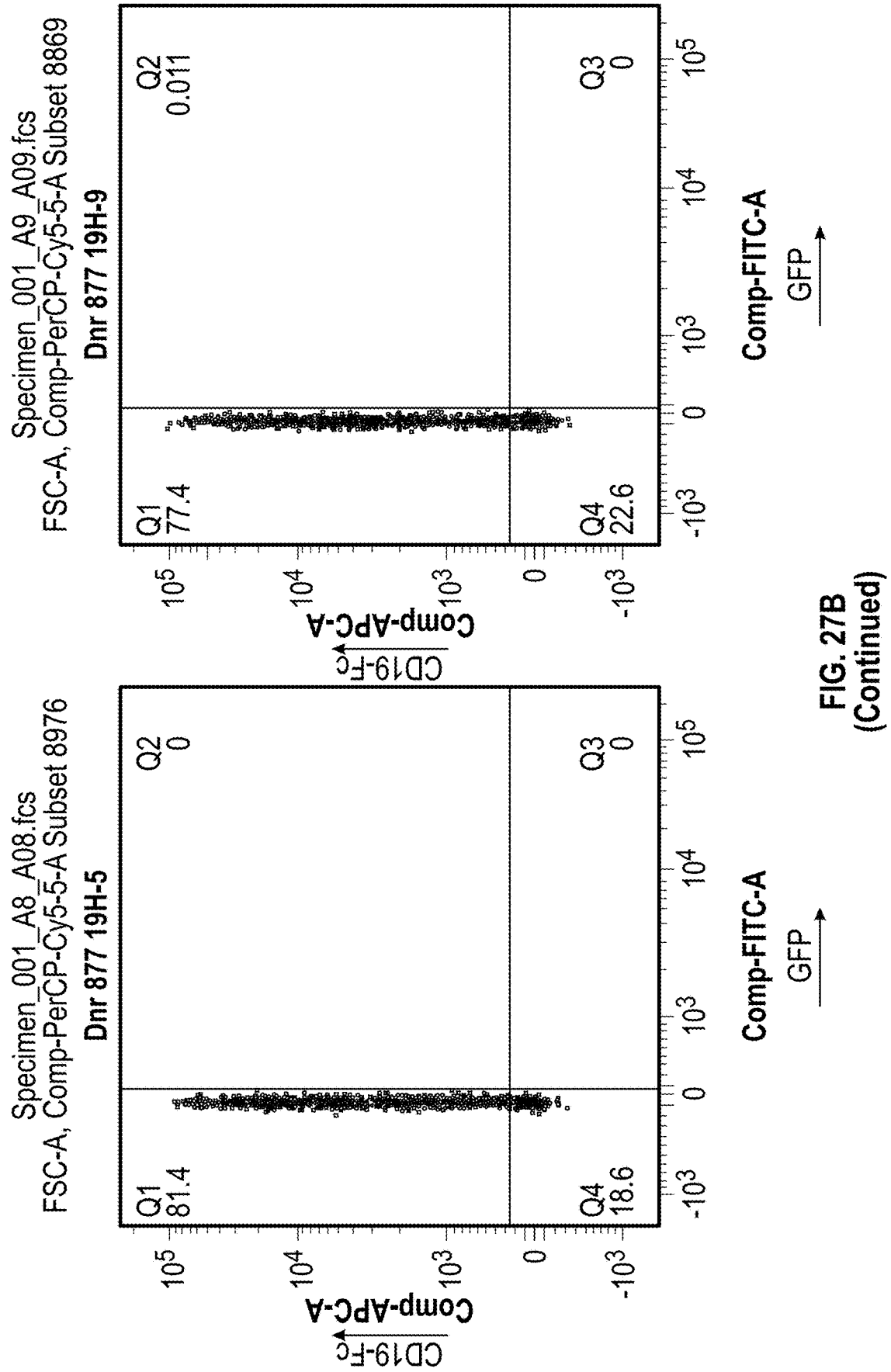

FIGS. 27A-27B show flow cytometry data that characterizes NK cells from two donors (276 in FIG. 17A and 877 in 27B) transduced with non-limiting examples of anti-CD19 CAR constructs as disclosed herein. FIGS. 27A and 27B both show that NK cells transduced with GFP express little to no CD19-Flag. Each of the other panels demonstrates that the NK cells from these donors can express not only the positive control non-humanized NK19-1 construct, but also efficiently express the selected humanized anti-CD19 CAR constructs. This is indicative of the limited impact that humanization of the anti-CD19 binder has on expression characteristics.

Figure 28A:
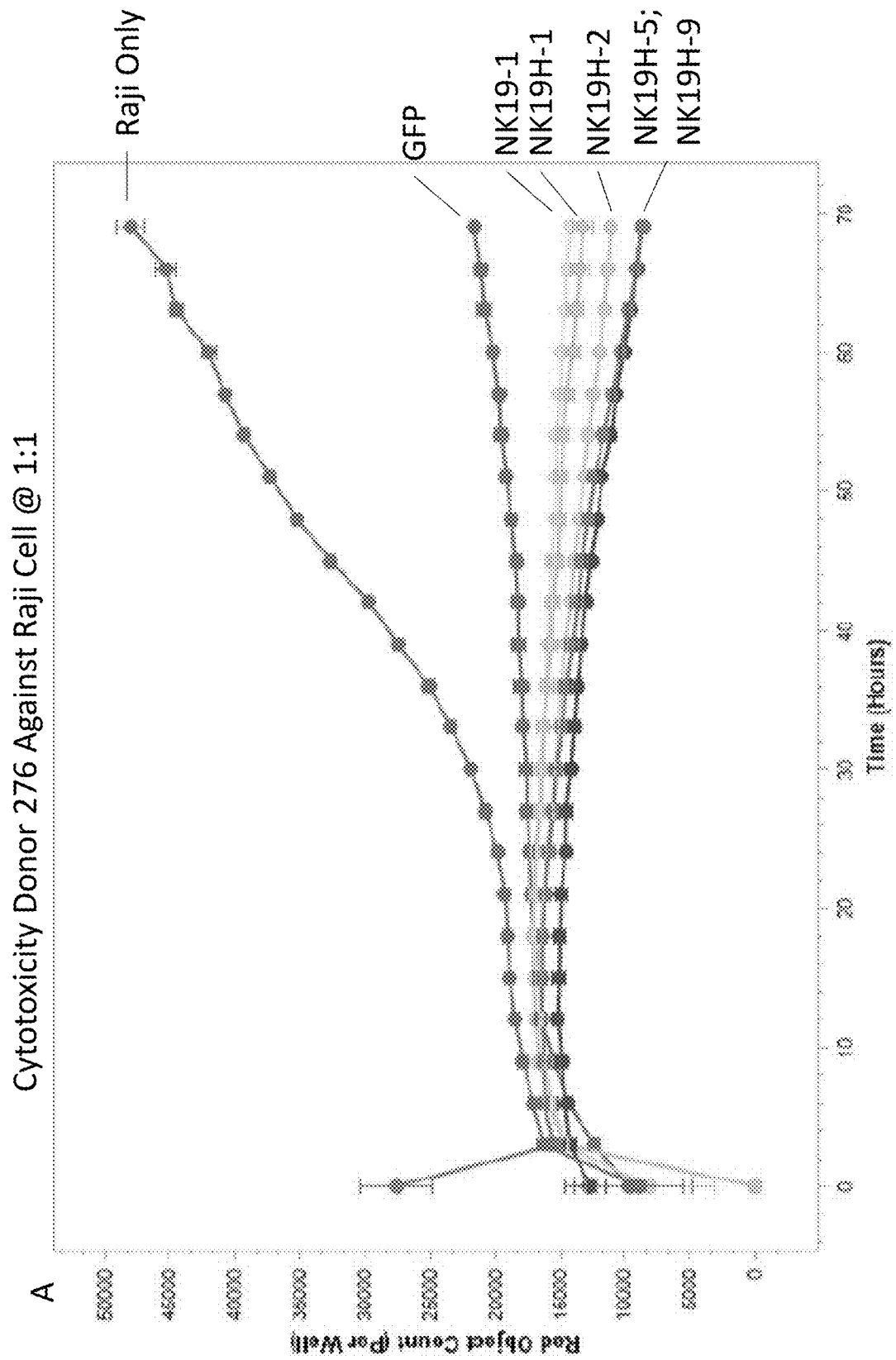

FIGS. 28A-28B show initial data for NK cell cytotoxicity of those two donors from FIG. 27 against Raji cells at an E:T ratio of 1:1. Consistent with results discussed above, each of the selected humanized anti-CD19 CAR constructs endowed transduced NK cells with significant cytotoxic potential against the target Raji cells. Each of the indicated non-limiting examples of anti-CD19 CAR constructs effectively controlled Raji cell growth (equivalent to, or enhanced as compared to, the non-humanized NK19-1 construct) with the trend of decreasing Raji cell numbers even as long as 70 hours after inception of the experiment. Similarly, FIG. 28B shows that transduced NK cells from donor 877 also effectively control Raji cell growth, equivalent to, or enhanced as compared to, the non-humanized NK19-1 construct. These data are in line with those presented for NK cells from other donors, discussed above, and indicate that, in accordance with several embodiments disclosed herein, transduction of NK cells with humanized anti-CD19 CARs enable the engineered NK cells to exert significant cytotoxic effects against target tumor cells and can effectively control growth of tumor cells. According to several embodiments, such engineered anti-CD19 NK cells (whether allogeneic or autologous) allow for robust and effective cellular immunotherapy to treat cancers.

Example 8

Figure 29A:
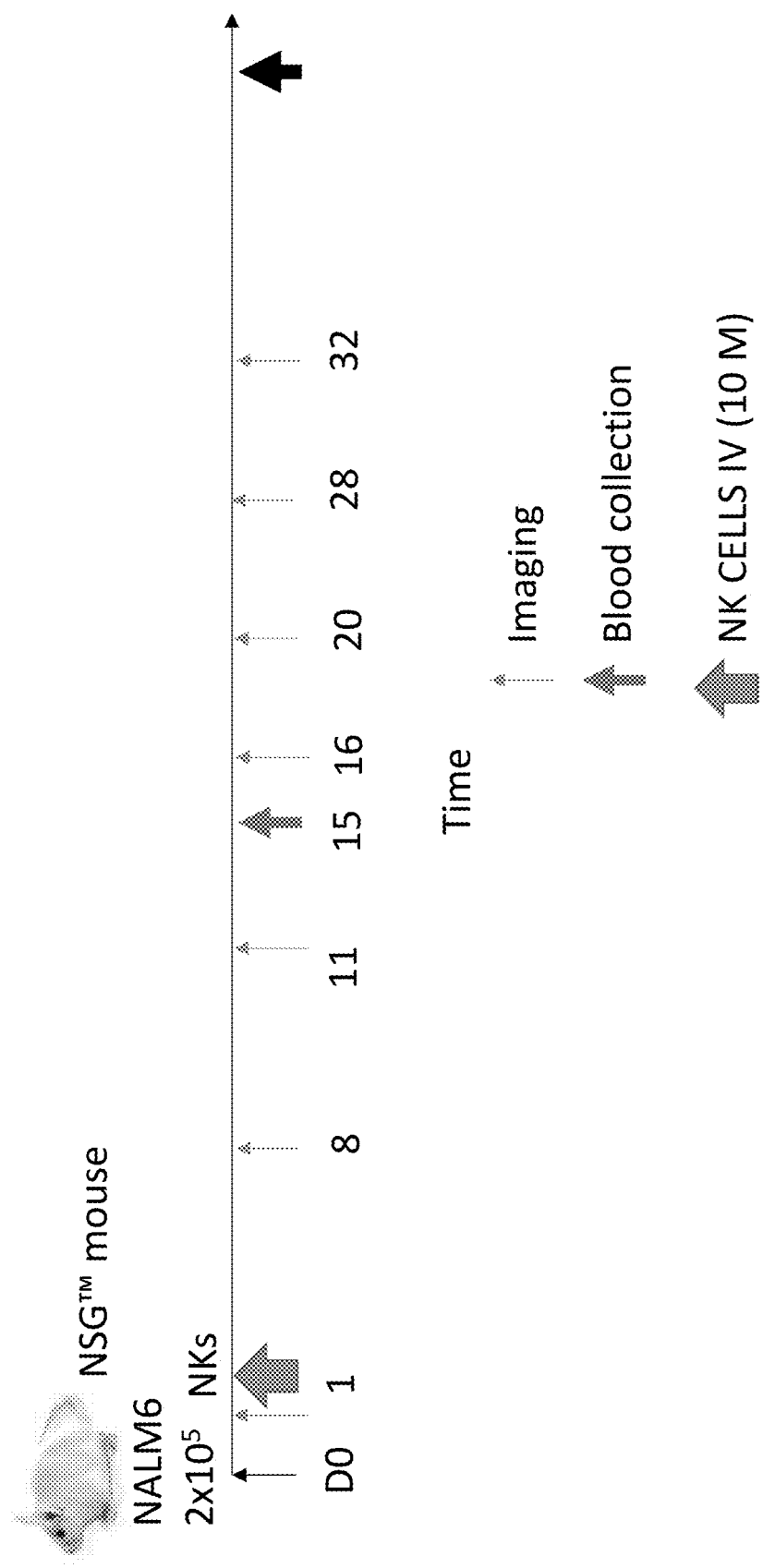
FIGS. 29A-29E show data related to various humanized CD19-directed CAR constructs and their efficacy in an in vivo model.
Figure 29B:
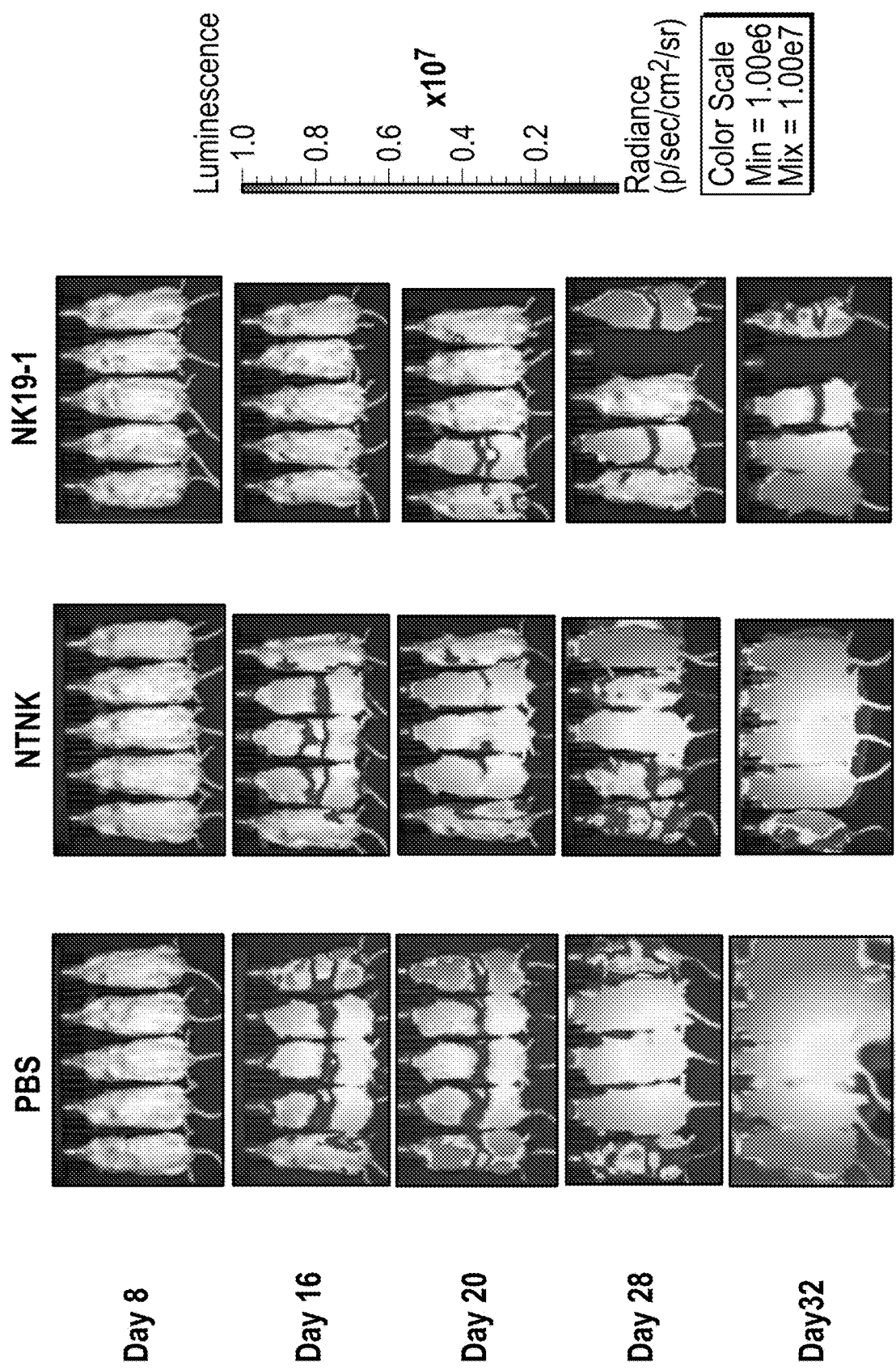
Figure 29B:
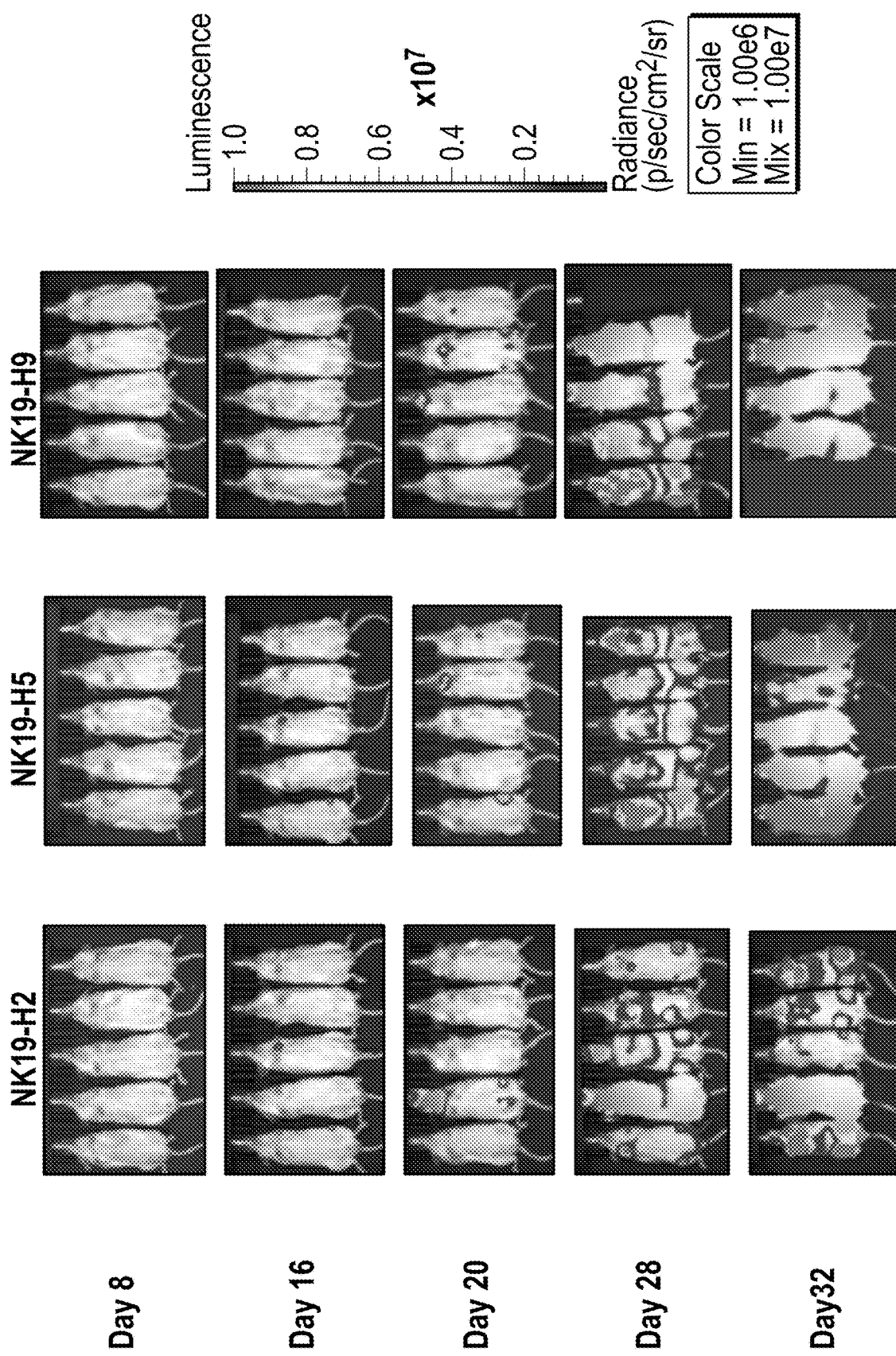
Figure 29C:
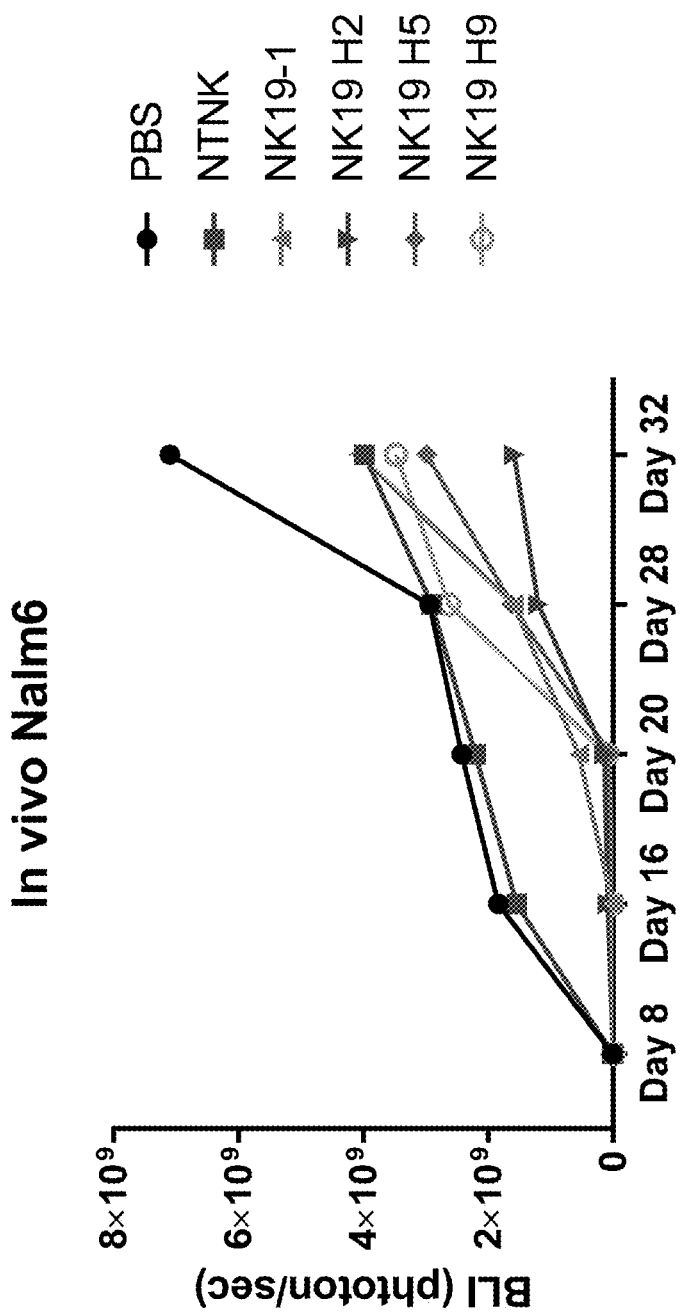
Figure 29D:
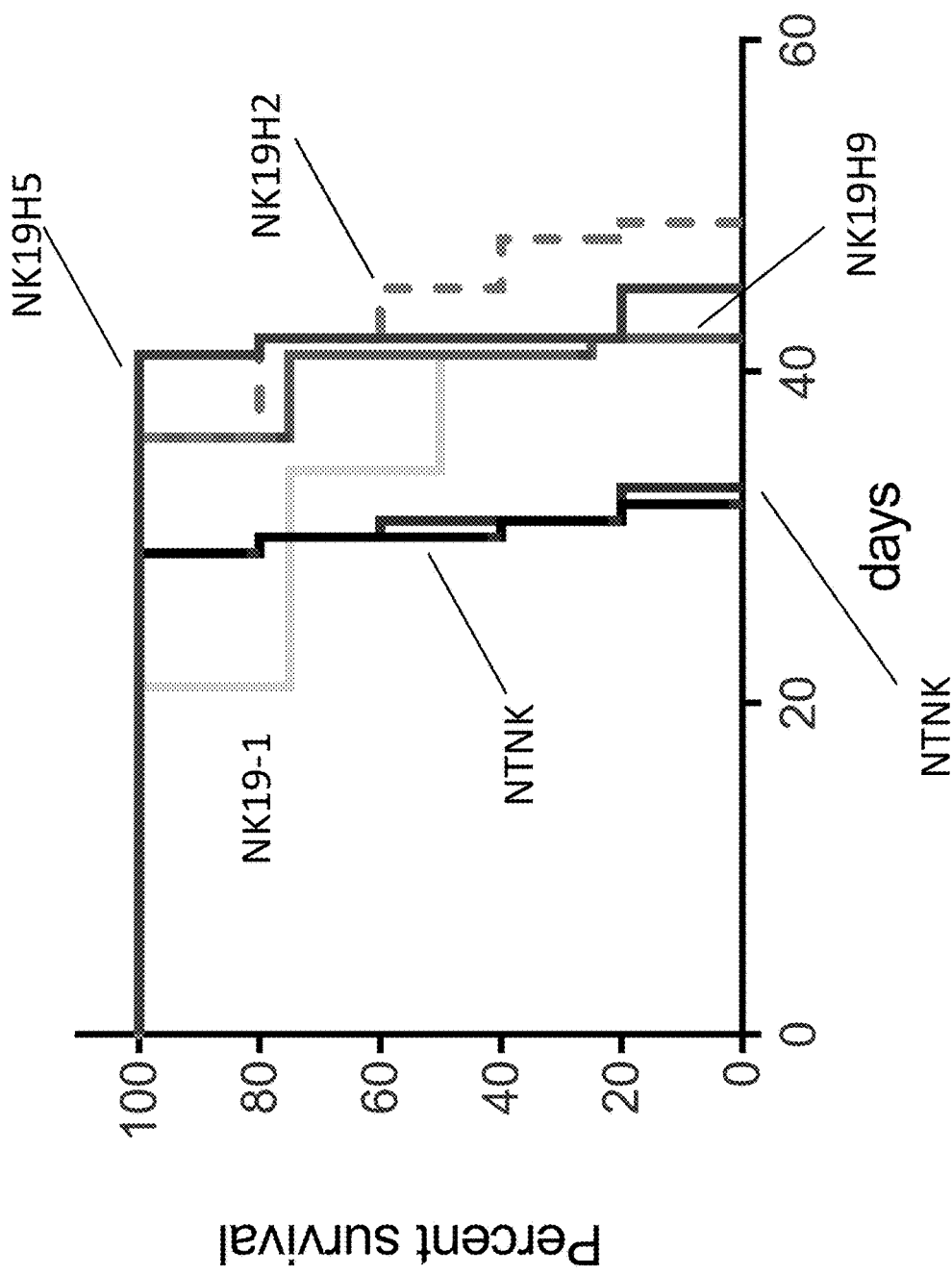
Figure 29E:
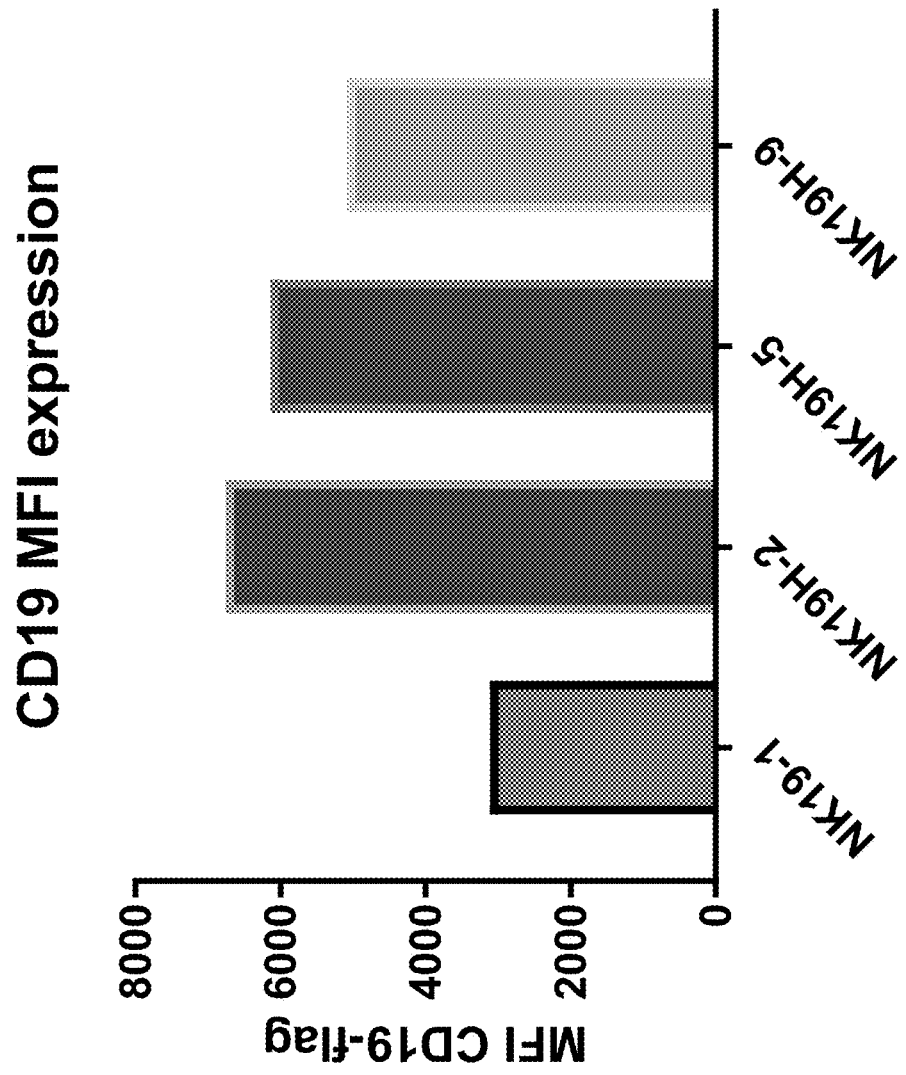

Further experiments were conducted to evaluate humanized CD19 CAR constructs as disclosed herein. FIG. 29A shows a schematic of the experimental protocol. Briefly, NSG mice were injected on Day 0 with 1×10⁵ Nalm6 cells (expressing a fluorescent reporter) intravenously. At Day 1, mice received either a PBS control injection, non-transduced K cells ("NTNK", 10M), 10 million NK cells expressing the non-humanized NK19-1 CAR, or 10 million NK cells expressing one of various humanized CD19 CAR constructs. Blood collection and fluorescent imaging were performed as indicated. Bioluminescence data is shown in FIG. 29B. As shown, the injection of NK cells expressing any CD19 CAR construct resulted in a reduced progression of Nalm6 growth. The humanized constructs tested (NK19-H2, NK19-H5, and NK19H-9) each showed significant delay in Nalm6 growth compared to controls. FIG. 29C is a line graph depicting the measured bioluminescence over 31 days. As shown, each of the humanized constructs tested in this experiment showed reduced tumor progression as compared to controls, and slightly reduced as compared to non-humanized NK19-1. FIG. 29D shows a survival curve that reflects the reduction in tumor progression, with the mice treated with NK19-1 or any of the selected humanized constructs surviving longer than the control groups. FIG. 29E shows data related to an evaluation of the expression of each of the humanized constructs on the NK cells. As shown, each of the humanized constructs expressed more robustly than the non-humanized NK19-1 construct. In accordance with several embodiments disclosed herein, the use of a humanized construct results in a more efficacious therapeutic, at least in part due to the enhanced expression (and/or activity) of the CAR by the NK cells.

Figures 30A, 30B:
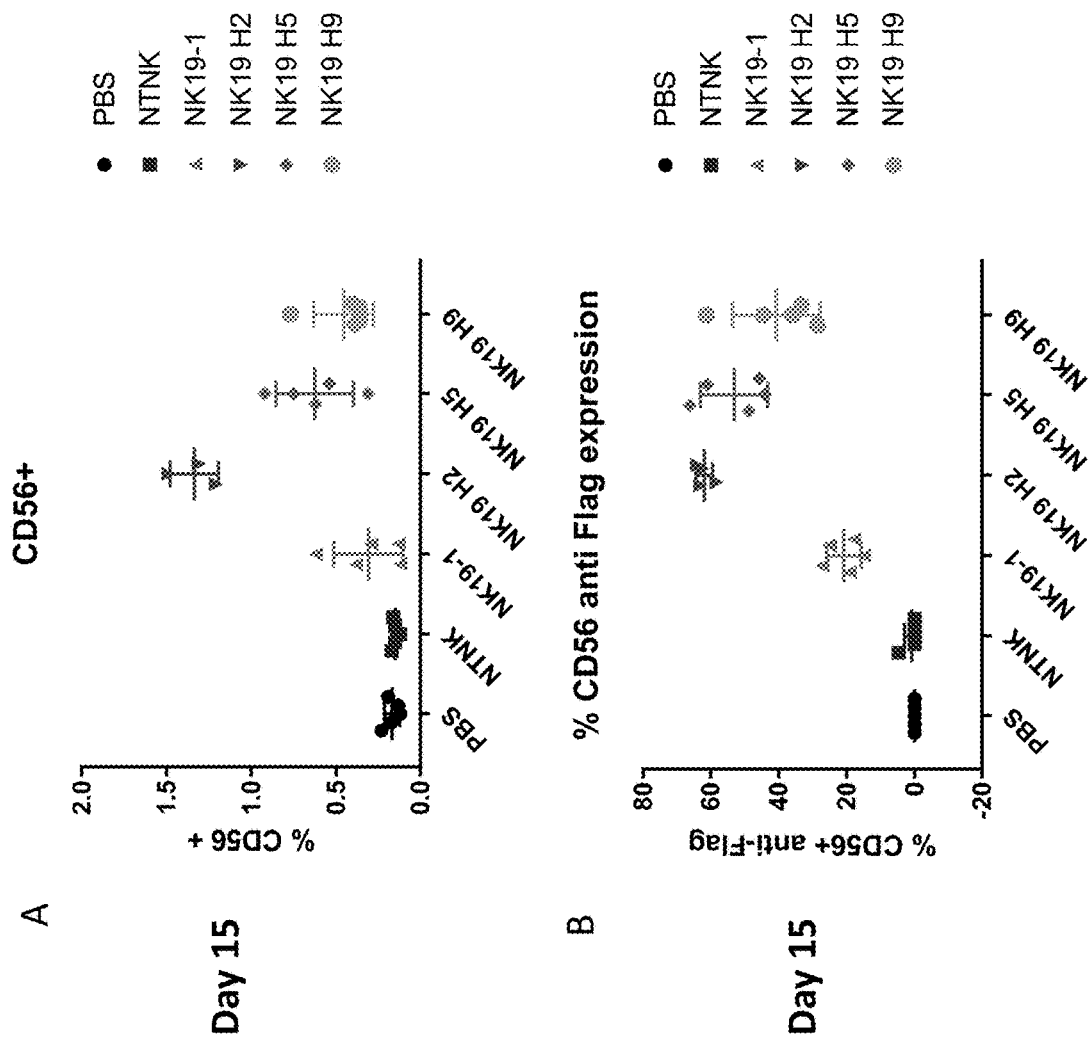
FIGS. 30A-30F relate to expression of the indicated CD19-directed CAR constructs.
Figures 30C, 30D:
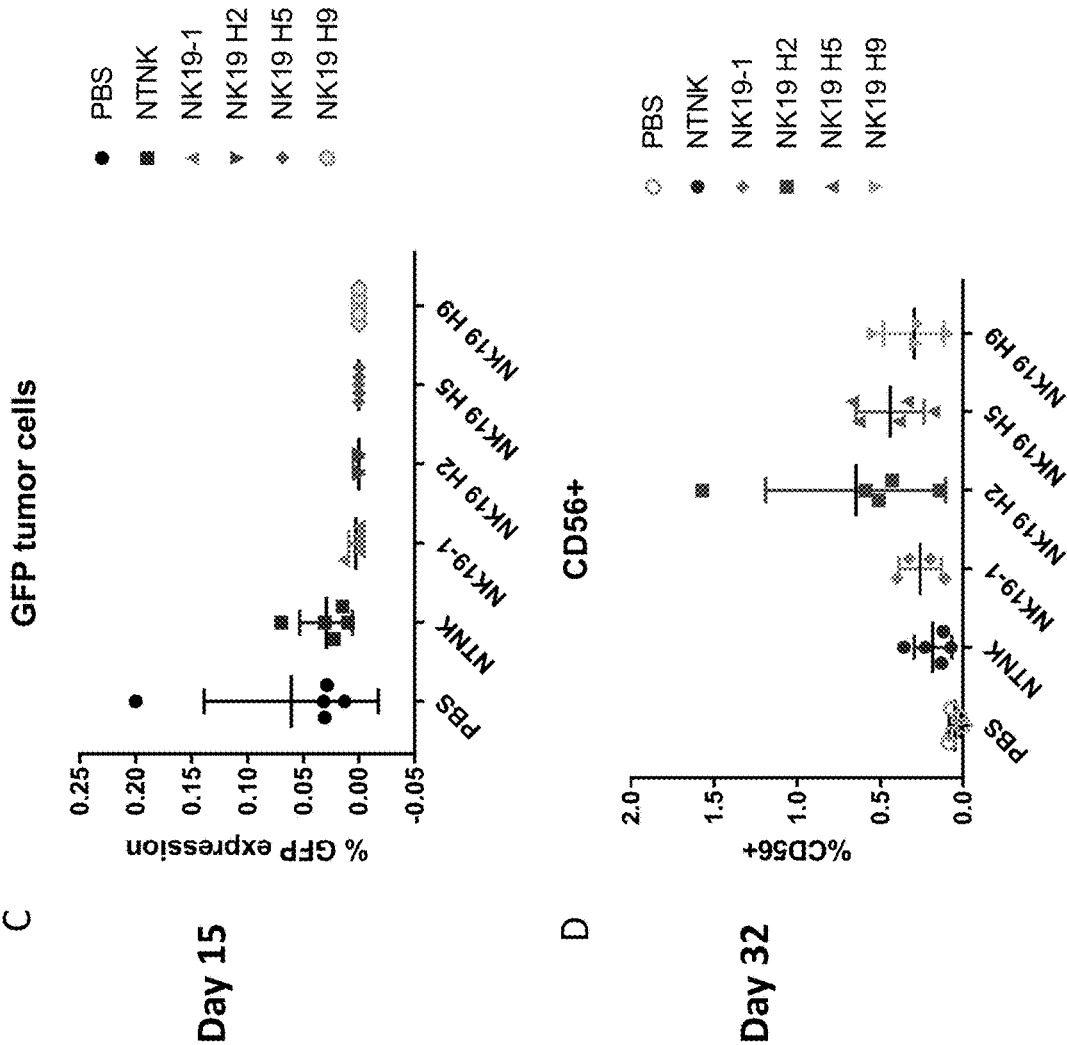
Figures 30E, 30F:
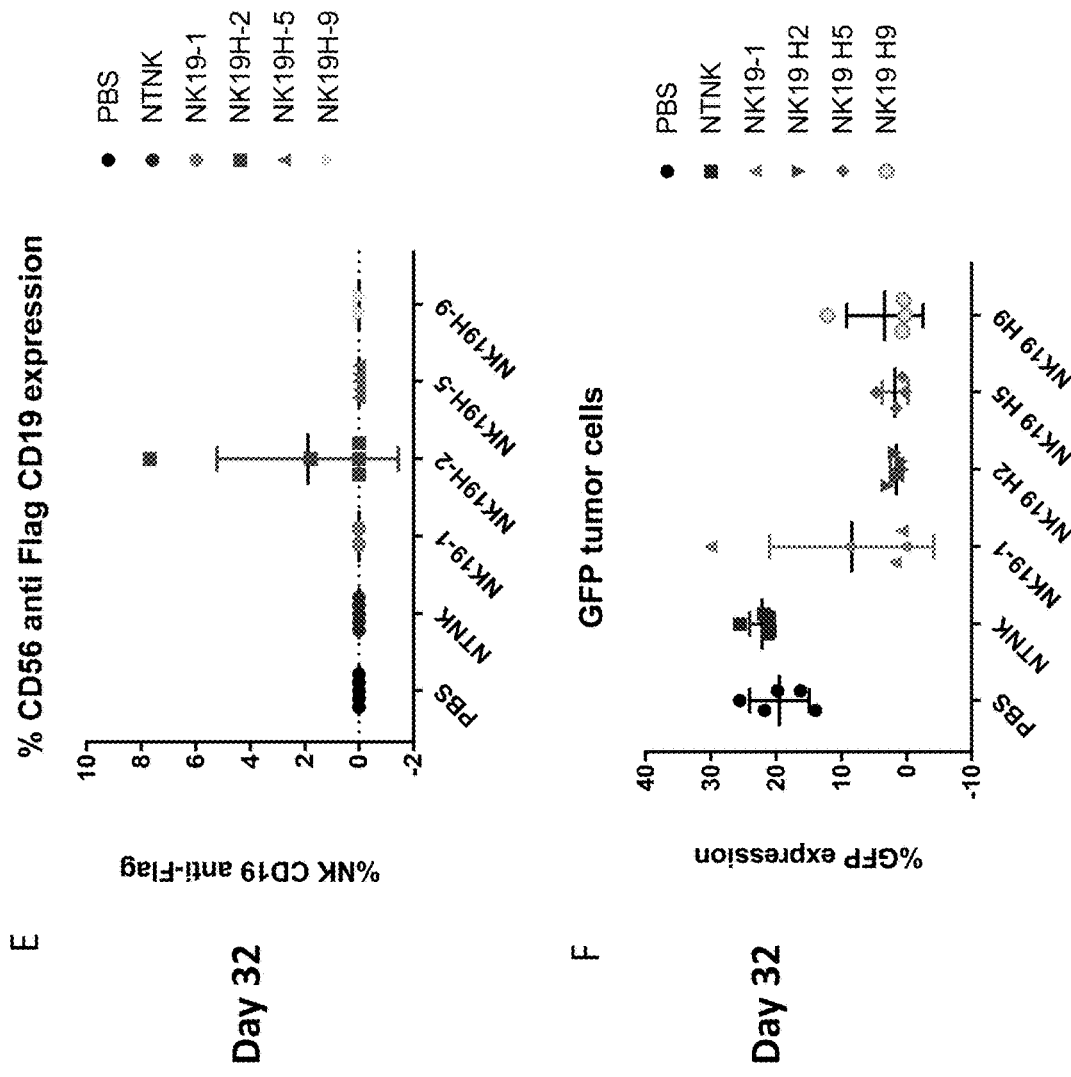

FIGS. 30A-30F relate to characteristics of cells in the blood of the mice treated with the indicated constructs at various time points during the experiment. FIG. 30A shows the percentage of human CD56+ cells in the peripheral blood of the mice, which represents the survival of the administered NK cells through the first fifteen days of the experiment. Each of the experimental groups exhibit a higher percentage of cells, with the NK19-H2 construct exhibiting the most persistence of those tested. FIG. 30B shows similar data, based on the detection of the flag expression tag used in these constructs (though, in several embodiments, no tag is used). These data show that the humanized constructs are expressed at greater levels than the non-humanized constructs. FIG. 30C shows the detection of GFP positive tumor cells after 15 days. The CAR-expressing NK cells show nearly zero GFP expression, reflective of their inhibition of Nalm6 growth at Day 15. FIGS. 30D-30F show similar data at Day 32. These data show that the NK cells expressing humanized CD19 CAR constructs make up a greater percentage of the cells present in the peripheral blood of the mice tested, which is consistent with the increased efficacy of these constructs at controlling tumor growth at later time points. FIG. 30F shows that there is little difference in expression among the humanized CD19 CAR constructs at day 32. FIG. 32F reflects the enhanced ability of NK cells expressing the humanized CD19 CAR constructs at controlling tumor growth, with the detected GFP-positive cells being lower in the humanized treatment groups, even as compared to the animals receiving NK19-1. In several embodiments, the enhanced efficacy is due, at least in part, to the enhanced expression of the humanized CD19 CAR constructs.

Example 9

Figures 31A, 31B:
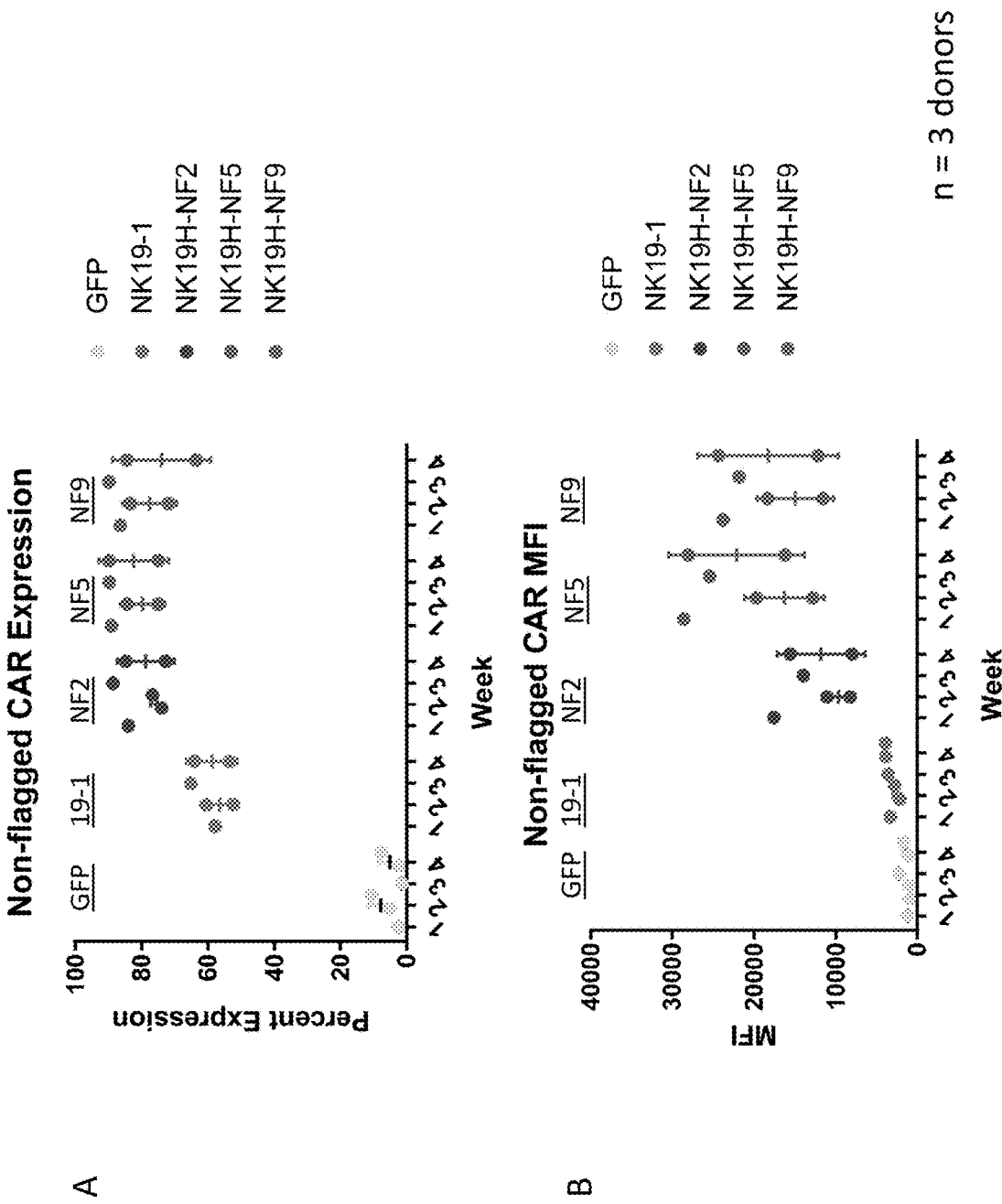
FIGS. 31A-31B show data related to the expression of non-tagged CD19 CAR constructs. As discussed herein, in several embodiments the CD19 CAR constructs comprise a Flag, or other tag, for detection purposes. However, all constructs disclosed herein with a tag are also included herein without a tag.

As discussed above, in some embodiments, CAR constructs comprise a detection tag. However, in several embodiments, no tag is used. Experiments were performed in order to evaluate the expression of non-flagged humanized CARS. This experiment employed NK19H-NK-2, -5 and -9 as non-limiting examples of non-flagged humanized CARs. FIGS. 31A-31B show expression data (percent expression in 31A, mean fluorescence in 31B) of the indicated construct by NK cells from three different donors, measured each week for 4 weeks. These data demonstrate that non-flagged versions of the CD19 CAR constructs as provided for herein express relatively similarly to one another, but more robustly than non-humanized constructs. Each of the non-flagged humanized constructs were expressed on at least about 70-80% of the NK cells.

Example 10

Figures 32A, 32B:
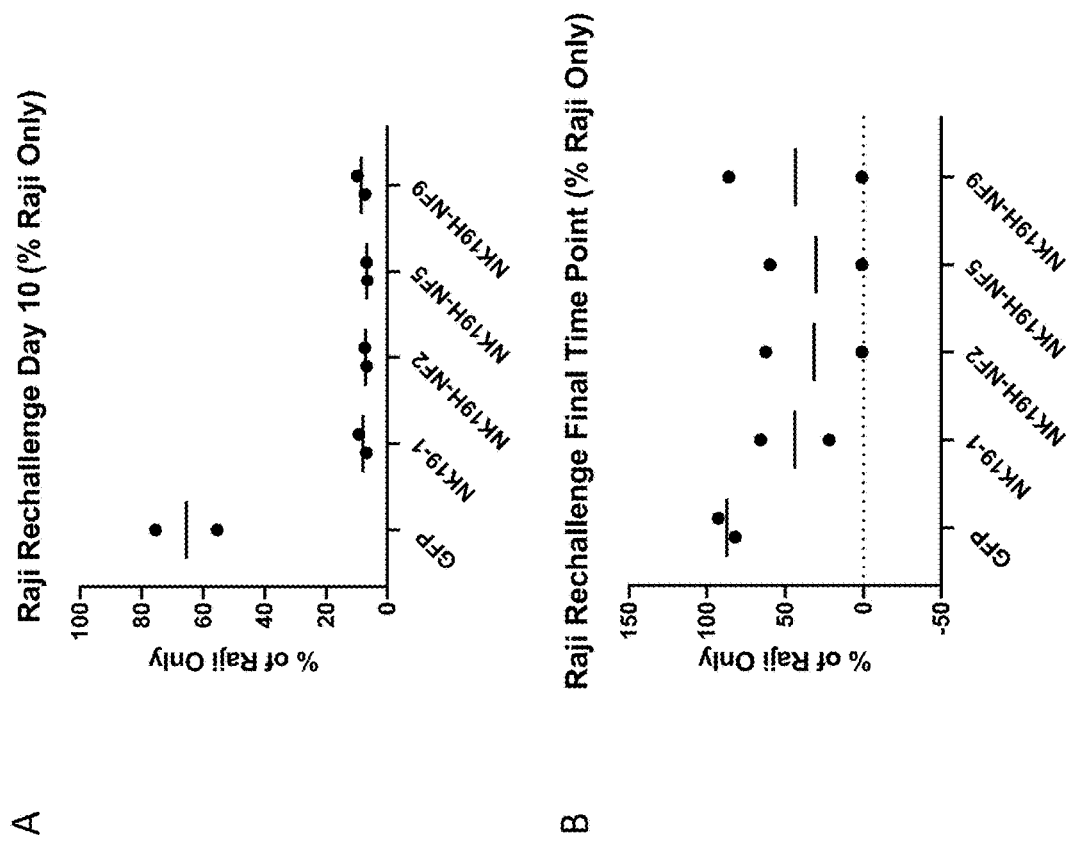
FIGS. 32A-32D show data related to an in vitro re-challenge experiment in which a first population of tumor cells were co-cultured with NK cells expressing the indicated constructs and the NK cells were "rechallenged" with an additional bolus of tumor cells.
Figures 32C, 32D:
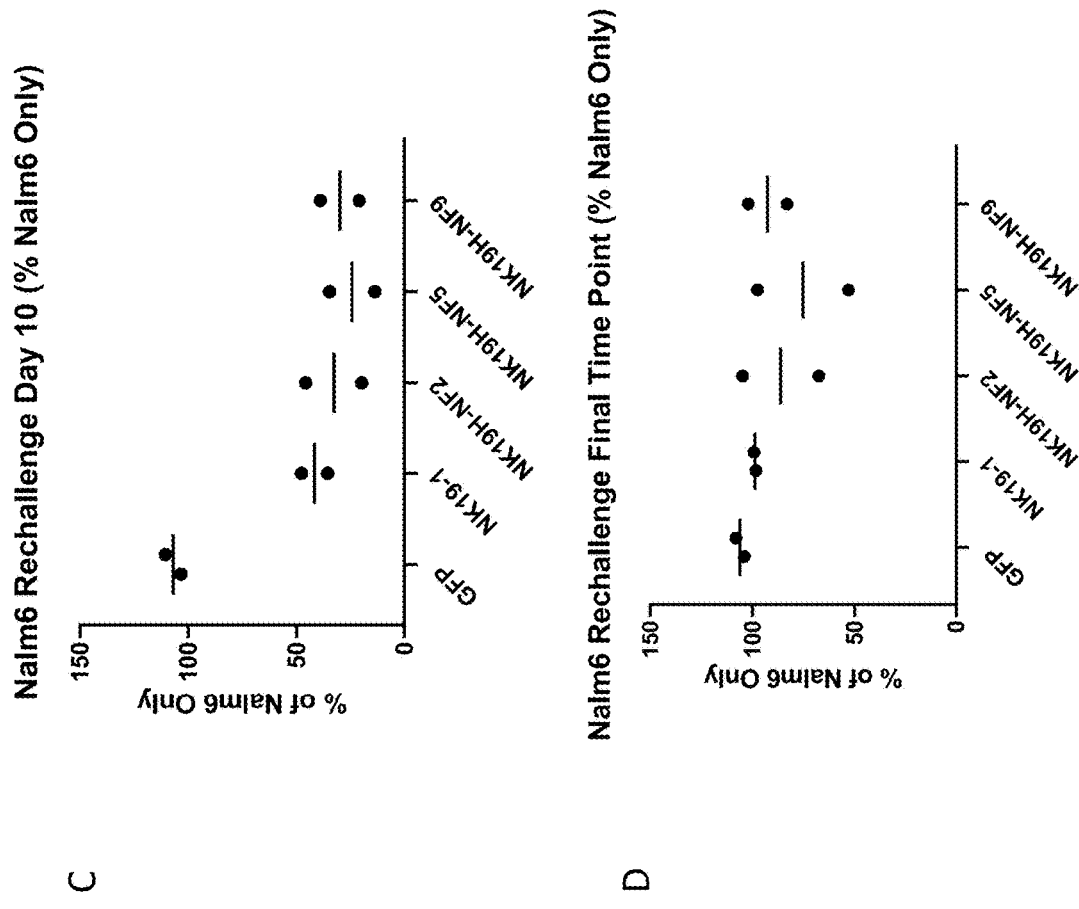
Figures 33A, 33B:
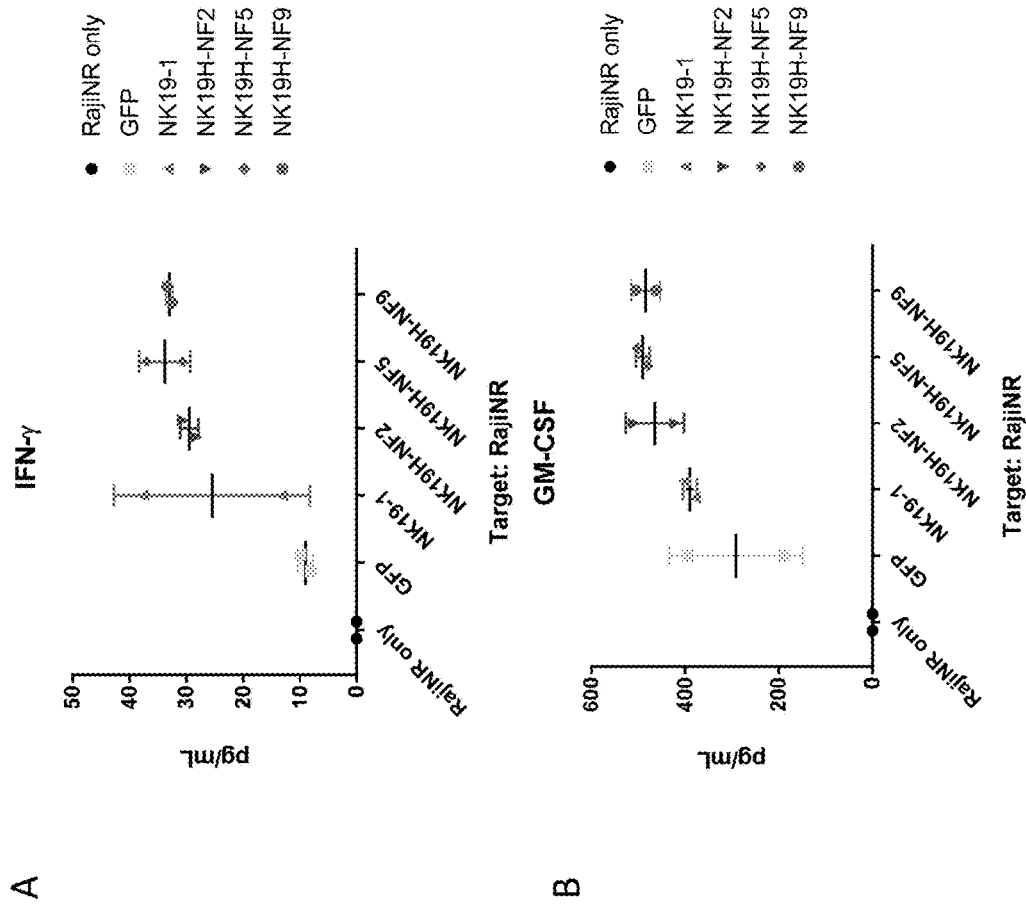
FIGS. 33A-33J relate to evaluation of cytokine production by NK cells expressing the indicated constructs.
Figures 33C, 33D:
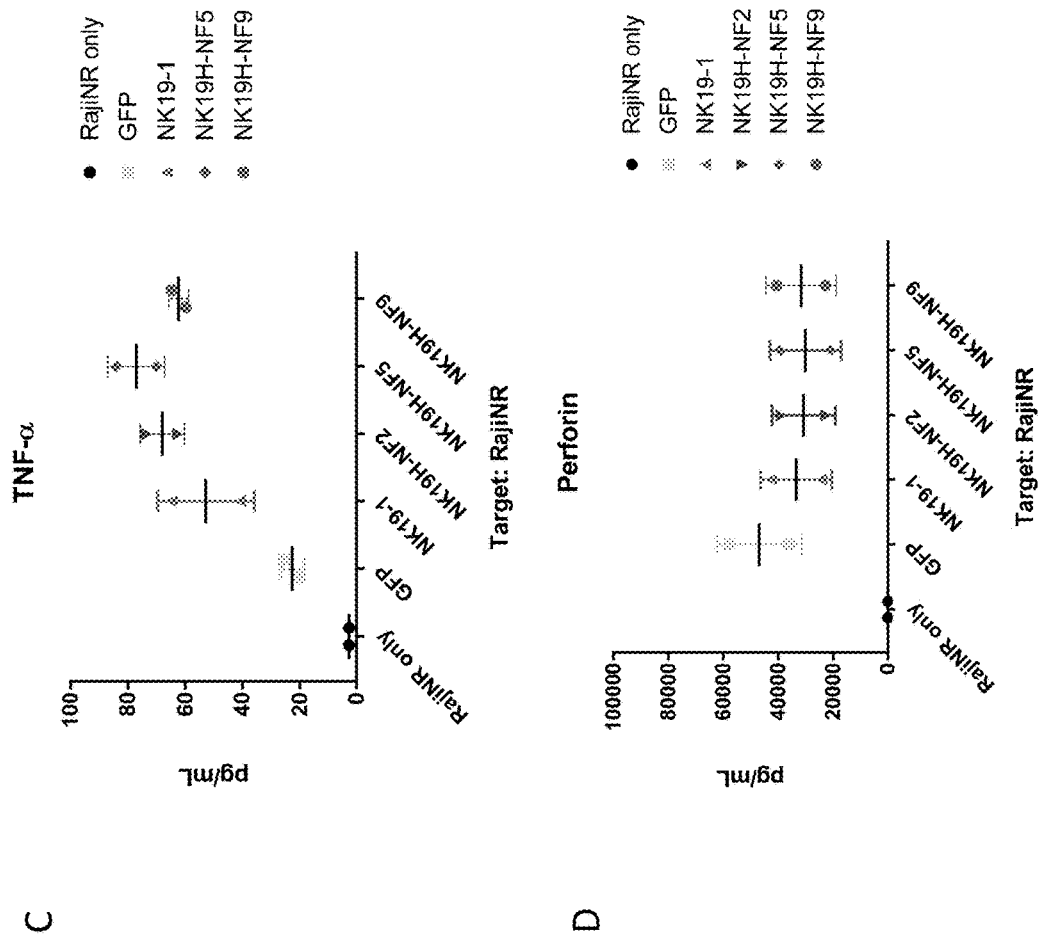
Figures 33E, 33F:
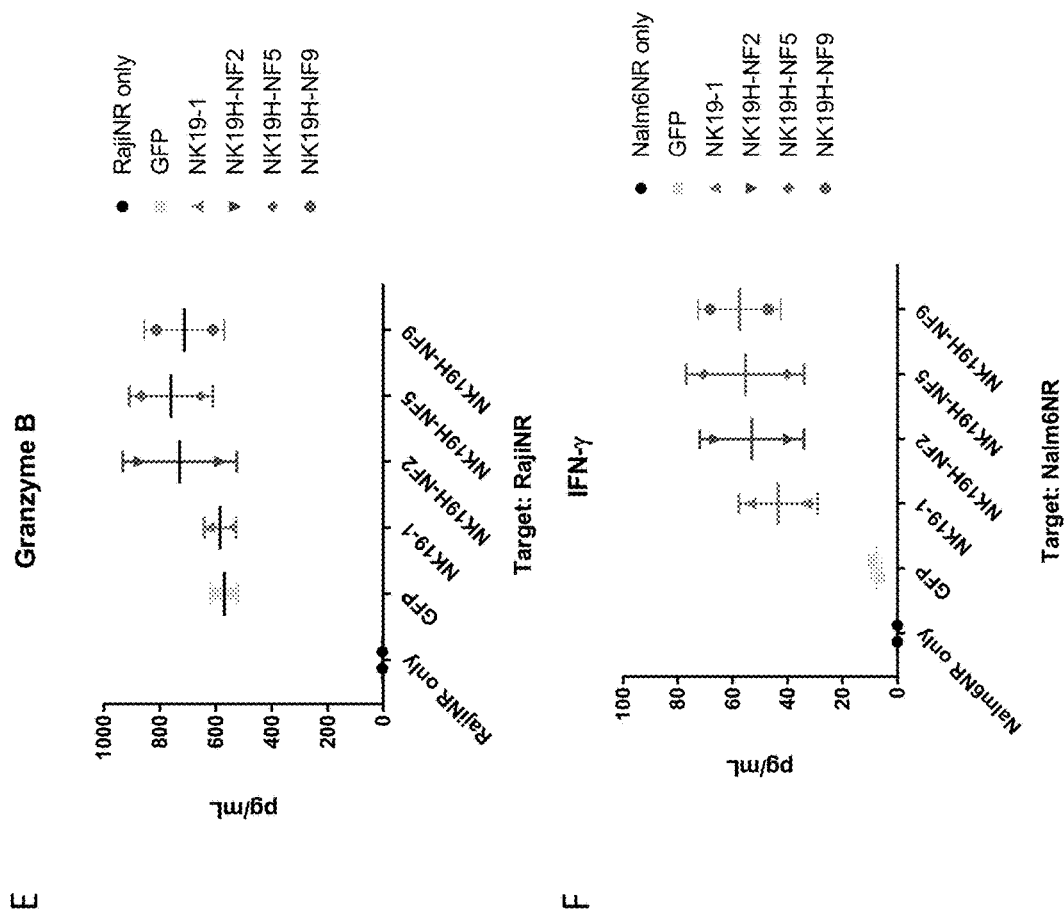
Figures 33G, 33H:
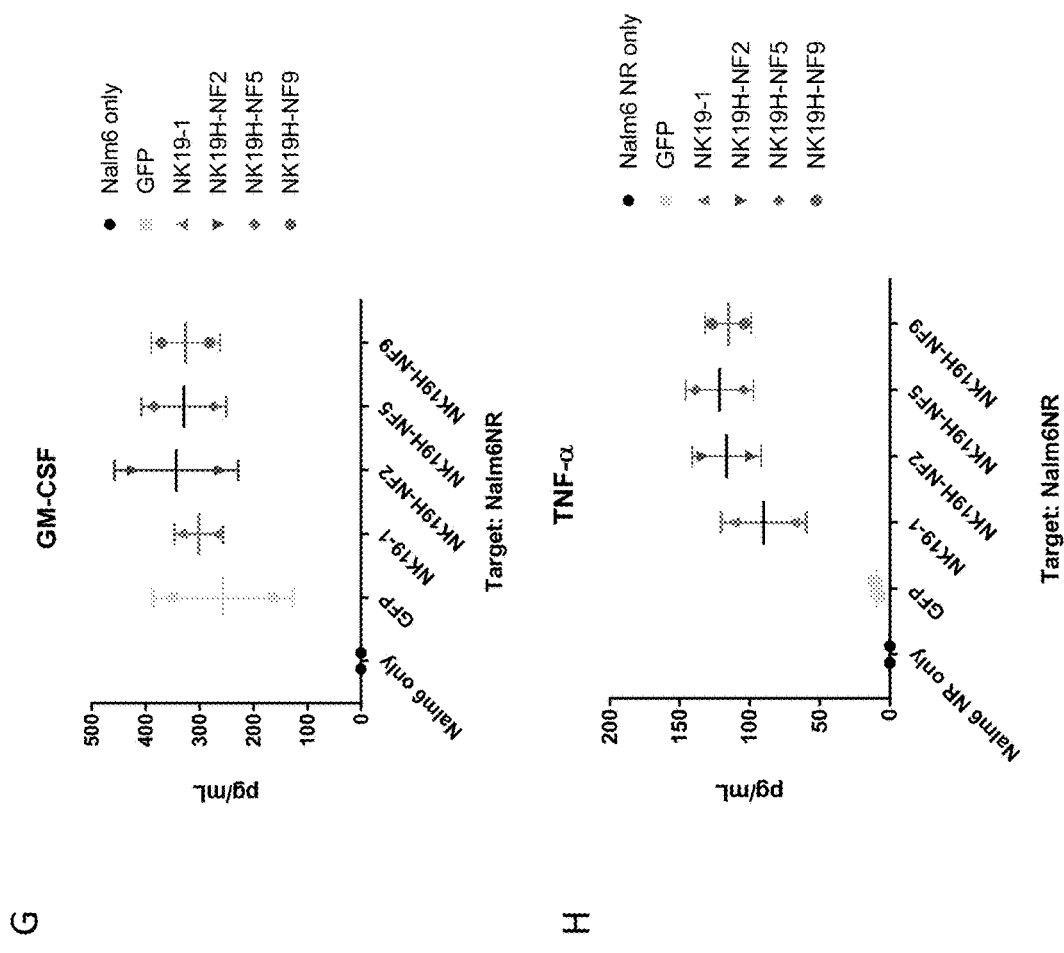
Figures 33I, 33J:
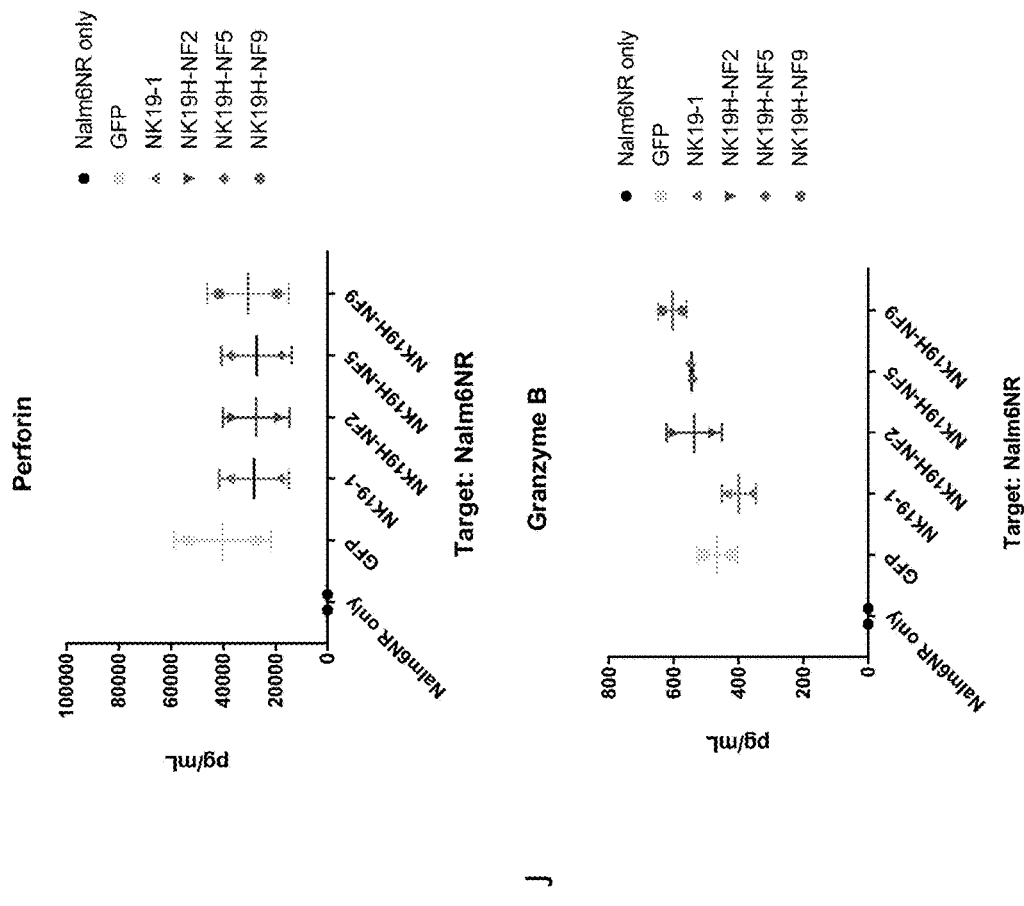

Experiments to evaluate the cytotoxicity of NK cells expressing humanized, non-flagged CD19 CAR constructs were performed. An in vitro re-challenge assay was performed as described above, using Raji cells (FIGS. 32A-32B) or Nalm6 cells (FIGS. 32C-32D) as the target cell. FIG. 32A shows the percent of Raji cells co-cultured with the indicated treatment, measured as a percent of the number of cells measured in a Raji-only control group at day 10 of the experiment. As shown, each of the CD19 CAR constructs, whether humanized or not, and whether tagged or not, substantially eliminated Raji cell growth through Day 10. FIG. 32B shows the final time point, and there remains limited Raji cell growth in each of the experimental groups with CD19 CARs, though the data show a small trend to greater prevention of Raji growth in with the NK19H-NF-2 and NK19H-NF-5 groups. FIGS. 32C and 32D show the corresponding data using Nalm6 cells. FIG. 32C shows that, similar to Raji cells, each of the CD19 CAR constructs, whether humanized or not, and whether tagged or not, substantially eliminated Nalm6 cell growth through 10 days. At the final time point, there was Nalm6 cell growth across all groups, though the data trends to the humanized constructs being more effective at preventing growth.

Figure 34:
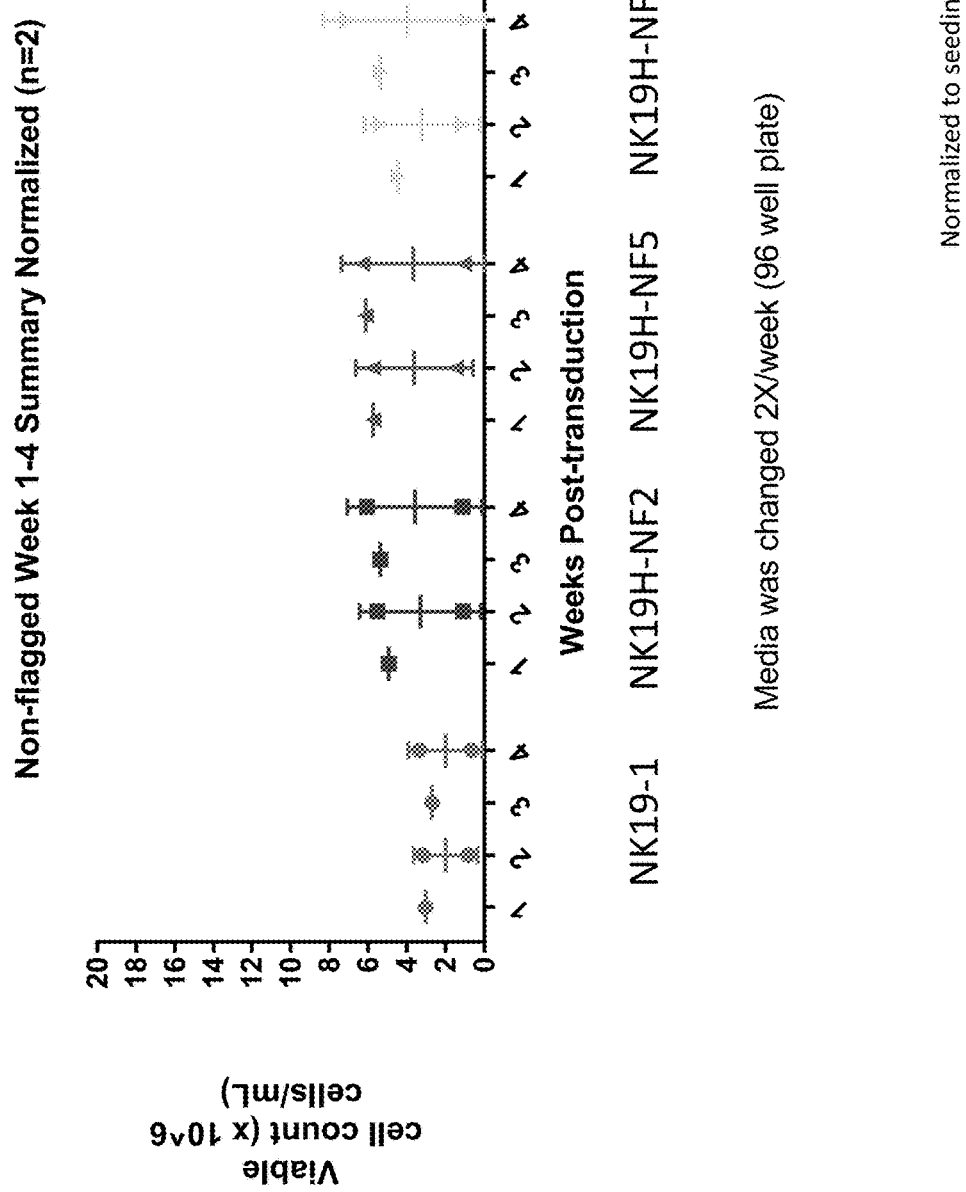
FIG. 34 shows data related to the viability of NK cells expressing humanized non-tagged CD19 CAR constructs over four weeks post-transduction.

FIGS. 33A-33J relate to the detected cytokine profile for NK cells expressing the indicated constructs. As discussed above, the culture media from each treatment group was assayed for interferon gamma (33A/33F), GM-CSF (33B/33G), TNF-alpha (33C/33H), Perforin (33D/33I), and Granzyme B (33E/33J). FIGS. 33A-33E show data from the Raji cell rechallenge, while 33F-33J show data from the Nalm6 rechallenge. As shown, the non-flagged, humanized CD19 CAR expressing NK cells release similar levels of similar amount of IFN-gamma into the media, with those levels being slightly greater than the amount released by NK cells expressing the non-humanized NK19-1 CAR. Similarly, GM-CSF release was fairly consistent among the humanized, non-flagged CAR bearing NK cells, and at a level slightly about the NK19-1 expressing cells. TNF-alpha release showed a similar pattern, while perforin release was consistent among all the CD19 CAR expressing NK cells, and at a level below control. Lastly in the Raji cells, granzyme B showed a similar degree of release for the non-flagged, humanized CD19 CARs, at a level slightly above the NK19-1 expressing cells. For the most part, the data collected from the Nalm6 experiment showed similar patterns. According to several embodiments, the greater degree of release of cytotoxicity-mediating cytokines leads to a more effective therapeutic. In some embodiments, the greater degree of cytokine release is due, at least in part, to the enhanced expression of the non-flagged, humanized CD19 CAR constructs by the NK cells and/or due, at least in part, to the enhanced persistence of the NK cells expressing the non-flagged, humanized CD19 CAR constructs. Further supporting these concepts, FIG. 34 shows data related to the persistence of NK cells expressing the indicated non-flagged, humanized constructs over four weeks in culture, as compared to NK cells expressing NK19-1. While the overall cell counts appear similar among the NK cells expressing the humanized constructs, the cell counts show the same basic pattern as the cytokines, that is, slightly greater than NK cells expressing non-humanized NK19-1.

Example 11

Figure 35A:
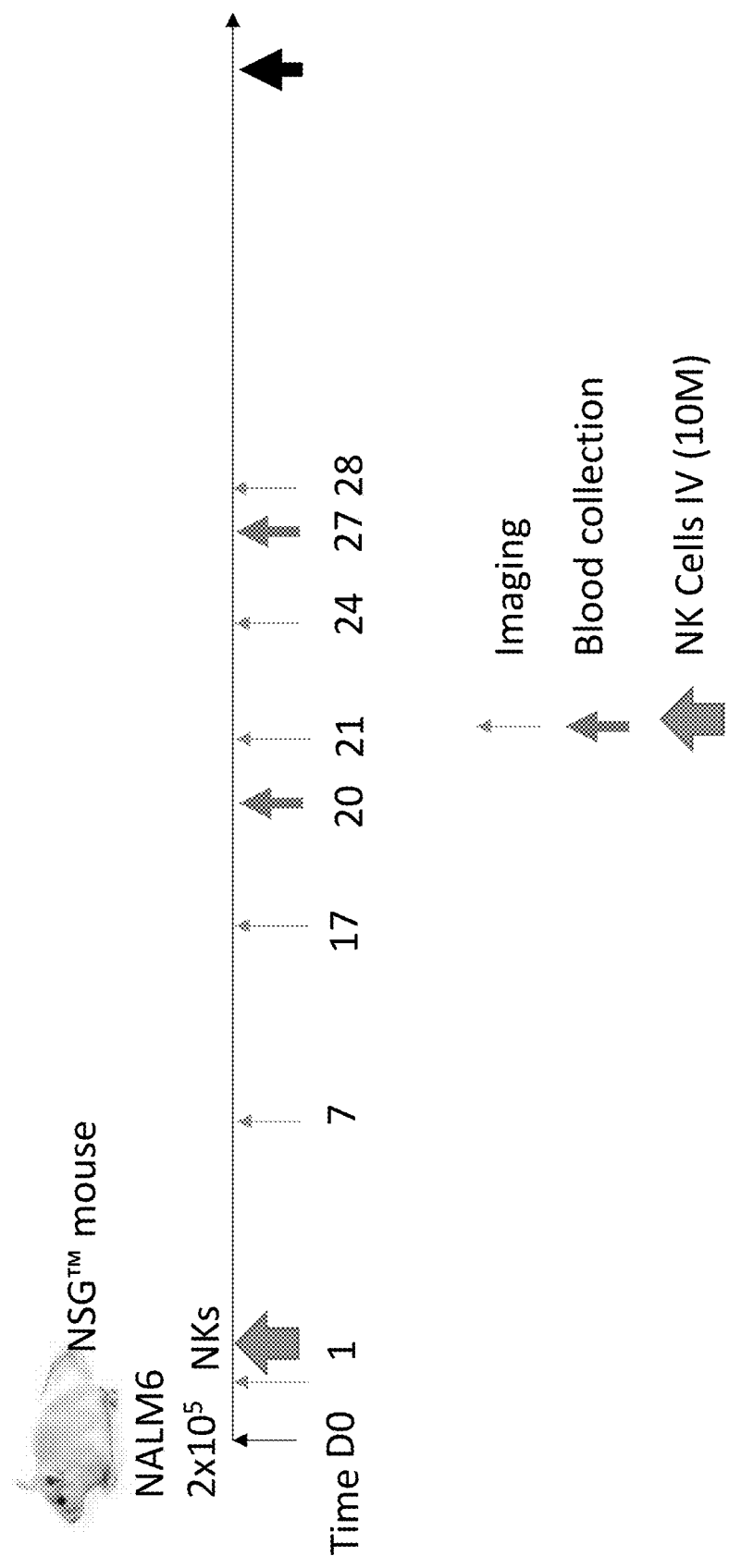
FIGS. 35A-35D show data related to various humanized, non-tagged, CD19-directed CAR constructs and their efficacy in an in vivo model.
Figure 35B:
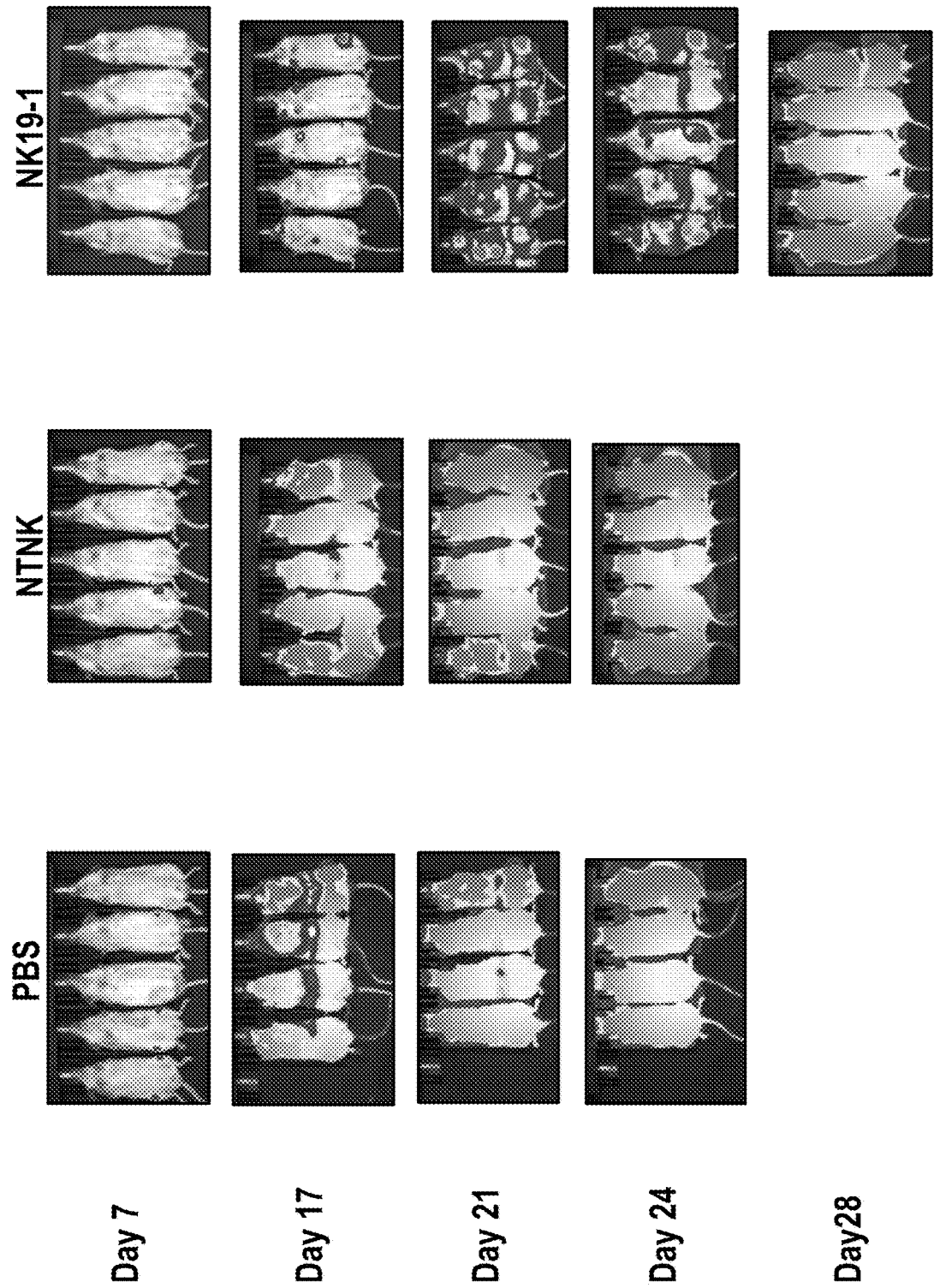
Figure 35B:
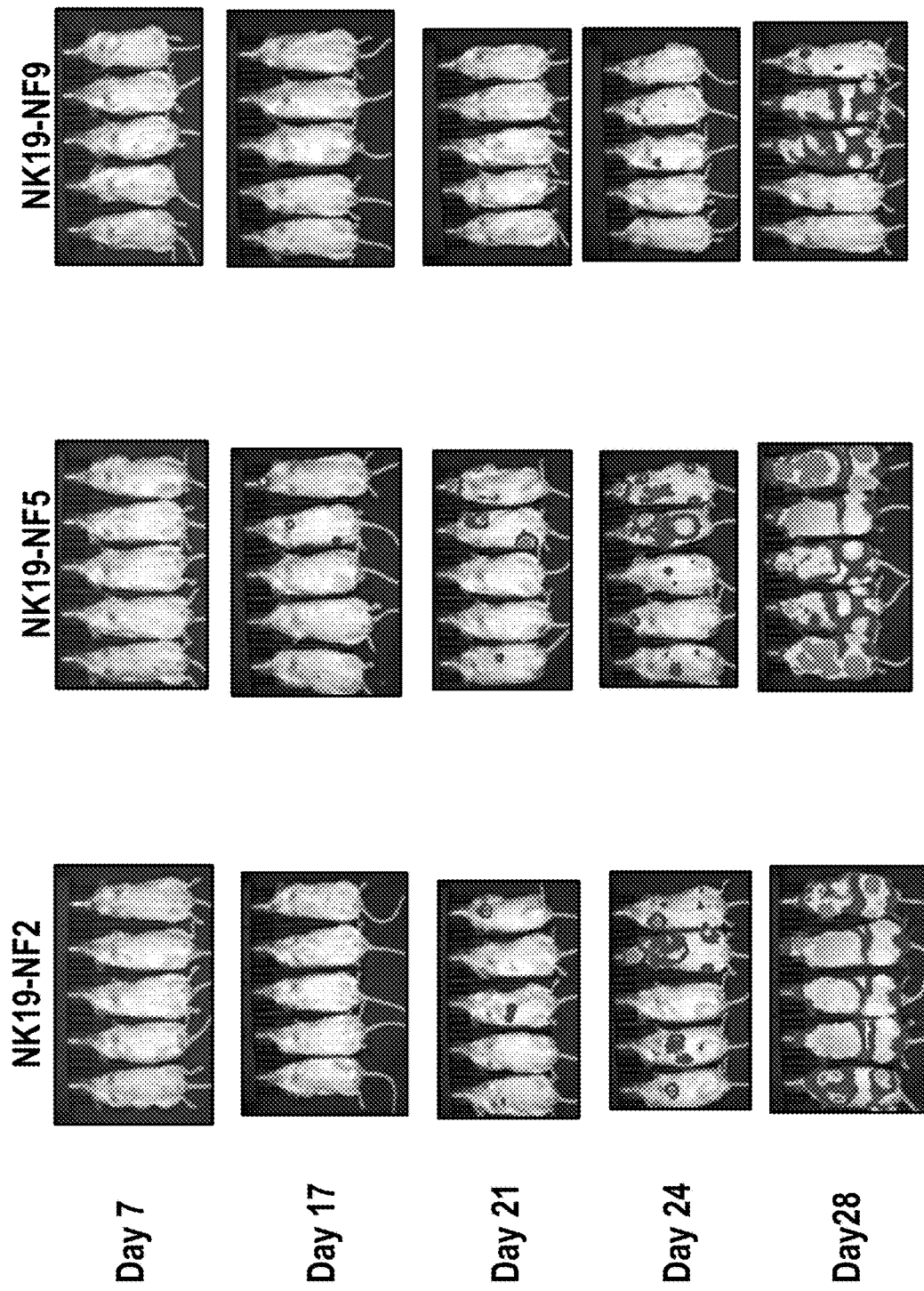
Figures 35C, 35D:
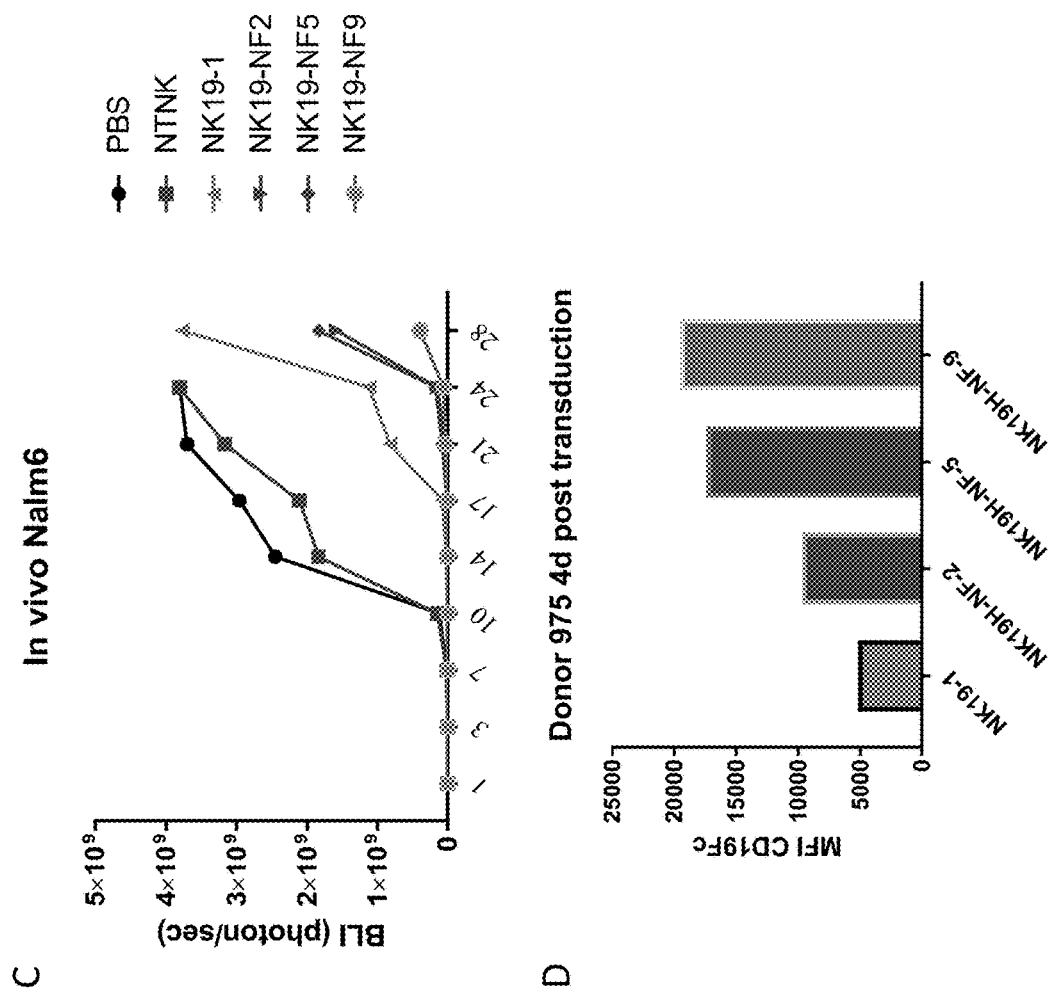
Figures 36A, 36B:
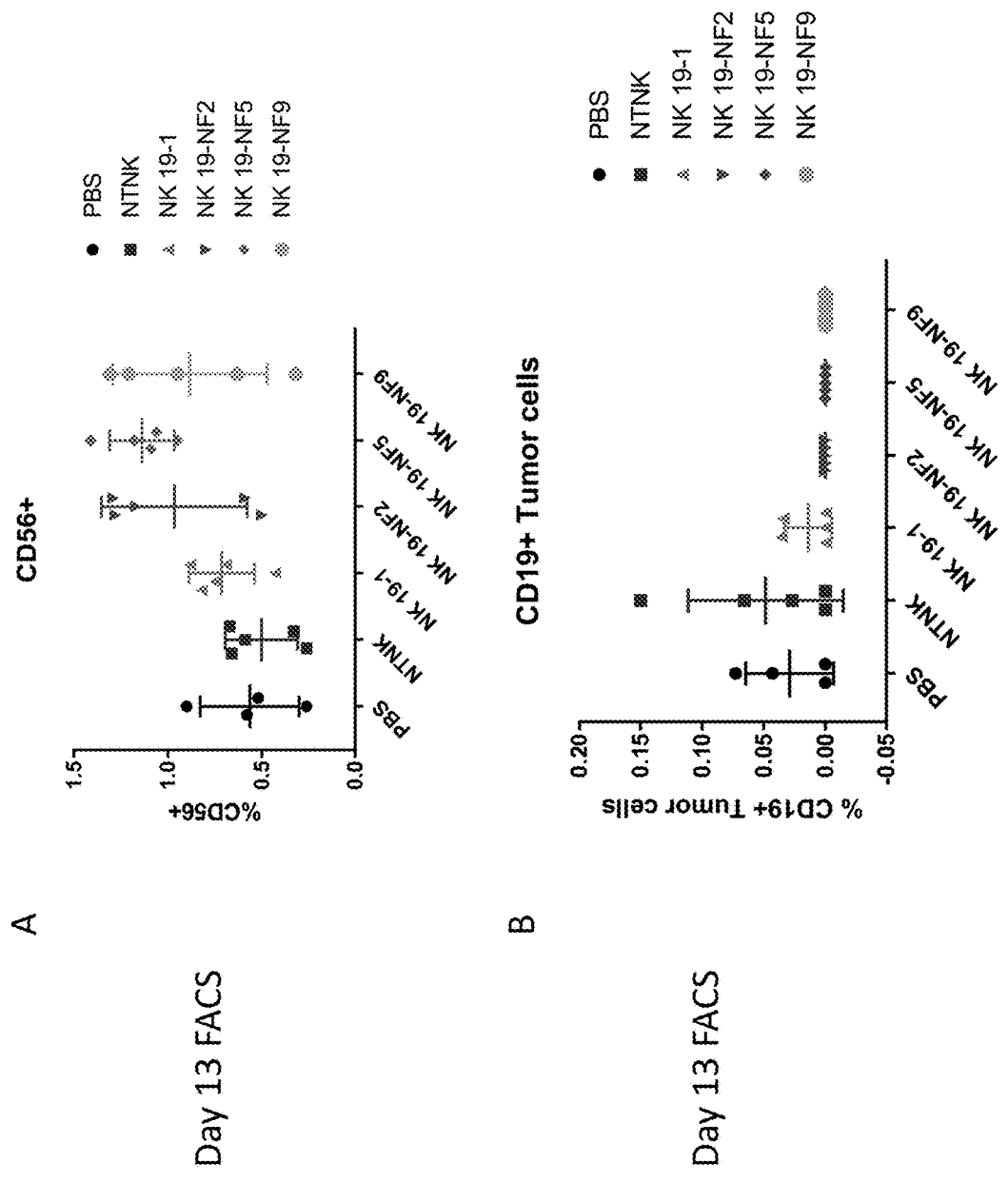
FIGS. 36A-36F relate to expression of the indicated CD19-directed CAR constructs.
Figures 36C, 36D:
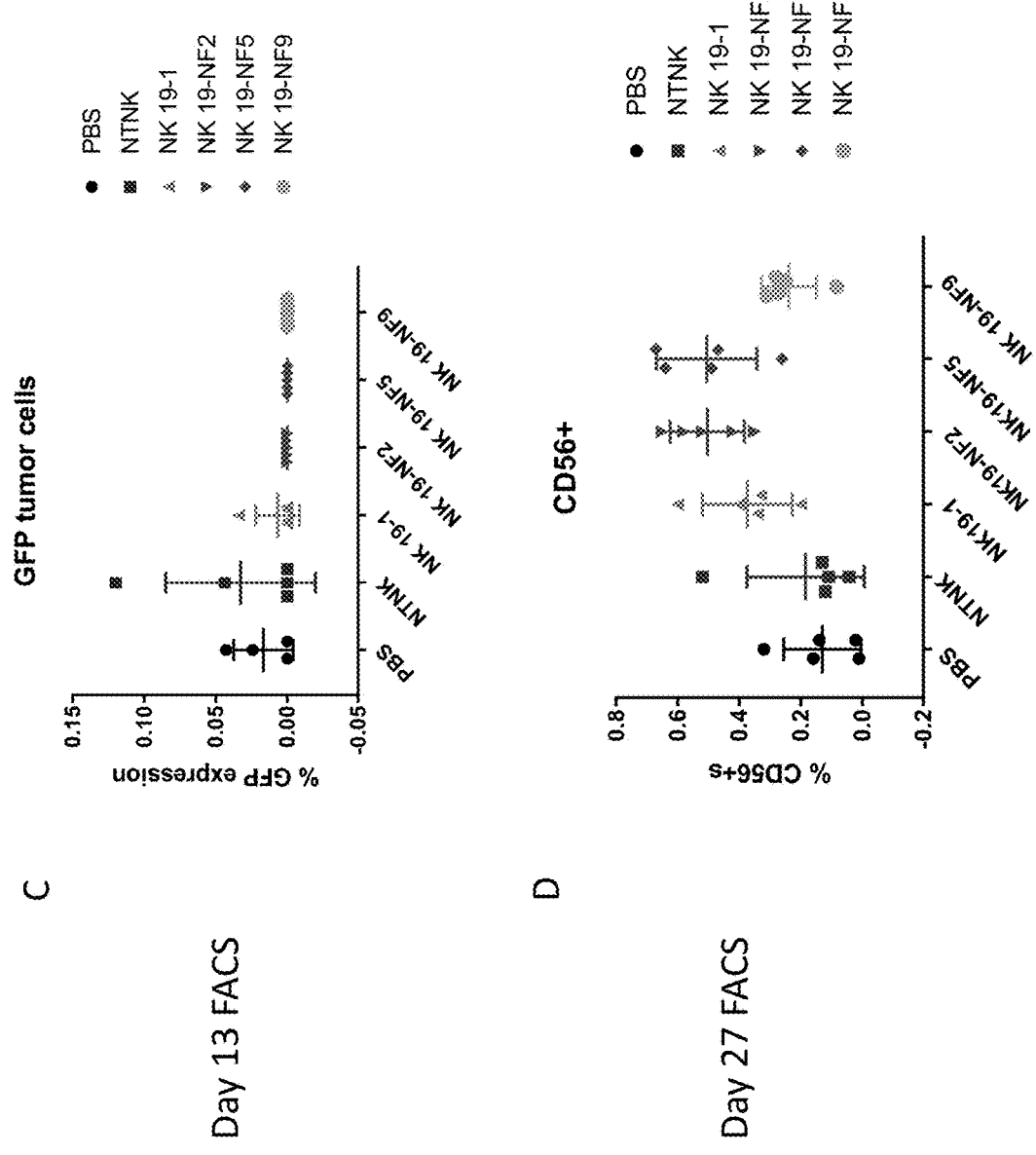
Figures 36E, 36F:
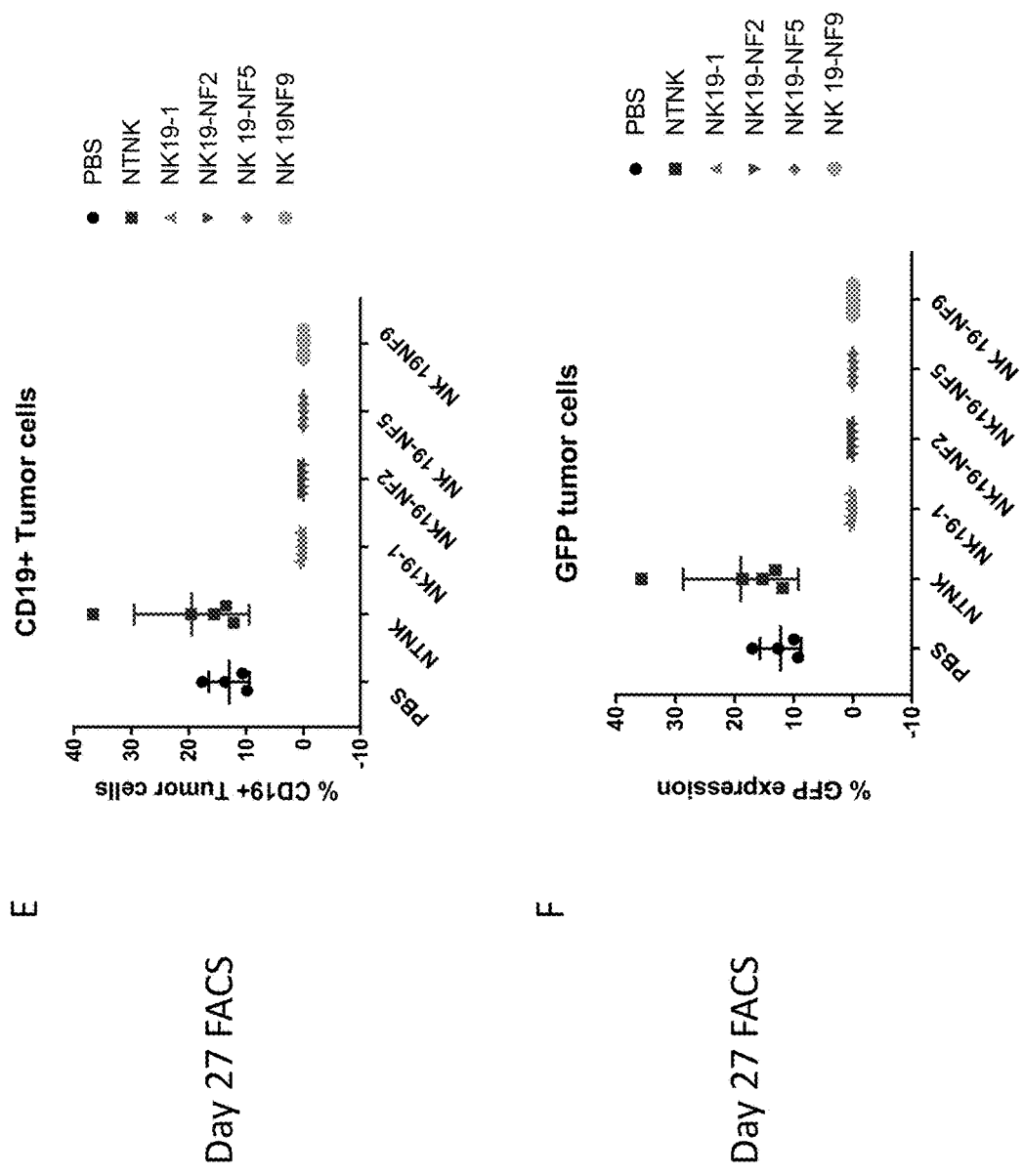

Similar to the experiments above, an in vivo assessment of the efficacy of non-flagged, humanized constructs was performed. FIG. 35A shows a schematic of the protocol used. FIG. 35B shows the in vivo bioluminescence measurements, which show that humanized, non-flagged constructs appear to slow tumor progression to a greater extent than NK cells expressing the NK19-1 construct. FIG. 35C, recapitulates the imaging data in a line graph, where the enhanced inhibition of tumor cell growth can clearly be seen when the mice received NK cells expressing any of the non-flagged, humanized CD19 CAR constructs. FIG. 35D reflects the enhanced expression of the non-flagged, humanized constructs by NK cells. FIGS. 36A-36F relate to the persistence of NK cells expressing the indicated constructs over the timeline of the experiment. FIG. 36A indicates that NK cells expressing the non-flagged, humanized CD19 CAR constructs are more persistent in vivo, making up a larger percentage of the overall CD56+ cells in the peripheral blood at Day 13. FIG. 36B demonstrates that, at Day 13, NK cells expressing any CD19 CAR inhibit tumor growth better than control, with the that NK cells expressing the non-flagged, humanized CD19 CAR constructs showing a slight advantage over the NK19-1 expressing NK cells in terms of limiting CD19+ tumor cell growth. FIG. 36C shows similar data to 36B, using GFP positive tumor cell count as the benchmark. FIG. 36D shows persistence data at day 27, wherein the NK19-NF-2 and -9 expressing NK cells have elevated population numbers compared to the other groups, indicating enhanced persistence over a longer period of time. Similar to the earlier time-point, FIGS. 36E and 36F show that the CD19-targeting CAR constructs are all effective at limiting tumor cell growth, compared to controls. According to several embodiments provided for herein, expression of a non-flagged, humanized CD19 targeting CAR by NK cells engenders those NK cells with enhanced in vivo persistence and cytotoxicity.

Example 11

Figure 37A:
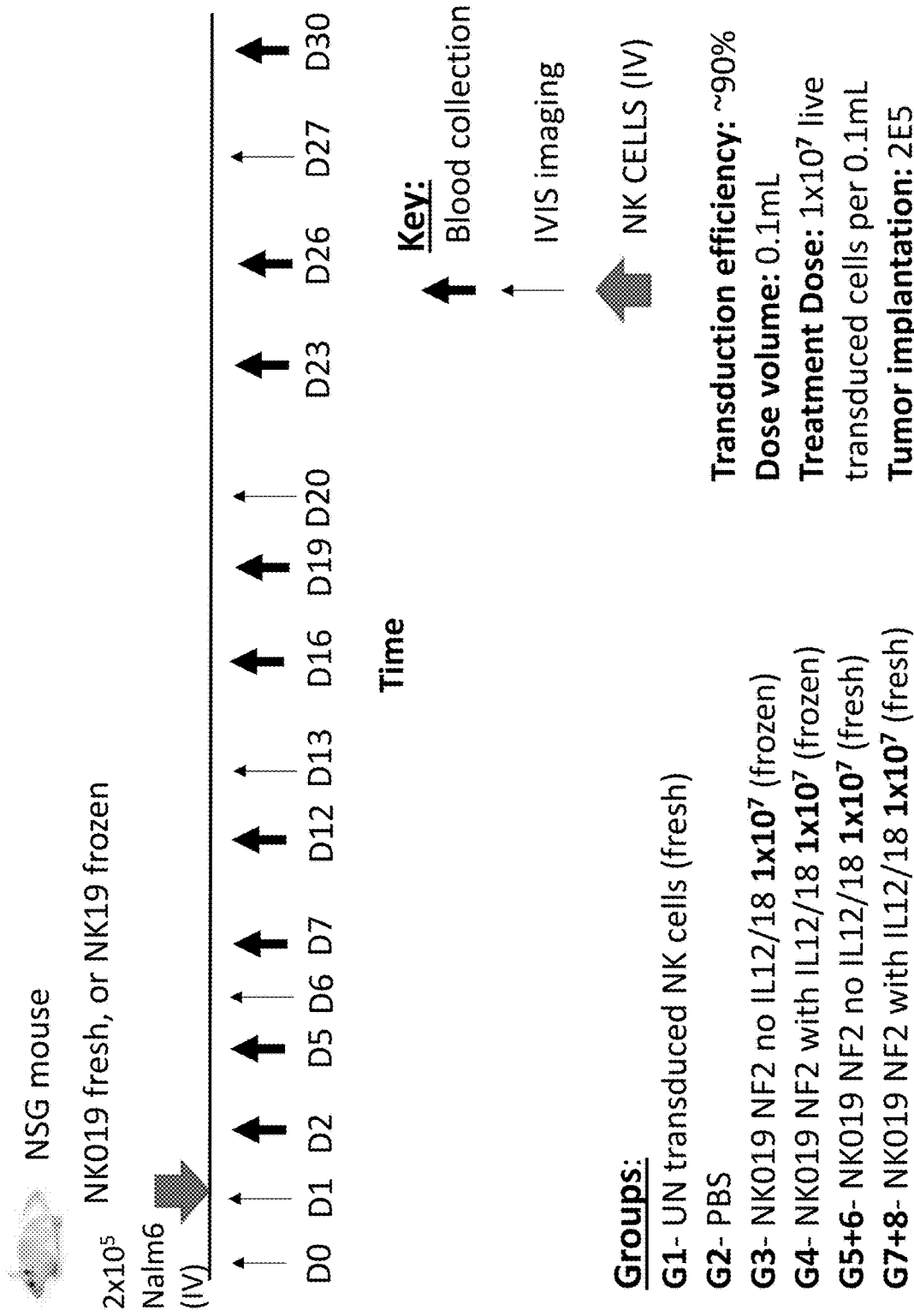
FIGS. 37A-37C relate to the in vivo efficacy of various CD19-directed CAR according to embodiments disclosed herein.
Figure 37B:
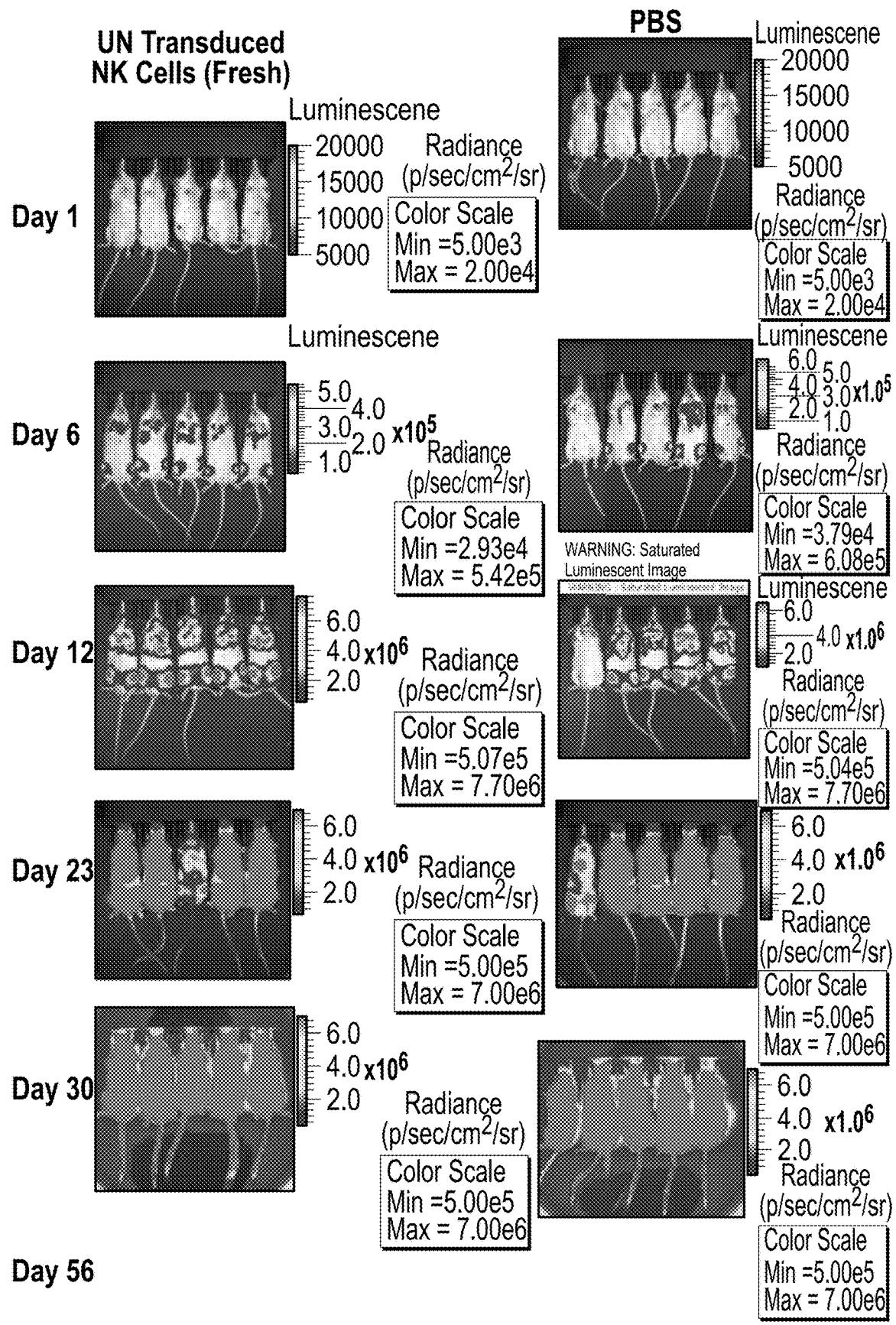
Figure 37B:
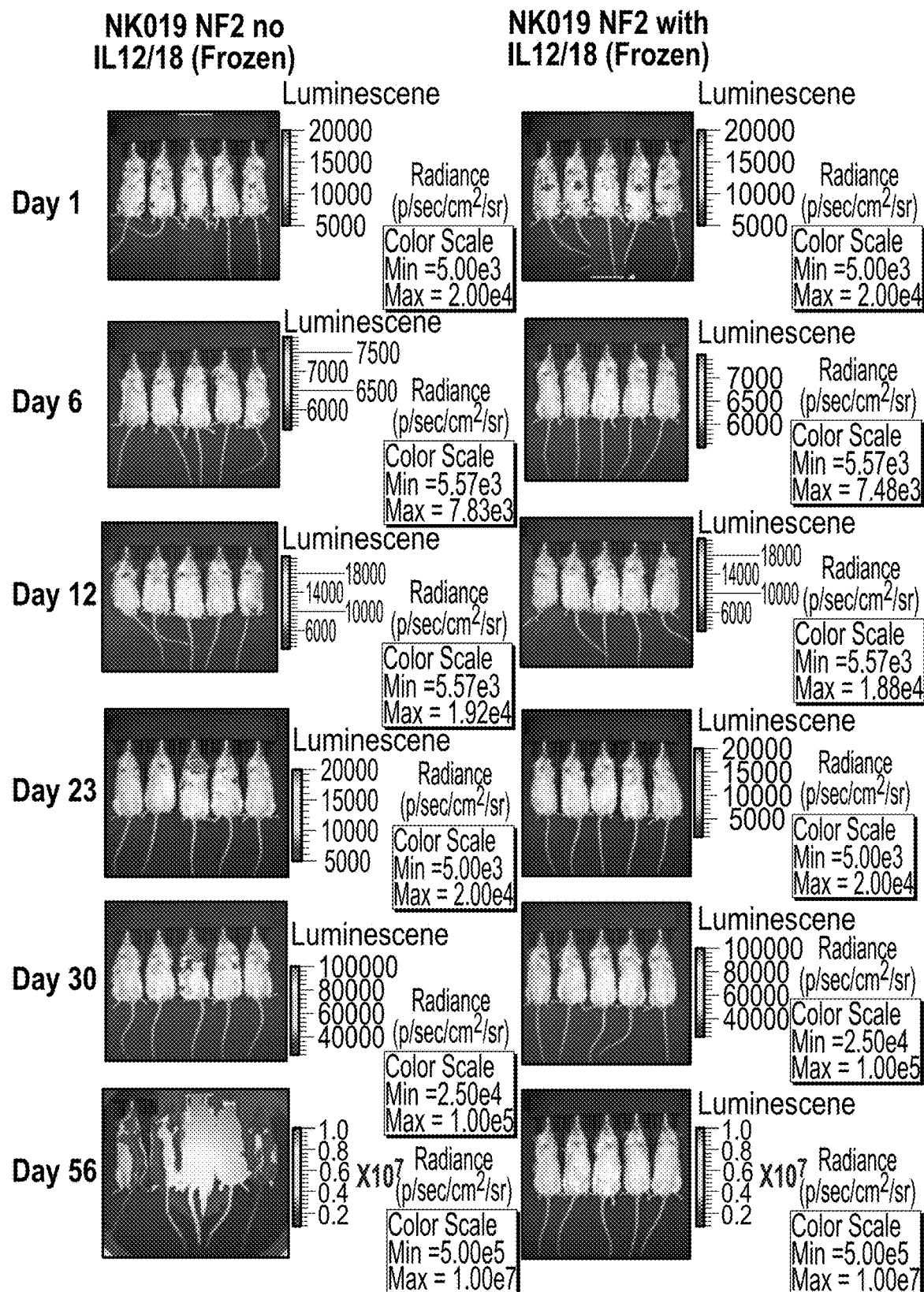
Figure 37B:
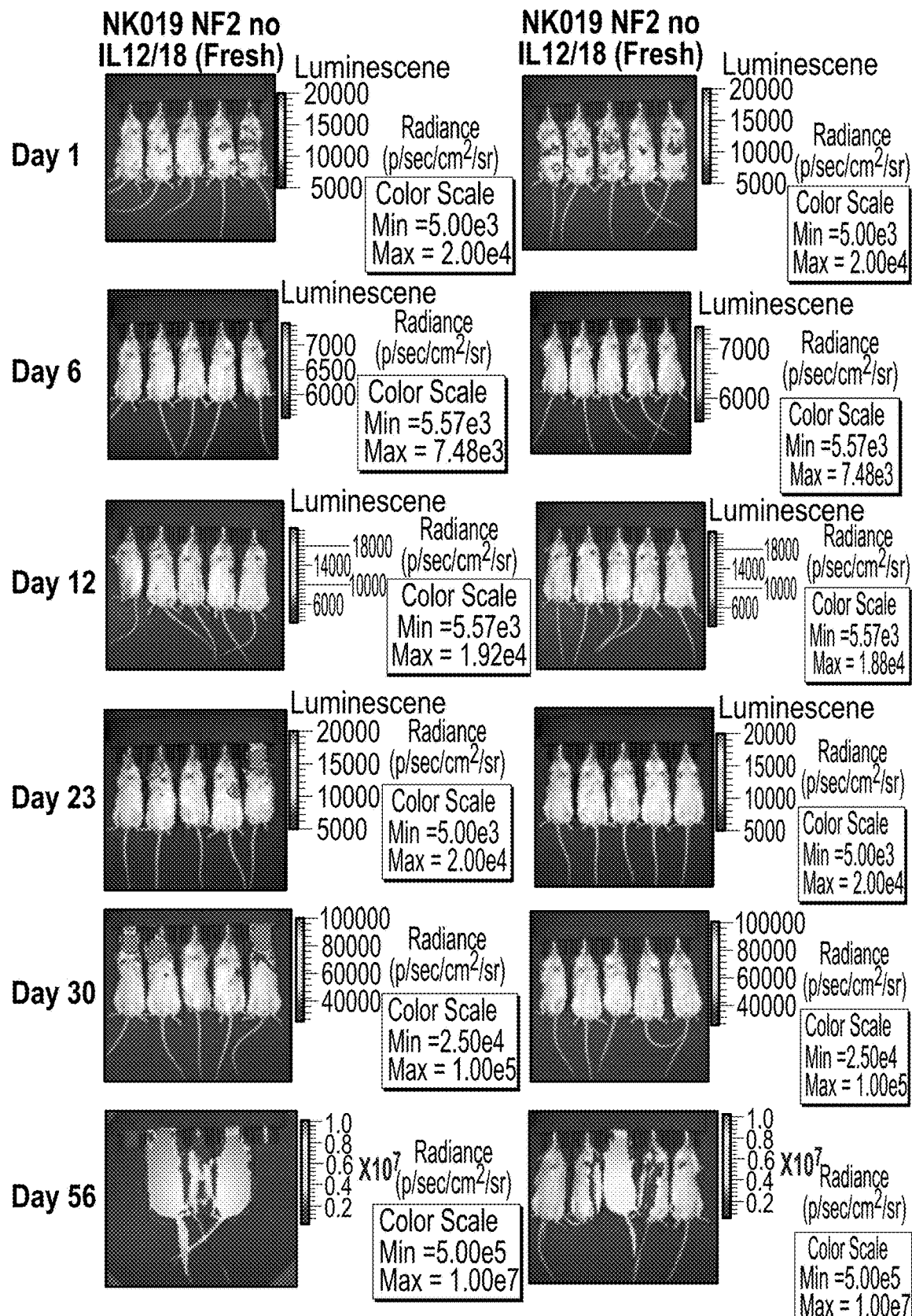
Figure 37B:
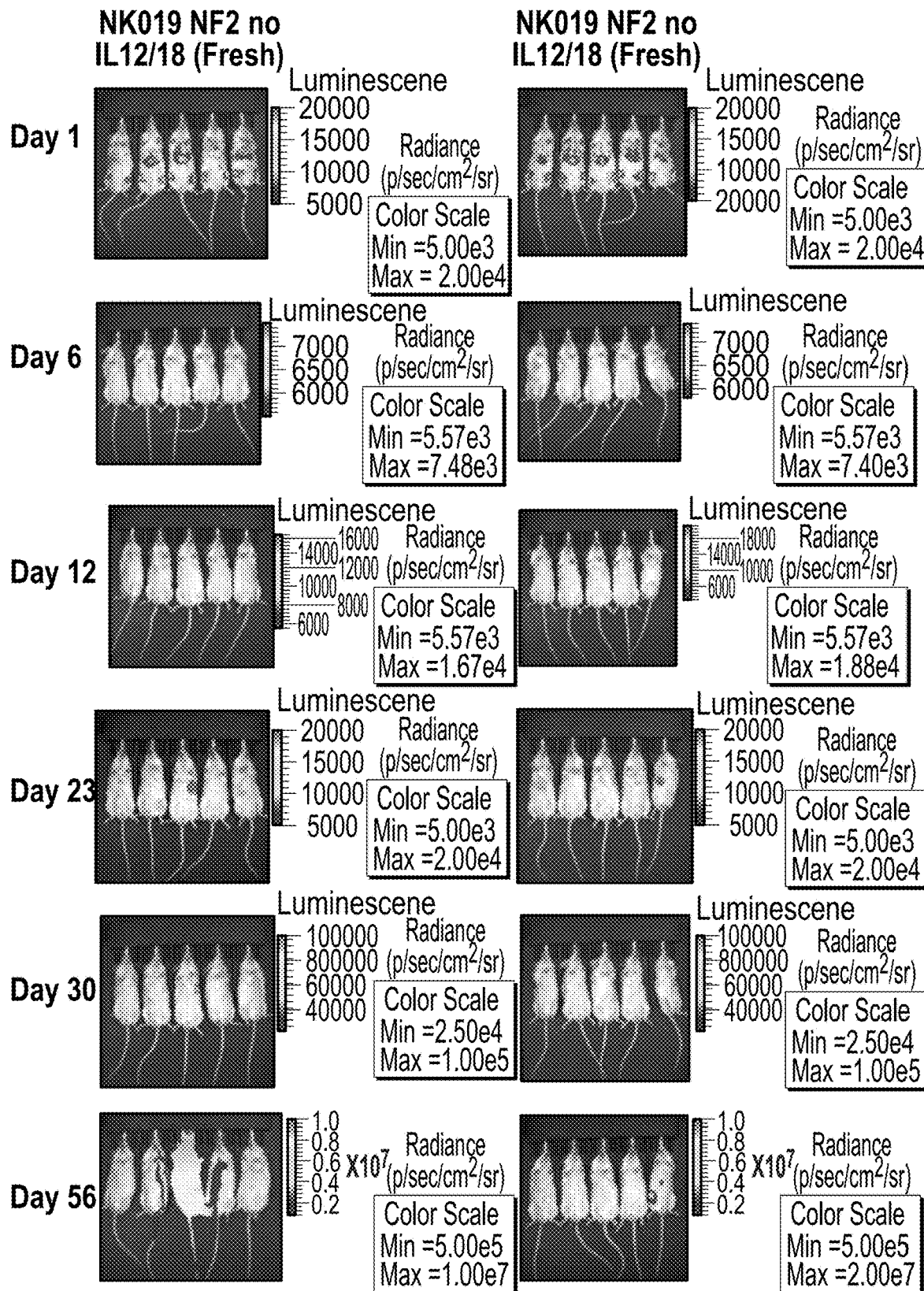
Figure 37C:
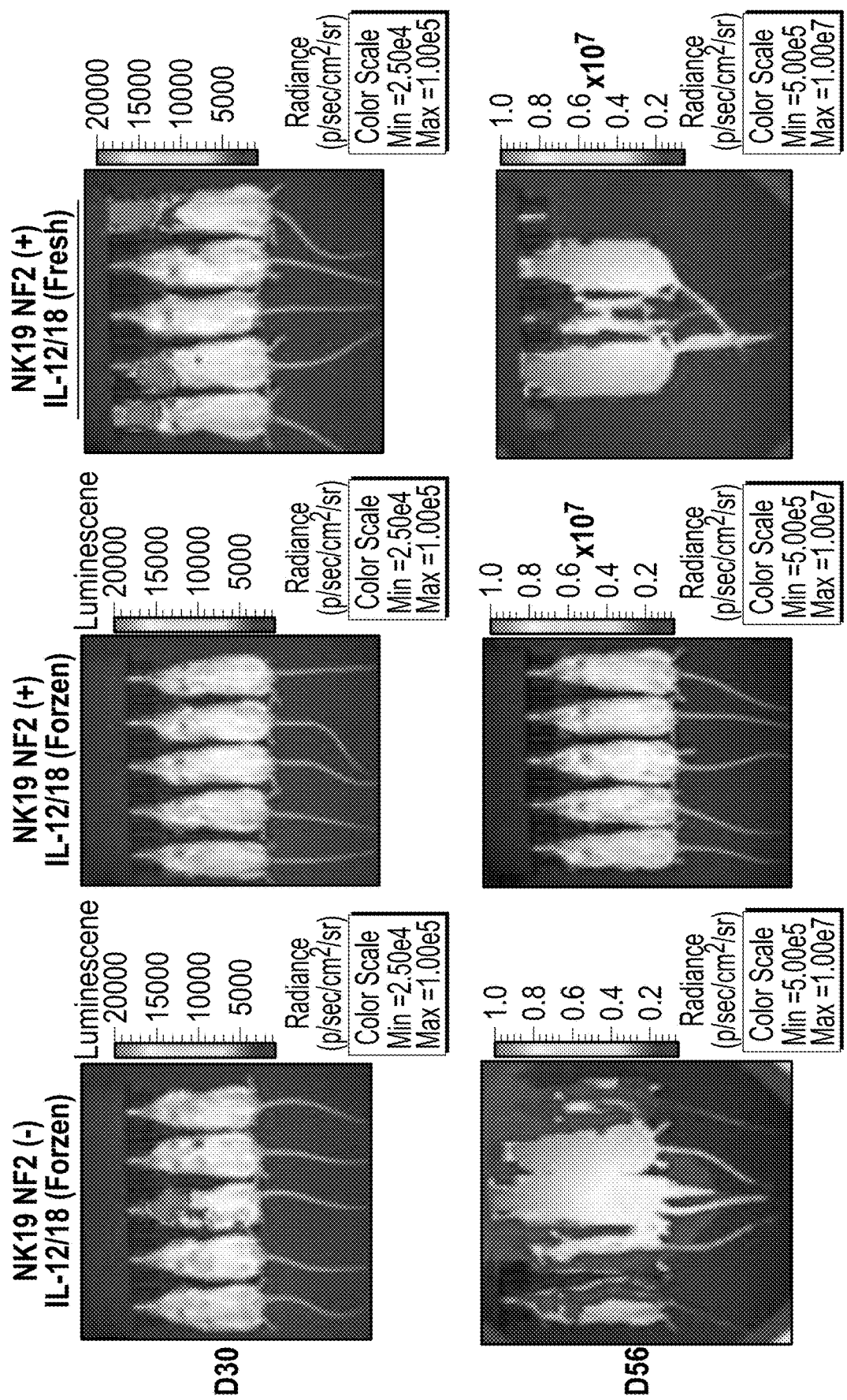
Figure 37C:
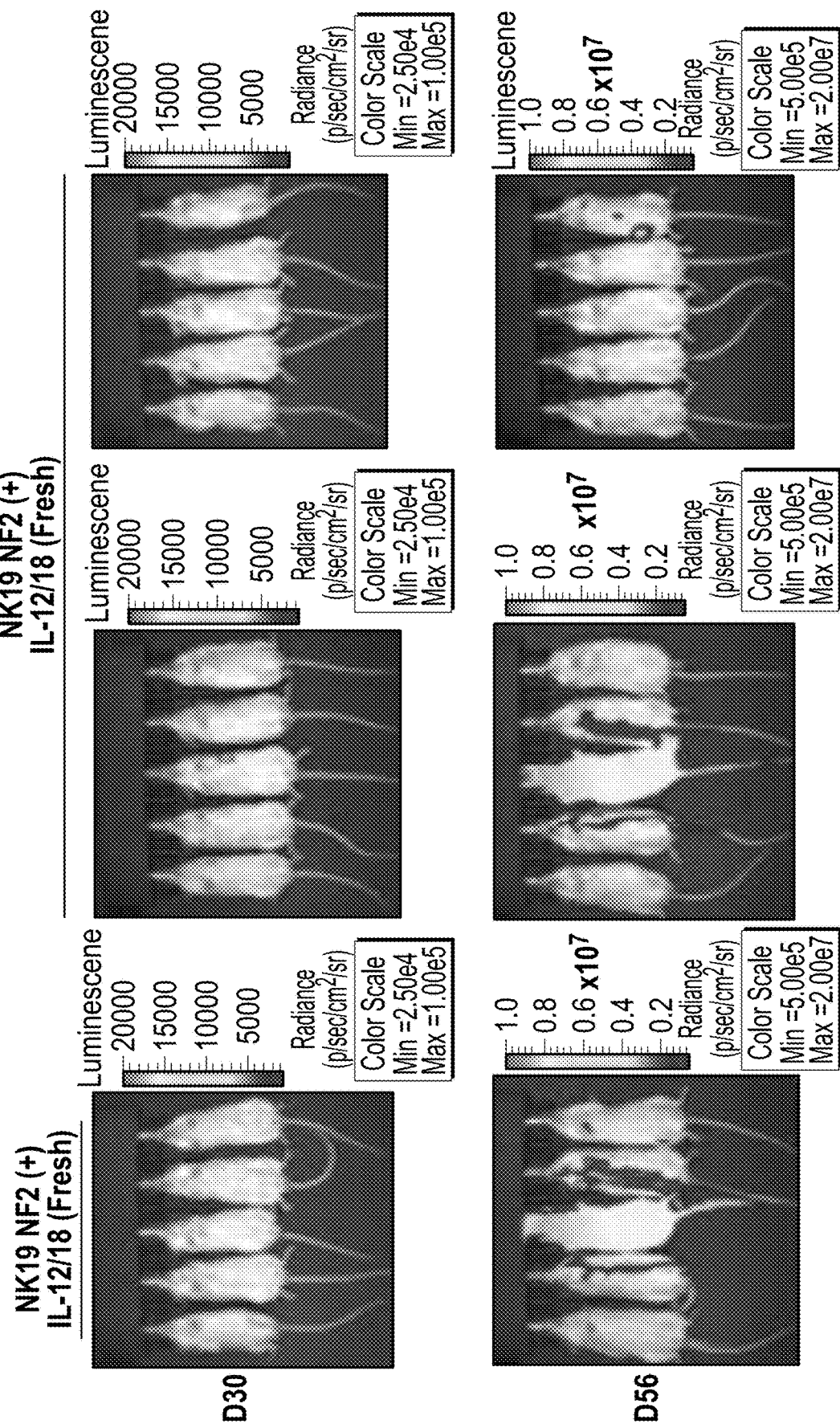
Figure 38A:
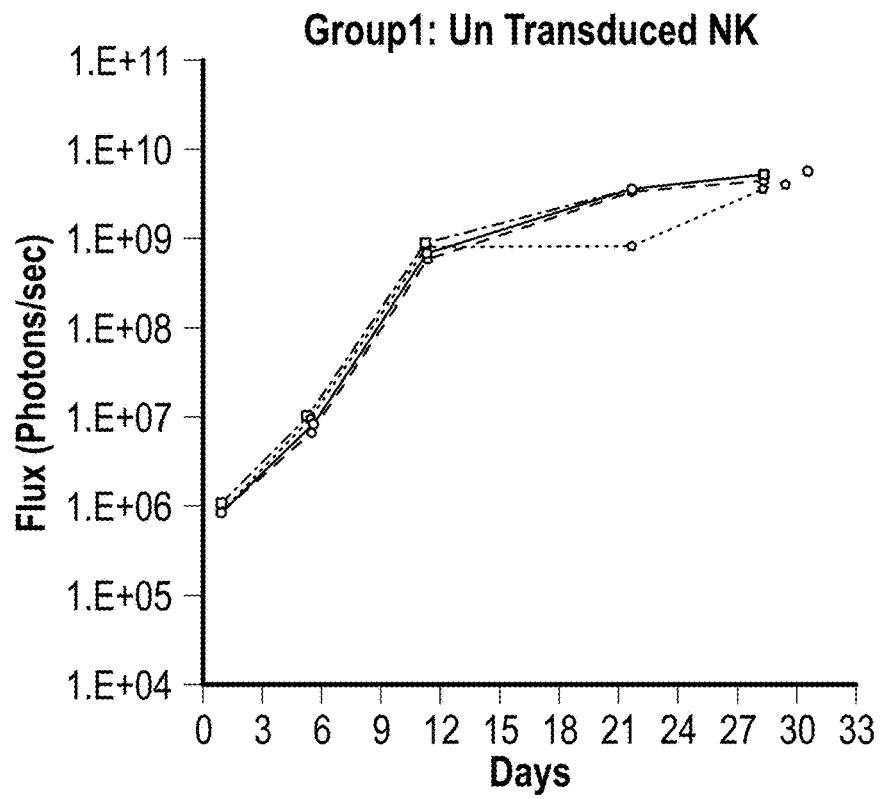
FIGS. 38A-38J show graphical depictions of the bioluminescence data from FIG. 37B.
Figure 38B:
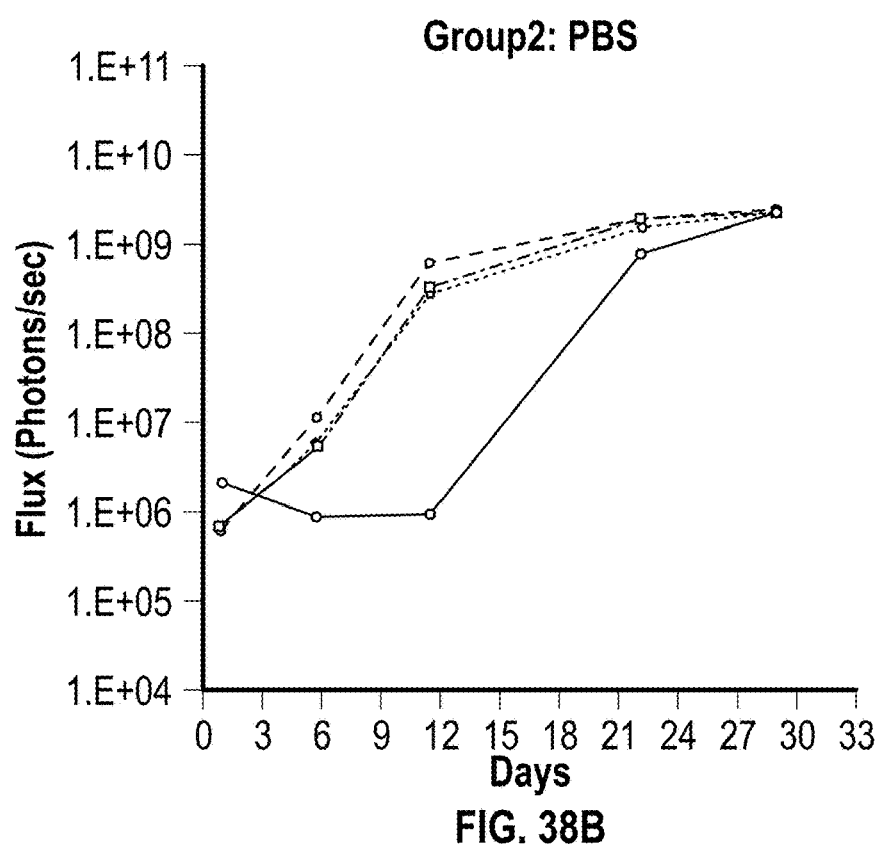
Figure 38C:
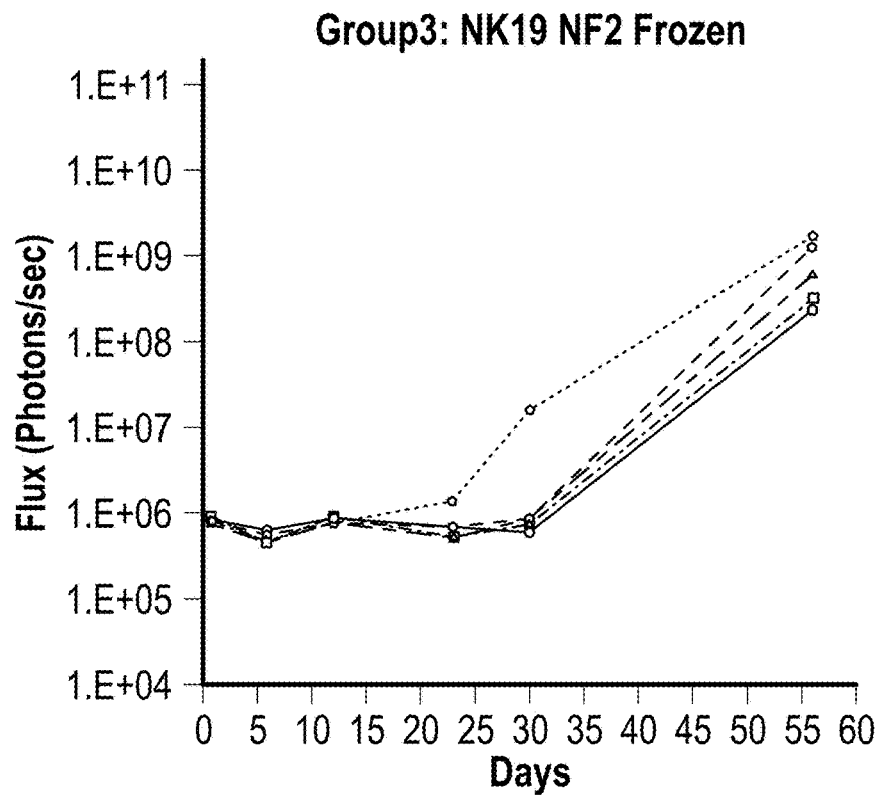
Figure 38D:
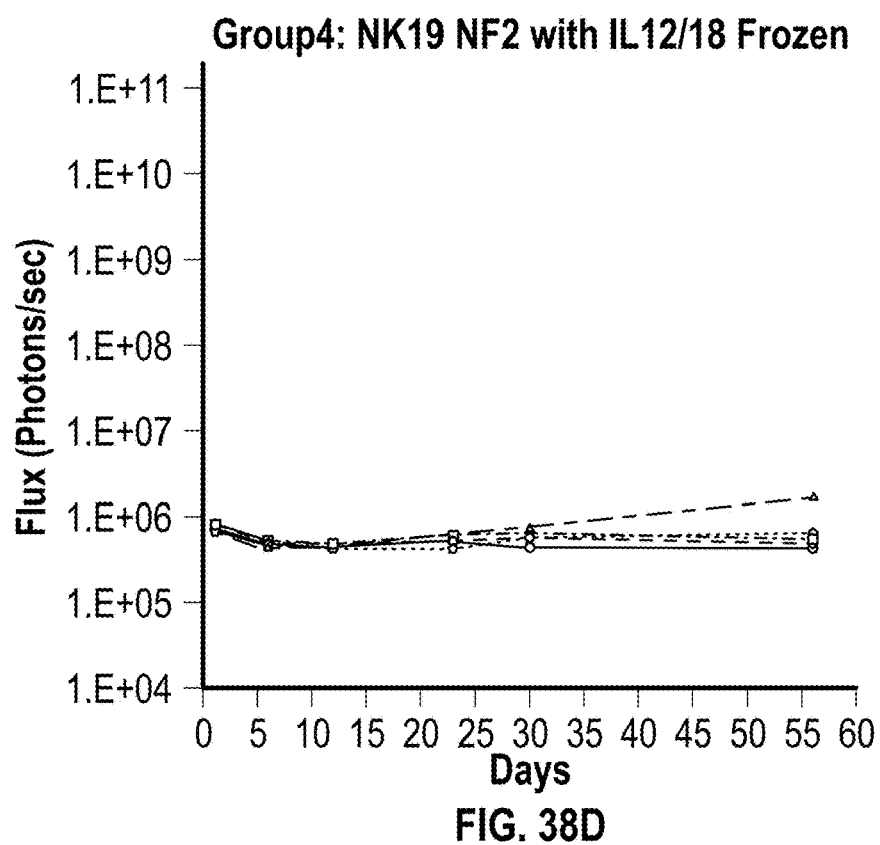
Figure 38E:
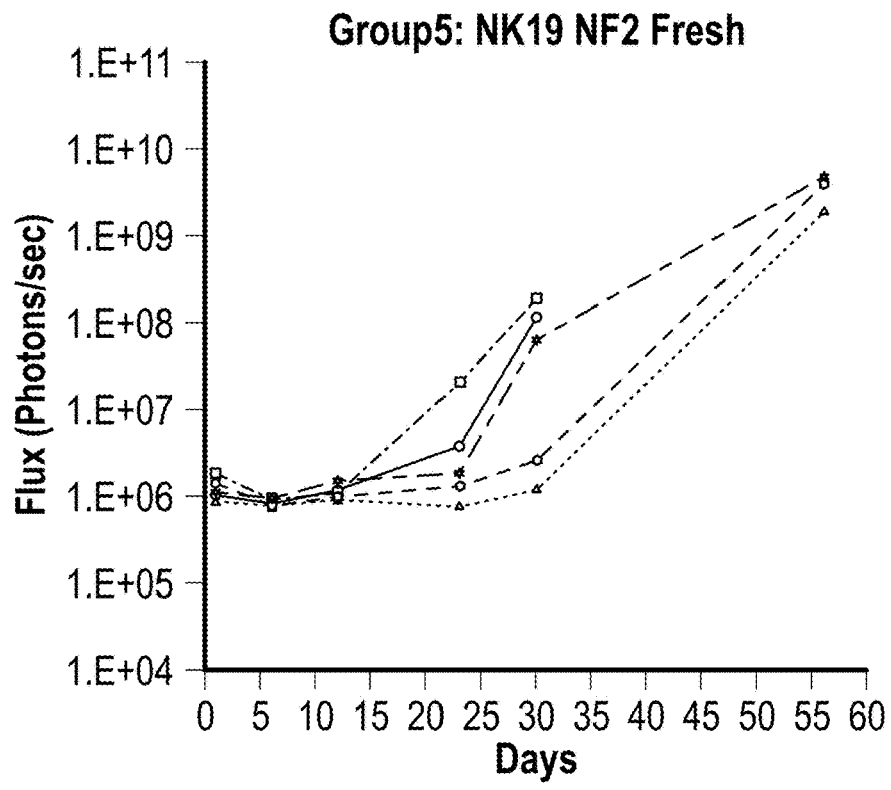
Figure 38F:
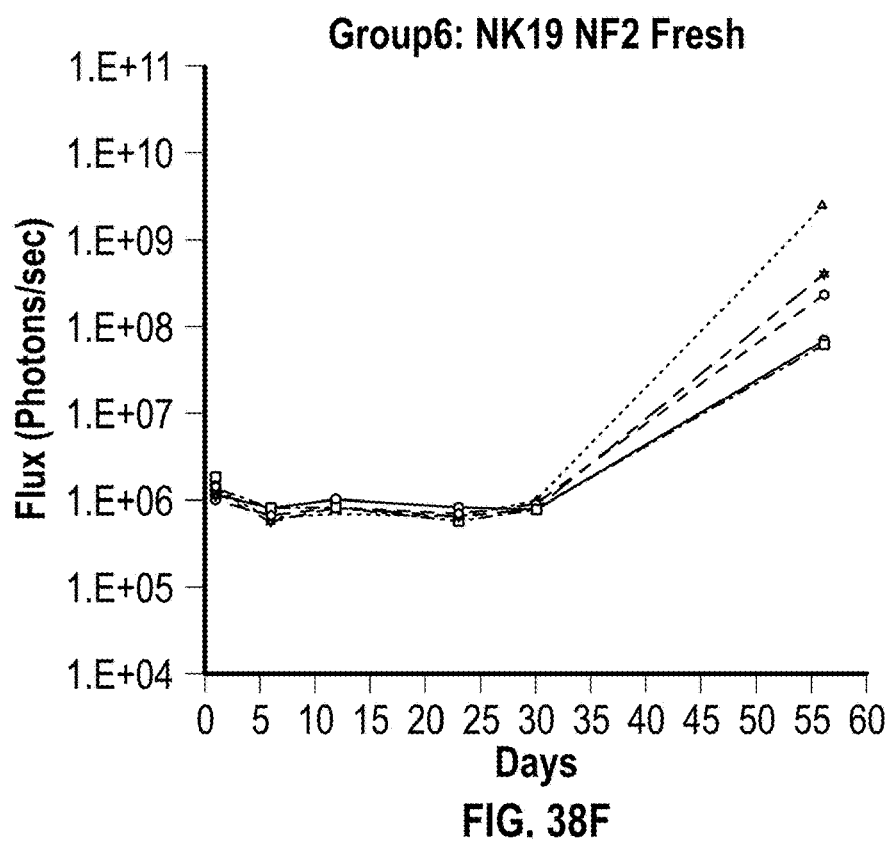
Figure 38G:
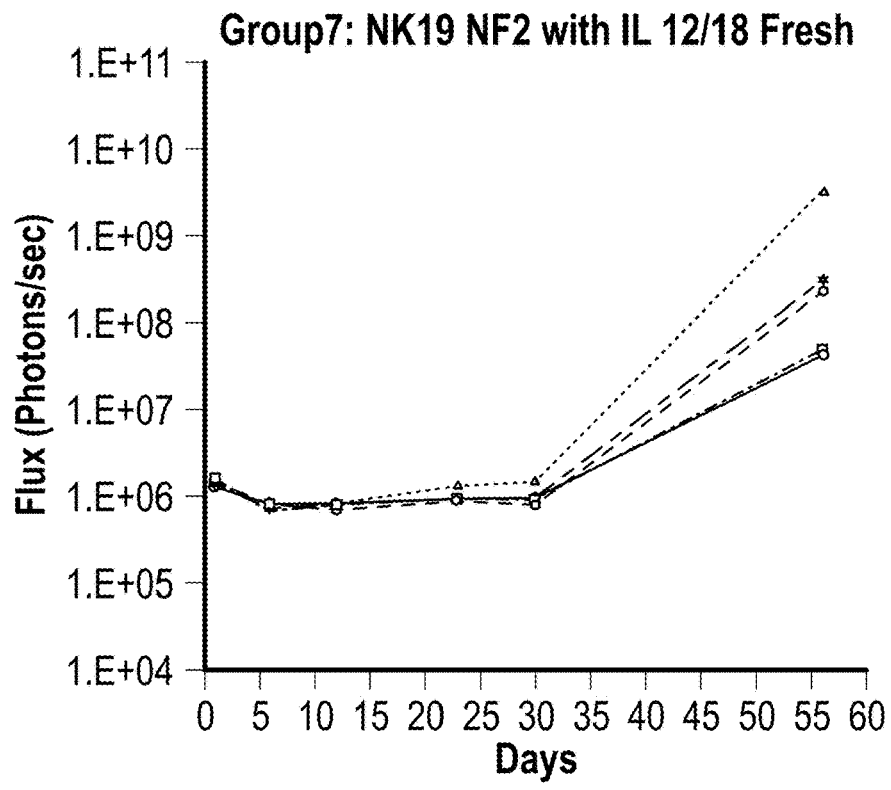
Figure 38H:
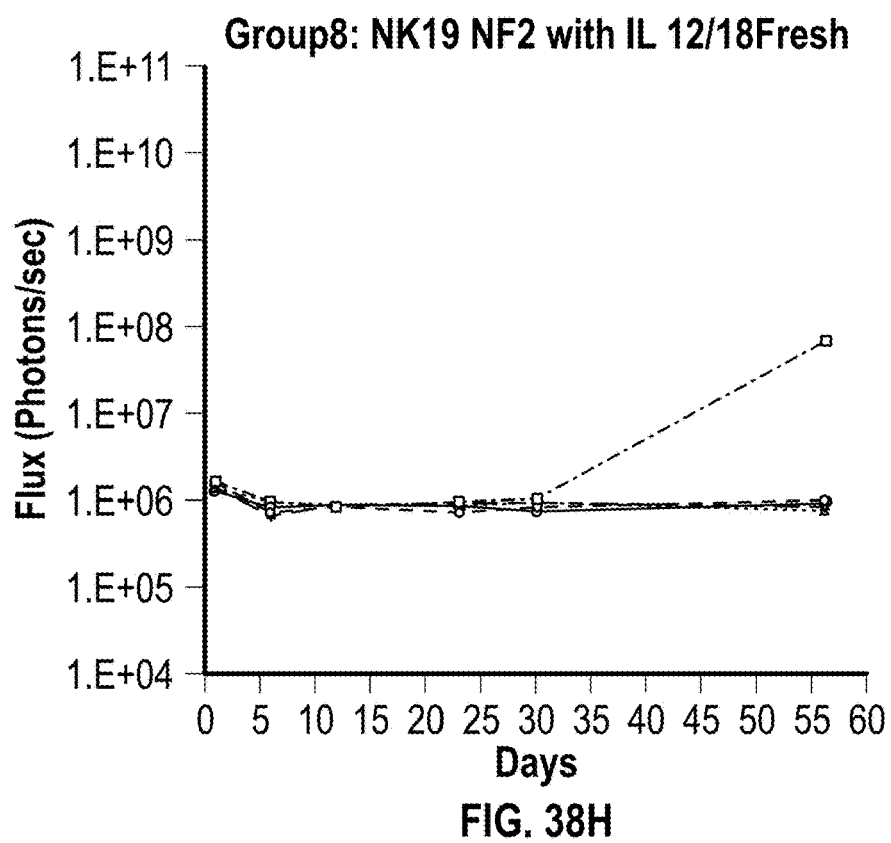
Figure 38I:
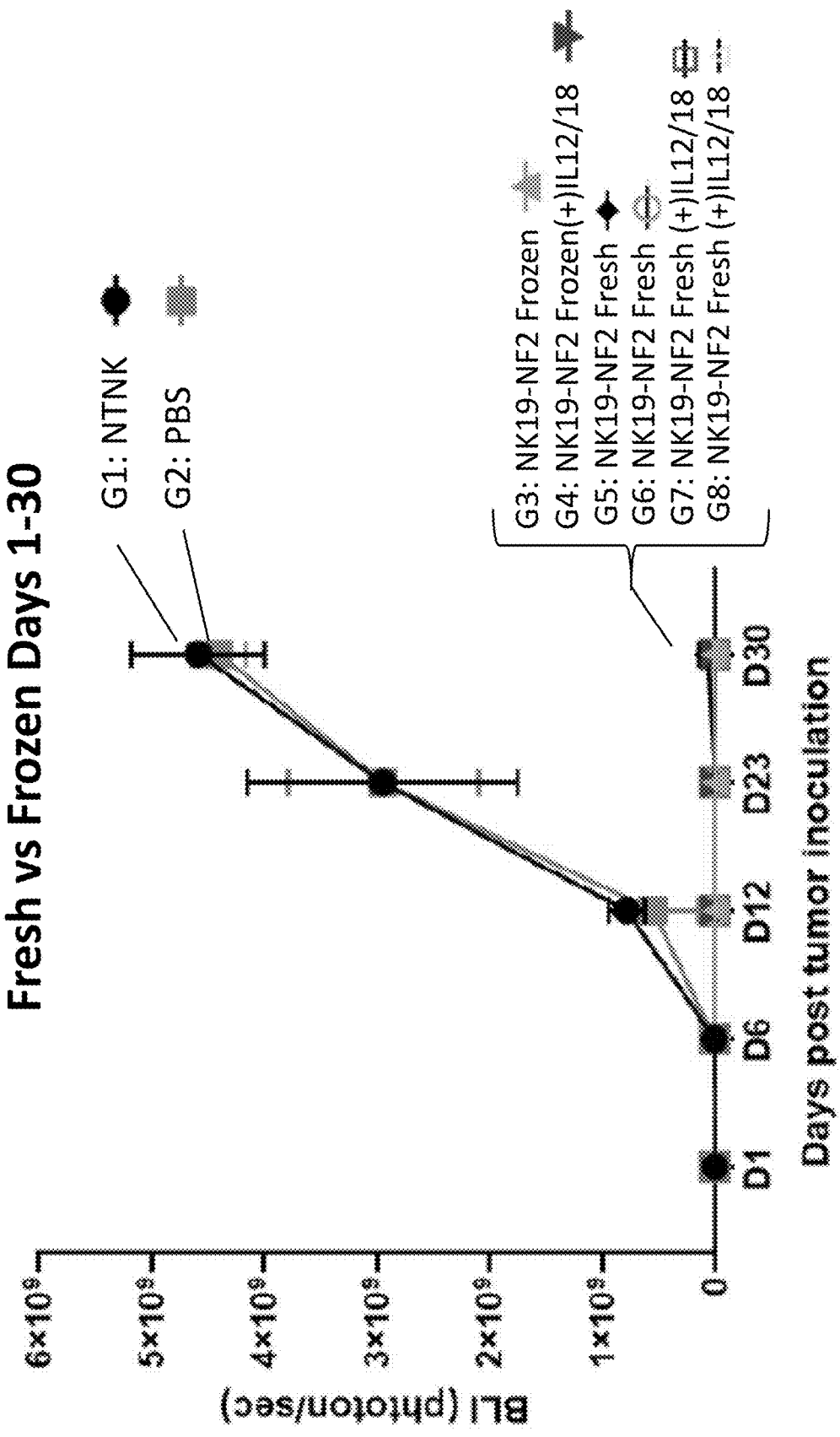
Figure 38J:
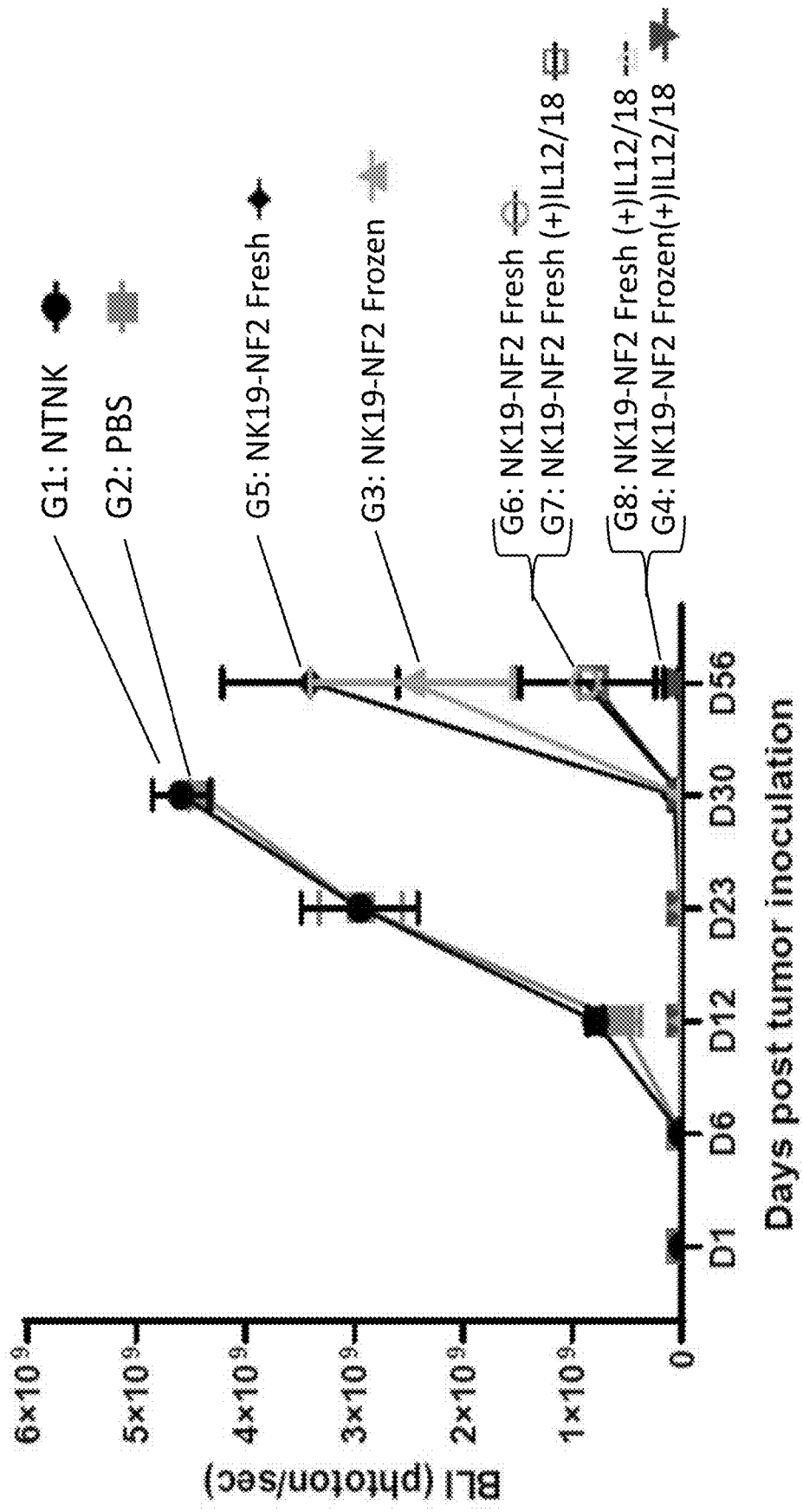

As discussed herein, in several embodiments engineered NK cells are prepared for allogeneic cell therapy. As such, in several embodiments, the engineered NK cells to be administered are prepared and then frozen for later use in a subject. Experiments were performed to determine whether the process of cryopreservation followed by thawing would adversely impact the engineered NK cells, such as by reducing their viability, persistence or cytotoxicity. FIG. 37A shows the schematic experimental protocol employed, as well as the experimental groups and other conditions used. For cells with an "IL12/IL18" designation, the cells were expanded in the presence of soluble IL12 and/or IL18, as described in in U.S. Provisional Patent Application No. 62/881,311, filed Jul. 31, 2019 and Application No. 62/932,342, filed Nov. 7, 2019, each of which is incorporated in its entirety by reference herein. FIGS. 37B and 37C shows the in vivo bioluminescence imaging from the indicated experimental groups. FIG. 38A-38H show line graphs that reflect the bioluminescence intensity over time. These data are recapitulated in FIG. 38I, which shows the first 30 days, and FIG. 38J which shows data through 56 days. While FIG. 38I shows a clear distinction between the NK cells expressing CD19 CARs and the controls, there is nominal separation among the experimental groups. However, FIG. 38J shows data through 56 days, and there is a greater distinction of the ability of NK cells expressing the various CAR constructs and processed under the indicated conditions at inhibiting tumor cell growth. Of note is that the "pairs" of groups (same CAR construct, fresh vs. frozen) show fairly similar anti-tumor activity. This indicates, that, according to several embodiments, engineered NK cells expressing anti-CD19 CARs are effective not only when prepared and administered fresh. Additionally, according to several embodiments, engineered NK cells expressing anti-CD19 CARs are effective not only when prepared, frozen, then thawed and administered (e.g., as in an allogeneic context).

Figure 39:
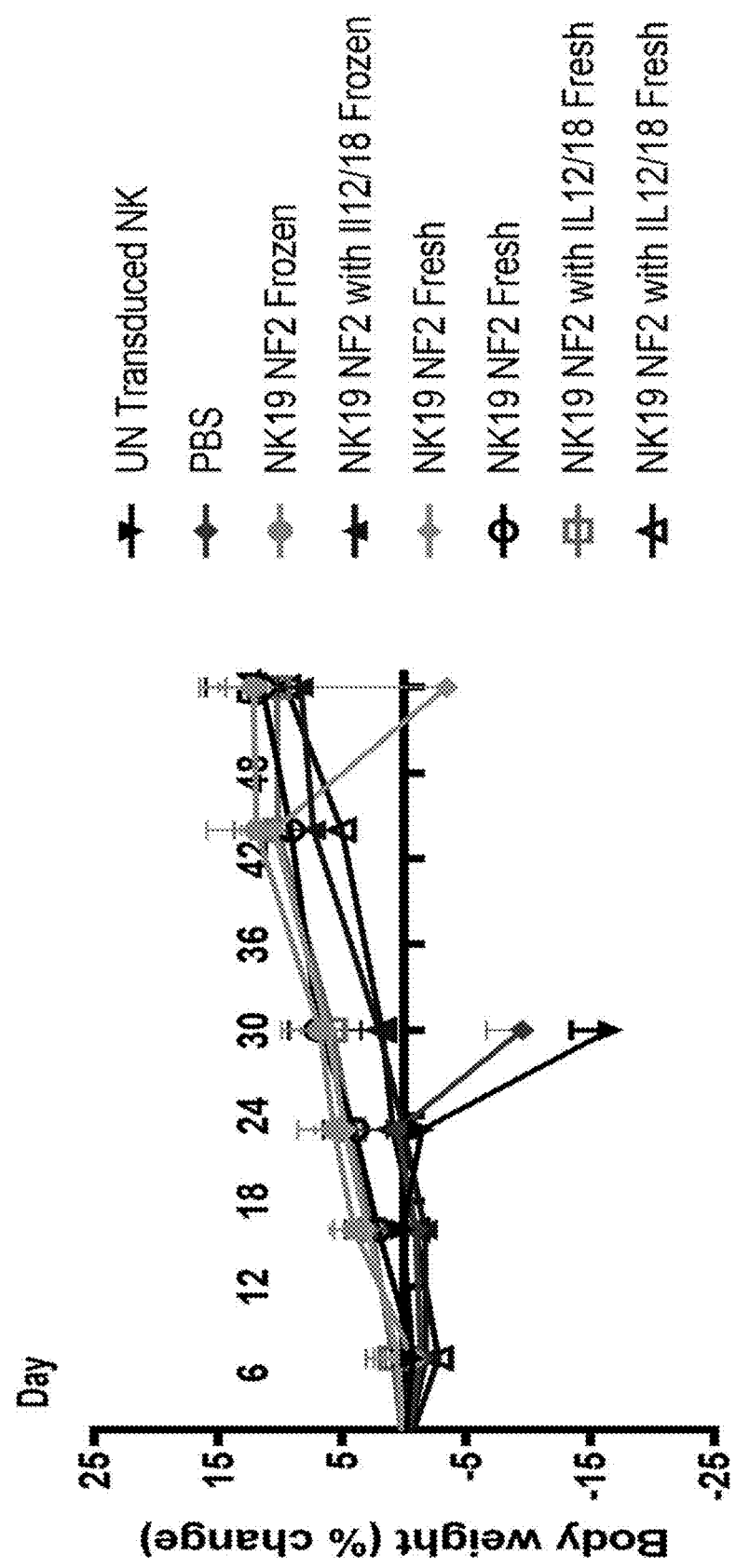
FIG. 39 shows data related to the body mass of mice over time when receiving the indicated therapy.

FIG. 39 shows a line graph of body mass of the mice treated with the indicated constructs over 56 days of the experiment. A reduction in body weight is correlated with increased tumor growth, e.g., progression of the tumor results in a decreased health of the mice, and corresponding loss of body weight (e.g., wasting). As shown, the control groups show substantial loss of body mass by 30 days, while experimental groups are increasing in body mass for the majority of the experiment. As with the bioluminescence data discussed above, there is a notable trend that many of the fresh versus frozen preparations exhibit substantially similar effects on body weight. According to several embodiments, engineered NK cells expressing anti-CD19 CARs are effective not only when prepared and administered fresh. Additionally, according to several embodiments, engineered NK cells expressing anti-CD19 CARs are effective not only when prepared, frozen, then thawed and administered (e.g., as in an allogeneic context).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% sequence identity or homology includes 96%, 97%, 98%, 99%, and 100% sequence identity or homology to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

In several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

Any titles or subheadings used herein are for organization purposes and should not be used to limit the scope of embodiments disclosed herein.

What is claimed is:

1. A polynucleotide encoding a CD19-directed chimeric antigen receptor, the chimeric antigen receptor comprising:
   an extracellular anti-CD19 binding moiety comprising a single chain Fragment variable (scFv), wherein the scFv comprises:
      a variable heavy (VH) domain, wherein the encoded VH domain comprises the amino acid sequence of SEQ ID NO: 120, and
      a variable light (VL) domain;
   a hinge, wherein the hinge is a CD8 alpha hinge;
   a transmembrane domain, wherein the transmembrane domain comprises a CD8 alpha transmembrane domain; and
   an intracellular signaling domain, wherein the intracellular signaling domain comprises:
      an OX40 subdomain, wherein the OX40 subdomain is encoded by a sequence having at least 95% sequence identity to SEQ ID NO: 5,
      a CD3 zeta subdomain, wherein the CD3 zeta subdomain is encoded by a sequence having at least 95% sequence identity to SEQ ID NO: 7, and
   wherein the polynucleotide also encodes membrane-bound interleukin-15 (mbIL15), wherein the mbIL15 comprises a sequence having at least 95% sequence identity to SEQ ID NO. 12.

2. The polynucleotide of claim 1, wherein the OX40 subdomain is encoded by SEQ ID NO. 5, and wherein the CD3 zeta subdomain is encoded by SEQ ID NO. 7.

3. The polynucleotide of claim 1, wherein the encoded OX40 subdomain comprises the amino acid sequence of SEQ ID NO: 6.

4. The polynucleotide of claim 1, wherein the encoded CD3 zeta subdomain comprises the amino acid sequence of SEQ ID NO: 8.

5. A polynucleotide encoding a CD19-directed chimeric antigen receptor, the chimeric antigen receptor comprising:
   an extracellular anti-CD19 binding moiety comprising a single chain Fragment variable (scFv), wherein the scFv comprises:
      a variable heavy (VH) domain,
         wherein the encoded VH domain comprises an amino acid sequence having at least 95% sequence identity to SEQ ID NO: 120; and
      a variable light (VL) domain,
         wherein the encoded VL domain comprises an amino acid sequence having at least 95% sequence identity to SEQ ID NO: 118;
   a hinge;
   a transmembrane domain; and
   an intracellular signaling domain, wherein the intracellular signaling domain comprises:
      an OX40 subdomain,
      a CD3 zeta subdomain; and
   wherein the polynucleotide also encodes membrane-bound interleukin-15 (mbIL15), wherein the mbIL15 comprises a sequence having at least 95% sequence identity to SEQ ID NO. 12.

6. The polynucleotide of claim 5, wherein the OX40 subdomain is encoded by a sequence having at least 95% sequence identity to SEQ ID NO. 5.

7. The polynucleotide of claim 5, wherein the CD3 zeta subdomain is encoded by a sequence having at least 95% sequence identity to SEQ ID NO. 7.

8. The polynucleotide of claim 5, wherein the polynucleotide does not encode SEQ ID NO: 112, SEQ ID NO: 113, SEQ ID NO: 114, or SEQ ID NO: 116.

9. The polynucleotide of claim 5, wherein the encoded VH domain comprises the amino acid sequence of SEQ ID NO: 120.

10. The polynucleotide of claim 5, wherein the encoded VL domain comprises the amino acid sequence of SEQ ID NO: 118.

11. A polynucleotide encoding a CD19-directed chimeric antigen receptor, the chimeric antigen receptor comprising:
    an extracellular anti-CD19 binding moiety comprising a single chain Fragment variable (scFv), wherein the scFv comprises:
       a variable heavy (VH) domain, and
       a variable light (VL) domain, wherein the encoded VL domain comprises
    the amino acid sequence of SEQ ID NO: 118;
    a hinge, wherein the hinge is a CD8 alpha hinge;
    a transmembrane domain, wherein the transmembrane domain comprises a CD8 alpha transmembrane domain; and
    an intracellular signaling domain, wherein the intracellular signaling domain comprises:
       an OX40 subdomain, wherein the OX40 subdomain is encoded by a sequence having at least 95% sequence identity to SEQ ID NO. 5, a CD3 zeta subdomain, wherein the CD3 zeta subdomain is encoded by a sequence having at least 95% sequence identity to SEQ ID NO. 7, and wherein the polynucleotide also encodes membrane-bound interleukin-15 (mbIL15), wherein the mbIL15 comprises a sequence having at least 95% sequence identity to SEQ ID NO. 12.

12. The polynucleotide of claim 11, wherein the OX40 subdomain is encoded by SEQ ID NO. 5, and wherein the CD3 zeta subdomain is encoded by SEQ ID NO. 7.

13. The polynucleotide of claim 11, wherein the encoded OX40 subdomain comprises the amino acid sequence of SEQ ID NO: 6 and wherein the encoded CD3 zeta subdomain comprises the amino acid sequence of SEQ ID NO: 8.

14. A polynucleotide encoding a CD19-directed chimeric antigen receptor, the chimeric antigen receptor comprising:
an extracellular anti-CD19 binding moiety comprising a single chain Fragment variable (scFv), wherein the scFv comprises:
a variable heavy (VH) domain, and
a variable light (VL) domain;
a hinge, wherein the hinge is a CD8 alpha hinge;
a transmembrane domain, wherein the transmembrane domain comprises a CD8 alpha transmembrane domain; and
an intracellular signaling domain, wherein the intracellular signaling domain comprises:
an OX40 subdomain, wherein the OX40 subdomain is encoded by a sequence having at least 95% sequence identity to SEQ ID NO. 5,
a CD3 zeta subdomain, wherein the CD3 zeta subdomain is encoded by a sequence having at least 95% sequence identity to SEQ ID NO. 7, and
wherein the polynucleotide also encodes membrane-bound interleukin-15 (mbIL15), wherein the comprises a sequence having at least 95% sequence identity to SEQ ID NO. 12, and
wherein the encoded CD19-directed chimeric antigen receptor has at least 95% sequence identity to the amino acid sequence set forth in SEQ ID NO: 187.

15. The polynucleotide of claim 14, wherein the OX40 subdomain is encoded by SEQ ID NO. 5, and wherein the CD3 zeta subdomain is encoded by SEQ ID NO. 7.

16. The polynucleotide of claim 14, wherein the encoded OX40 subdomain comprises the amino acid sequence of SEQ ID NO: 6 and wherein the encoded CD3 zeta subdomain comprises the amino acid sequence of SEQ ID NO: 8.

17. A polynucleotide encoding a CD19-directed chimeric antigen receptor, the chimeric antigen receptor comprising:
an extracellular anti-CD19 binding moiety comprising a single chain Fragment variable (scFv), wherein the scFv comprises:
a variable heavy (VH) domain, and
a variable light (VL) domain;
a hinge, wherein the hinge is a CD8 alpha hinge;
a transmembrane domain, wherein the transmembrane domain comprises a CD8 alpha transmembrane domain; and
an intracellular signaling domain, wherein the intracellular signaling domain comprises:
an OX40 subdomain, wherein the OX40 subdomain is encoded by a sequence having at least 95% sequence identity to SEQ ID NO. 5,
a CD3 zeta subdomain, wherein the CD3 zeta subdomain is encoded by a sequence having at least 95% sequence identity to SEQ ID NO. 7, and
wherein the polynucleotide also encodes membrane-bound interleukin-15 (mbIL15), wherein the mbIL15 comprises a sequence having at least 95% sequence identity to SEQ ID NO. 12, and
wherein the encoded CD19-directed chimeric antigen receptor comprises the amino acid sequence set forth in SEQ ID NO: 187.

18. The polynucleotide of claim 17, wherein the OX40 subdomain is encoded by SEQ ID NO. 5, and wherein the CD3 zeta subdomain is encoded by SEQ ID NO. 7.

19. The polynucleotide of claim 17, wherein the encoded OX40 subdomain comprises the amino acid sequence of SEQ ID NO: 6 and wherein the encoded CD3 zeta subdomain comprises the amino acid sequence of SEQ ID NO: 8.

\* \* \* \* \*